US006183752B1

(12) United States Patent
Epstein et al.

(10) Patent No.: US 6,183,752 B1
(45) Date of Patent: Feb. 6, 2001

(54) RESTENOSIS/ATHEROSCLEROSIS DIAGNOSIS, PROPHYLAXIS AND THERAPY

(75) Inventors: Stephen E. Epstein, Rockville; Toren Finkel, Bethesda, both of MD (US); Edith Speir, Annandale, VA (US); Yi Fu Zhou; Jianhui Zhu, both of Bethesda, MD (US); Lorne Erdile, Loudonville; Steven Pincus, East Greenbush, both of NY (US)

(73) Assignees: Pasteur Merieux Serums et Vaccins, Lyons (FR); The United States of America as represented by the Department of Health and Human Services, Washington, DC (US)

( * ) Notice: Under 35 U.S.C. 154(b), the term of this patent shall be extended for 0 days.

(21) Appl. No.: 08/796,101

(22) Filed: Feb. 5, 1997

(51) Int. Cl.[7] ...................... A61K 39/245; A61K 39/275; C12N 15/38; C12N 15/12

(52) U.S. Cl. .................................... 424/199.1; 424/199.1; 424/230.1; 424/277.1; 424/93.2; 435/320.1; 514/44

(58) Field of Search ............................... 435/173.3, 69.3, 435/320.1; 424/199.1, 230.1, 93.2, 277.1; 514/44

(56) References Cited

U.S. PATENT DOCUMENTS

| | | | | |
|---|---|---|---|---|
| 5,338,683 | * | 8/1994 | Paoletti | 435/320.1 |
| 5,747,469 | * | 5/1998 | Roth et al. | 514/44 |
| 5,837,262 | * | 11/1998 | Golubev et al. | 424/231.1 |

FOREIGN PATENT DOCUMENTS 2723697 2/1996 (FR) .

OTHER PUBLICATIONS

Epstein et al., "The Basis of Molecular Strategies for Treating Coronary Restenosis After Angioplasty," *JACC*. vol. 23, pp. 1278–1288, May 1994.

Chang et al., "Cytostatic Gene Therapy for Vascular Proliferative Disorders with a Constitutively Active Form of the Retinoblastoma Gene Product," *Science*, vol. 267, pp. 518–522, Jan. 27, 1995.

P. Rowe, "Casual Link Found Between CMV and Restenosis," *The Lancet*, vol. 347, p. 1755, Jun. 22, 1996.

"The Infected Heart," *The Economist*, p. 95, Sep. 14, 1996.

S. Squires, "Virus Linked to Blocked Arteries," *Washington Post Health*, p. 7, Sep. 3, 1996.

Speir et al., "Potential Role of Human Cytomegalovirus and p53 Interaction in Coronary Restenosis," *Science*, vol. 265, pp. 391–394, Jul. 15, 1994.

Speir et al., "Role of Reactive Oxygen Intermediates in Cytomegalovirus Gene Expression and in the Response of Human Smooth Muscle Cells to Viral Infection," *Circulation Research*, vol. 79, pp. 1143–1152, Dec. 1996.

Muganda et al (Journal of Virology 68:8024–2034), 1994.*

Tsai et al (Journal of Biological Chemistry 271:3534–3540), Feb. 16, 1996.*

Minar et al, Circulation, 91 (8) p2167–73, abstract only cited, Apr. 15, 1995.*

Ranke et al, Circulation, 87 (6) p1873–9, abstract only cited, Jun. 1993.*

Melnick et al, Bioessays 17(10):899–903, abstract only cited, Nov. 1995.*

Vossen, et al (1996) Intervirology, vol. 39 pp. 213–221.*

Vercellotti (1995) Trends Cardiovascular Medicine, vol. 5(4) pp. 128–133.*

Baar (1996) Human Pathology, vol. 27 (4) pp. 324–329.*

* cited by examiner

*Primary Examiner*—Mary E. Mosher
(74) *Attorney, Agent, or Firm*—Frommer Lawrence & Haug LLP; William S. Frommer; Thomas J. Kowalski

(57) ABSTRACT

Disclosed and claimed are compositions and methods for therapy and/or prevention of restenosis and/or atherosclerosis. The compositions can include an agent for decreasing viral load of cytomegalovirus, such as an immunological composition or vaccine against cytomegalovirus (CMV) containing at least one epitope of interest of CMV and/or an expression system which expresses at least one epitope of interest of CMV. Such compositions can include at least one epitope of p53. Alternatively, the compositions can include at least one epitope of p53 and/or an expression system which expresses the epitope. The methods can include administering the compositions to a patient in need of such therapy and/or prevention. Additionally, compositions and methods for diagnosing atherosclerosis and/or restenosis, or susceptibility thereto, including screening a sample from a patient for antibodies to CMV and/or CMV proteins and/or screening a sample from a patient for specific viral proteins that predict whether the virus has been reactivated and/or antibodies thereto and/or detecting whether CMV nucleic acid, e.g., mRNA is present in peripheral blood monocytes (PBMCs) and/or detecting a cellular-mediated immune response to CMV peptides or proteins is present and/or HLA phenotyping and/or HLA genotyping. Embodiements can include a skin test.

22 Claims, 102 Drawing Sheets

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC ACAGGGTACG
 301 GATCTTATTC GCTTTGAACG TAATATCGTC TGCACCTCGA TGAAGCCCAT CAATGAAGAC
 361 CTGGACGAGG GCATCATGGT GGTCTACAAA CGCAACATCG TCGCGCACAC CTTTAAGGTA
 421 CGAGTCTACC AGAAGGTTTT GACGTTTCGT CGTAGCTACG CTTACATCCA CACCACTTAT
 481 CTGCTGGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTGAACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA AATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCAAAAGA
1381 AGTACAGATG GCAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTG TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TTCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG GCAACCACCG CACTGAGGAA TGTCAGCTTC CCAGCCTCAA GATCTTCATC
1861 GCCGGCAACT CGGCCTACGA GTACGTGGAC TACCTCTTCA AACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTGCCGCC CTACCTCAAG GGTCTGGACG ACCTCATGAG CGGCCTGGGC
2161 GCCGCGGGAA AGGCCGTTGG CGTAGCCATT GGGGCCGTGG GTGGCGCGGT GGCCTCCGTG
2221 GTCGAAGGCG TTGCCACCTT CCTCAAAAAC CCCTTCGGAG CCTTCACCAT CATCCTCGTG
2281 GCCATAGCCG TCGTCATTAT CATTTATTTG ATCTATATCC GACAGCGGCG TCTCTGCATG
2341 CAGCCGCTGC AGAACCTCTT TCCCTATCTG GTGTCCGCCG ACGGGACCAC CGTGACGTCG
2401 GGCAACACCA AAGACACGTC GTTACAGGCT CCGCCTTCCT ACGAGGAAAG TGTTTATAAT
2461 TCTGGTCGCA AAGGACCGGG ACCACCGTCG TCTGATGCAT CCACGGCGGC TCCGCCTTAC
2521 ACCAACGAGC AGGCTTACCA GATGCTTCTG GCCCTGGTCC GTCTGGACGC AGAGCAGCGA
2581 GCGCACGAGA ACGGTACAGA TTCTTTGGAC GGACAGACTG GCACGCAGGA CAAGGGACAG
2641 AAGCCCAACC TGCTAGACCG ACTGCGACAC CGCAAAAACG GCTACCGACA CTTGAAAGAC
2701 TCCGACGAAG AAGAGAACGT CTGA
```

Figure 8

```
   1 AAGCTTTTGC GATCAATAAA TGGATCACAA CCAGTATCTC TTAACGATGT TCTTCGCAGA
  61 TGATGATTCA TTTTTTAAGT ATTTGGCTAG TCAAGATGAT GAATCTTCAT TATCTGATAT
 121 ATTGCAAATC ACTCAATATC TAGACTTTCT GTTATTATTA TTGATCCAAT CAAAAAATAA
 181 ATTAGAAGCC GTGGGTCATT GTTATGAATC TCTTTCAGAG GAATACAGAC AATTGACAAA
 241 ATTCACAGAC TCTCAAGATT TTAAAAAACT GTTTAACAAG GTCCCTATTG TTACAGATGG
 301 AAGGGTCAAA CTTAATAAAG GATATTTGTT CGACTTTGTG ATTAGTTTGA TGCGATTCAA
 361 AAAAGAATCC TCTCTAGCTA CCACCGCAAT AGATCCTATT AGATACATAG ATCCTCGTCG
 421 CGATATCGCA TTTTCTAACG TGATGGATAT ATTAAAGTCG AATAAAGTGA ACAATAATTA
 481 ATTCTTTATT GTCATCATGT AATTAACTAG CTACCCGGGA GATCTCTCGA GCTGCAGAAG
 541 CTTATAAAAA TCACAAGTCT CTGTCACTTT TTTTGTCTAG TTTTTTTTTC TCCTCTTGGT
 601 TCAGACGTTC TCTTCTTCGT CGGAGTCTTT CAAGTGTCGG TAGCCGTTTT TGCGGTGTCG
 661 CAGTCGGTCT AGCAGGTTGG GCTTCTGTCC CTTGTCCTGC GTGCCAGTCT GTCCGTCCAA
 721 AGAATCTGTA CCGTTCTCGT GCGCTCGCTG CTCTGCGTCC AGACGGACCA GGGCCAGAAG
 781 CATCTGGTAA GCCTGCTCGT TGGTGTAAGG CGGAGCCGCC GTGGATGCAT CAGACGACGG
 841 TGGTCCCGGT CCTTTGCGAC CAGAATTATA AACACTTTCC TCGTAGGAAG GCGGAGCCTG
 901 TAACGACGTG TCTTTGGTGT TGCCCGACGT CACGGTGGTC CCGTCGGCGG ACACCAGATA
 961 GGGAAAGAGG TTCTGCAGCG GCTGCATGCA GAGACGCCGC TGTCGAGTAT AGATCAAATA
1021 AATGATAATG ACGACGGCTA TGGCCACGAG GATGATGGTG AAGGCTCCGA AGGGGTTTTT
1081 GAGGAAGGTG GCAACGCCTT CGACCACGGA GGCCACCGCG CCACCCACGG CCCCAATGGC
1141 TACGCCAACG GCCTTTCCCG CGGCGCCCAG GCCGCTCATG AGGTCGTCCA GACCCTTGAG
1201 GTAGGGCGGC AGCGGGTCGA CTACCTTGTC CTCCACGTAC TTTACCCGCT GCTTATACGA
1261 ATTGAACTCG CGCATGATCT CCTCGAGATC AAAAACGTTG CTGGAACGCA ATTCTTTCTG
1321 CGAGTAAAGT TCCAGTACCC TGAAGTCGGT GTTTTCCAGC GGGTCGATGT CTAGGGCGAT
1381 CATGCTGTCG ACGGTGGAGA TGCTGCTGAG GTCAATCATG CGTTTGAAGA GGTAGTCCAC
1441 GTACTCGTAG GCCGAGTTGC CGGCGATGAA GATCTTGAGG CTGGGAAGCT GACATTCCTC
1501 AGTGCGGTGG TTGCCCAACA GGATTTCGTT ATCCTCGCCC AGTTGACCGT ACTGCACGTA
1561 CGAGCTGTTG GCGAAATTAA AGATGACCAC TGGTCGTGAG TAGCAGCGTC CTGGCGATTC
1621 CTTCACATTC ATATCACGCA GCACCTTGAC GCTGGTTTGG TTAATGGTCA CGCAGCTGGC
1681 CAGACCCAGG ACATCACCCA TGAAACGCGC GGCAATCGGT TTGTTGTAGA TGGCCGAGAG
1741 AATAGCTGAC GGGTTGATCT TGCTAAGTTC CTTGAAGACC TCTAGGGTGC GCCGTTGATC
1801 CACACACCAG GCTTCTGCGA TTTCGGCCAG CGCCCGGTTG ATGTAACCGC GCAACGTGTC
1861 ATAGGTGAAC TGCAGCTGGG CGTAGACCAG ATTGTGCACC GACTCCATGT TGGATAAATG
1921 AGTTGCATTG TTGCCATCTG TACTTCTTTT GGTTCTATTA TGAGTAAGAT TCAGACTGGA
1981 GCGGTTGGCC AAACGTTCGA GTTCCACCAG AGATTTTTGC TTGATACCTT GCCAGAACAC
2041 CACCAAACCA CCAGTGGTTT CAAAGACGGA CACGTTTCCA TATTTTTCAT ATGTTTGATT
2101 GTATGAAGTA TTGAAAATCT GCTGTAACTT ATTTATGGCC TCATCACGTA CACAGTCCAG
2161 CGCAGAGTCG GACATGTTCA CCTCTTGCTT CTTAGATAAG AAAGTGGCGG TCATTTTGGC
2221 AGAAGAAAAG TGATACGAGT CCTCGGCTTC GGAACGAATG GTGCGTTCCG AGGCTTCCCA
2281 GAAAGTGAGT TGACAAGTAA CATTCTTCTC GTCCTGTATA TCCCAGGAGA TCACTGAGTC
2341 CGCACGTTCA AGAAAAGCCA CCAACCTGTG GGTCTCTAAC GCAGAATTCG GTCTTTCAAA
2401 GTCGGAGACG ATAGTGTAGT TCGGAAAAAT GAAAAACTTG TCGGCGTTTT CTCCAAAATA
2461 GCTGGCATTG CGATTAGTTC CGTTGTAGAA AGGAGAAATG TCAACCACAT CACCCGTGGA
2521 AGTTGCGAAA AAATGATAGG GATACTTGGA GCGCGCAGTA GTGATGGTCA CCATACAATT
2581 CAGATTACAG GTCTCACGAT AGAGCCAGGT GCTGCCGCGG CTGTGCCATT GATCCTTGAC
2641 CGTCACGTAA CGGGTACTGT GGGTGTTGGA ATAATCGTCG GGCATTAATT GCATGGTTTT
2701 GTTTTCATAG CTGTCCCTAT GATAAGCCAC GAAAACCGTG CCTGCTATAA CGCGGCTGTA
2761 GGAACTGTAG CACTGACTGT GACTGTTGAT ATGATGAATC TCCCACATAG GAGGCGCCAC
2821 GTATTCCGTG TTGCTGCCCA GCAGATAAGT GGTGTGGATG TAAGCGTAGC TACGACGAAA
2881 CGTCAAAACC TTCTGGTAGA CTCGTACCTT AAAGGTGTGC GCGACGATGT TGCGTTTGTA
2941 GACCACCATG ATGCCCTCGT CCAGGTCTTC ATTGATGGGC TTCATCGAGG TGCAGACGAT
3001 ATTACGTTCA AAGCGAATAA GATCCGTACC CTGAGCCATA GAACACACGC GATAGGGGTA
3061 CTTGGTGGTG TTGACCCCCA CCACATCTCC GTACTTGAGG GTAGTGTTGT AGATGGTCTC
```

Figure 9A

| | | | | | | |
|---|---|---|---|---|---|---|
| 3121 | GTTAACACCA | TGGCTGACCG | TTTGGGAAGA | AGTTACGCGT | TGAGAGACTG | AACCGGATCG |
| 3181 | AGAATGAGCA | GCAGACGTCG | TATGAGAGGA | ATGGTGACTG | TGAGTAGCAG | AAGTTCCACG |
| 3241 | AGTAGAAGAT | GAGGAAACCG | CAGCACCCAG | ACAGACGATA | CACAAGTTAA | CGCAGACTAC |
| 3301 | CAGGCACCAG | ATCCTGGATT | CCATTACGAT | ACAAACTTAA | CGGATATCGC | GATAATGAAA |
| 3361 | TAATTTATGA | TTATTTCTCG | CTTTCAATTT | AACACAACCC | TCAAGAACCT | TTGTATTTAT |
| 3421 | TTTCACTTTT | AAGTATAGAA | TAAAGAAGCT | TGCATGCCAC | GCGTCTCGAG | GGCCCCTGCA |
| 3481 | GGTCGACTCT | AGAGGATCCT | GATCCTTTTT | CTGGGTAAGT | AATACGTCAA | GGAGAAAACG |
| 3541 | AAACGATCTG | TAGTTAGCGG | CCGCCTAATT | AACTAATATT | ATATTTTTTA | TCTAAAAAAC |
| 3601 | TAAAAATAAA | CATTGATTAA | ATTTTAATAT | AATACTTAAA | AATGGATGTT | GTGTCGTTAG |
| 3661 | ATAAACCGTT | TATGTATTTT | GAGGAAATTG | ATAATGAGTT | AGATTACGAA | CCAGAAAGTG |
| 3721 | CAAATGAGGT | CGCAAAAAAA | CTGCCGTATC | AAGGACAGTT | AAAACTATTA | CTAGGAGAAT |
| 3781 | TATTTTTTCT | TAGTAAGTTA | CAGCGACACG | GTATATTAGA | TGGTGCCACC | GTAGTGTATA |
| 3841 | TAGGATCGGC | TCCTGGTACA | CATATACGTT | ATTTGAGAGA | TCATTTCTAT | AATTTAGGAA |
| 3901 | TGATTATCAA | ATGGATGCTA | ATTGACGGAC | GCCATCATGA | TCCTATTTTA | AATGGATTGC |
| 3961 | GTGATGTGAC | TCTAGTGACT | CGGTTCGTTG | ATGAGGAATA | TCTACGATCC | ATCAAAAAAC |
| 4021 | AACTGCATCC | TTCTAAGATT | ATTTTAATTT | CTGATGTGAG | ATCCAAACGA | GGAGGAAATG |
| 4081 | AACCTAGTAC | GGCGGATTTA | CTAAGTAATT | ACGCTCTACA | AAATGTCATG | ATTAGTATTT |
| 4141 | TAAACCCCGT | GGCGTCTAGT | CTTAAATGGA | GATGCCCGTT | TCCAGATCAA | TGGATCAAGG |
| 4201 | ACTTTTATAT | CCCACACGGT | AATAAAATGT | TACAACCTTT | TGCTCCTTCA | TATTCAGCTG |

Figure 9B

1 AGATATTTGT TAGCTTCTGC CGGAGATACC GTGAAAATCT ATTTTCTGGA AGGAAAGGGA
61 GGTCTTATCT ATTCTGTCAG CAGAGTAGGT TCCTCTAATG ACGAAGACAA TAGTGAATAC
121 TTGCATGAAG GTCACTGTGT AGAGTTCAAA ACTGATCATC AGTGTTTGAT AACTCTAGCG
181 TGTACGAGTC CTTCTAACAC TGTGGTTTAT TGGCTGGAAT AAAAGGATAA AGACACCTAT
241 ACTGATTCAT TTTCATCTGT CAACGTTTCT CTAAGAGATT CATAGGTATT ATTATTACAT
301 CGATCTAGAA GTCTAATAAC TGCTAAGTAT ATTATTGGAT TTAACGCGCT ATAAACGCAT
361 CCAAAACCTA CAAATATAGG AGAAGCTTCT CTTATGAAAC TTCTTAAAGC TTTACTCTTA
421 CTATTACTAC TCAAAAGAGA TATTACATTA ATTATGTGAT GAGGCATCCA ACATATAAAG
481 AAGACTAAAG CTGTAGAAGC TGTTATGAAG AATATCTTAT CAGATATATT AGATGCATTG
541 TTAGTTCTGT AGATCAGTAA CGTATAGCAT ACGAGTATAA TTATCGTAGG TAGTAGGTAT
601 CCTAAAATAA ATCTGATACA GATAATAACT TTGTAAATCA ATTCAGCAAT TTCTCTATTA
661 TCATGATAAT GATTAATACA CAGCGTGTCG TTATTTTTTG TTACGATAGT ATTTCTAAAG
721 TAAAGAGCAG GAATCCCTAG TATAATAGAA ATAATCCATA TGAAAAATAT AGTAATGTAC
781 ATATTTCTAA TGTTAACATA TTTATAGGTA AATCCAGGAA GGGTAATTTT TACATATCTA
841 TATACGCTTA TTACAGTTAT TAAAAATATA CTTGCAAACA TGTTAGAAGT AAAAAAGAAA
901 GAACTAATTT TACAAAGTGC TTTACCAAAA TGCCAATGGA AATTACTTAG TATGTATATA
961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTATG AATACTACTA ATCACGAAGA ATGCAGTAAA ACATATGATA
1501 CAAACATGTT AACAGTTTTA AAAGCCATTA GTAATAAACA GTACAATATA ATTAAGTCTT
1561 TACTTAAAAA AGATATTAAT GTTAATAGAT TATTAACTAG TTATTCTAAC GAAATATATA
1621 AACATTTAGA CATTACATTA TGTAATATAC TTATAGAACG TGCAGCAGAC ATAAACATTA
1681 TAGATAAGAA CAATCGTACA CCGTTGTTTT ATGCGGTAAA GAATAATGAT TATGATATGG
1741 TTAAACTCCT ATTAAAAAAT GGCGCGAATG TAAATTTACA AGATAGTATA GGATATTCAT
1801 GTCTTCACAT CGCAGGTATA CATAATAGTA ACATAGAAAT AGTAGATGCA TTGATATCAT
1861 ACAAACCAGA TTTAAACTCC CGCGATTGGG TAGGTAGAAC ACCGCTACAT ATCTTCGTGA
1921 TAGAATCTAA CTTTGAAGCT GTGAAATTAT TATTAAAGTC AGGTGCATAT GTAGGTTTGA
1981 AAGACAAATG TAAGCATTTT CCTATACACC ATTCTGTAAT GAAATTAGAT CACTTAATAT
2041 CAGGATTGTT ATTAAAATAT GGAGCAAATC CAAATACAAT TAACGGCAAT GGAAAAACAT
2101 TATTAAGCAT TGCTGTAACA TCTAATAATA CACTACTGGT AGAACAGCTG CTGTTATATG
2161 GAGCAGAAGT TAATAATGGT GGTTATGATG TTCCAGCTCC TATTATATCC GCTGTCAGTG
2221 TTAACAATTA TGATATTGTT AAGATACTGA TACATAATGG TGCGAATATA AATGTATCCA
2281 CGGAAGATGG TAGAACGTCT TTACATACAG CTATGTTTTG GAATAACGCT AAAATAATAG
2341 ATGAGTTGCT TAACTATGGA AGTGACATAA ACAGCGTAGA TACTTATGGT AGAACTCCGT
2401 TATCTTGTTA TCGTAGCTTA AGTTATGATA TCGCTACTAA ACTAATATCA CGTATCATTA
2461 TAACAGATGT CTATCGTGAA GCACCAGTAA ATATCAGCGG ATTTATAATT AATTTAAAAA
2521 CTATAGAAAA TAATGATATA TTCAAATTAA TTAAAGATGA TTGTATTAAA GAGATAAACA
2581 TACTTAAAAG TATAACCCTT AATAAATTTC ATTCATCTGA CATATTTATA CGATATAATA
2641 CTGATATATG TTTATTAACG AGATTTATTC AACATCCAAA GATAATAGAA CTAGACAAAA
2701 AACTCTACGC TTATAAATCT ATAGTCAACG AGAGAAAAAT CAAAGCTACT TACAGGTATT
2761 ATCAAATAAA AAAAGTATTA ACTGTACTAC CTTTTTCAGG ATATTTCTCT ATATTGCCGT
2821 TTGATGTGTT AGTATATATA CTTGAATTCA TCTATGATAA TAATATGTTG GTACTTATGA
2881 GAGCGTTATC ATTAAAATGA AATAAAAAGC ATACAAGCTA TTGCTTCGCT ATCGTTACAA
2941 AATGGCAGGA ATTTTGTGTA AACTAAGCCA CATACTTGCC AATGAAAAAA ATAGTAGAAA
3001 GGATACTATT TTAATGGGAT TAGATGTTAA GGTTCCTTGG GATTATAGTA ACTGGGCATC

Figure 10A

```
3061 TGTTAACTTT TACGACGTTA GGTTAGATAC TGATGTTACA GATTATAATA ATGTTACAAT
3121 AAAATACATG ACAGGATGTG ATATTTTTCC TCATATAACT CTTGGAATAG CAAATATGGA
3181 TCAATGTGAT AGATTTGAAA ATTTCAAAAA GCAAATAACT GATCAAGATT TACAGACTAT
3241 TTCTATAGTC TGTAAAGAAG AGATGTGTTT TCCTCAGAGT AACGCCTCTA AACAGTTGGG
3301 AGCGAAAGGA TGCGCTGTAG TTATGAAACT GGAGGTATCT GATGAACTTA GAGCCCTAAG
3361 AAATGTTCTG CTGAATGCGG TACCCTGTTC GAAGGACGTG TTTGGTGATA TCACAGTAGA
3421 TAATCCGTGG AATCCTCACA TAACAGTAGG ATATGTTAAG GAGGACGATG TCGAAAACAA
3481 GAAACGCCTA ATGGAGTGCA TGTCCAAGTT TAGGGGGCAA GAAATACAAG TTCTAGGATG
3541 GTATTAATAA GTATCTAAGT ATTTGGTATA ATTTATTAAA TAGTATAATT ATAACAAATA
3601 ATAAATAACA TGATAACGGT TTTTATTAGA ATAAAATAGA GATAATATCA TAATGATATA
3661 TAATACTTCA TTACCAGAAA TGAGTAATGG AAGACTTATA AATGAACTGC ATAAAGCTAT
3721 AAGGTATAGA GATATAAATT TAGTAAGGTA TATACTTAAA AAATGCAAAT ACAATAACGT
3781 AAATATACTA TCAACGTCTT TGTATTTAGC CGTAAGTATT TCTGATATAG AAATGGTAAA
3841 ATTATTACTA GAACACGGTG CCGATATTTT AAAATGTAAA AATCCTCCTC TTCATAAAGC
3901 TGCTAGTTTA GATAATACAG AAATTGCTAA ACTACTAATA GATTCTGGCG CTGACATAGA
3961 ACAGATACAT TCTGGAAATA GTCCGTTATA TATTTCTGTA TATAGAAACA ATAAGTCATT
4021 AACTAGATAT TTATTAAAAA AAGGTGTTAA TTGTAATAGA TTCTTTCTAA ATTATTACGA
4081 TGTACTGTAT GATAAGATAT CTGATGATAT GTATAAAATA TTTATAGATT TTAATATTGA
4141 TCTTAATATA CAAACTAGAA ATTTTGAAAC TCCGTTACAT TACGCTATAA AGTATAAGAA
4201 TATAGATTTA ATTAGGATAT TGTTAGATAA TAGTATTAAA ATAGATAAAA GTTTATTTTT
4261 GCATAAACAG TATCTCATAA AGGCACTTAA AAATAATTGT AGTTACGATA TAATAGCGTT
4321 ACTTATAAAT CACGGAGTGC CTATAAACGA ACAAGATGAT TTAGGTAAAA CCCCATTACA
4381 TCATTCGGTA ATTAATAGAA GAAAAGATGT AACAGCACTT CTGTTAAATC TAGGAGCTGA
4441 TATAAACGTA ATAGATGACT GTATGGGCAG TCCCTTACAT TACGCTGTTT CACGTAACGA
4501 TATCGAAACA ACAAAGACAC TTTTAGAAAG AGGATCTAAT GTTAATGTGG TTAATAATCA
4561 TATAGATACC GTTCTAAATA TAGCTGTTGC ATCTAAAAAC AAAACTATAG TAAACTTATT
4621 ACTGAAGTAC GGTACTGATA CAAAGTTGGT AGGATTAGAT AAACATGTTA TTCACATAGC
4681 TATAGAAATG AAAGATATTA ATATACTGAA TGCGATCTTA TTATATGGTT GCTATGTAAA
4741 CGTCTATAAT CATAAAGGTT TCACTCCTCT ATACATGGCA GTTAGTTCTA TGAAAACAGA
4801 ATTTGTTAAA CTCTTACTTG ACCACGGTGC TTACGTAAAT GCTAAAGCTA AGTTATCTGG
4861 AAATACTCCT TTACATAAAG CTATGTTATC TAATAGTTTT AATAATATAA AATTACTTTT
4921 ATCTTATAAC GCCGACTATA ATTCTCTAAA TAATCACGGT AATACGCCTC TAACTTGTGT
4981 TAGCTTTTTA GATGACAAGA TAGCTATTAT GATAATATCT AAAATGATGT TAGAAATATC
5041 TAAAAATCCT GAAATAGCTA ATTCAGAAGG TTTTATAGTA AACATGGAAC ATATAAACAG
5101 TAATAAAAGA CTACTATCTA TAAAAGAATC ATGCGAAAAA GAACTAGATG TTATAACACA
5161 TATAAAGTTA AATTCTATAT ATTCTTTTAA TATCTTTCTT GACAATAACA TAGATCTTAT
5221 GGTAAAGTTC GTAACTAATC CTAGAGTTAA TAAGATACCT GCATGTATAC GTATATATAG
5281 GGAATTAATA CGGAAAAATA AATCATTAGC TTTTCATAGA CATCAGCTAA TAGTTAAAGC
5341 TGTAAAAGAG AGTAAGAATC TAGGAATAAT AGGTAGGTTA CCTATAGATA TCAAACATAT
5401 AATAATGGAA CTATTAAGTA ATAATGATTT ACATTCTGTT ATCACCAGCT GTTGTAACCC
5461 AGTAGTATAA AGTGATTTTA TTCAATTACG AAGATAAACA TTAAATTTGT TAACAGATAT
5521 GAGTTATGAG TATTTAACTA AAGTTACTTT AGGTACAAAT AAAATATTAT GTAATATAAT
5581 AGAAAATTAT CTTGAGTCTT CATTTCCATC ACCGTCTAAA TTTATTATTA AAACCTTATT
5641 ATATAAGGCT GTTGAGTTTA GAAATGTAAA TGCTGTAAAA AAAATATTAC AGAATGATAT
5701 TGAATATGTT AAAGTAGATA GTCATGGTGT CTCGCCTTTA CATATTATAG CTATGCCTTC
5761 AAATTTTTCT CTCATAGACG CTGACATGTA TTCAGAATTT AATGAAATTA GTAATAGACT
5821 TCAAAAATCT AAAGATAGTA ACGAATTTCA ACGAGTTAGT CTACTAAGGA CAATTATAGA
5881 ATATGGTAAT GATAGTGATA TTAATAAGTG TCTAACATTA GTAAAAACGG ATATACAGAG
5941 TAACGAAGAG ATAGATATTA TAGATCTTTT GATAAATAAA GGAATAGATA TAAATATTAA
6001 AGACGATTTA GGAAACACAG CTTTGCATTA CTCGTGTGAT TATGCTAAGG GATCAAAGAT
6061 AGCTAAAAAG TTACTAGATT GTGGAGCAGA TCCTAACATA GTTAATGATT TAGGTGTTAC
```

Figure 10B

6121 ACCACTAGCG TGTGCCGTTA ATACTTGCAA CGAGATACTA GTAGATATTC TGTTAAATAA
6181 TGATGCGAAT CCTGATTCAT CTTCCTCATA TTTTTTAGGT ACTAATGTGT TACATACAGC
6241 CGTAGGTACC GGTAATATAG ATATTGTAAG ATCTTTACTT ACGGCTGGTG CCAATCCTAA
6301 TGTAGGAGAT AAATCTGGAG TTACTCCTTT GCACGTTGCT GCAGCTGATA AAGACAGTTA
6361 TCTGTTAATG GAGATGCTAC TAGATAGCGG GGCAGATCCA AATATAAAAT GCGCAAACGG
6421 TTTTACTCCT TTGTTTAATG CAGTATATGA TCATAACCGT ATAAAGTTAT TATTTCTTTA
6481 CGGGGCTGAT ATCAATATTA CTGACTCTTA CGGAAATACT CCTCTTACTT ATATGACTAA
6541 TTTTGATAAT AAATATGTAA ATTCAATAAT TATCTTACAA ATATATCTAC TTAAAAAAGA
6601 ATATAACGAT GAAAGATTGT TTCCACCTGG TATGATAAAA AATTTAAACT TTATAGAATC
6661 AAACGATAGT CTTAAAGTTA TAGCTAAAAA GTGTAATTCG TTAATACGCT ATAAGAAAAA
6721 TAAAGACATA GATGCAGATA ACGTATTATT GGAGCTTTTA GAGGAAGAGG AAGAAGATGA
6781 AATAGACAGA TGGCATACTA CATGTAAAAT ATCTTAAATA GTAATTAAAT CATTGAAATA
6841 TTAACTTACA AGATGATCGA GGTCACTTAT TATACTCTTT AATAATGGGT ACAAAGAGTA
6901 TTCATACGTT AGTTAAATCT AACGATGTAA TACGTGTTCG TGAATTAATA AAGGATGATA
6961 GATGTTTGAT AAATAAAAGA AATAGAAGAA ATCAGTCACC TGTATATATA GCTATATACA
7021 AAGGACTTTA TGAAATGACT GAAATGTTAT TGCTAAATAA TGCAAGTCTA GATACTAAAA
7081 TACCTTCTTT AATTATAGCA GCTAAAAATA ATGACTTACC TATGATAAAA TTATTGATAC
7141 AATACGGGGC AAAATTAAAT GATATTTATT TAAGGGACAC AGCATTAATG ATAGCTCTCA
7201 GAAATGGTTA CCTAGATATA GCTGAATATT TACTTTCATT AGGAGCAGAA TTTGTTAAAT
7261 ACAGACATAA GGTAATATAT AAATATCTAT CAAAAGATGC GTATGAATTA CTTTTTAGAT
7321 TTAATTATGA CGTTAATATA ATAGATTGAG A

Figure 10C

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTTGA CTAATTAGCT ATAAAAACCC GGGCTGCAGG AATTCCTCGA
1501 GACGCGTGGC ATGCAAGCTT ATAAAAATCA CAAGTCTCTG TCACTTTTTT TGTCTAGTTT
1561 TTTTTTCTCC TCTTGGTTCA GACGTTCTCT TCTTCGTCGG AGTCTTTCAA GTGTCGGTAG
1621 CCGTTTTTGC GGTGTCGCAG TCGGTCTAGC AGGTTGGGCT TCTGTCCCTT GTCCTGCGTG
1681 CCAGTCTGTC CGTCCAAAGA ATCTGTACCG TTCTCGTGCG CTCGCTGCTC TGCGTCCAGA
1741 CGGACCAGGG CCAGAAGCAT CTGGTAAGCC TGCTCGTTGG TGTAAGGCGG AGCCGCCGTG
1801 GATGCATCAG ACGACGGTGG TCCCGGTCCT TTGCGACCAG AATTATAAAC ACTTTCCTCG
1861 TAGGAAGGCG GAGCCTGTAA CGACGTGTCT TTGGTGTTGC CCGACGTCAC GGTGGTCCCG
1921 TCGGCGGACA CCAGATAGGG AAAGAGGTTC TGCAGCGGCT GCATGCAGAG ACGCCGCTGT
1981 CGAGTATAGA TCAAATAAAT GATAATGACG ACGGCTATGG CCACGAGGAT GATGGTGAAG
2041 GCTCCGAAGG GGTTTTTGAG GAAGGTGGCA ACGCCTTCGA CCACGGAGGC CACCGCGCCA
2101 CCCACGGCCC CAATGGCTAC GCCAACGGCC TTTCCCGCGG CGCCCAGGCC GCTCATGAGG
2161 TCGTCCAGAC CCTTGAGGTA GGGCGGCAGC GGGTCGACTA CCTTGTCCTC CACGTACTTT
2221 ACCCGCTGCT TATACGAATT GAACTCGCGC ATGATCTCCT CGAGATCAAA AACGTTGCTG
2281 GAACGCAATT CTTTCTGCGA GTAAAGTTCC AGTACCCTGA AGTCGGTGTT TTCCAGCGGG
2341 TCGATGTCTA GGGCGATCAT GCTGTCGACG GTGGAGATGC TGCTGAGGTC AATCATGCGT
2401 TTGAAGAGGT AGTCCACGTA CTCGTAGGCC GAGTTGCCGG CGATGAAGAT CTTGAGGCTG
2461 GGAAGCTGAC ATTCCTCAGT GCGGTGGTTG CCCAACAGGA TTTCGTTATC CTCGCCCAGT
2521 TGACCGTACT GCACGTACGA GCTGTTGGCG AAATTAAAGA TGACCACTGG TCGTGAGTAG
2581 CAGCGTCCTG GCGATTCCTT CACATTCATA TCACGCAGCA CCTTGACGCT GGTTTGGTTA
2641 ATGGTCACGC AGCTGGCCAG ACCCAGGACA TCACCCATGA AACGCGCGGC AATCGGTTTG
2701 TTGTAGATGG CCGAGAGAAT AGCTGACGGG TTGATCTTGC TAAGTTCCTT GAAGACCTCT
2761 AGGGTGCGCC GTTGATCCAC ACACCAGGCT TCTGCGATTT CGGCCAGCGC CCGGTTGATG
2821 TAACCGCGCA ACGTGTCATA GGTGAACTGC AGCTGGGCGT AGACCAGATT GTGCACCGAC
2881 TCCATGTTGG ATAAATGAGT TGCATTGTTG CCATCTGTAC TTCTTTTGGT TCTATTATGA
2941 GTAAGATTCA GACTGGAGCG GTTGGCCAAA CGTTCGAGTT CCACCAGAGA TTTTTGCTTG
3001 ATACCTTGCC AGAACACCAC CAAACCACCA GTGGTTTCAA AGACGGACAC GTTTCCATAT
3061 TTTTCATATG TTTGATTGTA TGAAGTATTG AAAATCTGCT GTAACTTATT TATGGCCTCA
```

Figure 11A

3121 TCACGTACAC AGTCCAGCGC AGAGTCGGAC ATGTTCACCT CTTGCTTCTT AGATAAGAAA
3181 GTGGCGGTCA TTTTGGCAGA AGAAAAGTGA TACGAGTCCT CGGCTTCGGA ACGAATGGTG
3241 CGTTCCGAGG CTTCCCAGAA AGTGAGTTGA CAAGTAACAT TCTTCTCGTC CTGTATATCC
3301 CAGGAGATCA CTGAGTCCGC ACGTTCAAGA AAAGCCACCA ACCTGTGGGT CTCTAACGCA
3361 GAATTCGGTC TTTCAAAGTC GGAGACGATA GTGTAGTTCG GAAAAATGAA AAACTTGTCG
3421 GCGTTTTCTC CAAAATAGCT GGCATTGCGA TTAGTTCCGT TGTAGAAAGG AGAAATGTCA
3481 ACCACATCAC CCGTGGAAGT TGCGAAAAAA TGATAGGGAT ACTTGGAGCG CGCAGTAGTG
3541 ATGGTCACCA TACAATTCAG ATTACAGGTC TCACGATAGA GCCAGGTGCT GCCGCGGCTG
3601 TGCCATTGAT CCTTGACCGT CACGTAACGG GTACTGTGGG TGTTGGAATA ATCGTCGGGC
3661 ATTAATTGCA TGGTTTTGTT TTCATAGCTG TCCCTATGAT AAGCCACGAA AACCGTGCCT
3721 GCTATAACGC GGCTGTAGGA ACTGTAGCAC TGACTGTGAC TGTTGATATG ATGAATCTCC
3781 CACATAGGAG GCGCCACGTA TTCCGTGTTG CTGCCCAGCA GATAAGTGGT GTGGATGTAA
3841 GCGTAGCTAC GACGAAACGT CAAAACCTTC TGGTAGACTC GTACCTTAAA GGTGTGCGCG
3901 ACGATGTTGC GTTTGTAGAC CACCATGATG CCCTCGTCCA GGTCTTCATT GATGGGCTTC
3961 ATCGAGGTGC AGACGATATT ACGTTCAAAG CGAATAAGAT CCGTACCCTG AGCCATAGAA
4021 CACACGCGAT AGGGGTACTT GGTGGTGTTG ACCCCCACCA CATCTCCGTA CTTGAGGGTA
4081 GTGTTGTAGA TGGTCTCGTT AACACCATGG CTGACCGTTT GGGAAGAAGT TACGCGTTGA
4141 GAGACTGAAC CGGATCGAGA ATGAGCAGCA GACGTCGTAT GAGAGGAATG GTGACTGTGA
4201 GTAGCAGAAG TTCCACGAGT AGAAGATGAG GAAACCGCAG CACCCAGACA GACGATACAC
4261 AAGTTAACGC AGACTACCAG GCACCAGATC CTGGATTCCA TTACGATACA AACTTAACGG
4321 ATATCGCGAT AATGAAATAA TTTATGATTA TTTCTCGCTT TCAATTTAAC ACAACCCTCA
4381 AGAACCTTTG TATTTATTTT CACTTTTTAA GTATAGAATA AAGAAGCTCT AATTAATTAA
4441 GCTACAAATA GTTTCGTTTT CACCTTGTCT AATAACTAAT TAATTAACCC GGATCCCGAT
4501 TTTTATGACT AGTTAATCAA ATAAAAAGCA TACAAGCTAT TGCTTCGCTA TCGTTACAAA
4561 ATGGCAGGAA TTTTGTGTAA ACTAAGCCAC ATACTTGCCA ATGAAAAAAA TAGTAGAAAG
4621 GATACTATTT TAATGGGATT AGATGTTAAG GTTCCTTGGG ATTATAGTAA CTGGGCATCT
4681 GTTAACTTTT ACGACGTTAG GTTAGATACT GATGTTACAG ATTATAATAA TGTTACAATA
4741 AAATACATGA CAGGATGTGA TATTTTTCCT CATATAACTC TTGGAATAGC AAATATGGAT
4801 CAATGTGATA GATTTGAAAA TTTCAAAAAG CAAATAACTG ATCAAGATTT ACAGACTATT
4861 TCTATAGTCT GTAAAGAAGA GATGTGTTTT CCTCAGAGTA ACGCCTCTAA ACAGTTGGGA
4921 GCGAAAGGAT GCGCTGTAGT TATGAAACTG GAGGTATCTG ATGAACTTAG AGCCCTAAGA
4981 AATGTTCTGC TGAATGCGGT ACCCTGTTCG AAGGACGTGT TTGGTGATAT CACAGTAGAT
5041 AATCCGTGGA ATCCTCACAT AACAGTAGGA TATGTTAAGG AGGACGATGT CGAAAACAAG
5101 AAACGCCTAA TGGAGTGCAT GTCCAAGTTT AGGGGGCAAG AAATACAAGT TCTAGGATGG
5161 TATTAATAAG TATCTAAGTA TTTGGTATAA TTTATTAAAT AGTATAATTA TAACAAATAA
5221 TAAATAACAT GATAACGGTT TTTATTAGAA TAAAATAGAG ATAATATCAT AATGATATAT
5281 AATACTTCAT TACCAGAAAT GAGTAATGGA AGACTTATAA ATGAACTGCA TAAAGCTATA
5341 AGGTATAGAG ATATAAATTT AGTAAGGTAT ATACTTAAAA AATGCAAATA CAATAACGTA
5401 AATATACTAT CAACGTCTTT GTATTTAGCC GTAAGTATTT CTGATATAGA AATGGTAAAA
5461 TTATTACTAG AACACGGTGC CGATATTTTA AAATGTAAAA ATCCTCCTCT TCATAAAGCT
5521 GCTAGTTTAG ATAATACAGA AATTGCTAAA CTACTAATAG ATTCTGGCGC TGACATAGAA
5581 CAGATACATT CTGGAAATAG TCCGTTATAT ATTTCTGTAT ATAGAAACAA TAAGTCATTA
5641 ACTAGATATT TATTAAAAAA AGGTGTTAAT TGTAATAGAT TCTTTCTAAA TTATTACGAT
5701 GTACTGTATG ATAAGATATC TGATGATATG TATAAAATAT TTATAGATTT TAATATTGAT
5761 CTTAATATAC AAACTAGAAA TTTTGAAACT CCGTTACATT ACGCTATAAA GTATAAGAAT
5821 ATAGATTTAA TTAGGATATT GTTAGATAAT AGTATTAAAA TAGATAAAAG TTTATTTTTG
5881 CATAAACAGT ATCTCATAAA GGCACTTAAA AATAATTGTA GTTACGATAT AATAGCGTTA
5941 CTTATAAATC ACGGAGTGCC TATAAACGAA CAAGATGATT TAGGTAAAAC CCCATTACAT
6001 CATTCGGTAA TTAATAGAAG AAAAGATGTA ACAGCACTTC TGTTAAATCT AGGAGCTGAT
6061 ATAAACGTAA TAGATGACTG TATGGGCAGT CCCTTACATT ACGCTGTTTC ACGTAACGAT
6121 ATCGAAACAA CAAAGACACT TTTAGAAAGA GGATCTAATG TTAATGTGGT TAATAATCAT

Figure 11B

```
6181 ATAGATACCG TTCTAAATAT AGCTGTTGCA TCTAAAAACA AAACTATAGT AAACTTATTA
6241 CTGAAGTACG GTACTGATAC AAAGTTGGTA GGATTAGATA AACATGTTAT TCACATAGCT
6301 ATAGAAATGA AAGATATTAA TATACTGAAT GCGATCTTAT TATATGGTTG CTATGTAAAC
6361 GTCTATAATC ATAAAGGTTT CACTCCTCTA TACATGGCAG TTAGTTCTAT GAAAACAGAA
6421 TTTGTTAAAC TCTTACTTGA CCACGGTGCT TACGTAAATG CTAAAGCTAA GTTATCTGGA
6481 AATACTCCTT TACATAAAGC TATGTTATCT AATAGTTTTA ATAATATAAA ATTACTTTTA
6541 TCTTATAACG CCGACTATAA TTCTCTAAAT AATCACGGTA ATACGCCTCT AACTTGTGTT
6601 AGCTTTTTAG ATGACAAGAT AGCTATTATG ATAATATCTA AAATGATGTT AGAAATATCT
6661 AAAAATCCTG AAATAGCTAA TTCAGAAGGT TTTATAGTAA ACATGGAACA TATAAACAGT
6721 AATAAAAGAC TACTATCTAT AAAAGAATCA TGCGAAAAAG AACTAGATGT TATAACACAT
6781 ATAAAGTTAA ATTCTATATA TTCTTTTAAT ATCTTTCTTG ACAATAACAT AGATCTTATG
6841 GTAAAGTTCG TAACTAATCC TAGAGTTAAT AAGATACCTG CATGTATACG TATATATAGG
6901 GAATTAATAC GGAAAAATAA ATCATTAGCT TTTCATAGAC ATCAGCTAAT AGTTAAAGCT
6961 GTAAAAGAGA GTAAGAATCT AGGAATAATA GGTAGGTTAC CTATAGATAT CAAACATATA
7021 ATAATGGAAC TATTAAGTAA TAATGATTTA CATTCTGTTA TCACCAGCTG TTGTAACCCA
7081 GTAGTATAAA G
```

Figure 11C

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGTCT CTGACACTTT TTTTGTCTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAAGAGG TTCTGCAGCG GCTGCATGCA GAGACGCCGC
 901 TGTCGAGTAT AGATCAAATA AATGATAATG ACGACGGCTA TGGCCACGAG GATGATGGTG
 961 AAGGCTCCGA AGGGGTTTTT GAGGAAGGTG GCAACGCCTT CGACCACGGA GGCCACCGCG
1021 CCACCCACGG CCCCAATGGC TACGCCAACG GCCTTTCCCG CGGCGCCCAG GCCGCTCATG
1081 AGGTCGTCCA GACCCTTGAG GTAGGGCGGC AGCGGGTCGA CTACCTTGTC CTCCACGTAC
1141 TTTACCCGCT GCTTATACGA ATTGAACTCG CGCATGATCT CCTCGAGATC AAAAACGTTG
1201 CTGGAACGCA ATTCTTTCTG CGAGTAAAGT TCCAGTACCC TGAAGTCGGT GTTTTCCAGC
1261 GGGTCGATGT CTAGGGCGAT CATGCTGTCG ACGGTGGAGA TGCTGCTGAG GTCAATCATG
1321 CGTTTGAAGA GGTAGTCCAC GTACTCGTAG GCCGAGTTGC CGGCGATGAA GATCTTGAGG
1381 CTGGGAAGCT GACATTCCTC AGTGCGGTGG TTGCCCAACA GGATTTCGTT ATCCTCGCCC
1441 AGTTGACCGT ACTGCACGTA CGAGCTGTTG GCGAAATTAA AGATGACCAC TGGTCGTGAG
1501 TAGCAGCGTC CTGGCGATTC CTTCACATTC ATATCACGCA GCACCTTGAC GCTGGTTTGG
1561 TTAATGGTCA CGCAGCTGGC CAGACCCAGG ACATCACCCA TGAAACGCGC GGCAATCGGT
1621 TTGTTGTAGA TGGCCGAGAG AATAGCTGAC GGGTTGATCT TGCTAAGTTC CTTGAAGACC
1681 TCTAGGGTGC GCCGTTGATC CACACACCAG GCTTCTGCGA TTTCGGCCAG CGCCCGGTTG
1741 ATGTAACCGC GCAACGTGTC ATAGGTGAAC TGCAGCTGGG CGTAGACCAG ATTGTGCACC
1801 GACTCCATGT TGGATAAATG AGTTGCATTG TTGCCATCTG TACTTCTTTT GGTTCTATTA
1861 TGAGTAAGAT TCAGACTGGA GCGGTTGGCC AAACGTTCGA GTTCCACCAG AGATTTTTGC
1921 TTGATACCTT GCCAGAACAC CACCAAACCA CCAGTGGTTT CAAAGACGGA CACGTTTCCA
1981 TATTTTTCAT ATGTTTGATT GTATGAAGTA TTGAAAATCT GCTGTAACTT ATTTATGGCC
2041 TCATCACGTA CACAGTCCAG CGCAGAGTCG GACATGTTCA CCTCTTGCTT CTTAGATAAG
2101 AAAGTGGCGG TCATTTTGGC AGAAGAAAAG TGATACGAGT CCTCGGCTTC GGAACGAATG
2161 GTGCGTTCCG AGGCTTCCCA GAAAGTGAGT TGACAAGTAA CATTCTTCTC GTCCTGTATA
2221 TCCCAGGAGA TCACTGAGTC CGCACGTTCA AGAAAAGCCA CCAACCTGTG GGTCTCTAAC
2281 GCAGAATTCG GTCTTTCAAA GTCGGAGACG ATAGTGTAGT TCGGAAAAAT GAAAAACTTG
2341 TCGGCGTTTT CTCCAAAATA GCTGGCATTG CGATTAGTTC CGTTGTAGAA AGGAGAAATG
2401 TCAACCACAT CACCCGTGGA AGTTGCGAAA AAATGATAGG GATACTTGGA GCGCGCAGTA
2461 GTGATGGTCA CCATACAATT CAGATTACAG GTCTCACGAT AGAGCCAGGT GCTGCCGCGG
2521 CTGTGCCATT GATCCTTGAC CGTCACGTAA CGGGTACTGT GGGTGTTGGA ATAATCGTCG
2581 GGCATTAATT GCATGGTTTT GTTTTCATAG CTGTCCCTAT GATAAGCCAC GAAAACCGTG
2641 CCTGCTATAA CGCGGCTGTA GGAACTGTAG CACTGACTGT GACTGTTGAT ATGATGAATC
2701 TCCCACATAG GAGGCGCCAC GTATTCCGTG TTGCTGCCCA GCAGATAAGT GGTGTGGATG
2761 TAAGCGTAGC TACGACGAAA CGTCAAAACC TTCTGGTAGA CTCGTACCTT AAAGGTGTGC
2821 GCGACGATGT TGCGTTTGTA GACCACCATG ATGCCCTCGT CCAGGTCTTC ATTGATGGGC
2881 TTCATCGAGG TGCAGACGAT ATTACGTTCA AAGCGAATAA GATCCGTACC CTGAGCCATA
2941 GAACACACGC GATAGGGGTA CTTGGTGGTG TTGACCCCCA CCACATCTCC GTACTTGAGG
3001 GTAGTGTTGT AGATGGTCTC GTTAACACCA TGGCTGACCG TTTGGGAAGA AGTTACGCGT
3061 TGAGAGACTG AACCGGATCG AGAATGAGCA GCAGACGTCG TATGAGAGGA ATGGTGACTG
```

Figure 12A

```
3121 TGAGTAGCAG AAGTTCCACG AGTAGAAGAT GAGGAAACCG CAGCACCCAG ACAGACGATA
3181 CACAAGTTAA CGCAGACTAC CAGGCACCAG ATCCTGGATT CCATTACGAT ACAAACTTAA
3241 CGGATATCGC GATAATGAAA TAATTTATGA TTATTTCTCG CTTTCAATTT AACACAACCC
3301 TCAAGAACCT TTGTATTTAT TTTCACTTTT TAAGTATAGA ATAAAGAAGC TGGGAATCGA
3361 TTCGCGATAG CTGATTAGTT TTTGTTAACA AAAATGTGGG AGAATCTAAT TAGTTTTTCT
3421 TTACACAATT GACGTACATG AGTCTGAGTT CCTTGTTTTT GCTAATTATT TCATCCAATT
3481 TATTATTCTT GACGATATCG AGATCTTTTG TATAGGAGTC AGACTTGTAT TCAACATGCT
3541 TTTCTATAAT CATCTTAGTT ATTTCGGCAT CATCCAATAG TACATTTTCC AGATTAACAG
3601 AGTAGATATT AATGTCGTAT TTGAACAGAG CCTGTAACAT CTCAATGTCT TTATTATCTA
3661 TAGCCAATTT AATGTCCGGA ATGAAGAGAA GGGAATTATT GGTGTTTGTC GACGTCATAT
3721 AGTCGAGCAA GAGAATCATC ATATCCACGT GTCCATTTTT TATAGTGGTG TGAATACAAC
3781 TAAGGAGAAT AGCCAGATCA AAAGTAGATG GTATTTCTGA AAGAAAGTAT GATACAATAC
3841 TTACATCATT AAGCATGACG GCATGATAAA ATGAAGTTTT CCATCCAGTT TTCCCATAGA
3901 ACATCAGTCT CCAATTTTTC TTAAACAGTT TCACCGTTTG CATGTTACCA CTATCAACCG
3961 CATAATACAA TGCGGTGTTT CCTTTGTCAT CAAATTGTGA ATCATCCATT CCACTGAATA
4021 GCAAAATCTT TACTATTTTG GTATCTTCTA ATGTGGCTGC CTGATGTAAT GGAAATTCAT
4081 TCTCTAGAAG ATTTTTCAAT GCTCCAGCGT TCAACAACGT ACATACTAGA CGCACGTTAT
4141 TATCAGCTAT TGCATAATAC AAGGCACTAT GTCCATGGAC ATCCGCCTTA AATGTATCTT
4201 TACTAGAGAG AAAGCTTTTC AGCTGCTTAG ACTTCCAAGT ATTAATTCGT GACAGATCCA
4261 TGTCTGAAAC GAGACGCTAA TTAGTGTATA TTTTTTCATT TTTTATAATT TTGTCATATT
4321 GCACCAGAAT TAATAATATC TCTAATAGAT CTAATTTAAT TTAATTTATA TAACTTATTT
4381 TTTGAATATA CTTTTAATTA ACAAAAGAGT TAAGTTACTC ATATGGACGC CGTCCAGTCT
4441 GAACATCAAT CTTTTTAGCC AGAGATATCA TAGCCGCTCT TAGAGTTTCA GCGTGATTTT
4501 CCAACCTAAA TAGAACTTCA TCGTTGCGTT TACAACACTT TTCTATTTGT TCAAACTTTG
4561 TTGTTACATT AGTAATCTTT TTTTCCAAAT TAGTTAGCCG TTGTTTGAGA GTTTCCTCAT
4621 TGTCGTCTTC ATCGGCTTTA ACAATTGCTT CGCGTTTAGC CTCCTGGCTG TTCTTATCAG
4681 CCTTTGTAGA AAAAAATTCA GTTGCTGGAA TTGCAAGATC GTCATCTCCG GGGAAAAGAG
4741 TTCCGTCCAT TTAAAGCCGC GGGAATTC
```

Figure 12B

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC TCAGGGTACG
 301 GATCTTATTC GCTTTGAACG TAATATCGTC TGCACCTCGA TGAAGCCCAT CAATGAAGAC
 361 CTGGACGAGG GCATCATGGT GGTCTACAAA CGCAACATCG TCGCGCACAC CTTTAAGGTA
 421 CGAGTCTACC AGAAGGTTTT GACGTTTCGT CGTAGCTACG CTTACATCCA CACCACTTAT
 481 CTGCTGGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTGAACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA AATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCAAAAGA
1381 AGTACAGATG GCAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTG TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TTCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG GCAACCACCG CACTGAGGAA TGTCAGCTTC CCAGCCTCAA GATCTTCATC
1861 GCCGGCAACT CGGCCTACGA GTACGTGGAC TACCTCTTCA AACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTGCCGCC CTACCTCAAG GGTCTGGACG ACACTCGACA GCGGCGTCTC
2161 TGCATGCAGC CGCTGCAGAA CCTCTTTCCC TATCTGGTGT CCGCCGACGG GACCACCGTG
2221 ACGTCGGGCA ACACCAAAGA CACGTCGTTA CAGGCTCCGC CTTCCTACGA GGAAAGTGTT
2281 TATAATTCTG GTCGCAAAGG ACCGGGACCA CCGTCGTCTG ATGCATCCAC GGCGGCTCCG
2341 CCTTACACCA ACGAGCAGGC TTACCAGATG CTTCTGGCCC TGGTCCGTCT GGACGCAGAG
2401 CAGCGAGCGC ACGAGAACGG TACAGATTCT TTGGACGGAC AGACTGGCAC GCAGGACAAG
2461 GGACAGAAGC CCAACCTGCT AGACCGACTG CGACACCGCA AAAACGGCTA CCGACACTTG
2521 AAAGACTCCG ACGAAGAAGA GAACGTCTGA
```

Figure 13

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGACT CTGTCACTTT TTTTGACTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAAGAGG TTCTGCAGCG GCTGCATGCA GAGACGCCGC
 901 TGTCGAGTGT CGTCCAGACC CTTGAGGTAG GGCGGCAGCG GGTCGACTAC CTTGTCCTCC
 961 ACGTACTTTA CCCGCTGCTT ATACGAATTG AACTCGCGCA TGATCTCCTC GAGATCAAAA
1021 ACGTTGCTGG AACGCAATTC TTTCTGCGAG TAAAGTTCCA GTACCCTGAA GTCGGTGTTT
1081 TCCAGCGGGT CGATGTCTAG GGCGATCATG CTGTCGACGG TGGAGATGCT GCTGAGGTCA
1141 ATCATGCGTT TGAAGAGGTA GTCCACGTAC TCGTAGGCCG AGTTGCCGGC GATGAAGATC
1201 TTGAGGCTGG GAAGCTGACA TTCCTCAGTG CGGTGGTTGC CCAACAGGAT TTCGTTATCC
1261 TCGCCCAGTT GACCGTACTG CACGTACGAG CTGTTGGCGA AATTAAAGAT GACCACTGGT
1321 CGTGAGTAGC AGCGTCCTGG CGATTCCTTC ACATTCATAT CACGCAGCAC CTTGACGCTG
1381 GTTTGGTTAA TGGTCACGCA GCTGGCCAGA CCCAGGACAT CACCCATGAA ACGCGCGGCA
1441 ATCGGTTTGT TGTAGATGGC CGAGAGAATA GCTGACGGGT TGATCTTGCT AAGTTCCTTG
1501 AAGACCTCTA GGGTGCGCCG TTGATCCACA CACCAGGCTT CTGCGATTTC GGCCAGCGCC
1561 CGGTTGATGT AACCGCGCAA CGTGTCATAG GTGAACTGCA GCTGGGCGTA GACCAGATTG
1621 TGCACCGACT CCATGTTGGA TAAATGAGTT GCATTGTTGC CATCTGTACT TCTTTTGGTT
1681 CTATTATGAG TAAGATTCAG ACTGGAGCGG TTGGCCAAAC GTTCGAGTTC CACCAGAGAT
1741 TTTTGCTTGA TACCTTGCCA GAACACCACC AAACCACCAG TGGTTTCAAA GACGGACACG
1801 TTTCCATATT TTTCATATGT TTGATTGTAT GAAGTATTGA AAATCTGCTG TAACTTATTT
1861 ATGGCCTCAT CACGTACACA GTCCAGCGCA GAGTCGGACA TGTTCACCTC TTGCTTCTTA
1921 GATAAGAAAG TGGCGGTCAT TTTGGCAGAA GAAAAGTGAT ACGAGTCCTC GGCTTCGGAA
1981 CGAATGGTGC GTTCCGAGGC TTCCCAGAAA GTGAGTTGAC AAGTAACATT CTTCTCGTCC
2041 TGTATATCCC AGGAGATCAC TGAGTCCGCA CGTTCAAGAA AAGCCACCAA CCTGTGGGTC
2101 TCTAACGCAG AATTCGGTCT TTCAAAGTCG GAGACGATAG TGTAGTTCGG AAAAATGAAA
2161 AACTTGTCGG CGTTTTCTCC AAAATAGCTG GCATTGCGAT TAGTTCCGTT GTAGAAAGGA
2221 GAAATGTCAA CCACATCACC CGTGGAAGTT GCGAAAAAAT GATAGGGATA CTTGGAGCGC
2281 GCAGTAGTGA TGGTCACCAT ACAATTCAGA TTACAGGTCT CACGATAGAG CCAGGTGCTG
2341 CCGCGGCTGT GCCATTGATC CTTGACCGTC ACGTAACGGG TACTGTGGGT GTTGGAATAA
2401 TCGTCGGGCA TTAATTGCAT GGTTTTGTTT TCATAGCTGT CCCTATGATA AGCCACGAAA
2461 ACCGTGCCTG CTATAACGCG GCTGTAGGAA CTGTAGCACT GACTGTGACT GTTGATATGA
2521 TGAATCTCCC ACATAGGAGG CGCCACGTAT TCCGTGTTGC TGCCCAGCAG ATAAGTGGTG
2581 TGGATGTAAG CGTAGCTACG ACGAAACGTC AAAACCTTCT GGTAGACTCG TACCTTAAAG
2641 GTGTGCGCGA CGATGTTGCG TTTGTAGACC ACCATGATGC CCTCGTCCAG GTCTTCATTG
2701 ATGGGCTTCA TCGAGGTGCA GACGATATTA CGTTCAAAGC GAATAAGATC CGTACCCTGA
2761 GCCATAGAAC ACACGCGATA GGGGTACTTG GTGGTGTTGA CCCCCACCAC ATCTCCGTAC
2821 TTGAGGGTAG TGTTGTAGAT GGTCTCGTTA ACACCATGGC TGACCGTTTG GGAAGAAGTT
2881 ACGCGTTGAG AGACTGAACC GGATCGAGAA TGAGCAGCAG ACGTCGTATG AGAGGAATGG
2941 TGACTGTGAG TAGCAGAAGT TCCACGAGTA GAAGATGAGG AAACCGCAGC ACCCAGACAG
3001 ACGATACACA AGTTAACGCA GACTACCAGG CACCAGATCC TGGATTCCAT TACGATACAA
3061 ACTTAACGGA TATCGCGATA ATGAAATAAT TTATGATTAT TTCTCGCTTT CAATTTAACA
```

Figure 14A

```
3121 CAACCCTCAA GAACCTTTGT ATTTATTTTC ACTTTTTAAG TATAGAATAA AGAAGCTGGG
3181 AATCGATTCG CGATAGCTGA TTAGTTTTTG TTAACAAAAA TGTGGGAGAA TCTAATTAGT
3241 TTTTCTTTAC ACAATTGACG TACATGAGTC TGAGTTCCTT GTTTTTGCTA ATTATTTCAT
3301 CCAATTTATT ATTCTTGACG ATATCGAGAT CTTTTGTATA GGAGTCAGAC TTGTATTCAA
3361 CATGCTTTTC TATAATCATC TTAGTTATTT CGGCATCATC CAATAGTACA TTTTCCAGAT
3421 TAACAGAGTA .GATATTAATG TCGTATTTGA ACAGAGCCTG TAACATCTCA ATGTCTTTAT
3481 TATCTATAGC CAATTTAATG TCCGGAATGA AGAGAAGGGA ATTATTGGTG TTTGTCGACG
3541 TCATATAGTC GAGCAAGAGA ATCATCATAT CCACGTGTCC ATTTTTTATA GTGGTGTGAA
3601 TACAACTAAG GAGAATAGCC AGATCAAAAG TAGATGGTAT TTCTGAAAGA AAGTATGATA
3661 CAATACTTAC ATCATTAAGC ATGACGGCAT GATAAAATGA AGTTTTCCAT CCAGTTTTCC
3721 CATAGAACAT CAGTCTCCAA TTTTTCTTAA ACAGTTTCAC CGTTTGCATG TTACCACTAT
3781 CAACCGCATA ATACAATGCG GTGTTTCCTT TGTCATCAAA TTGTGAATCA TCCATTCCAC
3841 TGAATAGCAA AATCTTTACT ATTTTGGTAT CTTCTAATGT GGCTGCCTGA TGTAATGGAA
3901 ATTCATTCTC TAGAAGATTT TTCAATGCTC CAGCGTTCAA CAACGTACAT ACTAGACGCA
3961 CGTTATTATC AGCTATTGCA TAATACAAGG CACTATGTCC ATGGACATCC GCCTTAAATG
4021 TATCTTTACT AGAGAGAAAG CTTTTCAGCT GCTTAGACTT CCAAGTATTA ATTCGTGACA
4081 GATCCATGTC TGAAACGAGA CGCTAATTAG TGTATATTTT TTCATTTTTT ATAATTTTGT
4141 CATATTGCAC CAGAATTAAT AATATCTCTA ATAGATCTAA TTTAATTTAA TTTATATAAC
4201 TTATTTTTTG AATATACTTT TAATTAACAA AAGAGTTAAG TTACTCATAT GGACGCCGTC
4261 CAGTCTGAAC ATCAATCTTT TTAGCCAGAG ATATCATAGC CGCTCTTAGA GTTTCAGCGT
4321 GATTTTCCAA CCTAAATAGA ACTTCATCGT TGCGTTTACA ACACTTTTCT ATTTGTTCAA
4381 ACTTTGTTGT TACATTAGTA ATCTTTTTTT CCAAATTAGT TAGCCGTTGT TTGAGAGTTT
4441 CCTCATTGTC GTCTTCATCG GCTTTAACAA TTGCTTCGCG TTTAGCCTCC TGGCTGTTCT
4501 TATCAGCCTT TGTAGAAAAA AATTCAGTTG CTGGAATTGC AAGATCGTCA TCTCCGGGGA
4561 AAAGAGTTCC GTCCATTTAA AGCCGCGGGA ATTC
```

Figure 14B

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC TCAGGGTACG
 301 GATCTTATTC GCTTTGAACG TAATATCGTC TGCACCTCGA TGAAGCCCAT CAATGAAGAC
 361 CTGGACGAGG GCATCATGGT GGTCTACAAA CGCAACATCG TCGCGCACAC CTTTAAGGTA
 421 CGAGTCTACC AGAAGGTTTT GACGTTTCGT CGTAGCTACG CTTACATCCA CACCACTTAT
 481 CTGCTGGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTGAACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA AATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCATAAGA
1381 TCTACAGATG GCAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTG TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TTCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG GCAACCACCG CACTGAGGAA TGTCAGCTTC CCAGCCTCAA GATCTTCATC
1861 GCCGGCAACT CGGCCTACGA GTACGTGGAC TACCTCTTCA AACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTGCCGCC CTACCTCAAG GGTCTGGACG ACACTCGACA GCGGCGTCTC
2161 TGCATGCAGC CGCTGCAGAA CCTCTTTCCC TATCTGGTGT CCGCCGACGG GACCACCGTG
2221 ACGTCGGGCA ACACCAAAGA CACGTCGTTA CAGGCTCCGC CTTCCTACGA GGAAAGTGTT
2281 TATAATTCTG GTCGCAAAGG ACCGGGACCA CCGTCGTCTG ATGCATCCAC GGCGGCTCCG
2341 CCTTACACCA ACGAGCAGGC TTACCAGATG CTTCTGGCCC TGGTCCGTCT GGACGCAGAG
2401 CAGCGAGCGC ACGAGAACGG TACAGATTCT TTGGACGGAC AGACTGGCAC GCAGGACAAG
2461 GGACAGAAGC CCAACCTGCT AGACCGACTG CGACACCGCA AAAACGGCTA CCGACACTTG
2521 AAAGACTCCG ACGAAGAAGA GAACGTCTGA
```

Figure 15

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGTCT CTGACACTTT TTTTGTCTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAAGAGG TTCTGCAGCG GCTGCATGCA GAGACGCCGC
 901 TGTCGAGTGT CGTCCAGACC CTTGAGGTAG GGCGGCAGCG GGTCGACTAC CTTGTCCTCC
 961 ACGTACTTTA CCCGCTGCTT ATACGAATTG AACTCGCGCA TGATCTCCTC GAGATCAAAA
1021 ACGTTGCTGG AACGCAATTC TTTCTGCGAG TAAAGTTCCA GTACCCTGAA GTCGGTGTTT
1081 TCCAGCGGGT CGATGTCTAG GGCGATCATG CTGTCGACGG TGGAGATGCT GCTGAGGTCA
1141 ATCATGCGTT TGAAGAGGTA GTCCACGTAC TCGTAGGCCG AGTTGCCGGC GATGAAGATC
1201 TTGAGGCTGG GAAGCTGACA TTCCTCAGTG CGGTGGTTGC CCAACAGGAT TTCGTTATCC
1261 TCGCCCAGTT GACCGTACTG CACGTACGAG CTGTTGGCGA AATTAAAGAT GACCACTGGT
1321 CGTGAGTAGC AGCGTCCTGG CGATTCCTTC ACATTCATAT CACGCAGCAC CTTGACGCTG
1381 GTTTGGTTAA TGGTCACGCA GCTGGCCAGA CCCAGGACAT CACCCATGAA ACGCGCGGCA
1441 ATCGGTTTGT TGTAGATGGC CGAGAGAATA GCTGACGGGT TGATCTTGCT AAGTTCCTTG
1501 AAGACCTCTA GGGTGCGCCG TTGATCCACA CACCAGGCTT CTGCGATTTC GGCCAGCGCC
1561 CGGTTGATGT AACCGCGCAA CGTGTCATAG GTGAACTGCA GCTGGGCGTA GACCAGATTG
1621 TGCACCGACT CCATGTTGGA TAAATGAGTT GCATTGTTGC CATCTGTAGA TCTTATGGTT
1681 CTATTATGAG TAAGATTCAG ACTGGAGCGG TTGGCCAAAC GTTCGAGTTC CACCAGAGAT
1741 TTTTGCTTGA TACCTTGCCA GAACACCACC AAACCACCAG TGGTTTCAAA GACGGACACG
1801 TTTCCATATT TTTCATATGT TTGATTGTAT GAAGTATTGA AAATCTGCTG TAACTTATTT
1861 ATGGCCTCAT CACGTACACA GTCCAGCGCA GAGTCGGACA TGTTCACCTC TTGCTTCTTA
1921 GATAAGAAAG TGGCGGTCAT TTTGGCAGAA GAAAAGTGAT ACGAGTCCTC GGCTTCGGAA
1981 CGAATGGTGC GTTCCGAGGC TTCCCAGAAA GTGAGTTGAC AAGTAACATT CTTCTCGTCC
2041 TGTATATCCC AGGAGATCAC TGAGTCCGCA CGTTCAAGAA AAGCCACCAA CCTGTGGGTC
2101 TCTAACGCAG AATTCGGTCT TTCAAAGTCG GAGACGATAG TGTAGTTCGG AAAAATGAAA
2161 AACTTGTCGG CGTTTTCTCC AAAATAGCTG GCATTGCGAT TAGTTCCGTT GTAGAAAGGA
2221 GAAATGTCAA CCACATCACC CGTGGAAGTT GCGAAAAAAT GATAGGGATA CTTGGAGCGC
2281 GCAGTAGTGA TGGTCACCAT ACAATTCAGA TTACAGGTCT CACGATAGAG CCAGGTGCTG
2341 CCGCGGCTGT GCCATTGATC CTTGACCGTC ACGTAACGGG TACTGTGGGT GTTGGAATAA
2401 TCGTCGGGCA TTAATTGCAT GGTTTTGTTT TCATAGCTGT CCCTATGATA AGCCACGAAA
2461 ACCGTGCCTG CTATAACGCG GCTGTAGGAA CTGTAGCACT GACTGTGACT GTTGATATGA
2521 TGAATCTCCC ACATAGGAGG CGCCACGTAT TCCGTGTTGC TGCCCAGCAG ATAAGTGGTG
2581 TGGATGTAAG CGTAGCTACG ACGAAACGTC AAAACCTTCT GGTAGACTCG TACCTTAAAG
2641 GTGTGCGCGA CGATGTTGCG TTTGTAGACC ACCATGATGC CCTCGTCCAG GTCTTCATTG
2701 ATGGGCTTCA TCGAGGTGCA GACGATATTA CGTTCAAAGC GAATAAGATC CGTACCCTGA
2761 GCCATAGAAC ACACGCGATA GGGGTACTTG GTGGTGTTGA CCCCCACCAC ATCTCCGTAC
2821 TTGAGGGTAG TGTTGTAGAT GGTCTCGTTA ACACCATGGC TGACCGTTTG GGAAGAAGTT
2881 ACGCGTTGAG AGACTGAACC GGATCGAGAA TGAGCAGCAG ACGTCGTATG AGAGGAATGG
2941 TGACTGTGAG TAGCAGAAGT TCCACGAGTA GAAGATGAGG AAACCGCAGC ACCCAGACAG
3001 ACGATACACA AGTTAACGCA GACTACCAGG CACCAGATCC TGGATTCCAT TACGATACAA
3061 ACTTAACGGA TATCGCGATA ATGAAATAAT TTATGATTAT TTCTCGCTTT CAATTTAACA
```

Figure 16A

```
3121 CAACCCTCAA GAACCTTTGT ATTTATTTTC ACTTTTTAAG TATAGAATAA AGAAGCTGGG
3181 AATCGATTCG CGATAGCTGA TTAGTTTTTG TTAACAAAAA TGTGGGAGAA TCTAATTAGT
3241 TTTTCTTTAC ACAATTGACG TACATGAGTC TGAGTTCCTT GTTTTTGCTA ATTATTTCAT
3301 CCAATTTATT ATTCTTGACG ATATCGAGAT CTTTTGTATA GGAGTCAGAC TTGTATTCAA
3361 CATGCTTTTC TATAATCATC TTAGTTATTT CGGCATCATC CAATAGTACA TTTTCCAGAT
3421 TAACAGAGTA GATATTAATG TCGTATTTGA ACAGAGCCTG TAACATCTCA ATGTCTTTAT
3481 TATCTATAGC CAATTTAATG TCCGGAATGA AGAGAAGGGA ATTATTGGTG TTTGTCGACG
3541 TCATATAGTC GAGCAAGAGA ATCATCATAT CCACGTGTCC ATTTTTTATA GTGGTGTGAA
3601 TACAACTAAG GAGAATAGCC AGATCAAAAG TAGATGGTAT TTCTGAAAGA AAGTATGATA
3661 CAATACTTAC ATCATTAAGC ATGACGGCAT GATAAAATGA AGTTTTCCAT CCAGTTTTCC
3721 CATAGAACAT CAGTCTCCAA TTTTTCTTAA ACAGTTTCAC CGTTTGCATG TTACCACTAT
3781 CAACCGCATA ATACAATGCG GTGTTTCCTT TGTCATCAAA TTGTGAATCA TCCATTCCAC
3841 TGAATAGCAA AATCTTTACT ATTTTGGTAT CTTCTAATGT GGCTGCCTGA TGTAATGGAA
3901 ATTCATTCTC TAGAAGATTT TTCAATGCTC CAGCGTTCAA CAACGTACAT ACTAGACGCA
3961 CGTTATTATC AGCTATTGCA TAATACAAGG CACTATGTCC ATGGACATCC GCCTTAAATG
4021 TATCTTTACT AGAGAGAAAG CTTTTCAGCT GCTTAGACTT CCAAGTATTA ATTCGTGACA
4081 GATCCATGTC TGAAACGAGA CGCTAATTAG TGTATATTTT TTCATTTTTT ATAATTTTGT
4141 CATATTGCAC CAGAATTAAT AATATCTCTA ATAGATCTAA TTTAATTTAA TTTATATAAC
4201 TTATTTTTTG AATATACTTT TAATTAACAA AAGAGTTAAG TTACTCATAT GGACGCCGTC
4261 CAGTCTGAAC ATCAATCTTT TTAGCCAGAG ATATCATAGC CGCTCTTAGA GTTTCAGCGT
4321 GATTTTCCAA CCTAAATAGA ACTTCATCGT TGCGTTTACA ACACTTTTCT ATTTGTTCAA
4381 ACTTTGTTGT TACATTAGTA ATCTTTTTTT CCAAATTAGT TAGCCGTTGT TTGAGAGTTT
4441 CCTCATTGTC GTCTTCATCG GCTTTAACAA TTGCTTCGCG TTTAGCCTCC TGGCTGTTCT
4501 TATCAGCCTT TGTAGAAAAA AATTCAGTTG CTGGAATTGC AAGATCGTCA TCTCCGGGGA
4561 AAAGAGTTCC GTCCATTTAA AGCCGCGGGA ATTC
```

Figure 16B

```
   1 ATGCGGCCAG GCCTCCCCTC CTACCTCATC GTCCTCGCCG TCTGTCTCCT CAGCCACCTA
  61 CTTTCGTCAC GATATGGCGC AGAAGCCATA TCCGAACCGC TGGACAAAGC GTTTCACCTA
 121 CTGCTCAACA CCTACGGGAG ACCCATCCGC TTCCTGCGTG AAAACACCAC CCAGTGTACC
 181 TACAATAGCA GCCTCCGTAA CAGCACGGTC GTCAGGGAAA ACGCCATCAG TTTCAACTTT
 241 TTCCAAAGCT ATAATCAATA CTATGTATTC CATATGCCTC GATGTCTTTT TGCGGGTCCT
 301 CTGGCGGAGC AGTTTCTGAA CCAGGTAGAT CTGACCGAAA CCCTGGAAAG ATACCAACAG
 361 AGACTTAACA CTTACGCGCT GGTATCCAAA GACCTGGCCA GCTACCGATC TTTTTCGCAG
 421 CAGCTAAAGG CACAGGACAG CCTAGGTGAA CAGCCCACCA CTGTGCCACC ACCCATTGAC
 481 CTGTCAATAC CTCACGTTTG GATGCCACCG CAAACCACTC CACACGGCTG GACAGAATCA
 541 CATACCACCT CAGGACTACA CCGACCACAC TTTAACCAGA CCTGTATCCT CTTTGATGGA
 601 CACGATCTAC TATTCAGCAC CGTCACACCT TGTTTGCACC AAGGCTTTTA CCTCATCGAC
 661 GAACTACGTT ACGTTAAAAT AACACTGACC GAGGACTTCT TCGTAGTTAC GGTGTCCATA
 721 GACGACGACA CACCCATGCT GCTTATCTTC GGCCATCTTC CACGCGTACT CTTTAAAGCG
 781 CCCTATCAAC GCGACAACTT TATACTACGA CAAACTGAAA AACACGAGCT CCTGGTGCTA
 841 GTTAAGAAAG ATCAACTGAA CCGTCACTCT TATCTCAAAG ACCCGGACTT TCTTGACGCC
 901 GCACTTGACT TCAACTACCT GGACCTCAGC GCACTACTAC GTAACAGCTT TCACCGTTAC
 961 GCCGTGGATG TACTCAAAAG CGGTCGATGT CAGATGCTGG ACCGCCGCAC GGTAGAAATG
1021 GCCTTCGCCT ACGCATTAGC ACTGTTCGCA GCAGCCCGAC AAGAAGAGGC CGGCGCCCAA
1081 GTCTCCGTCC CACGGGCCCT AGACCGCCAG GCCGCACTCT TACAAATACA AGAATTTATG
1141 ATCACCTGCC TCTCACAAAC ACCACCACGC ACCACGTTGC TGCTGTATCC CACGGCCGTG
1201 GACCTGGCCA AACGAGCCCT TTGGACACCG AATCAGATCA CCGACATCAC CAGCCTCGTA
1261 CGCCTGGTCT ACATACTCTC TAAACAGAAT CAGCAACATC TCATCCCCCA GTGGGCACTA
1321 CGACAGATCG CCGACTTTGC CCTAAAACTA CACAAAACGC ACCTGGCCTC TTTTCTTTCA
1381 GCCTTCGCGC GTCAAGAACT CTACCTCATG GGCAGCCTCG TCCACTCCAT GCTAGTACAT
1441 ACGACGGAGA GACGCGAAAT CTTCATCGTA GAAACGGGCC TCTGTTCATT AGCCGAGCTA
1501 TCACACTTTA CGCAGTTGCT AGCTCATCCG CACCACGAAT ACCTCAGCGA CCTGTACACA
1561 CCCTGTTCCA GTAGCGGGCG ACGCGATCAC TCGCTCGAAC GCCTCACACG TCTCTTCCCC
1621 GATGCCACCG TCCCCACTAC CGTTCCCGCC GCCCTCTCCA TCCTATCTAC CATGCAACCA
1681 AGCACGCTAG AAACCTTCCC CGACCTGTTT TGTCTGCCGC TCGGCGAATC CTTCTCCGCG
1741 CTGACCGTCT CCGAACACGT CAGTTATGTC GTAACAAACC AGTACCTGAT CAAAGGTATC
1801 TCCTACCCTG TCTCCACCAC CGTCGTAGGC CAGAGCCTCA TCATCACCCA GACGGACAGT
1861 CAAACTAAAT GCGAACTGAC GCGCAACATG CATACCACAC ACAGCATCAC AGCGGCGCTC
1921 AACATTTCCC TAGAAAACTG CGCCTTTTGC CAAAGCGCCC TACTAGAATA CGACGACACG
1981 CAAGGCGTCA TCAACATCAT GTACATGCAC GACTCGGACG ACGTCCTTTT CGCCCTGGAT
2041 CCCTACAACG AAGTGGTGGT CTCATCTCCG CGAACTCACT ACCTCATGCT TTTGAAAAAC
2101 GGTACGGTCC TAGAAGTAAC TGACGTCGTC GTGGACGCTA CCGACAGTCG TCTCCTCATG
2161 ATGTCCGTCT ACGCGCTATC GGCCATCATC GGCATCTATC TGCTCTACCG CATGCTCAAG
2221 ACATGCTGA
```

Figure 17

1 CTGCAGGTCG ACGGATCTGA GAATGGATGA TTCTCCAGCC GAAACATATT CTACCATGGC
61 TCCGTTTAAT TTGTTGATGA AGATGGATTC ATCCTTAAAT GTTTTCTCTG TAATAGTTTC
121 CACCGAAAGA CTATGCAAAG AATTTGGAAT GCGTTCCTTG TGCTTAATGT TTCCATAGAC
181 GGCTTCTAGA AGTTGATACA ACATAGGACT AGCCGCGGTA ACTTTTATTT TTAGAAAGTA
241 TCCATCGCTT CTATCTTGTT TAGATTTATT TTTATAAAGT TTAGTCTCTC CTTCCAACAT
301 AATAAAAGTG GAAGTCATTT GACTAGATAA ACTATCAGTA AGTTTTATAG AGATAGACGA
361 ACAATTAGCG TATTGAGAAG CATTTAGTGT AACGTATTCG ATACATTTTG CATTAGATTT
421 ACTAATCGAT TTTGCATACT CTATAACACC CGCACAAGTC TGTAGAGAAT CGCTAGATGC
481 AGTAGGTCTT GGTGAAGTTT CAACTCTCTT CTTGATTACC TTACTCATGA TTAAACCTAA
541 ATAATTGTAC TTTGTAATAT AATGATATAT ATTTTCACTT TATCTCATTT GAGAATAAAA
601 AGATCACAAA AATTAACTAA TCAGGATCCG GTACCCTCGA GTTTATTGGG AAGAATATGA
661 TAATATTTTG GGATTTCAAA ATTGAAAATA TATAATTACA ATATAAAATG CGGCCCGGGC
721 TCCCCTCCTA CCTCATCGTC CTCGCCGTCT GTCTCCTCAG CCACCTACTT TCGTCACGAT
781 ATGGCGCAGA AGCCATATCC GAACCGCTGG ACAAAGCGTT TCACCTACTG CTCAACACCT
841 ACGGGAGACC CATCCGCTTC CTGCGTGAAA ACACCACCCA GTGTACCTAC AATAGCAGCC
901 TCCGTAACAG CACGGTCGTC AGGGAAAACG CCATCAGTTT CAACTTTTTC CAAAGCTATA
961 ATCAATACTA TGTATTCCAT ATGCCTCGAT GTCTTTTTGC GGGTCCTCTG GCGGAGCAGT
1021 TTCTGAACCA GGTAGATCTG ACCGAAACCC TGGAAAGATA CCAACAGAGA CTTAACACTT
1081 ACGCGCTGGT ATCCAAAGAC CTGGCCAGCT ACCGATCTTT TTCGCAGCAG CTAAAGGCAC
1141 AGGACAGCCT AGGTGAACAG CCCACCACTG TGCCACCACC CATTGACCTG TCAATACCTC
1201 ACGTTTGGAT GCCACCGCAA ACCACTCCAC ACGGCTGGAC AGAATCACAT ACCACCTCAG
1261 GACTACACCG ACCACACTTT AACCAGACCT GTATCCTCTT TGATGGACAC GATCTACTAT
1321 TCAGCACCGT CACACCTTGT TTGCACCAAG GCTTTTACCT CATCGACGAA CTACGTTACG
1381 TTAAAATAAC ACTGACCGAG GACTTCTTCG TAGTTACGGT GTCCATAGAC GACGACACAC
1441 CCATGCTGCT TATCTTCGGC CATCTTCCAC GCGTACTCTT TAAAGCGCCC TATCAACGCG
1501 ACAACTTTAT ACTACGACAA ACTGAAAAAC ACGAGCTCCT GGTGCTAGTT AAGAAAGATC
1561 AACTGAACCG TCACTCTTAT CTCAAAGACC CGGACTTTCT TGACGCCGCA CTTGACTTCA
1621 ACTACCTGGA CCTCAGCGCA CTACTACGTA ACAGCTTTCA CCGTTACGCC GTGGATGTAC
1681 TCAAAAGCGG TCGATGTCAG ATGCTGGACC GCCGCACGGT AGAAATGGCC TTCGCCTACG
1741 CATTAGCACT GTTCGCAGCA GCCCGACAAG AAGAGGCCGG CGCCCAAGTC TCCGTCCCAC
1801 GGGCCCTAGA CCGCCAGGCC GCACTCTTAC AAATACAAGA ATTTATGATC ACCTGCCTCT
1861 CACAAACACC ACCACGCACC ACGTTGCTGC TGTATCCCAC GGCCGTGGAC CTGGCCAAAC
1921 GAGCCCTTTG GACACCGAAT CAGATCACCG ACATCACCAG CCTCGTACGC CTGGTCTACA
1981 TACTCTCTAA ACAGAATCAG CAACATCTCA TCCCCCAGTG GGCACTACGA CAGATCGCCG
2041 ACTTTGCCCT AAAACTACAC AAAACGCACC TGGCCTCTTT TCTTTCAGCC TTCGCGCGTC
2101 AAGAACTCTA CCTCATGGGC AGCCTCGTCC ACTCCATGCT AGTACATACG ACGGAGAGAC
2161 GCGAAATCTT CATCGTAGAA ACGGGCCTCT GTTCATTAGC CGAGCTATCA CACTTTACGC
2221 AGTTGCTAGC TCATCCGCAC CACGAATACC TCAGCGACCT GTACACACCC TGTTCCAGTA
2281 GCGGGCGACG CGATCACTCG CTCGAACGCC TCACACGTCT CTTCCCCGAT GCCACCGTCC
2341 CCACTACCGT TCCCGCCGCC CTCTCCATCC TATCTACCAT GCAACCAAGC ACGCTAGAAA
2401 CCTTCCCCGA CCTGTTTTGT CTGCCGCTCG GCGAATCCTT CTCCGCGCTG ACCGTCTCCG
2461 AACACGTCAG TTATGTCGTA ACAAACCAGT ACCTGATCAA AGGTATCTCC TACCCTGTCT
2521 CCACCACCGT CGTAGGCCAG AGCCTCATCA TCACCCAGAC GGACAGTCAA ACTAAATGCG
2581 AACTGACGCG CAACATGCAT ACCACACACA GCATCACAGC GGCGCTCAAC ATTTCCCTAG
2641 AAAACTGCGC CTTTTGCCAA AGCGCCCTAC TAGAATACGA CGACACGCAA GGCGTCATCA
2701 ACATCATGTA CATGCACGAC TCGGACGACG TCCTTTTCGC CCTGGATCCC TACAACGAAG
2761 TGGTGGTCTC ATCTCCGCGA ACTCACTACC TCATGCTTTT GAAAAACGGT ACGGTCCTAG
2821 AAGTAACTGA CGTCGTCGTG GACGCTACCG ACAGTCGTCT CCTCATGATG TCCGTCTACG
2881 CGCTATCGGC CATCATCGGC ATCTATCTGC TCTACCGCAT GCTCAAGACA TGCTGATTTT
2941 TATCTCGAGC CCGGGAGATC TTAGCTAACT GATTTTTCTG GGAAAAAAAT TATTTAACTT
3001 TTCATTAATA GGGATTTGAC GTATGTAGCG TACAAAATTA TCGTTCCTGG TATATAGATA
3061 AAGAGTCCTA TATATTTGAA AATCGTTACG GCTCGATTAA ACTTTAATGA TTGCATAGTG

Figure 18A

```
3121 AATATATCAT TAGGATTTAA CTCCTTGACT ATCATGGCGG CGCCAGAAAT TACCATCAAA
3181 AGCATTAATA CAGTTATGCC GATCGCAGTT AGAACGGTTA TAGCATCCAC CATTTATATC
3241 TAAAAATTAG ATCAAAGAAT ATGTGACAAA GTCCTAGTTG TATACTGAGA ATTGACGAAA
3301 CAATGTTTCT TACATATTTT TTTCTTATTA GTAACTGACT TAATAGTAGG AACTGGAAAG
3361 CTAGACTTGA TTATTCTATA AGTATAGATA CCCTTCCAGA TAATGTTCTC TTTGATAAAA
3421 GTTCCAGAAA ATGTAGAATT TTTTAAAAAG TTATCTTTTG CTATTACCAA GATTGTGTTT
3481 AGACGCTTAT TATTAATATG AGTAATGAAA TCCACACCGC CTCTAGATAT GGGGAATTC
```

Figure 18B

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGGA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC TTAATTAATT AGTCATCAGG CAGGGCGAGA ACGAGACTAT
1621 CTGCTCGTTA ATTAATTAGG TCGACGGATC CGGTACCCTC GAGTTTATTG GGAAGAATAT
1681 GATAATATTT TGGGATTTCA AAATTGAAAA TATATAATTA CAATATAAAA TGCGGCCCGG
1741 GCTCCCCTCC TACCTCATCG TCCTCGCCGT CTGTCTCCTC AGCCACCTAC TTTCGTCACG
1801 ATATGGCGCA GAAGCCATAT CCGAACCGCT GGACAAAGCG TTTCACCTAC TGCTCAACAC
1861 CTACGGGAGA CCCATCCGCT TCCTGCGTGA AAACACCACC CAGTGTACCT ACAATAGCAG
1921 CCTCCGTAAC AGCACGGTCG TCAGGGAAAA CGCCATCAGT TTCAACTTTT TCCAAAGCTA
1981 TAATCAATAC TATGTATTCC ATATGCCTCG ATGTCTTTTT GCGGGTCCTC TGGCGGAGCA
2041 GTTTCTGAAC CAGGTAGATC TGACCGAAAC CCTGGAAAGA TACCAACAGA GACTTAACAC
2101 TTACGCGCTG GTATCCAAAG ACCTGGCCAG CTACCGATCT TTTTCGCAGC AGCTAAAGGC
2161 ACAGGACAGC CTAGGTGAAC AGCCCACCAC TGTGCCACCA CCCATTGACC TGTCAATACC
2221 TCACGTTTGG ATGCCACCGC AAACCACTCC ACACGGCTGG ACAGAATCAC ATACCACCTC
2281 AGGACTACAC CGACCACACT TTAACCAGAC CTGTATCCTC TTTGATGGAC ACGATCTACT
2341 ATTCAGCACC GTCACACCTT GTTTGCACCA AGGCTTTTAC CTCATCGACG AACTACGTTA
2401 CGTTAAAATA ACACTGACCG AGGACTTCTT CGTAGTTACG GTGTCCATAG ACGACGACAC
2461 ACCCATGCTG CTTATCTTCG GCCATCTTCC ACGCGTACTC TTTAAAGCGC CCTATCAACG
2521 CGACAACTTT ATACTACGAC AAACTGAAAA ACACGAGCTC CTGGTGCTAG TTAAGAAAGA
2581 TCAACTGAAC CGTCACTCTT ATCTCAAAGA CCCGGACTTT CTTGACGCCG CACTTGACTT
2641 CAACTACCTG GACCTCAGCG CACTACTACG TAACAGCTTT CACCGTTACG CCGTGGATGT
2701 ACTCAAAAGC GGTCGATGTC AGATGCTGGA CCGCCGCACG GTAGAAATGG CCTTCGCCTA
2761 CGCATTAGCA CTGTTCGCAG CAGCCCGACA AGAAGAGGCC GGCGCCCAAG TCTCCGTCCC
2821 ACGGGCCCTA GACCGCCAGG CCGCACTCTT ACAAATACAA GAATTTATGA TCACCTGCCT
2881 CTCACAAACA CCACCACGCA CCACGTTGCT GCTGTATCCC ACGGCCGTGG ACCTGGCCAA
2941 ACGAGCCCTT TGGACACCGA ATCAGATCAC CGACATCACC AGCCTCGTAC GCCTGGTCTA
3001 CATACTCTCT AAACAGAATC AGCAACATCT CATCCCCCAG TGGGCACTAC GACAGATCGC
3061 CGACTTTGCC CTAAAACTAC ACAAAACGCA CCTGGCCTCT TTTCTTTCAG CCTTCGCGCG
```

Figure 19A

```
3121 TCAAGAACTC TACCTCATGG GCAGCCTCGT CCACTCCATG CTAGTACATA CGACGGAGAG
3181 ACGCGAAATC TTCATCGTAG AAACGGGCCT CTGTTCATTA GCCGAGCTAT CACACTTTAC
3241 GCAGTTGCTA GCTCATCCGC ACCACGAATA CCTCAGCGAC CTGTACACAC CCTGTTCCAG
3301 TAGCGGGCGA CGCGATCACT CGCTCGAACG CCTCACACGT CTCTTCCCCG ATGCCACCGT
3361 CCCCACTACC GTTCCCGCCG CCCTCTCCAT CCTATCTACC ATGCAACCAA GCACGCTAGA
3421 AACCTTCCCC GACCTGTTTT GTCTGCCGCT CGGCGAATCC TTCTCCGCGC TGACCGTCTC
3481 CGAACACGTC AGTTATGTCG TAACAAACCA GTACCTGATC AAAGGTATCT CCTACCCTGT
3541 CTCCACCACC GTCGTAGGCC AGAGCCTCAT CATCACCCAG ACGGACAGTC AAACTAAATG
3601 CGAACTGACG CGCAACATGC ATACCACACA CAGCATCACA GCGGCGCTCA ACATTTCCCT
3661 AGAAAACTGC GCCTTTTGCC AAAGCGCCCT ACTAGAATAC GACGACACGC AAGGCGTCAT
3721 CAACATCATG TACATGCACG ACTCGGACGA CGTCCTTTTC GCCCTGGATC CCTACAACGA
3781 AGTGGTGGTC TCATCTCCGC GAACTCACTA CCTCATGCTT TTGAAAAACG GTACGGTCCT
3841 AGAAGTAACT GACGTCGTCG TGGACGCTAC CGACAGTCGT CTCCTCATGA TGTCCGTCTA
3901 CGCGCTATCG GCCATCATCG GCATCTATCT GCTCTACCGC ATGCTCAAGA CATGCTGATT
3961 TTTATCTCGA GTCTAGAATC GATCCCGGGT TTTTATGACT AGTTAATCAC GGCCGCTTAT
4021 AAAGATCTAA AATGCATAAT TTCTAAATAA TGAAAAAAAA GTACATCATG AGCAACGCGT
4081 TAGTATATTT TACAATGGAG ATTAACGCTC TATACCGTTC TATGTTTATT GATTCAGATG
4141 ATGTTTTAGA AAAGAAAGTT ATTGAATATG AAAACTTTAA TGAAGATGAA GATGACGACG
4201 ATGATTATTG TTGTAAATCT GTTTTAGATG AAGAAGATGA CGCGCTAAAG TATACTATGG
4261 TTACAAAGTA TAAGTCTATA CTACTAATGG CGACTTGTGC AAGAAGGTAT AGTATAGTGA
4321 AAATGTTGTT AGATTATGAT TATGAAAAAC CAAATAAATC AGATCCATAT CTAAAGGTAT
4381 CTCCTTTGCA CATAATTTCA TCTATTCCTA GTTTAGAATA CCTGCAG
```

Figure 19 B

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGATAAA AATCAGCATG TCTTGAGCAT
 181 GCGGTAGAGC AGATAGATGC CGATGATGGC CGATAGCGCG TAGACGGACA TCATGAGGAG
 241 ACGACTGTCG GTAGCGTCCA CGACGACGTC AGTTACTTCT AGGACCGTAC CGTTTTTCAA
 301 AAGCATGAGG TAGTGAGTTC GCGGAGATGA GACCACCACT TCGTTGTAGG GATCCAGGGC
 361 GAAAAGGACG TCGTCCGAGT CGTGCATGTA CATGATGTTG ATGACGCCTT GCGTGTCGTC
 421 GTATTCTAGT AGGGCGCTTT GGCAAAAGGC GCAGTTTTCT AGGGAAATGT TGAGCGCCGC
 481 TGTGATGCTG TGTGTGGTAT GCATGTTGCG CGTCAGTTCG CATTTAGTTT GACTGTCCGT
 541 CTGGGTGATG ATGAGGCTCT GGCCTACGAC GGTGGTGGAG ACAGGGTAGG AGATACCTTT
 601 GATCAGGTAC TGGTTTGTTA CGACATAACT GACGTGTTCG GAGACGGTCA GCGCGGAGAA
 661 GGATTCGCCG AGCGGCAGAC AAAACAGGTC GGGGAAGGTT TCTAGCGTGC TTGGTTGCAT
 721 GGTAGATAGG ATGGAGAGGG CGGCGGGAAC GGTAGTGGGG ACGGTGGCAT CGGGGAAGAG
 781 ACGTGTGAGG CGTTCGAGCG AGTGATCGCG TCGCCCGCTA CTGGAACAGG GTGTGTACAG
 841 GTCGCTGAGG TATTCGTGGT GCGGATGAGC TAGCAACTGC GTAAAGTGTG ATAGCTCGGC
 901 TAATGAACAG AGGCCCGTTT CTACGATGAA GATTTCGCGT CTCTCCGTCG TATGTACTAG
 961 CATGGAGTGG ACGAGGCTGC CCATGAGGTA GAGTTCTTGA CGCGCGAAGG CTGAAAGAAA
1021 AGAGGCCAGG TGCGTTTTGT GTAGTTTTAG GGCAAAGTCG GCGATCTGTC GTAGTGCCCA
1081 CTGGGGGATG AGATGTTGCT GATTCTGTTT AGAGAGTATG TAGACCAGGC GTACGAGGCT
1141 GGTGATGTCG GTGATCTGAT TCGGTGTCCA AAGGGCTCGT TTGGCCAGGT CCACGGCCGT
1201 GGGATACAGC AGCAACGTGG TGCGTGGTGG TGTTTGTGAG AGGCAGGTGA TCATAAATTC
1261 TTGTATTTGT AAGAGTGCGG CCTGGCGGTC TAGGGCCCGT GGGACGGAGA CTTGGGCGCC
1321 GGCCTCTTCT TGTCGGGCTG CTGCGAACAG TGCTAATGCG TAGGCGAAGG CCATTTCTAC
1381 CGTGCGGCGG TCCAGCATCT GACATCGACC GCTTTTGAGT ACATCCACGG CGTAACGGTG
1441 AAAGCTGTTA CGTAGTAGTG CGCTGAGGTC CAGGTAGTTG AAGTCAAGTG CGGCGTCAAG
1501 AAAGTCCGGG TCTTTGAGAT AAGAGTGACG GTTCAGTTGA TCTTTCTTAA CTAGCACCAG
1561 GAGCTCGTGT TTTTCAGTTT GTCGTAGTAT AAAGTTGTCG CGTTGATAGG GCGCTTTAAA
1621 GAGTACGCGT GGAAGATGGC CGAAGATAAG CAGCATGGGT GTGTCGTCGT CTATGGACAC
1681 CGTAACTACG AAGAAGTCCT CGGTCAGTGT TATTTTAACG TAACGTAGTT CGTCGATGAG
1741 GTAAAAGCCT TGGTGCAAAC AAGGTGTGAC GGTGCTGAAT AGTAGATCGT GTCCATCAAA
1801 GAGGATACAG GTCTGGTTAA AGTGTGGTCG GTGTAGTCCT GAGGTGGTAT GTGATTCTGT
1861 CCAGCCGTGT GGAGTGGTTT GCGGTGGCAT CCAAACGTGA GGTATTGACA GGTCAATGGG
1921 TGGTGGCACA GTGGTGGGCT GTTCACCTAG GCTGTCCTGT GCCTTTAGCT GCTGCGAAAA
1981 AGATCGGTAG CTGGCCAGGT CTTTGGATAC CAGCGCGTAA GTGTTAAGTC TCTGTTGGTA
2041 TCTTTCCAGG GTTTCGGTCA GATCTACCTG GTTCAGAAAC TGCTCCGCCA GAGGACCCGC
2101 AAAAAGACAT CGAGGCATAT GGAATACATA GTATTGATTA TAGCTTTGGA AAAAGTTGAA
2161 ACTGATGGCG TTTTCCCTGA CGACCGTGCT GTTACGGAGG CTGCTATTGT AGGTACACTG
2221 GGTGGTGTTT TCACGCAGGA AGCGGATGGG TCTCCCGTAG GTGTTGAGCA GTAGGTGAAA
2281 CGCTTTGTCC AGCGGTTCGG ATATGGCTTC TGCGCCATAT CGTGACGAAA GTAGGTGGCT
2341 GAGGAGACAG ACGGCGAGGA CGATGAGGTA GGAGGGGAGC CCGGGCCGCA TTTTATATTG
2401 TAATTATATA TTTTCAATTT TGAAATCCCA AAATATTATC ATATTCTTCC CAATAAACTC
2461 GAGCCCGGGG AATTCGGATC CTCGCGACTG CAGGGTACCT GAGTAGCTAA TTTTTAAACA
2521 AAAATGTGGG AGAATCTAAT TAGTTTTTCT TTACACAATT GACGTACATG AGTCTGAGTT
2581 CCTTGTTTTT GCTAATTATT TCATCCAATT TATTATTCTT GACGATATCG AGATCTTTTG
2641 TATAGGAGTC A
```

Figure 20

```
   1 ATGGAGTCCT CTGCCAAGAG AAAGATGGAC CCTGATAATC CTGACGAGGG CCCTTCCTCC
  61 AAGGTGCCAC GGCCCGAGAC ACCCGTGACC AAGGCCACGA CGTTCCTGCA GACTATGTTG
 121 AGGAAGGAGG TTAACAGTCA GCTGAGTCTG GGAGACCCGC TGTTTCCAGA GTTGGCCGAA
 181 GAATCCCTCA AAACTTTTGA ACAAGTGACC GAGGATTGCA ACGAGAACCC CGAGAAAGAT
 241 GTCCTGGCAG AACTCGTCAA ACAGATTAAG GTTCGAGTGG ACATGGTGCG GCATAGAATC
 301 AAGGAGCACA TGCTGAAAAA ATATACCCAG ACGGAAGAGA AATTCACTGG CGCCTTTAAT
 361 ATGATGGGAG GATGTTTGCA GAATGCCTTA GATATCTTAG ATAAGGTTCA TGAGCCTTTC
 421 GAGGAGATGA AGTGTATTGG GCTAACTATG CAGAGCATGT ATGAGAACTA CATTGTACCT
 481 GAGGATAAGC GGGAGATGTG GATGGCTTGT ATTAAGGAGC TGCATGATGT GAGCAAGGGC
 541 GCCGCTAACA AGTTGGGGGG TGCACTGCAG GCTAAGGCCC GTGCTAAAAA GGATGAACTT
 601 AGGAGAAAGA TGATGTATAT GTGCTACAGG AATATAGAGT TCTTTACCAA GAACTCAGCC
 661 TTCCCTAAGA CCACCAATGG CTGCAGTCAG GCCATGGCGG CACTGCAGAA CTTGCCTCAG
 721 TGCTCCCCTG ATGAGATTAT GGCTTATGCC CAGAAAATAT TTAAGATTTT GGATGAGGAG
 781 AGAGACAAGG TGCTCACGCA CATTGATCAC ATATTTATGG ATATCCTCAC TACATGTGTG
 841 GAAACAATGT GTAATGAGTA CAAGGTCACT AGTGACGCTT GTATGATGAC CATGTACGGG
 901 GGCATCTCTC TCTTAAGTGA GTTCTGTCGG GTGCTGTGCT GCTATGTCTT AGAGGAGACT
 961 AGTGTGATGC TGGCCAAGCG GCCTCTGATA ACCAAGCCTG AGGTTATCAG TGTAATGAAG
1021 CGCCGCATTG AGGAGATCTG CATGAAGGTC TTTGCCCAGT ACATTCTGGG GGCCGATCCT
1081 CTGAGAGTCT GCTCTCCTAG TGTGGATGAC CTACGGGCCA TCGCCGAGGA GTCAGATGAG
1141 GAAGAGGCTA TTGTAGCCTA CACTTTGGCC ACCGCTGGTG TCAGCTCCTC TGATTCTCTG
1201 GTGTCACCCC CAGAGTCCCC TGTACCCGCG ACTATCCCTC TGTCCTCAGT AATTGTGGCT
1261 GAGAACAGTG ATCAGGAAGA AAGTGAGCAG AGTGATGAGG AAGAGGAGGA GGGTGCTCAG
1321 GAGGAGCGGG AGGACACTGT GTCTGTCAAG TCTGAGCCAG TGTCTGAGAT AGAGGAAGTT
1381 GCCCCAGAGG AAGAGGAGGA TGGTGCTGAG GAACCCACCG CCTCTGGAGG TAAGAGTACC
1441 CACCCTATGG TGACTAGAAG CAAGGCTGAC CAGTAA
```

Figure 21

```
   1 ATATAATCCT CCACCAAAAT AGAGAATATA TATATCATCA TTTCATGATG TATACTACTG
  61 ACATAGTTTC AATGTGAACT TTTCACTTTC TTGCCGGTTA TGAAGAATAT TTTTTATTTT
 121 AATGGTCATT ACTAATCGTA TATTATAATT GAAAATGAAT TAGTTTAATA TGACGCTCGT
 181 CATGGGATCC ATAAAAATTA CTGGTCAGCC TTGCTTCTAG TCACCATAGG GTGGGTACTC
 241 TTACCTCCAG AGGCGGTGGG TTCCTCAGCA CCATCCTCCT CTTCCTCTGG GGCAACTTCC
 301 TCTATCTCAG ACACTGGCTC AGACTTGACA GACACAGTGT CCTCCCGCTC CTCCTGAGCA
 361 CCCTCCTCCT CTTCCTCATC ACTCTGCTCA CTTTCTTCCT GATCACTGTT CTCAGCCACA
 421 ATTACTGAGG ACAGAGGGAT AGTCGCGGGT ACAGGGGACT CTGGGGGTGA CACCAGAGAA
 481 TCAGAGGAGC TGACACCAGC GGTGGCCAAA GTGTAGGCTA CAATAGCCTC TTCCTCATCT
 541 GACTCCTCGG CGATGGCCCG TAGGTCATCC ACACTAGGAG AGCAGACTCT CAGAGGATCG
 601 GCCCCCAGAA TGTACTGGGC AAAGACCTTC ATGCAGATCT CCTCAATGCG GCGCTTCATT
 661 ACACTGATAA CCTCAGGCTT GGTTATCAGA GGCCGCTTGG CCAGCATCAC ACTAGTCTCC
 721 TCTAAGACAT AGCAGCACAG CACCCGACAG AACTCACTTA AGAGAGAGAT GCCCCCGTAC
 781 ATGGTCATCA TACAAGCGTC ACTAGTGACC TTGTACTCAT TACACATTGT TTCCACACAT
 841 GTAGTGAGGA TATCCATAAA TATGTGATCA ATGTGCGTGA GCACCTTGTC TCTCTCCTCA
 901 TCCAAAATCT TAAATATTTT CTGGGCATAA GCCATAATCT CATCAGGGGA GCACTGAGGC
 961 AAGTTCTGCA GTGCCGCCAT GGCCTGACTG CAGCCATTGG TGGTCTTAGG GAAGGCTGAG
1021 TTCTTGGTAA AGAACTCTAT ATTCCTGTAG CACATATACA TCATCTTTCT CCTAAGTTCA
1081 TCCTTTTTAG CACGGGCCTT AGCCTGCAGT GCACCCCCCA ACTTGTTAGC GGCGCCCTTG
1141 CTCACATCAT GCAGCTCCTT AATACAAGCC ATCCACATCT CCCGCTTATC CTCAGGTACA
1201 ATGTAGTTCT CATACATGCT CTGCATAGTT AGCCCAATAC ACTTCATCTC CTCGAAAGGC
1261 TCATGAACCT TATCTAAGAT ATCTAAGGCA TTCTGCAAAC ATCCTCCCAT CATATTAAAG
1321 GCGCCAGTGA ATTTCTCTTC CGTCTGGGTA TATTTTTTCA GCATGTGCTC CTTGATTCTA
1381 TGCCGCACCA TGTCCACTCG AACCTTAATC TGTTTGACGA GTTCTGCCAG GACATCTTTC
1441 TCGGGGTTCT CGTTGCAATC CTCGGTCACT TGTTCAAAAG TTTTGAGGGA TTCTTCGGCC
1501 AACTCTGGAA ACAGCGGGTC TCCCAGACTC AGCTGACTGT TAACCTCCTT CCTCAACATA
1561 GTCTGCAGGA ACGTCGTGGC CTTGGTCACG GGTGTCTCGG GCCGTGGCAC CTTGGAGGAA
1621 GGGCCCTCGT CAGGATTATC AGGGTCCATC TTTCTCTTGG CAGAGGACTC CATTACGATA
1681 CAAACTTAAC GGATATCGCG ATAATGAAAT AATTTATGAT TATTTCTCGC TTTCAATTTA
1741 ACACAACCCT CAAGAACCTT TGTATTTATT TTCACTTTTT AAGTATAGAA TAAAGAGATC
1801 CTGCTGTGGT AGATTCTGTG ACGCTAAGAA TAAGAATAAG AAGGAAGATG TAGAAGAGGG
1861 AAGAGAAGGA TGTTACAATT ATAAGAACCT TAATGATCTG GATGAATCCG AAGCACGTGT
1921 AGAATTTGGA CCATTATATA TGATAAATGA AGAAAAATCA GACATAAATA CATTG
```

Figure 22

1 AAGCTTGCGG CCGCTCATTA GACAAGCGAA TGAGGGACGA AAACGTGGAG GAGGTATTAA
61 GTTTGGAGAA ATGGAGAGAG ACTGTTTAAT AGCGCATGGC GCAGCCAATA CTATTACAGA
121 AGTTTTGAAA GATTCGGAAG AAGATTATCA AGATGTGTAT GTTTGTGAAA ATTGTGGAGA
181 CATAGCAGCA CAAATCAAGG GTATTAATAC ATGTCTTAGA TGTTCAAAAC TTAATCTCTC
241 TCCTCTCTTA ACAAAAATTG ATACCACGCA CGTATCTAAA GTATTTCTTA CTCAAATGAA
301 CGCCAGAGGC GTAAAAGTCA AATTAGATTT CGAACGAAGG CCTCCTTCGT TTTATAAACC
361 ATTAGATAAA GTTGATCTCA AGCCGTCTTT TCTGGTGTAA TAAAAATTAA TTAATTACTC
421 GAGATAAAAA TTACTGGTCA GCCTTGCTTC TAGTCACCAT AGGGTGGGTA CTCTTACCTC
481 CAGAGGCGGT GGGTTCCTCA GCACCATCCT CCTCTTCCTC TGGGGCAACT TCCTCTATCT
541 CAGACACTGG CTCAGACTTG ACAGACACAG TGTCCTCCCG CTCCTCCTGA GCACCCTCCT
601 CCTCTTCCTC ATCACTCTGC TCACTTTCTT CCTGATCACT GTTCTCAGCC ACAATTACTG
661 AGGACAGAGG GATAGTCGCG GGTACAGGGG ACTCTGGGGG TGACACCAGA GAATCAGAGG
721 AGCTGACACC AGCGGTGGCC AAAGTGTAGG CTACAATAGC CTCTTCCTCA TCTGACTCCT
781 CGGCGATGGC CCGTAGGTCA TCCACACTAG GAGAGCAGAC TCTCAGAGGA TCGGCCCCCA
841 GAATGTACTG GGCAAAGACC TTCATGCAGA TCTCCTCAAT GCGGCGCTTC ATTACACTGA
901 TAACCTCAGG CTTGGTTATC AGAGGCCGCT TGGCCAGCAT CACACTAGTC TCCTCTAAGA
961 CATAGCAGCA CAGCACCCGA CAGAACTCAC TTAAGAGAGA GATGCCCCCG TACATGGTCA
1021 TCATACAAGC GTCACTAGTG ACCTTGTACT CATTACACAT TGTTTCCACA CATGTAGTGA
1081 GGATATCCAT AAATATGTGA TCAATGTGCG TGAGCACCTT GTCTCTCTCC TCATCCAAAA
1141 TCTTAAATAT TTTCTGGGCA TAAGCCATAA TCTCATCAGG GGAGCACTGA GGCAAGTTCT
1201 GCAGTGCCGC CATGGCCTGA CTGCAGCCAT TGGTGGTCTT AGGGAAGGCT GAGTTCTTGG
1261 TAAAGAACTC TATATTCCTG TAGCACATAT ACATCATCTT TCTCCTAAGT TCATCCTTTT
1321 TAGCACGGGC CTTAGCCTGC AGTGCACCCC CCAACTTGTT AGCGGCGCCC TTGCTCACAT
1381 CATGCAGCTC CTTAATACAA GCCATCCACA TCTCCCGCTT ATCCTCAGGT ACAATGTAGT
1441 TCTCATACAT GCTCTGCATA GTTAGCCCAA TACACTTCAT CTCCTCGAAA GGCTCATGAA
1501 CCTTATCTAA GATATCTAAG GCATTCTGCA AACATCCTCC CATCATATTA AAGGCGCCAG
1561 TGAATTTCTC TTCCGTCTGG GTATATTTTT TCAGCATGTG CTCCTTGATT CTATGCCGCA
1621 CCATGTCCAC TCGAACCTTA ATCTGTTTGA CGAGTTCTGC CAGGACATCT TTCTCGGGGT
1681 TCTCGTTGCA ATCCTCGGTC ACTTGTTCAA AAGTTTTGAG GGATTCTTCG GCCAACTCTG
1741 GAAACAGCGG GTCTCCCAGA CTCAGCTGAC TGTTAACCTC CTTCCTCAAC ATAGTCTGCA
1801 GGAACGTCGT GGCCTTGGTC ACGGGTGTCT CGGGCCGTGG CACCTTGGAG GAAGGGCCCT
1861 CGTCAGGATT ATCAGGGTCC ATCTTTCTCT TGGCAGAGGA CTCCATTACG ATACAAACTT
1921 AACGGATATC GCGATAATGA AATAATTTAT GATTATTTCT CGCTTTCAAT TTAACACAAC
1981 CCTCAAGAAC CTTTGTATTT ATTTTCACTT TTTAAGTATA GAATAAAGAA GCTCTAATTA
2041 ATTAAGCTAC AAATAGTTTC GTTTTCACCT TGTCTAATAA CTAATTAATT AACCCCGATA
2101 GCTGATTAGT TTTTGTTAAC AAAAATGTGG GAGAATCTAA TTAGTTTTTC TTTACACAAT
2161 TGACGTACAT GAGTCTGAGT TCCTTGTTTT TGCTAATTAT TTCATCCAAT TTATTATTCT
2221 TGACGATATC GAGATCTTTT GTATAGGAGT CAGACTTGTA TTCAACATGC TTTTCTATAA
2281 TCATCTTAGT TATTTCGGCA TCATCCAATA GTACATTTTC CAGATTAACA GAGTAGATAT
2341 TAATGTCGTA TTTGAACAGA GCCTGTAACA TCTCAATGTC TTTATTATCT ATAGCCAATT
2401 TAATGTCCGG AATGAAGAGA AGGGAATTAT TGGTGTTTGT CGACGTCATA TAGTCGAGCA
2461 AGAGAATCAT CATATCCACG TGTCCATTTT TTATAGTGGT GTGAATACAA CTAAGGAGAA
2521 TAGCCAGATC AAAAGTAGAT GGTATTTCTG AAAGAAAGTA TGATACAATA CTTACATCAT
2581 TAAGCATGAC GGCATGATAA AATGAAGTTT TCCATCCAGT TTTCCCATAG AACATCAGTC
2641 TCCAATTTTT CTTAAACAGT TTCACCGTTT GCATGTTACC ACTATCAACC GCATAATACA
2701 ATGCGGTGTT TCCTTTGTCA TCAAATTGTG AATCATCCAT TCCACTGAAT AGCAAAATCT
2761 TTACTATTTT GGTATCTTCT AATGTGGCTG CCTGATGTAA TGGAAATTCA TTCTCTAGAA
2821 GATTTTTCAA TGCTCCAGCG TTCAACAACG TACATACTAG ACGCACGTTA TTATCAGCTA
2881 TTGCATAATA CAAGGCACTA TGTCCATGGA CATCCGCCTT AAATGTATCT TTACTAGAGA
2941 GAAAGCTTTT CAGCTGCTTA GACTTCCAAG TATTAATTCG TGACAGATCC ATGTCTGAAA
3001 CGAGACGCTA ATTAGTGTAT ATTTTTTCAT TTTTTATAAT TTTGTCATAT TGCACCAGAA
3061 TTAATAATAT CTCTAATAGA TCTAATTTAA TTTAATTTAT ATAACTTATT TTTTGAATAT

Figure 23A

```
3121 ACTTTTAATT AACAAAAGAG TTAAGTTACT CATATGGACG CCGTCCAGTC TGAACATCAA
3181 TCTTTTTAGC CAGAGATATC ATAGCCGCTC TTAGAGTTTC AGCGTGATTT TCCAACCTAA
3241 ATAGAACTTC ATCGTTGCGT TTACAACACT TTTCTATTTG TTCAAACTTT GTTGTTACAT
3301 TAGTAATCTT TTTTTCCAAA TTAGTTAGCC GTTGTTTGAG AGTTTCCTCA TTGTCGTCTT
3361 CATCGGCTTT AACAATTGCT TCGCGTTTAG CCTCCTGGCT GTTCTTATCA GCCTTTGTAG
3421 AAAAAAATTC AGTTGCTGGA ATTGCAAGAT CGTCATCTCC GGGGAAAAGA GTTCCGTCCA
3481 TTTAAAGCCG CGGGAATTC
```

Figure 23B

```
   1 ATGGAGTCCT CTGCCAAGAG AAAGATGGAC CCTGATAATC CTGACGAGGG CCCTTCCTCC
  61 AAGGTGCCAC GGCCCGAGAC ACCCGTGACC AAGGCCACGA CGTTCCTGCA GACTATGTTG
 121 AGGAAGGAGG TTAACAGTCA GCTGAGTCTG GGAGACCCGC TGTTTCCAGA GTTGGCCGAA
 181 GAATCCCTCA AAACTTTTGA ACAAGTGACC GAGGATTGCA ACGAGAACCC CGAGAAAGAT
 241 GTCCTGGCAG AACTCGTCAA ACAGATTAAG GTTCGAGTGG ACATGGTGCG GCATAGAATC
 301 AAGGAGCACA TGCTGAAAAA ATATACCCAG ACGGAAGAGA AATTCACTGG CGCCTTTAAT
 361 ATGATGGGAG GATGTTTGCA GAATGCCTTA GATATCTTAG ATAAGGTTCA TGAGCCTTTC
 421 GAGGAGATGA AGTGTATTGG GCTAACTATG CAGAGCATGT ATGAGAACTA CATTGTACCT
 481 GAGGATAAGC GGGAGATGTG GATGGCTTGT ATTAAGGAGC TGCATGATGT GAGCAAGGGC
 541 GCCGCTAACA AGTTGGGGGG TGCACTGCAG GCTAAGGCCC GTGCTAAAAA GGATGAACTT
 601 AGGAGAAAGA TGATGTATAT GTGCTACAGG AATATAGAGT TCTTTACCAA GAACTCAGCC
 661 TTCCCTAAGA CCACCAATGG CTGCAGTCAG GCCATGGCGG CACTGCAGAA CTTGCCTCAG
 721 TGCTCCCCTG ATGAGATTAT GGCTTATGCC CAGAAAATAT TTAAGATTTT GGATGAGGAG
 781 AGAGACAAGG TGCTCACGCA CATTGATCAC ATATTTATGG ATATCCTCAC TACATGTGTG
 841 GAAACAATGT GTAATGAGTA CAAGGTCACT AGTGTGATGC TGGCCAAGCG GCCTCTGATA
 901 ACCAAGCCTG AGGTTATCAG TGTAATGAAG CGCCGCATTG AGGAGATCTG CATGAAGGTC
 961 TTTGCCCAGT ACATTCTGGG GGCCGATCCT CTGAGAGTCT GCTCTCCTAG TGTGGATGAC
1021 CTACGGGCCA TCGCCGAGGA GTCAGATGAG GAAGAGGCTA TTGTAGCCTA CACTTTGGCC
1081 ACCGCTGGTG TCAGCTCCTC TGATTCTCTG GTGTCACCCC CAGAGTCCCC TGTACCCGCG
1141 ACTATCCCTC TGTCCTCAGT AATTGTGGCT GAGAACAGTG ATCAGGAAGA AAGTGAGCAG
1201 AGTGATGAGG AAGAGGAGGA GGGTGCTCAG GAGGAGCGGG AGGACACTGT GTCTGTCAAG
1261 TCTGAGCCAG TGTCTGAGAT AGAGGAAGTT GCCCCAGAGG AAGAGGAGGA TGGTGCTGAG
1321 GAACCCACCG CCTCTGGAGG TAAGAGTACC CACCCTATGG TGACTAGAAG CAAGGCTGAC
1381 CAGTAA
```

Figure 24

1 AAGCTTGCGG CCGCTCATTA GACAAGCGAA TGAGGGACGA AAACGTGGAG GAGGTATTAA
61 GTTTGGAGAA ATGGAGAGAG ACTGTTTAAT AGCGCATGGC GCAGCCAATA CTATTACAGA
121 AGTTTTGAAA GATTCGGAAG AAGATTATCA AGATGTGTAT GTTTGTGAAA ATTGTGGAGA
181 CATAGCAGCA CAAATCAAGG GTATTAATAC ATGTCTTAGA TGTTCAAAAC TTAATCTCTC
241 TCCTCTCTTA ACAAAAATTG ATACCACGCA CGTATCTAAA GTATTTCTTA CTCAAATGAA
301 CGCCAGAGGC GTAAAAGTCA AATTAGATTT CGAACGAAGG CCTCCTTCGT TTTATAAACC
361 ATTAGATAAA GTTGATCTCA AGCCGTCTTT TCTGGTGTAA TAAAAATTAA TTAATTACTC
421 GAGATAAAAA TTACTGGTCA GCCTTGCTTC TAGTCACCAT AGGGTGGGTA CTCTTACCTC
481 CAGAGGCGGT GGGTTCCTCA GCACCATCCT CCTCTTCCTC TGGGGCAACT TCCTCTATCT
541 CAGACACTGG CTCAGACTTG ACAGACACAG TGTCCTCCCG CTCCTCCTGA GCACCCTCCT
601 CCTCTTCCTC ATCACTCTGC TCACTTTCTT CCTGATCACT GTTCTCAGCC ACAATTACTG
661 AGGACAGAGG GATAGTCGCG GGTACAGGGG ACTCTGGGGG TGACACCAGA GAATCAGAGG
721 AGCTGACACC AGCGGTGGCC AAAGTGTAGG CTACAATAGC CTCTTCCTCA TCTGACTCCT
781 CGGCGATGGC CCGTAGGTCA TCCACACTAG GAGAGCAGAC TCTCAGAGGA TCGGCCCCCA
841 GAATGTACTG GGCAAAGACC TTCATGCAGA TCTCCTCAAT GCGGCGCTTC ATTACACTGA
901 TAACCTCAGG CTTGGTTATC AGAGGCCGCT TGGCCAGCAT CACACTAGTG ACCTTGTACT
961 CATTACACAT TGTTTCCACA CATGTAGTGA GGATATCCAT AAATATGTGA TCAATGTGCG
1021 TGAGCACCTT GTCTCTCTCC TCATCCAAAA TCTTAAATAT TTTCTGGGCA TAAGCCATAA
1081 TCTCATCAGG GGAGCACTGA GGCAAGTTCT GCAGTGCCGC CATGGCCTGA CTGCAGCCAT
1141 TGGTGGTCTT AGGGAAGGCT GAGTTCTTGG TAAAGAACTC TATATTCCTG TAGCACATAT
1201 ACATCATCTT TCTCCTAAGT TCATCCTTTT TAGCACGGGC CTTAGCCTGC AGTGCACCCC
1261 CCAACTTGTT AGCGGCGCCC TTGCTCACAT CATGCAGCTC CTTAATACAA GCCATCCACA
1321 TCTCCCGCTT ATCCTCAGGT ACAATGTAGT TCTCATACAT GCTCTGCATA GTTAGCCCAA
1381 TACACTTCAT CTCCTCGAAA GGCTCATGAA CCTTATCTAA GATATCTAAG GCATTCTGCA
1441 AACATCCTCC CATCATATTA AAGGCGCCAG TGAATTTCTC TTCCGTCTGG GTATATTTTT
1501 TCAGCATGTG CTCCTTGATT CTATGCCGCA CCATGTCCAC TCGAACCTTA ATCTGTTTGA
1561 CGAGTTCTGC CAGGACATCT TTCTCGGGGT TCTCGTTGCA ATCCTCGGTC ACTTGTTCAA
1621 AAGTTTTGAG GGATTCTTCG GCCAACTCTG GAAACAGCGG GTCTCCCAGA CTCAGCTGAC
1681 TGTTAACCTC CTTCCTCAAC ATAGTCTGCA GGAACGTCGT GGCCTTGGTC ACGGGTGTCT
1741 CGGGCCGTGG CACCTTGGAG GAAGGGCCCT CGTCAGGATT ATCAGGGTCC ATCTTTCTCT
1801 TGGCAGAGGA CTCCATTACG ATACAAACTT AACGGATATC GCGATAATGA AATAATTTAT
1861 GATTATTTCT CGCTTTCAAT TTAACACAAC CCTCAAGAAC CTTTGTATTT ATTTTCACTT
1921 TTTAAGTATA GAATAAAGAA GCTCTAATTA ATTAAGCTAC AAATAGTTTC GTTTTCACCT
1981 TGTCTAATAA CTAATTAATT AACCCCGATA GCTGATTAGT TTTTGTTAAC AAAAATGTGG
2041 GAGAATCTAA TTAGTTTTTC TTTACACAAT TGACGTACAT GAGTCTGAGT TCCTTGTTTT
2101 TGCTAATTAT TTCATCCAAT TTATTATTCT TGACGATATC GAGATCTTTT GTATAGGAGT
2161 CAGACTTGTA TTCAACATGC TTTTCTATAA TCATCTTAGT TATTTCGGCA TCATCCAATA
2221 GTACATTTTC CAGATTAACA GAGTAGATAT TAATGTCGTA TTTGAACAGA GCCTGTAACA
2281 TCTCAATGTC TTTATTATCT ATAGCCAATT TAATGTCCGG AATGAAGAGA AGGGAATTAT
2341 TGGTGTTTGT CGACGTCATA TAGTCGAGCA AGAGAATCAT CATATCCACG TGTCCATTTT
2401 TTATAGTGGT GTGAATACAA CTAAGGAGAA TAGCCAGATC AAAAGTAGAT GGTATTTCTG
2461 AAAGAAAGTA TGATACAATA CTTACATCAT TAAGCATGAC GGCATGATAA AATGAAGTTT
2521 TCCATCCAGT TTTCCCATAG AACATCAGTC TCCAATTTTT CTTAAACAGT TTCACCGTTT
2581 GCATGTTACC ACTATCAACC GCATAATACA ATGCGGTGTT TCCTTTGTCA TCAAATTGTG
2641 AATCATCCAT TCCACTGAAT AGCAAAATCT TTACTATTTT GGTATCTTCT AATGTGGCTG
2701 CCTGATGTAA TGGAAATTCA TTCTCTAGAA GATTTTTCAA TGCTCCAGCG TTCAACAACG
2761 TACATACTAG ACGCACGTTA TTATCAGCTA TTGCATAATA CAAGGCACTA TGTCCATGGA
2821 CATCCGCCTT AAATGTATCT TTACTAGAGA GAAAGCTTTT CAGCTGCTTA GACTTCCAAG
2881 TATTAATTCG TGACAGATCC ATGTCTGAAA CGAGACGCTA ATTAGTGTAT ATTTTTTCAT
2941 TTTTTATAAT TTTGTCATAT TGCACCAGAA TTAATAATAT CTCTAATAGA TCTAATTTAA
3001 TTTAATTTAT ATAACTTATT TTTTGAATAT ACTTTTAATT AACAAAAGAG TTAAGTTACT
3061 CATATGGACG CCGTCCAGTC TGAACATCAA TCTTTTTAGC CAGAGATATC ATAGCCGCTC

Figure 25A

```
3121 TTAGAGTTTC AGCGTGATTT TCCAACCTAA ATAGAACTTC ATCGTTGCGT TTACAACACT
3181 TTTCTATTTG TTCAAACTTT GTTGTTACAT TAGTAATCTT TTTTTCCAAA TTAGTTAGCC
3241 GTTGTTTGAG AGTTTCCTCA TTGTCGTCTT CATCGGCTTT AACAATTGCT TCGCGTTTAG
3301 CCTCCTGGCT GTTCTTATCA GCCTTTGTAG AAAAAAATTC AGTTGCTGGA ATTGCAAGAT
3361 CGTCATCTCC GGGGAAAAGA GTTCCGTCCA TTTAAAGCCG CGGGAATTC
```

Figure 25B

```
   1 ATGAAACAGA TTAAGGTTCG AGTGGACATG GTGCGGCATA GAATCAAGGA GCACATGCTG
  61 AAAAAATATA CCCAGACGGA AGAGAAATTC ACTGGCGCCT TTAATATGAT GGGAGGATGT
 121 TTGCAGAATG CCTTAGATAT CTTAGATAAG GTTCATGAGC CTTTCGAGGA GATGAAGTGT
 181 ATTGGGCTAA CTATGCAGAG CATGTATGAG AACTACATTG TACCTGAGGA TAAGCGGGAG
 241 ATGTGGATGG CTTGTATTAA GGAGCTGCAT GATGTGAGCA AGGGCGCCGC TAACAAGTTG
 301 GGGGGTGCAC TGCAGGCTAA GGCCCGTGCT AAAAAGGATG AACTTAGGAG AAAGATGATG
 361 TATATGTGCT ACAGGAATAT AGAGTTCTTT ACCAAGAACT CAGCCTTCCC TAAGACCACC
 421 AATGGCTGCA GTCAGGCCAT GGCGGCACTG CAGAACTTGC CTCAGTGCTC CCCTGATGAG
 481 ATTATGGCTT ATGCCCAGAA AATATTTAAG ATTTTGGATG AGGAGAGAGA CAAGGTGCTC
 541 ACGCACATTG ATCACATATT TATGGATATC CTCACTACAT GTGTGGAAAC AATGTGTAAT
 601 GAGTACAAGG TCACTAGTGA CGCTTGTATG ATGACCATGT ACGGGGGCAT CTCTCTCTTA
 661 AGTGAGTTCT GTCGGGTGCT GTGCTGCTAT GTCTTAGAGG AGACTAGTGT GATGCTGGCC
 721 AAGCGGCCTC TGATAACCAA GCCTGAGGTT ATCAGTGTAA TGAAGCGCCG CATTGAGGAG
 781 ATCTGCATGA AGGTCTTTGC CCAGTACATT CTGGGGGCCG ATCCTCTGAG AGTCTGCTCT
 841 CCTAGTGTGG ATGACCTACG GGCCATCGCC GAGGAGTCAG ATGAGGAAGA GGCTATTGTA
 901 GCCTACACTT TGGCCACCGC TGGTGTCAGC TCCTCTGATT CTCTGGTGTC ACCCCCAGAG
 961 TCCCCTGTAC CCGCGACTAT CCCTCTGTCC TCAGTAATTG TGGCTGAGAA CAGTGATCAG
1021 GAAGAAAGTG AGCAGAGTGA TGAGGAAGAG GAGGAGGGTG CTCAGGAGGA GCGGGAGGAC
1081 ACTGTGTCTG TCAAGTCTGA GCCAGTGTCT GAGATAGAGG AAGTTGCCCC AGAGGAAGAG
1141 GAGGATGGTG CTGAGGAACC CACCGCCTCT GGAGGTAAGA GTACCCACCC TATGGTGACT
1201 AGAAGCAAGG CTGACCAGTA A
```

Figure 26

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCCT TCTTTATTCT ATACTTAAAA AGTGAAAATA
 661 AATACAAAGG TTCTTGAGGG TTGTGTTAAA TTGAAAGCGA GAAATAATCA TAAATTATTT
 721 CATTATCGCG ATATCCGTTA AGTTTGTATC GTAATGAAAC AGATTAAGGT TCGAGTGGAC
 781 ATGGTGCGGC ATAGAATCAA GGAGCACATG CTGAAAAAAT ATACCCAGAC GGAAGAGAAA
 841 TTCACTGGCG CCTTTAATAT GATGGGAGGA TGTTTGCAGA ATGCCTTAGA TATCTTAGAT
 901 AAGGTTCATG AGCCTTTCGA GGAGATGAAG TGTATTGGGC TAACTATGCA GAGCATGTAT
 961 GAGAACTACA TTGTACCTGA GGATAAGCGG GAGATGTGGA TGGCTTGTAT TAAGGAGCTG
1021 CATGATGTGA GCAAGGGCGC CGCTAACAAG TTGGGGGGTG CACTGCAGGC TAAGGCCCGT
1081 GCTAAAAAGG ATGAACTTAG GAGAAAGATG ATGTATATGT GCTACAGGAA TATAGAGTTC
1141 TTTACCAAGA ACTCAGCCTT CCCTAAGACC ACCAATGGCT GCAGTCAGGC CATGGCGGCA
1201 CTGCAGAACT TGCCTCAGTG CTCCCCTGAT GAGATTATGG CTTATGCCCA GAAAATATTT
1261 AAGATTTTGG ATGAGGAGAG AGACAAGGTG CTCACGCACA TTGATCACAT ATTTATGGAT
1321 ATCCTCACTA CATGTGTGGA AACAATGTGT AATGAGTACA AGGTCACTAG TGACGCTTGT
1381 ATGATGACCA TGTACGGGGG CATCTCTCTC TTAAGTGAGT TCTGTCGGGT GCTGTGCTGC
1441 TATGTCTTAG AGGAGACTAG TGTGATGCTG GCCAAGCGGC CTCTGATAAC CAAGCCTGAG
1501 GTTATCAGTG TAATGAAGCG CCGCATTGAG GAGATCTGCA TGAAGGTCTT TGCCCAGTAC
1561 ATTCTGGGGG CCGATCCTCT GAGAGTCTGC TCTCCTAGTG TGGATGACCT ACGGGCCATC
1621 GCCGAGGAGT CAGATGAGGA AGAGGCTATT GTAGCCTACA CTTTGGCCAC CGCTGGTGTC
1681 AGCTCCTCTG ATTCTCTGGT GTCACCCCCA GAGTCCCCTG TACCCGCGAC TATCCCTCTG
1741 TCCTCAGTAA TTGTGGCTGA GAACAGTGAT CAGGAAGAAA GTGAGCAGAG TGATGAGGAA
1801 GAGGAGGAGG GTGCTCAGGA GGAGCGGGAG GACACTGTGT CTGTCAAGTC TGAGCCAGTG
1861 TCTGAGATAG AGGAAGTTGC CCCAGAGGAA GAGGAGGATG GTGCTGAGGA ACCCACCGCC
1921 TCTGGAGGTA AGAGTACCCA CCCTATGGTG ACTAGAAGCA AGGCTGACCA GTAATTTTTA
1981 TCTCGAGCCC GGGAGATCTT AGCTAACTGA TTTTTCTGGG AAAAAAATTA TTTAACTTTT
2041 CATTAATAGG GATTTGACGT ATGTAGCGTA CAAAATTATC GTTCCTGGTA TATAGATAAA
2101 GAGTCCTATA TATTTGAAAA TCGTTACGGC TCGATTAAAC TTTAATGATT GCATAGTGAA
2161 TATATCATTA GGATTTAACT CCTTGACTAT CATGGCGGCG CCAGAAATTA CCATCAAAAG
2221 CATTAATACA GTTATGCCGA TCGCAGTTAG AACGGTTATA GCATCCACCA TTTATATCTA
2281 AAAATTAGAT CAAAGAATAT GTGACAAAGT CCTAGTTGTA TACTGAGAAT TGACGAAACA
2341 ATGTTTCTTA CATATTTTTT TCTTATTAGT AACTGACTTA ATAGTAGGAA CTGGAAAGCT
2401 AGACTTGATT ATTCTATAAG TATAGATACC CTTCCAGATA ATGTTCTCTT TGATAAAAGT
2461 TCCAGAAAAT GTAGAATTTT TTAAAAAGTT ATCTTTTGCT ATTACCAAGA TTGTGTTTAG
2521 ACGCTTATTA TTAATATGAG TAATGAAATC CACACCGCCT CTAGATATGG GGAATTC
```

Figure 27

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGGA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC CGGGTTAATT AATTAGTCAT CAGGCAGGGC GAGAACGAGA
1621 CTATCTGCTC GTTAATTAAT TAGAGCTTCT TTATTCTATA CTTAAAAAGT GAAAATAAAT
1681 ACAAAGGTTC TTGAGGGTTG TGTTAAATTG AAAGCGAGAA ATAATCATAA ATTATTTCAT
1741 TATCGCGATA TCCGTTAAGT TTGTATCGTA ATGAAACAGA TTAAGGTTCG AGTGGACATG
1801 GTGCGGCATA GAATCAAGGA GCACATGCTG AAAAAATATA CCCAGACGGA AGAGAAATTC
1861 ACTGGCGCCT TTAATATGAT GGGAGGATGT TTGCAGAATG CCTTAGATAT CTTAGATAAG
1921 GTTCATGAGC CTTTCGAGGA GATGAAGTGT ATTGGGCTAA CTATGCAGAG CATGTATGAG
1981 AACTACATTG TACCTGAGGA TAAGCGGGAG ATGTGGATGG CTTGTATTAA GGAGCTGCAT
2041 GATGTGAGCA AGGGCGCCGC TAACAAGTTG GGGGGTGCAC TGCAGGCTAA GGCCCGTGCT
2101 AAAAAGGATG AACTTAGGAG AAAGATGATG TATATGTGCT ACAGGAATAT AGAGTTCTTT
2161 ACCAAGAACT CAGCCTTCCC TAAGACCACC AATGGCTGCA GTCAGGCCAT GGCGGCACTG
2221 CAGAACTTGC CTCAGTGCTC CCCTGATGAG ATTATGGCTT ATGCCCAGAA AATATTTAAG
2281 ATTTTGGATG AGGAGAGAGA CAAGGTGCTC ACGCACATTG ATCACATATT TATGGATATC
2341 CTCACTACAT GTGTGGAAAC AATGTGTAAT GAGTACAAGG TCACTAGTGA CGCTTGTATG
2401 ATGACCATGT ACGGGGGCAT CTCTCTCTTA AGTGAGTTCT GTCGGGTGCT GTGCTGCTAT
2461 GTCTTAGAGG AGACTAGTGT GATGCTGGCC AAGCGGCCTC TGATAACCAA GCCTGAGGTT
2521 ATCAGTGTAA TGAAGCGCCG CATTGAGGAG ATCTGCATGA AGGTCTTTGC CCAGTACATT
2581 CTGGGGGCCG ATCCTCTGAG AGTCTGCTCT CCTAGTGTGG ATGACCTACG GGCCATCGCC
2641 GAGGAGTCAG ATGAGGAAGA GGCTATTGTA GCCTACACTT TGGCCACCGC TGGTGTCAGC
2701 TCCTCTGATT CTCTGGTGTC ACCCCCAGAG TCCCCTGTAC CCGCGACTAT CCCTCTGTCC
2761 TCAGTAATTG TGGCTGAGAA CAGTGATCAG GAAGAAAGTG AGCAGAGTGA TGAGGAAGAG
2821 GAGGAGGGTG CTCAGGAGGA GCGGGAGGAC ACTGTGTCTG TCAAGTCTGA GCCAGTGTCT
2881 GAGATAGAGG AAGTTGCCCC AGAGGAAGAG GAGGATGGTG CTGAGGAACC CACCGCCTCT
2941 GGAGGTAAGA GTACCCACCC TATGGTGACT AGAAGCAAGG CTGACCAGTA ATTTTTATCT
3001 CGAGTCTAGA ATCGATCCCG GGTTTTTATG ACTAGTTAAT CACGGCCGCT TATAAAGATC
3061 TAAAATGCAT AATTTCTAAA TAATGAAAAA AAAGTACATC ATGAGCAACG CGTTAGTATA
```

Figure 28A

```
3121 TTTTACAATG GAGATTAACG CTCTATACCG TTCTATGTTT ATTGATTCAG ATGATGTTTT
3181 AGAAAAGAAA GTTATTGAAT ATGAAAACTT TAATGAAGAT GAAGATGACG ACGATGATTA
3241 TTGTTGTAAA TCTGTTTTAG ATGAAGAAGA TGACGCGCTA AAGTATACTA TGGTTACAAA
3301 GTATAAGTCT ATACTACTAA TGGCGACTTG TGCAAGAAGG TATAGTATAG TGAAAATGTT
3361 GTTAGATTAT GATTATGAAA AACCAAATAA ATCAGATCCA TATCTAAAGG TATCTCCTTT
3421 GCACATAATT TCATCTATTC CTAGTTTAGA ATACCTGCAG
```

Figure 28B

```
   1 ATGACGACGT TCCTGCAGAC TATGTTGAGG AAGGAGGTTA ACAGTCAGCT GAGTCTGGGA
  61 GACCCGCTGT TTCCAGAGTT GGCCGAAGAA TCCCTCAAAA CTTTTGAACA AGTGACCGAG
 121 GATTGCAACG AGAACCCCGA GAAAGATGTC CTGGCAGAAC TCGTCAAACA GATTAAGGTT
 181 CGAGTGGACA TGGTGCGGCA TAGAATCAAG GAGCACATGC TGAAAAAATA TACCCAGACG
 241 GAAGAGAAAT TCACTGGCGC CTTTAATATG ATGGGAGGAT GTTTGCAGAA TGCCTTAGAT
 301 ATCTTAGATA AGGTTCATGA GCCTTTCGAG GAGATGAAGT GTATTGGGCT AACTATGCAG
 361 AGCATGTATG AGAACTACAT TGTACCTGAG GATAAGCGGG AGATGTGGAT GGCTTGTATT
 421 AAGGAGCTGC ATGATGTGAG CAAGGGCGCC GCTAACAAGT TGGGGGGTGC ACTGCAGGCT
 481 AAGGCCCGTG CTAAAAAGGA TGAACTTAGG AGAAAGATGA TGTATATGTG CTACAGGAAT
 541 ATAGAGTTCT TTACCAAGAA CTCAGCCTTC CCTAAGACCA CCAATGGCTG CAGTCAGGCC
 601 ATGGCGGCAC TGCAGAACTT GCCTCAGTGC TCCCCTGATG AGATTATGGC TTATGCCCAG
 661 AAAATATTTA AGATTTTGGA TGAGGAGAGA GACAAGGTGC TCACGCACAT TGATCACATA
 721 TTTATGGATA TCCTCACTAC ATGTGTGGAA ACAATGTGTA ATGAGTACAA GGTCACTAGT
 781 GACGCTTGTA TGATGACCAT GTACGGGGGC ATCTCTCTCT TAAGTGAGTT CTGTCGGGTG
 841 CTGTGCTGCT ATGTCTTAGA GGAGACTAGT GTGATGCTGG CCAAGCGGCC TCTGATAACC
 901 AAGCCTGAGG TTATCAGTGT AATGAAGCGC CGCATTGAGG AGATCTGCAT GAAGGTCTTT
 961 GCCCAGTACA TTCTGGGGGC CGATCCTCTG AGAGTCTGCT CTCCTAGTGT GGATGACCTA
1021 CGGGCCATCG CCGAGGAGTC AGATGAGGAA GAGGCTATTG TAGCCTACAC TTTGGCCACC
1081 GCTGGTGTCA GCTCCTCTGA TTCTCTGGTG TCACCCCCAG AGTCCCCTGT ACCCGCGACT
1141 ATCCCTCTGT CCTCAGTAAT TGTGGCTGAG AACAGTGATC AGGAAGAAAG TGAGCAGAGT
1201 GATGAGGAAG AGGAGGAGGG TGCTCAGGAG GAGCGGGAGG ACACTGTGTC TGTCAAGTCT
1261 GAGCCAGTGT CTGAGATAGA GGAAGTTGCC CCAGAGGAAG AGGAGGATGG TGCTGAGGAA
1321 CCCACCGCCT CTGGAGGTAA GAGTACCCAC CCTATGGTGA CTAGAAGCAA GGCTGACCAG
1381 TAA
```

Figure 29

1 CTGCAGGTCG ACGGATCTGA GAATGGATGA TTCTCCAGCC GAAACATATT CTACCATGGC
61 TCCGTTTAAT TTGTTGATGA AGATGGATTC ATCCTTAAAT GTTTTCTCTG TAATAGTTTC
121 CACCGAAAGA CTATGCAAAG AATTTGGAAT GCGTTCCTTG TGCTTAATGT TTCCATAGAC
181 GGCTTCTAGA AGTTGATACA ACATAGGACT AGCCGCGGTA ACTTTTATTT TTAGAAAGTA
241 TCCATCGCTT CTATCTTGTT TAGATTTATT TTTATAAAGT TTAGTCTCTC CTTCCAACAT
301 AATAAAAGTG GAAGTCATTT GACTAGATAA ACTATCAGTA AGTTTTATAG AGATAGACGA
361 ACAATTAGCG TATTGAGAAG CATTTAGTGT AACGTATTCG ATACATTTTG CATTAGATTT
421 ACTAATCGAT TTTGCATACT CTATAACACC CGCACAAGTC TGTAGAGAAT CGCTAGATGC
481 AGTAGGTCTT GGTGAAGTTT CAACTCTCTT CTTGATTACC TTACTCATGA TTAAACCTAA
541 ATAATTGTAC TTTGTAATAT AATGATATAT ATTTTCACTT TATCTCATTT GAGAATAAAA
601 AGATCACAAA AATTAACTAA TCAGGATCCT TCTTTATTCT ATACTTAAAA AGTGAAAATA
661 AATACAAAGG TTCTTGAGGG TTGTGTTAAA TTGAAAGCGA GAAATAATCA TAAATTATTT
721 CATTATCGCG ATATCCGTTA AGTTTGTATC GTAATGACGA CGTTCCTGCA GACTATGTTG
781 AGGAAGGAGG TTAACAGTCA GCTGAGTCTG GGAGACCCGC TGTTTCCAGA GTTGGCCGAA
841 GAATCCCTCA AAACTTTTGA ACAAGTGACC GAGGATTGCA ACGAGAACCC CGAGAAAGAT
901 GTCCTGGCAG AACTCGTCAA ACAGATTAAG GTTCGAGTGG ACATGGTGCG GCATAGAATC
961 AAGGAGCACA TGCTGAAAAA ATATACCCAG ACGGAAGAGA AATTCACTGG CGCCTTTAAT
1021 ATGATGGGAG GATGTTTGCA GAATGCCTTA GATATCTTAG ATAAGGTTCA TGAGCCTTTC
1081 GAGGAGATGA AGTGTATTGG GCTAACTATG CAGAGCATGT ATGAGAACTA CATTGTACCT
1141 GAGGATAAGC GGGAGATGTG GATGGCTTGT ATTAAGGAGC TGCATGATGT GAGCAAGGGC
1201 GCCGCTAACA AGTTGGGGGG TGCACTGCAG GCTAAGGCCC GTGCTAAAAA GGATGAACTT
1261 AGGAGAAAGA TGATGTATAT GTGCTACAGG AATATAGAGT TCTTTACCAA GAACTCAGCC
1321 TTCCCTAAGA CCACCAATGG CTGCAGTCAG GCCATGGCGG CACTGCAGAA CTTGCCTCAG
1381 TGCTCCCCTG ATGAGATTAT GGCTTATGCC CAGAAAATAT TTAAGATTTT GGATGAGGAG
1441 AGAGACAAGG TGCTCACGCA CATTGATCAC ATATTTATGG ATATCCTCAC TACATGTGTG
1501 GAAACAATGT GTAATGAGTA CAAGGTCACT AGTGACGCTT GTATGATGAC CATGTACGGG
1561 GGCATCTCTC TCTTAAGTGA GTTCTGTCGG GTGCTGTGCT GCTATGTCTT AGAGGAGACT
1621 AGTGTGATGC TGGCCAAGCG GCCTCTGATA ACCAAGCCTG AGGTTATCAG TGTAATGAAG
1681 CGCCGCATTG AGGAGATCTG CATGAAGGTC TTTGCCCAGT ACATTCTGGG GGCCGATCCT
1741 CTGAGAGTCT GCTCTCCTAG TGTGGATGAC CTACGGGCCA TCGCCGAGGA GTCAGATGAG
1801 GAAGAGGCTA TTGTAGCCTA CACTTTGGCC ACCGCTGGTG TCAGCTCCTC TGATTCTCTG
1861 GTGTCACCCC CAGAGTCCCC TGTACCCGCG ACTATCCCTC TGTCCTCAGT AATTGTGGCT
1921 GAGAACAGTG ATCAGGAAGA AAGTGAGCAG AGTGATGAGG AAGAGGAGGA GGGTGCTCAG
1981 GAGGAGCGGG AGGACACTGT GTCTGTCAAG TCTGAGCCAG TGTCTGAGAT AGAGGAAGTT
2041 GCCCCAGAGG AAGAGGAGGA TGGTGCTGAG GAACCCACCG CCTCTGGAGG TAAGAGTACC
2101 CACCCTATGG TGACTAGAAG CAAGGCTGAC CAGTAATTTT TATCTCGAGC CCGGGAGATC
2161 TTAGCTAACT GATTTTTCTG GGAAAAAAAT TATTTAACTT TTCATTAATA GGGATTTGAC
2221 GTATGTAGCG TACAAAATTA TCGTTCCTGG TATATAGATA AAGAGTCCTA TATATTTGAA
2281 AATCGTTACG GCTCGATTAA ACTTTAATGA TTGCATAGTG AATATATCAT TAGGATTTAA
2341 CTCCTTGACT ATCATGGCGG CGCCAGAAAT TACCATCAAA AGCATTAATA CAGTTATGCC
2401 GATCGCAGTT AGAACGGTTA TAGCATCCAC CATTTATATC TAAAAATTAG ATCAAAGAAT
2461 ATGTGACAAA GTCCTAGTTG TATACTGAGA ATTGACGAAA CAATGTTTCT TACATATTTT
2521 TTTCTTATTA GTAACTGACT TAATAGTAGG AACTGGAAAG CTAGACTTGA TTATTCTATA
2581 AGTATAGATA CCCTTCCAGA TAATGTTCTC TTTGATAAAA GTTCCAGAAA ATGTAGAATT
2641 TTTTAAAAAG TTATCTTTTG CTATTACCAA GATTGTGTTT AGACGCTTAT TATTAATATG
2701 AGTAATGAAA TCCACACCGC CTCTAGATAT GGGGAATTC

Figure 30

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGGA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC CGGGTTAATT AATTAGTCAT CAGGCAGGGC GAGAACGAGA
1621 CTATCTGCTC GTTAATTAAT TAGAGCTTCT TTATTCTATA CTTAAAAAGT GAAAATAAAT
1681 ACAAAGGTTC TTGAGGGTTG TGTTAAATTG AAAGCGAGAA ATAATCATAA ATTATTTCAT
1741 TATCGCGATA TCCGTTAAGT TTGTATCGTA ATGACGACGT TCCTGCAGAC TATGTTGAGG
1801 AAGGAGGTTA ACAGTCAGCT GAGTCTGGGA GACCCGCTGT TTCCAGAGTT GGCCGAAGAA
1861 TCCCTCAAAA CTTTTGAACA AGTGACCGAG GATTGCAACG AGAACCCCGA GAAAGATGTC
1921 CTGGCAGAAC TCGTCAAACA GATTAAGGTT CGAGTGGACA TGGTGCGGCA TAGAATCAAG
1981 GAGCACATGC TGAAAAAATA TACCCAGACG GAAGAGAAAT TCACTGGCGC CTTTAATATG
2041 ATGGGAGGAT GTTTGCAGAA TGCCTTAGAT ATCTTAGATA AGGTTCATGA GCCTTTCGAG
2101 GAGATGAAGT GTATTGGGCT AACTATGCAG AGCATGTATG AGAACTACAT TGTACCTGAG
2161 GATAAGCGGG AGATGTGGAT GGCTTGTATT AAGGAGCTGC ATGATGTGAG CAAGGGCGCC
2221 GCTAACAAGT TGGGGGGTGC ACTGCAGGCT AAGGCCCGTG CTAAAAAGGA TGAACTTAGG
2281 AGAAAGATGA TGTATATGTG CTACAGGAAT ATAGAGTTCT TTACCAAGAA CTCAGCCTTC
2341 CCTAAGACCA CCAATGGCTG CAGTCAGGCC ATGGCGGCAC TGCAGAACTT GCCTCAGTGC
2401 TCCCCTGATG AGATTATGGC TTATGCCCAG AAAATATTTA AGATTTTGGA TGAGGAGAGA
2461 GACAAGGTGC TCACGCACAT TGATCACATA TTTATGGATA TCCTCACTAC ATGTGTGGAA
2521 ACAATGTGTA ATGAGTACAA GGTCACTAGT GACGCTTGTA TGATGACCAT GTACGGGGGC
2581 ATCTCTCTCT TAAGTGAGTT CTGTCGGGTG CTGTGCTGCT ATGTCTTAGA GGAGACTAGT
2641 GTGATGCTGG CCAAGCGGCC TCTGATAACC AAGCCTGAGG TTATCAGTGT AATGAAGCGC
2701 CGCATTGAGG AGATCTGCAT GAAGGTCTTT GCCCAGTACA TTCTGGGGGC CGATCCTCTG
2761 AGAGTCTGCT CTCCTAGTGT GGATGACCTA CGGGCCATCG CCGAGGAGTC AGATGAGGAA
2821 GAGGCTATTG TAGCCTACAC TTTGGCCACC GCTGGTGTCA GCTCCTCTGA TTCTCTGGTG
2881 TCACCCCCAG AGTCCCCTGT ACCCGCGACT ATCCCTCTGT CCTCAGTAAT TGTGGCTGAG
2941 AACAGTGATC AGGAAGAAAG TGAGCAGAGT GATGAGGAAG AGGAGGAGGG TGCTCAGGAG
3001 GAGCGGGAGG ACACTGTGTC TGTCAAGTCT GAGCCAGTGT CTGAGATAGA GGAAGTTGCC
3061 CCAGAGGAAG AGGAGGATGG TGCTGAGGAA CCCACCGCCT CTGGAGGTAA GAGTACCCAC
```

Figure 31A

```
3121 CCTATGGTGA CTAGAAGCAA GGCTGACCAG TAATTTTTAT CTCGAGTCTA GAATCGATCC
3181 CGGGTTTTTA TGACTAGTTA ATCACGGCCG CTTATAAAGA TCTAAAATGC ATAATTTCTA
3241 AATAATGAAA AAAAAGTACA TCATGAGCAA CGCGTTAGTA TATTTTACAA TGGAGATTAA
3301 CGCTCTATAC CGTTCTATGT TTATTGATTC AGATGATGTT TTAGAAAAGA AAGTTATTGA
3361 ATATGAAAAC TTTAATGAAG ATGAAGATGA CGACGATGAT TATTGTTGTA AATCTGTTTT
3421 AGATGAAGAA GATGACGCGC TAAAGTATAC TATGGTTACA AAGTATAAGT CTATACTACT
3481 AATGGCGACT TGTGCAAGAA GGTATAGTAT AGTGAAAATG TTGTTAGATT ATGATTATGA
3541 AAAACCAAAT AAATCAGATC CATATCTAAA GGTATCTCCT TTGCACATAA TTTCATCTAT
3601 TCCTAGTTTA GAATACCTGC AG
```

Figure 31B

```
   1 ATGGAGTCGC GCGGTCGCCG TTGTCCCGAA ATGATATCCG TACTGGGTCC CATTTCGGGG
  61 CACGTGCTGA AAGCCGTGTT TAGTCGCGGC GACACGCCGG TGCTGCCGCA CGAGACGCGA
 121 CTCCTGCAGA CGGGTATCCA CGTGCGCGTG AGCCAGCCCT CGCTGATCCT GGTGTCGCAG
 181 TACACGCCCG ACTCGACGCC ATGCCACCGC GGCGACAATC AGCTGCAGGT GCAGCACACG
 241 TACTTTACGG GCAGCGAGGT GGAGAACGTG TCGGTCAACG TGCACAACCC CACGGGCCGG
 301 AGCATCTGCC CCAGCCAAGA GCCCATGTCG ATCTATGTGT ACGCGCTGCC GCTCAAGATG
 361 CTGAACATCC CCAGCATCAA CGTGCACCAC TACCCGTCGG CGGCCGAGCG CAAACACCGA
 421 CACCTGCCCG TAGCTGACGC TGTGATTCAC GCGTCGGGCA AGCAGATGTG GCAGGCGCGT
 481 CTCACGGTCT CGGGACTGGC CTGGACGCGT CAGCAGAACC AGTGGAAAGA GCCCGACGTC
 541 TACTACACGT CAGCGTTCGT GTTTCCCACC AAGGACGTGG CACTGCGGCA CGTGGTGTGC
 601 GCGCACGAGC TGGTTTGCTC CATGGAGAAC ACGCGCGCAA CCAAGATGCA GGTGATAGGT
 661 GACCAGTACG TCAAGGTGTA CCTGGAGTCC TTCTGCGAGG ACGTGCCCTC CGGCAAGCTC
 721 TTTATGCACG TCACGCTGGG CTCTGACGTG GAAGAGGACC TGACGATGAC CCGCAACCCG
 781 CAACCCTTCA TGCGCCCCCA CGAGCGCAAC GGCTTTACGG TGTTGTGTCC CAAAAATATG
 841 ATAATCAAAC CGGGCAAGAT CTCGCACATC ATGCTGGATG TGGCTTTTAC CTCACACGAG
 901 CATTTTGGGC TGCTGTGTCC CAAGAGCATC CCGGGCCTGA GCATCTCAGG TAACCTATTG
 961 ATGAACGGGC AGCAGATCTT CCTGGAGGTG CAAGCGATAC GCGAGACCGT GGAACTGCGT
1021 CAGTACGATC CCGTGGCTGC GCTCTTCTTT TTCGATATCG ACTTGCTGCT GCAGCGCGGG
1081 CCTCAGTACA GCGAACACCC CACCTTCACC AGCCAGTATC GCATCCAGGG CAAGCTTGAG
1141 TACCGACACA CCTGGGACCG GCACGACGAG GGTGCCGCCC AGGGCGACGA CGACGTCTGG
1201 ACCAGCGGAT CGGACTCCGA CGAGGAACTC GTAACCACCG AGCGCAAGAC GCCCCGCGTT
1261 ACCGGCGGCG GCGCCATGGC GGGCGCCTCC ACTTCCGCGG GCCGCAAACG CAAATCAGCA
1321 TCCTCGGCGA CGGCGTGCAC GGCGGGCGTT ATGACACGCG GCCGCCTTAA GGCCGAGTCC
1381 ACCGTCGCGC CCGAAGAGGA CACCGACGAG GATTCCGACA ACGAAATCCA CAATCCGGCC
1441 GTGTTCACCT GGCCGCCCTG GCAGGCCGGC ATCCTGGCCC GCAACCTGGT GCCCATGGTG
1501 GCTACGGTTC AGGGTCAGAA TCTGAAGTAC CAGGAGTTCT TCTGGGACGC CAACGACATC
1561 TACCGCATCT TCGCCGAATT GGAAGGCGTA TGGCAGCCCG CTGCGCAACC CAAACGTCGC
1621 CGCCACCGGC AAGACGCCTT GCCCGGGCCA TGCATCGCCT CGACGCCCAA AAAGCACCGA
1681 GGTTGA
```

Figure 32

```
   1 GTCGACGATT GTTCATGATG GCAAGATTTA TATATCTGGA GGTTACAACA ATAGTAGTGT
  61 AGTTAATGTA ATATCGAATC TAGTCCTTAG CTATAATCCG ATATATGATG AATGGACCAA
 121 ATTATCATCA TTAAACATTC CTAGAATTAA TCCCGCTCTA TGGTCAGCGC ATAATAAATT
 181 ATATGTAGGA GGAGGAATAT CTGATGATGT TCGAACTAAT ACATCTGAAA CATACGATAA
 241 AGAAAAAGAT TGTTGGACAT TGGATAATGG TCACGTGTTA CCACGCAATT ATATAATGTA
 301 TAAATGCGAA CCGATTAAAC ATAAATATCC ATTGGAAAAA ACACAGTACA CGAATGATTT
 361 TCTAAAGTAT TTGGAAAGTT TTATAGGTAG TTGATAGAAC AAAATACATA ATTTTGTAAA
 421 AATAAATCAC TTTTTATACT AATATTTAAT TAATTAAGCT TGGTACCCTC GAAGCTTCTT
 481 TATTCTATAC TTAAAAAGTG AAAATAAATA CAAAGGTTCT TGAGGGTTGT GTTAAATTGA
 541 AAGCGAGAAA TAATCATAAA TTATTTCATT ATCGCGATAT CCGTTAAGTT TGTATCGTAA
 601 TGGAGTCGCG CGGTCGCCGT TGTCCCGAAA TGATATCCGT ACTGGGTCCC ATTTCGGGGC
 661 ACGTGCTGAA AGCCGTGTTT AGTCGCGGCG ACACGCCGGT GCTGCCGCAC GAGACGCGAC
 721 TCCTGCAGAC GGGTATCCAC GTGCGCGTGA GCCAGCCCTC GCTGATCCTG GTGTCGCAGT
 781 ACACGCCCGA CTCGACGCCA TGCCACCGCG GCGACAATCA GCTGCAGGTG CAGCACACGT
 841 ACTTTACGGG CAGCGAGGTG GAGAACGTGT CGGTCAACGT GCACAACCCC ACGGGCCGGA
 901 GCATCTGCCC CAGCCAAGAG CCCATGTCGA TCTATGTGTA CGCGCTGCCG CTCAAGATGC
 961 TGAACATCCC CAGCATCAAC GTGCACCACT ACCCGTCGGC GGCCGAGCGC AAACACCGAC
1021 ACCTGCCCGT AGCTGACGCT GTGATTCACG CGTCGGGCAA GCAGATGTGG CAGGCGCGTC
1081 TCACGGTCTC GGGACTGGCC TGGACGCGTC AGCAGAACCA GTGGAAAGAG CCCGACGTCT
1141 ACTACACGTC AGCGTTCGTG TTTCCCACCA AGGACGTGGC ACTGCGGCAC GTGGTGTGCG
1201 CGCACGAGCT GGTTTGCTCC ATGGAGAACA CGCGCGCAAC CAAGATGCAG GTGATAGGTG
1261 ACCAGTACGT CAAGGTGTAC CTGGAGTCCT TCTGCGAGGA CGTGCCCTCC GGCAAGCTCT
1321 TTATGCACGT CACGCTGGGC TCTGACGTGG AAGAGGACCT GACGATGACC CGCAACCCGC
1381 AACCCTTCAT GCGCCCCCAC GAGCGCAACG GCTTTACGGT GTTGTGTCCC AAAAATATGA
1441 TAATCAAACC GGGCAAGATC TCGCACATCA TGCTGGATGT GGCTTTTACC TCACACGAGC
1501 ATTTTGGGCT GCTGTGTCCC AAGAGCATCC CGGGCCTGAG CATCTCAGGT AACCTATTGA
1561 TGAACGGGCA GCAGATCTTC CTGGAGGTGC AAGCGATACG CGAGACCGTG GAACTGCGTC
1621 AGTACGATCC CGTGGCTGCG CTCTTCTTTT TCGATATCGA CTTGCTGCTG CAGCGCGGGC
1681 CTCAGTACAG CGAACACCCC ACCTTCACCA GCCAGTATCG CATCCAGGGC AAGCTTGAGT
1741 ACCGACACAC CTGGGACCGG CACGACGAGG GTGCCGCCCA GGGCGACGAC GACGTCTGGA
1801 CCAGCGGATC GGACTCCGAC GAGGAACTCG TAACCACCGA GCGCAAGACG CCCCGCGTTA
1861 CCGGCGGCGG CGCCATGGCG GGCGCCTCCA CTTCCGCGGG CCGCAAACGC AAATCAGCAT
1921 CCTCGGCGAC GGCGTGCACG GCGGGCGTTA TGACACGCGG CCGCCTTAAG GCCGAGTCCA
1981 CCGTCGCGCC CGAAGAGGAC ACCGACGAGG ATTCCGACAA CGAAATCCAC AATCCGGCCG
2041 TGTTCACCTG GCCGCCCTGG CAGGCCGGCA TCCTGGCCCG CAACCTGGTG CCCATGGTGG
2101 CTACGGTTCA GGGTCAGAAT CTGAAGTACC AGGAGTTCTT CTGGGACGCC AACGACATCT
2161 ACCGCATCTT CGCCGAATTG GAAGGCGTAT GGCAGCCCGC TGCGCAACCC AAACGTCGCC
2221 GCCACCGGCA AGACGCCTTG CCCGGGCCAT GCATCGCCTC GACGCCCAAA AAGCACCGAG
2281 GTTGATTTTT ATGGATCCCC CGGGTAGCTA GCTAATTTTT CTTTTACGTA TTATATATGT
2341 AATAAACGTT CACGTAAATA CAAAACAGAG AACAAAGTCT AGATTTTTGA CTTACATAAA
2401 TGTCTGGGAT AGTAAAATCT ATCATATTGA GCGGACCATC TGGTTCAGGA AAGACAGCCA
2461 TAGCCAAAAG ACTATGGGAA TATATTTGGA TTTGTGGTGT CCCATACCAC TAGATTTCCT
2521 CGTCCTATGG AACGAGAAGG TGTCGATTAC CATTACGTTA ACAGAGAGGC CATCTGGAAG
2581 GGAATAGCCG CCGGAAACTT TCTAGAACAT ACTGAGTTTT TAGGAAATAT TTACGGAACT
2641 TCTAAAACTG CTGTGAATAC AGCGGCTATT AATAATCGTA TTTGTGTGAT GGATTTAAAC
2701 ATCGACGGTG TTAGAAGTTT TAAAAATACT TACCTGCAGA AGCTT
```

Figure 33

```
   1 AAGCTTCTAT CAAAAGTCTT AATGAGTTAG GTGTAGATAG TATAGATATT ACTACAAAGG
  61 TATTCATATT TCCTATCAAT TCTAAAGTAG ATGATATTAA TAACTCAAAG ATGATGATAG
 121 TAGATAATAG ATACGCTCAT ATAATGACTG CAAATTTGGA CGGTTCACAT TTTAATCATC
 181 ACGCGTTCAT AAGTTTCAAC TGCATAGATC AAAATCTCAC TAAAAAGATA GCCGATGTAT
 241 TTGAGAGAGA TTGGACATCT AACTACGCTA AAGAAATTAC AGTTATAAAT AATACATAAT
 301 GGATTTTGTT ATCATCAGTT ATATTTAACA TAAGTACAAT AAAAAGTATT AAATAAAAAT
 361 ACTTACTTAC GAAAAAATGT CATTATTACA AAAACTATAT TTTACAGAAC AATCTATAGT
 421 AGAGTCCTTT AAGAGTTATA ATTTAAAAGA TAACCATAAT GTAATATTTA CCACATCAGA
 481 TGTTGATACT GTTGTAGTAA TAAATGAAGA TAATGTACTG TTATCTACAA GATTATTATC
 541 ATTTGATAAA ATTCTGTTTT TTAACTCCTT TAATAACGGT TTATCAAAAT ACGAAACTAT
 601 TAGTGATACA ATATTAGATA TAGATACTCA TAATTATTAT ATACCTAGTT CTTCTTCTTT
 661 GTTAGATATT CTAAAAAAAA GAGCGTGTGA TTTAGAATTA GAAGATCTAA ATTATGCGTT
 721 AATAGGAGAC AATAGTAACT TATATTATAA AGATATGACT TACATGAATA ATTGGTTATT
 781 TACTAAAGGA TTATTAGATT ACAAGTTTGT ATTATTGCGC GATGTAGATA AATGTTACAA
 841 ACAGTATAAT AAAAAGAATA CTATAATAGA TATAATACAT CGCGATAACA GACAGTATAA
 901 CATATGGGTT AAAAATGTTA TAGAATACTG TTCTCCTGGC TATATATTAT GGTTACATGA
 961 TCTAAAAGCC GCTGCTGAAG ATGATTGGTT AAGATACGAT AACCGTATAA ACGAATTATC
1021 TGCGGATAAA TTATACACTT TCGAGTTCAT AGTTATATTA GAAAATAATA TAAAACATTT
1081 ACGAGTAGGT ACAATAATTG TACATCCAAA CAAGATAATA GCTAATGGTA CATCTAATAA
1141 TATACTTACT GATTTTCTAT CTTACGTAGA AGAACTAATA TATCATCATA ATTCATCTAT
1201 AATATTGGCC GGATATTTTT TAGAATTCTT TGAGACCACT ATTTTATCAG AATTTATTTC
1261 TTCATCTTCT GAATGGGTAA TGAATAGTAA CTGTTTAGTA CACCTGAAAA CAGGGTATGA
1321 AGCTATACTC TTTGATGCTA GTTTATTTTT CCAACTCTCT ACTAAAAGCA ATTATGTAAA
1381 ATATTGGACA AAGAAAACTT TGCAGTATAA GAACTTTTTT AAAGACGGTA AACAGTTAGC
1441 AAAATATATA ATTAAGAAAG ATAGTCAGGT GATAGATAGA GTATGTTATT TACACGCAGC
1501 TGTATATAAT CACGTAACTT ACTTAATGGA TACGTTTAAA ATTCCTGGTT TTGATTTTAA
1561 ATTCTCCGGA ATGATAGATA TACTACTGTT TGGAATATTG CATAAGGATA ATGAGAATAT
1621 ATTTTATCCG AAACGTGTTT CTGTAACTAA TATAATATCA GAATCTATCT ATGCAGATTT
1681 TTACTTTATA TCAGATGTTA ATAAATTCAG TAAAAAGATA GAATATAAAA CTATGTTTCC
1741 TATACTCGCA GAAAACTACT ATCCAAAAGG AAGGCCCTAT TTTACACATA CATCTAACGA
1801 AGATCTTCTG TCTATCTGTT TATGCGAAGT AACAGTTTGT AAAGATATAA AAAATCCATT
1861 ATTATATTCT AAAAAGGATA TATCAGCAAA ACGATTCATA GGTTTATTTA CATCTGTCGA
1921 TATAAATACG GCTGTTGAGT TAAGAGGATA TAAAATAAGA GTAATAGGAT GTTTAGAATG
1981 GCCTGAAAAG ATAAAAATAT TTAATTCTAA TCCTACATAC ATTAGATTAT TACTAACAGA
2041 AAGACGTTTA GATATTCTAC ATTCCTATCT GCTTAAATTT AATATAACAG AGGATATAGC
2101 TACCAGAGAT GGAGTCAGAA ATAATTTACC TATAATTTCT TTTATCGTCA GTTATTGTAG
2161 ATCGTATACT TATAAATTAC TAAATTGCCA TATGTACAAT TCGTGTAAGA TAACAAAGTG
2221 TAAATATAAT CAGGTAATAT ATAATCCTAT ATAGGAGTAT ATATAATTGA AAAAGTAAAA
2281 ATAAATCATA TAATAATGAA ACGAAATATC AGTAATAGAC AGGAACTGGC AGATTCTTCT
2341 TCTAATGAAG TAAGTACTGC TAAATCTCCA AAATTAGATA AAAATGATAC AGCAAATACA
2401 GCTTCATTCA ACGAATTACC TTTTAATTTT TTCAGACACA CCTTATTACA AACTAACTAA
2461 GTCAGATGAT GAGAAAGTAA ATATAAATTT AACTTATGGG TATAATATAA TAAAGATTCA
2521 TGATATTAAT AATTTACTTA ACGATGTTAA TAGACTTATT CCATCAACCC CTTCAAACCT
2581 TTCTGGATAT TATAAAATAC CAGTTAATGA TATTAAAATA GATTGTTTAA GAGATGTAAA
2641 TAATTATTTG GAGGTAAAGG ATATAAAATT AGTCTATCTT TCACATGGAA ATGAATTACC
2701 TAATATTAAT AATTATGATA GGAATTTTTT AGGATTTACA GCTGTTATAT GTATCAACAA
2761 TACAGGCAGA TCTATGGTTA TGGTAAAACA CTGTAACGGG AAGCAGCATT CTATGGTAAC
2821 TGGCCTATGT TTAATAGCCA GATCATTTTA CTCTATAAAC ATTTTACCAC AAATAATAGG
2881 ATCCTCTAGA TATTTAATAT TATATCTAAC AACAACAAAA AAATTTAACG ATGTATGGCC
2941 AGAAGTATTT TCTACTAATA AAGATAAAGA TAGTCTATCT TATCTACAAG ATATGAAAGA
3001 AGATAATCAT TTAGTAGTAG CTACTAATAT GGAAAGAAAT GTATACAAAA ACGTGGAAGC
3061 TTTTATATTA AATAGCATAT TACTAGAAGA TTTAAAATCT AGACTTAGTA TAACAAAACA
```

Figure 34A

```
3121 GTTAAATGCC AATATCGATT CTATATTTCA TCATAACAGT AGTACATTAA TCAGTGATAT
3181 ACTGAAACGA TCTACAGACT CAACTATGCA AGGAATAAGC AATATGCCAA TTATGTCTAA
3241 TATTTTAACT TTAGAACTAA AACGATTCTA CCAATACTAA AAATAGGATA CGTGATAGGC
3301 TGTTAAAAGC TGCAATAAAT AGTAAGGATG TAGAAGAAAT ACTTTGTTCT ATACCTTCGG
3361 AGGAAAGAAC TTTAGAACAA CTTAAGTTTA ATCAAACTTG TATTTATGAA CACTATAAAA
3421 AAATTATGGA AGATACAAGT AAAAGAATGG ATGTTGAATG TCGTAGTTTA GAACATAACT
3481 ATACGGCTAA CTTATATAAA GTGTACGGAC AAAACGAATA TATGATTACT TATATACTAG
3541 CTCTCATAAG TAGGATTAAT AATATTATAG AAACTTTAAA ATATAATCTG GTGGGGCTAG
3601 ACGAATCTAC AATACGTAAT ATAAATTATA TAATTTCACA AAGAACAAAA AAAAATCAGT
3661 TTCTAATACC TTATAGATAA ACTATATTTT TTACCACTGA CAACAC
```

Figure 34B

1 GAGCTCGCGG CCGCCTATCA AAAGTCTTAA TGAGTTAGGT GTAGATAGTA TAGATATTAC
61 TACAAAGGTA TTCATATTTC CTATCAATTC TAAAGTAGAT GATATTAATA ACTCAAAGAT
121 GATGATAGTA GATAATAGAT ACGCTCATAT AATGACTGCA AATTTGGACG GTTCACATTT
181 TAATCATCAC GCGTTCATAA GTTTCAACTG CATAGATCAA AATCTCACTA AAAAGATAGC
241 CGATGTATTT GAGAGAGATT GGACATCTAA CTACGCTAAA GAAATTACAG TTATAAATAA
301 TACATAATGG ATTTTGTTAT CATCAGTTAT ATTTAACATA AGTACAATAA AAAGTATTAA
361 ATAAAAATAC TTACTTACGA AAAAATGACT AATTAGCTAT AAAAACCCAA CAAAAACTAA
421 TCAGCTATCG GGGTTAATTA ATTAGTTATT AGACAAGGTG AAAACGAAAC TATTTGTAGC
481 TTAATTAATT AGAGCTTCTT TATTCTATAC TTAAAAAGTG AAAATAAATA CAAAGGTTCT
541 TGAGGGTTGT GTTAAATTGA AAGCGAGAAA TAATCATAAA TTATTTCATT ATCGCGATAT
601 CCGTTAAGTT TGTATCGTAA TGGAGTCGCG CGGTCGCCGT TGTCCCGAAA TGATATCCGT
661 ACTGGGTCCC ATTTCGGGGC ACGTGCTGAA AGCCGTGTTT AGTCGCGGCG ACACGCCGGT
721 GCTGCCGCAC GAGACGCGAC TCCTGCAGAC GGGTATCCAC GTGCGCGTGA GCCAGCCCTC
781 GCTGATCCTG GTGTCGCAGT ACACGCCCGA CTCGACGCCA TGCCACCGCG GCGACAATCA
841 GCTGCAGGTG CAGCACACGT ACTTTACGGG CAGCGAGGTG GAGAACGTGT CGGTCAACGT
901 GCACAACCCC ACGGGCCGGA GCATCTGCCC CAGCCAAGAG CCCATGTCGA TCTATGTGTA
961 CGCGCTGCCG CTCAAGATGC TGAACATCCC CAGCATCAAC GTGCACCACT ACCCGTCGGC
1021 GGCCGAGCGC AAACACCGAC ACCTGCCCGT AGCTGACGCT GTGATTCACG CGTCGGGCAA
1081 GCAGATGTGG CAGGCGCGTC TCACGGTCTC GGGACTGGCC TGGACGCGTC AGCAGAACCA
1141 GTGGAAAGAG CCCGACGTCT ACTACACGTC AGCGTTCGTG TTTCCCACCA AGGACGTGGC
1201 ACTGCGGCAC GTGGTGTGCG CGCACGAGCT GGTTTGCTCC ATGGAGAACA CGCGCGCAAC
1261 CAAGATGCAG GTGATAGGTG ACCAGTACGT CAAGGTGTAC CTGGAGTCCT TCTGCGAGGA
1321 CGTGCCCTCC GGCAAGCTCT TTATGCACGT CACGCTGGGC TCTGACGTGG AAGAGGACCT
1381 GACGATGACC CGCAACCCGC AACCCTTCAT GCGCCCCCAC GAGCGCAACG GCTTTACGGT
1441 GTTGTGTCCC AAAAATATGA TAATCAAACC GGGCAAGATC TCGCACATCA TGCTGGATGT
1501 GGCTTTTACC TCACACGAGC ATTTTGGGCT GCTGTGTCCC AAGAGCATCC CGGGCCTGAG
1561 CATCTCAGGT AACCTATTGA TGAACGGGCA GCAGATCTTC CTGGAGGTGC AAGCGATACG
1621 CGAGACCGTG GAACTGCGTC AGTACGATCC CGTGGCTGCG CTCTTCTTTT TCGATATCGA
1681 CTTGCTGCTG CAGCGCGGGC CTCAGTACAG CGAACACCCC ACCTTCACCA GCCAGTATCG
1741 CATCCAGGGC AAGCTTGAGT ACCGACACAC CTGGGACCGG CACGACGAGG GTGCCGCCCA
1801 GGGCGACGAC GACGTCTGGA CCAGCGGATC GGACTCCGAC GAGGAACTCG TAACCACCGA
1861 GCGCAAGACG CCCCGCGTTA CCGGCGGCGG CGCCATGGCG GGCGCCTCCA CTTCCGCGGG
1921 CCGCAAACGC AAATCAGCAT CCTCGGCGAC GGCGTGCACG GCGGGCGTTA TGACACGCGG
1981 CCGCCTTAAG GCCGAGTCCA CCGTCGCGCC CGAAGAGGAC ACCGACGAGG ATTCCGACAA
2041 CGAAATCCAC AATCCGGCCG TGTTCACCTG GCCGCCCTGG CAGGCCGGCA TCCTGGCCCG
2101 CAACCTGGTG CCCATGGTGG CTACGGTTCA GGGTCAGAAT CTGAAGTACC AGGAGTTCTT
2161 CTGGGACGCC AACGACATCT ACCGCATCTT CGCCGAATTG GAAGGCGTAT GGCAGCCCGC
2221 TGCGCAACCC AAACGTCGCC GCCACCGGCA AGACGCCTTG CCCGGGCCAT GCATCGCCTC
2281 GACGCCCAAA AAGCACCGAG GTTGATTTTT ATGGATCCGG TACCCTCGAG GAATTCTTTT
2341 TATTGATTAA CTAGTCAAAT GAGTATATAT AATTGAAAAA GTAAAATATA AATCATATAA
2401 TAATGAAACG AAATATCAGT AATAGACAGG AACTGGCAGA TTCTTCTTCT AATGAAGTAA
2461 GTACTGCTAA ATCTCCAAAA TTAGATAAAA ATGATACAGC AAATACAGCT TCATTCAACG
2521 AATTACCTTT TAATTTTTTC AGACACACCT TATTACAAAC TAACTAAGTC AGATGATGAG
2581 AAAGTAAATA TAAATTTAAC TTATGGGTAT AATATAATAA AGATTCATGA TATTAATAAT
2641 TTACTTAACG ATGTTAATAG ACTTATTCCA TCAACCCCTT CAAACCTTTC TGGATATTAT
2701 AAAATACCAG TTAATGATAT TAAAATAGAT TGTTTAAGAG ATGTAAATAA TTATTTGGAG
2761 GTAAAGGATA TAAAATTAGT CTATCTTTCA CATGGAAATG AATTACCTAA TATTAATAAT
2821 TATGATAGGA ATTTTTTAGG ATTTACAGCT GTTATATGTA TCAACAATAC AGGCAGATCT
2881 ATGGTTATGG TAAAACACTG TAACGGGAAG CAGCATTCTA TGGTAACTGG CCTATGTTTA
2941 ATAGCCAGAT CATTTTACTC TATAAACATT TTACCACAAA TAATAGGATC CTCTAGATAT
3001 TTAATATTAT ATCTAACAAC AACAAAAAAA TTTAACGATG TATGGCCAGA AGTATTTTCT
3061 ACTAATAAAG ATAAAGATAG TCTATCTTAT CTACAAGATA TGAAAGAAGA TAATCATTTA

Figure 35A

```
3121 GTAGTAGCTA CTAATATGGA AAGAAATGTA TACAAAAACG TGGAAGCTTT TATATTAAAT
3181 AGCATATTAC TAGAAGATTT AAAATCTAGA CTTAGTATAA CAAAACAGTT AAATGCCAAT
3241 ATCGATTCTA TATTTCATCA TAACAGTAGT ACATTAATCA GTGATATACT GAAACGATCT
3301 ACAGACTCAA CTATGCAAGG AATAAGCAAT ATGCCAATTA TGTCTAATAT TTTAACTTTA
3361 GAACTAAAAC GTTCTACCAA TACTAAAAAT AGGATACGTG ATAGGCTGTT AAAAGCTGCA
3421 ATAAATAGTA AGGATGTAGA AGAAATACTT TGTTCTATAC CTTCGGAGGA AAGAACTTTA
3481 GAACAACTTA AGTTTAATCA AACTTGTATT TATGAAGGTA C
```

Figure 35B

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGCCCCC TCGAAGCTTC TTTATTCTAT
 181 ACTTAAAAAG TGAAAATAAA TACAAAGGTT CTTGAGGGTT GTGTTAAATT GAAAGCGAGA
 241 AATAATCATA AATTATTTCA TTATCGCGAT ATCCGTTAAG TTTGTATCGT AATGGAGTCG
 301 CGCGGTCGCC GTTGTCCCGA AATGATATCC GTACTGGGTC CCATTTCGGG GCACGTGCTG
 361 AAAGCCGTGT TTAGTCGCGG CGACACGCCG GTGCTGCCGC ACGAGACGCG ACTCCTGCAG
 421 ACGGGTATCC ACGTGCGCGT GAGCCAGCCC TCGCTGATCC TGGTGTCGCA GTACACGCCC
 481 GACTCGACGC CATGCCACCG CGGCGACAAT CAGCTGCAGG TGCAGCACAC GTACTTTACG
 541 GGCAGCGAGG TGGAGAACGT GTCGGTCAAC GTGCACAACC CCACGGGCCG GAGCATCTGC
 601 CCCAGCCAAG AGCCCATGTC GATCTATGTG TACGCGCTGC CGCTCAAGAT GCTGAACATC
 661 CCCAGCATCA ACGTGCACCA CTACCCGTCG GCGGCCGAGC GCAAACACCG ACACCTGCCC
 721 GTAGCTGACG CTGTGATTCA CGCGTCGGGC AAGCAGATGT GGCAGGCGCG TCTCACGGTC
 781 TCGGGACTGG CCTGGACGCG TCAGCAGAAC CAGTGGAAAG AGCCCGACGT CTACTACACG
 841 TCAGCGTTCG TGTTTCCCAC CAAGGACGTG GCACTGCGGC ACGTGGTGTG CGCGCACGAG
 901 CTGGTTTGCT CCATGGAGAA CACGCGCGCA ACCAAGATGC AGGTGATAGG TGACCAGTAC
 961 GTCAAGGTGT ACCTGGAGTC CTTCTGCGAG GACGTGCCCT CCGGCAAGCT CTTTATGCAC
1021 GTCACGCTGG GCTCTGACGT GGAAGAGGAC CTGACGATGA CCCGCAACCC GCAACCCTTC
1081 ATGCGCCCCC ACGAGCGCAA CGGCTTTACG GTGTTGTGTC CCAAAAATAT GATAATCAAA
1141 CCGGGCAAGA TCTCGCACAT CATGCTGGAT GTGGCTTTTA CCTCACACGA GCATTTTGGG
1201 CTGCTGTGTC CCAAGAGCAT CCCGGGCCTG AGCATCTCAG GTAACCTATT GATGAACGGG
1261 CAGCAGATCT TCCTGGAGGT GCAAGCGATA CGCGAGACCG TGGAACTGCG TCAGTACGAT
1321 CCCGTGGCTG CGCTCTTCTT TTTCGATATC GACTTGCTGC TGCAGCGCGG GCCTCAGTAC
1381 AGCGAACACC CCACCTTCAC CAGCCAGTAT CGCATCCAGG GCAAGCTTGA GTACCGACAC
1441 ACCTGGGACC GGCACGACGA GGGTGCCGCC CAGGGCGACG ACGACGTCTG GACCAGCGGA
1501 TCGGACTCCG ACGAGGAACT CGTAACCACC GAGCGCAAGA CGCCCCGCGT TACCGGCGGC
1561 GGCGCCATGG CGGGCGCCTC CACTTCCGCG GGCCGCAAAC GCAAATCAGC ATCCTCGGCG
1621 ACGGCGTGCA CGGCGGGCGT TATGACACGC GGCCGCCTTA AGGCCGAGTC CACCGTCGCG
1681 CCCGAAGAGG ACACCGACGA GGATTCCGAC AACGAAATCC ACAATCCGGC CGTGTTCACC
1741 TGGCCGCCCT GGCAGGCCGG CATCCTGGCC CGCAACCTGG TGCCCATGGT GGCTACGGTT
1801 CAGGGTCAGA ATCTGAAGTA CCAGGAGTTC TTCTGGGACG CCAACGACAT CTACCGCATC
1861 TTCGCCGAAT TGGAAGGCGT ATGGCAGCCC GCTGCGCAAC CCAAACGTCG CCGCCACCGG
1921 CAAGACGCCT TGCCCGGGCC ATGCATCGCC TCGACGCCCA AAAAGCACCG AGGTTGATTT
1981 TTATGGATCC TCGCGACTGC AGGGTACCTG AGTAGCTAAT TTTTAAACAA AAATGTGGGA
2041 GAATCTAATT AGTTTTTCTT TACACAATTG ACGTACATGA GTCTGAGTTC CTTGTTTTTG
2101 CTAATTATTT CATCCAATTT ATTATTCTTG ACGATATCGA GATCTTTTGT ATAGGAGTCA
```

Figure 36

| | | | | | | |
|---|---|---|---|---|---|---|
| 1 | ATGAGTTTGC | AGTTTATCGG | TCTACAGCGG | CGCGATGTGG | TGGCCCTGGT | CAACTTTCTG |
| 61 | CGCCATCTCA | CGCAAAAGCC | CGACGTGGAT | CTCGAGGCAC | ACCCCAAGAT | CCTGAAAAAA |
| 121 | TGTGGCGAAA | AACGCCTGCA | CCGGCGTACG | GTGCTGTTCA | ACGAGCTCAT | GCTTTGGTTG |
| 181 | GGATACTACC | GCGAGCTGCG | TTTCCACAAC | CCCGACCTCT | CCTCGGTTCT | CGAGGAGTTC |
| 241 | GAGGTGCGTT | GCGCGGCCGT | GGCGCGTCGC | GGCTACACTT | ACCCGTTCGG | TGATCGTGGT |
| 301 | AAGGCGCGTG | ACCACCTGGC | TGTGCTAGAC | CGTACCGAAT | TCGATACGGA | CGTACGCCAC |
| 361 | GATGCTGAGA | TTGTGGAGCG | CGCGCTCGTA | AGCGCGGTCA | TTCTGGCCAA | GATGTCGGTG |
| 421 | CGCGAGACGC | TGGTCACAGC | CATCGGCCAG | ACGGAACCCA | TCGCTTTTGT | GCACCTCAAG |
| 481 | GATACGGAGG | TGCAGCGCAT | TGAAGAAAAC | CTGGAGGGTG | TGCGCCGTAA | CATGTTCTGC |
| 541 | GTGAAACCGC | TCGACCTTAA | CCTGGACCGG | CACGCCAACA | CGGCGCTGGT | CAACGCCGTC |
| 601 | AACAAGCTCG | TGTACACGGG | CCGTCTCATC | ATGAACGTGC | GCAGGTCTTG | GGAGGAGCTG |
| 661 | GAGCGCAAAT | GTCTGGCGCG | CATTCAGGAG | CGCTGCAAGC | TGCTGGTCAA | GGAGCTGCGC |
| 721 | ATGTGCCTTT | CCTTTGATTC | CAACTACTGT | CGCAATATCC | TCAAACACGC | CGTGGAAAAC |
| 781 | GGTGACTCGG | CCGACACGCT | GCTGGAGCTG | CTCATCGAGG | ACTTTGACAT | CTACGTGGAC |
| 841 | AGCTTCCCGC | AGTCGGCGCA | CACCTTTTTG | GGCGCGCGCC | CGCCGTCGTT | GGAGTTTGAC |
| 901 | GATGACGCCA | ATCTCCTCTC | GCTCGGCGGC | GGTTCAGCCT | TCTCGTCGGT | ACCCAAGAAA |
| 961 | CATGTCCCCA | CGCAGCCGCT | GGACGGCTGG | AGCTGGATCG | CCAGTCCCTG | GAAGGGACAC |
| 1021 | AAACCGTTCC | GCTTCGAGGC | CCATGGTTCT | CTGGCACCGG | CCGCCGACGC | CCACGCCGCC |
| 1081 | CGTTCGGCGC | GCGTCGGCTA | TTACGACGAA | GAGGAAAAGC | GTCGCGAGCG | GCAGAAACGG |
| 1141 | GTGGACGACG | AGGTGGTGCA | GCGTGAGAAA | CAGCAGCTGA | AGGCTTGGGA | GGAGAGGCAG |
| 1201 | CAGAACCTGC | AGCAACGTCA | GCAGCAACCG | CCGCCCCCGA | CACGTAAACC | GGGCGCCTCC |
| 1261 | CGGAGGCTCT | TTGGCTCCAG | TGCCGATGAG | GACGACGACG | ATGATGATGA | CGAGAAAAAC |
| 1321 | ATCTTTACGC | CCATCAAGAA | ACCGGGAACT | AGCGGCAAGG | GCGCCGCTAG | TGGCAACGGT |
| 1381 | GTTTCCAGCA | TTTTCAGCGG | CATGTTATCC | TCGGGCAGTC | AGAAACCGAC | CAGCGGTCCC |
| 1441 | TTGAACATCC | CGCAGCAACA | ACAGCGTCAC | GCGGCTTTCA | GTCTCGTCTC | CCCGCAGGTA |
| 1501 | ACCAAGGCCA | GCCCGGGAAG | GGTCCGTCGG | GACAGCGCGT | GGGACGTGAG | GCCGCTCACG |
| 1561 | GAGACAAGAG | GGGATCTTTT | CTCGGGCGAC | GAGGATTCCG | ACAGCTCGGA | TGGCTATCCC |
| 1621 | CCCAACCGTC | AAGATCCGCG | TTTCACCGAC | ACGCTGGTGG | ACATCACGGA | TACCGAGACG |
| 1681 | AGCGCCAAAC | CGCCCGTCAC | CACCGCGTAC | AAGTTCGAGC | AACCGACGTT | GACGTTCGGC |
| 1741 | GCCGGAGTTA | ACGTCCCTGC | TGGCGCCGGC | GCTGCCATCC | TCACGCCGAC | GCCTGTCAAT |
| 1801 | CCTTCCACGG | CCCCCGCTCC | GGCCCCGACA | CCTACCTTCG | CGGGTACCCA | AACCCCGGTC |
| 1861 | AACGGTAACT | CGCCCTGGGC | TCCGACGGCG | CCGTTGCCCG | GGGATATGAA | CCCCGCCAAC |
| 1921 | TGGCCGCGCG | AACGCGCGTG | GGCCCTCAAG | AATCCTCACC | TGGCTTACAA | TCCCTTCAGG |
| 1981 | ATGCCTACGA | CTTCCACGAC | TTCTCAAAAC | AACGTGTCCA | CCACCCCTCG | GAGGCCGTCG |
| 2041 | ACTCCACGCG | CCGCGGTGAC | ACAAACAGCG | TCTCAGAACG | CCGCTGATGA | GGTTTGGGCT |
| 2101 | TTAAGGGACC | AAACTGCAGA | GTCACCGGTC | GAAGACAGCG | AGGAGGAAGA | CGACGACTCC |
| 2161 | TCGGACACCG | GCTCCGTCGT | CAGCCTGGGA | CACACAACAC | CGTCGTCCGA | TTACAACGAC |
| 2221 | GTCATTTCGC | CTCCCAGTCA | GACGCCCGAG | CAGTCGACGC | CGTCCAGAAT | ACGTAAAGCT |
| 2281 | AAGTTATCGT | CTCCAATGAC | GACGACATCC | ACGAGCCAGA | AACCGGTGCT | GGGCAAGCGA |
| 2341 | GTCGCGACGC | CGCACGCGTC | CGCCCGAGCG | CAGACGGTGA | CGTCGACACC | GGTTCAGGGA |
| 2401 | AGGGTAGAGA | AACAGGTATC | GGGCACGCCG | TCGACGGTAC | CCGCCACGCT | GTTGCAACCT |
| 2461 | CAACCGGCTT | CGTCTAAAAC | AACGTCATCA | AGGAACGTGA | CTTCTGGCGC | GAGAACCTCT |
| 2521 | TCCGCTTCGG | CTCGACAGCC | GTCAGCCTCG | GCGTCCGTTT | TGTCGCCCAC | GGAGGATGAT |
| 2581 | GTCGTGTCCC | CCGTCACGTC | GCCGCTGTCC | ATGCTTTCGT | CAGCCTCTCC | GTCCCCGGCC |
| 2641 | AAGAGTGCCC | CTCCGTCTCC | GGTGAAAGGT | CGGGGCAGCC | GCGTCGGTGT | TCCTTCTTTG |
| 2701 | AAACCTACTT | TGGGCGGCAA | GGCGGTGGTA | GGTCGACCGC | CCTCGGTCCC | CGTGAGCGGT |
| 2761 | AGCGCGCCGG | GTCGCCTGTC | CGGCACCAGC | CGGGCCGCCT | CGACCACGCC | GACGTATCCC |
| 2821 | GCGGTAACCA | CCGTTTACCC | ACCGTCGTCT | ACGGCCAAAA | GCAGCGTATC | GAATGCGCCG |
| 2881 | CCTGTGGCCT | CCCCCTCCAT | CCTGAAACCG | GGGGCGAGCG | CGGCTTTGCA | ATCACGCCGC |
| 2941 | TCGACGGGGA | CCGCCGCCGT | AGGTTCCCCC | GTCAAGAGCA | CGACGGGCAT | GAAAACGGTG |
| 3001 | GCTTTCGACC | TATCGTCGCC | CCAGAAGAGC | GGTACGGGGC | CGCAACCGGG | TTCTGCCGGC |
| 3061 | ATGGGGGGCG | CCAAAACGCC | GTCGGACGCC | GTGCAGAACA | TCCTCCAAAA | GATCGAGAAG |
| 3121 | ATTAAGAACA | CGGAGGAATA | G | | | |

Figure 37

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGCCCCTAG CAATAAAAAC TATTCCTCCG TGTTCTTAAT CTTCTCGATC TTTTGGAGGA
 481 TGTTCTGCAC GGCGTCCGAC GGCGTTTTGG CGCCCCCCAT GCCGGCAGAA CCCGGTTGCG
 541 GCCCCGTACC GCTCTTCTGG GGCGACGATA GGTCGAAAGC CACCGTTTTC ATGCCCGTCG
 601 TGCTCTTGAC GGGGGAACCT ACGGCGGCGG TCCCCGTCGA GCGGCGTGAT TGCAAAGCCG
 661 CGCTCGCCCC CGGTTTCAGG ATGGAGGGGG AGGCCACAGG CGGCGCATTC GATACGCTGC
 721 TTTTGGCCGT AGACGACGGT GGGTAAACGG TGGTTACCGC GGGATACGTC GGCGTGGTCG
 781 AGGCGGCCCG GCTGGTGCCG GACAGGCGAC CCGGCGCGCT ACCGCTCACG GGTACCGAGG
 841 GCGGTCGACC TACCACCGCC TTGCCGCCCA AAGTAGGTTT CAAAGAAGGA ACACCGACGC
 901 GGCTGCCCCG ACCTTTCACC GGAGACGGAG GGGCACTCTT GGCCGGGGAC GGAGAGGCTG
 961 ACGAAAGCAT GGACAGCGGC GACGTGACGG GGGACACGAC ATCATCCTCC GTGGGCGACA
1021 AAACGGACGC CGAGGCTGAC GGCTGTCGAG CCGAAGCGGA AGAGGTTCTC GCGCCAGAAG
1081 TCACGTTCCT TGATGACGTT GTTTTAGACG AAGCCGGTTG AGGTTGCAAC AGCGTGGCGG
1141 GTACCGTCGA CGGCGTGCCC GATACCTGTT TCTCTACCCT TCCCTGAACC GGTGTCGACG
1201 TCACCGTCTG CGCTCGGGCG GACGCGTGCG GCGTCGCGAC TCGCTTGCCC AGCACCGGTT
1261 TCTGGCTCGT GGATGTCGTC GTCATTGGAG ACGATAACTT AGCTTTACGT ATTCTGGACG
1321 GCGTCGACTG CTCGGGCGTC TGACTGGGAG GCGAAATGAC GTCGTTGTAA TCGGACGACG
1381 GTGTTGTGTG TCCCAGGCTG ACGACGGAGC CGGTGTCCGA GGAGTCGTCG TCTTCCTCCT
1441 CGCTGTCTTC GACCGGTGAC TCTGCAGTTT GGTCCCTTAA AGCCCAAACC TCATCAGCGG
1501 CGTTCTGAGA CGCTGTTTGT GTCACCGCGG CGCGTGGAGT CGACGGCCTC CGAGGGGTGG
1561 TGGACACGTT GTTTTGAGAA GTCGTGGAAG TCGTAGGCAT CCTGAAGGGA TTGTAAGCCA
1621 GGTGAGGATT CTTGAGGGCC CACGCGCGTT CGCGCGGCCA GTTGGCGGGG TTCATATCCC
1681 CGGGCAACGG CGCCGTCGGA GCCCAGGGCG AGTTACCGTT GACCGGGGTT TGGGTACCCG
1741 CGAAGGTAGG TGTCGGGGCC GGAGCGGGGG CCGTGGAAGG ATTGACAGGC GTCGGCGTGA
1801 GGATGGCAGC GCCGGCGCCA GCAGGGACGT TAACTCCGGC GCCGAACGTC AACGTCGGTT
1861 GCTCGAACTT GTACGCGGTG GTGACGGGCG GTTTGGCGCT CGTCTCGGTA TCCGTGATGT
1921 CCACCAGCGT GTCGGTGAAA CGCGGATCTT GACGGTTGGG GGGATAGCCA TCCGAGCTGT
1981 CGGAATCCTC GTCGCCCGAG AAAAGATCCC CTCTTGTCTC CGTGAGCGGC CTCACGTCCC
2041 ACGCGCTGTC CCGACGGACC CTTCCCGGGC TGGCCTTGGT TACCTGCGGG GAGACGAGAC
2101 TGAAAGCCGC GTGACGCTGT TGTTGCTGCG GGATGTTCAA GGGACCGCTG GTCGGTTTCT
2161 GACTGCCCGA GGATAACATG CCGCTGAAAA TGCTGGAAAC ACCGTTGCCA CTAGCGGCGC
2221 CCTTGCCGCT AGTTCCCGGT TTCTTGATGG GCGTAAAGAT GTTTTTCTCG TCATCATCAT
2281 CGTCGTCGTC CTCATCGGCA CTGGAGCCAA AGAGCCTCCG GGAGGCGCCC GGTTTACGTG
2341 TCGGGGGCGG CGGTTGCTGC TGACGTTGCT GCAGGTTCTG CTGCCTCTCC TCCCAAGCCT
2401 TCAGCTGCTG TTTCTCACGC TGCACCACCT CGTCGTCCAC CCGTTTCTGC CGCTCGCGAC
2461 GCTTTTCCTC TTCGTCGTAA TAGCCGACGC GCGCCGAACG GGCGGCGTGG GCGTCGGCGG
2521 CCGGTGCCAG AGAACCATGG GCCTCGAAGC GGAACGGTTT GTGTCCCTTC CAGGGACTGG
2581 CGATCCAGCT CCAGCCGTCC AGCGGCTGCG TGGGGACATG TTTCTTGGGT ACCGACGAGA
2641 AGGCTGAACC GCCGCCGAGC GAGAGGAGAT TGGCGTCATC GTCAAACTCC AACGACGGCG
2701 GGCGCGCGCC CAAAAAGGTG TGCGCCGACT GCGGGAAGCT GTCCACGTAG ATGTCAAAGT
2761 CCTCGATGAG CAGCTCCAGC AGCGTGTCGG CCGAGTCACC GTTTTCCACG GCGTGTTTGA
2821 GGATATTGCG ACAGTAGTTG GAATCAAAGG AAAGGCACAT GCGCAGCTCC TTGACCAGCA
2881 GCTTGCAGCG CTCCTGAATG CGCGCCAGAC ATTTGCGCTC CAGCTCCTCC CAAGACCTGC
2941 GCACGTTCAT GATGAGACGG CCCGTGTACA CGAGCTTGTT GACGGCGTTG ACCAGCGCCG
3001 TGTTGGCGTG CCGGTCCAGG TTAAGGTCGA GCGGTTTCAC GCAGAACATG TTACGGCGCA
3061 CACCCTCCAG GTTTTCTTCA ATGCGCTGCA CCTCCGTATC CTTGAGGTGC ACAAAAGCGA
```

Figure 38A

```
3121 TGGGTTCCGT CTGGCCGATG GCTGTGACCA GCGTCTCGCG CACCGACATC TTGGCCAGAA
3181 TGACCGCGCT TACGAGCGCG CGCTCCACAA TCTCAGCATC GTGGCGTACG TCCGTATCGA
3241 ATTCGGTACG GTCTAGCACA GCCAGGTGGT CACGCGCCTT ACCACGATCA CCGAACGGGT
3301 AAGTGTAGCC GCGACGCGCC ACGGCCGCGC AACGCACCTC GAACTCCTCG AGAACCGAGG
3361 AGAGGTCGGG GTTGTGGAAA CGCAGCTCGC GGTAGTATCC CAACCAAAGC ATGAGCTCGT
3421 TGAACAGCAC CGTACGCCGG TGCAGGCGTT TTTCGCCACA TTTTTTCAGG ATCTTGGGGT
3481 GTGCCTCGAG ATCCACGTCG GGCTTTTGCG TGAGATGGCG CAGAAAGTTG ACCAGGGCCA
3541 CCACATCGCG CCGCTGTAGA CCGATAAACT GCAAACTCAT TTTATATTGT AATTATATAT
3601 TTTCAATTTT GAAATCCCAA AATATTATCA TATCTTCCCA ATAAAGCTAG GGGAGATCTA
3661 ATTTAATTTA ATTTATATAA CTTATTTTTT GAATATACTT TTAATTAACA AAAGAGTTAA
3721 GTTACTCATA TGGACGCCGT CCAGTCTGAA CATCAATCTT TTTAGCCAGA GATATCATAG
3781 CCGCTCTTAG AGTTTCAGCG TGATTTTCCA ACCTAAATAG AACTTCATCG TTGCGTTTAC
3841 AACACTTTTC TATTTGTTCA AACTTTGTTG TTACATTAGT AATCTTTTTT TCCAAATTAG
3901 TTAGCCGTTG TTTGAGAGTT TCCTCATTGT CGTCTTCATC GGCTTTAACA ATTGCTTCGC
3961 GTTTAGCCTC CTGGCTGTTC TTATCAGCCT TTGTAGAAAA AAATTCAGTT GCTGGAATTG
4021 CAAGATCGTC ATCTCCGGGG AAAAGAGTTC CGTCCATTTA AAGCCGCGGG AATTC
```

Figure 38B

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCGG GGGATCCTTA
 421 ATTAATTAGT TATTAGACAA GGTGAAAACG AAACTATTTG TAGCTTAATT AATTAGCTGC
 481 AGGGCTGCAG GAATTCTAGC AATAAAAACT ATTCCTCCGT GTTCTTAATC TTCTCGATCT
 541 TTTGGAGGAT GTTCTGCACG GCGTCCGACG GCGTTTTGGC GCCCCCCATG CCGGCAGAAC
 601 CCGGTTGCGG CCCCGTACCG CTCTTCTGGG GCGACGATAG GTCGAAAGCC ACCGTTTTCA
 661 TGCCCGTCGT GCTCTTGACG GGGGAACCTA CGGCGGCGGT CCCCGTCGAG CGGCGTGATT
 721 GCAAAGCCGC GCTCGCCCCC GGTTTCAGGA TGGAGGGGGA GGCCACAGGC GGCGCATTCG
 781 ATACGCTGCT TTTGGCCGTA GACGACGGTG GGTAAACGGT GGTTACCGCG GGATACGTCG
 841 GCGTGGTCGA GGCGGCCCGG CTGGTGCCGG ACAGGCGACC CGGCGCGCTA CCGCTCACGG
 901 GTACCGAGGG CGGTCGACCT ACCACCGCCT TGCCGCCCAA AGTAGGTTTC AAAGAAGGAA
 961 CACCGACGCG GCTGCCCCGA CCTTTCACCG GAGACGGAGG GGCACTCTTG GCCGGGGACG
1021 GAGAGGCTGA CGAAAGCATG GACAGCGGCG ACGTGACGGG GGACACGACA TCATCCTCCG
1081 TGGGCGACAA AACGGACGCC GAGGCTGACG GCTGTCGAGC CGAAGCGGAA GAGGTTCTCG
1141 CGCCAGAAGT CACGTTCCTT GATGACGTTG TTTTAGACGA AGCCGGTTGA GGTTGCAACA
1201 GCGTGGCGGG TACCGTCGAC GGCGTGCCCG ATACCTGTTT CTCTACCCTT CCCTGAACCG
1261 GTGTCGACGT CACCGTCTGC GCTCGGGCGG ACGCGTGCGG CGTCGCGACT CGCTTGCCCA
1321 GCACCGGTTT CTGGCTCGTG GATGTCGTCG TCATTGGAGA CGATAACTTA GCTTTACGTA
1381 TTCTGGACGG CGTCGACTGC TCGGGCGTCT GACTGGGAGG CGAAATGACG TCGTTGTAAT
1441 CGGACGACGG TGTTGTGTGT CCCAGGCTGA CGACGGAGCC GGTGTCCGAG GAGTCGTCGT
1501 CTTCCTCCTC GCTGTCTTCG ACCGGTGACT CTGCAGTTTG GTCCCTTAAA GCCCAAACCT
1561 CATCAGCGGC GTTCTGAGAC GCTGTTTGTG TCACCGCGGC GCGTGGAGTC GACGGCCTCC
1621 GAGGGGTGGT GGACACGTTG TTTTGAGAAG TCGTGGAAGT CGTAGGCATC CTGAAGGGAT
1681 TGTAAGCCAG GTGAGGATTC TTGAGGGCCC ACGCGCGTTC GCGCGGCCAG TTGGCGGGGT
1741 TCATATCCCC GGGCAACGGC GCCGTCGGAG CCCAGGGCGA GTTACCGTTG ACCGGGGTTT
1801 GGGTACCCGC GAAGGTAGGT GTCGGGGCCG GAGCGGGGGC CGTGGAAGGA TTGACAGGCG
1861 TCGGCGTGAG GATGGCAGCG CCGGCGCCAG CAGGGACGTT AACTCCGGCG CCGAACGTCA
1921 ACGTCGGTTG CTCGAACTTG TACGCGGTGG TGACGGGCGG TTTGGCGCTC GTCTCGGTAT
1981 CCGTGATGTC CACCAGCGTG TCGGTGAAAC GCGGATCTTG ACGGTTGGGG GGATAGCCAT
2041 CCGAGCTGTC GGAATCCTCG TCGCCCGAGA AAAGATCCCC TCTTGTCTCC GTGAGCGGCC
2101 TCACGTCCCA CGCGCTGTCC CGACGGACCC TTCCCGGGCT GGCCTTGGTT ACCTGCGGGG
2161 AGACGAGACT GAAAGCCGCG TGACGCTGTT GTTGCTGCGG GATGTTCAAG GGACCGCTGG
2221 TCGGTTTCTG ACTGCCCGAG GATAACATGC CGCTGAAAAT GCTGGAAACA CCGTTGCCAC
2281 TAGCGGCGCC CTTGCCGCTA GTTCCCGGTT TCTTGATGGG CGTAAAGATG TTTTTCTCGT
2341 CATCATCATC GTCGTCGTCC TCATCGGCAC TGGAGCCAAA GAGCCTCCGG GAGGCGCCCG
2401 GTTTACGTGT CGGGGGCGGC GGTTGCTGCT GACGTTGCTG CAGGTTCTGC TGCCTCTCCT
2461 CCCAAGCCTT CAGCTGCTGT TTCTCACGCT GCACCACCTC GTCGTCCACC CGTTTCTGCC
2521 GCTCGCGACG CTTTTCCTCT TCGTCGTAAT AGCCGACGCG CGCCGAACGG GCGGCGTGGG
2581 CGTCGGCGGC CGGTGCCAGA GAACCATGGG CCTCGAAGCG GAACGGTTTG TGTCCCTTCC
2641 AGGGACTGGC GATCCAGCTC CAGCCGTCCA GCGGCTGCGT GGGGACATGT TTCTTGGGTA
2701 CCGACGAGAA GGCTGAACCG CCGCCGAGCG AGAGGAGATT GGCGTCATCG TCAAACTCCA
2761 ACGACGGCGG GCGCGCGCCC AAAAAGGTGT GCGCCGACTG CGGGAAGCTG TCCACGTAGA
2821 TGTCAAAGTC CTCGATGAGC AGCTCCAGCA GCGTGTCGGC CGAGTCACCG TTTTCCACGG
2881 CGTGTTTGAG GATATTGCGA CAGTAGTTGG AATCAAAGGA AAGGCACATG CGCAGCTCCT
2941 TGACCAGCAG CTTGCAGCGC TCCTGAATGC GCGCCAGACA TTTGCGCTCC AGCTCCTCCC
3001 AAGACCTGCG CACGTTCATG ATGAGACGGC CCGTGTACAC GAGCTTGTTG ACGGCGTTGA
3061 CCAGCGCCGT GTTGGCGTGC CGGTCCAGGT TAAGGTCGAG CGGTTTCACG CAGAACATGT
```

Figure 39A

```
3121 TACGGCGCAC ACCCTCCAGG TTTTCTTCAA TGCGCTGCAC CTCCGTATCC TTGAGGTGCA
3181 CAAAAGCGAT GGGTTCCGTC TGGCCGATGG CTGTGACCAG CGTCTCGCGC ACCGACATCT
3241 TGGCCAGAAT GACCGCGCTT ACGAGCGCGC GCTCCACAAT CTCAGCATCG TGGCGTACGT
3301 CCGTATCGAA TTCGGTACGG TCTAGCACAG CCAGGTGGTC ACGCGCCTTA CCACGATCAC
3361 CGAACGGGTA AGTGTAGCCG CGACGCGCCA CGGCCGCGCA ACGCACCTCG AACTCCTCGA
3421 GAACCGAGGA GAGGTCGGGG TTGTGGAAAC GCAGCTCGCG GTAGTATCCC AACCAAAGCA
3481 TGAGCTCGTT GAACAGCACC GTACGCCGGT GCAGGCGTTT TTCGCCACAT TTTTTCAGGA
3541 TCTTGGGGTG TGCCTCGAGA TCCACGTCGG GCTTTTGCGT GAGATGGCGC AGAAAGTTGA
3601 CCAGGGCCAC CACATCGCGC CGCTGTAGAC CGATAAACTG CAAACTCATT TTATATTGTA
3661 ATTATATATT TTCAATTTTG AAATCCCAAA ATATTATCAT ATCTTCCCAA TAAAGCTAGA
3721 TTCTTTTTAT TGATTAACTA GTCAAATGAG TATATATAAT TGAAAAAGTA AAATATAAAT
3781 CATATAATAA TGAAACGAAA TATCAGTAAT AGACAGGAAC TGGCAGATTC TTCTTCTAAT
3841 GAAGTAAGTA CTGCTAAATC TCCAAAATTA GATAAAAATG ATACAGCAAA TACAGCTTCA
3901 TTCAACGAAT TACCTTTTAA TTTTTTCAGA CACACCTTAT TACAAACTAA CTAAGTCAGA
3961 TGATGAGAAA GTAAATATAA ATTTAACTTA TGGGTATAAT ATAATAAAGA TTCATGATAT
4021 TAATAATTTA CTTAACGATG TTAATAGACT TATTCCATCA ACCCCTTCAA ACCTTTCTGG
4081 ATATTATAAA ATACCAGTTA ATGATATTAA AATAGATTGT TTAAGAGATG TAAATAATTA
4141 TTTGGAGGTA AAGGATATAA AATTAGTCTA TCTTTCACAT GGAAATGAAT TACCTAATAT
4201 TAATAATTAT GATAGGAATT TTTTAGGATT TACAGCTGTT ATATGTATCA ACAATACAGG
4261 CAGATCTATG GTTATGGTAA AACACTGTAA CGGGAAGCAG CATTCTATGG TAACTGGCCT
4321 ATGTTTAATA GCCAGATCAT TTTACTCTAT AAACATTTTA CCACAAATAA TAGGATCCTC
4381 TAGATATTTA ATATTATATC TAACAACAAC AAAAAAATTT AACGATGTAT GGCCAGAAGT
4441 ATTTTCTACT AATAAAGATA AAGATAGTCT ATCTTATCTA CAAGATATGA AAGAAGATAA
4501 TCATTTAGTA GTAGCTACTA ATATGGAAAG AAATGTATAC AAAAACGTGG AAGCTTTTAT
4561 ATTAAATAGC ATATTACTAG AAGATTTAAA ATCTAGACTT AGTATAACAA AACAGTTAAA
4621 TGCCAATATC GATTCTATAT TTCATCATAA CAGTAGTACA TTAATCAGTG ATATACTGAA
4681 ACGATCTACA GACTCAACTA TGCAAGGAAT AAGCAATATG CCAATTATGT CTAATATTTT
4741 AACTTTAGAA CTAAAACGTT CTACCAATAC TAAAAATAGG ATACGTGATA GGCTGTTAAA
4801 AGCTGCAATA AATAGTAAGG ATGTAGAAGA AATACTTTGT TCTATACCTT CGGAGGAAAG
4861 AACTTTAGAA CAACTTAAGT TTAATCAAAC TTGTATTTAT GAAGGTACC
```

Figure 39B

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGCCCCT AGCAATAAAA ACTATTCCTC
 181 CGTGTTCTTA ATCTTCTCGA TCTTTTGGAG GATGTTCTGC ACGGCGTCCG ACGGCGTTTT
 241 GGCGCCCCCC ATGCCGGCAG AACCCGGTTG CGGCCCCGTA CCGCTCTTCT GGGGCGACGA
 301 TAGGTCGAAA GCCACCGTTT TCATGCCCGT CGTGCTCTTG ACGGGGGAAC CTACGGCGGC
 361 GGTCCCCGTC GAGCGGCGTG ATTGCAAAGC CGCGCTCGCC CCCGGTTTCA GGATGGAGGG
 421 GGAGGCCACA GGCGGCGCAT TCGATACGCT GCTTTTGGCC GTAGACGACG GTGGGTAAAC
 481 GGTGGTTACC GCGGGATACG TCGGCGTGGT CGAGGCGGCC CGGCTGGTGC CGGACAGGCG
 541 ACCCGGCGCG CTACCGCTCA CGGGTACCGA GGGCGGTCGA CCTACCACCG CCTTGCCGCC
 601 CAAAGTAGGT TTCAAAGAAG GAACACCGAC GCGGCTGCCC CGACCTTTCA CCGGAGACGG
 661 AGGGGCACTC TTGGCCGGGG ACGGAGAGGC TGACGAAAGC ATGGACAGCG GCGACGTGAC
 721 GGGGGACACG ACATCATCCT CCGTGGGCGA CAAAACGGAC GCCGAGGCTG ACGGCTGTCG
 781 AGCCGAAGCG GAAGAGGTTC TCGCGCCAGA AGTCACGTTC CTTGATGACG TTGTTTTAGA
 841 CGAAGCCGGT TGAGGTTGCA ACAGCGTGGC GGGTACCGTC GACGGCGTGC CCGATACCTG
 901 TTTCTCTACC CTTCCCTGAA CCGGTGTCGA CGTCACCGTC TGCGCTCGGG CGGACGCGTG
 961 CGGCGTCGCG ACTCGCTTGC CCAGCACCGG TTTCTGGCTC GTGGATGTCG TCGTCATTGG
1021 AGACGATAAC TTAGCTTTAC GTATTCTGGA CGGCGTCGAC TGCTCGGGCG TCTGACTGGG
1081 AGGCGAAATG ACGTCGTTGT AATCGGACGA CGGTGTTGTG TGTCCCAGGC TGACGACGGA
1141 GCCGGTGTCC GAGGAGTCGT CGTCTTCCTC CTCGCTGTCT TCGACCGGTG ACTCTGCAGT
1201 TTGGTCCCTT AAAGCCCAAA CCTCATCAGC GGCGTTCTGA GACGCTGTTT GTGTCACCGC
1261 GGCGCGTGGA GTCGACGGCC TCCGAGGGGT GGTGGACACG TTGTTTTGAG AAGTCGTGGA
1321 AGTCGTAGGC ATCCTGAAGG GATTGTAAGC CAGGTGAGGA TTCTTGAGGG CCCACGCGCG
1381 TTCGCGCGGC CAGTTGGCGG GGTTCATATC CCCGGGCAAC GGCGCCGTCG GAGCCCAGGG
1441 CGAGTTACCG TTGACCGGGG TTTGGGTACC CGCGAAGGTA GGTGTCGGGG CCGGAGCGGG
1501 GGCCGTGGAA GGATTGACAG GCGTCGGCGT GAGGATGGCA GCGCCGGCGC CAGCAGGGAC
1561 GTTAACTCCG GCGCCGAACG TCAACGTCGG TTGCTCGAAC TTGTACGCGG TGGTGACGGG
1621 CGGTTTGGCG CTCGTCTCGG TATCCGTGAT GTCCACCAGC GTGTCGGTGA AACGCGGATC
1681 TTGACGGTTG GGGGGATAGC CATCCGAGCT GTCGGAATCC TCGTCGCCCG AGAAAAGATC
1741 CCCTCTTGTC TCCGTGAGCG GCCTCACGTC CCACGCGCTG TCCCGACGGA CCCTTCCCGG
1801 GCTGGCCTTG GTTACCTGCG GGGAGACGAG ACTGAAAGCC GCGTGACGCT GTTGTTGCTG
1861 CGGGATGTTC AAGGGACCGC TGGTCGGTTT CTGACTGCCC GAGGATAACA TGCCGCTGAA
1921 AATGCTGGAA ACACCGTTGC CACTAGCGGC GCCCTTGCCG CTAGTTCCCG GTTTCTTGAT
1981 GGGCGTAAAG ATGTTTTTCT CGTCATCATC ATCGTCGTCG TCCTCATCGG CACTGGAGCC
2041 AAAGAGCCTC CGGGAGGCGC CCGGTTTACG TGTCGGGGGC GGCGGTTGCT GCTGACGTTG
2101 CTGCAGGTTC TGCTGCCTCT CCTCCCAAGC CTTCAGCTGC TGTTTCTCAC GCTGCACCAC
2161 CTCGTCGTCC ACCCGTTTCT GCCGCTCGCG ACGCTTTTCC TCTTCGTCGT AATAGCCGAC
2221 GCGCGCCGAA CGGGCGGCGT GGGCGTCGGC GGCCGGTGCC AGAGAACCAT GGGCCTCGAA
2281 GCGGAACGGT TTGTGTCCCT TCCAGGGACT GGCGATCCAG CTCCAGCCGT CCAGCGGCTG
2341 CGTGGGGACA TGTTTCTTGG GTACCGACGA GAAGGCTGAA CCGCCGCCGA GCGAGAGGAG
2401 ATTGGCGTCA TCGTCAAACT CCAACGACGG CGGGCGCGCG CCCAAAAAGG TGTGCGCCGA
2461 CTGCGGGAAG CTGTCCACGT AGATGTCAAA GTCCTCGATG AGCAGCTCCA GCAGCGTGTC
2521 GGCCGAGTCA CCGTTTTCCA CGGCGTGTTT GAGGATATTG CGACAGTAGT TGGAATCAAA
2581 GGAAAGGCAC ATGCGCAGCT CCTTGACCAG CAGCTTGCAG CGCTCCTGAA TGCGCGCCAG
2641 ACATTTGCGC TCCAGCTCCT CCCAAGACCT GCGCACGTTC ATGATGAGAC GGCCCGTGTA
2701 CACGAGCTTG TTGACGGCGT TGACCAGCGC CGTGTTGGCG TGCCGGTCCA GGTTAAGGTC
2761 GAGCGGTTTC ACGCAGAACA TGTTACGGCG CACACCCTCC AGGTTTTCTT CAATGCGCTG
2821 CACCTCCGTA TCCTTGAGGT GCACAAAAGC GATGGGTTCC GTCTGGCCGA TGGCTGTGAC
2881 CAGCGTCTCG CGCACCGACA TCTTGGCCAG AATGACCGCG CTTACGAGCG CGCGCTCCAC
2941 AATCTCAGCA TCGTGGCGTA CGTCCGTATC GAATTCGGTA CGGTCTAGCA CAGCCAGGTG
3001 GTCACGCGCC TTACCACGAT CACCGAACGG GTAAGTGTAG CCGCGACGCG CCACGGCCGC
3061 GCAACGCACC TCGAACTCCT CGAGAACCGA GGAGAGGTCG GGGTTGTGGA AACGCAGCTC
```

Figure 40A

```
3121 GCGGTAGTAT CCCAACCAAA GCATGAGCTC GTTGAACAGC ACCGTACGCC GGTGCAGGCG
3181 TTTTTCGCCA CATTTTTTCA GGATCTTGGG GTGTGCCTCG AGATCCACGT CGGGCTTTTG
3241 CGTGAGATGG CGCAGAAAGT TGACCAGGGC CACCACATCG CGCCGCTGTA GACCGATAAA
3301 CTGCAAACTC ATTTTATATT GTAATTATAT ATTTTCAATT TTGAAATCCC AAAATATTAT
3361 CATATCTTCC CAATAAAGCT AGGGGGAATT CGGATCCTCG CGACTGCAGG GTACCTGAGT
3421 AGCTAATTTT TAAACAAAAA TGTGGGAGAA TCTAATTAGT TTTTCTTTAC ACAATTGACG
3481 TACATGAGTC TGAGTTCCTT GTTTTTGCTA ATTATTTCAT CCAATTTATT ATTCTTGACG
3541 ATATCGAGAT CTTTTGTATA GGAGTCA
```

Figure 40B

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCTC GAGATAAAAA TCAGCATGTC TTGAGCATGC
 661 GGTAGAGCAG ATAGATGCCG ATGATGGCCG ATAGCGCGTA GACGGACATC ATGAGGAGAC
 721 GACTGTCGGT AGCGTCCACG ACGACGTCAG TTACTTCTAG GACCGTACCG TTTTTCAAAA
 781 GCATGAGGTA GTGAGTTCGC GGAGATGAGA CCACCACTTC GTTGTAGGGA TCCAGGGCGA
 841 AAAGGACGTC GTCCGAGTCG TGCATGTACA TGATGTTGAT GACGCCTTGC GTGTCGTCGT
 901 ATTCTAGTAG GGCGCTTTGG CAAAAGGCGC AGTTTTCTAG GGAAATGTTG AGCGCCGCTG
 961 TGATGCTGTG TGTGGTATGC ATGTTGCGCG TCAGTTCGCA TTTAGTTTGA CTGTCCGTCT
1021 GGGTGATGAT GAGGCTCTGG CCTACGACGG TGGTGGAGAC AGGGTAGGAG ATACCTTTGA
1081 TCAGGTACTG GTTTGTTACG ACATAACTGA CGTGTTCGGA GACGGTCAGC GCGGAGAAGG
1141 ATTCGCCGAG CGGCAGACAA AACAGGTCGG GGAAGGTTTC TAGCGTGCTT GGTTGCATGG
1201 TAGATAGGAT GGAGAGGGCG GCGGGAACGG TAGTGGGGAC GGTGGCATCG GGGAAGAGAC
1261 GTGTGAGGCG TTCGAGCGAG TGATCGCGTC GCCCGCTACT GGAACAGGGT GTGTACAGGT
1321 CGCTGAGGTA TTCGTGGTGC GGATGAGCTA GCAACTGCGT AAAGTGTGAT AGCTCGGCTA
1381 ATGAACAGAG GCCCGTTTCT ACGATGAAGA TTTCGCGTCT CTCCGTCGTA TGTACTAGCA
1441 TGGAGTGGAC GAGGCTGCCC ATGAGGTAGA GTTCTTGACG CGCGAAGGCT GAAAGAAAAG
1501 AGGCCAGGTG CGTTTTGTGT AGTTTTAGGG CAAAGTCGGC GATCTGTCGT AGTGCCCACT
1561 GGGGGATGAG ATGTTGCTGA TTCTGTTTAG AGAGTATGTA GACCAGGCGT ACGAGGCTGG
1621 TGATGTCGGT GATCTGATTC GGTGTCCAAA GGGCTCGTTT GGCCAGGTCC ACGGCCGTGG
1681 GATACAGCAG CAACGTGGTG CGTGGTGGTG TTTGTGAGAG GCAGGTGATC ATAAATTCTT
1741 GTATTTGTAA GAGTGCGGCC TGGCGGTCTA GGGCCCGTGG GACGGAGACT TGGGCGCCGG
1801 CCTCTTCTTG TCGGGCTGCT GCGAACAGTG CTAATGCGTA GGCGAAGGCC ATTTCTACCG
1861 TGCGGCGGTC CAGCATCTGA CATCGACCGC TTTTGAGTAC ATCCACGGCG TAACGGTGAA
1921 AGCTGTTACG TAGTAGTGCG CTGAGGTCCA GGTAGTTGAA GTCAAGTGCG GCGTCAAGAA
1981 AGTCCGGGTC TTTGAGATAA GAGTGACGGT TCAGTTGATC TTTCTTAACT AGCACCAGGA
2041 GCTCGTGTTT TTCAGTTTGT CGTAGTATAA AGTTGTCGCG TTGATAGGGC GCTTTAAAGA
2101 GTACGCGTGG AAGATGGCCG AAGATAAGCA GCATGGGTGT GTCGTCGTCT ATGGACACCG
2161 TAACTACGAA GAAGTCCTCG GTCAGTGTTA TTTTAACGTA ACGTAGTTCG TCGATGAGGT
2221 AAAAGCCTTG GTGCAAACAA GGTGTGACGG TGCTGAATAG TAGATCGTGT CCATCAAAGA
2281 GGATACAGGT CTGGTTAAAG TGTGGTCGGT GTAGTCCTGA GGTGGTATGT GATTCTGTCC
2341 AGCCGTGTGG AGTGGTTTGC GGTGGCATCC AAACGTGAGG TATTGACAGG TCAATGGGTG
2401 GTGGCACAGT GGTGGGCTGT TCACCTAGGC TGTCCTGTGC CTTTAGCTGC TGCGAAAAAG
2461 ATCGGTAGCT GGCCAGGTCT TTGGATACCA GCGCGTAAGT GTTAAGTCTC TGTTGGTATC
2521 TTTCCAGGGT TTCGGTCAGA TCTACCTGGT TCAGAAACTG CTCCGCCAGA GGACCCGCAA
2581 AAAGACATCG AGGCATATGG AATACATAGT ATTGATTATA GCTTTGGAAA AAGTTGAAAC
2641 TGATGGCGTT TTCCCTGACG ACCGTGCTGT TACGGAGGCT GCTATTGTAG GTACACTGGG
2701 TGGTGTTTTC ACGCAGGAAG CGGATGGGTC TCCCGTAGGT GTTGAGCAGT AGGTGAAACG
2761 CTTTGTCCAG CGGTTCGGAT ATGGCTTCTG CGCCATATCG TGACGAAAGT AGGTGGCTGA
2821 GGAGACAGAC GGCGAGGACG ATGAGGTAGG AGGGGAGCCC GGGCCGCATT TTATATTGTA
2881 ATTATATATT TTCAATTTTG AAATCCCAAA ATATTATCAT ATTCTTCCCA ATAAACTCGA
2941 GATCCTTCTT TATTCTATAC TTAAAAAGTG AAAATAAATA CAAAGGTTCT TGAGGGTTGT
3001 GTTAAATTGA AAGCGAGAAA TAATCATAAA TTATTTCATT ATCGCGATAT CCGTTAAGTT
3061 TGTATCGTAA TGAAACAGAT TAAGGTTCGA GTGGACATGG TGCGGCATAG AATCAAGGAG
```

Figure 41A

```
3121 CACATGCTGA AAAAATATAC CCAGACGGAA GAGAAATTCA CTGGCGCCTT TAATATGATG
3181 GGAGGATGTT TGCAGAATGC CTTAGATATC TTAGATAAGG TTCATGAGCC TTTCGAGGAG
3241 ATGAAGTGTA TTGGGCTAAC TATGCAGAGC ATGTATGAGA ACTACATTGT ACCTGAGGAT
3301 AAGCGGGAGA TGTGGATGGC TTGTATTAAG GAGCTGCATG ATGTGAGCAA GGGCGCCGCT
3361 AACAAGTTGG GGGGTGCACT GCAGGCTAAG GCCCGTGCTA AAAAGGATGA ACTTAGGAGA
3421 AAGATGATGT ATATGTGCTA CAGGAATATA GAGTTCTTTA CCAAGAACTC AGCCTTCCCT
3481 AAGACCACCA ATGGCTGCAG TCAGGCCATG GCGGCACTGC AGAACTTGCC TCAGTGCTCC
3541 CCTGATGAGA TTATGGCTTA TGCCCAGAAA ATATTTAAGA TTTTGGATGA GGAGAGAGAC
3601 AAGGTGCTCA CGCACATTGA TCACATATTT ATGGATATCC TCACTACATG TGTGGAAACA
3661 ATGTGTAATG AGTACAAGGT CACTAGTGAC GCTTGTATGA TGACCATGTA CGGGGGCATC
3721 TCTCTCTTAA GTGAGTTCTG TCGGGTGCTG TGCTGCTATG TCTTAGAGGA GACTAGTGTG
3781 ATGCTGGCCA AGCGGCCTCT GATAACCAAG CCTGAGGTTA TCAGTGTAAT GAAGCGCCGC
3841 ATTGAGGAGA TCTGCATGAA GGTCTTTGCC CAGTACATTC TGGGGGCCGA TCCTCTGAGA
3901 GTCTGCTCTC CTAGTGTGGA TGACCTACGG GCCATCGCCG AGGAGTCAGA TGAGGAAGAG
3961 GCTATTGTAG CCTACACTTT GGCCACCGCT GGTGTCAGCT CCTCTGATTC TCTGGTGTCA
4021 CCCCCAGAGT CCCCTGTACC CGCGACTATC CCTCTGTCCT CAGTAATTGT GGCTGAGAAC
4081 AGTGATCAGG AAGAAAGTGA GCAGAGTGAT GAGGAAGAGG AGGAGGGTGC TCAGGAGGAG
4141 CGGGAGGACA CTGTGTCTGT CAAGTCTGAG CCAGTGTCTG AGATAGAGGA AGTTGCCCCA
4201 GAGGAAGAGG AGGATGGTGC TGAGGAACCC ACCGCCTCTG GAGGTAAGAG TACCCACCCT
4261 ATGGTGACTA GAAGCAAGGC TGACCAGTAA TTTTTATCTC GAGCCCGGGA GATCTTAGCT
4321 AACTGATTTT TCTGGGAAAA AAATTATTTA ACTTTTCATT AATAGGGATT TGACGTATGT
4381 AGCGTACAAA ATTATCGTTC CTGGTATATA GATAAAGAGT CCTATATATT TGAAAATCGT
4441 TACGGCTCGA TTAAACTTTA ATGATTGCAT AGTGAATATA TCATTAGGAT TTAACTCCTT
4501 GACTATCATG GCGGCGCCAG AAATTACCAT CAAAAGCATT AATACAGTTA TGCCGATCGC
4561 AGTTAGAACG GTTATAGCAT CCACCATTTA TATCTAAAAA TTAGATCAAA GAATATGTGA
4621 CAAAGTCCTA GTTGTATACT GAGAATTGAC GAAACAATGT TTCTTACATA TTTTTTTCTT
4681 ATTAGTAACT GACTTAATAG TAGGAACTGG AAAGCTAGAC TTGATTATTC TATAAGTATA
4741 GATACCCTTC CAGATAATGT TCTCTTTGAT AAAAGTTCCA GAAAATGTAG AATTTTTTAA
4801 AAAGTTATCT TTTGCTATTA CCAAGATTGT GTTTAGACGC TTATTATTAA TATGAGTAAT
4861 GAAATCCACA CCGCCTCTAG ATATGGGGAA TTC
```

Figure 41B

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAA CAAAAACTAA
 421 TCAGCTATCG GGGTTAATTA ATTAGTTATT AGACAAGGTG AAAACGAAAC TATTTGTAGC
 481 TTAATTAATT AGAGCTTCTT TATTCTATAC TTAAAAAGTG AAAATAAATA CAAAGGTTCT
 541 TGAGGGTTGT GTTAAATTGA AAGCGAGAAA TAATCATAAA TTATTTCATT ATGGCGATAT
 601 CCGTTAAGTT TGTATCGTAA TGGAGTCGCG CGGTCGCCGT TGTCCCGAAA TGATATCCGT
 661 ACTGGGTCCC ATTTCGGGGC ACGTGCTGAA AGCCGTGTTT AGTCGCGGCG ACACGCCGGT
 721 GCTGCCGCAC GAGACGCGAC TCCTGCAGAC GGGTATCCAC GTGCGCGTGA GCCAGCCCTC
 781 GCTGATCCTG GTGTCGCAGT ACACGCCCGA CTCGACGCCA TGCCACCGCG GCGACAATCA
 841 GCTGCAGGTG CAGCACACGT ACTTTACGGG CAGCGAGGTG GAGAACGTGT CGGTCAACGT
 901 GCACAACCCC ACGGGCCGGA GCATCTGCCC CAGCCAAGAG CCCATGTCGA TCTATGTGTA
 961 CGCGCTGCCG CTCAAGATGC TGAACATCCC CAGCATCAAC GTGCACCACT ACCCGTCGGC
1021 GGCCGAGCGC AAACACCGAC ACCTGCCCGT AGCTGACGCT GTGATTCACG CGTCGGGCAA
1081 GCAGATGTGG CAGGCGCGTC TCACGGTCTC GGGACTGGCC TGGACGCGTC AGCAGAACCA
1141 GTGGAAAGAG CCCGACGTCT ACTACACGTC AGCGTTCGTG TTTCCCACCA AGGACGTGGC
1201 ACTGCGGCAC GTGGTGTGCG CGCACGAGCT GGTTTGCTCC ATGGAGAACA CGCGCGCAAC
1261 CAAGATGCAG GTGATAGGTG ACCAGTACGT CAAGGTGTAC CTGGAGTCCT TCTGCGAGGA
1321 CGTGCCCTCC GGCAAGCTCT TTATGCACGT CACGCTGGGC TCTGACGTGG AAGAGGACCT
1381 GACGATGACC CGCAACCCGC AACCCTTCAT GCGCCCCCAC GAGCGCAACG GCTTTACGGT
1441 GTTGTGTCCC AAAAATATGA TAATCAAACC GGGCAAGATC TCGCACATCA TGCTGGATGT
1501 GGCTTTTACC TCACACGAGC ATTTTGGGCT GCTGTGTCCC AAGAGCATCC CGGGCCTGAG
1561 CATCTCAGGT AACCTATTGA TGAACGGGCA GCAGATCTTC CTGGAGGTGC AAGCGATACG
1621 CGAGACCGTG GAACTGCGTC AGTACGATCC CGTGGCTGCG CTCTTCTTTT TCGATATCGA
1681 CTTGCTGCTG CAGCGCGGGC CTCAGTACAG CGAACACCCC ACCTTCACCA GCCAGTATCG
1741 CATCCAGGGC AAGCTTGAGT ACCGACACAC CTGGGACCGG CACGACGAGG GTGCCGCCCA
1801 GGGCGACGAC GACGTCTGGA CCAGCGGATC GGACTCCGAC GAGGAACTCG TAACCACCGA
1861 GCGCAAGACG CCCCGCGTTA CCGGCGGCGG CGCCATGGCG GGCGCCTCCA CTTCCGCGGG
1921 CCGCAAACGC AAATCAGCAT CCTCGGCGAC GGCGTGCACG GCGGGCGTTA TGACACGCGG
1981 CCGCCTTAAG GCCGAGTCCA CCGTCGCGCC CGAAGAGGAC ACCGACGAGG ATTCCGACAA
2041 CGAAATCCAC AATCCGGCCG TGTTCACCTG GCCGCCCTGG CAGGCCGGCA TCCTGGCCCG
2101 CAACCTGGTG CCCATGGTGG CTACGGTTCA GGGTCAGAAT CTGAAGTACC AGGAGTTCTT
2161 CTGGGACGCC AACGACATCT ACCGCATCTT CGCCGAATTG GAAGGCGTAT GGCAGCCCGC
2221 TGCGCAACCC AAACGTCGCC GCCACCGGCA AGACGCCTTG CCCGGGCCAT GCATCGCCTC
2281 GACGCCCAAA AAGCACCGAG GTTGATTTTT ATGGATCCGG TACCCTCGAG GAATTCTAGC
2341 AATAAAAACT ATTCCTCCGT GTTCTTAATC TTCTCGATCT TTTGGAGGAT GTTCTGCACG
2401 GCGTCCGACG GCGTTTTGGC GCGCCCCATG CCGGCAGAAC CCGGTTGCGG CCCCGTACCG
2461 CTCTTCTGGG GCGACGATAG GTCGAAAGCC ACCGTTTTCA TGCCCGTCGT GCTCTTGACG
2521 GGGGAACCTA CGGCGGCGGT CCCCGTCGAG CGGCGTGATT GCAAAGCCGC GCTCGCCCCC
2581 GGTTTCAGGA TGGAGGGGGA GGCCACAGGC GGCGCATTCG ATACGCTGCT TTTGGCCGTA
2641 GACGACGGTG GGTAAACGGT GGTTACCGCG GGATACGTCG GCGTGGTCGA GGCGGCCCGG
2701 CTGGTGCCGG ACAGGCGACC CGGCGCGCTA CCGCTCACGG GTACCGAGGG CGGTCGACCT
2761 ACCACCGCCT TGCCGCCCAA AGTAGGTTTC AAAGAAGGAA CACCGACGCG GCTGCCCCGA
2821 CCTTTCACCG GAGACGGAGG GGCACTCTTG GCCGGGGACG GAGAGGCTGA CGAAAGCATG
2881 GACAGCGGCG ACGTGACGGG GGACACGACA TCATCCTCCG TGGGCGACAA AACGGACGCC
2941 GAGGCTGACG GCTGTCGAGC CGAAGCGGAA GAGGTTCTCG CGCCAGAAGT CACGTTCCTT
3001 GATGACGTTG TTTTAGACGA AGCCGGTTGA GGTTGCAACA GCGTGGCGGG TACCGTCGAC
3061 GGCGTGCCCG ATACCTGTTT CTCTACCCTT CCCTGAACCG GTGTCGACGT CACCGTCTGC
```

Figure 42A

3121 GCTCGGGCGG ACGCGTGCGG CGTCGCGACT CGCTTGCCCA GCACCGGTTT CTGGCTCGTG
3181 GATGTCGTCG TCATTGGAGA CGATAACTTA GCTTTACGTA TTCTGGACGG CGTCGACTGC
3241 TCGGGCGTCT GACTGGGAGG CGAAATGACG TCGTTGTAAT CGGACGACGG TGTTGTGTGT
3301 CCCAGGCTGA CGACGGAGCC GGTGTCCGAG GAGTCGTCGT CTTCCTCCTC GCTGTCTTCG
3361 ACCGGTGACT CTGCAGTTTG GTCCCTTAAA GCCCAAACCT CATCAGCGGC GTTCTGAGAC
3421 GCTGTTTGTG TCACCGCGGC GCGTGGAGTC GACGGCCTCC GAGGGGTGGT GGACACGTTG
3481 TTTTGAGAAG TCGTGGAAGT CGTAGGCATC CTGAAGGGAT TGTAAGCCAG GTGAGGATTC
3541 TTGAGGGCCC ACGCGCGTTC GCGCGGCCAG TTGGCGGGGT TCATATCCCC GGGCAACGGC
3601 GCCGTCGGAG CCCAGGGCGA GTTACCGTTG ACCGGGGTTT GGGTACCCGC GAAGGTAGGT
3661 GTCGGGGCCG GAGCGGGGGC CGTGGAAGGA TTGACAGGCG TCGGCGTGAG GATGGCAGCG
3721 CCGGCGCCAG CAGGGACGTT AACTCCGGCG CCGAACGTCA ACGTCGGTTG CTCGAACTTG
3781 TACGCGGTGG TGACGGGCGG TTTGGCGCTC GTCTCGGTAT CCGTGATGTC CACCAGCGTG
3841 TCGGTGAAAC GCGGATCTTG ACGGTTGGGG GGATAGCCAT CCGAGCTGTC GGAATCCTCG
3901 TCGCCCGAGA AAAGATCCCC TCTTGTCTCC GTGAGCGGCC TCACGTCCCA CGCGCTGTCC
3961 CGACGGACCC TTCCCGGGCT GGCCTTGGTT ACCTGCGGGG AGACGAGACT GAAAGCCGCG
4021 TGACGCTGTT GTTGCTGCGG GATGTTCAAG GGACCGCTGG TCGGTTTCTG ACTGCCCGAG
4081 GATAACATGC CGCTGAAAAT GCTGGAAACA CCGTTGCCAC TAGCGGCGCC CTTGCCGCTA
4141 GTTCCCGGTT TCTTGATGGG CGTAAAGATG TTTTTCTCGT CATCATCATC GTCGTCGTCC
4201 TCATCGGCAC TGGAGCCAAA GAGCCTCCGG GAGGCGCCCG GTTTACGTGT CGGGGGCGGC
4261 GGTTGCTGCT GACGTTGCTG CAGGTTCTGC TGCCTCTCCT CCCAAGCCTT CAGCTGCTGT
4321 TTCTCACGCT GCACCACCTC GTCGTCCACC CGTTTCTGCC GCTCGCGACG CTTTTCCTCT
4381 TCGTCGTAAT AGCCGACGCG CGCCGAACGG GCGGCGTGGG CGTCGGCGGC CGGTGCCAGA
4441 GAACCATGGG CCTCGAAGCG GAACGGTTTG TGTCCCTTCC AGGGACTGGC GATCCAGCTC
4501 CAGCCGTCCA GCGGCTGCGT GGGGACATGT TTCTTGGGTA CCGACGAGAA GGCTGAACCG
4561 CCGCCGAGCG AGAGGAGATT GGCGTCATCG TCAAACTCCA ACGACGGCGG GCGCGCGCCC
4621 AAAAAGGTGT GCGCCGACTG CGGGAAGCTG TCCACGTAGA TGTCAAAGTC CTCGATGAGC
4681 AGCTCCAGCA GCGTGTCGGC CGAGTCACCG TTTTCCACGG CGTGTTTGAG GATATTGCGA
4741 CAGTAGTTGG AATCAAAGGA AAGGCACATG CGCAGCTCCT TGACCAGCAG CTTGCAGCGC
4801 TCCTGAATGC GCGCCAGACA TTTGCGCTCC AGCTCCTCCC AAGACCTGCG CACGTTCATG
4861 ATGAGACGGC CCGTGTACAC GAGCTTGTTG ACGGCGTTGA CCAGCGCCGT GTTGGCGTGC
4921 CGGTCCAGGT TAAGGTCGAG CGGTTTCACG CAGAACATGT TACGGCGCAC ACCCTCCAGG
4981 TTTTCTTCAA TGCGCTGCAC CTCCGTATCC TTGAGGTGCA CAAAAGCGAT GGGTTCCGTC
5041 TGGCCGATGG CTGTGACCAG CGTCTCGCGC ACCGACATCT TGGCCAGAAT GACCGCGCTT
5101 ACGAGCGCGC GCTCCACAAT CTCAGCATCG TGGCGTACGT CCGTATCGAA TTCGGTACGG
5161 TCTAGCACAG CCAGGTGGTC ACGCGCCTTA CCACGATCAC CGAACGGGTA AGTGTAGCCG
5221 CGACGCGCCA CGGCCGCGCA ACGCACCTCG AACTCCTCGA GAACCGAGGA GAGGTCGGGG
5281 TTGTGGAAAC GCAGCTCGCG GTAGTATCCC AACCAAAGCA TGAGCTCGTT GAACAGCACC
5341 GTACGCCGGT GCAGGCGTTT TTCGCCACAT TTTTTCAGGA TCTTGGGGTG TGCCTCGAGA
5401 TCCACGTCGG GCTTTTGCGT GAGATGGCGC AGAAAGTTGA CCAGGGCCAC CACATCGCGC
5461 CGCTGTAGAC CGATAAACTG CAAACTCATT TTATATTGTA ATTATATATT TTCAATTTTG
5521 AAATCCCAAA ATATTATCAT ATCTTCCCAA TAAAGCTAGA ATTCTTTTTA TTGATTAACT
5581 AGTCAAATGA GTATATATAA TTGAAAAAGT AAAATATAAA TCATATAATA ATGAAACGAA
5641 ATATCAGTAA TAGACAGGAA CTGGCAGATT CTTCTTCTAA TGAAGTAAGT ACTGCTAAAT
5701 CTCCAAAATT AGATAAAAAT GATACAGCAA ATACAGCTTC ATTCAACGAA TTACCTTTTA
5761 ATTTTTTCAG ACACACCTTA TTACAAACTA ACTAAGTCAG ATGATGAGAA AGTAAATATA
5821 AATTTAACTT ATGGGTATAA TATAATAAAG ATTCATGATA TTAATAATTT ACTTAACGAT
5881 GTTAATAGAC TTATTCCATC AACCCCTTCA AACCTTTCTG GATATTATAA AATACCAGTT
5941 AATGATATTA AAATAGATTG TTTAAGAGAT GTAAATAATT ATTTGGAGGT AAAGGATATA
6001 AAATTAGTCT ATCTTTCACA TGGAAATGAA TTACCTAATA TTAATAATTA TGATAGGAAT
6061 TTTTTAGGAT TTACAGCTGT TATATGTATC AACAATACAG GCAGATCTAT GGTTATGGTA
6121 AAACACTGTA ACGGGAAGCA GCATTCTATG GTAACTGGCC TATGTTTAAT AGCCAGATCA
6181 TTTTACTCTA TAAACATTTT ACCACAAATA ATAGGATCCT CTAGATATTT AATATTATAT

Figure 42B

```
6241 CTAACAACAA CAAAAAAATT TAACGATGTA TGGCCAGAAG TATTTTCTAC TAATAAAGAT
6301 AAAGATAGTC TATCTTATCT ACAAGATATG AAAGAAGATA ATCATTTAGT AGTAGCTACT
6361 AATATGGAAA GAAATGTATA CAAAAACGTG GAAGCTTTTA TATTAAATAG CATATTACTA
6421 GAAGATTTAA AATCTAGACT TAGTATAACA AAACAGTTAA ATGCCAATAT CGATTCTATA
6481 TTTCATCATA ACAGTAGTAC ATTAATCAGT GATATACTGA AACGATCTAC AGACTCAACT
6541 ATGCAAGGAA TAAGCAATAT GCCAATTATG TCTAATATTT TAACTTTAGA ACTAAAACGT
6601 TCTACCAATA CTAAAAATAG GATACGTGAT AGGCTGTTAA AAGCTGCAAT AAATAGTAAG
6661 GATGTAGAAG AAATACTTTG TTCTATACCT TCGGAGGAAA GAACTTTAGA ACAACTTAAG
6721 TTTAATCAAA CTTGTATTTA TGAAGGTAC
```

Figure 42C

```
  1 ATGTGCCGCC GCCCGGATTG CGGCTTCTCT TTCTCACCTG GACCGGTGGC ACTGCTGTGG
 61 TGTTGCCTTC TGCTGCCCAT CGTTTCCTCA GCCACCGTCA GCGTCGCTCC TACCGTCGCC
121 GAGAAAGTTC CCGCGGAGTG CCCCGAACTA ACGCGTCGAT GCCTGTTGGG TGAGGTGTTT
181 CAGGGTGACA AGTATGAAAG TTGGCTGCGC CCGTTGGTGA ATGTTACCAG ACGCGATGGC
241 CCGCTATCGC AACTTATTCG TTACCGTCCC GTTACGCCGG AGGCCGCCAA CTCCGTGCTG
301 TTGGACGATG CTTTCCTGGA CACTCTGGCC CTGCTGTACA ACAATCCGGA TCAATTGCGG
361 GCCTTGCTGA CGCTGTTGAG CTCGGACACA GCGCCGCGCT GGATGACGGT GATGCGCGGT
421 TACAGCGAGT GCGGCGATGG CTCGCCGGCC GTGTACACGT GCGTGGACGA CCTGTGCCGC
481 GGCTACGACC TCACGCGACT GTCATACGGG CGCAGCATCT TCACGGAACA CGTGTTAGGC
541 TTCGAGCTGG TGCCACCGTC TCTCTTTAAC GTGGTGGTGG CCATACGCAA CGAAGCCACG
601 CGTACCAACC GCGCCGTGCG TCTGCCCGTG AGCACCGCTG CCGCGCCCGA GGGCATCACG
661 CTCTTTTACG GCCTGTACAA CGCAGTGAAG GAATTCTGCC TGCGTCACCA GCTGGACCCG
721 CCGCTGCTAC GCCACCTAGA TAAATACTAC GCCGGACTGC CGCCCGAGCT GAAGCAGACG
781 CGCGTCAACC TGCCGGCTCA CTCGCGCTAT GGCCCTCAAG CAGTGGATGC TCGCTAA
```

Figure 43

```
   1 AAGCTTTTGC GATCAATAAA TGGATCACAA CCAGTATCTC TTAACGATGT TCTTCGCAGA
  61 TGATGATTCA TTTTTTAAGT ATTTGGCTAG TCAAGATGAT GAATCTTCAT TATCTGATAT
 121 ATTGCAAATC ACTCAATATC TAGACTTTCT GTTATTATTA TTGATCCAAT CAAAAAATAA
 181 ATTAGAAGCC GTGGGTCATT GTTATGAATC TCTTTCAGAG GAATACAGAC AATTGACAAA
 241 ATTCACAGAC TCTCAAGATT TTAAAAAACT GTTTAACAAG GTCCCTATTG TTACAGATGG
 301 AAGGGTCAAA CTTAATAAAG GATATTTGTT CGACTTTGTG ATTAGTTTGA TGCGATTCAA
 361 AAAAGAATCC TCTCTAGCTA CCACCGCAAT AGATCCTATT AGATACATAG ATCCTCGTCG
 421 CGATATCGCA TTTTCTAACG TGATGGATAT ATTAAAGTCG AATAAAGTGA ACAATAATTA
 481 ATTCTTTATT GTCATCATGT AATTAACTAG CTACCCGGGA GATCTCTCGA GCTGCAGAAG
 541 CTTATAAAAA TCACAAGTCT CTGTCACTTT TTTTGTCTAG TTTTTTTTTC TCCTCTTGGT
 601 TCAGACGTTC TCTTCTTCGT CGGAGTCTTT CAAGTGTCGG TAGCCGTTTT TGCGGTGTCG
 661 CAGTCGGTCT AGCAGGTTGG GCTTCTGTCC CTTGTCCTGC GTGCCAGTCT GTCCGTCCAA
 721 AGAATCTGTA CCGTTCTCGT GCGCTCGCTG CTCTGCGTCC AGACGGACCA GGGCCAGAAG
 781 CATCTGGTAA GCCTGCTCGT TGGTGTAAGG CGGAGCCGCC GTGGATGCAT CAGACGACGG
 841 TGGTCCCGGT CCTTTGCGAC CAGAATTATA AACACTTTCC TCGTAGGAAG GCGGAGCCTG
 901 TAACGACGTG TCTTTGGTGT TGCCCGACGT CACGGTGGTC CCGTCGGCGG ACACCAGATA
 961 GGGAAAGAGG TTCTGCAGCG GCTGCATGCA GAGACGCCGC TGTCGAGTAT AGATCAAATA
1021 AATGATAATG ACGACGGCTA TGGCCACGAG GATGATGGTG AAGGCTCCGA AGGGGTTTTT
1081 GAGGAAGGTG GCAACGCCTT CGACCACGGA GGCCACCGCG CCACCCACGG CCCCAATGGC
1141 TACGCCAACG GCCTTTCCCG CGGCGCCCAG GCCGCTCATG AGGTCGTCCA GACCCTTGAG
1201 GTAGGGCGGC AGCGGGTCGA CTACCTTGTC CTCCACGTAC TTTACCCGCT GCTTATACGA
1261 ATTGAACTCG CGCATGATCT CCTCGAGATC AAAAACGTTG CTGGAACGCA ATTCTTTCTG
1321 CGAGTAAAGT TCCAGTACCC TGAAGTCGGT GTTTTCCAGC GGGTCGATGT CTAGGGCGAT
1381 CATGCTGTCG ACGGTGGAGA TGCTGCTGAG GTCAATCATG CGTTTGAAGA GGTAGTCCAC
1441 GTACTCGTAG GCCGAGTTGC CGGCGATGAA GATCTTGAGG CTGGGAAGCT GACATTCCTC
1501 AGTGCGGTGG TTGCCCAACA GGATTTCGTT ATCCTCGCCC AGTTGACCGT ACTGCACGTA
1561 CGAGCTGTTG GCGAAATTAA AGATGACCAC TGGTCGTGAG TAGCAGCGTC CTGGCGATTC
1621 CTTCACATTC ATATCACGCA GCACCTTGAC GCTGGTTTGG TTAATGGTCA CGCAGCTGGC
1681 CAGACCCAGG ACATCACCCA TGAAACGCGC GGCAATCGGT TTGTTGTAGA TGGCCGAGAG
1741 AATAGCTGAC GGGTTGATCT TGCTAAGTTC CTTGAAGACC TCTAGGGTGC GCCGTTGATC
1801 CACACACCAG GCTTCTGCGA TTTCGGCCAG CGCCCGGTTG ATGTAACCGC GCAACGTGTC
1861 ATAGGTGAAC TGCAGCTGGG CGTAGACCAG ATTGTGCACC GACTCCATGT TGGATAAATG
1921 AGTTGCATTG TTGCCATCTG TACTTCTTTT GGTTCTATTA TGAGTAAGAT TCAGACTGGA
1981 GCGGTTGGCC AAACGTTCGA GTTCCACCAG AGATTTTTGC TTGATACCTT GCCAGAACAC
2041 CACCAAACCA CCAGTGGTTT CAAAGACGGA CACGTTTCCA TATTTTTCAT ATGTTTGATT
2101 GTATGAAGTA TTGAAAATCT GCTGTAACTT ATTTATGGCC TCATCACGTA CACAGTCCAG
2161 CGCAGAGTCG GACATGTTCA CCTCTTGCTT CTTAGATAAG AAAGTGGCGG TCATTTTGGC
2221 AGAAGAAAAG TGATACGAGT CCTCGGCTTC GGAACGAATG GTGCGTTCCG AGGCTTCCCA
2281 GAAAGTGAGT TGACAAGTAA CATTCTTCTC GTCCTGTATA TCCCAGGAGA TCACTGAGTC
2341 CGCACGTTCA AGAAAAGCCA CCAACCTGTG GGTCTCTAAC GCAGAATTCG GTCTTTCAAA
2401 GTCGGAGACG ATAGTGTAGT TCGGAAAAAT GAAAAACTTG TCGGCGTTTT CTCCAAAATA
2461 GCTGGCATTG CGATTAGTTC CGTTGTAGAA AGGAGAAATG TCAACCACAT CACCCGTGGA
2521 AGTTGCGAAA AAATGATAGG GATACTTGGA GCGCGCAGTA GTGATGGTCA CCATACAATT
2581 CAGATTACAG GTCTCACGAT AGAGCCAGGT GCTGCCGCGG CTGTGCCATT GATCCTTGAC
2641 CGTCACGTAA CGGGTACTGT GGGTGTTGGA ATAATCGTCG GGCATTAATT GCATGGTTTT
2701 GTTTTCATAG CTGTCCCTAT GATAAGCCAC GAAAACCGTG CCTGCTATAA CGCGGCTGTA
2761 GGAACTGTAG CACTGACTGT GACTGTTGAT ATGATGAATC TCCCACATAG GAGGCGCCAC
2821 GTATTCCGTG TTGCTGCCCA GCAGATAAGT GGTGTGGATG TAAGCGTAGC TACGACGAAA
2881 CGTCAAAACC TTCTGGTAGA CTCGTACCTT AAAGGTGTGC GCGACGATGT TGCGTTTGTA
2941 GACCACCATG ATGCCCTCGT CCAGGTCTTC ATTGATGGGC TTCATCGAGG TGCAGACGAT
3001 ATTACGTTCA AAGCGAATAA GATCCGTACC CTGTGCCATA GAACACACGC GATAGGGGTA
3061 CTTGGTGGTG TTGACCCCCA CCACATCTCC GTACTTGAGG GTAGTGTTGT AGATGGTCTC
```

Figure 44A

```
3121 GTTAACACCA TGGCTGACCG TTTGGGAAGA AGTTACGCGT TGAGAGACTG AACCGGATCG
3181 AGAATGAGCA GCAGACGTCG TATGAGAGGA ATGGTGACTG TGAGTAGCAG AAGTTCCACG
3241 AGTAGAAGAT GAGGAAACCG CAGCACCCAG ACAGACGATA CACAAGTTAA CGCAGACTAC
3301 CAGGCACCAG ATCCTGGATT CCATTACGAT ACAAACTTAA CGGATATCGC GATAATGAAA
3361 TAATTTATGA TTATTTCTCG CTTTCAATTT AACACAACCC TCAAGAACCT TTGTATTTAT
3421 TTTCACTTTT AAGTATAGAA TAAAGAAGCT TGCATGCCAC GCGTCTCGAG GGCCCCTGCA
3481 GGTCGACTCT AGAGGATCCT TCTTTATTCT ATACTTAAAA AGTGAAAATA AATACAAAGG
3541 TTCTTGAGGG TTGTGTTAAA TTGAAAGCGA GAAATAATCA TAAATTATTT CATTATCGCG
3601 ATATCCGTTA AGTTTGTATC GTAATGTGCC GCCGCCCGGA TTGCGGCTTC TCTTTCTCAC
3661 CTGGACCGGT GGCACTGCTG TGGTGTTGCC TTCTGCTGCC CATCGTTTCC TCAGCCACCG
3721 TCAGCGTCGC TCCTACCGTC GCCGAGAAAG TTCCCGCGGA GTGCCCCGAA CTAACGCGTC
3781 GATGCCTGTT GGGTGAGGTG TTTCAGGGTG ACAAGTATGA AAGTTGGCTG CGCCCGTTGG
3841 TGAATGTTAC CAGACGCGAT GGCCCGCTAT CGCAACTTAT TCGTTACCGT CCCGTTACGC
3901 CGGAGGCCGC CAACTCCGTG CTGTTGGACG ATGCTTTCCT GGACACTCTG GCCCTGCTGT
3961 ACAACAATCC GGATCAATTG CGGGCCTTGC TGACGCTGTT GAGCTCGGAC ACAGCGCCGC
4021 GCTGGATGAC GGTGATGCGC GGTTACAGCG AGTGCGGCGA TGGCTCGCCG GCCGTGTACA
4081 CGTGCGTGGA CGACCTGTGC CGCGGCTACG ACCTCACGCG ACTGTCATAC GGGCGCAGCA
4141 TCTTCACGGA ACACGTGTTA GGCTTCGAGC TGGTGCCACC GTCTCTCTTT AACGTGGTGG
4201 TGGCCATACG CAACGAAGCC ACGCGTACCA ACCGCGCCGT GCGTCTGCCC GTGAGCACCG
4261 CTGCCGCGCC CGAGGGCATC ACGCTCTTTT ACGGCCTGTA CAACGCAGTG AAGGAATTCT
4321 GCCTGCGTCA CCAGCTGGAC CCGCCGCTGC TACGCCACCT AGATAAATAC TACGCCGGAC
4381 TGCCGCCCGA GCTGAAGCAG ACGCGCGTCA ACCTGCCGGC TCACTCGCGC TATGGCCCTC
4441 AAGCAGTGGA TGCTCGCTAA TTTTTATAGA TCCTGATCCT TTTTCTGGGT AAGTAATACG
4501 TCAAGGAGAA AACGAAACGA TCTGTAGTTA GCGGCCGCCT AATTAACTAA TATTATATTT
4561 TTTATCTAAA AAACTAAAAA TAAACATTGA TTAAATTTTA ATATAATACT TAAAAATGGA
4621 TGTTGTGTCG TTAGATAAAC CGTTTATGTA TTTTGAGGAA ATTGATAATG AGTTAGATTA
4681 CGAACCAGAA AGTGCAAATG AGGTCGCAAA AAAACTGCCG TATCAAGGAC AGTTAAAACT
4741 ATTACTAGGA GAATTATTTT TTCTTAGTAA GTTACAGCGA CACGGTATAT TAGATGGTGC
4801 CACCGTAGTG TATATAGGAT CGGCTCCTGG TACACATATA CGTTATTTGA GAGATCATTT
4861 CTATAATTTA GGAATGATTA TCAAATGGAT GCTAATTGAC GGACGCCATC ATGATCCTAT
4921 TTTAAATGGA TTGCGTGATG TGACTCTAGT GACTCGGTTC GTTGATGAGG AATATCTACG
4981 ATCCATCAAA AAACAACTGC ATCCTTCTAA GATTATTTTA ATTTCTGATG TGAGATCCAA
5041 ACGAGGAGGA AATGAACCTA GTACGGCGGA TTTACTAAGT AATTACGCTC TACAAAATGT
5101 CATGATTAGT ATTTTAAACC CCGTGGCGTC TAGTCTTAAA TGGAGATGCC CGTTTCCAGA
5161 TCAATGGATC AAGGACTTTT ATATCCCACA CGGTAATAAA ATGTTACAAC CTTTTGCTCC
5221 TTCATATTCA GCTG
```

Figure 44B

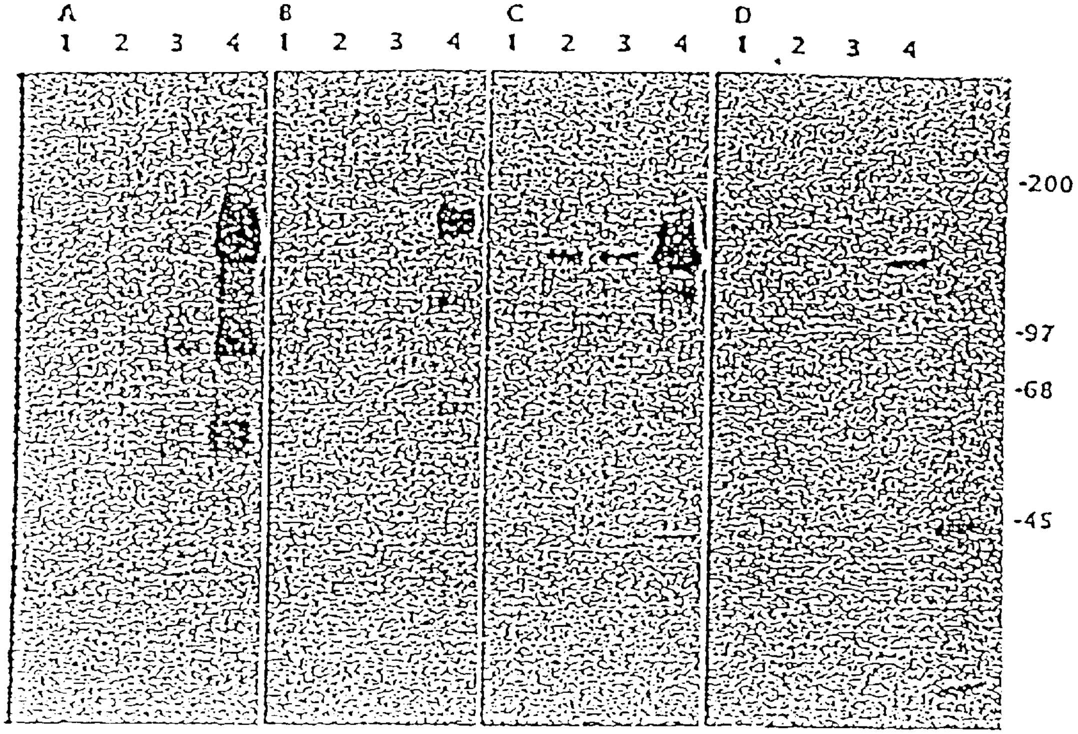
FIGURE 48 A - D

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAA CAAAAACTAA
 421 TCAGCTATCG GGGTTAATTA ATTAGTTATT AGACAAGGTG AAAACGAAAC TATTTGTAGC
 481 TTAATTAATT AGAGCTTCTT TATTCTATAC TTAAAAAGTG AAAATAAATA CAAAGGTTCT
 541 TGAGGGTTGT GTTAAATTGA AAGCGAGAAA TAATCATAAA TTATTTCATT ATGGCGATAT
 601 CCGTTAAGTT TGTATCGTAA TGGAGTCGCG CGGTCGCCGT TGTCCCGAAA TGATATCCGT
 661 ACTGGGTCCC ATTTCGGGGC ACGTGCTGAA AGCCGTGTTT AGTCGCGGCG ACACGCCGGT
 721 GCTGCCGCAC GAGACGCGAC TCCTGCAGAC GGGTATCCAC GTGCGCGTGA GCCAGCCCTC
 781 GCTGATCCTG GTGTCGCAGT ACACGCCCGA CTCGACGCCA TGCCACCGCG GCGACAATCA
 841 GCTGCAGGTG CAGCACACGT ACTTTACGGG CAGCGAGGTG GAGAACGTGT CGGTCAACGT
 901 GCACAACCCC ACGGGCCGGA GCATCTGCCC CAGCCAAGAG CCCATGTCGA TCTATGTGTA
 961 CGCGCTGCCG CTCAAGATGC TGAACATCCC CAGCATCAAC GTGCACCACT ACCCGTCGGC
1021 GGCCGAGCGC AAACACCGAC ACCTGCCCGT AGCTGACGCT GTGATTCACG CGTCGGGCAA
1081 GCAGATGTGG CAGGCGCGTC TCACGGTCTC GGGACTGGCC TGGACGCGTC AGCAGAACCA
1141 GTGGAAAGAG CCCGACGTCT ACTACACGTC AGCGTTCGTG TTTCCCACCA AGGACGTGGC
1201 ACTGCGGCAC GTGGTGTGCG CGCACGAGCT GGTTTGCTCC ATGGAGAACA CGCGCGCAAC
1261 CAAGATGCAG GTGATAGGTG ACCAGTACGT CAAGGTGTAC CTGGAGTCCT TCTGCGAGGA
1321 CGTGCCCTCC GGCAAGCTCT TTATGCACGT CACGCTGGGC TCTGACGTGG AAGAGGACCT
1381 GACGATGACC CGCAACCCGC AACCCTTCAT GCGCCCCCAC GAGCGCAACG GCTTTACGGT
1441 GTTGTGTCCC AAAAATATGA TAATCAAACC GGGCAAGATC TCGCACATCA TGCTGGATGT
1501 GGCTTTTACC TCACACGAGC ATTTTGGGCT GCTGTGTCCC AAGAGCATCC CGGGCCTGAG
1561 CATCTCAGGT AACCTATTGA TGAACGGGCA GCAGATCTTC CTGGAGGTGC AAGCGATACG
1621 CGAGACCGTG GAACTGCGTC AGTACGATCC CGTGGCTGCG CTCTTCTTTT TCGATATCGA
1681 CTTGCTGCTG CAGCGCGGGC CTCAGTACAG CGAACACCCC ACCTTCACCA GCCAGTATCG
1741 CATCCAGGGC AAGCTTGAGT ACCGACACAC CTGGGACCGG CACGACGAGG GTGCCGCCCA
1801 GGGCGACGAC GACGTCTGGA CCAGCGGATC GGACTCCGAC GAGGAACTCG TAACCACCGA
1861 GCGCAAGACG CCCCGCGTTA CCGGCGGCGG CGCCATGGCG GGCGCCTCCA CTTCCGCGGG
1921 CCGCAAACGC AAATCAGCAT CCTCGGCGAC GGCGTGCACG GCGGGCGTTA TGACACGCGG
1981 CCGCCTTAAG GCCGAGTCCA CCGTCGCGCC CGAAGAGGAC ACCGACGAGG ATTCCGACAA
2041 CGAAATCCAC AATCCGGCCG TGTTCACCTG GCCGCCCTGG CAGGCCGGCA TCCTGGCCCG
2101 CAACCTGGTG CCCATGGTGG CTACGGTTCA GGGTCAGAAT CTGAAGTACC AGGAGTTCTT
2161 CTGGGACGCC AACGACATCT ACCGCATCTT CGCCGAATTG GAAGGCGTAT GGCAGCCCGC
2221 TGCGCAACCC AAACGTCGCC GCCACCGGCA AGACGCCTTG CCCGGGCCAT GCATCGCCTC
2281 GACGCCCAAA AAGCACCGAG GTTGATTTTT ATGGATCCGG TACCCTCGAG GAATTCTAGC
2341 TTTATTGGGA AGATATGATA ATATTTTGGG ATTTCAAAAT TGAAAATATA TAATTACAAT
2401 ATAAAATGAG TTTGCAGTTT ATCGGTCTAC AGCGGCGCGA TGTGGTGGCC CTGGTCAACT
2461 TTCTGCGCCA TCTCACGCAA AAGCCCGACG TGGATCTCGA GGCACACCCC AAGATCCTGA
2521 AAAAATGTGG CGAAAAACGC CTGCACCGGC GTACGGTGCT GTTCAACGAG CTCATGCTTT
2581 GGTTGGGATA CTACCGCGAG CTGCGTTTCC ACAACCCCGA CCTCTCCTCG GTTCTCGAGG
2641 AGTTCGAGGT GCGTTGCGCG GCCGTGGCGC GTCGCGGCTA CACTTACCCG TTCGGTGATC
2701 GTGGTAAGGC GCGTGACCAC CTGGCTGTGC TAGACCGTAC CGAATTCGAT ACGGACGTAC
2761 GCCACGATGC TGAGATTGTG GAGCGCGCGC TCGTAAGCGC GGTCATTCTG GCCAAGATGT
2821 CGGTGCGCGA GACGCTGGTC ACAGCCATCG GCCAGACGGA ACCCATCGCT TTTGTGCACC
2881 TCAAGGATAC GGAGGTGCAG CGCATTGAAG AAAACCTGGA GGGTGTGCGC CGTAACATGT
2941 TCTGCGTGAA ACCGCTCGAC CTTAACCTGG ACCGGCACGC CAACACGGCG CTGGTCAACG
3001 CCGTCAACAA GCTCGTGTAC ACGGGCCGTC TCATCATGAA CGTGCGCAGG TCTTGGGAGG
3061 AGCTGGAGCG CAAATGTCTG GCGCGCATTC AGGAGCGCTG CAAGCTGCTG GTCAAGGAGC
```

Figure 59A

3121 TGCGCATGTG CCTTTCCTTT GATTCCAACT ACTGTCGCAA TATCCTCAAA CACGCCGTGG
3181 AAAACGGTGA CTCGGCCGAC ACGCTGCTGG AGCTGCTCAT CGAGGACTTT GACATCTACG
3241 TGGACAGCTT CCCGCAGTCG GCGCACACCT TTTTGGGCGC GCGCCCGCCG TCGTTGGAGT
3301 TTGACGATGA CGCCAATCTC CTCTCGCTCG GCGGCGGTTC AGCCTTCTCG TCGGTACCCA
3361 AGAAACATGT CCCCACGCAG CCGCTGGACG GCTGGAGCTG GATCGCCAGT CCCTGGAAGG
3421 GACACAAACC GTTCCGCTTC GAGGCCCATG GTTCTCTGGC ACCGGCCGCC GACGCCCACG
3481 CCGCCCGTTC GGCGCGCGTC GGCTATTACG ACGAAGAGGA AAAGCGTCGC GAGCGGCAGA
3541 AACGGGTGGA CGACGAGGTG GTGCAGCGTG AGAAACAGCA GCTGAAGGCT TGGGAGGAGA
3601 GGCAGCAGAA CCTGCAGCAA CGTCAGCAGC AACCGCCGCC CCCGACACGT AAACCGGGCG
3661 CCTCCCGGAG GCTCTTTGGC TCCAGTGCCG ATGAGGACGA CGACGATGAT GATGACGAGA
3721 AAAACATCTT TACGCCCATC AAGAAACCGG GAACTAGCGG CAAGGGCGCC GCTAGTGGCA
3781 ACGGTGTTTC CAGCATTTTC AGCGGCATGT TATCCTCGGG CAGTCAGAAA CCGACCAGCG
3841 GTCCCTTGAA CATCCCGCAG CAACAACAGC GTCACGCGGC TTTCAGTCTC GTCTCCCCGC
3901 AGGTAACCAA GGCCAGCCCG GGAAGGGTCC GTCGGGACAG CGCGTGGGAC GTGAGGCCGC
3961 TCACGGAGAC AAGAGGGGAT CTTTTCTCGG GCGACGAGGA TTCCGACAGC TCGGATGGCT
4021 ATCCCCCCAA CCGTCAAGAT CCGCGTTTCA CCGACACGCT GGTGGACATC ACGGATACCG
4081 AGACGAGCGC CAAACCGCCC GTCACCACCG CGTACAAGTT CGAGCAACCG ACGTTGACGT
4141 TCGGCGCCGG AGTTAACGTC CCTGCTGGCG CCGGCGCTGC CATCCTCACG CCGACGCCTG
4201 TCAATCCTTC CACGGCCCCC GCTCCGGCCC CGACACCTAC CTTCGCGGGT ACCCAAACCC
4261 CGGTCAACGG TAACTCGCCC TGGGCTCCGA CGGCGCCGTT GCCCGGGGAT ATGAACCCCG
4321 CCAACTGGCC GCGCGAACGC GCGTGGGCCC TCAAGAATCC TCACCTGGCT TACAATCCCT
4381 TCAGGATGCC TACGACTTCC ACGACTTCTC AAAACAACGT GTCCACCACC CCTCGGAGGC
4441 CGTCGACTCC ACGCGCCGCG GTGACACAAA CAGCGTCTCA GAACGCCGCT GATGAGGTTT
4501 GGGCTTTAAG GGACCAAACT GCAGAGTCAC CGGTCGAAGA CAGCGAGGAG GAAGACGACG
4561 ACTCCTCGGA CACCGGCTCC GTCGTCAGCC TGGGACACAC AACACCGTCG TCCGATTACA
4621 ACGACGTCAT TTCGCCTCCC AGTCAGACGC CCGAGCAGTC GACGCCGTCC AGAATACGTA
4681 AAGCTAAGTT ATCGTCTCCA ATGACGACGA CATCCACGAG CCAGAAACCG GTGCTGGGCA
4741 AGCGAGTCGC GACGCCGCAC GCGTCCGCCC GAGCGCAGAC GGTGACGTCG ACACCGGTTC
4801 AGGGAAGGGT AGAGAAACAG GTATCGGGCA CGCCGTCGAC GGTACCCGCC ACGCTGTTGC
4861 AACCTCAACC GGCTTCGTCT AAAACAACGT TATCAAGGAA CGTGACTTCT GGCGCGAGAA
4921 CCTCTTCCGC TTCGGCTCGA CAGCCGTCAG CCTCGGCGTC CGTTTTGTCG CCCACGGAGG
4981 ATGATGTCGT GTCCCCCGTC ACGTCGCCGC TGTCCATGCT TTCGTCAGCC TCTCCGTCCC
5041 CGGCCAAGAG TGCCCCTCCG TCTCCGGTGA AAGGTCGGGG CAGCCGCGTC GGTGTTCCTT
5101 CTTTGAAACC TACTTTGGGC GGCAAGGCGG TGGTAGGTCG ACCGCCCTCG GTACCCGTGA
5161 GCGGTAGCGC GCCGGGTCGC CTGTCCGGCA CCAGCCGGGC CGCCTCGACC ACGCCGACGT
5221 ATCCCGCGGT AACCACCGTT TACCCACCGT CGTCTACGGC CAAAAGCAGC GTATCGAATG
5281 CGCCGCCTGT GGCCTCCCCC TCCATCCTGA AACCGGGGGC GAGCGCGGCT TTGCAATCAC
5341 GCCGCTCGAC GGGGACCGCC GCCGTAGGTT CCCCCGTCAA GAGCACGACG GGCATGAAAA
5401 CGGTGGCTTT CGACCTATCG TCGCCCCAGA AGAGCGGTAC GGGGCCGCAA CCGGGTTCTG
5461 CCGGCATGGG GGGCGCCAAA ACGCCGTCGG ACGCCGTGCA GAACATCCTC CAAAAGATCG
5521 AGAAGATTAA GAACACGGAG GAATAGTTTT TATTGCTAGA ATTCTTTTTA TTGATTAACT
5581 AGTCAAATGA GTATATATAA TTGAAAAAGT AAAATATAAA TCATATAATA ATGAAACGAA
5641 ATATCAGTAA TAGACAGGAA CTGGCAGATT CTTCTTCTAA TGAAGTAAGT ACTGCTAAAT
5701 CTCCAAAATT AGATAAAAAT GATACAGCAA ATACAGCTTC ATTCAACGAA TTACCTTTTA
5761 ATTTTTTCAG ACACACCTTA TTACAAACTA ACTAAGTCAG ATGATGAGAA AGTAAATATA
5821 AATTTAACTT ATGGGTATAA TATAATAAAG ATTCATGATA TTAATAATTT ACTTAACGAT
5881 GTTAATAGAC TTATTCCATC AACCCCTTCA AACCTTTCTG GATATTATAA AATACCAGTT
5941 AATGATATTA AAATAGATTG TTTAAGAGAT GTAAATAATT ATTTGGAGGT AAAGGATATA
6001 AAATTAGTCT ATCTTTCACA TGGAAATGAA TTACCTAATA TTAATAATTA TGATAGGAAT
6061 TTTTTAGGAT TTACAGCTGT TATATGTATC AACAATACAG GCAGATCTAT GGTTATGGTA
6121 AAACACTGTA ACGGGAAGCA GCATTCTATG GTAACTGGCC TATGTTTAAT AGCCAGATCA
6181 TTTTACTCTA TAAACATTTT ACCACAAATA ATAGGATCCT CTAGATATTT AATATTATAT

Figure 59B

```
6241 CTAACAACAA CAAAAAAATT TAACGATGTA TGGCCAGAAG TATTTTCTAC TAATAAAGAT
6301 AAAGATAGTC TATCTTATCT ACAAGATATG AAAGAAGATA ATCATTTAGT AGTAGCTACT
6361 AATATGGAAA GAAATGTATA CAAAAACGTG GAAGCTTTTA TATTAAATAG CATATTACTA
6421 GAAGATTTAA AATCTAGACT TAGTATAACA AAACAGTTAA ATGCCAATAT CGATTCTATA
6481 TTTCATCATA ACAGTAGTAC ATTAATCAGT GATATACTGA AACGATCTAC AGACTCAACT
6541 ATGCAAGGAA TAAGCAATAT GCCAATTATG TCTAATATTT TAACTTTAGA ACTAAAACGT
6601 TCTACCAATA CTAAAAATAG GATACGTGAT AGGCTGTTAA AAGCTGCAAT AAATAGTAAG
6661 GATGTAGAAG AAATACTTTG TTCTATACCT TCGGAGGAAA GAACTTTAGA ACAACTTAAG
6721 TTTAATCAAA CTTGTATTTA TGAAGGTAC
```

Figure 59C

```
   1 TCTAGAACTA GTGGATCTTC TGGTAATGAC AAATTAAACT GTTTAGCGTA TATTATATAC
  61 TCGTATAAAA AATCATGATC TATATTCTTA ATAGCTTTTA GAAGGTTCAT ATCGTAGAAA
 121 TAAACATAAG TTCCTTTCAT CACTCTACCT ACACGACCTT TACGTTGCGT CATCATAGAT
 181 TTTGATATAA ACATCTGAAC ACCACCAAAA GGTCTAGGTA CGTATACTCT ACCGGTATCG
 241 TATACGTGAG TCGCTGTACG TATAGTAATA CTAGATTCCA AATAAGGGGT AGATACTAGA
 301 ATACAAGGTC TTTCTCTATT AGGTCGTTGA ACATCTTGTA GGATTTCTGC TATATTTTTT
 361 AATTTTCCAT GTATTACTAT AAAATCAATA TTCTTATTCT TAGATTCTAA GTACTCTTTA
 421 TACTTAATAC ATTCTGATAC AGAAGGTAAG AATAAAATAC CACACATTCC ATTATCTGGC
 481 TTACACCACA ATAAAGTAGA CGATATATTC TTTCTCTCAT TATCAAAATA AACTCTCTTA
 541 TCCGGAGAAT ACCTATTTTT TACGTATATT TCTTTTATGG AGTAAAGAAC TGGTCCTTCT
 601 ATATGGTAAA ATTCAACATC AGGAAGAAAT TCCATTAGTC TATCTTTATC ATCTTCTAGA
 661 GTGGCAGACA TCAATACTAG CGAATGAATG CTATCTATAT TTTTTCTTAG AACGGCTATC
 721 ATAATATCGG CTATCCTATC ATGTTCATGT ATTTCATCTA TTATGACTAT ATTATACTTT
 781 GATAGAGAGT AACTAGTCAG TTTATTAGTA GAAAGTACTA TACCTTGAAA TCCTTTTTTG
 841 GTTTTTTCTG TATGTCCTCC GTATTTAAGT TCTACAGGAG AACCTTCGAA CTGTGAAAAT
 901 CCCAACGATT GTAAAAAATT ATTTCCGTTG CTCTTTACCA AAGTCACCCT AGGAAGAGAT
 961 AAAACTATAG GTTTGGGTAT AAAATCTAGC CTTATCCTGT CTATATCATC CCATCCTCCG
1021 AATAAATAGT TATACCACAT TATTACTTTT GGTAACTGAG ATGTTTTACC TATGCCTGTA
1081 CTACCGGTAA CTACTATCTG TTTCCTCTTC TTTAACATAT CAAAGATATG AACCTGTGTT
1141 GTTAAACTAA GGGATTTGAA CGATATGATA GCGAAAGGAT TTGGATTATT GAGTATTCCT
1201 ATAGAATTCT TAATGGGTAC CTTCTTATTG GAAGAGAAAA TAGACAGATG ATTTCCAGCT
1261 ACTAGTAATC CTCTTTTATC GTCAAGCGTT ATATCAGATA CATGATTATA ACCGATACAT
1321 TTTACGTAAC TATAGCATTC AAACGTTATA AATCTATCGT TACCTATATA GTATACCTGT
1381 TTACTGTAGT TGATACTGAC GGGTATTATA TCTATAAGTT TACTAACAGG TATTTTAGCG
1441 GGTATTGAAT TAGTAGTTTC TATATTCAGC ATATAAGTAT CGTCCTTTAA GCAGATAAAT
1501 ACTTTATTCC ACCTATGTTT TATTATAGGA AATACAGAAT GAGAAAAAAA TAACGTATCT
1561 TTATTATGAT ATTCTTCTAA TTCTTTTTGG GTATACTTAC TTGGGAATAT ATCGTACATA
1621 TTAGGGAAAG CGTATATCGA AAATAGCTCG TTAGTGGCCA TAGTTCCTAC AGTATGTATA
1681 TTTAGTTAGT AATAAATGGA TAGATACACA GAACTAGTTA TTAATAAAAT ACCAGAATTA
1741 GGATTCGTTA ACTTGCTTTC TCATATCTAT CAAACAGTTG GGTTATCCTA CGATATAGAT
1801 GTATCAAAAT TCAAAACTAA TTGCAATGGT TACGTCGTAG AGAGATTTGA TAACTCAGAA
1861 ACAGTTGGCA AAGTGTCCTG CGTGCCTATA TCTATACTGT TAGAATTGGT AGACAGAAAA
1921 ATATTATCTA AACCAGATAC GTCTAAAACA GAAATAGAGA TTAAAGAAGA TTTAGTAAAC
1981 GAATTAATTG AAAATACCAA TAGTTTCGAA GATATAATGA CTATACCTAC CAGTATCCCT
2041 ATGAGATATT TTTTTAAACC GGTACTAAGA GAAAAAGTAT CTAAAGCTGT AGATTTTTCC
2101 AGAATGGATA TTAAGGGAGA TGATATTAGC AAAATGGGAA TAAAACACGG AGAAAAAAGT
2161 AATAATATAT CTAATATTAA GATTGTACCA GAAAAAGATG CCTGGATGAC TAATACTAGT
2221 ATTCAGCAAT TAATAGGACC TATGTCGTAC GGAACAGAAG TTAGCTATAT AGGTCAATTT
2281 AACTTTAATT TTATTAACAC ATATCCTGTA TACGAAAAAT CTGCAGCCCT TAACAGAAGT
2341 CCAGAACTTT TTAAGATTAA AGATAGAATT AAAGGATTAC GTACAAGATT TGTTATGTTC
2401 GGTTTCTGTT ATATGTTCCA TTGGAAATGT TTGATATATG ATAGAGAAAA CGATTTTGTA
2461 TGTTTCTATG ATTCAGGAGG ATCTAATCCA AATGACTTTG ATCACTATGA TAATTTTTTC
2521 TACTATAGTC ATTCGAGAGG ATTCAATAGA AATTCTAAGA GGTCATCTAG CTTATCTAAT
2581 GAAAATGCAG ATATAGATAT TCTGTTCAAC TTTTTCGTGG ATAATTACGA AGTTACTTCA
2641 GGATGTATAA ACGTAGAAGT CAATCAGCTG ATGGAATCAG AATGTGGTAT GTTTACTTGT
2701 TTGTTTATGA CTATGTGCTG TCTCCATCCT CCTAAAGGAT TTAAAGGGAT AAGAAAGACA
2761 TATACCTATT TTAAGTTTTT AGCCGATAAA AAAATGACTA TGCTAAAGTC TATACTTTTC
2821 AACGCTGACA AGATGGAATT TAAAGTGAAA GAATCAAGCA GTAAAGGCAT ACAAGAATAT
2881 AAAAAAATGG AAGAGTGGTG TGGTAAAACT ATAAACATTT TAGCTGATAA AATAACAACA
2941 CGTGTAAATA GTATAATAGA GTAGTAAAAT GGATAATTTT ATAAAGCAGA TATCGTCAAA
3001 GATAGTAAAA CCTATAGCAG AATTAGAACC TCCAGATTCT AAAGTACAAT ATTATTACAT
3061 GACTATATCG TTTAATTTTC CTGACTTATA TTATTGTAAT AAAAATTTAT TTGCGAAACC
```

Figure 60A

3121 CGATAATACT TTGCTAGATG TTTCTAAGTC TTTGCTTACT TTAAACTCAT TTCCGTATGA
3181 AAACTTTGTG ATAAATGATT TACTAAGAAC TATTAGGCGT TACTGTCACG TATATGATGT
3241 CTATTTTTTA CCCGTAGGGT GGTTTGTAGG AAAAGAAGAT GTATTACCCA ATTACCAAGT
3301 ATCGATAAAA ATAATAAGAA GTACTAATCA AGAAGTAATA GAAAACATTA TTAGGAATTA
3361 TTTATCACGA CACGGTATTT ATGGAGATAA CCTATCTATA GAAACAGACC GATTAAACGA
3421 AGTATCTATA AACAGACATT CTATTGTAGG AGCTAGACAG TTAGCACCTA TATGCGTTGT
3481 TTCTTTTTAT CCTTTCGACC CTGAAAATAA AATACTTTTC GTTATATATG TAGGTAGATA
3541 CAAAGACAGA CATTGCGGTG TATCTTATGT AGTTGATAGA GAGGATATGT ATAAAGTAAT
3601 TAACAGAATA TATTCTTACG TAGTTTGTAT TTATCTAGTT TCCGATGATA TGGTCACGTT
3661 TCATACTACT CCTCTAGCTA ATCACAGTAA AAAATTAATA CCGTTACCCA TAAATCATTG
3721 CAATACCTTA TGCGAGATAG TTCACGACTT TGAGTTTTTA AGATTTGAGC AATCCACTAT
3781 GCCAATACCC GTTTTCACTC CTTTTATTCC TAAACAGCTA GTTAATATAA TCAACTTACC
3841 TGATGATATA CCTATTACTT GTGCATCAAT AAACAGATTA GAATATGTTA CACATATAGA
3901 TGATAAAAAA TTAAAAAGAG TACTGATTAT CGTAAAGGAT AAATTTCTTA GAAATACTAT
3961 TCTTCACGGT ACATTTAAAA AAAGGAATAT AGTCAGAAAC AGGAAATATA CTTTCACTAT
4021 AACATGGTCT AATTTCGAAT GTCCGACGTT AGGAGACGTT AAGTCTTCTT CACCTAATAC
4081 CTGTAATAGA GTAGTTTTAG ACGGTAGTAG ATACGTTACA AAAACCTTTA ATGATACAAT
4141 ATAAATGGAA CTAACTAGAG AAACGCTGAT ATTTGTAGGC ATTACTGTAC TAGTAGTAGT
4201 AATGATCATA TCTGGTTTCT CACTAATATT GCGATTGATA CCTGGTGTAT ATTCATCAGT
4261 TATTAGATCG TCGTTCGTAG GAGGGAAAAT ATTAAGATTT ATGGAGGTAT TCTCTACTGT
4321 TATGTTTATA CCATCATTAG TAATACTTTA TACAGCATAT ATAAGGAAAT CTAAAGTGAA
4381 AAATAACTAA ATATTATAGT ATTTGTAATA AATGGCTACT GGAGAGATTC GTCTTATTAT
4441 AGGGCCTATG TTTTCAGGTA AAACAACAGA ATTAGTTAGA TTAATAAGAA GATTTATGAT
4501 ATCGGGACGT AAATGTATAA TAATAAAACA TTGTAGTGAT TCCCGTTATA CCGAAGGAGA
4561 TTTAGAAGCT ATATATACTC ATGATAAAAT TTCGATGGAA GCACTATCGT GTAGCAAATT
4621 ATTACCTTTA ATACCTAAAA TTGATAACTT TGAAGTAATA GGTATAGACG AAGGACAGTT
4681 TTTTGAAGAT ATAGTAGAAT TTAGTGAGAT TATGGCTAAT AAGGGTAAAA CTGTAATCAT
4741 AGCGGCTTTA AATGGAGATT TCAAACGACA ATTATTTGGA AACATATTTA AACTATTATC
4801 TTTATCAGAA TCAGTTACTA GTTTAACTGC TATTTGTGCA GTTTGTAAAA ACGAAGCATC
4861 TTTTTCTAAG CGCATGACTG ATGATAAAGA TGTAAAAGTT ATAGGAGGTA AAGAAATGTA
4921 TACTGCTGTT TGTAGAAAAT GCTTTTTATG AGTCTAATAT ACGTACTAAA TACTTGTACG
4981 TACAACTATG TTAGAATAAT TTGCTTAGTA TAGTATATAA ACAAGTATGT AAAAAATAAA
5041 ATTGATATAA AAGTAGTCTT CTATTCCGAA CAATAACTAT ACAAAATGGA TTTAGATATT
5101 AAATCTTGCA GAAGTATTTA CAAAATATGG GATAAATATC ATTTTATGAC AGGGTATAAA
5161 TATAAAAATG ATAAACAGAG ATTTAAAATT ACAATTTACT GTAAATGTGA TTGTTCTATC
5221 AAAGAATATC CTTATAGATT TGTTACTGAG AAACTGCTTT TAATGTATAT TATTAATAAG
5281 TTTAGAGGAA AGTATCTAAT CAAAATTAGG ATAGAACCCA TAGTTAAAAA TTAAATCATA
5341 TATCAATACA TGTCAGTTTT TTATCGAAAA ATGGATTTAT AAATAAAATG AAAAATAACT
5401 TGAATGAAGG AAAAAATAAC CATGAGTAAA AAACCAGTAA AGACGGTCCA GCGTAGACGT
5461 GGAAACGATG AGGATAATAA GTTTACTTGT ATCCAAGCGC TAGAACATGC AAAAAGCTTA
5521 TGTACTAAAA ATAATAAAAT AGTTAAATCT GTTAAACTAT CACAATCTCT CTTTAAGTCA
5581 TCTAACAATA TTTCTGTGAT ATTAGAACCA GAATATAAAG ACAAATTAGT GACTCCTCTT
5641 ATTATTGTAG AAGGTGAAGG AAAAATATAC CATAATAAGA ATGATAGTTT TAATCGTGAA
5701 GAACCGTATT TTCTAAAAAT ACGACCTACG TTAATGAATC CTATATTATA TCAGATTATG
5761 GAATGCATTT ATAGAGATCC CCCGGGCTGC AGGAATTC

Figure 60B

```
   1 GCCCTTAACA GAAGTCCAGA ACTTTTTAAG ATTAAAGATA GAATTAAAGG ATTACGTACA
  61 AGATTTGTTA TGTTCGGTTT CTGTTATATG TTCCATTGGA AATGTTTGAT ATATGATAGA
 121 GAAAACGATT TTGTATGTTT CTATGATTCA GGAGGATCTA ATCCAAATGA CTTTGATCAC
 181 TATGATAATT TTTTCTACTA TAGTCATTCG AGAGGATTCA ATAGAAATTC TAAGAGGTCA
 241 TCTAGCTTAT CTAATGAAAA TGCAGATATA GATATTCTGT TCAACTTTTT CGTGGATAAT
 301 TACGAAGTTA CTTCAGGATG TATAAACGTA GAAGTCAATC AGCTGATGGA ATCAGAATGT
 361 GGTATGTTTA CTTGTTTGTT TATGACTATG TGCTGTCTCC ATCCTCCTAA AGGATTTAAA
 421 GGGATAAGAA AGACATATAC CTATTTTAAG TTTTTAGCCG ATAAAAAAAT GACTATGCTA
 481 AAGTCTATAC TTTTCAACGC TGACAAGATG GAATTTAAAG TGAAAGAATC AAGCAGTAAA
 541 GGCATACAAG AATATAAAAA AATGGAAGAG TGGTGTGGTA AAACTATAAA CATTTTAGCT
 601 GATAAAATAA CAACACGTGT AAATAGTATA ATAGAGTAGT AAAATGGATA ATTTTATAAA
 661 GCAGATATCG TCAAAGATAG TAAAACCTAT AGCAGAATTA GAACCTCCAG ATTCTAAAGT
 721 ACAATATTAT TACATGACTA TATCGTTTAA TTTTCCTGAC TTATATTATT GTAATAAAAA
 781 TTTATTTGCG AAACCCGATA ATACTTTGCT AGATGTTTCT AAGTCTTTGC TTACTTTAAA
 841 CTCATTTCCG TATGAAAACT TTGTGATAAA TGATTTACTA AGAACTATTA GGCGTTACTG
 901 TCACGTATAT GATGTCTATT TTTTACCCGT AGGTGGTTTG TAGGAAAAGA AGATGTATTA
 961 CCCAATTACC AAGTATCGAT AAAAATAATA AGAAGTACTA ATCAAGAAGT AATAGAAAAC
1021 ATTATTAGGA ATTATTTATC ACGACACGGT ATTTATGGAG ATAACCTATC TATAGAAACA
1081 GACCGATTAA ACGAAGTATC TATAAACAGA CATTCTATTG TAGGAGCTAG ACAGTTAGCA
1141 CCTATATGCG TTGTTTCTTT TTATCCTTTC GACCCTGAAA ATAAAATACT TTTCGTTATA
1201 TATGTAGGTA GATACAAAGA CAGACATTGC GGTGTATCTT ATGTAGTTGA TAGAGAGGAT
1261 ATGTATAAAG TAATTAACAG AATATATTCT TACGTAGTTT GTATTTATCT AGTTTCCGAT
1321 GATATGGTCA CGTTTCATAC TACTCCTCTA GCTAATCACA GTAAAAAATT AATACCGTTA
1381 CCCATAAATC ATTGCAATAC CTTATGCGAG ATAGTTCACG ACTTTGAGTT TTTGAGATTT
1441 GAGCAATCCA CTATGCCAAT ACCCGTTTTC ACTCCTTTTA TTCCTAAACA GCTAGTTAAT
1501 ATAATCAACT TACCTGATGA TATACCTATT ACTTGTGCAT CAATAAACAG ATTAGAATAT
1561 GTTACACATA TAGATGATAA AAAATTAAAA AGAGTACTGA TTATCGTAAA GGATAAATTT
1621 CTTAGAAATA CTATTCTTCA CGGTACATTT AAAAAAAGGA ATATAGTCAG AAACAGGAAA
1681 TATACTTTCA CTATAACATG GTCTAATTTC GAATGTCCGA CGTTAGGAGA CGTTAAGTCT
1741 TCTTCACCTA ATACCTGTAA TAGAGTAGTT TTAGACGGTA GTAGATACGT TACAAAAACC
1801 TTTAATGATA CAATATAAAT GGAACTAACT AGAGAAACGC TGATATTTGT AGGCATTACT
1861 GTACTAGTAG TAGTAATGAT CATATCTGGT TTCTCACTAA TATTGCGATT GATACCTGGT
1921 GTATATTCAT CAGTTATTAG ATCGTCGTTC GTAGGAGGGA AAATATTAAG ATTTATGGAG
1981 GTATTCTCTA CTGTTATGTT TATACCATCA TTAGTAATAC TTTATACAGC ATATATAAGG
2041 AAATCTAAAG TGAAAAATAA CTAAATATTA TAGTATTTGT AATAAGTACT AATTAGCTAT
2101 AAAAACCCGG GTCGCGAGAA TTCGTCGACG GATCCTTCTT TATTCTATAC TTAAAAAGTG
2161 AAAATAAATA CAAAGGTTCT TGAGGGTTGT GTTAAATTGA AAGCGAGAAA TAATCATAAA
2221 TTATTTCATT ATCGCGATAT CCGTTAAGTT TGTATCGTAA TGTGCCGCCG CCCGGATTGC
2281 GGCTTCTCTT TCTCACCTGG ACCGGTGGCA CTGCTGTGGT GTTGCCTTCT GCTGCCCATC
2341 GTTTCCTCAG CCACCGTCAG CGTCGCTCCT ACCGTCGCCG AGAAAGTTCC CGCGGAGTGC
2401 CCCGAACTAA CGCGTCGATG CCTGTTGGGT GAGGTGTTTC AGGGTGACAA GTATGAAAGT
2461 TGGCTGCGCC CGTTGGTGAA TGTTACCAGA CGCGATGGCC CGCTATCGCA ACTTATTCGT
2521 TACCGTCCCG TTACGCCGGA GGCCGCCAAC TCCGTGCTGT TGGACGATGC TTTCCTGGAC
2581 ACTCTGGCCC TGCTGTACAA CAATCCGGAT CAATTGCGGG CCTTGCTGAC GCTGTTGAGC
2641 TCGGACACAG CGCCGCGCTG GATGACGGTG ATGCGCGGTT ACAGCGAGTG CGGCGATGGC
2701 TCGCCGGCCG TGTACACGTG CGTGGACGAC CTGTGCCGCG GCTACGACCT CACGCGACTG
2761 TCATACGGGC GCAGCATCTT CACGGAACAC GTGTTAGGCT TCGAGCTGGT GCCACCGTCT
2821 CTCTTTAACG TGGTGGTGGC CATACGCAAC GAAGCCACGC GTACCAACCG CGCCGTGCGT
2881 CTGCCCGTGA GCACCGCTGC CGCGCCCGAG GGCATCACGC TCTTTTACGG CCTGTACAAC
2941 GCAGTGAAGG AATTCTGCCT GCGTCACCAG CTGGACCCGC CGCTGCTACG CCACCTAGAT
3001 AAATACTACG CCGGACTGCC GCCCGAGCTG AAGCAGACGC GCGTCAACCT GCCGGCTCAC
3061 TCGCGCTATG GCCCTCAAGC AGTGGATGCT CGCTAATTTT TATAGATCCC TCGAGGGTAC
```

Figure 61A

```
3121 CGCATGCCCT TTTTATTGAC TAGTTAATCA GTCTAATATA CGTACTAAAT ACTTGTACGT
3181 ACAACTATGT TAGAATAATT TGCTTAGTAT AGTATATAAA CAAGTATGTA AAAAATAAAA
3241 TTGATATAAA AGTAGTCTTC TATTCCGAAC AATAACTATA CAAAATGGAT TTAGATATTA
3301 AATCTTGCAG AAGTATTTAC AAAATATGGG ATAAATATCA TTTTATGACA GGGTATAAAT
3361 ATAAAAATGA TAAACAGAGA TTTAAAATTA CAATTTACTG TAAATGTGAT TGTTCTATCA
3421 AAGAATATCC TTATAGATTT GTTACTGAGA AACTGCTTTT AATGTATATT ATTAATAAGT
3481 TTAGAGGAAA GTATCTAATC AAAATTAGGA TAGAACCCAT AGTTAAAAAT TAAATCATAT
3541 ATCAATACAT GTCAGTTTTT TATCGAAAAA TGGATTTATA AATAAAATGA AAAATAACTT
3601 GAATGAAGGA AAAAATAACC ATGAGTAAAA AACCAGTAAA GACGGTCCAG CGTAGACGTG
3661 GAAACGATGA GGATAATAAG TTTACTTGTA TCCAAGCGCT AGAACATGCA AAAAGCTTAT
3721 GTACTAAAAA TAATAAAATA GTTAAATCTG TTAAACTATC ACAATCTCTC TTTAAGTCAT
3781 CTAACAATAT TTCTGTGATA TTAGAACCAG AATATAAAGA CAAATTAGTG ACTCCTCTTA
3841 TTATTGTAGA AGGTGAAGGA AAAATATACC ATAATAAGAA TGATAGTTTT AATCGTGAAG
3901 AACCGTATTT TCTAAAAATA CGACCTACGT TAATGAATCC TATATTATAT CAGATTATGG
3961 AA
```

Figure 61B

1 GCCCTTAACA GAAGTCCAGA ACTTTTTAAG ATTAAAGATA GAATTAAAGG ATTACGTACA
61 AGATTTGTTA TGTTCGGTTT CTGTTATATG TTCCATTGGA AATGTTTGAT ATATGATAGA
121 GAAAACGATT TTGTATGTTT CTATGATTCA GGAGGATCTA ATCCAAATGA CTTTGATCAC
181 TATGATAATT TTTTCTACTA TAGTCATTCG AGAGGATTCA ATAGAAATTC TAAGAGGTCA
241 TCTAGCTTAT CTAATGAAAA TGCAGATATA GATATTCTGT TCAACTTTTT CGTGGATAAT
301 TACGAAGTTA CTTCAGGATG TATAAACGTA GAAGTCAATC AGCTGATGGA ATCAGAATGT
361 GGTATGTTTA CTTGTTTGTT TATGACTATG TGCTGTCTCC ATCCTCCTAA AGGATTTAAA
421 GGGATAAGAA AGACATATAC CTATTTTAAG TTTTTAGCCG ATAAAAAAAT GACTATGCTA
481 AAGTCTATAC TTTTCAACGC TGACAAGATG GAATTTAAAG TGAAAGAATC AAGCAGTAAA
541 GGCATACAAG AATATAAAAA AATGGAAGAG TGGTGTGGTA AAACTATAAA CATTTTAGCT
601 GATAAAATAA CAACACGTGT AAATAGTATA ATAGAGTAGT AAAATGGATA ATTTTATAAA
661 GCAGATATCG TCAAAGATAG TAAAACCTAT AGCAGAATTA GAACCTCCAG ATTCTAAAGT
721 ACAATATTAT TACATGACTA TATCGTTTAA TTTTCCTGAC TTATATTATT GTAATAAAAA
781 TTTATTTGCG AAACCCGATA ATACTTTGCT AGATGTTTCT AAGTCTTTGC TTACTTTAAA
841 CTCATTTCCG TATGAAAACT TTGTGATAAA TGATTTACTA AGAACTATTA GGCGTTACTG
901 TCACGTATAT GATGTCTATT TTTTACCCGT AGGTGGTTTG TAGGAAAAGA AGATGTATTA
961 CCCAATTACC AAGTATCGAT AAAAATAATA AGAAGTACTA ATCAAGAAGT AATAGAAAAC
1021 ATTATTAGGA ATTATTTATC ACGACACGGT ATTTATGGAG ATAACCTATC TATAGAAACA
1081 GACCGATTAA ACGAAGTATC TATAAACAGA CATTCTATTG TAGGAGCTAG ACAGTTAGCA
1141 CCTATATGCG TTGTTTCTTT TTATCCTTTC GACCCTGAAA ATAAAATACT TTTCGTTATA
1201 TATGTAGGTA GATACAAAGA CAGACATTGC GGTGTATCTT ATGTAGTTGA TAGAGAGGAT
1261 ATGTATAAAG TAATTAACAG AATATATTCT TACGTAGTTT GTATTTATCT AGTTTCCGAT
1321 GATATGGTCA CGTTTCATAC TACTCCTCTA GCTAATCACA GTAAAAAATT AATACCGTTA
1381 CCCATAAATC ATTGCAATAC CTTATGCGAG ATAGTTCACG ACTTTGAGTT TTTGAGATTT
1441 GAGCAATCCA CTATGCCAAT ACCCGTTTTC ACTCCTTTTA TTCCTAAACA GCTAGTTAAT
1501 ATAATCAACT TACCTGATGA TATACCTATT ACTTGTGCAT CAATAAACAG ATTAGAATAT
1561 GTTACACATA TAGATGATAA AAAATTAAAA AGAGTACTGA TTATCGTAAA GGATAAATTT
1621 CTTAGAAATA CTATTCTTCA CGGTACATTT AAAAAAAGGA ATATAGTCAG AAACAGGAAA
1681 TATACTTTCA CTATAACATG GTCTAATTTC GAATGTCCGA CGTTAGGAGA CGTTAAGTCT
1741 TCTTCACCTA ATACCTGTAA TAGAGTAGTT TTAGACGGTA GTAGATACGT TACAAAAACC
1801 TTTAATGATA CAATATAAAT GGAACTAACT AGAGAAACGC TGATATTTGT AGGCATTACT
1861 GTACTAGTAG TAGTAATGAT CATATCTGGT TTCTCACTAA TATTGCGATT GATACCTGGT
1921 GTATATTCAT CAGTTATTAG ATCGTCGTTC GTAGGAGGGA AAATATTAAG ATTTATGGAG
1981 GTATTCTCTA CTGTTATGTT TATACCATCA TTAGTAATAC TTTATACAGC ATATATAAGG
2041 AAATCTAAAG TGAAAAATAA CTAAATATTA TAGTATTTGT AATAAGTACT AATTAGCTAT
2101 AAAAACCCGG GCTCGAGATA AAAATTACTG GTCAGCCTTG CTTCTAGTCA CCATAGGGTG
2161 GGTACTCTTA CCTCCAGAGG CGGTGGGTTC CTCAGCACCA TCCTCCTCTT CCTCTGGGGC
2221 AACTTCCTCT ATCTCAGACA CTGGCTCAGA CTTGACAGAC ACAGTGTCCT CCCGCTCCTC
2281 CTGAGCACCC TCCTCCTCTT CCTCATCACT CTGCTCACTT TCTTCCTGAT CACTGTTCTC
2341 AGCCACAATT ACTGAGGACA GAGGGATAGT CGCGGGTACA GGGGACTCTG GGGGTGACAC
2401 CAGAGAATCA GAGGAGCTGA CACCAGCGGT GGCCAAAGTG TAGGCTACAA TAGCCTCTTC
2461 CTCATCTGAC TCCTCGGCGA TGGCCCGTAG GTCATCCACA CTAGGAGAGC AGACTCTCAG
2521 AGGATCGGCC CCCAGAATGT ACTGGGCAAA GACCTTCATG CAGATCTCCT CAATGCGGCG
2581 CTTCATTACA CTGATAACCT CAGGCTTGGT TATCAGAGGC CGCTTGGCCA GCATCACACT
2641 AGTCTCCTCT AAGACATAGC AGCACAGCAC CCGACAGAAC TCACTTAAGA GAGAGATGCC
2701 CCCGTACATG GTCATCATAC AAGCGTCACT AGTGACCTTG TACTCATTAC ACATTGTTTC
2761 CACACATGTA GTGAGGATAT CCATAAATAT GTGATCAATG TGCGTGAGCA CCTTGTCTCT
2821 CTCCTCATCC AAAATCTTAA ATATTTTCTG GGCATAAGCC ATAATCTCAT CAGGGGAGCA
2881 CTGAGGCAAG TTCTGCAGTG CCGCCATGGC CTGACTGCAG CCATTGGTGG TCTTAGGGAA
2941 GGCTGAGTTC TTGGTAAAGA ACTCTATATT CCTGTAGCAC ATATACATCA TCTTTCTCCT
3001 AAGTTCATCC TTTTTAGCAC GGGCCTTAGC CTGCAGTGCA CCCCCCAACT TGTTAGCGGC
3061 GCCCTTGCTC ACATCATGCA GCTCCTTAAT ACAAGCCATC CACATCTCCC GCTTATCCTC

Figure 62A

```
3121 AGGTACAATG TAGTTCTCAT ACATGCTCTG CATAGTTAGC CCAATACACT TCATCTCCTC
3181 GAAAGGCTCA TGAACCTTAT CTAAGATATC TAAGGCATTC TGCAAACATC CTCCCATCAT
3241 ATTAAAGGCG CCAGTGAATT TCTCTTCCGT CTGGGTATAT TTTTTCAGCA TGTGCTCCTT
3301 GATTCTATGC CGCACCATGT CCACTCGAAC CTTAATCTGT TTCATTACGA TACAAACTTA
3361 ACGGATATCG CGATAATGAA ATAATTTATG ATTATTTCTC GCTTTCAATT TAACACAACC
3421 CTCAAGAACC TTTGTATTTA TTTTCACTTT TTAAGTATAG AATAAAGAAG GATCCTTCTT
3481 TATTCTATAC TTAAAAAGTG AAAATAAATA CAAAGGTTCT TGAGGGTTGT GTTAAATTGA
3541 AAGCGAGAAA TAATCATAAA TTATTTCATT ATCGCGATAT CCGTTAAGTT TGTATCGTAA
3601 TGTGCCGCCG CCCGGATTGC GGCTTCTCTT TCTCACCTGG ACCGGTGGCA CTGCTGTGGT
3661 GTTGCCTTCT GCTGCCCATC GTTTCCTCAG CCACCGTCAG CGTCGCTCCT ACCGTCGCCG
3721 AGAAAGTTCC CGCGGAGTGC CCCGAACTAA CGCGTCGATG CCTGTTGGGT GAGGTGTTTC
3781 AGGGTGACAA GTATGAAAGT TGGCTGCGCC CGTTGGTGAA TGTTACCAGA CGCGATGGCC
3841 CGCTATCGCA ACTTATTCGT TACCGTCCCG TTACGCCGGA GGCCGCCAAC TCCGTGCTGT
3901 TGGACGATGC TTTCCTGGAC ACTCTGGCCC TGCTGTACAA CAATCCGGAT CAATTGCGGG
3961 CCTTGCTGAC GCTGTTGAGC TCGGACACAG CGCCGCGCTG GATGACGGTG ATGCGCGGTT
4021 ACAGCGAGTG CGGCGATGGC TCGCCGGCCG TGTACACGTG CGTGGACGAC CTGTGCCGCG
4081 GCTACGACCT CACGCGACTG TCATACGGGC GCAGCATCTT CACGGAACAC GTGTTAGGCT
4141 TCGAGCTGGT GCCACCGTCT CTCTTTAACG TGGTGGTGGC CATACGCAAC GAAGCCACGC
4201 GTACCAACCG CGCCGTGCGT CTGCCCGTGA GCACCGCTGC CGCGCCCGAG GGCATCACGC
4261 TCTTTTACGG CCTGTACAAC GCAGTGAAGG AATTCTGCCT GCGTCACCAG CTGGACCCGC
4321 CGCTGCTACG CCACCTAGAT AAATACTACG CCGGACTGCC GCCCGAGCTG AAGCAGACGC
4381 GCGTCAACCT GCCGGCTCAC TCGCGCTATG GCCCTCAAGC AGTGGATGCT CGCTAATTTT
4441 TATAGATCCC TCGAGGGTAC CGCATGCCCT TTTTATTGAC TAGTTAATCA GTCTAATATA
4501 CGTACTAAAT ACTTGTACGT ACAACTATGT TAGAATAATT TGCTTAGTAT AGTATATAAA
4561 CAAGTATGTA AAAAATAAAA TTGATATAAA AGTAGTCTTC TATTCCGAAC AATAACTATA
4621 CAAAATGGAT TTAGATATTA AATCTTGCAG AAGTATTTAC AAAATATGGG ATAAATATCA
4681 TTTTATGACA GGGTATAAAT ATAAAAATGA TAAACAGAGA TTTAAAATTA CAATTTACTG
4741 TAAATGTGAT TGTTCTATCA AAGAATATCC TTATAGATTT GTTACTGAGA AACTGCTTTT
4801 AATGTATATT ATTAATAAGT TTAGAGGAAA GTATCTAATC AAAATTAGGA TAGAACCCAT
4861 AGTTAAAAAT TAAATCATAT ATCAATACAT GTCAGTTTTT TATCGAAAAA TGGATTTATA
4921 AATAAAATGA AAAATAACTT GAATGAAGGA AAAAATAACC ATGAGTAAAA AACCAGTAAA
4981 GACGGTCCAG CGTAGACGTG GAAACGATGA GGATAATAAG TTTACTTGTA TCCAAGCGCT
5041 AGAACATGCA AAAAGCTTAT GTACTAAAAA TAATAAAATA GTTAAATCTG TTAAACTATC
5101 ACAATCTCTC TTTAAGTCAT CTAACAATAT TTCTGTGATA TTAGAACCAG AATATAAAGA
5161 CAAATTAGTG ACTCCTCTTA TTATTGTAGA AGGTGAAGGA AAAATATACC ATAATAAGAA
5221 TGATAGTTTT AATCGTGAAG AACCGTATTT TCTAAAAATA CGACCTACGT TAATGAATCC
5281 TATATTATAT CAGATTATGG AA
```

Figure 62B

```
   1 ATGCGGCCAG GCCTCCCCTC CTACCTCATC GTCCTCGCCG TCTGTCTCCT CAGCCACCTA
  61 CTTTCGTCAC GATATGGCGC AGAAGCCATA TCCGAACCGC TGGACAAAGC GTTTCACCTA
 121 CTGCTCAACA CCTACGGGAG ACCCATCCGC TTCCTGCGTG AAAACACCAC CCAGTGTACC
 181 TACAATAGCA GCCTCCGTAA CAGCACGGTC GTCAGGGAAA ACGCCATCAG TTTCAACTTT
 241 TTCCAAAGCT ATAATCAATA CTATGTATTC CATATGCCTC GATGTCTTTT TGCGGGTCCT
 301 CTGGCGGAGC AGTTTCTGAA CCAGGTAGAT CTGACCGAAA CCCTGGAAAG ATACCAACAG
 361 AGACTTAACA CTTACGCGCT GGTATCCAAA GACCTGGCCA GCTACCGATC TTTTTCGCAG
 421 CAGCTAAAGG CACAGGACAG CCTAGGTGAA CAGCCCACCA CTGTGCCACC ACCCATTGAC
 481 CTGTCAATAC CTCACGTTTG GATGCCACCG CAAACCACTC CACACGGCTG GACAGAATCA
 541 CATACCACCT CAGGACTACA CCGACCACAC TTTAACCAGA CCTGTATCCT CTTTGATGGA
 601 CACGATCTAC TATTCAGCAC CGTCACACCT TGTTTGCACC AAGGCTTTTA CCTCATCGAC
 661 GAACTACGTT ACGTTAAAAT AACACTGACC GAGGACTTCT TCGTAGTTAC GGTGTCCATA
 721 GACGACGACA CACCCATGCT GCTTATCTTC GGCCATCTTC CACGCGTACT CTTTAAAGCG
 781 CCCTATCAAC GCGACAACTT TATACTACGA CAAACTGAAA AACACGAGCT CCTGGTGCTA
 841 GTTAAGAAAG ATCAACTGAA CCGTCACTCT TATCTCAAAG ACCCGGACTT TCTTGACGCC
 901 GCACTTGACT TCAACTACCT GGACCTCAGC GCACTACTAC GTAACAGCTT TCACCGTTAC
 961 GCCGTGGATG TACTCAAAAG CGGTCGATGT CAGATGCTGG ACCGCCGCAC GGTAGAAATG
1021 GCCTTCGCCT ACGCATTAGC ACTGTTCGCA GCAGCCCGAC AAGAAGAGGC CGGCGCCCAA
1081 GTCTCCGTCC CACGGGCCCT AGACCGCCAG GCCGCACTCT TACAAATACA AGAATTTATG
1141 ATCACCTGCC TCTCACAAAC ACCACCACGC ACCACGTTGC TGCTGTATCC CACGGCCGTG
1201 GACCTGGCCA AACGAGCCCT TTGGACACCG AATCAGATCA CCGACATCAC CAGCCTCGTA
1261 CGCCTGGTCT ACATACTCTC TAAACAGAAT CAGCAACATC TCATCCCCCA GTGGGCACTA
1321 CGACAGATCG CCGACTTTGC CCTAAAACTA CACAAAACGC ACCTGGCCTC TTTTCTTTCA
1381 GCCTTCGCGC GTCAAGAACT CTACCTCATG GGCAGCCTCG TCCACTCCAT GCTAGTACAT
1441 ACGACGGAGA GACGCGAAAT CTTCATCGTA GAAACGGGCC TCTGTTCATT AGCCGAGCTA
1501 TCACACTTTA CGCAGTTGCT AGCTCATCCG CACCACGAAT ACCTCAGCGA CCTGTACACA
1561 CCCTGTTCCA GTAGCGGGCG ACGCGATCAC TCGCTCGAAC GCCTCACACG TCTCTTCCCC
1621 GATGCCACCG TCCCCACTAC CGTTCCCGCC GCCCTCTCCA TCCTATCTAC CATGCAACCA
1681 AGCACGCTAG AAACCTTCCC CGACCTGTTT TGTCTGCCGC TCGGCGAATC CTTCTCCGCG
1741 CTGACCGTCT CCGAACACGT CAGTTATGTC GTAACAAACC AGTACCTGAT CAAAGGTATC
1801 TCCTACCCTG TCTCCACCAC CGTCGTAGGC CAGAGCCTCA TCATCACCCA GACGGACAGT
1861 CAAACTAAAT GCGAACTGAC GCGCAACATG CATACCACAC ACAGCATCAC AGCGGCGCTC
1921 AACATTTCCC TAGAAAACTG CGCCTTTTGC CAAAGCGCCC TACTAGAATA CGACGACACG
1981 CAAGGCGTCA TCAACATCAT GTACATGCAC GACTCGGACG ACGTCCTTTT CGCCCTGGAT
2041 CCCTACAACG AAGTGGTGGT CTCATCTCCG CGAACTCACT ACCTCATGCT TTTGAAAAAC
2101 GGTACGGTCC TAGAAGTAAC TGACGTCGTC GTGGACGCTA CCGACAGTCG T
```

Figure 63

1 AAGCTTGCGG CCGCTCATTA GACAAGCGAA TGAGGGACGA AAACGTGGAG GAGGTATTAA
61 GTTTGGAGAA ATGGAGAGAG ACTGTTTAAT AGCGCATGGC GCAGCCAATA CTATTACAGA
121 AGTTTTGAAA GATTCGGAAG AAGATTATCA AGATGTGTAT GTTTGTGAAA ATTGTGGAGA
181 CATAGCAGCA CAAATCAAGG GTATTAATAC ATGTCTTAGA TGTTCAAAAC TTAATCTCTC
241 TCCTCTCTTA ACAAAAATTG ATACCACGCA CGTATCTAAA GTATTTCTTA CTCAAATGAA
301 CGCCAGAGGC GTAAAAGTCA AATTAGATTT CGAACGAAGG CCTCCTTCGT TTTATAAACC
361 ATTAGATAAA GTTGATCTCA AGCCGTCTTT TCTGGTGTAA TAAAAATTAA TTAATTACTC
421 GAGATAAAAA TCAACGACTG TCGGTAGCGT CCACGACGAC GTCAGTTACT TCTAGGACCG
481 TACCGTTTTT CAAAAGCATG AGGTAGTGAG TTCGCGGAGA TGAGACCACC ACTTCGTTGT
541 AGGGATCCAG GGCGAAAAGG ACGTCGTCCG AGTCGTGCAT GTACATGATG TTGATGACGC
601 CTTGCGTGTC GTCGTATTCT AGTAGGGCGC TTTGGCAAAA GGCGCAGTTT TCTAGGGAAA
661 TGTTGAGCGC CGCTGTGATG CTGTGTGTGG TATGCATGTT GCGCGTCAGT TCGCATTTAG
721 TTTGACTGTC CGTCTGGGTG ATGATGAGGC TCTGGCCTAC GACGGTGGTG GAGACAGGGT
781 AGGAGATACC TTTGATCAGG TACTGGTTTG TTACGACATA ACTGACGTGT TCGGAGACGG
841 TCAGCGCGGA GAAGGATTCG CCGAGCGGCA GACAAAACAG GTCGGGGAAG GTTTCTAGCG
901 TGCTTGGTTG CATGGTAGAT AGGATGGAGA GGGCGGCGGG AACGGTAGTG GGGACGGTGG
961 CATCGGGGAA GAGACGTGTG AGGCGTTCGA GCGAGTGATC GCGTCGCCCG CTACTGGAAC
1021 AGGGTGTGTA CAGGTCGCTG AGGTATTCGT GGTGCGGATG AGCTAGCAAC TGCGTAAAGT
1081 GTGATAGCTC GGCTAATGAA CAGAGGCCCG TTTCTACGAT GAAGATTTCG CGTCTCTCCG
1141 TCGTATGTAC TAGCATGGAG TGGACGAGGC TGCCCATGAG GTAGAGTTCT TGACGCGCGA
1201 AGGCTGAAAG AAAAGAGGCC AGGTGCGTTT TGTGTAGTTT TAGGGCAAAG TCGGCGATCT
1261 GTCGTAGTGC CCACTGGGGG ATGAGATGTT GCTGATTCTG TTTAGAGAGT ATGTAGACCA
1321 GGCGTACGAG GCTGGTGATG TCGGTGATCT GATTCGGTGT CCAAAGGGCT CGTTTGGCCA
1381 GGTCCACGGC CGTGGGATAC AGCAGCAACG TGGTGCGTGG TGGTGTTTGT GAGAGGCAGG
1441 TGATCATAAA TTCTTGTATT TGTAAGAGTG CGGCCTGGCG GTCTAGGGCC CGTGGGACGG
1501 AGACTTGGGC GCCGGCCTCT TCTTGTCGGG CTGCTGCGAA CAGTGCTAAT GCGTAGGCGA
1561 AGGCCATTTC TACCGTGCGG CGGTCCAGCA TCTGACATCG ACCGCTTTTG AGTACATCCA
1621 CGGCGTAACG GTGAAAGCTG TTACGTAGTA GTGCGCTGAG GTCCAGGTAG TTGAAGTCAA
1681 GTGCGGCGTC AAGAAAGTCC GGGTCTTTGA GATAAGAGTG ACGGTTCAGT TGATCTTTCT
1741 TAACTAGCAC CAGGAGCTCG TGTTTTTCAG TTTGTCGTAG TATAAAGTTG TCGCGTTGAT
1801 AGGGCGCTTT AAAGAGTACG CGTGGAAGAT GGCCGAAGAT AAGCAGCATG GGTGTGTCGT
1861 CGTCTATGGA CACCGTAACT ACGAAGAAGT CCTCGGTCAG TGTTATTTTA ACGTAACGTA
1921 GTTCGTCGAT GAGGTAAAAG CCTTGGTGCA AACAAGGTGT GACGGTGCTG AATAGTAGAT
1981 CGTGTCCATC AAAGAGGATA CAGGTCTGGT TAAAGTGTGG TCGGTGTAGT CCTGAGGTGG
2041 TATGTGATTC TGTCCAGCCG TGTGGAGTGG TTTGCGGTGG CATCCAAACG TGAGGTATTG
2101 ACAGGTCAAT GGGTGGTGGC ACAGTGGTGG GCTGTTCACC TAGGCTGTCC TGTGCCTTTA
2161 GCTGCTGCGA AAAAGATCGG TAGCTGGCCA GGTCTTTGGA TACCAGCGCG TAAGTGTTAA
2221 GTCTCTGTTG GTATCTTTCC AGGGTTTCGG TCAGATCTAC CTGGTTCAGA AACTGCTCCG
2281 CCAGAGGACC CGCAAAAAGA CATCGAGGCA TATGGAATAC ATAGTATTGA TTATAGCTTT
2341 GGAAAAAGTT GAAACTGATG GCGTTTTCCC TGACGACCGT GCTGTTACGG AGGCTGCTAT
2401 TGTAGGTACA CTGGGTGGTG TTTTCACGCA GGAAGCGGAT GGGTCTCCCG TAGGTGTTGA
2461 GCAGTAGGTG AAACGCTTTG TCCAGCGGTT CGGATATGGC TTCTGCGCCA TATCGTGACG
2521 AAAGTAGGTG GCTGAGGAGA CAGACGGCGA GGACGATGAG GTAGGAGGGG AGCCCGGGCC
2581 GCATTTTATA TTGTAATTAT ATATTTTCAA TTTTGAAATC CCAAAATATT ATCATATTCT
2641 TCCCAATAAA CTCGAGGGTA CCGGATCCTT CTTTATTCTA TACTTAAAAA GTGAAAATAA
2701 ATACAAAGGT TCTTGAGGGT TGTGTTAAAT TGAAAGCGAG AAATAATCAT AAATTATTTC
2761 ATTATCGCGA TATCCGTTAA GTTTGTATCG TAATGTGCCG CCGCCCGGAT TGCGGCTTCT
2821 CTTTCTCACC TGGACCGGTG GCACTGCTGT GGTGTTGCCT TCTGCTGCCC ATCGTTTCCT
2881 CAGCCACCGT CAGCGTCGCT CCTACCGTCG CCGAGAAAGT TCCCGCGGAG TGCCCCGAAC
2941 TAACGCGTCG ATGCCTGTTG GGTGAGGTGT TTCAGGGTGA CAAGTATGAA AGTTGGCTGC
3001 GCCCGTTGGT GAATGTTACC AGACGCGATG GCCCGCTATC GCAACTTATT CGTTACCGTC
3061 CCGTTACGCC GGAGGCCGCC AACTCCGTGC TGTTGGACGA TGCTTTCCTG GACACTCTGG

Figure 64A

```
3121 CCCTGCTGTA CAACAATCCG GATCAATTGC GGGCCTTGCT GACGCTGTTG AGCTCGGACA
3181 CAGCGCCGCG CTGGATGACG GTGATGCGCG GTTACAGCGA GTGCGGCGAT GGCTCGCCGG
3241 CCGTGTACAC GTGCGTGGAC GACCTGTGCC GCGGCTACGA CCTCACGCGA CTGTCATACG
3301 GGCGCAGCAT CTTCACGGAA CACGTGTTAG GCTTCGAGCT GGTGCCACCG TCTCTCTTTA
3361 ACGTGGTGGT GGCCATACGC AACGAAGCCA CGCGTACCAA CCGCGCCGTG CGTCTGCCCG
3421 TGAGCACCGC TGCCGCGCCC GAGGGCATCA CGCTCTTTTA CGGCCTGTAC AACGCAGTGA
3481 AGGAATTCTG CCTGCGTCAC CAGCTGGACC CGCCGCTGCT ACGCCACCTA GATAAATACT
3541 ACGCCGGACT GCCGCCCGAG CTGAAGCAGA CGCGCGTCAA CCTGCCGGCT CACTCGCGCT
3601 ATGGCCCTCA AGCAGTGGAT GCTCGCTAAT TTTTATAGAT CCCCCGGGAA TCGATTCGCG
3661 ATAGCTGATT AGTTTTTGTT AACAAAAATG TGGGAGAATC TAATTAGTTT TTCTTTACAC
3721 AATTGACGTA CATGAGTCTG AGTTCCTTGT TTTTGCTAAT TATTTCATCC AATTTATTAT
3781 TCTTGACGAT ATCGAGATCT TTTGTATAGG AGTCAGACTT GTATTCAACA TGCTTTTCTA
3841 TAATCATCTT AGTTATTTCG GCATCATCCA ATAGTACATT TTCCAGATTA ACAGAGTAGA
3901 TATTAATGTC GTATTTGAAC AGAGCCTGTA ACATCTCAAT GTCTTTATTA TCTATAGCCA
3961 ATTTAATGTC CGGAATGAAG AGAAGGGAAT TATTGGTGTT TGTCGACGTC ATATAGTCGA
4021 GCAAGAGAAT CATCATATCC ACGTGTCCAT TTTTTATAGT GGTGTGAATA CAACTAAGGA
4081 GAATAGCCAG ATCAAAAGTA GATGGTATTT CTGAAAGAAA GTATGATACA ATACTTACAT
4141 CATTAAGCAT GACGGCATGA TAAAATGAAG TTTTCCATCC AGTTTTCCCA TAGAACATCA
4201 GTCTCCAATT TTTCTTAAAC AGTTTCACCG TTTGCATGTT ACCACTATCA ACCGCATAAT
4261 ACAATGCGGT GTTTCCTTTG TCATCAAATT GTGAATCATC CATTCCACTG AATAGCAAAA
4321 TCTTTACTAT TTTGGTATCT TCTAATGTGG CTGCCTGATG TAATGGAAAT TCATTCTCTA
4381 GAAGATTTTT CAATGCTCCA GCGTTCAACA ACGTACATAC TAGACGCACG TTATTATCAG
4441 CTATTGCATA ATACAAGGCA CTATGTCCAT GGACATCCGC CTTAAATGTA TCTTTACTAG
4501 AGAGAAAGCT TTTCAGCTGC TTAGACTTCC AAGTATTAAT TCGTGACAGA TCCATGTCTG
4561 AAACGAGACG CTAATTAGTG TATATTTTTT CATTTTTTAT AATTTTGTCA TATTGCACCA
4621 GAATTAATAA TATCTCTAAT AGATCTAATT TAATTTAATT TATATAACTT ATTTTTTGAA
4681 TATACTTTTA ATTAACAAAA GAGTTAAGTT ACTCATATGG ACGCCGTCCA GTCTGAACAT
4741 CAATCTTTTT AGCCAGAGAT ATCATAGCCG CTCTTAGAGT TTCAGCGTGA TTTTCCAACC
4801 TAAATAGAAC TTCATCGTTG CGTTTACAAC ACTTTTCTAT TTGTTCAAAC TTTGTTGTTA
4861 CATTAGTAAT CTTTTTTTCC AAATTAGTTA GCCGTTGTTT GAGAGTTTCC TCATTGTCGT
4921 CTTCATCGGC TTTAACAATT GCTTCGCGTT TAGCCTCCTG GCTGTTCTTA TCAGCCTTTG
4981 TAGAAAAAAA TTCAGTTGCT GGAATTGCAA GATCGTCATC TCCGGGGAAA AGAGTTCCGT
5041 CCATTTAAAG CCGCGGGAAT TC
```

Figure 64B

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTATGACAA TAAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGGTGTTGA GAGACGACTA CAAAATAGTG
1021 AAAGATCTGT TGAAGAATAA CTATGTAAAC AATGTTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAAGCTG TTAATCGATC ATGGAGCTGA TGTAAACTCT TTAACTATTG
2581 CTAAAGATAA TCTTATTAAA AAAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAATAGGA TGTAAGAACT TACTAGAATG TTTTATCAAT AATGATATGA ATACAGTATC
2821 TAGGGCTATA AACAATGAAA CGATTAAAAA TTATAAAAAT CATTTCCCTA TATATAATAC
2881 GCTCATAGAA AAATTCATTT CTGAAAGTAT ACTAAGACAC GAATTATTGG ATGGAGTTAT
2941 AAATTCTTTT CAAGGATTCA ATAATAAATT GCCTTACGAG ATTCAGTACA TTATACTGGA
3001 GAATCTTAAT AACCATGAAC TAAAAAAAAT TTTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

Figure 65

```
   1 GGTACGTGACTAATTAGCTATAAAAAGGATCTTAATTAATTAGTCATCAGGCAGGGCGAG
  61 AACGAGACTATCTGCTCGTTAATTAATTAGGTCGACGGATCCCCCGGGTTCTTTATTCTA
 121 TACTTAAAAAGTGAAAATAAATACAAAGGTTCTTGAGGGTTGTGTTAAATTGAAAGCGAG
 181 AAATAATCATAAATTATTTCATTATCGCGATATCCGTTAAGTTTGTATCGTAATGGAGGA
 241 GCCGCAGTCAGATCCTAGCGTCGAGCCCCCTCTGAGTCAGGAAACATTTTCAGACCTATG
 301 GAAACTACTTCCTGAAAACAACGTTCTGTCCCCCTTGCCGTCCCAAGCAATGGATGATTT
 361 GATGCTGTCCCCGGACGATATTGAACAATGGTTCACTGAAGACCCAGGTCCAGATGAAGC
 421 TCCCAGAATGCCAGAGGCTGCTCCCCGCGTGGCCCCTGGACCAGCAGCTCCTACACCGGC
 481 GGCCCCTGCACCAGCCCCCTCCTGGCCCCTGTCATCTTCTGTCCCTTCCCAGAAAACCTA
 541 CCAGGGCAGCTACGGTTTCCGTCTGGGCTTCTTGCATTCTGGGACAGCCAAGTCTGTGAC
 601 TTGCACGTACTCCCCTGCCCTCAACAAGATGTTTTGCCAACTGGCCAAGACCTGCCCTGT
 661 GCAGCTGTGGGTTGATTCCACACCCCCGCCCGGCACCCGCGTCCGCGCCATGGCCATCTA
 721 CAAGCAGTCACAGCACATGACGGAGGTTGTGAGGCGCTGCCCCCACCATGAGCGCTGCTC
 781 AGATAGCGATGGTCTGGCCCCTCCTCAGCATCTTATCCGAGTGGAAGGAAATTTGCGTGT
 841 GGAGTATTTGGATGACAGAAACACTTTTCGACATAGTGTGGTGGTGCCCTATGAGCCGCC
 901 TGAGGTTGGCTCTGACTGTACCACCATCCACTACAACTACATGTGTAACAGTTCCTGCAT
 961 GGGCGGCATGAACCGGAGGCCCATCCTCACCATCATCACACTGGAAGACTCCAGTGGTAA
1021 TCTACTGGGACGGAACAGCTTTGAGGTGCGTGTTTGTGCCTGTCCTGGGAGAGACCGGCG
1081 CACAGAGGAAGAGAATCTCCGCAAGAAAGGGGAGCCTCACCACGAGCTGCCCCCAGGGAG
1141 CACTAAGCGAGCACTGCCCAACAACACCAGCTCCTCTCCCCAGCCAAAGAAGAAACCACT
1201 GGATGGAGAATATTTCACCCTTCAGATCCGTGGGCGTGAGCGCTTCGAGATGTTCCGAGA
1261 GCTGAATGAGGCCTTGGAACTCAAGGATGCCCAGGCTGGGAAGGAGCCAGGGGGGAGCAG
1321 GGCTCACTCCAGCCACCTGAAGTCCAAAAAGGGTCAGTCTACCTCCCGCCATAAAAAACT
1381 CATGTTCAAGACAGAAGGGCCTGACTCAGACTGAACGCGTTTTTATCCCGGGCTCGAGTC
1441 TAGAATCGATCCCGGGTTTTTATGACTAGTTAATCACGGCCGC
```

Figure 66

```
1    ATGACTGCCATGGAGGAGTCACAGTCGGATATCAGCCTCGAGCTCCCTCTGAGCCAGGAG
61   ACATTTTCAGGCTTATGGAAACTACTTCCTCCAGAAGATATCCTGCCATCACCTCACTGC
121  ATGGACGATCTGTTGCTGCCCCAGGATGTTGAGGAGTTTTTTGAAGGCCCAAGTGAAGCC
181  CTCCGAGTGTCAGGAGCTCCTGCAGCACAGGACCCTGTCACCGAGACCCCTGGGCCAGTG
241  GCCCCTGCCCCAGCCACTCCATGGCCCCTGTCATCTTTTGTCCCTTCTCAAAAAACTTAC
301  CAGGGCAACTATGGCTTCCACCTGGGCTTCCTGCAGTCTGGGACAGCCAAGTCTGTTATG
361  TGCACGTACTCTCCTCCCCTCAATAAGCTATTCTGCCAGCTGGCGAAGACGTGCCCTGTG
421  CAGTTGTGGGTCAGCGCCACACCTCCAGCTGGGAGCCGTGTCCGCGCCATGGCCATCTAC
481  AAGAAGTCACAGCACATGACGGAGGTCGTGAGACGCTGCCCCCACCATGAGCGCTGCTCC
541  GATGGTGATGGCCTGGCTCCTCCCCAGCATCTTATCCGGGTGGAAGGAAATTTGTATCCC
601  GAGTATCTGGAAGACAGGCAGACTTTTCGCCACAGCGTGGTGGTACCTTATGAGCCACCC
661  GAGGCCGGCTCTGAGTATACCACCATCCACTACAAGTACATGTGTAATAGCTCCTGCATG
721  GGGGGCATGAACCGCCGACCTATCCTTACCATCATCACACTGGAAGACTCCAGTGGGAAC
781  CTTCTGGGACGGACAGCTTTGAGGTTCGTGTTTGTGCCTGCCCTGGGAGAGACCGCCGT
841  ACAGAAGAAGAAAATTTCCGCAAAAAGGAAGTCCTTTGCCCTGAACTGCCCCCAGGGAGC
901  GCAAAGAGAGCGCTGCCCACCTGCACAAGCGCCTCTCCCCCGCAAAAGAAAAAACCACTT
961  GATGGAGAGTATTTCACCCTCAAGATCCGCGGGCGTAAACGCTTCGAGATGTTCCGGGAG
1021 CTGAATGAGGCCTTAGAGTTAAAGGATGCCCATGCTACAGAGGAGTCTGGAGACAGCAGG
1081 GCTCACTCCAGCTACCTGAAGACCAAGAAGGGCCAGTCTACTTCCCGCCATAAAAAAACA
1141 ATGGTCAAGAAAGTGGGGCCTGACTCAGACTGA
```

Figure 67

1 ATGGAGGAGCCGCAGTCAGATCCTAGCGTCGAGCCCCCTCTGAGTCAGGAAACATTTTCA
61 GACCTATGGAAACTACTTCCTGAAAACAACGTTCTGTCCCCCTTGCCGTCCCAAGCAATG
121 GATGATTTGATGCTGTCCCCGGACGATATTGAACAATGGTTCACTGAAGACCCAGGTCCA
181 GATGAAGCTCCCAGAATGCCAGAGGCTGCTCCCCGCGTGGCCCCTGCACCAGCAGCTCCT
241 ACACCGGCGGCCCCTGCACCAGCCCCCTCCTGGCCCCTGTCATCTTCTGTCCCTTCCCAG
301 AAAACCTACCAGGGCAGCTACGGTTTCCGTCTGGGCTTCTTGCATTCTGGGACAGCCAAG
361 TCTGTGACTTGCACGTACTCCCCTGCCCTCAACAAGATGTTTTGCCAACTGGCCAAGACC
421 TGCCCTGTGCAGCTGTGGGTTGATTCCACACCCCCGCCCGGCACCCGCGTCCGCGCCATG
481 GCCATCTACAAGCAGTCACAGCACATGACGGAGGTTGTGAGGCGCTGCCCCCACCATGAG
541 CGCTGCTCAGATAGCGATGGTCTGGCCCCTCCTCAGCATCTTATCCGAGTGGAAGGAAAT
601 TTGCGTGTGGAGTATTTGGATGACAGAAACACTTTTCGACATAGTGTGGTGGTGCCCTAT
661 GAGCCGCCTGAGGTTGGCTCTGACTGTACCACCATCCACTACAACTACATGTGTAACAGT
721 TCCTGCATGGGCGGCATGAACCGGAGGCCCATCCTCACCATCATCACACTGGAAGACTCC
781 AGTGGTAATCTACTGGGACGGAACAGCTTTGAGGTGCGTGTTTGTGCCTGTCCTGGGAGA
841 GACCGGCGCACAGAGGAAGAGAATCTCCGCAAGAAAGGGGAGCCTCACCACGAGCTGCCC
901 CCAGGGAGCACTAAGCGAGCACTGCCCAACAACACCAGCTCCTCTCCCCAGCCAAAGAAG
961 AAACCACTGGATGGAGAATATTTCACCCTTCAGATCCGTGGGCGTGAGCGCTTCGAGATG
1021 TTCCGAGAGCTGAATGAGGCCTTGGAACTCAAGGATGCCCAGGCTGGGAAGGAGCCAGGG
1081 GGGAGCAGGGCTCACTCCAGCCACCTGAAGTCCAAAAAGGGTCAGTCTACCTCCCGCCAT
1141 AAAAAACTCATGTTCAAGACAGAAGGCCTGACTCAGACTGA

Figure 68

```
   1 TATAAATCTC CTAACGCCGT TCGGGCAGTC ACAGTCTTCG GATCGGACGC CGTGGAACGC
  61 AGTTCTCAGC GAAGAAGGAC ACCGCCCGAC TCCAGAAGAC ACCGCTGCCC GAAGAAGAGA
 121 AGACTTCATC GGTAAGAGAC CCAGCTTCTC CTCCCCGGAG CTTCGGCCAC GCCGCTCCAC
 181 ACCCGGGAAC CGAGGCTTCG GAGCCCGATA CCCGGACAGA AGCTTCTCCC CGGCCGCTCC
 241 ACATCAGGGA GCCTTGACCG GCGAGCCTGC TATCCGGGTA GAGACTGTCC TGCGGCCGCT
 301 TCAGCAGCTC CACGATCGAC GACTGTGACC GTTGAGCCCG CCGTTTAGGC AGAGGCTCCG
 361 CTTCAACTAC CCTACCGACA CATTCGCGGT TCTTCCTCCA GAACATCTTA CCCTCTACTC
 421 GGCCACTCTA CAAGGACCGG TAATGGATCC AACTCTTTTC ACACAATCAA GACTTCTCAG
 481 AGTGAATGAT TATGATGAAG TGCGTGAGTC GGTAAATCAA CCGAGACAGG AACAGCAGCC
 541 AGGAGACAGG TGCCCTAGAC ATGTGGCAAG AATCATTGCC GAGAACGATC CTCCAATCAG
 601 ATGTGACCTG ACTCTCCAAG AGCTATTGAG TGAGGTGCAG GTGGATTTCG AACCATCGGC
 661 ATCAGAGGTC GTGGCAATGG AAGGCCTGAT GGACGAACAA CACTTCATTC CACATGATCC
 721 ACATTCTAAA AAAGCAGCCG TTCAAAGTCT TGTAATTGCC ATCAAGACCG CGGACCTCCT
 781 GTTGCAAATG ATACATGAGA ATGTTAAAAG AGACATCCGC ACGACATGCA TCCAAATGGC
 841 TAATGAATCT TATGCACGTG CGGACATAGT CAGAGATTCA CTGATAGCAG CATCGCAAGG
 901 AAAATACACA GCACTCGGGA AAATAGTATT CCACTCCTAT ACAAATTTCA TGCCAGTGAA
 961 TGCAAATGAG TCCGAAAAGA GAGCATGGAT GGAAATGCTA GGCGAGTGTA CCAGCCATGG
1021 AAACAAGCTG TGTGAGATGG CAAATGCGCA AGTAGAGCAG GAGACGCGCG ATATAATCAA
1081 TATAATGTTC AAAAATATAG ATGATGTAGT CACACAAACA ACAAGAGCAA TGAGAGGCGT
1141 GTTCGATCCA CCTGACACAG TTAAAGCTCT CTCTGCCGCA GCCCAACTGA TCAGAGTATG
1201 GGAACATGAT AACGTTATAA ATGACCAAAG TGTGTCAACA TCTTCTGTCG TAACGGCTGC
1261 ATTGGAGGCT AACGAGAATT TGGCAAAGGC ACTTAGAGAT GTGTCAGGGT ACGCTGAGGT
1321 GCAATTTAAC AGATTATGCC TTTCTATACT AACATCGGCA AAGGAACGAA TAGACATAAT
1381 CTATCATTCG GCAAGGTCCC AACACCTCGC GTGCAATGTC AGGATGAACG TGGCACAACA
1441 AAACCTAGCA ACTTTCATCC TAACGAATGC CAGAGAGAGG CCAAATGATG CTGTGATCAG
1501 AACACGCAGA GCAGTTGCAA ATACAGGTAT ACTGCTGTTC ACAGGACAAC ATATCACAAG
1561 AGATGCTTTA GATAAAGCTG CAGAGTCAAA AAGTGTAGAA GAAATTGTAG GGATGTCAGT
1621 ACAGGCTAGA CAAGCGCTAG TTGAACAAGA TATGCCTCCA CTAGAGGGAG AAGGTGAGGA
1681 AGCTAGAGAG GAACATGCCG GAGAAGGACA GGCTAGAGAA GGACAGGCCG AAGAAGAACA
1741 GGCCGGAGAA TCTGCGGGAG ATGAGTCCGA AGATGAAGAT GGCGAAGGAA GAAGGTCTCT
1801 GGTCCGTGTG ATCAACATTC CACTCGCGCA ACCTCAGCCG ATAGTGGCGC ACGAGCCTCC
1861 ACCTCAGCCC CAAGAATCGG ATGACAGCGA TACCGAATCT GATGGCGAAG ATCCAATCGC
1921 TAGGCAACAG AATCCCACAC CAACACAAGA GAGCGAACCC ATAACCGAAG ATCCTGAAGA
1981 CTGGCCGGAC GCTCAGAGAC TGATAGAAGA GGAATCTAGC CAAGAAACAC CCCAAGAACC
2041 GGCATCTGAG CAAGAACCAT CCACACCAGG TCCACGCACT AGGAGACGCT CACACCCCCC
2101 AACTGAAGGT TCAGCACCCA AGAGAGGCAG GAGATCATAA GGTGCCAACC AATATCAAAC
2161 CGATCGGGGT ACCAATCATA TAAATCATAA ATGCCAGGAT ACCAATCACA TAATCATATC
2221 AATATGCATC AATAAAATTT TATAATCATA CTCAGAGGGA ACTGCCCACC CTCAATTACC
2281 TATTGATTTT ACAATATATA ATGTAACTGC AATTAATAAA GTACACATGT ACATGA
```

Figure 69

```
   1 TATAAATCTC CTAACGCCGT TCGGGCAGTC ACAGTCTTCG GATCGGACGC CGTGGAACGC
  61 AGTTCTCAGC GAAGAAGGAC ACCGCCCGAC TCCAGAAGAC ACCGCTGCCC GAAGAAGAGA
 121 AGACTTCATC GGTAAGAGAC CCAGCTTCTC CTCCCCGGAG CTTCGGCCAC GCCGCTCCAC
 181 ACCCGGGAAC CGAGGCTTCG GAGCCCGATA CCCGGACAGA AGCTTCTCCC CGGCCGCTCC
 241 ACATCAGGGA GCCTTGACCG GCGAGCCTGC TATCCGGGTA GAGACTGTCC TGCGGCCGCT
 301 TCAGCAGCTC CACGATCGAC GACTGTGACC GTTGAGCCCG CCGTTTAGGC AGAGGCTCCG
 361 CTTCAACTAC CCTACCGACA CATTCGCGGT TCTTCCTCCA GAACATCTTA CCCTCTACTC
 421 GGCCACTCTA CAAGGACCGG TAATGGATCC AACTCTTTTC ACACAATCAA GACTTCTCAG
 481 AGTGAATGAT TATGATGAAG TGCGTGAGTC GGTAAATCAA CCGAGACAGG AACAGCAGCC
 541 AGGAGACAGG TGCCCTAGAC ATGTGGCAAG AATCATTGCC GAGAACGATC CTCCAATCAG
 601 ATGTGACCTG ACTCTCCAAG AGCTATTGAG TGAGGTGCAG GTGGATTTCG AACCATCGGC
 661 ATCAGAGGTC GTGGCAATGG AAGGCCTGAT GGACGAACAA CACTTCATTC CACATGATCC
 721 ACATTCTAAA AAAGCAGCCG GGCCTAACGT GAGGCATATA GACATTGTTA CCGCAGCCGC
 781 GTCGATGTCA GGGATATCCG GATCAACAGA GAGACCATTA GATGATGGAC AGAGACCCTT
 841 AGCTGATGGA TGTTATAGCA AGAAACATAA GAAGCAGAAA CACAGCGAAC CTATAGACAC
 901 CAAGGTGCAC ATCCAACGGG GGGAGGAAAC AGACTCTGAT TCAGACTCAG ACACCGGTAA
 961 ATCACCGGGA TGCGATGAAA TATCTTTTTA CTTGTCCAGT GCTTCGGATG ATGAACATGG
1021 CAATGGGAAT CGTTCTGGGT TAGAAGGAAA TTGTAGTTCA TATACTTCAC ATTCATCACG
1081 TAGATCAAAA TCGCCGCTAA GAAGTCCTTC AAACAGGCCC CAAAAGAGAA AATTATGTAA
1141 GAATATGTTT ATTACAAAAA GCAAACGTAG GGTAATATGT GAATCTGATT CAGATACAGA
1201 CTCCGAAATC GAGACCAGGC CATTTATCAG ACCACAAGAA CCTCCCAGAC AAAAGAATAA
1261 GGGGAAAAGA TGTCCCAAGA AACATAGAAA GATAAAAGAG CTCATGGATG GGCCAGGATT
1321 CGTGGCTCCG AATGCACACA AACGAGGTAA AAATAGAAAT GAGGGAAACA ACGATGGACG
1381 AGGGAAACCG ACCACACGAG CTTTAGAATA CAAACAGATG CCATACAAAC AGCAAACGGT
1441 CCAGTTTCTC TATGGAAATG CGATAAGGAC ATGTAGAGAG AGCACCGTAC ACGATAAAAT
1501 TATTATGGTG ATGTTTACAC GGGGTCAAGA TATCAGGCAG GCCATAGAAA AGTTGAGATC
1561 CCAACTTGGT CAAATAACCA ACCTTTCCAT ATCTGCTCCC TTCAACACAG AACACACAAA
1621 ACCACAGATA CACACACCAA ACACGGTTAA CATGACATCG CAGGCACTTG CGGCAGGTCT
1681 TCAAGCCTCC TGGAACCTAG ACGAGGATAA TAAACACAAT AATGCACCTA GGATGTCAGA
1741 TTACAGAACC ATGATAATCC AAGCGGCAAC ACCACCAGAT TTTCTAGGTG CACTCAAACT
1801 ATGCATACAG TTCGCACAAA CCTTTCCCAA GAATGCGTGT ATAAGGTTAT GTAATATAGT
1861 TGGAGGCCTA CAACCCCTTC CCATCTACGA AAAAGTCGTC ACCGCTTACA CTGACACGCA
1921 ATATAACTTT AGCCCAATCA CTAACAAAGA TAGTAACGGT GGTATGAGCA CAATATTGGA
1981 TCAGGACTCC GATTCAGAAT AATGAAGAAA CTATCATATT AAATCGTGTA CATATTTTAT
2041 TAAACACTAT TTCCAACCAT GAGACGAGGC TTGTTGATGC AGCTGCTGTT CCTTGGAATA
2101 AATGTAATAT ACTGT
```

Figure 70

1 AAGCTTGCGG CCGCTCATTA GACAAGCGAA TGAGGGACGA AAACGTGGAG GAGGTATTAA
61 GTTTGGAGAA ATGGAGAGAG ACTGTTTAAT AGCGCATGGC GCAGCCAATA CTATTACAGA
121 AGTTTTGAAA GATTCGGAAG AAGATTATCA AGATGTGTAT GTTTGTGAAA ATTGTGGAGA
181 CATAGCAGCA CAAATCAAGG GTATTAATAC ATGTCTTAGA TGTTCAAAAC TTAATCTCTC
241 TCCTCTCTTA ACAAAAATTG ATACCACGCA CGTATCTAAA GTATTTCTTA CTCAAATGAA
301 CGCCAGAGGC GTAAAAGTCA AATTAGATTT CGAACGAAGG CCTCCTTCGT TTTATAAACC
361 ATTAGATAAA GTTGATCTCA AGCCGTCTTT TCTGGTGTAA TAAAAATTAA TTAATTACTC
421 GAGATAAAAA TTATGATCTC CTGCCTCTCT TGGGTGCTGA ACCTTCAGTT GGGGGGTGTG
481 AGCGTCTCCT AGTGCGTGGA CCTGGTGTGG ATGGTTCTTG CTCAGATGCC GGTTCTTGGG
541 GTGTTTCTTG GCTAGATTCC TCTTCTATCA GTCTCTGAGC GTCCGGCCAG TCTTCAGGAT
601 CTTCGGTTAT GGGTTCGCTC TCTTGTGTTG GTGTGGGATT CTGTTGCCTA GCGATTGGAT
661 CTTCGCCATC AGATTCGGTA TCGCTGTCAT CCGATTCTTG GGGCTGAGGT GGAGGCTCGT
721 GCGCCACTAT CGGCTGAGGT TGCGCGAGTG GAATGTTGAT CACACGGACC AGAGACCTTC
781 TTCCTTCGCC ATCTTCATCT TCGGACTCAT CTCCCGCAGA TTCTCCGGCC TGTTCTTCTT
841 CGGCCTGTCC TTCTCTAGCC TGTCCTTCTC CGGCATGTTC CTCTCTAGCT TCCTCACCTT
901 CTCCCTCTAG TGGAGGCATA TCTTGTTCAA CTAGCGCTTG TCTAGCCTGT ACTGACATCC
961 CTACAATTTC TTCTACACTT TTTGACTCTG CAGCTTTATC TAAAGCATCT CTTGTGATAT
1021 GTTGTCCTGT GAACAGCAGT ATACCTGTAT TTGCAACTGC TCTGCGTGTT CTGATCACAG
1081 CATCATTTGG CCTCTCTCTG GCATTCGTTA GGATGAAAGT TGCTAGGTTT TGTTGTGCCA
1141 CGTTCATCCT GACATTGCAC GCGAGGTGTT GGGACCTTGC CGAATGATAG ATTATGTCTA
1201 TTCGTTCCTT TGCCGATGTT AGTATAGAAA GGCATAATCT GTTAAATTGC ACCTCAGCGT
1261 ACCCTGACAC ATCTCTAAGT GCCTTTGCCA AATTCTCGTT AGCCTCCAAT GCAGCCGTTA
1321 CGACAGAAGA TGTTGACACA CTTTGGTCAT TTATAACGTT ATCATGTTCC CATACTCTGA
1381 TCAGTTGGGC TGCGGCAGAG AGAGCTTTAA CTGTGTCAGG TGGATCGAAC ACGCCTCTCA
1441 TTGCTCTTGT TGTTTGTGTG ACTACATCAT CTATATTTTT GAACATTATA TTGATTATAT
1501 CGCGCGTCTC CTGCTCTACT TGCGCATTTG CCATCTCACA CAGCTTGTTT CCATGGCTGG
1561 TACACTCGCC TAGCATTTCC ATCCATGCTC TCTTTTCGGA CTCATTTGCA TTCACTGGCA
1621 TGAAATTTGT ATAGGAGTGG AATACTATTT TCCCGAGTGC TGTGTATTTT CCTTGCGATG
1681 CTGCTATCAG TGAATCTCTG ACTATGTCCG CACGTGCATA AGATTCATTA GCCATTTGGA
1741 TGCATGTCGT GCGGATGTCT CTTTTAACAT TCTCATGTAT CATTTGCAAC AGGAGGTCCG
1801 CGGTCTTGAT GGCAATTACA AGACTTTGAA CGGCTGCTTT TTTAGAATGT GGATCATGTG
1861 GAATGAAGTG TTGTTCGTCC ATCAGGCCTT CCATTGCCAC GACCTCTGAT GCCGATGGTT
1921 CGAAATCCAC CTGCACCTCA CTCAATAGCT CTTGGAGAGT CAGGTCACAT CTGATTGGAG
1981 GATCGTTCTC GGCAATGATT CTTGCCACAT GTCTAGGGCA CCTGTCTCCT GGCTGCTGTT
2041 CCTGTCTCGG TTGATTTACC GACTCACGCA CTTCATCATA ATCATTCACT CTGAGAAGTC
2101 TTGATTGTGT GAAAAGAGTT GGATCCATTA CGATACAAAC TTAACGGATA TCGCGATAAT
2161 GAAATAATTT ATGATTATTT CTCGCTTTCA ATTTAACACA ACCCTCAAGA ACCTTTGTAT
2221 TTATTTTCAC TTTTTAAGTA TAGAATAAAG AAGAATTGGG TTTTGGGATT TCAAAATTGA
2281 AAATATATAA TTACAATATA AAATGGATCC AACTCTTTTC ACACAATCAA GACTTCTCAG
2341 AGTGAATGAT TATGATGAAG TGCGTGAGTC GGTAAATCAA CCGAGACAGG AACAGCAGCC
2401 AGGAGACAGG TGCCCTAGAC ATGTGGCAAG AATCATTGCC GAGAACGATC CTCCAATCAG
2461 ATGTGACCTG ACTCTCCAAG AGCTATTGAG TGAGGTGCAG GTGGATTTCG AACCATCGGC
2521 ATCAGAGGTC GTGGCAATGG AAGGCCTGAT GGACGAACAA CACTTCATTC CACATGATCC
2581 ACATTCTAAA AAAGCAGCCG GGCCTAACGT GAGGCATATA GACATTGTTA CCGCAGCCGC
2641 GTCGATGTCA GGGATATCCG GATCAACAGA GAGACCATTA GATGATGGAC AGAGACCCTT
2701 AGCTGATGGA TGTTATAGCA AGAAACATAA GAAGCAGAAA CACAGCGAAC CTATAGACAC
2761 CAAGGTGCAC ATCCAACGGG GGGAGGAAAC AGACTCTGAT TCAGACTCAG ACACCGGTAA
2821 ATCACCGGGA TGCGATGAAA TATCTTTTTA CTTGTCCAGT GCTTCGGATG ATGAACATGG
2881 CAATGGGAAT CGTTCTGGGT TAGAAGGAAA TTGTAGTTCA TATACTTCAC ATTCATCACG
2941 TAGATCAAAA TCGCCGCTAA GAAGTCCTTC AAACAGGCCC CAAAAGAGAA AATTATGTAA
3001 GAATATGTTT ATTACAAAAA GCAAACGTAG GGTAATATGT GAATCTGATT CAGATACAGA
3061 CTCCGAAATC GAGACCAGGC CATTTATCAG ACCACAAGAA CCTCCCAGAC AAAAGAATAA

Figure 71A

3121 GGGGAAAAGA CGTCCCAAGA AACATAGAAA GATAACAGAG CTCATGGATG GGCCAGGATT
3181 CGTGGCTCCG AATGCACACA AACGAGGTAA AAATAGAAAT GAGGGAAACA ACGATGGACG
3241 AGGGAAACCG ACCACACGAG CTTTAGAATA CAAACAGATG CCATACAAAC AGCAAACGGT
3301 CCAGTTTCTC TATGGAAATG CGATAAGGAC ATGTAGAGAG AGCACCGTAC ACGATAAAAT
3361 TATTATGGTG ATGTTTACAC GGGGTCAAGA TATCAGGCAG GCCATAGAAA AGTTGAGATC
3421 CCAACTTGGT CAAATAACCA ACCTTTCCAT ATCTGCTCCC TTCAACACAG AACACACAAA
3481 ACCACAGATA CACACACCAA ACACGGTTAA CATGACATCG CAGGCACTTG CGGCAGGTCT
3541 TCAAGCCTCC TGGAACCTAG ACGAGGATAA TAAACACAAT AATGCACCTA GGATGTCAGA
3601 TTACAGAACC ATGATAATCC AAGCGGCAAC ACCACCAGAT TTTCTAGGTG CACTCAAACT
3661 ATGCATACAG TTCGCACAAA CCTTTCCCAA GAATGCGTGT ATAAGGTTAT GTAATATAGT
3721 TGGAGGCCTA CAACCCCTTC CCATCTACGA AAAAGTCGTC ACCGCTTACA CTGACACGCA
3781 ATATAACTTT AGCCCAATCA CTAACAAAGA TAGTAACGGT GGTATGAGCA CAATATTGGA
3841 TCAGGACTCC GATTCAGAAT AATTTTTATC GCGATAGCTG ATTAGTTTTT GTTAACAAAA
3901 ATGTGGGAGA ATCTAATTAG TTTTTCTTTA CACAATTGAC GTACATGAGT CTGAGTTCCT
3961 TGTTTTTGCT AATTATTTCA TCCAATTTAT TATTCTTGAC GATATCGAGA TCTTTTGTAT
4021 AGGAGTCAGA CTTGTATTCA ACATGCTTTT CTATAATCAT CTTAGTTATT TCGGCATCAT
4081 CCAATAGTAC ATTTTCCAGA TTAACAGAGT AGATATTAAT GTCGTATTTG AACAGAGCCT
4141 GTAACATCTC AATGTCTTTA TTATCTATAG CCAATTTAAT GTCCGGAATG AAGAGAAGGG
4201 AATTATTGGT GTTTGTCGAC GTCATATAGT CGAGCAAGAG AATCATCATA TCCACGTGTC
4261 CATTTTTTAT AGTGGTGTGA ATACAACTAA GGAGAATAGC CAGATCAAAA GTAGATGGTA
4321 TTTCTGAAAG AAAGTATGAT ACAATACTTA CATCATTAAG CATGACGGCA TGATAAAATG
4381 AAGTTTTCCA TCCAGTTTTC CCATAGAACA TCAGTCTCCA ATTTTTCTTA AACAGTTTCA
4441 CCGTTTGCAT GTTACCACTA TCAACCGCAT AATACAATGC GGTGTTTCCT TTGTCATCAA
4501 ATTGTGAATC ATCCATTCCA CTGAATAGCA AAATCTTTAC TATTTTGGTA TCTTCTAATG
4561 TGGCTGCCTG ATGTAATGGA AATTCATTCT CTAGAAGATT TTTCAATGCT CCAGCGTTCA
4621 ACAACGTACA TACTAGACGC ACGTTATTAT CAGCTATTGC ATAATACAAG GCACTATGTC
4681 CATGGACATC CGCCTTAAAT GTATCTTTAC TAGAGAGAAA GCTTTTCAGC TGCTTAGACT
4741 TCCAAGTATT AATTCGTGAC AGATCCATGT CTGAAACGAG ACGCTAATTA GTGTATATTT
4801 TTTCATTTTT TATAATTTTG TCATATTGCA CCAGAATTAA TAATATCTCT AATAGATCTA
4861 ATTTAATTTA ATTTATATAA CTTATTTTTT GAATATACTT TTAATTAACA AAAGAGTTAA
4921 GTTACTCATA TGGACGCCGT CCAGTCTGAA CATCAATCTT TTTAGCCAGA GATATCATAG
4981 CCGCTCTTAG AGTTTCAGCG TGATTTTCCA ACCTAAATAG AACTTCATCG TTGCGTTTAC
5041 AACACTTTTC TATTTGTTCA AACTTTGTTG TTACATTAGT AATCTTTTTT TCCAAATTAG
5101 TTAGCCGTTG TTTGAGAGTT TCCTCATTGT CGTCTTCATC GGCTTTAACA ATTGCTTCGC
5161 GTTTAGCCTC CTGGCTGTTC TTATCAGCCT TTGTAGAAAA AAATTCAGTT GCTGGAATTG
5221 CAAGATCGTC ATCTCCGGGG AAAAGAGTTC CGTCCATTTA AAGCCGCGGG AATTC

Figure 71B

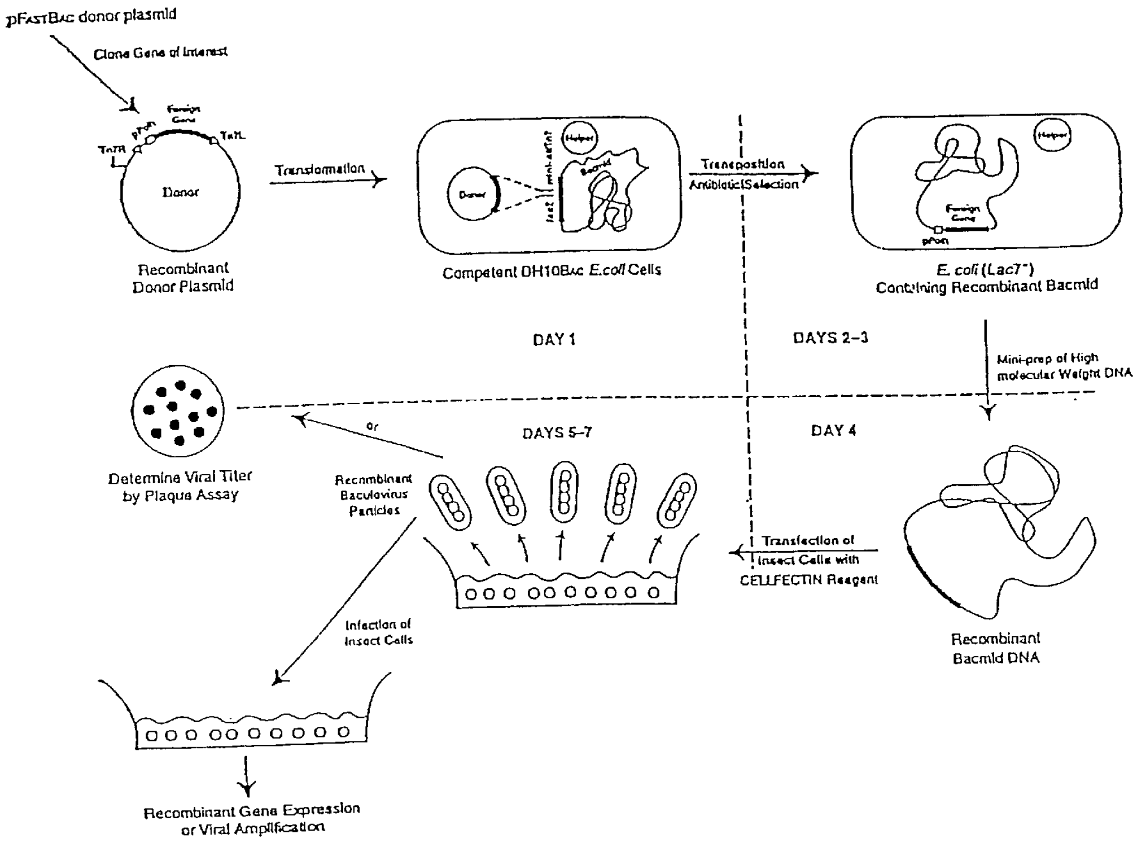

Generation of recombinant baculoviruses and gene expression with the Bac-to-Bac Expression System. The gene of interest is cloned into a pFastBac donor plasmid, and the recombinant plasmid is transformed into DH10Bac competent cells which contain the bacmid with a mini-attTn7 target site and the helper plasmid. The mini-Tn7 element on the pFastBac donor plasmid can transpose to the mini-attTn7 target site on the bacmid in the presence of transposition proteins provided by the helper plasmid. Colonies containing recombinant bacmids are identified by disruption of the *lacZα* gene. High molecular weight mini-prep DNA is prepared from selected *E. coli* clones containing the recombinant bacmid, and this DNA is then used to transfect insect cells.

Figure 72

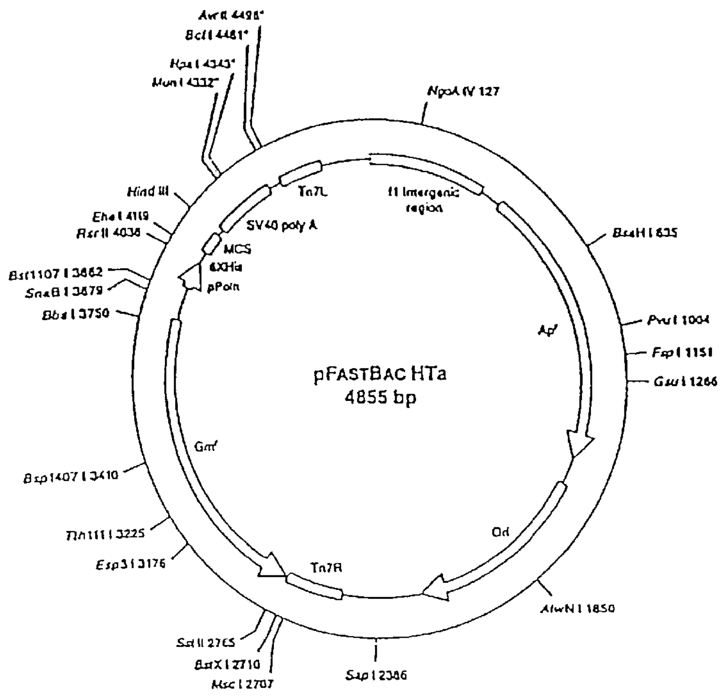

Map and restriction endonuclease sites for pFASTBAC HT expression vectors. The circle map of pFASTBAC HTa (4855 bp) is presented. A similar map can be drawn for pFASTBAC HTb (4856 bp) and pFASTBAC HTc (4857 bp) except that the starred restriction endonucleases are shifted by +1 and +2 bases respectively.

*Restriction endonucleases that do not cleave pFASTBAC HT DNAs:*

| | | | | | | | | |
|---|---|---|---|---|---|---|---|---|
| *Aat* II | *Bpu*1102 I | *Bst*E II | *Eco*72 I | *Nhe* I | *Pfl*M I | *Pvu* II | *Sma* I | *Sun* II |
| *Afl* II | *Bsg* I | *Cla* I | *Eco*O109 I | *Nru* I | *Pin*A I | *Sex*A I | *Srf* I | *Swa* I |
| *Apa* I | *Bsp*M I | *Cvn* I | *Mlu* I | *Nsi* I | *Pme* I | *Sfi* I | *Sse* I | *Xcm* I |
| *Asc* I | *Bss*H II | *Eco*47 III | *Nde* I | *Pac* I | *Psp*5 II | *Sgr*A I | *Sse*8387 I | |

*Restriction endonucleases that cleave pFASTBAC HTa DNA twice:*

| | | | | | | | | |
|---|---|---|---|---|---|---|---|---|
| *Acc* I | 3882 | 4150 | *Bsa*H I | 835 | 4119 | *Rca* I | 536 | 1544 |
| *Afl* III | 2264 | 3246 | *Bsm* I | 4327 | 4426 | *Sca* I | 893 | 4230 |
| *Ban* II | 157 | 4156 | *Dra* III | 230 | 3578 | *Tfi* I | 2290 | 4181 |
| *Bgl* II | 2547 | 3017 | *Eam*1105 I | 1371 | 4731 | *Xmn* I | 772 | 3797 |
| *Bsa* I | 1304 | 3661 | *Eco*R V | 2823 | 4086 | | | |

*Restriction endonucleases that cleave pFASTBAC HTb DNA twice:*

| | | | | | | | | |
|---|---|---|---|---|---|---|---|---|
| *Acc* I | 3882 | 4151 | *Bsa*H I | 835 | 4119 | *Rca* I | 536 | 1544 |
| *Afl* III | 2264 | 3246 | *Bsm* I | 4328 | 4427 | *Sca* I | 893 | 4231 |
| *Ban* II | 157 | 4157 | *Dra* III | 230 | 3578 | *Tfi* I | 2290 | 4182 |
| *Bgl* II | 2547 | 3017 | *Eam*1105 I | 1371 | 4732 | *Xmn* I | 772 | 3797 |
| *Bsa* I | 1304 | 3661 | | | | | | |

*Restriction endonucleases that cleave pFASTBAC HTc DNA twice:*

| | | | | | | | | |
|---|---|---|---|---|---|---|---|---|
| *Acc* I | 3882 | 4152 | *Bsm* I | 4329 | 4428 | *Rca* I | 536 | 1544 |
| *Afl* III | 2264 | 3246 | *Dra* III | 230 | 3578 | *Sca* I | 893 | 4232 |
| *Ban* II | 157 | 4158 | *Eam*1105 I | 1371 | 4733 | *Tfi* I | 2290 | 4183 |
| *Bsa* I | 1304 | 3661 | *Eco*R V | 2823 | 4086 | *Xmn* I | 772 | 3797 |
| *Bsa*H I | 835 | 4119 | | | | | | |

Figure73 pFastBac HTa

```
Rsr II
CTCGGTCCGAAACC ATG TCG TAC TAC CAT CAC CAT CAC CAT CAC GAT TAC GAT ATC CCA ACG ACC GAA AAC
               met ser tyr tyr his his his his his his asp tyr asp ile pro thr thr glu asn
                               6xHis                   spacer region               rTEV

                 EheI    NcoI BamHI EcoRI     StuI    SalI    SstI    SpeI
CTG TAT TTT CAG** GGC GCC ATG GAT CCG GAA TTC AAA GGC CTA CGT CGA CGA GCT CAA CTA GTG CGG
leu tyr phe gln   gly ala met asp pro glu phe lys gly leu arg arg arg ala glu leu val arg
protease cleavage site

NotI  NspV   XbaI    PstI    XhoI    SphI    KpnI    HindIII
CCG CTT TCG AAT CTA GAG CCT GCA GTC TCG AGG CAT GCG GTA CCA AGC TTG TCG AGA AGT ACT AGA
pro leu ser asp leu glu pro ala val ser arg his ala val pro ser leu ser arg ser thr arg

GGA TCA TAA TCA GCC ATA
gly ser stop
```

pFastBac HTb

```
Rsr II
CTCGGTCCGAAACC ATG TCG TAC TAC CAT CAC CAT CAC CAT CAC GAT TAC GAT ATC CCA ACG ACC GAA AAC
               met ser tyr tyr his his his his his his asp tyr asp ile pro thr thr glu asn
                               6xHis                   spacer region               rTEV

                 EheI    NcoI BamHI  EcoRI   StuI    SalI    SstI    SpeI
CTG TAT TTT CAG** GGC GCC ATG GGA TCC GGA ATT CAA AGG CCT ACG TCG ACG AGC TCA CTA GTC GCG
leu tyr phe gln   gly ala met gly ser gly ile glu arg pro thr ser thr ser ser leu val ala
protease cleavage site

NotI    NspV    XbaI    PstI    XhoI    SphI    KpnI    HindIII
GCC GCT TTC GAA TCT AGA GCC TGC AGT CTC GAG GCA TGC GGT ACC AAG CTT GTC GAG AAG TAC TAG
ala ala phe glu ser arg ala cys ser leu glu ala cys gly thr lys leu val glu lys tyr stop
```

pFastBac HTc

```
Rsr II
CTCGGTCCGAAACC ATG TCG TAC TAC CAT CAC CAT CAC CAT CAC GAT TAC GAT ATC CCA ACG ACC GAA AAC
               met ser tyr tyr his his his his his his asp tyr asp ile pro thr thr glu asn
                               6xHis                   spacer region               rTEV

                 EheI    NcoI BamHI  EcoRI   StuI    SalI    SstI    SpeI
CTG TAT TTT CAG** GGC GCC ATG GGG ATC CGG AAT TCA AAG GCC TAC GTC GAC GAG CTC ACT AGT CGC
leu tyr phe gln   gly ala met gly ile arg asn ser lys ala tyr leu asp glu leu thr ser arg
protease cleavage site

NotI    NspV    XbaI    PstI    XhoI    SphI    KpnI    HindIII
GGC CGC TTT CGA ATC TAG AGC CTG CAG TCT CGA GGC ATG CGG TAC CAA GCT TGT CGA GAA GTA CTA
gly arg phe arg ile stop
```

Multiple cloning site sequences of pFastBac HT expression vectors. The multiple cloning sites (MCS) for the three vectors are shown above. The sequence for the 6xHis, spacer region and rTEV protease cleavage site are underlined. The cleavage with rTEV protease occurs between the gln and gly and is signified by **. The shift in reading frame occurs at the *BamH* I site in each vector. The added base(s) are shown in bold. The stop codon for each vector is underlined and italicized. In pFastBac HTc the stop codon is within the MCS at the *Xba* I site. The 5' end of a gene must be cloned upstream of the *Xba* I site in pFastBac HTc to be translated.

Figure 74

```
   1 ATGGAGTCCT CTGCCAAGAG AAAGATGGAC CCTGATAATC CTGACGAGGG CCCTTCCTCC
  61 AAGGTGCCAC GGCCCGAGAC ACCCGTGACC AAGGCCACGA CGTTCCTGCA GACTATGTTG
 121 AGGAAGGAGG TTAACAGTCA GCTGAGTCTG GGAGACCCGC TGTTTCCAGA GTTGGCCGAA
 181 GAATCCCTCA AAACTTTTGA ACAAGTGACC GAGGATTGCA ACGAGAACCC CGAGAAAGAT
 241 GTCCTGGCAG AACTCGGTGA CATCCTCGCC CAGGCTGTCA ATCATGCCGG TATCGATTCC
 301 AGTAGCACCG GCCCCACGCT GACAACCCAC TTCCGCAGCG TTAGACGCGC CCCTCTTAAC
 361 AAGCCGACCC CCACCAGCGT CGCGGTTACT AACACTCCTC TCCCCGGGGC ATCCGCTACT
 421 CCCGAGCTCA GCCCGCGTAA GAAACCGCGC AAAACCACGC GTCCTTTCAA GGTGATTATT
 481 AAACCGCCCG TGCCTCCCGC GCCTATCATG CTGCCCCTCA TCAAACAGGA AGACATCAAG
 541 CCCGAGCCCG ACTTTACCAT CCAGTACCGC AACAAGATTA TCGATACCGC CGGCTGTATC
 601 GTGATCTCTG ATAGCGAGGA AGAACAGGGT GAAGAAGTCG AAACCCGCGG TGCTACCGCG
 661 TCTTCCCCTT CCACCGGCAG CGGCACGCCG CGAGTGACCT CTCCCACGCA CCCGCTCTCC
 721 CAGATGAACC ACCCTCCTCT TCCCGATCCC TTGGGCCGGC CCGATGAAGA TAGTTCCTCT
 781 TCGTCTTCCT CCTGCAGTTC GGCTTCGGAC TCGGAGAGTG AGTCCGAGGA GATGAAATGC
 841 AGCAGTGGCG GAGGAGCATC CGTGACCTCG AGCCACCATG GGCGCGGCGG TTTTGGTGGC
 901 GCGGCCTCCT CCTCTCTGCT GAGCTGCGGC CATCAGAGCA GCGGCGGGGC GAGCACCGGA
 961 CCCCGCAAGA AGAAGAGCAA ACGCATCTCC GAGTTGGACA ACGAGAAGGT GCGCAATATC
1021 ATGAAAGATA AGAACACCCC CTTCTGCACA CCCAACGTGC AGACTCGGCG GGGTCGCGTC
1081 AAGATTGACG AGGTGAGCCG CATGTTCCGC AACACCAATC GCTCTCTTGA GTACAAGAAC
1141 CTGCCCTTCA CGATTCCCAG TATGCACCAG GTGTTAGATG AGGCCATCAA AGCCTGCAAA
1201 ACCATGCAGG TGAACAACAA GGGCATCCAG ATTATCTACA CCCGCAATCA TGAGGTGAAG
1261 AGTGAGGTGG ATGCGGTGCG GTGTCGCCTG GGCACCATGT GCAACCTGGC CCTCTCCACT
1321 CCCTTCCTCA TGGAGCACAC CATGCCCGTG ACACATCCAC CCAAAGTGGC GCAGCGCACA
1381 GCCGATGCTT GTAACGAAGG CGTCAAGGCC GCGTGGAGCC TCAAAGAATT GCACACCCAC
1441 CAATTATGCC CCCGTTCCTC CGATTACCGC AACATGATCA TCCACGCTGC CACCCCCGTG
1501 GACCTGTTGG GCGCTCTCAA CCTGTGCCTG CCCCTGATGC AAAAGTTTCC CAAACAGGTC
1561 ATGGTGCGCA TCTTCTCCAC CAACCAGGGT GGGTTCATGC TGCCTATCTA CGAGACGGCC
1621 ACGAAGGCCT ACGCCGTGGG GCAGTTTGAG CAGCCCACCG AGACCCCTCC CGAAGACCTG
1681 GACACCCTGA GCCTGGCCAT CGAGGCAGCC ATCCAGGACC TGAGGAACAA GTCTCAGTAA
```

Figure 75

Western Blot

Lane 1 SF9 insect cell lysate
Lane 2 Baculovirus RCMVIE1 infected SF9 cell lysate
Lane 3 RCMVIE1 purified protein preparation
Lane 4 Baculovirus RCMVIE2 infected SF9 cell lysate
Lane 5 RK-13 cells
Lane 6 vP1479 infected RK-13 cell lysate
Lane 7 Prestained Molecular Weight Markers

Figure 76A

Coomassie Blue Stained Gel

Lane 1 RCMVIE1 purified protein preparation
Lane 2 Prestained Molecular Weight Markers

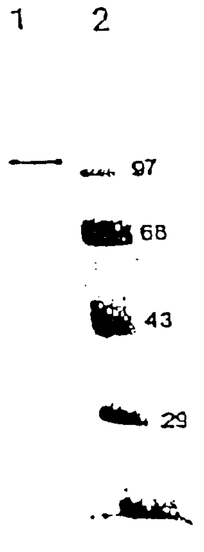

Figure 76B

GATTAAAGAAAGTTACTCTGAGACACAAAAGAGGTAGCTGAAGTGGTACTCTCAAAGGTA
CCCCCGGGTTAATTAATTAGTCATCAGGCAGGGCGAGAACGAGACTATCTGCTCGTTAAT
TAATTAGGTGACGGATCCCCGGGTTCTTTATTCTATACTTAAAAAGTGAAAATAAATAC
AAAGGTTCTTGAGGGTTGTGTTAAATTGAAAGCGAGAAATAATCATAAATTATTTCATTA
TCGCGATATCCGTTAAGTTTGTATCGTAATGGAGGAGCCGCAGTCAGATCCTAGCGTCGA
GCCCCCTCTGAGTCAGGAAACATTTTCAGACCTATGGAAACTACTTCCTGAAAACAACGT
TCTGTCCCCCTTGCCGTCCCAAGCAATGGATGATTTGATGCTGTCCCCGGACGATATTGA
ACAATGGTTCACTGAAGACCCAGGTCCAGATGAAGCTCCCAGAATGCCAGAGGCTGCTCC
CCGCGTGGCCCCTGGACCAGCAGCTCCTACACCGGCGGCCCCTGCACCAGCCCCCTCCTG
GCCCCTGTCATCTTCTGTCCCTTCCCAGAAAACCTACCAGGGCAGCTACGGTTTCCGTCT
GGGCTTCTTGCATTCTGGGACAGCCAAGTCTGTGACTTGCACGTACTCCCCTGCCCTCAA
CAAGATGTTTTGCCAACTGGCCAAGACCTGCCCTGTGCAGCTGTGGGTTGATTCCACACC
CCCGCCCGGCACCCGCGTCCGCGCCATGGCCATCTACAAGCAGTCACAGCACATGACGGA
GGTTGTGAGGCGCTGCCCCCACCATGAGCGCTGCTCAGATAGCGATGGTCTGGCCCCTCC
TCAGCATCTTATCCGAGTGGAAGGAAATTTGCGTGTGGAGTATTTGGATGACAGAAACAC
TTTTCGACATAGTGTGGTGGTGCCCTATGAGCCGCCTGAGGTTGGCTCTGACTGTACCAC
CATCCACTACAACTACATGTGTAACAGTTCCTGCATGGGCGGCATGAACCGGAGGCCCAT
CCTCACCATCATCACACTGGAAGACTCCAGTGGTAATCTACTGGGACGGAACAGCTTTGA
GGTGCGTGTTTGTGCCTGTCCTGGGAGAGACCGGCGCACAGAGGAAGAGAATCTCCGCAA
GAAAGGGGAGCCTCACCACGAGCTGCCCCCAGGGAGCACTAAGCGAGCACTGCCCAACAA
CACCAGCTCCTCTCCCCAGCCAAAGAAGAAACCACTGGATGGAGAATATTTCACCCTTCA
GATCCGTGGGCGTGAGCGCTTCGAGATGTTCCGAGAGCTGAATGAGGCCTTGGAACTCAA
GGATGCCCAGGCTGGGAAGGAGCCAGGGGGAGCCAGGGCTCACTCCAGCCACCTGAAGTC
CAAAAAGGGTCAGTCTACCTCCCGCCATAAAAAACTCATGTTCAAGACAGAAGGGCCTGA
CTCAGACTGAACGCGTTTTTATCCCGGGCTCGAGTCTAGAATCGATCCCGGGTTTTTATG
ACTAGTTAATCA

Figure 77

SEQUENCE LISTING (1) GENERAL INFORMATION:

(iii) NUMBER OF SEQUENCES: 184

(2) INFORMATION FOR SEQ ID NO:1:

(i) SEQUENCE CHARACTERISTICS:
(A) LENGTH: 2724 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
ATGGAATCCA GGATCTGGTG CCTGGTAGTC TGCGTTAACT TGTGTATCGT CTGTCTGGGT     60
GCTGCGGTTT CCTCATCTTC TACTCGTGGA ACTTCTGCTA CTCACAGTCA CCATTCCTCT    120
CATACGACGT CTGCTGCTCA TTCTCGATCC GGTTCAGTCT CTCAACGCGT AACTTCTTCC    180
CAAACGGTCA GCCATGGTGT TAACGAGACC ATCTACAACA CTACCCTCAA GTACGGAGAT    240
GTGGTGGGGG TCAACACCAC CAAGTACCCC TATCGCGTGT GTTCTATGGC ACAGGGTACG    300
GATCTTATTC GCTTTGAACG TAATATCGTC TGCACCTCGA TGAAGCCCAT CAATGAAGAC    360
CTGGACGAGG GCATCATGGT GGTCTACAAA CGCAACATCG TCGCGCACAC CTTTAAGGTA    420
CGAGTCTACC AGAAGGTTTT GACGTTTCGT CGTAGCTACG CTTACATCCA CACCACTTAT    480
CTGCTGGGCA GCAACACGGA ATACGTGGCG CCTCCTATGT GGGAGATTCA TCATATCAAC    540
AGTCACAGTC AGTGCTACAG TTCCTACAGC CGCGTTATAG CAGGCACGGT TTTCGTGGCT    600
TATCATAGGG ACAGCTATGA AAACAAAACC ATGCAATTAA TGCCCGACGA TTATTCCAAC    660
ACCCACAGTA CCCGTTACGT GACGGTCAAG GATCAATGGC ACAGCCGCGG CAGCACCTGG    720
CTCTATCGTG AGACCTGTAA TCTGAATTGT ATGGTGACCA TCACTACTGC GCGCTCCAAG    780
TATCCCTATC ATTTTTTCGC AACTTCCACG GGTGATGTGG TTGACATTTC TCCTTTCTAC    840
AACGGAACTA ATCGCAATGC CAGCTATTTT GGAGAAAACG CCGACAAGTT TTTCATTTTT    900
CCGAACTACA CTATCGTCTC CGACTTTGAA AGACCGAATT CTGCGTTAGA GACCCACAGG    960
TTGGTGGCTT TTCTTGAACG TGCGGACTCA GTGATCTCCT GGGATATACA GGACGAGAAG   1020
AATGTTACTT GTCAACTCAC TTTCTGGGAA GCCTCGGAAC GCACCATTCG TTCCGAAGCC   1080
GAGGACTCGT ATCACTTTTC TTCTGCCAAA ATGACCGCCA CTTTCTTATC TAAGAAGCAA   1140
GAGGTGAACA TGTCCGACTC TGCGCTGGAC TGTGTACGTG ATGAGGCCAT AAATAAGTTA   1200
CAGCAGATTT TCAATACTTC ATACAATCAA ACATATGAAA AATATGGAAA CGTGTCCGTC   1260
TTTGAAACCA CTGGTGGTTT GGTGGTGTTC TGGCAAGGTA TCAAGCAAAA ATCTCTGGTG   1320
GAACTCGAAC GTTTGGCCAA CCGCTCCAGT CTGAATCTTA CTCATAATAG AACCAAAAGA   1380
AGTACAGATG GCAACAATGC AACTCATTTA TCCAACATGG AGTCGGTGCA CAATCTGGTC   1440
TACGCCCAGC TGCAGTTCAC CTATGACACG TTGCGCGGTT ACATCAACCG GGCGCTGGCC   1500
GAAATCGCAG AAGCCTGGTG TGTGGATCAA CGGCGCACCC TAGAGGTCTT CAAGGAACTT   1560
AGCAAGATCA ACCCGTCAGC TATTCTCTCG GCCATCTACA ACAAACCGAT TGCCGCGCGT   1620
TTCATGGGTG ATGTCCTGGG TCTGGCCAGC TGCGTGACCA TTAACCAAAC CAGCGTCAAG   1680
GTGCTGCGTG ATATGAATGT GAAGGAATCG CCAGGACGCT GCTACTCACG ACCAGTGGTC   1740
ATCTTTAATT TCGCCAACAG CTCGTACGTG CAGTACGGTC AACTGGGCGA GGATAACGAA   1800
```

-continued

```
ATCCTGTTGG GCAACCACCG CACTGAGGAA TGTCAGCTTC CCAGCCTCAA GATCTTCATC   1860
GCCGGCAACT CGGCCTACGA GTACGTGGAC TACCTCTTCA AACGCATGAT TGACCTCAGC   1920
AGCATCTCCA CCGTCGACAG CATGATCGCC CTAGACATCG ACCCGCTGGA AAACACCGAC   1980
TTCAGGGTAC TGGAACTTTA CTCGCAGAAA GAATTGCGTT CCAGCAACGT TTTTGATCTC   2040
GAGGAGATCA TGCGCGAGTT CAATTCGTAT AAGCAGCGGG TAAAGTACGT GGAGGACAAG   2100
GTAGTCGACC CGCTGCCGCC CTACCTCAAG GGTCTGGACG ACCTCATGAG CGGCCTGGGC   2160
GCCGCGGGAA AGGCCGTTGG CGTAGCCATT GGGGCCGTGG GTGGCGCGGT GGCCTCCGTG   2220
GTCGAAGGCG TTGCCACCTT CCTCAAAAAC CCCTTCGGAG CCTTCACCAT CATCCTCGTG   2280
GCCATAGCCG TCGTCATTAT CATTTATTTG ATCTATATCC GACAGCGGCG TCTCTGCATG   2340
CAGCCGCTGC AGAACCTCTT TCCCTATCTG GTGTCCGCCG ACGGGACCAC CGTGACGTCG   2400
GGCAACACCA AAGACACGTC GTTACAGGCT CCGCCTTCCT ACGAGGAAAG TGTTTATAAT   2460
TCTGGTCGCA AAGGACCGGG ACCACCGTCG TCTGATGCAT CCACGGCGGC TCCGCCTTAC   2520
ACCAACGAGC AGGCTTACCA GATGCTTCTG GCCCTGGTCC GTCTGGACGC AGAGCAGCGA   2580
GCGCACGAGA ACGGTACAGA TTCTTTGGAC GGACAGACTG GCACGCAGGA CAAGGGACAG   2640
AAGCCCAACC TGCTAGACCG ACTGCGACAC CGCAAAAACG GCTACCGACA CTTGAAAGAC   2700
TCCGACGAAG AAGAGAACGT CTGA                                          2724
```

(2) INFORMATION FOR SEQ ID NO:2:

(i) SEQUENCE CHARACTERISTICS:
(A) LENGTH: 4260 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

```
AAGCTTTTGC GATCAATAAA TGGATCACAA CCAGTATCTC TTAACGATGT TCTTCGCAGA     60
TGATGATTCA TTTTTTAAGT ATTTGGCTAG TCAAGATGAT GAATCTTCAT TATCTGATAT    120
ATTGCAAATC ACTCAATATC TAGACTTTCT GTTATTATTA TTGATCCAAT CAAAAAATAA    180
ATTAGAAGCC GTGGGTCATT GTTATGAATC TCTTTCAGAG GAATACAGAC AATTGACAAA    240
ATTCACAGAC TCTCAAGATT TTAAAAAACT GTTTAACAAG GTCCCTATTG TTACAGATGG    300
AAGGGTCAAA CTTAATAAAG GATATTTGTT CGACTTTGTG ATTAGTTTGA TGCGATTCAA    360
AAAAGAATCC TCTCTAGCTA CCACCGCAAT AGATCCTATT AGATACATAG ATCCTCGTCG    420
CGATATCGCA TTTTCTAACG TGATGGATAT ATTAAAGTCG AATAAAGTGA ACAATAATTA    480
ATTCTTTATT GTCATCATGT AATTAACTAG CTACCCGGGA GATCTCTCGA GCTGCAGAAG    540
CTTATAAAAA TCACAAGTCT CTGTCACTTT TTTTGTCTAG TTTTTTTTTC TCCTCTTGGT    600
TCAGACGTTC TCTTCTTCGT CGGAGTCTTT CAAGTGTCGG TAGCCGTTTT TGCGGTGTCG    660
CAGTCGGTCT AGCAGGTTGG GCTTCTGTCC CTTGTCCTGC GTGCCAGTCT GTCCGTCCAA    720
AGAATCTGTA CCGTTCTCGT GCGCTCGCTG CTCTGCGTCC AGACGGACCA GGGCCAGAAG    780
CATCTGGTAA GCCTGCTCGT TGGTGTAAGG CGGAGCCGCC GTGGATGCAT CAGACGACGG    840
TGGTCCCGGT CCTTTGCGAC CAGAATTATA AACACTTTCC TCGTAGGAAG GCGGAGCCTG    900
TAACGACGTG TCTTTGGTGT TGCCCGACGT CACGGTGGTC CCGTCGGCGG ACACCAGATA    960
GGGAAAGAGG TTCTGCAGCG GCTGCATGCA GAGACGCCGC TGTCGAGTAT AGATCAAATA   1020
```

-continued

```
AATGATAATG ACGACGGCTA TGGCCACGAG GATGATGGTG AAGGCTCCGA AGGGGTTTTT   1080
GAGGAAGGTG GCAACGCCTT CGACCACGGA GGCCACCGCG CCACCCACGG CCCCAATGGC   1140
TACGCCAACG GCCTTTCCCG CGGCGCCCAG GCCGCTCATG AGGTCGTCCA GACCCTTGAG   1200
GTAGGGCGGC AGCGGGTCGA CTACCTTGTC CTCCACGTAC TTTACCCGCT GCTTATACGA   1260
ATTGAACTCG CGCATGATCT CCTCGAGATC AAAAACGTTG CTGGAACGCA ATTCTTTCTG   1320
CGAGTAAAGT TCCAGTACCC TGAAGTCGGT GTTTTCCAGC GGGTCGATGT CTAGGGCGAT   1380
CATGCTGTCG ACGGTGGAGA TGCTGCTGAG GTCAATCATG CGTTTGAAGA GGTAGTCCAC   1440
GTACTCGTAG GCCGAGTTGC CGGCGATGAA GATCTTGAGG CTGGGAAGCT GACATTCCTC   1500
AGTGCGGTGG TTGCCCAACA GGATTTCGTT ATCCTCGCCC AGTTGACCGT ACTGCACGTA   1560
CGAGCTGTTG GCGAAATTAA AGATGACCAC TGGTCGTGAG TAGCAGCGTC CTGGCGATTC   1620
CTTCACATTC ATATCACGCA GCACCTTGAC GCTGGTTTGG TTAATGGTCA CGCAGCTGGC   1680
CAGACCCAGG ACATCACCCA TGAAACGCGC GGCAATCGGT TTGTTGTAGA TGGCCGAGAG   1740
AATAGCTGAC GGGTTGATCT TGCTAAGTTC CTTGAAGACC TCTAGGGTGC GCCGTTGATC   1800
CACACACCAG GCTTCTGCGA TTTCGGCCAG CGCCCGGTTG ATGTAACCGC GCAACGTGTC   1860
ATAGGTGAAC TGCAGCTGGG CGTAGACCAG ATTGTGCACC GACTCCATGT TGGATAAATG   1920
AGTTGCATTG TTGCCATCTG TACTTCTTTT GGTTCTATTA TGAGTAAGAT TCAGACTGGA   1980
GCGGTTGGCC AAACGTTCGA GTTCCACCAG AGATTTTTGC TTGATACCTT GCCAGAACAC   2040
CACCAAACCA CCAGTGGTTT CAAAGACGGA CACGTTTCCA TATTTTTCAT ATGTTTGATT   2100
GTATGAAGTA TTGAAAATCT GCTGTAACTT ATTTATGGCC TCATCACGTA CACAGTCCAG   2160
CGCAGAGTCG GACATGTTCA CCTCTTGCTT CTTAGATAAG AAAGTGGCGG TCATTTTGGC   2220
AGAAGAAAAG TGATACGAGT CCTCGGCTTC GGAACGAATG GTGCGTTCCG AGGCTTCCCA   2280
GAAAGTGAGT TGACAAGTAA CATTCTTCTC GTCCTGTATA TCCCAGGAGA TCACTGAGTC   2340
CGCACGTTCA AGAAAAGCCA CCAACCTGTG GGTCTCTAAC GCAGAATTCG GTCTTTCAAA   2400
GTCGGAGACG ATAGTGTAGT TCGGAAAAAT GAAAAACTTG TCGGCGTTTT CTCCAAAATA   2460
GCTGGCATTG CGATTAGTTC CGTTGTAGAA AGGAGAAATG TCAACCACAT CACCCGTGGA   2520
AGTTGCGAAA AAATGATAGG GATACTTGGA GCGCGCAGTA GTGATGGTCA CCATACAATT   2580
CAGATTACAG GTCTCACGAT AGAGCCAGGT GCTGCCGCGG CTGTGCCATT GATCCTTGAC   2640
CGTCACGTAA CGGGTACTGT GGGTGTTGGA ATAATCGTCG GGCATTAATT GCATGGTTTT   2700
GTTTTCATAG CTGTCCCTAT GATAAGCCAC GAAAACCGTG CCTGCTATAA CGCGGCTGTA   2760
GGAACTGTAG CACTGACTGT GACTGTTGAT ATGATGAATC TCCCACATAG GAGGCGCCAC   2820
GTATTCCGTG TTGCTGCCCA GCAGATAAGT GGTGTGGATG TAAGCGTAGC TACGACGAAA   2880
CGTCAAAACC TTCTGGTAGA CTCGTACCTT AAAGGTGTGC GCGACGATGT TGCGTTTGTA   2940
GACCACCATG ATGCCCTCGT CCAGGTCTTC ATTGATGGGC TTCATCGAGG TGCAGACGAT   3000
ATTACGTTCA AAGCGAATAA GATCCGTACC CTGACCCATA GAACACACGC GATAGGGGTA   3060
CTTGGTGGTG TTGACCCCCA CCACATCTCC GTACTTGAGG GTAGTGTTGT AGATGGTCTC   3120
GTTAACACCA TGGCTGACCG TTTGGGAAGA AGTTACGCGT TGAGAGACTG AACCGGATCG   3180
AGAATGAGCA GCAGACGTCG TATGAGAGGA ATGGTGACTG TGAGTAGCAG AAGTTCCACG   3240
AGTAGAAGAT GAGGAAACCG CAGCACCCAG ACAGACGATA CACAAGTTAA CGCAGACTAC   3300
CAGGCACCAG ATCCTGGATT CCATTACGAT ACAAACTTAA CGGATATCGC GATAATGAAA   3360
```

-continued

```
TAATTTATGA TTATTTCTCG CTTTCAATTT AACACAACCC TCAAGAACCT TTGTATTTAT   3420

TTTCACTTTT AAGTATAGAA TAAAGAAGCT TGCATGCCAC GCGTCTCGAG GGCCCCTGCA   3480

GGTCGACTCT AGAGGATCCT GATCCTTTTT CTGGGTAAGT AATACGTCAA GGAGAAAACG   3540

AAACGATCTG TAGTTAGCGG CCGCCTAATT AACTAATATT ATATTTTTTA TCTAAAAAAC   3600

TAAAAATAAA CATTGATTAA ATTTTAATAT AATACTTAAA AATGGATGTT GTGTCGTTAG   3660

ATAAACCGTT TATGTATTTT GAGGAAATTG ATAATGAGTT AGATTACGAA CCAGAAAGTG   3720

CAAATGAGGT CGCAAAAAAA CTGCCGTATC AAGGACAGTT AAAACTATTA CTAGGAGAAT   3780

TATTTTTTCT TAGTAAGTTA CAGCGACACG GTATATTAGA TGGTGCCACC GTAGTGTATA   3840

TAGGATCGGC TCCTGGTACA CATATACGTT ATTTGAGAGA TCATTTCTAT AATTTAGGAA   3900

TGATTATCAA ATGGATGCTA ATTGACGGAC GCCATCATGA TCCTATTTTA AATGGATTGC   3960

GTGATGTGAC TCTAGTGACT CGGTTCGTTG ATGAGGAATA TCTACGATCC ATCAAAAAAC   4020

AACTGCATCC TTCTAAGATT ATTTTAATTT CTGATGTGAG ATCCAAACGA GGAGGAAATG   4080

AACCTAGTAC GGCGGATTTA CTAAGTAATT ACGCTCTACA AAATGTCATG ATTAGTATTT   4140

TAAACCCCGT GGCGTCTAGT CTTAAATGGA GATGCCCGTT TCCAGATCAA TGGATCAAGG   4200

ACTTTTATAT CCCACACGGT AATAAAATGT TACAACCTTT TGCTCCTTCA TATTCAGCTG   4260
```

(2) INFORMATION FOR SEQ ID NO:3:

(i) SEQUENCE CHARACTERISTICS:
(A) LENGTH: 7351 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

```
AGATATTTGT TAGCTTCTGC CGGAGATACC GTGAAAATCT ATTTTCTGGA AGGAAAGGGA     60

GGTCTTATCT ATTCTGTCAG CAGAGTAGGT TCCTCTAATG ACGAAGACAA TAGTGAATAC    120

TTGCATGAAG GTCACTGTGT AGAGTTCAAA ACTGATCATC AGTGTTTGAT AACTCTAGCG    180

TGTACGAGTC CTTCTAACAC TGTGGTTTAT TGGCTGGAAT AAAAGGATAA AGACACCTAT    240

ACTGATTCAT TTTCATCTGT CAACGTTTCT CTAAGAGATT CATAGGTATT ATTATTACAT    300

CGATCTAGAA GTCTAATAAC TGCTAAGTAT ATTATTGGAT TTAACGCGCT ATAAACGCAT    360

CCAAAACCTA CAAATATAGG AGAAGCTTCT CTTATGAAAC TTCTTAAAGC TTTACTCTTA    420

CTATTACTAC TCAAAAGAGA TATTACATTA ATTATGTGAT GAGGCATCCA ACATATAAAG    480

AAGACTAAAG CTGTAGAAGC TGTTATGAAG AATATCTTAT CAGATATATT AGATGCATTG    540

TTAGTTCTGT AGATCAGTAA CGTATAGCAT ACGAGTATAA TTATCGTAGG TAGTAGGTAT    600

CCTAAAATAA ATCTGATACA GATAATAACT TTGTAAATCA ATTCAGCAAT TTCTCTATTA    660

TCATGATAAT GATTAATACA CAGCGTGTCG TTATTTTTTG TTACGATAGT ATTTCTAAAG    720

TAAAGAGCAG GAATCCCTAG TATAATAGAA ATAATCCATA TGAAAAATAT AGTAATGTAC    780

ATATTTCTAA TGTTAACATA TTTATAGGTA AATCCAGGAA GGGTAATTTT TACATATCTA    840

TATACGCTTA TTACAGTTAT TAAAAATATA CTTGCAAACA TGTTAGAAGT AAAAAAGAAA    900

GAACTAATTT TACAAAGTGC TTTACCAAAA TGCCAATGGA AATTACTTAG TATGTATATA    960

ATGTATAAAG GTATGAATAT CACAAACAGC AAATCGGCTA TTCCCAAGTT GAGAAACGGT   1020

ATAATAGATA TATTTCTAGA TACCATTAAT AACCTTATAA GCTTGACGTT TCCTATAATG   1080
```

-continued

```
CCTACTAAGA AAACTAGAAG ATACATACAT ACTAACGCCA TACGAGAGTA ACTACTCATC   1140
GTATAACTAC TGTTGCTAAC AGTGACACTG ATGTTATAAC TCATCTTTGA TGTGGTATAA   1200
ATGTATAATA ACTATATTAC ACTGGTATTT TATTTCAGTT ATATACTATA TAGTATTAAA   1260
AATTATATTT GTATAATTAT ATTATTATAT TCAGTGTAGA AAGTAAAATA CTATAAATAT   1320
GTATCTCTTA TTTATAACTT ATTAGTAAAG TATGTACTAT TCAGTTATAT TGTTTTATAA   1380
AAGCTAAATG CTACTAGATT GATATAAATG AATATGTAAT AAATTAGTAA TGTAGTATAC   1440
TAATATTAAC TCACATTATG AATACTACTA ATCACGAAGA ATGCAGTAAA ACATATGATA   1500
CAAACATGTT AACAGTTTTA AAAGCCATTA GTAATAAACA GTACAATATA ATTAAGTCTT   1560
TACTTAAAAA AGATATTAAT GTTAATAGAT TATTAACTAG TTATTCTAAC GAAATATATA   1620
AACATTTAGA CATTACATTA TGTAATATAC TTATAGAACG TGCAGCAGAC ATAAACATTA   1680
TAGATAAGAA CAATCGTACA CCGTTGTTTT ATGCGGTAAA GAATAATGAT TATGATATGG   1740
TTAAACTCCT ATTAAAAAAT GGCGCGAATG TAAATTTACA AGATAGTATA GGATATTCAT   1800
GTCTTCACAT CGCAGGTATA CATAATAGTA ACATAGAAAT AGTAGATGCA TTGATATCAT   1860
ACAAACCAGA TTTAAACTCC CGCGATTGGG TAGGTAGAAC ACCGCTACAT ATCTTCGTGA   1920
TAGAATCTAA CTTTGAAGCT GTGAAATTAT TATTAAAGTC AGGTGCATAT GTAGGTTTGA   1980
AAGACAAATG TAAGCATTTT CCTATACACC ATTCTGTAAT GAAATTAGAT CACTTAATAT   2040
CAGGATTGTT ATTAAAATAT GGAGCAAATC CAAATACAAT TAACGGCAAT GGAAAAACAT   2100
TATTAAGCAT TGCTGTAACA TCTAATAATA CACTACTGGT AGAACAGCTG CTGTTATATG   2160
GAGCAGAAGT TAATAATGGT GGTTATGATG TTCCAGCTCC TATTATATCC GCTGTCAGTG   2220
TTAACAATTA TGATATTGTT AAGATACTGA TACATAATGG TGCGAATATA AATGTATCCA   2280
CGGAAGATGG TAGAACGTCT TTACATACAG CTATGTTTTG GAATAACGCT AAAATAATAG   2340
ATGAGTTGCT TAACTATGGA AGTGACATAA ACAGCGTAGA TACTTATGGT AGAACTCCGT   2400
TATCTTGTTA TCGTAGCTTA AGTTATGATA TCGCTACTAA ACTAATATCA CGTATCATTA   2460
TAACAGATGT CTATCGTGAA GCACCAGTAA ATATCAGCGG ATTTATAATT AATTTAAAAA   2520
CTATAGAAAA TAATGATATA TTCAAATTAA TTAAAGATGA TTGTATTAAA GAGATAAACA   2580
TACTTAAAAG TATAACCCTT AATAAATTTC ATTCATCTGA CATATTTATA CGATATAATA   2640
CTGATATATG TTTATTAACG AGATTTATTC AACATCCAAA GATAATAGAA CTAGACAAAA   2700
AACTCTACGC TTATAAATCT ATAGTCAACG AGAGAAAAAT CAAAGCTACT TACAGGTATT   2760
ATCAAATAAA AAAAGTATTA ACTGTACTAC CTTTTTCAGG ATATTTCTCT ATATTGCCGT   2820
TTGATGTGTT AGTATATATA CTTGAATTCA TCTATGATAA TAATATGTTG GTACTTATGA   2880
GAGCGTTATC ATTAAAATGA AATAAAAAGC ATACAAGCTA TTGCTTCGCT ATCGTTACAA   2940
AATGGCAGGA ATTTTGTGTA AACTAAGCCA CATACTTGCC AATGAAAAAA ATAGTAGAAA   3000
GGATACTATT TTAATGGGAT TAGATGTTAA GGTTCCTTGG GATTATAGTA ACTGGGCATC   3060
TGTTAACTTT TACGACGTTA GGTTAGATAC TGATGTTACA GATTATAATA ATGTTACAAT   3120
AAAATACATG ACAGGATGTG ATATTTTTCC TCATATAACT CTTGGAATAG CAAATATGGA   3180
TCAATGTGAT AGATTTGAAA ATTTCAAAAA GCAAATAACT GATCAAGATT TACAGACTAT   3240
TTCTATAGTC TGTAAAGAAG AGATGTGTTT TCCTCAGAGT AACGCCTCTA AACAGTTGGG   3300
AGCGAAAGGA TGCGCTGTAG TTATGAAACT GGAGGTATCT GATGAACTTA GAGCCCTAAG   3360
AAATGTTCTG CTGAATGCGG TACCCTGTTC GAAGGACGTG TTTGGTGATA TCACAGTAGA   3420
TAATCCGTGG AATCCTCACA TAACAGTAGG ATATGTTAAG GAGGACGATG TCGAAAACAA   3480
```

-continued

```
GAAACGCCTA ATGGAGTGCA TGTCCAAGTT TAGGGGGCAA GAAATACAAG TTCTAGGATG   3540
GTATTAATAA GTATCTAAGT ATTTGGTATA ATTTATTAAA TAGTATAATT ATAACAAATA   3600
ATAAATAACA TGATAACGGT TTTTATTAGA ATAAAATAGA GATAATATCA TAATGATATA   3660
TAATACTTCA TTACCAGAAA TGAGTAATGG AAGACTTATA AATGAACTGC ATAAAGCTAT   3720
AAGGTATAGA GATATAAATT TAGTAAGGTA TATACTTAAA AAATGCAAAT ACAATAACGT   3780
AAATATACTA TCAACGTCTT TGTATTTAGC CGTAAGTATT TCTGATATAG AAATGGTAAA   3840
ATTATTACTA GAACACGGTG CCGATATTTT AAAATGTAAA AATCCTCCTC TTCATAAAGC   3900
TGCTAGTTTA GATAATACAG AAATTGCTAA ACTACTAATA GATTCTGGCG CTGACATAGA   3960
ACAGATACAT TCTGGAAATA GTCCGTTATA TATTTCTGTA TATAGAAACA ATAAGTCATT   4020
AACTAGATAT TTATTAAAAA AAGGTGTTAA TTGTAATAGA TTCTTTCTAA ATTATTACGA   4080
TGTACTGTAT GATAAGATAT CTGATGATAT GTATAAAATA TTTATAGATT TTAATATTGA   4140
TCTTAATATA CAAACTAGAA ATTTTGAAAC TCCGTTACAT TACGCTATAA AGTATAAGAA   4200
TATAGATTTA ATTAGGATAT TGTTAGATAA TAGTATTAAA ATAGATAAAA GTTTATTTTT   4260
GCATAAACAG TATCTCATAA AGGCACTTAA AAATAATTGT AGTTACGATA TAATAGCGTT   4320
ACTTATAAAT CACGGAGTGC CTATAAACGA ACAAGATGAT TTAGGTAAAA CCCCATTACA   4380
TCATTCGGTA ATTAATAGAA GAAAAGATGT AACAGCACTT CTGTTAAATC TAGGAGCTGA   4440
TATAAACGTA ATAGATGACT GTATGGGCAG TCCCTTACAT TACGCTGTTT CACGTAACGA   4500
TATCGAAACA ACAAAGACAC TTTTAGAAAG AGGATCTAAT GTTAATGTGG TTAATAATCA   4560
TATAGATACC GTTCTAAATA TAGCTGTTGC ATCTAAAAAC AAAACTATAG TAAACTTATT   4620
ACTGAAGTAC GGTACTGATA CAAAGTTGGT AGGATTAGAT AAACATGTTA TTCACATAGC   4680
TATAGAAATG AAAGATATTA ATATACTGAA TGCGATCTTA TTATATGGTT GCTATGTAAA   4740
CGTCTATAAT CATAAAGGTT TCACTCCTCT ATACATGGCA GTTAGTTCTA TGAAAACAGA   4800
ATTTGTTAAA CTCTTACTTG ACCACGGTGC TTACGTAAAT GCTAAAGCTA AGTTATCTGG   4860
AAATACTCCT TTACATAAAG CTATGTTATC TAATAGTTTT AATAATATAA AATTACTTTT   4920
ATCTTATAAC GCCGACTATA ATTCTCTAAA TAATCACGGT AATACGCCTC TAACTTGTGT   4980
TAGCTTTTTA GATGACAAGA TAGCTATTAT GATAATATCT AAAATGATGT TAGAAATATC   5040
TAAAAATCCT GAAATAGCTA ATTCAGAAGG TTTTATAGTA AACATGGAAC ATATAAACAG   5100
TAATAAAAGA CTACTATCTA TAAAAGAATC ATGCGAAAAA GAACTAGATG TTATAACACA   5160
TATAAAGTTA AATTCTATAT ATTCTTTTAA TATCTTTCTT GACAATAACA TAGATCTTAT   5220
GGTAAAGTTC GTAACTAATC CTAGAGTTAA TAAGATACCT GCATGTATAC GTATATATAG   5280
GGAATTAATA CGGAAAAATA AATCATTAGC TTTTCATAGA CATCAGCTAA TAGTTAAAGC   5340
TGTAAAAGAG AGTAAGAATC TAGGAATAAT AGGTAGGTTA CCTATAGATA TCAAACATAT   5400
AATAATGGAA CTATTAAGTA ATAATGATTT ACATTCTGTT ATCACCAGCT GTTGTAACCC   5460
AGTAGTATAA AGTGATTTTA TTCAATTACG AAGATAAACA TTAAATTTGT TAACAGATAT   5520
GAGTTATGAG TATTTAACTA AAGTTACTTT AGGTACAAAT AAAATATTAT GTAATATAAT   5580
AGAAAATTAT CTTGAGTCTT CATTTCCATC ACCGTCTAAA TTTATTATTA AAACCTTATT   5640
ATATAAGGCT GTTGAGTTTA GAAATGTAAA TGCTGTAAAA AAAATATTAC AGAATGATAT   5700
TGAATATGTT AAAGTAGATA GTCATGGTGT CTCGCCTTTA CATATTATAG CTATGCCTTC   5760
AAATTTTTCT CTCATAGACG CTGACATGTA TTCAGAATTT AATGAAATTA GTAATAGACT   5820
```

-continued

```
TCAAAAATCT AAAGATAGTA ACGAATTTCA ACGAGTTAGT CTACTAAGGA CAATTATAGA   5880
ATATGGTAAT GATAGTGATA TTAATAAGTG TCTAACATTA GTAAAAACGG ATATACAGAG   5940
TAACGAAGAG ATAGATATTA TAGATCTTTT GATAAATAAA GGAATAGATA TAAATATTAA   6000
AGACGATTTA GGAAACACAG CTTTGCATTA CTCGTGTGAT TATGCTAAGG GATCAAAGAT   6060
AGCTAAAAAG TTACTAGATT GTGGAGCAGA TCCTAACATA GTTAATGATT TAGGTGTTAC   6120
ACCACTAGCG TGTGCCGTTA ATACTTGCAA CGAGATACTA GTAGATATTC TGTTAAATAA   6180
TGATGCGAAT CCTGATTCAT CTTCCTCATA TTTTTTAGGT ACTAATGTGT TACATACAGC   6240
CGTAGGTACC GGTAATATAG ATATTGTAAG ATCTTTACTT ACGGCTGGTG CCAATCCTAA   6300
TGTAGGAGAT AAATCTGGAG TTACTCCTTT GCACGTTGCT GCAGCTGATA AAGACAGTTA   6360
TCTGTTAATG GAGATGCTAC TAGATAGCGG GGCAGATCCA AATATAAAAT GCGCAAACGG   6420
TTTTACTCCT TTGTTTAATG CAGTATATGA TCATAACCGT ATAAAGTTAT TATTTCTTTA   6480
CGGGGCTGAT ATCAATATTA CTGACTCTTA CGGAAATACT CCTCTTACTT ATATGACTAA   6540
TTTTGATAAT AAATATGTAA ATTCAATAAT TATCTTACAA ATATATCTAC TTAAAAAAGA   6600
ATATAACGAT GAAAGATTGT TTCCACCTGG TATGATAAAA AATTTAAACT TTATAGAATC   6660
AAACGATAGT CTTAAAGTTA TAGCTAAAAA GTGTAATTCG TTAATACGCT ATAAGAAAAA   6720
TAAAGACATA GATGCAGATA ACGTATTATT GGAGCTTTTA GAGGAAGAGG AAGAAGATGA   6780
AATAGACAGA TGGCATACTA CATGTAAAAT ATCTTAAATA GTAATTAAAT CATTGAAATA   6840
TTAACTTACA AGATGATCGA GGTCACTTAT TATACTCTTT AATAATGGGT ACAAAGAGTA   6900
TTCATACGTT AGTTAAATCT AACGATGTAA TACGTGTTCG TGAATTAATA AAGGATGATA   6960
GATGTTTGAT AAATAAAAGA AATAGAAGAA ATCAGTCACC TGTATATATA GCTATATACA   7020
AAGGACTTTA TGAAATGACT GAAATGTTAT TGCTAAATAA TGCAAGTCTA GATACTAAAA   7080
TACCTTCTTT AATTATAGCA GCTAAAAATA ATGACTTACC TATGATAAAA TTATTGATAC   7140
AATACGGGGC AAAATTAAAT GATATTTATT TAAGGGACAC AGCATTAATG ATAGCTCTCA   7200
GAAATGGTTA CCTAGATATA GCTGAATATT TACTTTCATT AGGAGCAGAA TTTGTTAAAT   7260
ACAGACATAA GGTAATATAT AAATATCTAT CAAAAGATGC GTATGAATTA CTTTTTAGAT   7320
TTAATTATGA CGTTAATATA ATAGATTGAG A                                  7351
```

(2) INFORMATION FOR SEQ ID NO:4:

(i) SEQUENCE CHARACTERISTICS:
(A) LENGTH: 7091 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

```
AGATATTTGT TAGCTTCTGC CGGAGATACC GTGAAAATCT ATTTTCTGGA AGGAAAGGGA     60
GGTCTTATCT ATTCTGTCAG CAGAGTAGGT TCCTCTAATG ACGAAGACAA TAGTGAATAC    120
TTGCATGAAG GTCACTGTGT AGAGTTCAAA ACTGATCATC AGTGTTTGAT AACTCTAGCG    180
TGTACGAGTC CTTCTAACAC TGTGGTTTAT TGGCTGGAAT AAAAGGATAA AGACACCTAT    240
ACTGATTCAT TTTCATCTGT CAACGTTTCT CTAAGAGATT CATAGGTATT ATTATTACAT    300
CGATCTAGAA GTCTAATAAC TGCTAAGTAT ATTATTGGAT TTAACGCGCT ATAAACGCAT    360
CCAAAACCTA CAAATATAGG AGAAGCTTCT CTTATGAAAC TTCTTAAAGC TTTACTCTTA    420
```

-continued

```
CTATTACTAC TCAAAAGAGA TATTACATTA ATTATGTGAT GAGGCATCCA ACATATAAAG    480
AAGACTAAAG CTGTAGAAGC TGTTATGAAG AATATCTTAT CAGATATATT AGATGCATTG    540
TTAGTTCTGT AGATCAGTAA CGTATAGCAT ACGAGTATAA TTATCGTAGG TAGTAGGTAT    600
CCTAAAATAA ATCTGATACA GATAATAACT TTGTAAATCA ATTCAGCAAT TTCTCTATTA    660
TCATGATAAT GATTAATACA CAGCGTGTCG TTATTTTTTG TTACGATAGT ATTTCTAAAG    720
TAAAGAGCAG GAATCCCTAG TATAATAGAA ATAATCCATA TGAAAAATAT AGTAATGTAC    780
ATATTTCTAA TGTTAACATA TTTATAGGTA AATCCAGGAA GGGTAATTTT TACATATCTA    840
TATACGCTTA TTACAGTTAT TAAAAATATA CTTGCAAACA TGTTAGAAGT AAAAAAGAAA    900
GAACTAATTT TACAAAGTGC TTTACCAAAA TGCCAATGGA AATTACTTAG TATGTATATA    960
ATGTATAAAG GTATGAATAT CACAAACAGC AAATCGGCTA TTCCCAAGTT GAGAAACGGT   1020
ATAATAGATA TATTTCTAGA TACCATTAAT AACCTTATAA GCTTGACGTT TCCTATAATG   1080
CCTACTAAGA AAACTAGAAG ATACATACAT ACTAACGCCA TACGAGAGTA ACTACTCATC   1140
GTATAACTAC TGTTGCTAAC AGTGACACTG ATGTTATAAC TCATCTTTGA TGTGGTATAA   1200
ATGTATAATA ACTATATTAC ACTGGTATTT TATTTCAGTT ATATACTATA TAGTATTAAA   1260
AATTATATTT GTATAATTAT ATTATTATAT TCAGTGTAGA AAGTAAAATA CTATAAATAT   1320
GTATCTCTTA TTTATAACTT ATTAGTAAAG TATGTACTAT TCAGTTATAT TGTTTTATAA   1380
AAGCTAAATG CTACTAGATT GATATAAATG AATATGTAAT AAATTAGTAA TGTAGTATAC   1440
TAATATTAAC TCACATTTGA CTAATTAGCT ATAAAAACCC GGGCTGCAGG AATTCCTCGA   1500
GACGCGTGGC ATGCAAGCTT ATAAAAATCA CAAGTCTCTG TCACTTTTTT TGTCTAGTTT   1560
TTTTTTCTCC TCTTGGTTCA GACGTTCTCT TCTTCGTCGG AGTCTTTCAA GTGTCGGTAG   1620
CCGTTTTTGC GGTGTCGCAG TCGGTCTAGC AGGTTGGGCT TCTGTCCCTT GTCCTGCGTG   1680
CCAGTCTGTC CGTCCAAAGA ATCTGTACCG TTCTCGTGCG CTCGCTGCTC TGCGTCCAGA   1740
CGGACCAGGG CCAGAAGCAT CTGGTAAGCC TGCTCGTTGG TGTAAGGCGG AGCCGCCGTG   1800
GATGCATCAG ACGACGGTGG TCCCGGTCCT TTGCGACCAG AATTATAAAC ACTTTCCTCG   1860
TAGGAAGGCG GAGCCTGTAA CGACGTGTCT TTGGTGTTGC CCGACGTCAC GGTGGTCCCG   1920
TCGGCGGACA CCAGATAGGG AAAGAGGTTC TGCAGCGGCT GCATGCAGAG ACGCCGCTGT   1980
CGAGTATAGA TCAAATAAAT GATAATGACG ACGGCTATGG CCACGAGGAT GATGGTGAAG   2040
GCTCCGAAGG GGTTTTTGAG GAAGGTGGCA ACGCCTTCGA CCACGGAGGC CACCGCGCCA   2100
CCCACGGCCC CAATGGCTAC GCCAACGGCC TTTCCCGCGG CGCCCAGGCC GCTCATGAGG   2160
TCGTCCAGAC CCTTGAGGTA GGGCGGCAGC GGGTCGACTA CCTTGTCCTC CACGTACTTT   2220
ACCCGCTGCT TATACGAATT GAACTCGCGC ATGATCTCCT CGAGATCAAA AACGTTGCTG   2280
GAACGCAATT CTTTCTGCGA GTAAAGTTCC AGTACCCTGA AGTCGGTGTT TTCCAGCGGG   2340
TCGATGTCTA GGGCGATCAT GCTGTCGACG GTGGAGATGC TGCTGAGGTC AATCATGCGT   2400
TTGAAGAGGT AGTCCACGTA CTCGTAGGCC GAGTTGCCGG CGATGAAGAT CTTGAGGCTG   2460
GGAAGCTGAC ATTCCTCAGT GCGGTGGTTG CCCAACAGGA TTTCGTTATC CTCGCCCAGT   2520
TGACCGTACT GCACGTACGA GCTGTTGGCG AAATTAAAGA TGACCACTGG TCGTGAGTAG   2580
CAGCGTCCTG GCGATTCCTT CACATTCATA TCACGCAGCA CCTTGACGCT GGTTTGGTTA   2640
ATGGTCACGC AGCTGGCCAG ACCCAGGACA TCACCCATGA AACGCGCGGC AATCGGTTTG   2700
TTGTAGATGG CCGAGAGAAT AGCTGACGGG TTGATCTTGC TAAGTTCCTT GAAGACCTCT   2760
AGGGTGCGCC GTTGATCCAC ACACCAGGCT TCTGCGATTT CGGCCAGCGC CCGGTTGATG   2820
```

-continued

```
TAACCGCGCA ACGTGTCATA GGTGAACTGC AGCTGGGCGT AGACCAGATT GTGCACCGAC   2880
TCCATGTTGG ATAAATGAGT TGCATTGTTG CCATCTGTAC TTCTTTTGGT TCTATTATGA   2940
GTAAGATTCA GACTGGAGCG GTTGGCCAAA CGTTCGAGTT CCACCAGAGA TTTTTGCTTG   3000
ATACCTTGCC AGAACACCAC CAAACCACCA GTGGTTTCAA AGACCGACAC GTTTCCATAT   3060
TTTTCATATG TTTGATTGTA TGAAGTATTG AAAATCTGCT GTAACTTATT TATGGCCTCA   3120
TCACGTACAC AGTCCAGCGC AGAGTCGGAC ATGTTCACCT CTTGCTTCTT AGATAAGAAA   3180
GTGGCGGTCA TTTTGGCAGA AGAAAAGTGA TACGAGTCCT CGGCTTCGGA ACGAATGGTG   3240
CGTTCCGAGG CTTCCCAGAA AGTGAGTTGA CAAGTAACAT TCTTCTCGTC CTGTATATCC   3300
CAGGAGATCA CTGAGTCCGC ACGTTCAAGA AAAGCCACCA ACCTGTGGGT CTCTAACGCA   3360
GAATTCGGTC TTTCAAAGTC GGAGACGATA GTGTAGTTCG GAAAAATGAA AAACTTGTCG   3420
GCGTTTTCTC CAAAATAGCT GGCATTGCGA TTAGTTCCGT TGTAGAAAGG AGAAATGTCA   3480
ACCACATCAC CCGTGGAAGT TGCGAAAAAA TGATAGGGAT ACTTGGAGCG CGCAGTAGTG   3540
ATGGTCACCA TACAATTCAG ATTACAGGTC TCACGATAGA GCCAGGTGCT GCCGCGGCTG   3600
TGCCATTGAT CCTTGACCGT CACGTAACGG GTACTGTGGG TGTTGGAATA ATCGTCGGGC   3660
ATTAATTGCA TGGTTTTGTT TTCATAGCTG TCCCTATGAT AAGCCACGAA AACCGTGCCT   3720
GCTATAACGC GGCTGTAGGA ACTGTAGCAC TGACTGTGAC TGTTGATATG ATGAATCTCC   3780
CACATAGGAG GCGCCACGTA TTCCGTGTTG CTGCCCAGCA GATAAGTGGT GTGGATGTAA   3840
GCGTAGCTAC GACGAAACGT CAAAACCTTC TGGTAGACTC GTACCTTAAA GGTGTGCGCG   3900
ACGATGTTGC GTTTGTAGAC CACCATGATG CCCTCGTCCA GGTCTTCATT GATGGGCTTC   3960
ATCGAGGTGC AGACGATATT ACGTTCAAAG CGAATAAGAT CCGTACCCTG AGCCATAGAA   4020
CACACGCGAT AGGGGTACTT GGTGGTGTTG ACCCCCACCA CATCTCCGTA CTTGAGGGTA   4080
GTGTTGTAGA TGGTCTCGTT AACACCATGG CTGACCGTTT GGGAAGAAGT TACGCGTTGA   4140
GAGACTGAAC CGGATCGAGA ATGAGCAGCA GACGTCGTAT GAGAGGAATG GTGACTGTGA   4200
GTAGCAGAAG TTCCACGAGT AGAAGATGAG GAAACCGCAG CACCCAGACA GACGATACAC   4260
AAGTTAACGC AGACTACCAG GCACCAGATC CTGGATTCCA TTACGATACA AACTTAACGG   4320
ATATCGCGAT AATGAAATAA TTTATGATTA TTTCTCGCTT TCAATTTAAC ACAACCCTCA   4380
AGAACCTTTG TATTTATTTT CACTTTTTAA GTATAGAATA AAGAAGCTCT AATTAATTAA   4440
GCTACAAATA GTTTCGTTTT CACCTTGTCT AATAACTAAT TAATTAACCC GGATCCCGAT   4500
TTTTATGACT AGTTAATCAA ATAAAAAGCA TACAAGCTAT TGCTTCGCTA TCGTTACAAA   4560
ATGGCAGGAA TTTTGTGTAA ACTAAGCCAC ATACTTGCCA ATGAAAAAAA TAGTAGAAAG   4620
GATACTATTT TAATGGGATT AGATGTTAAG GTTCCTTGGG ATTATAGTAA CTGGGCATCT   4680
GTTAACTTTT ACGACGTTAG GTTAGATACT GATGTTACAG ATTATAATAA TGTTACAATA   4740
AAATACATGA CAGGATGTGA TATTTTTCCT CATATAACTC TTGGAATAGC AAATATGGAT   4800
CAATGTGATA GATTTGAAAA TTTCAAAAAG CAAATAACTG ATCAAGATTT ACAGACTATT   4860
TCTATAGTCT GTAAAGAAGA GATGTGTTTT CCTCAGAGTA ACGCCTCTAA ACAGTTGGGA   4920
GCGAAAGGAT GCGCTGTAGT TATGAAACTG GAGGTATCTG ATGAACTTAG AGCCCTAAGA   4980
AATGTTCTGC TGAATGCGGT ACCCTGTTCG AAGGACGTGT TTGGTGATAT CACAGTAGAT   5040
AATCCGTGGA ATCCTCACAT AACAGTAGGA TATGTTAAGG AGGACGATGT CGAAAACAAG   5100
AAACGCCTAA TGGAGTGCAT GTCCAAGTTT AGGGGGCAAG AAATACAAGT TCTAGGATGG   5160
```

-continued

```
TATTAATAAG TATCTAAGTA TTTGGTATAA TTTATTAAAT AGTATAATTA TAACAAATAA   5220

TAAATAACAT GATAACGGTT TTTATTAGAA TAAAATAGAG ATAATATCAT AATGATATAT   5280

AATACTTCAT TACCAGAAAT GAGTAATGGA AGACTTATAA ATGAACTGCA TAAAGCTATA   5340

AGGTATAGAG ATATAAATTT AGTAAGGTAT ATACTTAAAA AATGCAAATA CAATAACGTA   5400

AATATACTAT CAACGTCTTT GTATTTAGCC GTAAGTATTT CTGATATAGA AATGGTAAAA   5460

TTATTACTAG AACACGGTGC CGATATTTTA AAATGTAAAA ATCCTCCTCT TCATAAAGCT   5520

GCTAGTTTAG ATAATACAGA AATTGCTAAA CTACTAATAG ATTCTGGCGC TGACATAGAA   5580

CAGATACATT CTGGAAATAG TCCGTTATAT ATTTCTGTAT ATAGAAACAA TAAGTCATTA   5640

ACTAGATATT TATTAAAAAA AGGTGTTAAT TGTAATAGAT TCTTTCTAAA TTATTACGAT   5700

GTACTGTATG ATAAGATATC TGATGATATG TATAAAATAT TTATAGATTT TAATATTGAT   5760

CTTAATATAC AAACTAGAAA TTTTGAAACT CCGTTACATT ACGCTATAAA GTATAAGAAT   5820

ATAGATTTAA TTAGGATATT GTTAGATAAT AGTATTAAAA TAGATAAAAG TTTATTTTTG   5880

CATAAACAGT ATCTCATAAA GGCACTTAAA AATAATTGTA GTTACGATAT AATAGCGTTA   5940

CTTATAAATC ACGGAGTGCC TATAAACGAA CAAGATGATT TAGGTAAAAC CCCATTACAT   6000

CATTCGGTAA TTAATAGAAG AAAAGATGTA ACAGCACTTC TGTTAAATCT AGGAGCTGAT   6060

ATAAACGTAA TAGATGACTG TATGGGCAGT CCCTTACATT ACGCTGTTTC ACGTAACGAT   6120

ATCGAAACAA CAAAGACACT TTTAGAAAGA GGATCTAATG TTAATGTGGT TAATAATCAT   6180

ATAGATACCG TTCTAAATAT AGCTGTTGCA TCTAAAAACA AAACTATAGT AAACTTATTA   6240

CTGAAGTACG GTACTGATAC AAAGTTGGTA GGATTAGATA AACATGTTAT TCACATAGCT   6300

ATAGAAATGA AAGATATTAA TATACTGAAT GCGATCTTAT TATATGGTTG CTATGTAAAC   6360

GTCTATAATC ATAAAGGTTT CACTCCTCTA TACATGGCAG TTAGTTCTAT GAAAACAGAA   6420

TTTGTTAAAC TCTTACTTGA CCACGGTGCT TACGTAAATG CTAAAGCTAA GTTATCTGGA   6480

AATACTCCTT TACATAAAGC TATGTTATCT AATAGTTTTA ATAATATAAA ATTACTTTTA   6540

TCTTATAACG CCGACTATAA TTCTCTAAAT AATCACGGTA ATACGCCTCT AACTTGTGTT   6600

AGCTTTTTAG ATGACAAGAT AGCTATTATG ATAATATCTA AAATGATGTT AGAAATATCT   6660

AAAAATCCTG AAATAGCTAA TTCAGAAGGT TTTATAGTAA ACATGGAACA TATAAACAGT   6720

AATAAAAGAC TACTATCTAT AAAAGAATCA TGCGAAAAAG AACTAGATGT TATAACACAT   6780

ATAAAGTTAA ATTCTATATA TTCTTTTAAT ATCTTTCTTG ACAATAACAT AGATCTTATG   6840

GTAAAGTTCG TAACTAATCC TAGAGTTAAT AAGATACCTG CATGTATACG TATATATAGG   6900

GAATTAATAC GGAAAAATAA ATCATTAGCT TTTCATAGAC ATCAGCTAAT AGTTAAAGCT   6960

GTAAAAGAGA GTAAGAATCT AGGAATAATA GGTAGGTTAC CTATAGATAT CAAACATATA   7020

ATAATGGAAC TATTAAGTAA TAATGATTTA CATTCTGTTA TCACCAGCTG TTGTAACCCA   7080

GTAGTATAAA G                                                        7091
```

(2) INFORMATION FOR SEQ ID NO:5:

(i) SEQUENCE CHARACTERISTICS:
(A) LENGTH: 4768 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

-continued

```
AAGCTTGCGG CCGCTCATTA GACAAGCGAA TGAGGGACGA AAACGTGGAG GAGGTATTAA     60
GTTTGGAGAA ATGGAGAGAG ACTGTTTAAT AGCGCATGGC GCAGCCAATA CTATTACAGA    120
AGTTTTGAAA GATTCGGAAG AAGATTATCA AGATGTGTAT GTTTGTGAAA ATTGTGGAGA    180
CATAGCAGCA CAAATCAAGG GTATTAATAC ATGTCTTAGA TGTTCAAAAC TTAATCTCTC    240
TCCTCTCTTA ACAAAAATTG ATACCACGCA CGTATCTAAA GTATTTCTTA CTCAAATGAA    300
CGCCAGAGGC GTAAAAGTCA AATTAGATTT CGAACGAAGG CCTCCTTCGT TTTATAAACC    360
ATTAGATAAA GTTGATCTCA AGCCGTCTTT TCTGGTGTAA TAAAAATTAA TTAATTACTC    420
GAGGGTACCG GATCCCCCAG CTTATAAAAA TCACAAGTCT CTGACACTTT TTTTGTCTAG    480
TTTTTTTTTC TCCTCTTGGT TCAGACGTTC TCTTCTTCGT CGGAGTCTTT CAAGTGTCGG    540
TAGCCGTTTT TGCGGTGTCG CAGTCGGTCT AGCAGGTTGG GCTTCTGTCC CTTGTCCTGC    600
GTGCCAGTCT GTCCGTCCAA AGAATCTGTA CCGTTCTCGT GCGCTCGCTG CTCTGCGTCC    660
AGACGGACCA GGGCCAGAAG CATCTGGTAA GCCTGCTCGT TGGTGTAAGG CGGAGCCGCC    720
GTGGATGCAT CAGACGACGG TGGTCCCGGT CCTTTGCGAC CAGAATTATA AACACTTTCC    780
TCGTAGGAAG GCGGAGCCTG TAACGACGTG TCTTTGGTGT TGCCCGACGT CACGGTGGTC    840
CCGTCGGCGG ACACCAGATA GGGAAAGAGG TTCTGCAGCG GCTGCATGCA GAGACGCCGC    900
TGTCGAGTAT AGATCAAATA AATGATAATG ACGACGGCTA TGGCCACGAG GATGATGGTG    960
AAGGCTCCGA AGGGGTTTTT GAGGAAGGTG GCAACGCCTT CGACCACGGA GGCCACCGCG   1020
CCACCCACGG CCCCAATGGC TACGCCAACG GCCTTTCCCG CGGCGCCCAG GCCGCTCATG   1080
AGGTCGTCCA GACCCTTGAG GTAGGGCGGC AGCGGGTCGA CTACCTTGTC CTCCACGTAC   1140
TTTACCCGCT GCTTATACGA ATTGAACTCG CGCATGATCT CCTCGAGATC AAAAACGTTG   1200
CTGGAACGCA ATTCTTTCTG CGAGTAAAGT TCCAGTACCC TGAAGTCGGT GTTTTCCAGC   1260
GGGTCGATGT CTAGGGCGAT CATGCTGTCG ACGGTGGAGA TGCTGCTGAG GTCAATCATG   1320
CGTTTGAAGA GGTAGTCCAC GTACTCGTAG GCCGAGTTGC CGGCGATGAA GATCTTGAGG   1380
CTGGGAAGCT GACATTCCTC AGTGCGGTGG TTGCCCAACA GGATTTCGTT ATCCTCGCCC   1440
AGTTGACCGT ACTGCACGTA CGAGCTGTTG GCGAAATTAA AGATGACCAC TGGTCGTGAG   1500
TAGCAGCGTC CTGGCGATTC CTTCACATTC ATATCACGCA GCACCTTGAC GCTGGTTTGG   1560
TTAATGGTCA CGCAGCTGGC CAGACCCAGG ACATCACCCA TGAAACGCGC GGCAATCGGT   1620
TTGTTGTAGA TGGCCGAGAG AATAGCTGAC GGGTTGATCT TGCTAAGTTC CTTGAAGACC   1680
TCTAGGGTGC GCCGTTGATC CACACACCAG GCTTCTGCGA TTTCGGCCAG CGCCCGGTTG   1740
ATGTAACCGC GCAACGTGTC ATAGGTGAAC TGCAGCTGGG CGTAGACCAG ATTGTGCACC   1800
GACTCCATGT TGGATAAATG AGTTGCATTG TTGCCATCTG TACTTCTTTT GGTTCTATTA   1860
TGAGTAAGAT TCAGACTGGA GCGGTTGGCC AAACGTTCGA GTTCCACCAG AGATTTTTGC   1920
TTGATACCTT GCCAGAACAC CACCAAACCA CCAGTGGTTT CAAAGACGGA CACGTTTCCA   1980
TATTTTTCAT ATGTTTGATT GTATGAAGTA TTGAAAATCT GCTGTAACTT ATTTATGGCC   2040
TCATCACGTA CACAGTCCAG CGCAGAGTCG GACATGTTCA CCTCTTGCTT CTTAGATAAG   2100
AAAGTGGCGG TCATTTTGGC AGAAGAAAAG TGATACGAGT CCTCGGCTTC GGAACGAATG   2160
GTGCGTTCCG AGGCTTCCCA GAAAGTGAGT TGACAAGTAA CATTCTTCTC GTCCTGTATA   2220
TCCCAGGAGA TCACTGAGTC CGCACGTTCA AGAAAAGCCA CCAACCTGTG GGTCTCTAAC   2280
GCAGAATTCG GTCTTTCAAA GTCGGAGACG ATAGTGTAGT TCGGAAAAAT GAAAAACTTG   2340
TCGGCGTTTT CTCCAAAATA GCTGGCATTG CGATTAGTTC CGTTGTAGAA AGGAGAAATG   2400
```

-continued

```
TCAACCACAT CACCCGTGGA AGTTGCGAAA AAATGATAGG GATACTTGGA GCGCGCAGTA   2460
GTGATGGTCA CCATACAATT CAGATTACAG GTCTCACGAT AGAGCCAGGT GCTGCCGCGG   2520
CTGTGCCATT GATCCTTGAC CGTCACGTAA CGGGTACTGT GGGTGTTGGA ATAATCGTCG   2580
GGCATTAATT GCATGGTTTT GTTTTCATAG CTGTCCCTAT GATAAGCCAC GAAAACCGTG   2640
CCTGCTATAA CGCGGCTGTA GGAACTGTAG CACTGACTGT GACTGTTGAT ATGATGAATC   2700
TCCCACATAG GAGGCGCCAC GTATTCCGTG TTGCTGCCCA GCAGATAAGT GGTGTGGATG   2760
TAAGCGTAGC TACGACGAAA CGTCAAAACC TTCTGGTAGA CTCGTACCTT AAAGGTGTGC   2820
GCGACGATGT TGCGTTTGTA GACCACCATG ATGCCCTCGT CCAGGTCTTC ATTGATGGGC   2880
TTCATCGAGG TGCAGACGAT ATTACGTTCA AAGCGAATAA GATCCGTACC CTGAGCCATA   2940
GAACACACGC GATAGGGGTA CTTGGTGGTG TTGACCCCCA CCACATCTCC GTACTTGAGG   3000
GTAGTGTTGT AGATGGTCTC GTTAACACCA TGGCTGACCG TTTGGGAAGA AGTTACGCGT   3060
TGAGAGACTG AACCGGATCG AGAATGAGCA GCAGACGTCG TATGAGAGGA ATGGTGACTG   3120
TGAGTAGCAG AAGTTCCACG AGTAGAAGAT GAGGAAACCG CAGCACCCAG ACAGACGATA   3180
CACAAGTTAA CGCAGACTAC CAGGCACCAG ATCCTGGATT CCATTACGAT ACAAACTTAA   3240
CGGATATCGC GATAATGAAA TAATTTATGA TTATTTCTCG CTTTCAATTT AACACAACCC   3300
TCAAGAACCT TTGTATTTAT TTTCACTTTT TAAGTATAGA ATAAAGAAGC TGGGAATCGA   3360
TTCGCGATAG CTGATTAGTT TTTGTTAACA AAAATGTGGG AGAATCTAAT TAGTTTTTCT   3420
TTACACAATT GACGTACATG AGTCTGAGTT CCTTGTTTTT GCTAATTATT TCATCCAATT   3480
TATTATTCTT GACGATATCG AGATCTTTTG TATAGGAGTC AGACTTGTAT TCAACATGCT   3540
TTTCTATAAT CATCTTAGTT ATTTCGGCAT CATCCAATAG TACATTTTCC AGATTAACAG   3600
AGTAGATATT AATGTCGTAT TTGAACAGAG CCTGTAACAT CTCAATGTCT TTATTATCTA   3660
TAGCCAATTT AATGTCCGGA ATGAAGAGAA GGGAATTATT GGTGTTTGTC GACGTCATAT   3720
AGTCGAGCAA GAGAATCATC ATATCCACGT GTCCATTTTT TATAGTGGTG TGAATACAAC   3780
TAAGGAGAAT AGCCAGATCA AAAGTAGATG GTATTTCTGA AAGAAAGTAT GATACAATAC   3840
TTACATCATT AAGCATGACG GCATGATAAA ATGAAGTTTT CCATCCAGTT TTCCCATAGA   3900
ACATCAGTCT CCAATTTTTC TTAAACAGTT TCACCGTTTG CATGTTACCA CTATCAACCG   3960
CATAATACAA TGCGGTGTTT CCTTTGTCAT CAAATTGTGA ATCATCCATT CCACTGAATA   4020
GCAAAATCTT TACTATTTTG GTATCTTCTA ATGTGGCTGC CTGATGTAAT GGAAATTCAT   4080
TCTCTAGAAG ATTTTTCAAT GCTCCAGCGT TCAACAACGT ACATACTAGA CGCACGTTAT   4140
TATCAGCTAT TGCATAATAC AAGGCACTAT GTCCATGGAC ATCCGCCTTA AATGTATCTT   4200
TACTAGAGAG AAAGCTTTTC AGCTGCTTAG ACTTCCAAGT ATTAATTCGT GACAGATCCA   4260
TGTCTGAAAC GAGACGCTAA TTAGTGTATA TTTTTTCATT TTTTATAATT TTGTCATATT   4320
GCACCAGAAT TAATAATATC TCTAATAGAT CTAATTTAAT TTAATTTATA TAACTTATTT   4380
TTTGAATATA CTTTTAATTA ACAAAAGAGT TAAGTTACTC ATATGGACGC CGTCCAGTCT   4440
GAACATCAAT CTTTTTAGCC AGAGATATCA TAGCCGCTCT TAGAGTTTCA GCGTGATTTT   4500
CCAACCTAAA TAGAACTTCA TCGTTGCGTT TACAACACTT TTCTATTTGT TCAAACTTTG   4560
TTGTTACATT AGTAATCTTT TTTTCCAAAT TAGTTAGCCG TTGTTTGAGA GTTTCCTCAT   4620
TGTCGTCTTC ATCGGCTTTA ACAATTGCTT CGCGTTTAGC CTCCTGGCTG TTCTTATCAG   4680
CCTTTGTAGA AAAAAATTCA GTTGCTGGAA TTGCAAGATC GTCATCTCCG GGGAAAAGAG   4740
```

-continued

```
TTCCGTCCAT TTAAAGCCGC GGGAATTC                                     4768
```

(2) INFORMATION FOR SEQ ID NO:6:

(i) SEQUENCE CHARACTERISTICS:
(A) LENGTH: 2550 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
ATGGAATCCA GGATCTGGTG CCTGGTAGTC TGCGTTAACT TGTGTATCGT CTGTCTGGGT     60

GCTGCGGTTT CCTCATCTTC TACTCGTGGA ACTTCTGCTA CTCACAGTCA CCATTCCTCT    120

CATACGACGT CTGCTGCTCA TTCTCGATCC GGTTCAGTCT CTCAACGCGT AACTTCTTCC    180

CAAACGGTCA GCCATGGTGT TAACGAGACC ATCTACAACA CTACCCTCAA GTACGGAGAT    240

GTGGTGGGGG TCAACACCAC CAAGTACCCC TATCGCGTGT GTTCTATGGC TCAGGGTACG    300

GATCTTATTC GCTTTGAACG TAATATCGTC TGCACCTCGA TGAAGCCCAT CAATGAAGAC    360

CTGGACGAGG GCATCATGGT GGTCTACAAA CGCAACATCG TCGCGCACAC CTTTAAGGTA    420

CGAGTCTACC AGAAGGTTTT GACGTTTCGT CGTAGCTACG CTTACATCCA CACCACTTAT    480

CTGCTGGGCA GCAACACGGA ATACGTGGCG CCTCCTATGT GGGAGATTCA TCATATCAAC    540

AGTCACAGTC AGTGCTACAG TTCCTACAGC CGCGTTATAG CAGGCACGGT TTTCGTGGCT    600

TATCATAGGG ACAGCTATGA AAACAAAACC ATGCAATTAA TGCCCGACGA TTATTCCAAC    660

ACCCACAGTA CCCGTTACGT GACGGTCAAG GATCAATGGC ACAGCCGCGG CAGCACCTGG    720

CTCTATCGTG AGACCTGTAA TCTGAATTGT ATGGTGACCA TCACTACTGC GCGCTCCAAG    780

TATCCCTATC ATTTTTTCGC AACTTCCACG GGTGATGTGG TTGACATTTC TCCTTTCTAC    840

AACGGAACTA ATCGCAATGC CAGCTATTTT GGAGAAAACG CCGACAAGTT TTTCATTTTT    900

CCGAACTACA CTATCGTCTC CGACTTTGAA AGACCGAATT CTGCGTTAGA GACCCACAGG    960

TTGGTGGCTT TTCTTGAACG TGCGGACTCA GTGATCTCCT GGGATATACA GGACGAGAAG   1020

AATGTTACTT GTCAACTCAC TTTCTGGGAA GCCTCGGAAC GCACCATTCG TTCCGAAGCC   1080

GAGGACTCGT ATCACTTTTC TTCTGCCAAA ATGACCGCCA CTTTCTTATC TAAGAAGCAA   1140

GAGGTGAACA TGTCCGACTC TGCGCTGGAC TGTGTACGTG ATGAGGCCAT AAATAAGTTA   1200

CAGCAGATTT TCAATACTTC ATACAATCAA ACATATGAAA AATATGGAAA CGTGTCCGTC   1260

TTTGAAACCA CTGGTGGTTT GGTGGTGTTC TGGCAAGGTA TCAAGCAAAA ATCTCTGGTG   1320

GAACTCGAAC GTTTGGCCAA CCGCTCCAGT CTGAATCTTA CTCATAATAG AACCAAAAGA   1380

AGTACAGATG GCAACAATGC AACTCATTTA TCCAACATGG AGTCGGTGCA CAATCTGGTC   1440

TACGCCCAGC TGCAGTTCAC CTATGACACG TTGCGCGGTT ACATCAACCG GGCGCTGGCC   1500

GAAATCGCAG AAGCCTGGTG TGTGGATCAA CGGCGCACCC TAGAGGTCTT CAAGGAACTT   1560

AGCAAGATCA ACCCGTCAGC TATTCTCTCG GCCATCTACA ACAAACCGAT TGCCGCGCGT   1620

TTCATGGGTG ATGTCCTGGG TCTGGCCAGC TGCGTGACCA TTAACCAAAC CAGCGTCAAG   1680

GTGCTGCGTG ATATGAATGT GAAGGAATCG CCAGGACGCT GCTACTCACG ACCAGTGGTC   1740

ATCTTTAATT TCGCCAACAG CTCGTACGTG CAGTACGGTC AACTGGGCGA GGATAACGAA   1800

ATCCTGTTGG GCAACCACCG CACTGAGGAA TGTCAGCTTC CCAGCCTCAA GATCTTCATC   1860

GCCGGCAACT CGGCCTACGA GTACGTGGAC TACCTCTTCA AACGCATGAT TGACCTCAGC   1920
```

-continued

```
AGCATCTCCA CCGTCGACAG CATGATCGCC CTAGACATCG ACCCGCTGGA AAACACCGAC   1980

TTCAGGGTAC TGGAACTTTA CTCGCAGAAA GAATTGCGTT CCAGCAACGT TTTTGATCTC   2040

GAGGAGATCA TGCGCGAGTT CAATTCGTAT AAGCAGCGGG TAAAGTACGT GGAGGACAAG   2100

GTAGTCGACC CGCTGCCGCC CTACCTCAAG GGTCTGGACG ACACTCGACA GCGGCGTCTC   2160

TGCATGCAGC CGCTGCAGAA CCTCTTTCCC TATCTGGTGT CCGCCGACGG GACCACCGTG   2220

ACGTCGGGCA ACACCAAAGA CACGTCGTTA CAGGCTCCGC CTTCCTACGA GGAAAGTGTT   2280

TATAATTCTG GTCGCAAAGG ACCGGGACCA CCGTCGTCTG ATGCATCCAC GGCGGCTCCG   2340

CCTTACACCA ACGAGCAGGC TTACCAGATG CTTCTGGCCC TGGTCCGTCT GGACGCAGAG   2400

CAGCGAGCGC ACGAGAACGG TACAGATTCT TTGGACGGAC AGACTGGCAC GCAGGACAAG   2460

GGACAGAAGC CCAACCTGCT AGACCGACTG CGACACCGCA AAAACGGCTA CCGACACTTG   2520

AAAGACTCCG ACGAAGAAGA GAACGTCTGA                                    2550
```

(2) INFORMATION FOR SEQ ID NO:7:

(i) SEQUENCE CHARACTERISTICS:
(A) LENGTH: 4594 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

```
AAGCTTGCGG CCGCTCATTA GACAAGCGAA TGAGGGACGA AAACGTGGAG GAGGTATTAA     60

GTTTGGAGAA ATGGAGAGAG ACTGTTTAAT AGCGCATGGC GCAGCCAATA CTATTACAGA    120

AGTTTTGAAA GATTCGGAAG AAGATTATCA AGATGTGTAT GTTTGTGAAA ATTGTGGAGA    180

CATAGCAGCA CAAATCAAGG GTATTAATAC ATGTCTTAGA TGTTCAAAAC TTAATCTCTC    240

TCCTCTCTTA ACAAAAATTG ATACCACGCA CGTATCTAAA GTATTTCTTA CTCAAATGAA    300

CGCCAGAGGC GTAAAAGTCA AATTAGATTT CGAACGAAGG CCTCCTTCGT TTTATAAACC    360

ATTAGATAAA GTTGATCTCA AGCCGTCTTT TCTGGTGTAA TAAAAATTAA TTAATTACTC    420

GAGGGTACCG GATCCCCCAG CTTATAAAAA TCACAAGACT CTGTCACTTT TTTTGACTAG    480

TTTTTTTTTC TCCTCTTGGT TCAGACGTTC TCTTCTTCGT CGGAGTCTTT CAAGTGTCGG    540

TAGCCGTTTT TGCGGTGTCG CAGTCGGTCT AGCAGGTTGG GCTTCTGTCC CTTGTCCTGC    600

GTGCCAGTCT GTCCGTCCAA AGAATCTGTA CCGTTCTCGT GCGCTCGCTG CTCTGCGTCC    660

AGACGGACCA GGGCCAGAAG CATCTGGTAA GCCTGCTCGT TGGTGTAAGG CGGAGCCGCC    720

GTGGATGCAT CAGACGACGG TGGTCCCGGT CCTTTGCGAC CAGAATTATA AACACTTTCC    780

TCGTAGGAAG GCGGAGCCTG TAACGACGTG TCTTTGGTGT TGCCCGACGT CACGGTGGTC    840

CCGTCGGCGG ACACCAGATA GGGAAAGAGG TTCTGCAGCG GCTGCATGCA GAGACGCCGC    900

TGTCGAGTGT CGTCCAGACC CTTGAGGTAG GGCGGCAGCG GGTCGACTAC CTTGTCCTCC    960

ACGTACTTTA CCCGCTGCTT ATACGAATTG AACTCGCGCA TGATCTCCTC GAGATCAAAA   1020

ACGTTGCTGG AACGCAATTC TTTCTGCGAG TAAAGTTCCA GTACCCTGAA GTCGGTGTTT   1080

TCCAGCGGGT CGATGTCTAG GGCGATCATG CTGTCGACGG TGGAGATGCT GCTGAGGTCA   1140

ATCATGCGTT TGAAGAGGTA GTCCACGTAC TCGTAGGCCG AGTTGCCGGC GATGAAGATC   1200

TTGAGGCTGG GAAGCTGACA TTCCTCAGTG CGGTGGTTGC CCAACAGGAT TTCGTTATCC   1260

TCGCCCAGTT GACCGTACTG CACGTACGAG CTGTTGGCGA AATTAAAGAT GACCACTGGT   1320
```

-continued

```
CGTGAGTAGC AGCGTCCTGG CGATTCCTTC ACATTCATAT CACGCAGCAC CTTGACGCTG   1380
GTTTGGTTAA TGGTCACGCA GCTGGCCAGA CCCAGGACAT CACCCATGAA ACGCGCGGCA   1440
ATCGGTTTGT TGTAGATGGC CGAGAGAATA GCTGACGGGT TGATCTTGCT AAGTTCCTTG   1500
AAGACCTCTA GGGTGCGCCG TTGATCCACA CACCAGGCTT CTGCGATTTC GGCCAGCGCC   1560
CGGTTGATGT AACCGCGCAA CGTGTCATAG GTGAACTGCA GCTGGGCGTA GACCAGATTG   1620
TGCACCGACT CCATGTTGGA TAAATGAGTT GCATTGTTGC CATCTGTACT TCTTTTGGTT   1680
CTATTATGAG TAAGATTCAG ACTGGAGCGG TTGGCCAAAC GTTCGAGTTC CACCAGAGAT   1740
TTTTGCTTGA TACCTTGCCA GAACACCACC AAACCACCAG TGGTTTCAAA GACGGACACG   1800
TTTCCATATT TTTCATATGT TTGATTGTAT GAAGTATTGA AAATCTGCTG TAACTTATTT   1860
ATGGCCTCAT CACGTACACA GTCCAGCGCA GAGTCGGACA TGTTCACCTC TTGCTTCTTA   1920
GATAAGAAAG TGGCGGTCAT TTTGGCAGAA GAAAAGTGAT ACGAGTCCTC GGCTTCGGAA   1980
CGAATGGTGC GTTCCGAGGC TTCCCAGAAA GTGAGTTGAC AAGTAACATT CTTCTCGTCC   2040
TGTATATCCC AGGAGATCAC TGAGTCCGCA CGTTCAAGAA AAGCCACCAA CCTGTGGGTC   2100
TCTAACGCAG AATTCGGTCT TTCAAAGTCG GAGACGATAG TGTAGTTCGG AAAAATGAAA   2160
AACTTGTCGG CGTTTTCTCC AAAATAGCTG GCATTGCGAT TAGTTCCGTT GTAGAAAGGA   2220
GAAATGTCAA CCACATCACC CGTGGAAGTT GCGAAAAAAT GATAGGGATA CTTGGAGCGC   2280
GCAGTAGTGA TGGTCACCAT ACAATTCAGA TTACAGGTCT CACGATAGAG CCAGGTGCTG   2340
CCGCGGCTGT GCCATTGATC CTTGACCGTC ACGTAACGGG TACTGTGGGT GTTGGAATAA   2400
TCGTCGGGCA TTAATTGCAT GGTTTTGTTT TCATAGCTGT CCCTATGATA AGCCACGAAA   2460
ACCGTGCCTG CTATAACGCG GCTGTAGGAA CTGTAGCACT GACTGTGACT GTTGATATGA   2520
TGAATCTCCC ACATAGGAGG CGCCACGTAT TCCGTGTTGC TGCCCAGCAG ATAAGTGGTG   2580
TGGATGTAAG CGTAGCTACG ACGAAACGTC AAAACCTTCT GGTAGACTCG TACCTTAAAG   2640
GTGTGCGCGA CGATGTTGCG TTTGTAGACC ACCATGATGC CCTCGTCCAG GTCTTCATTG   2700
ATGGGCTTCA TCGAGGTGCA GACGATATTA CGTTCAAAGC GAATAAGATC CGTACCCTGA   2760
GCCATAGAAC ACACGCGATA GGGGTACTTG GTGGTGTTGA CCCCCACCAC ATCTCCGTAC   2820
TTGAGGGTAG TGTTGTAGAT GGTCTCGTTA ACACCATGGC TGACCGTTTG GGAAGAAGTT   2880
ACGCGTTGAG AGACTGAACC GGATCGAGAA TGAGCAGCAG ACGTCGTATG AGAGGAATGG   2940
TGACTGTGAG TAGCAGAAGT TCCACGAGTA GAAGATGAGG AAACCGCAGC ACCCAGACAG   3000
ACGATACACA AGTTAACGCA GACTACCAGG CACCAGATCC TGGATTCCAT TACGATACAA   3060
ACTTAACGGA TATCGCGATA ATGAAATAAT TTATGATTAT TTCTCGCTTT CAATTTAACA   3120
CAACCCTCAA GAACCTTTGT ATTTATTTTC ACTTTTTAAG TATAGAATAA AGAAGCTGGG   3180
AATCGATTCG CGATAGCTGA TTAGTTTTTG TTAACAAAAA TGTGGGAGAA TCTAATTAGT   3240
TTTTCTTTAC ACAATTGACG TACATGAGTC TGAGTTCCTT GTTTTTGCTA ATTATTTCAT   3300
CCAATTTATT ATTCTTGACG ATATCGAGAT CTTTTGTATA GGAGTCAGAC TTGTATTCAA   3360
CATGCTTTTC TATAATCATC TTAGTTATTT CGGCATCATC CAATAGTACA TTTTCCAGAT   3420
TAACAGAGTA GATATTAATG TCGTATTTGA ACAGAGCCTG TAACATCTCA ATGTCTTTAT   3480
TATCTATAGC CAATTTAATG TCCGGAATGA AGAGAAGGGA ATTATTGGTG TTTGTCGACG   3540
TCATATAGTC GAGCAAGAGA ATCATCATAT CCACGTGTCC ATTTTTTATA GTGGTGTGAA   3600
TACAACTAAG GAGAATAGCC AGATCAAAAG TAGATGGTAT TTCTGAAAGA AAGTATGATA   3660
CAATACTTAC ATCATTAAGC ATGACGGCAT GATAAAATGA AGTTTTCCAT CCAGTTTTCC   3720
```

-continued

```
CATAGAACAT CAGTCTCCAA TTTTTCTTAA ACAGTTTCAC CGTTTGCATG TTACCACTAT   3780
CAACCGCATA ATACAATGCG GTGTTTCCTT TGTCATCAAA TTGTGAATCA TCCATTCCAC   3840
TGAATAGCAA AATCTTTACT ATTTTGGTAT CTTCTAATGT GGCTGCCTGA TGTAATGGAA   3900
ATTCATTCTC TAGAAGATTT TTCAATGCTC CAGCGTTCAA CAACGTACAT ACTAGACGCA   3960
CGTTATTATC AGCTATTGCA TAATACAAGG CACTATGTCC ATGGACATCC GCCTTAAATG   4020
TATCTTTACT AGAGAGAAAG CTTTTCAGCT GCTTAGACTT CCAAGTATTA ATTCGTGACA   4080
GATCCATGTC TGAAACGAGA CGCTAATTAG TGTATATTTT TTCATTTTTT ATAATTTTGT   4140
CATATTGCAC CAGAATTAAT AATATCTCTA ATAGATCTAA TTTAATTTAA TTTATATAAC   4200
TTATTTTTTG AATATACTTT TAATTAACAA AAGAGTTAAG TTACTCATAT GGACGCCGTC   4260
CAGTCTGAAC ATCAATCTTT TTAGCCAGAG ATATCATAGC CGCTCTTAGA GTTTCAGCGT   4320
GATTTTCCAA CCTAAATAGA ACTTCATCGT TGCGTTTACA ACACTTTTCT ATTTGTTCAA   4380
ACTTTGTTGT TACATTAGTA ATCTTTTTTT CCAAATTAGT TAGCCGTTGT TTGAGAGTTT   4440
CCTCATTGTC GTCTTCATCG GCTTTAACAA TTGCTTCGCG TTTAGCCTCC TGGCTGTTCT   4500
TATCAGCCTT TGTAGAAAAA AATTCAGTTG CTGGAATTGC AAGATCGTCA TCTCCGGGGA   4560
AAAGAGTTCC GTCCATTTAA AGCCGCGGGA ATTC                               4594
```

(2) INFORMATION FOR SEQ ID NO:8:

(i) SEQUENCE CHARACTERISTICS:
(A) LENGTH: 2550 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
ATGGAATCCA GGATCTGGTG CCTGGTAGTC TGCGTTAACT TGTGTATCGT CTGTCTGGGT     60
GCTGCGGTTT CCTCATCTTC TACTCGTGGA ACTTCTGCTA CTCACAGTCA CCATTCCTCT    120
CATACGACGT CTGCTGCTCA TTCTCGATCC GGTTCAGTCT CTCAACGCGT AACTTCTTCC    180
CAAACGGTCA GCCATGGTGT TAACGAGACC ATCTACAACA CTACCCTCAA GTACGGAGAT    240
GTGGTGGGGG TCAACACCAC CAAGTACCCC TATCGCGTGT GTTCTATGGC TCAGGGTACG    300
GATCTTATTC GCTTTGAACG TAATATCGTC TGCACCTCGA TGAAGCCCAT CAATGAAGAC    360
CTGGACGAGG GCATCATGGT GGTCTACAAA CGCAACATCG TCGCGCACAC CTTTAAGGTA    420
CGAGTCTACC AGAAGGTTTT GACGTTTCGT CGTAGCTACG CTTACATCCA CACCACTTAT    480
CTGCTGGGCA GCAACACGGA ATACGTGGCG CCTCCTATGT GGGAGATTCA TCATATCAAC    540
AGTCACAGTC AGTGCTACAG TTCCTACAGC CGCGTTATAG CAGGCACGGT TTTCGTGGCT    600
TATCATAGGG ACAGCTATGA AAACAAAACC ATGCAATTAA TGCCCGACGA TTATTCCAAC    660
ACCCACAGTA CCCGTTACGT GACGGTCAAG GATCAATGGC ACAGCCGCGG CAGCACCTGG    720
CTCTATCGTG AGACCTGTAA TCTGAATTGT ATGGTGACCA TCACTACTGC GCGCTCCAAG    780
TATCCCTATC ATTTTTTCGC AACTTCCACG GGTGATGTGG TTGACATTTC TCCTTTCTAC    840
AACGGAACTA ATCGCAATGC CAGCTATTTT GGAGAAAACG CCGACAAGTT TTTCATTTTT    900
CCGAACTACA CTATCGTCTC CGACTTTGAA AGACCGAATT CTGCGTTAGA GACCCACAGG    960
TTGGTGGCTT TTCTTGAACG TGCGGACTCA GTGATCTCCT GGGATATACA GGACGAGAAG   1020
AATGTTACTT GTCAACTCAC TTTCTGGGAA GCCTCGGAAC GCACCATTCG TTCCGAAGCC   1080
```

```
GAGGACTCGT ATCACTTTTC TTCTGCCAAA ATGACCGCCA CTTTCTTATC TAAGAAGCAA      1140

GAGGTGAACA TGTCCGACTC TGCGCTGGAC TGTGTACGTG ATGAGGCCAT AAATAAGTTA      1200

CAGCAGATTT TCAATACTTC ATACAATCAA ACATATGAAA AATATGGAAA CGTGTCCGTC      1260

TTTGAAACCA CTGGTGGTTT GGTGGTGTTC TGGCAAGGTA TCAAGCAAAA ATCTCTGGTG      1320

GAACTCGAAC GTTTGGCCAA CCGCTCCAGT CTGAATCTTA CTCATAATAG AACCATAAGA      1380

TCTACAGATG GCAACAATGC AACTCATTTA TCCAACATGG AGTCGGTGCA CAATCTGGTC      1440

TACGCCCAGC TGCAGTTCAC CTATGACACG TTGCGCGGTT ACATCAACCG GGCGCTGGCC      1500

GAAATCGCAG AAGCCTGGTG TGTGGATCAA CGGCGCACCC TAGAGGTCTT CAAGGAACTT      1560

AGCAAGATCA ACCCGTCAGC TATTCTCTCG GCCATCTACA ACAAACCGAT TGCCGCGCGT      1620

TTCATGGGTG ATGTCCTGGG TCTGGCCAGC TGCGTGACCA TTAACCAAAC CAGCGTCAAG      1680

GTGCTGCGTG ATATGAATGT GAAGGAATCG CCAGGACGCT GCTACTCACG ACCAGTGGTC      1740

ATCTTTAATT TCGCCAACAG CTCGTACGTG CAGTACGGTC AACTGGGCGA GGATAACGAA      1800

ATCCTGTTGG GCAACCACCG CACTGAGGAA TGTCAGCTTC CCAGCCTCAA GATCTTCATC      1860

GCCGGCAACT CGGCCTACGA GTACGTGGAC TACCTCTTCA AACGCATGAT TGACCTCAGC      1920

AGCATCTCCA CCGTCGACAG CATGATCGCC CTAGACATCG ACCCGCTGGA AAACACCGAC      1980

TTCAGGGTAC TGGAACTTTA CTCGCAGAAA GAATTGCGTT CCAGCAACGT TTTTGATCTC      2040

GAGGAGATCA TGCGCGAGTT CAATTCGTAT AAGCAGCGGG TAAAGTACGT GGAGGACAAG      2100

GTAGTCGACC CGCTGCCGCC CTACCTCAAG GGTCTGGACG ACACTCGACA GCGGCGTCTC      2160

TGCATGCAGC CGCTGCAGAA CCTCTTTCCC TATCTGGTGT CCGCCGACGG GACCACCGTG      2220

ACGTCGGGCA ACACCAAAGA CACGTCGTTA CAGGCTCCGC CTTCCTACGA GGAAAGTGTT      2280

TATAATTCTG GTCGCAAAGG ACCGGGACCA CCGTCGTCTG ATGCATCCAC GGCGGCTCCG      2340

CCTTACACCA ACGAGCAGGC TTACCAGATG CTTCTGGCCC TGGTCCGTCT GGACGCAGAG      2400

CAGCGAGCGC ACGAGAACGG TACAGATTCT TTGGACGGAC AGACTGGCAC GCAGGACAAG      2460

GGACAGAAGC CCAACCTGCT AGACCGACTG CGACACCGCA AAAACGGCTA CCGACACTTG      2520

AAAGACTCCG ACGAAGAAGA GAACGTCTGA                                       2550

(2) INFORMATION FOR SEQ ID NO:9:

    (i) SEQUENCE CHARACTERISTICS:
        (A) LENGTH: 4594 base pairs
        (B) TYPE: nucleic acid
        (C) STRANDEDNESS: single
        (D) TOPOLOGY: linear

    (ii) MOLECULE TYPE: DNA (genomic)

    (xi) SEQUENCE DESCRIPTION: SEQ ID NO:9:

AAGCTTGCGG CCGCTCATTA GACAAGCGAA TGAGGGACGA AAACGTGGAG GAGGTATTAA       60

GTTTGGAGAA ATGGAGAGAG ACTGTTTAAT AGCGCATGGC GCAGCCAATA CTATTACAGA      120

AGTTTTGAAA GATTCGGAAG AAGATTATCA AGATGTGTAT GTTTGTGAAA ATTGTGGAGA      180

CATAGCAGCA CAAATCAAGG GTATTAATAC ATGTCTTAGA TGTTCAAAAC TTAATCTCTC      240

TCCTCTCTTA ACAAAAATTG ATACCACGCA CGTATCTAAA GTATTTCTTA CTCAAATGAA      300

CGCCAGAGGC GTAAAAGTCA AATTAGATTT CGAACGAAGG CCTCCTTCGT TTTATAAACC      360

ATTAGATAAA GTTGATCTCA AGCCGTCTTT TCTGGTGTAA TAAAAATTAA TTAATTACTC      420

GAGGGTACCG GATCCCCCAG CTTATAAAAA TCACAAGTCT CTGACACTTT TTTTGTCTAG      480
```

-continued

```
TTTTTTTTTC TCCTCTTGGT TCAGACGTTC TCTTCTTCGT CGGAGTCTTT CAAGTGTCGG    540
TAGCCGTTTT TGCGGTGTCG CAGTCGGTCT AGCAGGTTGG GCTTCTGTCC CTTGTCCTGC    600
GTGCCAGTCT GTCCGTCCAA AGAATCTGTA CCGTTCTCGT GCGCTCGCTG CTCTGCGTCC    660
AGACGGACCA GGGCCAGAAG CATCTGGTAA GCCTGCTCGT TGGTGTAAGG CGGAGCCGCC    720
GTGGATGCAT CAGACGACGG TGGTCCCGGT CCTTTGCGAC CAGAATTATA AACACTTTCC    780
TCGTAGGAAG GCGGAGCCTG TAACGACGTG TCTTTGGTGT TGCCCGACGT CACGGTGGTC    840
CCGTCGGCGG ACACCAGATA GGGAAAGAGG TTCTGCAGCG GCTGCATGCA GAGACGCCGC    900
TGTCGAGTGT CGTCCAGACC CTTGAGGTAG GGCGGCAGCG GGTCGACTAC CTTGTCCTCC    960
ACGTACTTTA CCCGCTGCTT ATACGAATTG AACTCGCGCA TGATCTCCTC GAGATCAAAA   1020
ACGTTGCTGG AACGCAATTC TTTCTGCGAG TAAAGTTCCA GTACCCTGAA GTCGGTGTTT   1080
TCCAGCGGGT CGATGTCTAG GGCGATCATG CTGTCGACGG TGGAGATGCT GCTGAGGTCA   1140
ATCATGCGTT TGAAGAGGTA GTCCACGTAC TCGTAGGCCG AGTTGCCGGC GATGAAGATC   1200
TTGAGGCTGG GAAGCTGACA TTCCTCAGTG CGGTGGTTGC CCAACAGGAT TTCGTTATCC   1260
TCGCCCAGTT GACCGTACTG CACGTACGAG CTGTTGGCGA AATTAAAGAT GACCACTGGT   1320
CGTGAGTAGC AGCGTCCTGG CGATTCCTTC ACATTCATAT CACGCAGCAC CTTGACGCTG   1380
GTTTGGTTAA TGGTCACGCA GCTGGCCAGA CCCAGGACAT CACCCATGAA ACGCGCGGCA   1440
ATCGGTTTGT TGTAGATGGC CGAGAGAATA GCTGACGGGT TGATCTTGCT AAGTTCCTTG   1500
AAGACCTCTA GGGTGCGCCG TTGATCCACA CACCAGGCTT CTGCGATTTC GGCCAGCGCC   1560
CGGTTGATGT AACCGCGCAA CGTGTCATAG GTGAACTGCA GCTGGGCGTA GACCAGATTG   1620
TGCACCGACT CCATGTTGGA TAAATGAGTT GCATTGTTGC CATCTGTAGA TCTTATGGTT   1680
CTATTATGAG TAAGATTCAG ACTGGAGCGG TTGGCCAAAC GTTCGAGTTC CACCAGAGAT   1740
TTTTGCTTGA TACCTTGCCA GAACACCACC AAACCACCAG TGGTTTCAAA GACGGACACG   1800
TTTCCATATT TTTCATATGT TTGATTGTAT GAAGTATTGA AAATCTGCTG TAACTTATTT   1860
ATGGCCTCAT CACGTACACA GTCCAGCGCA GAGTCGGACA TGTTCACCTC TTGCTTCTTA   1920
GATAAGAAAG TGGCGGTCAT TTTGGCAGAA GAAAAGTGAT ACGAGTCCTC GGCTTCGGAA   1980
CGAATGGTGC GTTCCGAGGC TTCCCAGAAA GTGAGTTGAC AAGTAACATT CTTCTCGTCC   2040
TGTATATCCC AGGAGATCAC TGAGTCCGCA CGTTCAAGAA AAGCCACCAA CCTGTGGGTC   2100
TCTAACGCAG AATTCGGTCT TTCAAAGTCG GAGACGATAG TGTAGTTCGG AAAAATGAAA   2160
AACTTGTCGG CGTTTTCTCC AAAATAGCTG GCATTGCGAT TAGTTCCGTT GTAGAAAGGA   2220
GAAATGTCAA CCACATCACC CGTGGAAGTT GCGAAAAAAT GATAGGGATA CTTGGAGCGC   2280
GCAGTAGTGA TGGTCACCAT ACAATTCAGA TTACAGGTCT CACGATAGAG CCAGGTGCTG   2340
CCGCGGCTGT GCCATTGATC CTTGACCGTC ACGTAACGGG TACTGTGGGT GTTGGAATAA   2400
TCGTCGGGCA TTAATTGCAT GGTTTTGTTT TCATAGCTGT CCCTATGATA AGCCACGAAA   2460
ACCGTGCCTG CTATAACGCG GCTGTAGGAA CTGTAGCACT GACTGTGACT GTTGATATGA   2520
TGAATCTCCC ACATAGGAGG CGCCACGTAT TCCGTGTTGC TGCCCAGCAG ATAAGTGGTG   2580
TGGATGTAAG CGTAGCTACG ACGAAACGTC AAAACCTTCT GGTAGACTCG TACCTTAAAG   2640
GTGTGCGCGA CGATGTTGCG TTTGTAGACC ACCATGATGC CCTCGTCCAG GTCTTCATTG   2700
ATGGGCTTCA TCGAGGTGCA GACGATATTA CGTTCAAAGC GAATAAGATC CGTACCCTGA   2760
GCCATAGAAC ACACGCGATA GGGGTACTTG GTGGTGTTGA CCCCCACCAC ATCTCCGTAC   2820
```

-continued

```
TTGAGGGTAG TGTTGTAGAT GGTCTCGTTA ACACCATGGC TGACCGTTTG GGAAGAAGTT   2880

ACGCGTTGAG AGACTGAACC GGATCGAGAA TGAGCAGCAG ACGTCGTATG AGAGGAATGG   2940

TGACTGTGAG TAGCAGAAGT TCCACGAGTA GAAGATGAGG AAACCGCAGC ACCCAGACAG   3000

ACGATACACA AGTTAACGCA GACTACCAGG CACCAGATCC TGGATTCCAT TACGATACAA   3060

ACTTAACGGA TATCGCGATA ATGAAATAAT TTATGATTAT TTCTCGCTTT CAATTTAACA   3120

CAACCCTCAA GAACCTTTGT ATTTATTTTC ACTTTTTAAG TATAGAATAA AGAAGCTGGG   3180

AATCGATTCG CGATAGCTGA TTAGTTTTTG TTAACAAAAA TGTGGGAGAA TCTAATTAGT   3240

TTTTCTTTAC ACAATTGACG TACATGAGTC TGAGTTCCTT GTTTTTGCTA ATTATTTCAT   3300

CCAATTTATT ATTCTTGACG ATATCGAGAT CTTTTGTATA GGAGTCAGAC TTGTATTCAA   3360

CATGCTTTTC TATAATCATC TTAGTTATTT CGGCATCATC CAATAGTACA TTTTCCAGAT   3420

TAACAGAGTA GATATTAATG TCGTATTTGA ACAGAGCCTG TAACATCTCA ATGTCTTTAT   3480

TATCTATAGC CAATTTAATG TCCGGAATGA AGAGAAGGGA ATTATTGGTG TTTGTCGACG   3540

TCATATAGTC GAGCAAGAGA ATCATCATAT CCACGTGTCC ATTTTTTATA GTGGTGTGAA   3600

TACAACTAAG GAGAATAGCC AGATCAAAAG TAGATGGTAT TTCTGAAAGA AAGTATGATA   3660

CAATACTTAC ATCATTAAGC ATGACGGCAT GATAAAATGA AGTTTTCCAT CCAGTTTTCC   3720

CATAGAACAT CAGTCTCCAA TTTTTCTTAA ACAGTTTCAC CGTTTGCATG TTACCACTAT   3780

CAACCGCATA ATACAATGCG GTGTTTCCTT TGTCATCAAA TTGTGAATCA TCCATTCCAC   3840

TGAATAGCAA AATCTTTACT ATTTTGGTAT CTTCTAATGT GGCTGCCTGA TGTAATGGAA   3900

ATTCATTCTC TAGAAGATTT TTCAATGCTC CAGCGTTCAA CAACGTACAT ACTAGACGCA   3960

CGTTATTATC AGCTATTGCA TAATACAAGG CACTATGTCC ATGGACATCC GCCTTAAATG   4020

TATCTTTACT AGAGAGAAAG CTTTTCAGCT GCTTAGACTT CCAAGTATTA ATTCGTGACA   4080

GATCCATGTC TGAAACGAGA CGCTAATTAG TGTATATTTT TTCATTTTTT ATAATTTTGT   4140

CATATTGCAC CAGAATTAAT AATATCTCTA ATAGATCTAA TTTAATTTAA TTTATATAAC   4200

TTATTTTTTG AATATACTTT TAATTAACAA AAGAGTTAAG TTACTCATAT GGACGCCGTC   4260

CAGTCTGAAC ATCAATCTTT TTAGCCAGAG ATATCATAGC CGCTCTTAGA GTTTCAGCGT   4320

GATTTTCCAA CCTAAATAGA ACTTCATCGT TGCGTTTACA ACACTTTTCT ATTTGTTCAA   4380

ACTTTGTTGT TACATTAGTA ATCTTTTTTT CCAAATTAGT TAGCCGTTGT TTGAGAGTTT   4440

CCTCATTGTC GTCTTCATCG GCTTTAACAA TTGCTTCGCG TTTAGCCTCC TGGCTGTTCT   4500

TATCAGCCTT TGTAGAAAAA AATTCAGTTG CTGGAATTGC AAGATCGTCA TCTCCGGGGA   4560

AAAGAGTTCC GTCCATTTAA AGCCGCGGGA ATTC                               4594
```

(2) INFORMATION FOR SEQ ID NO:10:

(i) SEQUENCE CHARACTERISTICS:
(A) LENGTH: 2229 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

```
ATGCGGCCAG GCCTCCCCTC CTACCTCATC GTCCTCGCCG TCTGTCTCCT CAGCCACCTA     60

CTTTCGTCAC GATATGGCGC AGAAGCCATA TCCGAACCGC TGGACAAAGC GTTTCACCTA    120

CTGCTCAACA CCTACGGGAG ACCCATCCGC TTCCTGCGTG AAAACACCAC CCAGTGTACC    180
```

-continued

```
TACAATAGCA GCCTCCGTAA CAGCACGGTC GTCAGGGAAA ACGCCATCAG TTTCAACTTT    240

TTCCAAAGCT ATAATCAATA CTATGTATTC CATATGCCTC GATGTCTTTT TGCGGGTCCT    300

CTGGCGGAGC AGTTTCTGAA CCAGGTAGAT CTGACCGAAA CCCTGGAAAG ATACCAACAG    360

AGACTTAACA CTTACGCGCT GGTATCCAAA GACCTGGCCA GCTACCGATC TTTTTCGCAG    420

CAGCTAAAGG CACAGGACAG CCTAGGTGAA CAGCCCACCA CTGTGCCACC ACCCATTGAC    480

CTGTCAATAC CTCACGTTTG GATGCCACCG CAAACCACTC CACACGGCTG GACAGAATCA    540

CATACCACCT CAGGACTACA CCGACCACAC TTTAACCAGA CCTGTATCCT CTTTGATGGA    600

CACGATCTAC TATTCAGCAC CGTCACACCT TGTTTGCACC AAGGCTTTTA CCTCATCGAC    660

GAACTACGTT ACGTTAAAAT AACACTGACC GAGGACTTCT TCGTAGTTAC GGTGTCCATA    720

GACGACGACA CACCCATGCT GCTTATCTTC GGCCATCTTC CACGCGTACT CTTTAAAGCG    780

CCCTATCAAC GCGACAACTT TATACTACGA CAAACTGAAA AACACGAGCT CCTGGTGCTA    840

GTTAAGAAAG ATCAACTGAA CCGTCACTCT TATCTCAAAG ACCCGGACTT TCTTGACGCC    900

GCACTTGACT TCAACTACCT GGACCTCAGC GCACTACTAC GTAACAGCTT TCACCGTTAC    960

GCCGTGGATG TACTCAAAAG CGGTCGATGT CAGATGCTGG ACCGCCGCAC GGTAGAAATG   1020

GCCTTCGCCT ACGCATTAGC ACTGTTCGCA GCAGCCCGAC AAGAAGAGGC CGGCGCCCAA   1080

GTCTCCGTCC CACGGGCCCT AGACCGCCAG GCCGCACTCT TACAAATACA AGAATTTATG   1140

ATCACCTGCC TCTCACAAAC ACCACCACGC ACCACGTTGC TGCTGTATCC CACGGCCGTG   1200

GACCTGGCCA AACGAGCCCT TTGGACACCG AATCAGATCA CCGACATCAC CAGCCTCGTA   1260

CGCCTGGTCT ACATACTCTC TAAACAGAAT CAGCAACATC TCATCCCCCA GTGGGCACTA   1320

CGACAGATCG CCGACTTTGC CCTAAAACTA CACAAAACGC ACCTGGCCTC TTTTCTTTCA   1380

GCCTTCGCGC GTCAAGAACT CTACCTCATG GGCAGCCTCG TCCACTCCAT GCTAGTACAT   1440

ACGACGGAGA GACGCGAAAT CTTCATCGTA GAAACGGGCC TCTGTTCATT AGCCGAGCTA   1500

TCACACTTTA CGCAGTTGCT AGCTCATCCG CACCACGAAT ACCTCAGCGA CCTGTACACA   1560

CCCTGTTCCA GTAGCGGGCG ACGCGATCAC TCGCTCGAAC GCCTCACACG TCTCTTCCCC   1620

GATGCCACCG TCCCCACTAC CGTTCCCGCC GCCCTCTCCA TCCTATCTAC CATGCAACCA   1680

AGCACGCTAG AAACCTTCCC CGACCTGTTT TGTCTGCCGC TCGGCGAATC CTTCTCCGCG   1740

CTGACCGTCT CCGAACACGT CAGTTATGTC GTAACAAACC AGTACCTGAT CAAAGGTATC   1800

TCCTACCCTG TCTCCACCAC CGTCGTAGGC CAGAGCCTCA TCATCACCCA GACGGACAGT   1860

CAAACTAAAT GCGAACTGAC GCGCAACATG CATACCACAC ACAGCATCAC AGCGGCGCTC   1920

AACATTTCCC TAGAAAACTG CGCCTTTTGC CAAAGCGCCC TACTAGAATA CGACGACACG   1980

CAAGGCGTCA TCAACATCAT GTACATGCAC GACTCGGACG ACGTCCTTTT CGCCCTGGAT   2040

CCCTACAACG AAGTGGTGGT CTCATCTCCG CGAACTCACT ACCTCATGCT TTTGAAAAAC   2100

GGTACGGTCC TAGAAGTAAC TGACGTCGTC GTGGACGCTA CCGACAGTCG TCTCCTCATG   2160

ATGTCCGTCT ACGCGCTATC GGCCATCATC GGCATCTATC TGCTCTACCG CATGCTCAAG   2220

ACATGCTGA                                                           2229
```

(2) INFORMATION FOR SEQ ID NO:11:

(i) SEQUENCE CHARACTERISTICS:
(A) LENGTH: 3539 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:11:

CTGCAGGTCG ACGGATCTGA GAATGGATGA TTCTCCAGCC GAAACATATT CTACCATGGC 60

TCCGTTTAAT TTGTTGATGA AGATGGATTC ATCCTTAAAT GTTTTCTCTG TAATAGTTTC 120

CACCGAAAGA CTATGCAAAG AATTTGGAAT GCGTTCCTTG TGCTTAATGT TTCCATAGAC 180

GGCTTCTAGA AGTTGATACA ACATAGGACT AGCCGCGGTA ACTTTTATTT TTAGAAAGTA 240

TCCATCGCTT CTATCTTGTT TAGATTTATT TTTATAAAGT TTAGTCTCTC CTTCCAACAT 300

AATAAAAGTG GAAGTCATTT GACTAGATAA ACTATCAGTA AGTTTTATAG AGATAGACGA 360

ACAATTAGCG TATTGAGAAG CATTTAGTGT AACGTATTCG ATACATTTTG CATTAGATTT 420

ACTAATCGAT TTTGCATACT CTATAACACC CGCACAAGTC TGTAGAGAAT CGCTAGATGC 480

AGTAGGTCTT GGTGAAGTTT CAACTCTCTT CTTGATTACC TTACTCATGA TTAAACCTAA 540

ATAATTGTAC TTTGTAATAT AATGATATAT ATTTTCACTT TATCTCATTT GAGAATAAAA 600

AGATCACAAA AATTAACTAA TCAGGATCCG GTACCCTCGA GTTTATTGGG AAGAATATGA 660

TAATATTTTG GGATTTCAAA ATTGAAAATA TATAATTACA ATATAAAATG CGGCCCGGGC 720

TCCCCTCCTA CCTCATCGTC CTCGCCGTCT GTCTCCTCAG CCACCTACTT TCGTCACGAT 780

ATGGCGCAGA AGCCATATCC GAACCGCTGG ACAAAGCGTT TCACCTACTG CTCAACACCT 840

ACGGGAGACC CATCCGCTTC CTGCGTGAAA ACACCACCCA GTGTACCTAC AATAGCAGCC 900

TCCGTAACAG CACGGTCGTC AGGGAAAACG CCATCAGTTT CAACTTTTTC CAAAGCTATA 960

ATCAATACTA TGTATTCCAT ATGCCTCGAT GTCTTTTTGC GGGTCCTCTG GCGGAGCAGT 1020

TTCTGAACCA GGTAGATCTG ACCGAAACCC TGGAAAGATA CCAACAGAGA CTTAACACTT 1080

ACGCGCTGGT ATCCAAAGAC CTGGCCAGCT ACCGATCTTT TTCGCAGCAG CTAAAGGCAC 1140

AGGACAGCCT AGGTGAACAG CCCACCACTG TGCCACCACC CATTGACCTG TCAATACCTC 1200

ACGTTTGGAT GCCACCGCAA ACCACTCCAC ACGGCTGGAC AGAATCACAT ACCACCTCAG 1260

GACTACACCG ACCACACTTT AACCAGACCT GTATCCTCTT TGATGGACAC GATCTACTAT 1320

TCAGCACCGT CACACCTTGT TTGCACCAAG GCTTTTACCT CATCGACGAA CTACGTTACG 1380

TTAAAATAAC ACTGACCGAG GACTTCTTCG TAGTTACGGT GTCCATAGAC GACGACACAC 1440

CCATGCTGCT TATCTTCGGC CATCTTCCAC GCGTACTCTT TAAAGCGCCC TATCAACGCG 1500

ACAACTTTAT ACTACGACAA ACTGAAAAAC ACGAGCTCCT GGTGCTAGTT AAGAAAGATC 1560

AACTGAACCG TCACTCTTAT CTCAAAGACC CGGACTTTCT TGACGCCGCA CTTGACTTCA 1620

ACTACCTGGA CCTCAGCGCA CTACTACGTA ACAGCTTTCA CCGTTACGCC GTGGATGTAC 1680

TCAAAAGCGG TCGATGTCAG ATGCTGGACC GCCGCACGGT AGAAATGGCC TTCGCCTACG 1740

CATTAGCACT GTTCGCAGCA GCCCGACAAG AAGAGGCCGG CGCCCAAGTC TCCGTCCCAC 1800

GGGCCCTAGA CCGCCAGGCC GCACTCTTAC AAATACAAGA ATTTATGATC ACCTGCCTCT 1860

CACAAACACC ACCACGCACC ACGTTGCTGC TGTATCCCAC GGCCGTGGAC CTGGCCAAAC 1920

GAGCCCTTTG GACACCGAAT CAGATCACCG ACATCACCAG CCTCGTACGC CTGGTCTACA 1980

TACTCTCTAA ACAGAATCAG CAACATCTCA TCCCCCAGTG GGCACTACGA CAGATCGCCG 2040

ACTTTGCCCT AAAACTACAC AAAACGCACC TGGCCTCTTT TCTTTCAGCC TTCGCGCGTC 2100

AAGAACTCTA CCTCATGGGC AGCCTCGTCC ACTCCATGCT AGTACATACG ACGGAGAGAC 2160

GCGAAATCTT CATCGTAGAA ACGGGCCTCT GTTCATTAGC CGAGCTATCA CACTTTACGC 2220

AGTTGCTAGC TCATCCGCAC CACGAATACC TCAGCGACCT GTACACACCC TGTTCCAGTA 2280

```
GCGGGCGACG CGATCACTCG CTCGAACGCC TCACACGTCT CTTCCCCGAT GCCACCGTCC    2340

CCACTACCGT TCCCGCCGCC CTCTCCATCC TATCTACCAT GCAACCAAGC ACGCTAGAAA    2400

CCTTCCCCGA CCTGTTTTGT CTGCCGCTCG GCGAATCCTT CTCCGCGCTG ACCGTCTCCG    2460

AACACGTCAG TTATGTCGTA ACAAACCAGT ACCTGATCAA AGGTATCTCC TACCCTGTCT    2520

CCACCACCGT CGTAGGCCAG AGCCTCATCA TCACCCAGAC GGACAGTCAA ACTAAATGCG    2580

AACTGACGCG CAACATGCAT ACCACACACA GCATCACAGC GGCGCTCAAC ATTTCCCTAG    2640

AAAACTGCGC CTTTTGCCAA AGCGCCCTAC TAGAATACGA CGACACGCAA GGCGTCATCA    2700

ACATCATGTA CATGCACGAC TCGGACGACG TCCTTTTCGC CCTGGATCCC TACAACGAAG    2760

TGGTGGTCTC ATCTCCGCGA ACTCACTACC TCATGCTTTT GAAAAACGGT ACGGTCCTAG    2820

AAGTAACTGA CGTCGTCGTG GACGCTACCG ACAGTCGTCT CCTCATGATG TCCGTCTACG    2880

CGCTATCGGC CATCATCGGC ATCTATCTGC TCTACCGCAT GCTCAAGACA TGCTGATTTT    2940

TATCTCGAGC CCGGGAGATC TTAGCTAACT GATTTTTCTG GGAAAAAAAT TATTTAACTT    3000

TTCATTAATA GGGATTTGAC GTATGTAGCG TACAAAATTA TCGTTCCTGG TATATAGATA    3060

AAGAGTCCTA TATATTTGAA AATCGTTACG GCTCGATTAA ACTTTAATGA TTGCATAGTG    3120

AATATATCAT TAGGATTTAA CTCCTTGACT ATCATGGCGG CGCCAGAAAT TACCATCAAA    3180

AGCATTAATA CAGTTATGCC GATCGCAGTT AGAACGGTTA TAGCATCCAC CATTTATATC    3240

TAAAAATTAG ATCAAAGAAT ATGTGACAAA GTCCTAGTTG TATACTGAGA ATTGACGAAA    3300

CAATGTTTCT TACATATTTT TTTCTTATTA GTAACTGACT TAATAGTAGG AACTGGAAAG    3360

CTAGACTTGA TTATTCTATA AGTATAGATA CCCTTCCAGA TAATGTTCTC TTTGATAAAA    3420

GTTCCAGAAA ATGTAGAATT TTTTAAAAAG TTATCTTTTG CTATTACCAA GATTGTGTTT    3480

AGACGCTTAT TATTAATATG AGTAATGAAA TCCACACCGC CTCTAGATAT GGGGAATTC     3539

(2) INFORMATION FOR SEQ ID NO:12:

    (i) SEQUENCE CHARACTERISTICS:
        (A) LENGTH: 4427 base pairs
        (B) TYPE: nucleic acid
        (C) STRANDEDNESS: single
        (D) TOPOLOGY: linear

    (ii) MOLECULE TYPE: DNA (genomic)

    (xi) SEQUENCE DESCRIPTION: SEQ ID NO:12:

GAATTGCGGC CGCTGAATGT TAAATGTTAT ACTTTGGATG AAGCTATAAA TATGCATTGG      60

AAAAATAATC CATTTAAAGA AAGGATTCAA ATACTACAAA ACCTAAGCGA TAATATGTTA     120

ACTAAGCTTA TTCTTAACGA CGCTTTAAAT ATACACAAAT AAACATAATT TTTGTATAAC     180

CTAACAAATA ACTAAAACAT AAAAATAATA AAAGGAAATG TAATATCGTA ATTATTTTAC     240

TCAGGAATGG GGTTAAATAT TTATATCACG TGTATATCTA TACTGTTATC GTATACTCTT     300

TACAATTACT ATTACGAATA TGCAAGAGAT AATAAGATTA CGTATTTAAG AGAATCTTCT     360

CATGATAATT GGGTACGACA TAGTGATAAA TGCTATTTCG CATCGTTACA TAAAGTCAGT     420

TGGAAAGATG GATTTGACAG ATGTAACTTA ATAGGTGCAA AAATGTTAAA TAACAGCATT     480

CTATCGGAAG ATAGGATACC AGTTATATTA TACAAAAATC ACTGGTTGGA TAAAACAGAT     540

TCTGCAATAT TCGTAAAAGA TGAAGATTAC TGCGAATTTG TAAACTATGA CAATAAAAAG     600

CCATTTATCT CAACGACATC GTGTAATTCT TCCATGTTTT ATGTATGTGT TTCAGATATT     660

ATGAGATTAC TATAAACTTT TTGTATACTT ATATTCCGTA AACTATATTA ATCATGAAGA     720
```

-continued

AAATGAAAAA GTATAGAAGC TGTTCACGAG CGGTTGTTGA AAACAACAAA ATTATACATT 780

CAAGATGGCT TACATATACG TCTGTGAGGC TATCATGGAT AATGACAATG CATCTCTAAA 840

TAGGTTTTTG GACAATGGAT TCGACCCTAA CACGGAATAT GGTACTCTAC AATCTCCTCT 900

TGAAATGGCT GTAATGTTCA AGAATACCGA GGCTATAAAA ATCTTGATGA GGTATGGAGC 960

TAAACCTGTA GTTACTGAAT GCACAACTTC TTGTCTGCAT GATGCGGTGT TGAGAGACGA 1020

CTACAAAATA GTGAAAGATC TGTTGAAGAA TAACTATGTA AACAATGTTC TTTACAGCGG 1080

AGGCTTTACT CCTTTGTGTT TGGCAGCTTA CCTTAACAAA GTTAATTTGG TTAAACTTCT 1140

ATTGGCTCAT TCGGCGGATG TAGATATTTC AAACACGGAT CGGTTAACTC CTCTACATAT 1200

AGCCGTATCA AATAAAAATT TAACAATGGT TAAACTTCTA TTGAACAAAG GTGCTGATAC 1260

TGACTTGCTG GATAACATGG GACGTACTCC TTTAATGATC GCTGTACAAT CTGGAAATAT 1320

TGAAATATGT AGCACACTAC TTAAAAAAAA TAAAATGTCC AGAACTGGGA AAAATTGATC 1380

TTGCCAGCTG TAATTCATGG TAGAAAAGAA GTGCTCAGGC TACTTTTCAA CAAAGGAGCA 1440

GATGTAAACT ACATCTTTGA AAGAAATGGA AAATCATATA CTGTTTTGGA ATTGATTAAA 1500

GAAAGTTACT CTGAGACACA AAAGAGGTAG CTGAAGTGGT ACTCTCAAAG GTACGTGACT 1560

AATTAGCTAT AAAAAGGATC TTAATTAATT AGTCATCAGG CAGGGCGAGA ACGAGACTAT 1620

CTGCTCGTTA ATTAATTAGG TCGACGGATC CGGTACCCTC GAGTTTATTG GGAAGAATAT 1680

GATAATATTT TGGGATTTCA AAATTGAAAA TATATAATTA CAATATAAAA TGCGGCCCGG 1740

GCTCCCCTCC TACCTCATCG TCCTCGCCGT CTGTCTCCTC AGCCACCTAC TTTCGTCACG 1800

ATATGGCGCA GAAGCCATAT CCGAACCGCT GGACAAAGCG TTTCACCTAC TGCTCAACAC 1860

CTACGGGAGA CCCATCCGCT TCCTGCGTGA AAACACCACC CAGTGTACCT ACAATAGCAG 1920

CCTCCGTAAC AGCACGGTCG TCAGGGAAAA CGCCATCAGT TTCAACTTTT TCCAAAGCTA 1980

TAATCAATAC TATGTATTCC ATATGCCTCG ATGTCTTTTT GCGGGTCCTC TGGCGGAGCA 2040

GTTTCTGAAC CAGGTAGATC TGACCGAAAC CCTGGAAAGA TACCAACAGA GACTTAACAC 2100

TTACGCGCTG GTATCCAAAG ACCTGGCCAG CTACCGATCT TTTTCGCAGC AGCTAAAGGC 2160

ACAGGACAGC CTAGGTGAAC AGCCCACCAC TGTGCCACCA CCCATTGACC TGTCAATACC 2220

TCACGTTTGG ATGCCACCGC AAACCACTCC ACACGGCTGG ACAGAATCAC ATACCACCTC 2280

AGGACTACAC CGACCACACT TTAACCAGAC CTGTATCCTC TTTGATGGAC ACGATCTACT 2340

ATTCAGCACC GTCACACCTT GTTTGCACCA AGGCTTTTAC CTCATCGACG AACTACGTTA 2400

CGTTAAAATA ACACTGACCG AGGACTTCTT CGTAGTTACG GTGTCCATAG ACGACGACAC 2460

ACCCATGCTG CTTATCTTCG GCCATCTTCC ACGCGTACTC TTTAAAGCGC CCTATCAACG 2520

CGACAACTTT ATACTACGAC AAACTGAAAA ACACGAGCTC CTGGTGCTAG TTAAGAAAGA 2580

TCAACTGAAC CGTCACTCTT ATCTCAAAGA CCCGGACTTT CTTGACGCCG CACTTGACTT 2640

CAACTACCTG GACCTCAGCG CACTACTACG TAACAGCTTT CACCGTTACG CCGTGGATGT 2700

ACTCAAAAGC GGTCGATGTC AGATGCTGGA CCGCCGCACG GTAGAAATGG CCTTCGCCTA 2760

CGCATTAGCA CTGTTCGCAG CAGCCCGACA AGAAGAGGCC GGCGCCCAAG TCTCCGTCCC 2820

ACGGGCCCTA GACCGCCAGG CCGCACTCTT ACAAATACAA GAATTTATGA TCACCTGCCT 2880

CTCACAAACA CCACCACGCA CCACGTTGCT GCTGTATCCC ACGGCCGTGG ACCTGGCCAA 2940

ACGAGCCCTT TGGACACCGA ATCAGATCAC CGACATCACC AGCCTCGTAC GCCTGGTCTA 3000

CATACTCTCT AAACAGAATC AGCAACATCT CATCCCCCAG TGGGCACTAC GACAGATCGC 3060

-continued

```
CGACTTTGCC CTAAAACTAC ACAAAACGCA CCTGGCCTCT TTTCTTTCAG CCTTCGCGCG   3120
TCAAGAACTC TACCTCATGG GCAGCCTCGT CCACTCCATG CTAGTACATA CGACGGAGAG   3180
ACGCGAAATC TTCATCGTAG AAACGGGCCT CTGTTCATTA GCCGAGCTAT CACACTTTAC   3240
GCAGTTGCTA GCTCATCCGC ACCACGAATA CCTCAGCGAC CTGTACACAC CCTGTTCCAG   3300
TAGCGGGCGA CGCGATCACT CGCTCGAACG CCTCACACGT CTCTTCCCCG ATGCCACCGT   3360
CCCCACTACC GTTCCCGCCG CCCTCTCCAT CCTATCTACC ATGCAACCAA GCACGCTAGA   3420
AACCTTCCCC GACCTGTTTT GTCTGCCGCT CGGCGAATCC TTCTCCGCGC TGACCGTCTC   3480
CGAACACGTC AGTTATGTCG TAACAAACCA GTACCTGATC AAAGGTATCT CCTACCCTGT   3540
CTCCACCACC GTCGTAGGCC AGAGCCTCAT CATCACCCAG ACGGACAGTC AAACTAAATG   3600
CGAACTGACG CGCAACATGC ATACCACACA CAGCATCACA GCGGCGCTCA ACATTTCCCT   3660
AGAAAACTGC GCCTTTTGCC AAAGCGCCCT ACTAGAATAC GACGACACGC AAGGCGTCAT   3720
CAACATCATG TACATGCACG ACTCGGACGA CGTCCTTTTC GCCCTGGATC CCTACAACGA   3780
AGTGGTGGTC TCATCTCCGC GAACTCACTA CCTCATGCTT TTGAAAAACG GTACGGTCCT   3840
AGAAGTAACT GACGTCGTCG TGGACGCTAC CGACAGTCGT CTCCTCATGA TGTCCGTCTA   3900
CGCGCTATCG GCCATCATCG GCATCTATCT GCTCTACCGC ATGCTCAAGA CATGCTGATT   3960
TTTATCTCGA GTCTAGAATC GATCCCGGGT TTTTATGACT AGTTAATCAC GGCCGCTTAT   4020
AAAGATCTAA AATGCATAAT TTCTAAATAA TGAAAAAAAA GTACATCATG AGCAACGCGT   4080
TAGTATATTT TACAATGGAG ATTAACGCTC TATACCGTTC TATGTTTATT GATTCAGATG   4140
ATGTTTTAGA AAAGAAAGTT ATTGAATATG AAAACTTTAA TGAAGATGAA GATGACGACG   4200
ATGATTATTG TTGTAAATCT GTTTTAGATG AAGAAGATGA CGCGCTAAAG TATACTATGG   4260
TTACAAAGTA TAAGTCTATA CTACTAATGG CGACTTGTGC AAGAAGGTAT AGTATAGTGA   4320
AAATGTTGTT AGATTATGAT TATGAAAAAC CAAATAAATC AGATCCATAT CTAAAGGTAT   4380
CTCCTTTGCA CATAATTTCA TCTATTCCTA GTTTAGAATA CCTGCAG                 4427
```

(2) INFORMATION FOR SEQ ID NO:13:

(i) SEQUENCE CHARACTERISTICS:
(A) LENGTH: 2651 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

```
AAGACTAATT TGTAAACCAT CTTACTCAAA ATATGTAACA ATAGTACGAT GCAATGAGTA     60
AGACAATAGG AAATCTATCT TATATACACA TAATTATTCT ATCAATTTTA CCAATTAGTT    120
AGTGTAATGT TATAAAAACT AATTAATCAC TCGAGATAAA AATCAGCATG TCTTGAGCAT    180
GCGGTAGAGC AGATAGATGC CGATGATGGC CGATAGCGCG TAGACGGACA TCATGAGGAG    240
ACGACTGTCG GTAGCGTCCA CGACGACGTC AGTTACTTCT AGGACCGTAC CGTTTTTCAA    300
AAGCATGAGG TAGTGAGTTC GCGGAGATGA GACCACCACT TCGTTGTAGG GATCCAGGGC    360
GAAAAGGACG TCGTCCGAGT CGTGCATGTA CATGATGTTG ATGACGCCTT GCGTGTCGTC    420
GTATTCTAGT AGGGCGCTTT GGCAAAAGGC GCAGTTTTCT AGGGAAATGT TGAGCGCCGC    480
TGTGATGCTG TGTGTGGTAT GCATGTTGCG CGTCAGTTCG CATTTAGTTT GACTGTCCGT    540
CTGGGTGATG ATGAGGCTCT GGCCTACGAC GGTGGTGGAG ACAGGGTAGG AGATACCTTT    600
```

-continued

```
GATCAGGTAC TGGTTTGTTA CGACATAACT GACGTGTTCG GAGACGGTCA GCGCGGAGAA    660

GGATTCGCCG AGCGGCAGAC AAAACAGGTC GGGGAAGGTT TCTAGCGTGC TTGGTTGCAT    720

GGTAGATAGG ATGGAGAGGG CGGCGGGAAC GGTAGTGGGG ACGGTGGCAT CGGGGAAGAG    780

ACGTGTGAGG CGTTCGAGCG AGTGATCGCG TCGCCCGCTA CTGGAACAGG GTGTGTACAG    840

GTCGCTGAGG TATTCGTGGT GCGGATGAGC TAGCAACTGC GTAAAGTGTG ATAGCTCGGC    900

TAATGAACAG AGGCCCGTTT CTACGATGAA GATTTCGCGT CTCTCCGTCG TATGTACTAG    960

CATGGAGTGG ACGAGGCTGC CCATGAGGTA GAGTTCTTGA CGCGCGAAGG CTGAAAGAAA   1020

AGAGGCCAGG TGCGTTTTGT GTAGTTTTAG GGCAAAGTCG GCGATCTGTC GTAGTGCCCA   1080

CTGGGGGATG AGATGTTGCT GATTCTGTTT AGAGAGTATG TAGACCAGGC GTACGAGGCT   1140

GGTGATGTCG GTGATCTGAT TCGGTGTCCA AAGGGCTCGT TTGGCCAGGT CCACGGCCGT   1200

GGGATACAGC AGCAACGTGG TGCGTGGTGG TGTTTGTGAG AGGCAGGTGA TCATAAATTC   1260

TTGTATTTGT AAGAGTGCGG CCTGGCGGTC TAGGGCCCGT GGGACGGAGA CTTGGGCGCC   1320

GGCCTCTTCT TGTCGGGCTG CTGCGAACAG TGCTAATGCG TAGGCGAAGG CCATTTCTAC   1380

CGTGCGGCGG TCCAGCATCT GACATCGACC GCTTTTGAGT ACATCCACGG CGTAACGGTG   1440

AAAGCTGTTA CGTAGTAGTG CGCTGAGGTC CAGGTAGTTG AAGTCAAGTG CGGCGTCAAG   1500

AAAGTCCGGG TCTTTGAGAT AAGAGTGACG GTTCAGTTGA TCTTTCTTAA CTAGCACCAG   1560

GAGCTCGTGT TTTTCAGTTT GTCGTAGTAT AAAGTTGTCG CGTTGATAGG GCGCTTTAAA   1620

GAGTACGCGT GGAAGATGGC CGAAGATAAG CAGCATGGGT GTGTCGTCGT CTATGGACAC   1680

CGTAACTACG AAGAAGTCCT CGGTCAGTGT TATTTTAACG TAACGTAGTT CGTCGATGAG   1740

GTAAAAGCCT TGGTGCAAAC AAGGTGTGAC GGTGCTGAAT AGTAGATCGT GTCCATCAAA   1800

GAGGATACAG GTCTGGTTAA AGTGTGGTCG GTGTAGTCCT GAGGTGGTAT GTGATTCTGT   1860

CCAGCCGTGT GGAGTGGTTT GCGGTGGCAT CCAAACGTGA GGTATTGACA GGTCAATGGG   1920

TGGTGGCACA GTGGTGGGCT GTTCACCTAG GCTGTCCTGT GCCTTTAGCT GCTGCGAAAA   1980

AGATCGGTAG CTGGCCAGGT CTTTGGATAC CAGCGCGTAA GTGTTAAGTC TCTGTTGGTA   2040

TCTTTCCAGG GTTTCGGTCA GATCTACCTG GTTCAGAAAC TGCTCCGCCA GAGGACCCGC   2100

AAAAAGACAT CGAGGCATAT GGAATACATA GTATTGATTA TAGCTTTGGA AAAAGTTGAA   2160

ACTGATGGCG TTTTCCCTGA CGACCGTGCT GTTACGGAGG CTGCTATTGT AGGTACACTG   2220

GGTGGTGTTT TCACGCAGGA AGCGGATGGG TCTCCCGTAG GTGTTGAGCA GTAGGTGAAA   2280

CGCTTTGTCC AGCGGTTCGG ATATGGCTTC TGCGCCATAT CGTGACGAAA GTAGGTGGCT   2340

GAGGAGACAG ACGGCGAGGA CGATGAGGTA GGAGGGGAGC CCGGGCCGCA TTTTATATTG   2400

TAATTATATA TTTTCAATTT TGAAATCCCA AAATATTATC ATATTCTTCC CAATAAACTC   2460

GAGCCCGGGG AATTCGGATC CTCGCGACTG CAGGGTACCT GAGTAGCTAA TTTTTAAACA   2520

AAAATGTGGG AGAATCTAAT TAGTTTTTCT TTACACAATT GACGTACATG AGTCTGAGTT   2580

CCTTGTTTTT GCTAATTATT TCATCCAATT TATTATTCTT GACGATATCG AGATCTTTTG   2640

TATAGGAGTC A                                                        2651
```

(2) INFORMATION FOR SEQ ID NO:14:

(i) SEQUENCE CHARACTERISTICS:
(A) LENGTH: 1476 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:14:

ATGGAGTCCT CTGCCAAGAG AAAGATGGAC CCTGATAATC CTGACGAGGG CCCTTCCTCC 60

AAGGTGCCAC GGCCCGAGAC ACCCGTGACC AAGGCCACGA CGTTCCTGCA GACTATGTTG 120

AGGAAGGAGG TTAACAGTCA GCTGAGTCTG GGAGACCCGC TGTTTCCAGA GTTGGCCGAA 180

GAATCCCTCA AAACTTTTGA ACAAGTGACC GAGGATTGCA ACGAGAACCC CGAGAAAGAT 240

GTCCTGGCAG AACTCGTCAA ACAGATTAAG GTTCGAGTGG ACATGGTGCG GCATAGAATC 300

AAGGAGCACA TGCTGAAAAA ATATACCCAG ACGGAAGAGA AATTCACTGG CGCCTTTAAT 360

ATGATGGGAG GATGTTTGCA GAATGCCTTA GATATCTTAG ATAAGGTTCA TGAGCCTTTC 420

GAGGAGATGA AGTGTATTGG GCTAACTATG CAGAGCATGT ATGAGAACTA CATTGTACCT 480

GAGGATAAGC GGGAGATGTG GATGGCTTGT ATTAAGGAGC TGCATGATGT GAGCAAGGGC 540

GCCGCTAACA AGTTGGGGGG TGCACTGCAG GCTAAGGCCC GTGCTAAAAA GGATGAACTT 600

AGGAGAAAGA TGATGTATAT GTGCTACAGG AATATAGAGT TCTTTACCAA GAACTCAGCC 660

TTCCCTAAGA CCACCAATGG CTGCAGTCAG GCCATGGCGG CACTGCAGAA CTTGCCTCAG 720

TGCTCCCCTG ATGAGATTAT GGCTTATGCC CAGAAAATAT TTAAGATTTT GGATGAGGAG 780

AGAGACAAGG TGCTCACGCA CATTGATCAC ATATTTATGG ATATCCTCAC TACATGTGTG 840

GAAACAATGT GTAATGAGTA CAAGGTCACT AGTGACGCTT GTATGATGAC CATGTACGGG 900

GGCATCTCTC TCTTAAGTGA GTTCTGTCGG GTGCTGTGCT GCTATGTCTT AGAGGAGACT 960

AGTGTGATGC TGGCCAAGCG GCCTCTGATA ACCAAGCCTG AGGTTATCAG TGTAATGAAG 1020

CGCCGCATTG AGGAGATCTG CATGAAGGTC TTTGCCCAGT ACATTCTGGG GGCCGATCCT 1080

CTGAGAGTCT GCTCTCCTAG TGTGGATGAC CTACGGGCCA TCGCCGAGGA GTCAGATGAG 1140

GAAGAGGCTA TTGTAGCCTA CACTTTGGCC ACCGCTGGTG TCAGCTCCTC TGATTCTCTG 1200

GTGTCACCCC CAGAGTCCCC TGTACCCGCG ACTATCCCTC TGTCCTCAGT AATTGTGGCT 1260

GAGAACAGTG ATCAGGAAGA AAGTGAGCAG AGTGATGAGG AAGAGGAGGA GGGTGCTCAG 1320

GAGGAGCGGG AGGACACTGT GTCTGTCAAG TCTGAGCCAG TGTCTGAGAT AGAGGAAGTT 1380

GCCCCAGAGG AAGAGGAGGA TGGTGCTGAG GAACCCACCG CCTCTGGAGG TAAGAGTACC 1440

CACCCTATGG TGACTAGAAG CAAGGCTGAC CAGTAA 1476

(2) INFORMATION FOR SEQ ID NO:15:

(i) SEQUENCE CHARACTERISTICS:
(A) LENGTH: 1975 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

ATATAATCCT CCACCAAAAT AGAGAATATA TATATCATCA TTTCATGATG TATACTACTG 60

ACATAGTTTC AATGTGAACT TTTCACTTTC TTGCCGGTTA TGAAGAATAT TTTTTATTTT 120

AATGGTCATT ACTAATCGTA TATTATAATT GAAAATGAAT TAGTTTAATA TGACGCTCGT 180

CATGGGATCC ATAAAAATTA CTGGTCAGCC TTGCTTCTAG TCACCATAGG GTGGGTACTC 240

TTACCTCCAG AGGCGGTGGG TTCCTCAGCA CCATCCTCCT CTTCCTCTGG GGCAACTTCC 300

TCTATCTCAG ACACTGGCTC AGACTTGACA GACACAGTGT CCTCCCGCTC CTCCTGAGCA 360

-continued

```
CCCTCCTCCT CTTCCTCATC ACTCTGCTCA CTTTCTTCCT GATCACTGTT CTCAGCCACA    420

ATTACTGAGG ACAGAGGGAT AGTCGCGGGT ACAGGGGACT CTGGGGGTGA CACCAGAGAA    480

TCAGAGGAGC TGACACCAGC GGTGGCCAAA GTGTAGGCTA CAATAGCCTC TTCCTCATCT    540

GACTCCTCGG CGATGGCCCG TAGGTCATCC ACACTAGGAG AGCAGACTCT CAGAGGATCG    600

GCCCCCAGAA TGTACTGGGC AAAGACCTTC ATGCAGATCT CCTCAATGCG GCGCTTCATT    660

ACACTGATAA CCTCAGGCTT GGTTATCAGA GGCCGCTTGG CCAGCATCAC ACTAGTCTCC    720

TCTAAGACAT AGCAGCACAG CACCCGACAG AACTCACTTA AGAGAGAGAT GCCCCCGTAC    780

ATGGTCATCA TACAAGCGTC ACTAGTGACC TTGTACTCAT TACACATTGT TTCCACACAT    840

GTAGTGAGGA TATCCATAAA TATGTGATCA ATGTGCGTGA GCACCTTGTC TCTCTCCTCA    900

TCCAAAATCT TAAATATTTT CTGGGCATAA GCCATAATCT CATCAGGGGA GCACTGAGGC    960

AAGTTCTGCA GTGCCGCCAT GGCCTGACTG CAGCCATTGG TGGTCTTAGG GAAGGCTGAG   1020

TTCTTGGTAA AGAACTCTAT ATTCCTGTAG CACATATACA TCATCTTTCT CCTAAGTTCA   1080

TCCTTTTTAG CACGGGCCTT AGCCTGCAGT GCACCCCCCA ACTTGTTAGC GGCGCCCTTG   1140

CTCACATCAT GCAGCTCCTT AATACAAGCC ATCCACATCT CCCGCTTATC CTCAGGTACA   1200

ATGTAGTTCT CATACATGCT CTGCATAGTT AGCCCAATAC ACTTCATCTC CTCGAAAGGC   1260

TCATGAACCT TATCTAAGAT ATCTAAGGCA TTCTGCAAAC ATCCTCCCAT CATATTAAAG   1320

GCGCCAGTGA ATTTCTCTTC CGTCTGGGTA TATTTTTTCA GCATGTGCTC CTTGATTCTA   1380

TGCCGCACCA TGTCCACTCG AACCTTAATC TGTTTGACGA GTTCTGCCAG GACATCTTTC   1440

TCGGGGTTCT CGTTGCAATC CTCGGTCACT TGTTCAAAAG TTTTGAGGGA TTCTTCGGCC   1500

AACTCTGGAA ACAGCGGGTC TCCCAGACTC AGCTGACTGT TAACCTCCTT CCTCAACATA   1560

GTCTGCAGGA ACGTCGTGGC CTTGGTCACG GGTGTCTCGG GCCGTGGCAC CTTGGAGGAA   1620

GGGCCCTCGT CAGGATTATC AGGGTCCATC TTTCTCTTGG CAGAGGACTC CATTACGATA   1680

CAAACTTAAC GGATATCGCG ATAATGAAAT AATTTATGAT TATTTCTCGC TTTCAATTTA   1740

ACACAACCCT CAAGAACCTT TGTATTTATT TTCACTTTTT AAGTATAGAA TAAAGAGATC   1800

CTGCTGTGGT AGATTCTGTG ACGCTAAGAA TAAGAATAAG AAGGAAGATG TAGAAGAGGG   1860

AAGAGAAGGA TGTTACAATT ATAAGAACCT TAATGATCTG GATGAATCCG AAGCACGTGT   1920

AGAATTTGGA CCATTATATA TGATAAATGA AGAAAAATCA GACATAAATA CATTG        1975
```

(2) INFORMATION FOR SEQ ID NO:16:

(i) SEQUENCE CHARACTERISTICS:
(A) LENGTH: 3499 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

```
AAGCTTGCGG CCGCTCATTA GACAAGCGAA TGAGGGACGA AAACGTGGAG GAGGTATTAA     60

GTTTGGAGAA ATGGAGAGAG ACTGTTTAAT AGCGCATGGC GCAGCCAATA CTATTACAGA    120

AGTTTTGAAA GATTCGGAAG AAGATTATCA AGATGTGTAT GTTTGTGAAA ATTGTGGAGA    180

CATAGCAGCA CAAATCAAGG GTATTAATAC ATGTCTTAGA TGTTCAAAAC TTAATCTCTC    240

TCCTCTCTTA ACAAAAATTG ATACCACGCA CGTATCTAAA GTATTTCTTA CTCAAATGAA    300

CGCCAGAGGC GTAAAAGTCA AATTAGATTT CGAACGAAGG CCTCCTTCGT TTTATAAACC    360
```

-continued

```
ATTAGATAAA GTTGATCTCA AGCCGTCTTT TCTGGTGTAA TAAAAATTAA TTAATTACTC    420
GAGATAAAAA TTACTGGTCA GCCTTGCTTC TAGTCACCAT AGGGTGGGTA CTCTTACCTC    480
CAGAGGCGGT GGGTTCCTCA GCACCATCCT CCTCTTCCTC TGGGGCAACT TCCTCTATCT    540
CAGACACTGG CTCAGACTTG ACAGACACAG TGTCCTCCCG CTCCTCCTGA GCACCCTCCT    600
CCTCTTCCTC ATCACTCTGC TCACTTTCTT CCTGATCACT GTTCTCAGCC ACAATTACTG    660
AGGACAGAGG GATAGTCGCG GGTACAGGGG ACTCTGGGGG TGACACCAGA GAATCAGAGG    720
AGCTGACACC AGCGGTGGCC AAAGTGTAGG CTACAATAGC CTCTTCCTCA TCTGACTCCT    780
CGGCGATGGC CCGTAGGTCA TCCACACTAG GAGAGCAGAC TCTCAGAGGA TCGGCCCCCA    840
GAATGTACTG GGCAAAGACC TTCATGCAGA TCTCCTCAAT GCGGCGCTTC ATTACACTGA    900
TAACCTCAGG CTTGGTTATC AGAGGCCGCT TGGCCAGCAT CACACTAGTC TCCTCTAAGA    960
CATAGCAGCA CAGCACCCGA CAGAACTCAC TTAAGAGAGA GATGCCCCCG TACATGGTCA   1020
TCATACAAGC GTCACTAGTG ACCTTGTACT CATTACACAT TGTTTCCACA CATGTAGTGA   1080
GGATATCCAT AAATATGTGA TCAATGTGCG TGAGCACCTT GTCTCTCTCC TCATCCAAAA   1140
TCTTAAATAT TTTCTGGGCA TAAGCCATAA TCTCATCAGG GGAGCACTGA GGCAAGTTCT   1200
GCAGTGCCGC CATGGCCTGA CTGCAGCCAT TGGTGGTCTT AGGGAAGGCT GAGTTCTTGG   1260
TAAAGAACTC TATATTCCTG TAGCACATAT ACATCATCTT TCTCCTAAGT TCATCCTTTT   1320
TAGCACGGGC CTTAGCCTGC AGTGCACCCC CCAACTTGTT AGCGGCGCCC TTGCTCACAT   1380
CATGCAGCTC CTTAATACAA GCCATCCACA TCTCCCGCTT ATCCTCAGGT ACAATGTAGT   1440
TCTCATACAT GCTCTGCATA GTTAGCCCAA TACACTTCAT CTCCTCGAAA GGCTCATGAA   1500
CCTTATCTAA GATATCTAAG GCATTCTGCA AACATCCTCC CATCATATTA AAGGCGCCAG   1560
TGAATTTCTC TTCCGTCTGG GTATATTTTT TCAGCATGTG CTCCTTGATT CTATGCCGCA   1620
CCATGTCCAC TCGAACCTTA ATCTGTTTGA CGAGTTCTGC CAGGACATCT TTCTCGGGGT   1680
TCTCGTTGCA ATCCTCGGTC ACTTGTTCAA AAGTTTTGAG GGATTCTTCG GCCAACTCTG   1740
GAAACAGCGG GTCTCCCAGA CTCAGCTGAC TGTTAACCTC CTTCCTCAAC ATAGTCTGCA   1800
GGAACGTCGT GGCCTTGGTC ACGGGTGTCT CGGGCCGTGG CACCTTGGAG GAAGGGCCCT   1860
CGTCAGGATT ATCAGGGTCC ATCTTTCTCT TGGCAGAGGA CTCCATTACG ATACAAACTT   1920
AACGGATATC GCGATAATGA AATAATTTAT GATTATTTCT CGCTTTCAAT TTAACACAAC   1980
CCTCAAGAAC CTTTGTATTT ATTTTCACTT TTTAAGTATA GAATAAAGAA GCTCTAATTA   2040
ATTAAGCTAC AAATAGTTTC GTTTTCACCT TGTCTAATAA CTAATTAATT AACCCCGATA   2100
GCTGATTAGT TTTTGTTAAC AAAAATGTGG GAGAATCTAA TTAGTTTTTC TTTACACAAT   2160
TGACGTACAT GAGTCTGAGT TCCTTGTTTT TGCTAATTAT TTCATCCAAT TTATTATTCT   2220
TGACGATATC GAGATCTTTT GTATAGGAGT CAGACTTGTA TTCAACATGC TTTTCTATAA   2280
TCATCTTAGT TATTTCGGCA TCATCCAATA GTACATTTTC CAGATTAACA GAGTAGATAT   2340
TAATGTCGTA TTTGAACAGA GCCTGTAACA TCTCAATGTC TTTATTATCT ATAGCCAATT   2400
TAATGTCCGG AATGAAGAGA AGGGAATTAT TGGTGTTTGT CGACGTCATA TAGTCGAGCA   2460
AGAGAATCAT CATATCCACG TGTCCATTTT TTATAGTGGT GTGAATACAA CTAAGGAGAA   2520
TAGCCAGATC AAAAGTAGAT GGTATTTCTG AAAGAAAGTA TGATACAATA CTTACATCAT   2580
TAAGCATGAC GGCATGATAA AATGAAGTTT TCCATCCAGT TTTCCCATAG AACATCAGTC   2640
TCCAATTTTT CTTAAACAGT TTCACCGTTT GCATGTTACC ACTATCAACC GCATAATACA   2700
ATGCGGTGTT TCCTTTGTCA TCAAATTGTG AATCATCCAT TCCACTGAAT AGCAAAATCT   2760
```

-continued

TTACTATTTT GGTATCTTCT AATGTGGCTG CCTGATGTAA TGGAAATTCA TTCTCTAGAA 2820

GATTTTTCAA TGCTCCAGCG TTCAACAACG TACATACTAG ACGCACGTTA TTATCAGCTA 2880

TTGCATAATA CAAGGCACTA TGTCCATGGA CATCCGCCTT AAATGTATCT TTACTAGAGA 2940

GAAAGCTTTT CAGCTGCTTA GACTTCCAAG TATTAATTCG TGACAGATCC ATGTCTGAAA 3000

CGAGACGCTA ATTAGTGTAT ATTTTTTCAT TTTTTATAAT TTTGTCATAT TGCACCAGAA 3060

TTAATAATAT CTCTAATAGA TCTAATTTAA TTTAATTTAT ATAACTTATT TTTTGAATAT 3120

ACTTTTAATT AACAAAAGAG TTAAGTTACT CATATGGACG CCGTCCAGTC TGAACATCAA 3180

TCTTTTTAGC CAGAGATATC ATAGCCGCTC TTAGAGTTTC AGCGTGATTT TCCAACCTAA 3240

ATAGAACTTC ATCGTTGCGT TTACAACACT TTTCTATTTG TTCAAACTTT GTTGTTACAT 3300

TAGTAATCTT TTTTTCCAAA TTAGTTAGCC GTTGTTTGAG AGTTTCCTCA TTGTCGTCTT 3360

CATCGGCTTT AACAATTGCT TCGCGTTTAG CCTCCTGGCT GTTCTTATCA GCCTTTGTAG 3420

AAAAAAATTC AGTTGCTGGA ATTGCAAGAT CGTCATCTCC GGGGAAAAGA GTTCCGTCCA 3480

TTTAAAGCCG CGGGAATTC 3499

(2) INFORMATION FOR SEQ ID NO:17:

(i) SEQUENCE CHARACTERISTICS:
(A) LENGTH: 1386 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

ATGGAGTCCT CTGCCAAGAG AAAGATGGAC CCTGATAATC CTGACGAGGG CCCTTCCTCC 60

AAGGTGCCAC GGCCCGAGAC ACCCGTGACC AAGGCCACGA CGTTCCTGCA GACTATGTTG 120

AGGAAGGAGG TTAACAGTCA GCTGAGTCTG GGAGACCCGC TGTTTCCAGA GTTGGCCGAA 180

GAATCCCTCA AAACTTTTGA ACAAGTGACC GAGGATTGCA ACGAGAACCC CGAGAAAGAT 240

GTCCTGGCAG AACTCGTCAA ACAGATTAAG GTTCGAGTGG ACATGGTGCG GCATAGAATC 300

AAGGAGCACA TGCTGAAAAA ATATACCCAG ACGGAAGAGA AATTCACTGG CGCCTTTAAT 360

ATGATGGGAG GATGTTTGCA GAATGCCTTA GATATCTTAG ATAAGGTTCA TGAGCCTTTC 420

GAGGAGATGA AGTGTATTGG GCTAACTATG CAGAGCATGT ATGAGAACTA CATTGTACCT 480

GAGGATAAGC GGGAGATGTG GATGGCTTGT ATTAAGGAGC TGCATGATGT GAGCAAGGGC 540

GCCGCTAACA AGTTGGGGGG TGCACTGCAG GCTAAGGCCC GTGCTAAAAA GGATGAACTT 600

AGGAGAAAGA TGATGTATAT GTGCTACAGG AATATAGAGT TCTTTACCAA GAACTCAGCC 660

TTCCCTAAGA CCACCAATGG CTGCAGTCAG GCCATGGCGG CACTGCAGAA CTTGCCTCAG 720

TGCTCCCCTG ATGAGATTAT GGCTTATGCC CAGAAAATAT TTAAGATTTT GGATGAGGAG 780

AGAGACAAGG TGCTCACGCA CATTGATCAC ATATTTATGG ATATCCTCAC TACATGTGTG 840

GAAACAATGT GTAATGAGTA CAAGGTCACT AGTGTGATGC TGGCCAAGCG GCCTCTGATA 900

ACCAAGCCTG AGGTTATCAG TGTAATGAAG CGCCGCATTG AGGAGATCTG CATGAAGGTC 960

TTTGCCCAGT ACATTCTGGG GGCCGATCCT CTGAGAGTCT GCTCTCCTAG TGTGGATGAC 1020

CTACGGGCCA TCGCCGAGGA GTCAGATGAG GAAGAGGCTA TTGTAGCCTA CACTTTGGCC 1080

ACCGCTGGTG TCAGCTCCTC TGATTCTCTG GTGTCACCCC CAGAGTCCCC TGTACCCGCG 1140

ACTATCCCTC TGTCCTCAGT AATTGTGGCT GAGAACAGTG ATCAGGAAGA AAGTGAGCAG 1200

-continued

AGTGATGAGG AAGAGGAGGA GGGTGCTCAG GAGGAGCGGG AGGACACTGT GTCTGTCAAG 1260

TCTGAGCCAG TGTCTGAGAT AGAGGAAGTT GCCCCAGAGG AAGAGGAGGA TGGTGCTGAG 1320

GAACCCACCG CCTCTGGAGG TAAGAGTACC CACCCTATGG TGACTAGAAG CAAGGCTGAC 1380

CAGTAA 1386

(2) INFORMATION FOR SEQ ID NO:18:

(i) SEQUENCE CHARACTERISTICS:
(A) LENGTH: 3409 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

AAGCTTGCGG CCGCTCATTA GACAAGCGAA TGAGGGACGA AAACGTGGAG GAGGTATTAA 60

GTTTGGAGAA ATGGAGAGAG ACTGTTTAAT AGCGCATGGC GCAGCCAATA CTATTACAGA 120

AGTTTTGAAA GATTCGGAAG AAGATTATCA AGATGTGTAT GTTTGTGAAA ATTGTGGAGA 180

CATAGCAGCA CAAATCAAGG GTATTAATAC ATGTCTTAGA TGTTCAAAAC TTAATCTCTC 240

TCCTCTCTTA ACAAAAATTG ATACCACGCA CGTATCTAAA GTATTTCTTA CTCAAATGAA 300

CGCCAGAGGC GTAAAAGTCA AATTAGATTT CGAACGAAGG CCTCCTTCGT TTTATAAACC 360

ATTAGATAAA GTTGATCTCA AGCCGTCTTT TCTGGTGTAA TAAAAATTAA TTAATTACTC 420

GAGATAAAAA TTACTGGTCA GCCTTGCTTC TAGTCACCAT AGGGTGGGTA CTCTTACCTC 480

CAGAGGCGGT GGGTTCCTCA GCACCATCCT CCTCTTCCTC TGGGGCAACT TCCTCTATCT 540

CAGACACTGG CTCAGACTTG ACAGACACAG TGTCCTCCCG CTCCTCCTGA GCACCCTCCT 600

CCTCTTCCTC ATCACTCTGC TCACTTTCTT CCTGATCACT GTTCTCAGCC ACAATTACTG 660

AGGACAGAGG GATAGTCGCG GGTACAGGGG ACTCTGGGGG TGACACCAGA GAATCAGAGG 720

AGCTGACACC AGCGGTGGCC AAAGTGTAGG CTACAATAGC CTCTTCCTCA TCTGACTCCT 780

CGGCGATGGC CCGTAGGTCA TCCACACTAG GAGAGCAGAC TCTCAGAGGA TCGGCCCCCA 840

GAATGTACTG GGCAAAGACC TTCATGCAGA TCTCCTCAAT GCGGCGCTTC ATTACACTGA 900

TAACCTCAGG CTTGGTTATC AGAGGCCGCT TGGCCAGCAT CACACTAGTG ACCTTGTACT 960

CATTACACAT TGTTTCCACA CATGTAGTGA GGATATCCAT AAATATGTGA TCAATGTGCG 1020

TGAGCACCTT GTCTCTCTCC TCATCCAAAA TCTTAAATAT TTTCTGGGCA TAAGCCATAA 1080

TCTCATCAGG GGAGCACTGA GGCAAGTTCT GCAGTGCCGC CATGGCCTGA CTGCAGCCAT 1140

TGGTGGTCTT AGGGAAGGCT GAGTTCTTGG TAAAGAACTC TATATTCCTG TAGCACATAT 1200

ACATCATCTT TCTCCTAAGT TCATCCTTTT TAGCACGGGC CTTAGCCTGC AGTGCACCCC 1260

CCAACTTGTT AGCGGCGCCC TTGCTCACAT CATGCAGCTC CTTAATACAA GCCATCCACA 1320

TCTCCCGCTT ATCCTCAGGT ACAATGTAGT TCTCATACAT GCTCTGCATA GTTAGCCCAA 1380

TACACTTCAT CTCCTCGAAA GGCTCATGAA CCTTATCTAA GATATCTAAG GCATTCTGCA 1440

AACATCCTCC CATCATATTA AAGGCGCCAG TGAATTTCTC TTCCGTCTGG GTATATTTTT 1500

TCAGCATGTG CTCCTTGATT CTATGCCGCA CCATGTCCAC TCGAACCTTA ATCTGTTTGA 1560

CGAGTTCTGC CAGGACATCT TTCTCGGGGT TCTCGTTGCA ATCCTCGGTC ACTTGTTCAA 1620

AAGTTTTGAG GGATTCTTCG GCCAACTCTG GAAACAGCGG GTCTCCCAGA CTCAGCTGAC 1680

TGTTAACCTC CTTCCTCAAC ATAGTCTGCA GGAACGTCGT GGCCTTGGTC ACGGGTGTCT 1740

-continued

CGGGCCGTGG CACCTTGGAG GAAGGGCCCT CGTCAGGATT ATCAGGGTCC ATCTTTCTCT 1800

TGGCAGAGGA CTCCATTACG ATACAAACTT AACGGATATC GCGATAATGA AATAATTTAT 1860

GATTATTTCT CGCTTTCAAT TTAACACAAC CCTCAAGAAC CTTTGTATTT ATTTTCACTT 1920

TTTAAGTATA GAATAAAGAA GCTCTAATTA ATTAAGCTAC AAATAGTTTC GTTTTCACCT 1980

TGTCTAATAA CTAATTAATT AACCCCGATA GCTGATTAGT TTTTGTTAAC AAAAATGTGG 2040

GAGAATCTAA TTAGTTTTTC TTTACACAAT TGACGTACAT GAGTCTGAGT TCCTTGTTTT 2100

TGCTAATTAT TTCATCCAAT TTATTATTCT TGACGATATC GAGATCTTTT GTATAGGAGT 2160

CAGACTTGTA TTCAACATGC TTTTCTATAA TCATCTTAGT TATTTCGGCA TCATCCAATA 2220

GTACATTTTC CAGATTAACA GAGTAGATAT TAATGTCGTA TTTGAACAGA GCCTGTAACA 2280

TCTCAATGTC TTTATTATCT ATAGCCAATT TAATGTCCGG AATGAAGAGA AGGGAATTAT 2340

TGGTGTTTGT CGACGTCATA TAGTCGAGCA AGAGAATCAT CATATCCACG TGTCCATTTT 2400

TTATAGTGGT GTGAATACAA CTAAGGAGAA TAGCCAGATC AAAAGTAGAT GGTATTTCTG 2460

AAAGAAAGTA TGATACAATA CTTACATCAT TAAGCATGAC GGCATGATAA AATGAAGTTT 2520

TCCATCCAGT TTTCCCATAG AACATCAGTC TCCAATTTTT CTTAAACAGT TTCACCGTTT 2580

GCATGTTACC ACTATCAACC GCATAATACA ATGCGGTGTT TCCTTTGTCA TCAAATTGTG 2640

AATCATCCAT TCCACTGAAT AGCAAAATCT TTACTATTTT GGTATCTTCT AATGTGGCTG 2700

CCTGATGTAA TGGAAATTCA TTCTCTAGAA GATTTTTCAA TGCTCCAGCG TTCAACAACG 2760

TACATACTAG ACGCACGTTA TTATCAGCTA TTGCATAATA CAAGGCACTA TGTCCATGGA 2820

CATCCGCCTT AAATGTATCT TTACTAGAGA GAAAGCTTTT CAGCTGCTTA GACTTCCAAG 2880

TATTAATTCG TGACAGATCC ATGTCTGAAA CGAGACGCTA ATTAGTGTAT ATTTTTTCAT 2940

TTTTTATAAT TTTGTCATAT TGCACCAGAA TTAATAATAT CTCTAATAGA TCTAATTTAA 3000

TTTAATTTAT ATAACTTATT TTTTGAATAT ACTTTTAATT AACAAAAGAG TTAAGTTACT 3060

CATATGGACG CCGTCCAGTC TGAACATCAA TCTTTTTAGC CAGAGATATC ATAGCCGCTC 3120

TTAGAGTTTC AGCGTGATTT TCCAACCTAA ATAGAACTTC ATCGTTGCGT TTACAACACT 3180

TTTCTATTTG TTCAAACTTT GTTGTTACAT TAGTAATCTT TTTTTCCAAA TTAGTTAGCC 3240

GTTGTTTGAG AGTTTCCTCA TTGTCGTCTT CATCGGCTTT AACAATTGCT TCGCGTTTAG 3300

CCTCCTGGCT GTTCTTATCA GCCTTTGTAG AAAAAAATTC AGTTGCTGGA ATTGCAAGAT 3360

CGTCATCTCC GGGGAAAAGA GTTCCGTCCA TTTAAAGCCG CGGGAATTC 3409

(2) INFORMATION FOR SEQ ID NO:19:

(i) SEQUENCE CHARACTERISTICS:
(A) LENGTH: 1221 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

ATGAAACAGA TTAAGGTTCG AGTGGACATG GTGCGGCATA GAATCAAGGA GCACATGCTG 60

AAAAAATATA CCCAGACGGA AGAGAAATTC ACTGGCGCCT TTAATATGAT GGGAGGATGT 120

TTGCAGAATG CCTTAGATAT CTTAGATAAG GTTCATGAGC CTTTCGAGGA GATGAAGTGT 180

ATTGGGCTAA CTATGCAGAG CATGTATGAG AACTACATTG TACCTGAGGA TAAGCGGGAG 240

ATGTGGATGG CTTGTATTAA GGAGCTGCAT GATGTGAGCA AGGGCGCCGC TAACAAGTTG 300

-continued

GGGGGTGCAC TGCAGGCTAA GGCCCGTGCT AAAAAGGATG AACTTAGGAG AAAGATGATG 360

TATATGTGCT ACAGGAATAT AGAGTTCTTT ACCAAGAACT CAGCCTTCCC TAAGACCACC 420

AATGGCTGCA GTCAGGCCAT GGCGGCACTG CAGAACTTGC CTCAGTGCTC CCCTGATGAG 480

ATTATGGCTT ATGCCCAGAA AATATTTAAG ATTTTGGATG AGGAGAGAGA CAAGGTGCTC 540

ACGCACATTG ATCACATATT TATGGATATC CTCACTACAT GTGTGGAAAC AATGTGTAAT 600

GAGTACAAGG TCACTAGTGA CGCTTGTATG ATGACCATGT ACGGGGGCAT CTCTCTCTTA 660

AGTGAGTTCT GTCGGGTGCT GTGCTGCTAT GTCTTAGAGG AGACTAGTGT GATGCTGGCC 720

AAGCGGCCTC TGATAACCAA GCCTGAGGTT ATCAGTGTAA TGAAGCGCCG CATTGAGGAG 780

ATCTGCATGA AGGTCTTTGC CCAGTACATT CTGGGGGCCG ATCCTCTGAG AGTCTGCTCT 840

CCTAGTGTGG ATGACCTACG GGCCATCGCC GAGGAGTCAG ATGAGGAAGA GGCTATTGTA 900

GCCTACACTT TGGCCACCGC TGGTGTCAGC TCCTCTGATT CTCTGGTGTC ACCCCCAGAG 960

TCCCCTGTAC CCGCGACTAT CCCTCTGTCC TCAGTAATTG TGGCTGAGAA CAGTGATCAG 1020

GAAGAAAGTG AGCAGAGTGA TGAGGAAGAG GAGGAGGGTG CTCAGGAGGA GCGGGAGGAC 1080

ACTGTGTCTG TCAAGTCTGA GCCAGTGTCT GAGATAGAGG AAGTTGCCCC AGAGGAAGAG 1140

GAGGATGGTG CTGAGGAACC CACCGCCTCT GGAGGTAAGA GTACCCACCC TATGGTGACT 1200

AGAAGCAAGG CTGACCAGTA A 1221

(2) INFORMATION FOR SEQ ID NO:20:

(i) SEQUENCE CHARACTERISTICS:
(A) LENGTH: 2577 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

CTGCAGGTCG ACGGATCTGA GAATGGATGA TTCTCCAGCC GAAACATATT CTACCATGGC 60

TCCGTTTAAT TTGTTGATGA AGATGGATTC ATCCTTAAAT GTTTTCTCTG TAATAGTTTC 120

CACCGAAAGA CTATGCAAAG AATTTGGAAT GCGTTCCTTG TGCTTAATGT TTCCATAGAC 180

GGCTTCTAGA AGTTGATACA ACATAGGACT AGCCGCGGTA ACTTTTATTT TTAGAAAGTA 240

TCCATCGCTT CTATCTTGTT TAGATTTATT TTTATAAAGT TTAGTCTCTC CTTCCAACAT 300

AATAAAAGTG GAAGTCATTT GACTAGATAA ACTATCAGTA AGTTTTATAG AGATAGACGA 360

ACAATTAGCG TATTGAGAAG CATTTAGTGT AACGTATTCG ATACATTTTG CATTAGATTT 420

ACTAATCGAT TTTGCATACT CTATAACACC CGCACAAGTC TGTAGAGAAT CGCTAGATGC 480

AGTAGGTCTT GGTGAAGTTT CAACTCTCTT CTTGATTACC TTACTCATGA TTAAACCTAA 540

ATAATTGTAC TTTGTAATAT AATGATATAT ATTTTCACTT TATCTCATTT GAGAATAAAA 600

AGATCACAAA AATTAACTAA TCAGGATCCT TCTTTATTCT ATACTTAAAA AGTGAAAATA 660

AATACAAAGG TTCTTGAGGG TTGTGTTAAA TTGAAAGCGA GAAATAATCA TAAATTATTT 720

CATTATCGCG ATATCCGTTA AGTTTGTATC GTAATGAAAC AGATTAAGGT TCGAGTGGAC 780

ATGGTGCGGC ATAGAATCAA GGAGCACATG CTGAAAAAAT ATACCCAGAC GGAAGAGAAA 840

TTCACTGGCG CCTTTAATAT GATGGGAGGA TGTTTGCAGA ATGCCTTAGA TATCTTAGAT 900

AAGGTTCATG AGCCTTTCGA GGAGATGAAG TGTATTGGGC TAACTATGCA GAGCATGTAT 960

GAGAACTACA TTGTACCTGA GGATAAGCGG GAGATGTGGA TGGCTTGTAT TAAGGAGCTG 1020

-continued

```
CATGATGTGA GCAAGGGCGC CGCTAACAAG TTGGGGGGTG CACTGCAGGC TAAGGCCCGT   1080

GCTAAAAAGG ATGAACTTAG GAGAAAGATG ATGTATATGT GCTACAGGAA TATAGAGTTC   1140

TTTACCAAGA ACTCAGCCTT CCCTAAGACC ACCAATGGCT GCAGTCAGGC CATGGCGGCA   1200

CTGCAGAACT TGCCTCAGTG CTCCCCTGAT GAGATTATGG CTTATGCCCA GAAAATATTT   1260

AAGATTTTGG ATGAGGAGAG AGACAAGGTG CTCACGCACA TTGATCACAT ATTTATGGAT   1320

ATCCTCACTA CATGTGTGGA AACAATGTGT AATGAGTACA AGGTCACTAG TGACGCTTGT   1380

ATGATGACCA TGTACGGGGG CATCTCTCTC TTAAGTGAGT TCTGTCGGGT GCTGTGCTGC   1440

TATGTCTTAG AGGAGACTAG TGTGATGCTG GCCAAGCGGC CTCTGATAAC CAAGCCTGAG   1500

GTTATCAGTG TAATGAAGCG CCGCATTGAG GAGATCTGCA TGAAGGTCTT TGCCCAGTAC   1560

ATTCTGGGGG CCGATCCTCT GAGAGTCTGC TCTCCTAGTG TGGATGACCT ACGGGCCATC   1620

GCCGAGGAGT CAGATGAGGA AGAGGCTATT GTAGCCTACA CTTTGGCCAC CGCTGGTGTC   1680

AGCTCCTCTG ATTCTCTGGT GTCACCCCCA GAGTCCCCTG TACCCGCGAC TATCCCTCTG   1740

TCCTCAGTAA TTGTGGCTGA GAACAGTGAT CAGGAAGAAA GTGAGCAGAG TGATGAGGAA   1800

GAGGAGGAGG GTGCTCAGGA GGAGCGGGAG GACACTGTGT CTGTCAAGTC TGAGCCAGTG   1860

TCTGAGATAG AGGAAGTTGC CCCAGAGGAA GAGGAGGATG GTGCTGAGGA ACCCACCGCC   1920

TCTGGAGGTA AGAGTACCCA CCCTATGGTG ACTAGAAGCA AGGCTGACCA GTAATTTTTA   1980

TCTCGAGCCC GGGAGATCTT AGCTAACTGA TTTTTCTGGG AAAAAAATTA TTTAACTTTT   2040

CATTAATAGG GATTTGACGT ATGTAGCGTA CAAAATTATC GTTCCTGGTA TATAGATAAA   2100

GAGTCCTATA TATTTGAAAA TCGTTACGGC TCGATTAAAC TTTAATGATT GCATAGTGAA   2160

TATATCATTA GGATTTAACT CCTTGACTAT CATGGCGGCG CCAGAAATTA CCATCAAAAG   2220

CATTAATACA GTTATGCCGA TCGCAGTTAG AACGGTTATA GCATCCACCA TTTATATCTA   2280

AAAATTAGAT CAAAGAATAT GTGACAAAGT CCTAGTTGTA TACTGAGAAT TGACGAAACA   2340

ATGTTTCTTA CATATTTTTT TCTTATTAGT AACTGACTTA ATAGTAGGAA CTGGAAAGCT   2400

AGACTTGATT ATTCTATAAG TATAGATACC CTTCCAGATA ATGTTCTCTT TGATAAAAGT   2460

TCCAGAAAAT GTAGAATTTT TTAAAAAGTT ATCTTTTGCT ATTACCAAGA TTGTGTTTAG   2520

ACGCTTATTA TTAATATGAG TAATGAAATC CACACCGCCT CTAGATATGG GGAATTC      2577
```

(2) INFORMATION FOR SEQ ID NO:21:

(i) SEQUENCE CHARACTERISTICS:
(A) LENGTH: 3460 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

```
GAATTGCGGC CGCTGAATGT TAAATGTTAT ACTTTGGATG AAGCTATAAA TATGCATTGG     60

AAAAATAATC CATTTAAAGA AAGGATTCAA ATACTACAAA ACCTAAGCGA TAATATGTTA    120

ACTAAGCTTA TTCTTAACGA CGCTTTAAAT ATACACAAAT AAACATAATT TTTGTATAAC    180

CTAACAAATA ACTAAAACAT AAAAATAATA AAAGGAAATG TAATATCGTA ATTATTTTAC    240

TCAGGAATGG GGTTAAATAT TTATATCACG TGTATATCTA TACTGTTATC GTATACTCTT    300

TACAATTACT ATTACGAATA TGCAAGAGAT AATAAGATTA CGTATTTAAG AGAATCTTGT    360

CATGATAATT GGGTACGACA TAGTGATAAA TGCTATTTCG CATCGTTACA TAAAGTCAGT    420
```

-continued

```
TGGAAAGATG GATTTGACAG ATGTAACTTA ATAGGTGCAA AAATGTTAAA TAACAGCATT    480
CTATCGGAAG ATAGGATACC AGTTATATTA TACAAAAATC ACTGGTTGGA TAAAACAGAT    540
TCTGCAATAT TCGTAAAAGA TGAAGATTAC TGCGAATTTG TAAACTATGA CAATAAAAAG    600
CCATTTATCT CAACGACATC GTGTAATTCT TCCATGTTTT ATGTATGTGT TTCAGATATT    660
ATGAGATTAC TATAAACTTT TTGTATACTT ATATTCCGTA AACTATATTA ATCATGAAGA    720
AAATGAAAAA GTATAGAAGC TGTTCACGAG CGGTTGTTGA AAACAACAAA ATTATACATT    780
CAAGATGGCT TACATATACG TCTGTGAGGC TATCATGGAT AATGACAATG CATCTCTAAA    840
TAGGTTTTTG GACAATGGAT TCGACCCTAA CACGGAATAT GGTACTCTAC AATCTCCTCT    900
TGAAATGGCT GTAATGTTCA AGAATACCGA GGCTATAAAA ATCTTGATGA GGTATGGAGC    960
TAAACCTGTA GTTACTGAAT GCACAACTTC TTGTCTGCAT GATGCGGTGT TGAGAGACGA   1020
CTACAAAATA GTGAAAGATC TGTTGAAGAA TAACTATGTA AACAATGTTC TTTACAGCGG   1080
AGGCTTTACT CCTTTGTGTT TGGCAGCTTA CCTTAACAAA GTTAATTTGG TTAAACTTCT   1140
ATTGGCTCAT TCGGCGGATG TAGATATTTC AAACACGGAT CGGTTAACTC CTCTACATAT   1200
AGCCGTATCA AATAAAAATT TAACAATGGT TAAACTTCTA TTGAACAAAG GTGCTGATAC   1260
TGACTTGCTG GATAACATGG GACGTACTCC TTTAATGATC GCTGTACAAT CTGGAAATAT   1320
TGAAATATGT AGCACACTAC TTAAAAAAAA TAAAATGTCC AGAACTGGGA AAAATTGATC   1380
TTGCCAGCTG TAATTCATGG TAGAAAAGAA GTGCTCAGGC TACTTTTCAA CAAAGGAGCA   1440
GATGTAAACT ACATCTTTGA AAGAAATGGA AAATCATATA CTGTTTTGGA ATTGATTAAA   1500
GAAAGTTACT CTGAGACACA AAAGAGGTAG CTGAAGTGGT ACTCTCAAAG GTACGTGACT   1560
AATTAGCTAT AAAAAGGATC CGGGTTAATT AATTAGTCAT CAGGCAGGGC GAGAACGAGA   1620
CTATCTGCTC GTTAATTAAT TAGAGCTTCT TTATTCTATA CTTAAAAAGT GAAAATAAAT   1680
ACAAAGGTTC TTGAGGGTTG TGTTAAATTG AAAGCGAGAA ATAATCATAA ATTATTTCAT   1740
TATCGCGATA TCCGTTAAGT TTGTATCGTA ATGAAACAGA TTAAGGTTCG AGTGGACATG   1800
GTGCGGCATA GAATCAAGGA GCACATGCTG AAAAAATATA CCCAGACGGA AGAGAAATTC   1860
ACTGGCGCCT TTAATATGAT GGGAGGATGT TTGCAGAATG CCTTAGATAT CTTAGATAAG   1920
GTTCATGAGC CTTTCGAGGA GATGAAGTGT ATTGGGCTAA CTATGCAGAG CATGTATGAG   1980
AACTACATTG TACCTGAGGA TAAGCGGGAG ATGTGGATGG CTTGTATTAA GGAGCTGCAT   2040
GATGTGAGCA AGGGCGCCGC TAACAAGTTG GGGGGTGCAC TGCAGGCTAA GGCCCGTGCT   2100
AAAAAGGATG AACTTAGGAG AAAGATGATG TATATGTGCT ACAGGAATAT AGAGTTCTTT   2160
ACCAAGAACT CAGCCTTCCC TAAGACCACC AATGGCTGCA GTCAGGCCAT GGCGGCACTG   2220
CAGAACTTGC CTCAGTGCTC CCCTGATGAG ATTATGGCTT ATGCCCAGAA AATATTTAAG   2280
ATTTTGGATG AGGAGAGAGA CAAGGTGCTC ACGCACATTG ATCACATATT TATGGATATC   2340
CTCACTACAT GTGTGGAAAC AATGTGTAAT GAGTACAAGG TCACTAGTGA CGCTTGTATG   2400
ATGACCATGT ACGGGGGCAT CTCTCTCTTA AGTGAGTTCT GTCGGGTGCT GTGCTGCTAT   2460
GTCTTAGAGG AGACTAGTGT GATGCTGGCC AAGCGGCCTC TGATAACCAA GCCTGAGGTT   2520
ATCAGTGTAA TGAAGCGCCG CATTGAGGAG ATCTGCATGA AGGTCTTTGC CCAGTACATT   2580
CTGGGGGCCG ATCCTCTGAG AGTCTGCTCT CCTAGTGTGG ATGACCTACG GGCCATCGCC   2640
GAGGAGTCAG ATGAGGAAGA GGCTATTGTA GCCTACACTT TGGCCACCGC TGGTGTCAGC   2700
TCCTCTGATT CTCTGGTGTC ACCCCCAGAG TCCCCTGTAC CCGCGACTAT CCCTCTGTCC   2760
```

-continued

```
TCAGTAATTG TGGCTGAGAA CAGTGATCAG GAAGAAAGTG AGCAGAGTGA TGAGGAAGAG   2820
GAGGAGGGTG CTCAGGAGGA GCGGGAGGAC ACTGTGTCTG TCAAGTCTGA GCCAGTGTCT   2880
GAGATAGAGG AAGTTGCCCC AGAGGAAGAG GAGGATGGTG CTGAGGAACC CACCGCCTCT   2940
GGAGGTAAGA GTACCCACCC TATGGTGACT AGAAGCAAGG CTGACCAGTA ATTTTTATCT   3000
CGAGTCTAGA ATCGATCCCG GGTTTTTATG ACTAGTTAAT CACGGCCGCT TATAAAGATC   3060
TAAAATGCAT AATTTCTAAA TAATGAAAAA AAAGTACATC ATGAGCAACG CGTTAGTATA   3120
TTTTACAATG GAGATTAACG CTCTATACCG TTCTATGTTT ATTGATTCAG ATGATGTTTT   3180
AGAAAAGAAA GTTATTGAAT ATGAAAACTT TAATGAAGAT GAAGATGACG ACGATGATTA   3240
TTGTTGTAAA TCTGTTTTAG ATGAAGAAGA TGACGCGCTA AAGTATACTA TGGTTACAAA   3300
GTATAAGTCT ATACTACTAA TGGCGACTTG TGCAAGAAGG TATAGTATAG TGAAAATGTT   3360
GTTAGATTAT GATTATGAAA AACCAAATAA ATCAGATCCA TATCTAAAGG TATCTCCTTT   3420
GCACATAATT TCATCTATTC CTAGTTTAGA ATACCTGCAG                         3460
```

(2) INFORMATION FOR SEQ ID NO:22:

(i) SEQUENCE CHARACTERISTICS:
(A) LENGTH: 1383 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

```
ATGACGACGT TCCTGCAGAC TATGTTGAGG AAGGAGGTTA ACAGTCAGCT GAGTCTGGGA     60
GACCCGCTGT TTCCAGAGTT GGCCGAAGAA TCCCTCAAAA CTTTTGAACA AGTGACCGAG    120
GATTGCAACG AGAACCCCGA GAAAGATGTC CTGGCAGAAC TCGTCAAACA GATTAAGGTT    180
CGAGTGGACA TGGTGCGGCA TAGAATCAAG GAGCACATGC TGAAAAAATA TACCCAGACG    240
GAAGAGAAAT TCACTGGCGC CTTTAATATG ATGGGAGGAT GTTTGCAGAA TGCCTTAGAT    300
ATCTTAGATA AGGTTCATGA GCCTTTCGAG GAGATGAAGT GTATTGGGCT AACTATGCAG    360
AGCATGTATG AGAACTACAT TGTACCTGAG GATAAGCGGG AGATGTGGAT GGCTTGTATT    420
AAGGAGCTGC ATGATGTGAG CAAGGGCGCC GCTAACAAGT TGGGGGGTGC ACTGCAGGCT    480
AAGGCCCGTG CTAAAAAGGA TGAACTTAGG AGAAAGATGA TGTATATGTG CTACAGGAAT    540
ATAGAGTTCT TTACCAAGAA CTCAGCCTTC CCTAAGACCA CCAATGGCTG CAGTCAGGCC    600
ATGGCGGCAC TGCAGAACTT GCCTCAGTGC TCCCCTGATG AGATTATGGC TTATGCCCAG    660
AAAATATTTA AGATTTTGGA TGAGGAGAGA GACAAGGTGC TCACGCACAT TGATCACATA    720
TTTATGGATA TCCTCACTAC ATGTGTGGAA ACAATGTGTA ATGAGTACAA GGTCACTAGT    780
GACGCTTGTA TGATGACCAT GTACGGGGGC ATCTCTCTCT TAAGTGAGTT CTGTCGGGTG    840
CTGTGCTGCT ATGTCTTAGA GGAGACTAGT GTGATGCTGG CCAAGCGGCC TCTGATAACC    900
AAGCCTGAGG TTATCAGTGT AATGAAGCGC CGCATTGAGG AGATCTGCAT GAAGGTCTTT    960
GCCCAGTACA TTCTGGGGGC CGATCCTCTG AGAGTCTGCT CTCCTAGTGT GGATGACCTA   1020
CGGGCCATCG CCGAGGAGTC AGATGAGGAA GAGGCTATTG TAGCCTACAC TTTGGCCACC   1080
GCTGGTGTCA GCTCCTCTGA TTCTCTGGTG TCACCCCCAG AGTCCCCTGT ACCCGCGACT   1140
ATCCCTCTGT CCTCAGTAAT TGTGGCTGAG AACAGTGATC AGGAAGAAAG TGAGCAGAGT   1200
GATGAGGAAG AGGAGGAGGG TGCTCAGGAG GAGCGGGAGG ACACTGTGTC TGTCAAGTCT   1260
```

-continued

GAGCCAGTGT CTGAGATAGA GGAAGTTGCC CCAGAGGAAG AGGAGGATGG TGCTGAGGAA 1320

CCCACCGCCT CTGGAGGTAA GAGTACCCAC CCTATGGTGA CTAGAAGCAA GGCTGACCAG 1380

TAA 1383

(2) INFORMATION FOR SEQ ID NO:23:

(i) SEQUENCE CHARACTERISTICS:
(A) LENGTH: 2739 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

CTGCAGGTCG ACGGATCTGA GAATGGATGA TTCTCCAGCC GAAACATATT CTACCATGGC 60

TCCGTTTAAT TTGTTGATGA AGATGGATTC ATCCTTAAAT GTTTTCTCTG TAATAGTTTC 120

CACCGAAAGA CTATGCAAAG AATTTGGAAT GCGTTCCTTG TGCTTAATGT TTCCATAGAC 180

GGCTTCTAGA AGTTGATACA ACATAGGACT AGCCGCGGTA ACTTTTATTT TTAGAAAGTA 240

TCCATCGCTT CTATCTTGTT TAGATTTATT TTTATAAAGT TTAGTCTCTC CTTCCAACAT 300

AATAAAAGTG GAAGTCATTT GACTAGATAA ACTATCAGTA AGTTTTATAG AGATAGACGA 360

ACAATTAGCG TATTGAGAAG CATTTAGTGT AACGTATTCG ATACATTTTG CATTAGATTT 420

ACTAATCGAT TTTGCATACT CTATAACACC CGCACAAGTC TGTAGAGAAT CGCTAGATGC 480

AGTAGGTCTT GGTGAAGTTT CAACTCTCTT CTTGATTACC TTACTCATGA TTAAACCTAA 540

ATAATTGTAC TTTGTAATAT AATGATATAT ATTTTCACTT TATCTCATTT GAGAATAAAA 600

AGATCACAAA AATTAACTAA TCAGGATCCT TCTTTATTCT ATACTTAAAA AGTGAAAATA 660

AATACAAAGG TTCTTGAGGG TTGTGTTAAA TTGAAAGCGA GAAATAATCA TAAATTATTT 720

CATTATCGCG ATATCCGTTA AGTTTGTATC GTAATGACGA CGTTCCTGCA GACTATGTTG 780

AGGAAGGAGG TTAACAGTCA GCTGAGTCTG GGAGACCCGC TGTTTCCAGA GTTGGCCGAA 840

GAATCCCTCA AAACTTTTGA ACAAGTGACC GAGGATTGCA ACGAGAACCC CGAGAAAGAT 900

GTCCTGGCAG AACTCGTCAA ACAGATTAAG GTTCGAGTGG ACATGGTGCG GCATAGAATC 960

AAGGAGCACA TGCTGAAAAA ATATACCCAG ACGGAAGAGA AATTCACTGG CGCCTTTAAT 1020

ATGATGGGAG GATGTTTGCA GAATGCCTTA GATATCTTAG ATAAGGTTCA TGAGCCTTTC 1080

GAGGAGATGA AGTGTATTGG GCTAACTATG CAGAGCATGT ATGAGAACTA CATTGTACCT 1140

GAGGATAAGC GGGAGATGTG GATGGCTTGT ATTAAGGAGC TGCATGATGT GAGCAAGGGC 1200

GCCGCTAACA AGTTGGGGGG TGCACTGCAG GCTAAGGCCC GTGCTAAAAA GGATGAACTT 1260

AGGAGAAAGA TGATGTATAT GTGCTACAGG AATATAGAGT TCTTTACCAA GAACTCAGCC 1320

TTCCCTAAGA CCACCAATGG CTGCAGTCAG GCCATGGCGG CACTGCAGAA CTTGCCTCAG 1380

TGCTCCCCTG ATGAGATTAT GGCTTATGCC CAGAAAATAT TTAAGATTTT GGATGAGGAG 1440

AGAGACAAGG TGCTCACGCA CATTGATCAC ATATTTATGG ATATCCTCAC TACATGTGTG 1500

GAAACAATGT GTAATGAGTA CAAGGTCACT AGTGACGCTT GTATGATGAC CATGTACGGG 1560

GGCATCTCTC TCTTAAGTGA GTTCTGTCGG GTGCTGTGCT GCTATGTCTT AGAGGAGACT 1620

AGTGTGATGC TGGCCAAGCG GCCTCTGATA ACCAAGCCTG AGGTTATCAG TGTAATGAAG 1680

CGCCGCATTG AGGAGATCTG CATGAAGGTC TTTGCCCAGT ACATTCTGGG GGCCGATCCT 1740

CTGAGAGTCT GCTCTCCTAG TGTGGATGAC CTACGGGCCA TCGCCGAGGA GTCAGATGAG 1800

-continued

```
GAAGAGGCTA TTGTAGCCTA CACTTTGGCC ACCGCTGGTG TCAGCTCCTC TGATTCTCTG   1860

GTGTCACCCC CAGAGTCCCC TGTACCCGCG ACTATCCCTC TGTCCTCAGT AATTGTGGCT   1920

GAGAACAGTG ATCAGGAAGA AAGTGAGCAG AGTGATGAGG AAGAGGAGGA GGGTGCTCAG   1980

GAGGAGCGGG AGGACACTGT GTCTGTCAAG TCTGAGCCAG TGTCTGAGAT AGAGGAAGTT   2040

GCCCCAGAGG AAGAGGAGGA TGGTGCTGAG GAACCCACCG CCTCTGGAGG TAAGAGTACC   2100

CACCCTATGG TGACTAGAAG CAAGGCTGAC CAGTAATTTT TATCTCGAGC CCGGGAGATC   2160

TTAGCTAACT GATTTTTCTG GGAAAAAAAT TATTTAACTT TTCATTAATA GGGATTTGAC   2220

GTATGTAGCG TACAAAATTA TCGTTCCTGG TATATAGATA AAGAGTCCTA TATATTTGAA   2280

AATCGTTACG GCTCGATTAA ACTTTAATGA TTGCATAGTG AATATATCAT TAGGATTTAA   2340

CTCCTTGACT ATCATGGCGG CGCCAGAAAT TACCATCAAA AGCATTAATA CAGTTATGCC   2400

GATCGCAGTT AGAACGGTTA TAGCATCCAC CATTTATATC TAAAAATTAG ATCAAAGAAT   2460

ATGTGACAAA GTCCTAGTTG TATACTGAGA ATTGACGAAA CAATGTTTCT TACATATTTT   2520

TTTCTTATTA GTAACTGACT TAATAGTAGG AACTGGAAAG CTAGACTTGA TTATTCTATA   2580

AGTATAGATA CCCTTCCAGA TAATGTTCTC TTTGATAAAA GTTCCAGAAA ATGTAGAATT   2640

TTTTAAAAAG TTATCTTTTG CTATTACCAA GATTGTGTTT AGACGCTTAT TATTAATATG   2700

AGTAATGAAA TCCACACCGC CTCTAGATAT GGGGAATTC                          2739
```

(2) INFORMATION FOR SEQ ID NO:24:

(i) SEQUENCE CHARACTERISTICS:
(A) LENGTH: 3622 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

```
GAATTGCGGC CGCTGAATGT TAAATGTTAT ACTTTGGATG AAGCTATAAA TATGCATTGG     60

AAAAATAATC CATTTAAAGA AAGGATTCAA ATACTACAAA ACCTAAGCGA TAATATGTTA    120

ACTAAGCTTA TTCTTAACGA CGCTTTAAAT ATACACAAAT AAACATAATT TTTGTATAAC    180

CTAACAAATA ACTAAAACAT AAAAATAATA AAAGGAAATG TAATATCGTA ATTATTTTAC    240

TCAGGAATGG GGTTAAATAT TTATATCACG TGTATATCTA TACTGTTATC GTATACTCTT    300

TACAATTACT ATTACGAATA TGCAAGAGAT AATAAGATTA CGTATTTAAG AGAATCTTGT    360

CATGATAATT GGGTACGACA TAGTGATAAA TGCTATTTCG CATCGTTACA TAAAGTCAGT    420

TGGAAAGATG GATTTGACAG ATGTAACTTA ATAGGTGCAA AAATGTTAAA TAACAGCATT    480

CTATCGGAAG ATAGGATACC AGTTATATTA TACAAAAATC ACTGGTTGGA TAAAACAGAT    540

TCTGCAATAT TCGTAAAAGA TGAAGATTAC TGCGAATTTG TAAACTATGA CAATAAAAAG    600

CCATTTATCT CAACGACATC GTGTAATTCT TCCATGTTTT ATGTATGTGT TTCAGATATT    660

ATGAGATTAC TATAAACTTT TTGTATACTT ATATTCCGTA AACTATATTA ATCATGAAGA    720

AAATGAAAAA GTATAGAAGC TGTTCACGAG CGGTTGTTGA AAACAACAAA ATTATACATT    780

CAAGATGGCT TACATATACG TCTGTGAGGC TATCATGGAT AATGACAATG CATCTCTAAA    840

TAGGTTTTTG GACAATGGAT TCGACCCTAA CACGGAATAT GGTACTCTAC AATCTCCTCT    900

TGAAATGGCT GTAATGTTCA AGAATACCGA GGCTATAAAA ATCTTGATGA GGTATGGAGC    960

TAAACCTGTA GTTACTGAAT GCACAACTTC TTGTCTGCAT GATGCGGTGT TGAGAGACGA   1020
```

-continued

```
CTACAAAATA GTGAAAGATC TGTTGAAGAA TAACTATGTA AACAATGTTC TTTACAGCGG   1080
AGGCTTTACT CCTTTGTGTT TGGCAGCTTA CCTTAACAAA GTTAATTTGG TTAAACTTCT   1140
ATTGGCTCAT TCGGCGGATG TAGATATTTC AAACACGGAT CGGTTAACTC CTCTACATAT   1200
AGCCGTATCA AATAAAAATT TAACAATGGT TAAACTTCTA TTGAACAAAG GTGCTGATAC   1260
TGACTTGCTG GATAACATGG GACGTACTCC TTTAATGATC GCTGTACAAT CTGGAAATAT   1320
TGAAATATGT AGCACACTAC TTAAAAAAAA TAAAATGTCC AGAACTGGGA AAAATTGATC   1380
TTGCCAGCTG TAATTCATGG TAGAAAAGAA GTGCTCAGGC TACTTTTCAA CAAAGGAGCA   1440
GATGTAAACT ACATCTTTGA AAGAAATGGA AAATCATATA CTGTTTTGGA ATTGATTAAA   1500
GAAAGTTACT CTGAGACACA AAAGAGGTAG CTGAAGTGGT ACTCTCAAAG GTACGTGACT   1560
AATTAGCTAT AAAAAGGATC CGGGTTAATT AATTAGTCAT CAGGCAGGGC GAGAACGAGA   1620
CTATCTGCTC GTTAATTAAT TAGAGCTTCT TTATTCTATA CTTAAAAAGT GAAAATAAAT   1680
ACAAAGGTTC TTGAGGGTTG TGTTAAATTG AAAGCGAGAA ATAATCATAA ATTATTTCAT   1740
TATCGCGATA TCCGTTAAGT TTGTATCGTA ATGACGACGT TCCTGCAGAC TATGTTGAGG   1800
AAGGAGGTTA ACAGTCAGCT GAGTCTGGGA GACCCGCTGT TTCCAGAGTT GGCCGAAGAA   1860
TCCCTCAAAA CTTTTGAACA AGTGACCGAG GATTGCAACG AGAACCCCGA GAAAGATGTC   1920
CTGGCAGAAC TCGTCAAACA GATTAAGGTT CGAGTGGACA TGGTGCGGCA TAGAATCAAG   1980
GAGCACATGC TGAAAAAATA TACCCAGACG GAAGAGAAAT TCACTGGCGC CTTTAATATG   2040
ATGGGAGGAT GTTTGCAGAA TGCCTTAGAT ATCTTAGATA AGGTTCATGA GCCTTTCGAG   2100
GAGATGAAGT GTATTGGGCT AACTATGCAG AGCATGTATG AGAACTACAT TGTACCTGAG   2160
GATAAGCGGG AGATGTGGAT GGCTTGTATT AAGGAGCTGC ATGATGTGAG CAAGGGCGCC   2220
GCTAACAAGT TGGGGGGTGC ACTGCAGGCT AAGGCCCGTG CTAAAAAGGA TGAACTTAGG   2280
AGAAAGATGA TGTATATGTG CTACAGGAAT ATAGAGTTCT TTACCAAGAA CTCAGCCTTC   2340
CCTAAGACCA CCAATGGCTG CAGTCAGGCC ATGGCGGCAC TGCAGAACTT GCCTCAGTGC   2400
TCCCCTGATG AGATTATGGC TTATGCCCAG AAAATATTTA AGATTTTGGA TGAGGAGAGA   2460
GACAAGGTGC TCACGCACAT TGATCACATA TTTATGGATA TCCTCACTAC ATGTGTGGAA   2520
ACAATGTGTA ATGAGTACAA GGTCACTAGT GACGCTTGTA TGATGACCAT GTACGGGGGC   2580
ATCTCTCTCT TAAGTGAGTT CTGTCGGGTG CTGTGCTGCT ATGTCTTAGA GGAGACTAGT   2640
GTGATGCTGG CCAAGCGGCC TCTGATAACC AAGCCTGAGG TTATCAGTGT AATGAAGCGC   2700
CGCATTGAGG AGATCTGCAT GAAGGTCTTT GCCCAGTACA TTCTGGGGGC CGATCCTCTG   2760
AGAGTCTGCT CTCCTAGTGT GGATGACCTA CGGGCCATCG CCGAGGAGTC AGATGAGGAA   2820
GAGGCTATTG TAGCCTACAC TTTGGCCACC GCTGGTGTCA GCTCCTCTGA TTCTCTGGTG   2880
TCACCCCCAG AGTCCCCTGT ACCCGCGACT ATCCCTCTGT CCTCAGTAAT TGTGGCTGAG   2940
AACAGTGATC AGGAAGAAAG TGAGCAGAGT GATGAGGAAG AGGAGGAGGG TGCTCAGGAG   3000
GAGCGGGAGG ACACTGTGTC TGTCAAGTCT GAGCCAGTGT CTGAGATAGA GGAAGTTGCC   3060
CCAGAGGAAG AGGAGGATGG TGCTGAGGAA CCCACCGCCT CTGGAGGTAA GAGTACCCAC   3120
CCTATGGTGA CTAGAAGCAA GGCTGACCAG TAATTTTTAT CTCGAGTCTA GAATCGATCC   3180
CGGGTTTTTA TGACTAGTTA ATCACGGCCG CTTATAAAGA TCTAAAATGC ATAATTTCTA   3240
AATAATGAAA AAAAAGTACA TCATGAGCAA CGCGTTAGTA TATTTTACAA TGGAGATTAA   3300
CGCTCTATAC CGTTCTATGT TTATTGATTC AGATGATGTT TTAGAAAAGA AAGTTATTGA   3360
ATATGAAAAC TTTAATGAAG ATGAAGATGA CGACGATGAT TATTGTTGTA AATCTGTTTT   3420
```

-continued

AGATGAAGAA GATGACGCGC TAAAGTATAC TATGGTTACA AAGTATAAGT CTATACTACT 3480

AATGGCGACT TGTGCAAGAA GGTATAGTAT AGTGAAAATG TTGTTAGATT ATGATTATGA 3540

AAAACCAAAT AAATCAGATC CATATCTAAA GGTATCTCCT TTGCACATAA TTTCATCTAT 3600

TCCTAGTTTA GAATACCTGC AG 3622

(2) INFORMATION FOR SEQ ID NO:25:

(i) SEQUENCE CHARACTERISTICS:
(A) LENGTH: 1686 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:25:

ATGGAGTCGC GCGGTCGCCG TTGTCCCGAA ATGATATCCG TACTGGGTCC CATTTCGGGG 60

CACGTGCTGA AAGCCGTGTT TAGTCGCGGC GACACGCCGG TGCTGCCGCA CGAGACGCGA 120

CTCCTGCAGA CGGGTATCCA CGTGCGCGTG AGCCAGCCCT CGCTGATCCT GGTGTCGCAG 180

TACACGCCCG ACTCGACGCC ATGCCACCGC GGCGACAATC AGCTGCAGGT GCAGCACACG 240

TACTTTACGG GCAGCGAGGT GGAGAACGTG TCGGTCAACG TGCACAACCC CACGGGCCGG 300

AGCATCTGCC CCAGCCAAGA GCCCATGTCG ATCTATGTGT ACGCGCTGCC GCTCAAGATG 360

CTGAACATCC CCAGCATCAA CGTGCACCAC TACCCGTCGG CGGCCGAGCG CAAACACCGA 420

CACCTGCCCG TAGCTGACGC TGTGATTCAC GCGTCGGGCA AGCAGATGTG GCAGGCGCGT 480

CTCACGGTCT CGGGACTGGC CTGGACGCGT CAGCAGAACC AGTGGAAAGA GCCCGACGTC 540

TACTACACGT CAGCGTTCGT GTTTCCCACC AAGGACGTGG CACTGCGGCA CGTGGTGTGC 600

GCGCACGAGC TGGTTTGCTC CATGGAGAAC ACGCGCGCAA CCAAGATGCA GGTGATAGGT 660

GACCAGTACG TCAAGGTGTA CCTGGAGTCC TTCTGCGAGG ACGTGCCCTC CGGCAAGCTC 720

TTTATGCACG TCACGCTGGG CTCTGACGTG GAAGAGGACC TGACGATGAC CCGCAACCCG 780

CAACCCTTCA TGCGCCCCCA CGAGCGCAAC GGCTTTACGG TGTTGTGTCC CAAAAATATG 840

ATAATCAAAC CGGGCAAGAT CTCGCACATC ATGCTGGATG TGGCTTTTAC CTCACACGAG 900

CATTTTGGGC TGCTGTGTCC CAAGAGCATC CCGGGCCTGA GCATCTCAGG TAACCTATTG 960

ATGAACGGGC AGCAGATCTT CCTGGAGGTG CAAGCGATAC GCGAGACCGT GGAACTGCGT 1020

CAGTACGATC CCGTGGCTGC GCTCTTCTTT TTCGATATCG ACTTGCTGCT GCAGCGCGGG 1080

CCTCAGTACA GCGAACACCC CACCTTCACC AGCCAGTATC GCATCCAGGG CAAGCTTGAG 1140

TACCGACACA CCTGGGACCG GCACGACGAG GGTGCCGCCC AGGGCGACGA CGACGTCTGG 1200

ACCAGCGGAT CGGACTCCGA CGAGGAACTC GTAACCACCG AGCGCAAGAC GCCCCGCGTT 1260

ACCGGCGGCG GCGCCATGGC GGGCGCCTCC ACTTCCGCGG GCCGCAAACG CAAATCAGCA 1320

TCCTCGGCGA CGGCGTGCAC GGCGGGCGTT ATGACACGCG GCCGCCTTAA GGCCGAGTCC 1380

ACCGTCGCGC CCGAAGAGGA CACCGACGAG GATTCCGACA ACGAAATCCA CAATCCGGCC 1440

GTGTTCACCT GGCCGCCCTG GCAGGCCGGC ATCCTGGCCC GCAACCTGGT GCCCATGGTG 1500

GCTACGGTTC AGGGTCAGAA TCTGAAGTAC CAGGAGTTCT TCTGGGACGC CAACGACATC 1560

TACCGCATCT TCGCCGAATT GGAAGGCGTA TGGCAGCCCG CTGCGCAACC CAAACGTCGC 1620

CGCCACCGGC AAGACGCCTT GCCCGGGCCA TGCATCGCCT CGACGCCCAA AAAGCACCGA 1680

GGTTGA 1686

(2) INFORMATION FOR SEQ ID NO:26:

(i) SEQUENCE CHARACTERISTICS:
(A) LENGTH: 2745 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

GTCGACGATT GTTCATGATG GCAAGATTTA TATATCTGGA GGTTACAACA ATAGTAGTGT 60

AGTTAATGTA ATATCGAATC TAGTCCTTAG CTATAATCCG ATATATGATG AATGGACCAA 120

ATTATCATCA TTAAACATTC CTAGAATTAA TCCCGCTCTA TGGTCAGCGC ATAATAAATT 180

ATATGTAGGA GGAGGAATAT CTGATGATGT TCGAACTAAT ACATCTGAAA CATACGATAA 240

AGAAAAAGAT TGTTGGACAT TGGATAATGG TCACGTGTTA CCACGCAATT ATATAATGTA 300

TAAATGCGAA CCGATTAAAC ATAAATATCC ATTGGAAAAA ACACAGTACA CGAATGATTT 360

TCTAAAGTAT TTGGAAAGTT TTATAGGTAG TTGATAGAAC AAAATACATA ATTTTGTAAA 420

AATAAATCAC TTTTTATACT AATATTTAAT TAATTAAGCT TGGTACCCTC GAAGCTTCTT 480

TATTCTATAC TTAAAAAGTG AAAATAAATA CAAAGGTTCT TGAGGGTTGT GTTAAATTGA 540

AAGCGAGAAA TAATCATAAA TTATTTCATT ATCGCGATAT CCGTTAAGTT TGTATCGTAA 600

TGGAGTCGCG CGGTCGCCGT TGTCCCGAAA TGATATCCGT ACTGGGTCCC ATTTCGGGGC 660

ACGTGCTGAA AGCCGTGTTT AGTCGCGGCG ACACGCCGGT GCTGCCGCAC GAGACGCGAC 720

TCCTGCAGAC GGGTATCCAC GTGCGCGTGA GCCAGCCCTC GCTGATCCTG GTGTCGCAGT 780

ACACGCCCGA CTCGACGCCA TGCCACCGCG GCGACAATCA GCTGCAGGTG CAGCACACGT 840

ACTTTACGGG CAGCGAGGTG GAGAACGTGT CGGTCAACGT GCACAACCCC ACGGGCCGGA 900

GCATCTGCCC CAGCCAAGAG CCCATGTCGA TCTATGTGTA CGCGCTGCCG CTCAAGATGC 960

TGAACATCCC CAGCATCAAC GTGCACCACT ACCCGTCGGC GGCCGAGCGC AAACACCGAC 1020

ACCTGCCCGT AGCTGACGCT GTGATTCACG CGTCGGGCAA GCAGATGTGG CAGGCGCGTC 1080

TCACGGTCTC GGGACTGGCC TGGACGCGTC AGCAGAACCA GTGGAAAGAG CCCGACGTCT 1140

ACTACACGTC AGCGTTCGTG TTTCCCACCA AGGACGTGGC ACTGCGGCAC GTGGTGTGCG 1200

CGCACGAGCT GGTTTGCTCC ATGGAGAACA CGCGCGCAAC CAAGATGCAG GTGATAGGTG 1260

ACCAGTACGT CAAGGTGTAC CTGGAGTCCT TCTGCGAGGA CGTGCCCTCC GGCAAGCTCT 1320

TTATGCACGT CACGCTGGGC TCTGACGTGG AAGAGGACCT GACGATGACC CGCAACCCGC 1380

AACCCTTCAT GCGCCCCCAC GAGCGCAACG GCTTTACGGT GTTGTGTCCC AAAAATATGA 1440

TAATCAAACC GGGCAAGATC TCGCACATCA TGCTGGATGT GGCTTTTACC TCACACGAGC 1500

ATTTTGGGCT GCTGTGTCCC AAGAGCATCC CGGGCCTGAG CATCTCAGGT AACCTATTGA 1560

TGAACGGGCA GCAGATCTTC CTGGAGGTGC AAGCGATACG CGAGACCGTG GAACTGCGTC 1620

AGTACGATCC CGTGGCTGCG CTCTTCTTTT TCGATATCGA CTTGCTGCTG CAGCGCGGGC 1680

CTCAGTACAG CGAACACCCC ACCTTCACCA GCCAGTATCG CATCCAGGGC AAGCTTGAGT 1740

ACCGACACAC CTGGGACCGG CACGACGAGG GTGCCGCCCA GGGCGACGAC GACGTCTGGA 1800

CCAGCGGATC GGACTCCGAC GAGGAACTCG TAACCACCGA GCGCAAGACG CCCCGCGTTA 1860

CCGGCGGCGG CGCCATGGCG GGCGCCTCCA CTTCCGCGGG CCGCAAACGC AAATCAGCAT 1920

CCTCGGCGAC GGCGTGCACG GCGGGCGTTA TGACACGCGG CCGCCTTAAG GCCGAGTCCA 1980

-continued

```
CCGTCGCGCC CGAAGAGGAC ACCGACGAGG ATTCCGACAA CGAAATCCAC AATCCGGCCG   2040

TGTTCACCTG GCCGCCCTGG CAGGCCGGCA TCCTGGCCCG CAACCTGGTG CCCATGGTGG   2100

CTACGGTTCA GGGTCAGAAT CTGAAGTACC AGGAGTTCTT CTGGGACGCC AACGACATCT   2160

ACCGCATCTT CGCCGAATTG GAAGGCGTAT GGCAGCCCGC TGCGCAACCC AAACGTCGCC   2220

GCCACCGGCA AGACGCCTTG CCCGGGCCAT GCATCGCCTC GACGCCCAAA AAGCACCGAG   2280

GTTGATTTTT ATGGATCCCC CGGGTAGCTA GCTAATTTTT CTTTTACGTA TTATATATGT   2340

AATAAACGTT CACGTAAATA CAAAACAGAG AACAAAGTCT AGATTTTTGA CTTACATAAA   2400

TGTCTGGGAT AGTAAAATCT ATCATATTGA GCGGACCATC TGGTTCAGGA AAGACAGCCA   2460

TAGCCAAAAG ACTATGGGAA TATATTTGGA TTTGTGGTGT CCCATACCAC TAGATTTCCT   2520

CGTCCTATGG AACGAGAAGG TGTCGATTAC CATTACGTTA ACAGAGAGGC CATCTGGAAG   2580

GGAATAGCCG CCGGAAACTT TCTAGAACAT ACTGAGTTTT TAGGAAATAT TTACGGAACT   2640

TCTAAAACTG CTGTGAATAC AGCGGCTATT AATAATCGTA TTTGTGTGAT GGATTTAAAC   2700

ATCGACGGTG TTAGAAGTTT TAAAAATACT TACCTGCAGA AGCTT                   2745
```

(2) INFORMATION FOR SEQ ID NO:27:

(i) SEQUENCE CHARACTERISTICS:
(A) LENGTH: 3706 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

```
AAGCTTCTAT CAAAAGTCTT AATGAGTTAG GTGTAGATAG TATAGATATT ACTACAAAGG     60

TATTCATATT TCCTATCAAT TCTAAAGTAG ATGATATTAA TAACTCAAAG ATGATGATAG    120

TAGATAATAG ATACGCTCAT ATAATGACTG CAAATTTGGA CGGTTCACAT TTTAATCATC    180

ACGCGTTCAT AAGTTTCAAC TGCATAGATC AAAATCTCAC TAAAAAGATA GCCGATGTAT    240

TTGAGAGAGA TTGGACATCT AACTACGCTA AAGAAATTAC AGTTATAAAT AATACATAAT    300

GGATTTTGTT ATCATCAGTT ATATTTAACA TAAGTACAAT AAAAAGTATT AAATAAAAAT    360

ACTTACTTAC GAAAAAATGT CATTATTACA AAAACTATAT TTTACAGAAC AATCTATAGT    420

AGAGTCCTTT AAGAGTTATA ATTTAAAAGA TAACCATAAT GTAATATTTA CCACATCAGA    480

TGTTGATACT GTTGTAGTAA TAAATGAAGA TAATGTACTG TTATCTACAA GATTATTATC    540

ATTTGATAAA ATTCTGTTTT TTAACTCCTT TAATAACGGT TTATCAAAAT ACGAAACTAT    600

TAGTGATACA ATATTAGATA TAGATACTCA TAATTATTAT ATACCTAGTT CTTCTTCTTT    660

GTTAGATATT CTAAAAAAAA GAGCGTGTGA TTTAGAATTA GAAGATCTAA ATTATGCGTT    720

AATAGGAGAC AATAGTAACT TATATTATAA AGATATGACT TACATGAATA ATTGGTTATT    780

TACTAAAGGA TTATTAGATT ACAAGTTTGT ATTATTGCGC GATGTAGATA AATGTTACAA    840

ACAGTATAAT AAAAAGAATA CTATAATAGA TATAATACAT CGCGATAACA GACAGTATAA    900

CATATGGGTT AAAAATGTTA TAGAATACTG TTCTCCTGGC TATATATTAT GGTTACATGA    960

TCTAAAAGCC GCTGCTGAAG ATGATTGGTT AAGATACGAT AACCGTATAA ACGAATTATC   1020

TGCGGATAAA TTATACACTT TCGAGTTCAT AGTTATATTA GAAAATAATA TAAAACATTT   1080

ACGAGTAGGT ACAATAATTG TACATCCAAA CAAGATAATA GCTAATGGTA CATCTAATAA   1140

TATACTTACT GATTTTCTAT CTTACGTAGA AGAACTAATA TATCATCATA ATTCATCTAT   1200
```

-continued

```
AATATTGGCC GGATATTTTT TAGAATTCTT TGAGACCACT ATTTTATCAG AATTTATTTC   1260
TTCATCTTCT GAATGGGTAA TGAATAGTAA CTGTTTAGTA CACCTGAAAA CAGGGTATGA   1320
AGCTATACTC TTTGATGCTA GTTTATTTTT CCAACTCTCT ACTAAAAGCA ATTATGTAAA   1380
ATATTGGACA AAGAAAACTT TGCAGTATAA GAACTTTTTT AAAGACGGTA AACAGTTAGC   1440
AAAATATATA ATTAAGAAAG ATAGTCAGGT GATAGATAGA GTATGTTATT TACACGCAGC   1500
TGTATATAAT CACGTAACTT ACTTAATGGA TACGTTTAAA ATTCCTGGTT TTGATTTTAA   1560
ATTCTCCGGA ATGATAGATA TACTACTGTT TGGAATATTG CATAAGGATA ATGAGAATAT   1620
ATTTTATCCG AAACGTGTTT CTGTAACTAA TATAATATCA GAATCTATCT ATGCAGATTT   1680
TTACTTTATA TCAGATGTTA ATAAATTCAG TAAAAAGATA GAATATAAAA CTATGTTTCC   1740
TATACTCGCA GAAAACTACT ATCCAAAAGG AAGGCCCTAT TTTACACATA CATCTAACGA   1800
AGATCTTCTG TCTATCTGTT TATGCGAAGT AACAGTTTGT AAAGATATAA AAAATCCATT   1860
ATTATATTCT AAAAAGGATA TATCAGCAAA ACGATTCATA GGTTTATTTA CATCTGTCGA   1920
TATAAATACG GCTGTTGAGT TAAGAGGATA TAAAATAAGA GTAATAGGAT GTTTAGAATG   1980
GCCTGAAAAG ATAAAAATAT TTAATTCTAA TCCTACATAC ATTAGATTAT TACTAACAGA   2040
AAGACGTTTA GATATTCTAC ATTCCTATCT GCTTAAATTT AATATAACAG AGGATATAGC   2100
TACCAGAGAT GGAGTCAGAA ATAATTTACC TATAATTTCT TTTATCGTCA GTTATTGTAG   2160
ATCGTATACT TATAAATTAC TAAATTGCCA TATGTACAAT TCGTGTAAGA TAACAAAGTG   2220
TAAATATAAT CAGGTAATAT ATAATCCTAT ATAGGAGTAT ATATAATTGA AAAAGTAAAA   2280
ATAAATCATA TAATAATGAA ACGAAATATC AGTAATAGAC AGGAACTGGC AGATTCTTCT   2340
TCTAATGAAG TAAGTACTGC TAAATCTCCA AAATTAGATA AAAATGATAC AGCAAATACA   2400
GCTTCATTCA ACGAATTACC TTTTAATTTT TTCAGACACA CCTTATTACA AACTAACTAA   2460
GTCAGATGAT GAGAAAGTAA ATATAAATTT AACTTATGGG TATAATATAA TAAAGATTCA   2520
TGATATTAAT AATTTACTTA ACGATGTTAA TAGACTTATT CCATCAACCC CTTCAAACCT   2580
TTCTGGATAT TATAAAATAC CAGTTAATGA TATTAAAATA GATTGTTTAA GAGATGTAAA   2640
TAATTATTTG GAGGTAAAGG ATATAAAATT AGTCTATCTT TCACATGGAA ATGAATTACC   2700
TAATATTAAT AATTATGATA GGAATTTTTT AGGATTTACA GCTGTTATAT GTATCAACAA   2760
TACAGGCAGA TCTATGGTTA TGGTAAAACA CTGTAACGGG AAGCAGCATT CTATGGTAAC   2820
TGGCCTATGT TTAATAGCCA GATCATTTTA CTCTATAAAC ATTTTACCAC AAATAATAGG   2880
ATCCTCTAGA TATTTAATAT TATATCTAAC AACAACAAAA AAATTTAACG ATGTATGGCC   2940
AGAAGTATTT TCTACTAATA AAGATAAAGA TAGTCTATCT TATCTACAAG ATATGAAAGA   3000
AGATAATCAT TTAGTAGTAG CTACTAATAT GGAAAGAAAT GTATACAAAA ACGTGGAAGC   3060
TTTTATATTA AATAGCATAT TACTAGAAGA TTTAAAATCT AGACTTAGTA TAACAAAACA   3120
GTTAAATGCC AATATCGATT CTATATTTCA TCATAACAGT AGTACATTAA TCAGTGATAT   3180
ACTGAAACGA TCTACAGACT CAACTATGCA AGGAATAAGC AATATGCCAA TTATGTCTAA   3240
TATTTTAACT TTAGAACTAA AACGATTCTA CCAATACTAA AAATAGGATA CGTGATAGGC   3300
TGTTAAAAGC TGCAATAAAT AGTAAGGATG TAGAAGAAAT ACTTTGTTCT ATACCTTCGG   3360
AGGAAAGAAC TTTAGAACAA CTTAAGTTTA ATCAAACTTG TATTTATGAA CACTATAAAA   3420
AAATTATGGA AGATACAAGT AAAAGAATGG ATGTTGAATG TCGTAGTTTA GAACATAACT   3480
ATACGGCTAA CTTATATAAA GTGTACGGAC AAAACGAATA TATGATTACT TATATACTAG   3540
```

-continued

CTCTCATAAG TAGGATTAAT AATATTATAG AAACTTTAAA ATATAATCTG GTGGGGCTAG 3600

ACGAATCTAC AATACGTAAT ATAAATTATA TAATTTCACA AAGAACAAAA AAAAATCAGT 3660

TTCTAATACC TTATAGATAA ACTATATTTT TTACCACTGA CAACAC 3706

(2) INFORMATION FOR SEQ ID NO:28:

(i) SEQUENCE CHARACTERISTICS:
(A) LENGTH: 3521 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

GAGCTCGCGG CCGCCTATCA AAAGTCTTAA TGAGTTAGGT GTAGATAGTA TAGATATTAC 60

TACAAAGGTA TTCATATTTC CTATCAATTC TAAAGTAGAT GATATTAATA ACTCAAAGAT 120

GATGATAGTA GATAATAGAT ACGCTCATAT AATGACTGCA AATTTGGACG GTTCACATTT 180

TAATCATCAC GCGTTCATAA GTTTCAACTG CATAGATCAA AATCTCACTA AAAAGATAGC 240

CGATGTATTT GAGAGAGATT GGACATCTAA CTACGCTAAA GAAATTACAG TTATAAATAA 300

TACATAATGG ATTTTGTTAT CATCAGTTAT ATTTAACATA AGTACAATAA AAAGTATTAA 360

ATAAAAATAC TTACTTACGA AAAAATGACT AATTAGCTAT AAAAACCCAA CAAAAACTAA 420

TCAGCTATCG GGGTTAATTA ATTAGTTATT AGACAAGGTG AAAACGAAAC TATTTGTAGC 480

TTAATTAATT AGAGCTTCTT TATTCTATAC TTAAAAAGTG AAAATAAATA CAAAGGTTCT 540

TGAGGGTTGT GTTAAATTGA AAGCGAGAAA TAATCATAAA TTATTTCATT ATCGCGATAT 600

CCGTTAAGTT TGTATCGTAA TGGAGTCGCG CGGTCGCCGT TGTCCCGAAA TGATATCCGT 660

ACTGGGTCCC ATTTCGGGGC ACGTGCTGAA AGCCGTGTTT AGTCGCGGCG ACACGCCGGT 720

GCTGCCGCAC GAGACGCGAC TCCTGCAGAC GGGTATCCAC GTGCGCGTGA GCCAGCCCTC 780

GCTGATCCTG GTGTCGCAGT ACACGCCCGA CTCGACGCCA TGCCACCGCG GCGACAATCA 840

GCTGCAGGTG CAGCACACGT ACTTTACGGG CAGCGAGGTG GAGAACGTGT CGGTCAACGT 900

GCACAACCCC ACGGGCCGGA GCATCTGCCC CAGCCAAGAG CCCATGTCGA TCTATGTGTA 960

CGCGCTGCCG CTCAAGATGC TGAACATCCC CAGCATCAAC GTGCACCACT ACCCGTCGGC 1020

GGCCGAGCGC AAACACCGAC ACCTGCCCGT AGCTGACGCT GTGATTCACG CGTCGGGCAA 1080

GCAGATGTGG CAGGCGCGTC TCACGGTCTC GGGACTGGCC TGGACGCGTC AGCAGAACCA 1140

GTGGAAAGAG CCCGACGTCT ACTACACGTC AGCGTTCGTG TTTCCCACCA AGGACGTGGC 1200

ACTGCGGCAC GTGGTGTGCG CGCACGAGCT GGTTTGCTCC ATGGAGAACA CGCGCGCAAC 1260

CAAGATGCAG GTGATAGGTG ACCAGTACGT CAAGGTGTAC CTGGAGTCCT TCTGCGAGGA 1320

CGTGCCCTCC GGCAAGCTCT TTATGCACGT CACGCTGGGC TCTGACGTGG AAGAGGACCT 1380

GACGATGACC CGCAACCCGC AACCCTTCAT GCGCCCCCAC GAGCGCAACG GCTTTACGGT 1440

GTTGTGTCCC AAAAATATGA TAATCAAACC GGGCAAGATC TCGCACATCA TGCTGGATGT 1500

GGCTTTTACC TCACACGAGC ATTTTGGGCT GCTGTGTCCC AAGAGCATCC CGGGCCTGAG 1560

CATCTCAGGT AACCTATTGA TGAACGGGCA GCAGATCTTC CTGGAGGTGC AAGCGATACG 1620

CGAGACCGTG GAACTGCGTC AGTACGATCC CGTGGCTGCG CTCTTCTTTT TCGATATCGA 1680

CTTGCTGCTG CAGCGCGGGC CTCAGTACAG CGAACACCCC ACCTTCACCA GCCAGTATCG 1740

CATCCAGGGC AAGCTTGAGT ACCGACACAC CTGGGACCGG CACGACGAGG GTGCCGCCCA 1800

-continued

```
GGGCGACGAC GACGTCTGGA CCAGCGGATC GGACTCCGAC GAGGAACTCG TAACCACCGA   1860

GCGCAAGACG CCCCGCGTTA CCGGCGGCGG CGCCATGGCG GGCGCCTCCA CTTCCGCGGG   1920

CCGCAAACGC AAATCAGCAT CCTCGGCGAC GGCGTGCACG GCGGGCGTTA TGACACGCGG   1980

CCGCCTTAAG GCCGAGTCCA CCGTCGCGCC CGAAGAGGAC ACCGACGAGG ATTCCGACAA   2040

CGAAATCCAC AATCCGGCCG TGTTCACCTG GCCGCCCTGG CAGGCCGGCA TCCTGGCCCG   2100

CAACCTGGTG CCCATGGTGG CTACGGTTCA GGGTCAGAAT CTGAAGTACC AGGAGTTCTT   2160

CTGGGACGCC AACGACATCT ACCGCATCTT CGCCGAATTG GAAGGCGTAT GGCAGCCCGC   2220

TGCGCAACCC AAACGTCGCC GCCACCGGCA AGACGCCTTG CCCGGGCCAT GCATCGCCTC   2280

GACGCCCAAA AAGCACCGAG GTTGATTTTT ATGGATCCGG TACCCTCGAG GAATTCTTTT   2340

TATTGATTAA CTAGTCAAAT GAGTATATAT AATTGAAAAA GTAAAATATA AATCATATAA   2400

TAATGAAACG AAATATCAGT AATAGACAGG AACTGGCAGA TTCTTCTTCT AATGAAGTAA   2460

GTACTGCTAA ATCTCCAAAA TTAGATAAAA ATGATACAGC AAATACAGCT TCATTCAACG   2520

AATTACCTTT TAATTTTTTC AGACACACCT TATTACAAAC TAACTAAGTC AGATGATGAG   2580

AAAGTAAATA TAAATTTAAC TTATGGGTAT AATATAATAA AGATTCATGA TATTAATAAT   2640

TTACTTAACG ATGTTAATAG ACTTATTCCA TCAACCCCTT CAAACCTTTC TGGATATTAT   2700

AAAATACCAG TTAATGATAT TAAAATAGAT TGTTTAAGAG ATGTAAATAA TTATTTGGAG   2760

GTAAAGGATA TAAAATTAGT CTATCTTTCA CATGGAAATG AATTACCTAA TATTAATAAT   2820

TATGATAGGA ATTTTTTAGG ATTTACAGCT GTTATATGTA TCAACAATAC AGGCAGATCT   2880

ATGGTTATGG TAAAACACTG TAACGGGAAG CAGCATTCTA TGGTAACTGG CCTATGTTTA   2940

ATAGCCAGAT CATTTTACTC TATAAACATT TTACCACAAA TAATAGGATC CTCTAGATAT   3000

TTAATATTAT ATCTAACAAC AACAAAAAAA TTTAACGATG TATGGCCAGA AGTATTTTCT   3060

ACTAATAAAG ATAAAGATAG TCTATCTTAT CTACAAGATA TGAAAGAAGA TAATCATTTA   3120

GTAGTAGCTA CTAATATGGA AAGAAATGTA TACAAAAACG TGGAAGCTTT TATATTAAAT   3180

AGCATATTAC TAGAAGATTT AAAATCTAGA CTTAGTATAA CAAAACAGTT AAATGCCAAT   3240

ATCGATTCTA TATTTCATCA TAACAGTAGT ACATTAATCA GTGATATACT GAAACGATCT   3300

ACAGACTCAA CTATGCAAGG AATAAGCAAT ATGCCAATTA TGTCTAATAT TTTAACTTTA   3360

GAACTAAAAC GTTCTACCAA TACTAAAAAT AGGATACGTG ATAGGCTGTT AAAAGCTGCA   3420

ATAAATAGTA AGGATGTAGA AGAAATACTT TGTTCTATAC CTTCGGAGGA AAGAACTTTA   3480

GAACAACTTA AGTTTAATCA AACTTGTATT TATGAAGGTA C                        3521
```

(2) INFORMATION FOR SEQ ID NO:29:

(i) SEQUENCE CHARACTERISTICS:
(A) LENGTH: 2160 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

```
AAGACTAATT TGTAAACCAT CTTACTCAAA ATATGTAACA ATAGTACGAT GCAATGAGTA     60

AGACAATAGG AAATCTATCT TATATACACA TAATTATTCT ATCAATTTTA CCAATTAGTT    120

AGTGTAATGT TATAAAAACT AATTAATCAC TCGAGCCCCC TCGAAGCTTC TTTATTCTAT    180

ACTTAAAAAG TGAAAATAAA TACAAAGGTT CTTGAGGGTT GTGTTAAATT GAAAGCGAGA    240
```

-continued

```
AATAATCATA AATTATTTCA TTATCGCGAT ATCCGTTAAG TTTGTATCGT AATGGAGTCG    300

CGCGGTCGCC GTTGTCCCGA AATGATATCC GTACTGGGTC CCATTTCGGG GCACGTGCTG    360

AAAGCCGTGT TTAGTCGCGG CGACACGCCG GTGCTGCCGC ACGAGACGCG ACTCCTGCAG    420

ACGGGTATCC ACGTGCGCGT GAGCCAGCCC TCGCTGATCC TGGTGTCGCA GTACACGCCC    480

GACTCGACGC CATGCCACCG CGGCGACAAT CAGCTGCAGG TGCAGCACAC GTACTTTACG    540

GGCAGCGAGG TGGAGAACGT GTCGGTCAAC GTGCACAACC CCACGGGCCG GAGCATCTGC    600

CCCAGCCAAG AGCCCATGTC GATCTATGTG TACGCGCTGC CGCTCAAGAT GCTGAACATC    660

CCCAGCATCA ACGTGCACCA CTACCCGTCG GCGGCCGAGC GCAAACACCG ACACCTGCCC    720

GTAGCTGACG CTGTGATTCA CGCGTCGGGC AAGCAGATGT GGCAGGCGCG TCTCACGGTC    780

TCGGGACTGG CCTGGACGCG TCAGCAGAAC CAGTGGAAAG AGCCCGACGT CTACTACACG    840

TCAGCGTTCG TGTTTCCCAC CAAGGACGTG GCACTGCGGC ACGTGGTGTG CGCGCACGAG    900

CTGGTTTGCT CCATGGAGAA CACGCGCGCA ACCAAGATGC AGGTGATAGG TGACCAGTAC    960

GTCAAGGTGT ACCTGGAGTC CTTCTGCGAG GACGTGCCCT CCGGCAAGCT CTTTATGCAC   1020

GTCACGCTGG GCTCTGACGT GGAAGAGGAC CTGACGATGA CCCGCAACCC GCAACCCTTC   1080

ATGCGCCCCC ACGAGCGCAA CGGCTTTACG GTGTTGTGTC CCAAAAATAT GATAATCAAA   1140

CCGGGCAAGA TCTCGCACAT CATGCTGGAT GTGGCTTTTA CCTCACACGA GCATTTTGGG   1200

CTGCTGTGTC CCAAGAGCAT CCCGGGCCTG AGCATCTCAG GTAACCTATT GATGAACGGG   1260

CAGCAGATCT TCCTGGAGGT GCAAGCGATA CGCGAGACCG TGGAACTGCG TCAGTACGAT   1320

CCCGTGGCTG CGCTCTTCTT TTTCGATATC GACTTGCTGC TGCAGCGCGG GCCTCAGTAC   1380

AGCGAACACC CCACCTTCAC CAGCCAGTAT CGCATCCAGG GCAAGCTTGA GTACCGACAC   1440

ACCTGGGACC GGCACGACGA GGGTGCCGCC CAGGGCGACG ACGACGTCTG GACCAGCGGA   1500

TCGGACTCCG ACGAGGAACT CGTAACCACC GAGCGCAAGA CGCCCCGCGT TACCGGCGGC   1560

GGCGCCATGG CGGGCGCCTC CACTTCCGCG GGCCGCAAAC GCAAATCAGC ATCCTCGGCG   1620

ACGGCGTGCA CGGCGGGCGT TATGACACGC GGCCGCCTTA AGGCCGAGTC CACCGTCGCG   1680

CCCGAAGAGG ACACCGACGA GGATTCCGAC AACGAAATCC ACAATCCGGC CGTGTTCACC   1740

TGGCCGCCCT GGCAGGCCGG CATCCTGGCC CGCAACCTGG TGCCCATGGT GGCTACGGTT   1800

CAGGGTCAGA ATCTGAAGTA CCAGGAGTTC TTCTGGGACG CCAACGACAT CTACCGCATC   1860

TTCGCCGAAT TGGAAGGCGT ATGGCAGCCC GCTGCGCAAC CCAAACGTCG CCGCCACCGG   1920

CAAGACGCCT TGCCCGGGCC ATGCATCGCC TCGACGCCCA AAAAGCACCG AGGTTGATTT   1980

TTATGGATCC TCGCGACTGC AGGGTACCTG AGTAGCTAAT TTTTAAACAA AAATGTGGGA   2040

GAATCTAATT AGTTTTTCTT TACACAATTG ACGTACATGA GTCTGAGTTC CTTGTTTTTG   2100

CTAATTATTT CATCCAATTT ATTATTCTTG ACGATATCGA GATCTTTTGT ATAGGAGTCA   2160
```

(2) INFORMATION FOR SEQ ID NO:30:

(i) SEQUENCE CHARACTERISTICS:
(A) LENGTH: 3141 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:30:

```
ATGAGTTTGC AGTTTATCGG TCTACAGCGG CGCGATGTGG TGGCCCTGGT CAACTTTCTG     60
```

-continued

| | | | | | | |
|---|---|---|---|---|---|---|
| CGCCATCTCA | CGCAAAAGCC | CGACGTGGAT | CTCGAGGCAC | ACCCCAAGAT | CCTGAAAAAA | 120 |
| TGTGGCGAAA | AACGCCTGCA | CCGGCGTACG | GTGCTGTTCA | ACGAGCTCAT | GCTTTGGTTG | 180 |
| GGATACTACC | GCGAGCTGCG | TTTCCACAAC | CCCGACCTCT | CCTCGGTTCT | CGAGGAGTTC | 240 |
| GAGGTGCGTT | GCGCGGCCGT | GGCGCGTCGC | GGCTACACTT | ACCCGTTCGG | TGATCGTGGT | 300 |
| AAGGCGCGTG | ACCACCTGGC | TGTGCTAGAC | CGTACCGAAT | TCGATACGGA | CGTACGCCAC | 360 |
| GATGCTGAGA | TTGTGGAGCG | CGCGCTCGTA | AGCGCGGTCA | TTCTGGCCAA | GATGTCGGTG | 420 |
| CGCGAGACGC | TGGTCACAGC | CATCGGCCAG | ACGGAACCCA | TCGCTTTTGT | GCACCTCAAG | 480 |
| GATACGGAGG | TGCAGCGCAT | TGAAGAAAAC | CTGGAGGGTG | TGCGCCGTAA | CATGTTCTGC | 540 |
| GTGAAACCGC | TCGACCTTAA | CCTGGACCGG | CACGCCAACA | CGGCGCTGGT | CAACGCCGTC | 600 |
| AACAAGCTCG | TGTACACGGG | CCGTCTCATC | ATGAACGTGC | GCAGGTCTTG | GGAGGAGCTG | 660 |
| GAGCGCAAAT | GTCTGGCGCG | CATTCAGGAG | CGCTGCAAGC | TGCTGGTCAA | GGAGCTGCGC | 720 |
| ATGTGCCTTT | CCTTTGATTC | CAACTACTGT | CGCAATATCC | TCAAACACGC | CGTGGAAAAC | 780 |
| GGTGACTCGG | CCGACACGCT | GCTGGAGCTG | CTCATCGAGG | ACTTTGACAT | CTACGTGGAC | 840 |
| AGCTTCCCGC | AGTCGGCGCA | CACCTTTTTG | GGCGCGCGCC | CGCCGTCGTT | GGAGTTTGAC | 900 |
| GATGACGCCA | ATCTCCTCTC | GCTCGGCGGC | GGTTCAGCCT | TCTCGTCGGT | ACCCAAGAAA | 960 |
| CATGTCCCCA | CGCAGCCGCT | GGACGGCTGG | AGCTGGATCG | CCAGTCCCTG | GAAGGGACAC | 1020 |
| AAACCGTTCC | GCTTCGAGGC | CCATGGTTCT | CTGGCACCGG | CCGCCGACGC | CCACGCCGCC | 1080 |
| CGTTCGGCGC | GCGTCGGCTA | TTACGACGAA | GAGGAAAAGC | GTCGCGAGCG | GCAGAAACGG | 1140 |
| GTGGACGACG | AGGTGGTGCA | GCGTGAGAAA | CAGCAGCTGA | AGGCTTGGGA | GGAGAGGCAG | 1200 |
| CAGAACCTGC | AGCAACGTCA | GCAGCAACCG | CCGCCCCCGA | CACGTAAACC | GGGCGCCTCC | 1260 |
| CGGAGGCTCT | TTGGCTCCAG | TGCCGATGAG | GACGACGACG | ATGATGATGA | CGAGAAAAAC | 1320 |
| ATCTTTACGC | CCATCAAGAA | ACCGGGAACT | AGCGGCAAGG | GCGCCGCTAG | TGGCAACGGT | 1380 |
| GTTTCCAGCA | TTTTCAGCGG | CATGTTATCC | TCGGGCAGTC | AGAAACCGAC | CAGCGGTCCC | 1440 |
| TTGAACATCC | CGCAGCAACA | ACAGCGTCAC | GCGGCTTTCA | GTCTCGTCTC | CCCGCAGGTA | 1500 |
| ACCAAGGCCA | GCCCGGGAAG | GGTCCGTCGG | GACAGCGCGT | GGGACGTGAG | GCCGCTCACG | 1560 |
| GAGACAAGAG | GGGATCTTTT | CTCGGGCGAC | GAGGATTCCG | ACAGCTCGGA | TGGCTATCCC | 1620 |
| CCCAACCGTC | AAGATCCGCG | TTTCACCGAC | ACGCTGGTGG | ACATCACGGA | TACCGAGACG | 1680 |
| AGCGCCAAAC | CGCCCGTCAC | CACCGCGTAC | AAGTTCGAGC | AACCGACGTT | GACGTTCGGC | 1740 |
| GCCGGAGTTA | ACGTCCCTGC | TGGCGCCGGC | GCTGCCATCC | TCACGCCGAC | GCCTGTCAAT | 1800 |
| CCTTCCACGG | CCCCCGCTCC | GGCCCCGACA | CCTACCTTCG | CGGGTACCCA | AACCCCGGTC | 1860 |
| AACGGTAACT | CGCCCTGGGC | TCCGACGGCG | CCGTTGCCCG | GGGATATGAA | CCCCGCCAAC | 1920 |
| TGGCCGCGCG | AACGCGCGTG | GGCCCTCAAG | AATCCTCACC | TGGCTTACAA | TCCCTTCAGG | 1980 |
| ATGCCTACGA | CTTCCACGAC | TTCTCAAAAC | AACGTGTCCA | CCACCCCTCG | GAGGCCGTCG | 2040 |
| ACTCCACGCG | CCGCGGTGAC | ACAAACAGCG | TCTCAGAACG | CCGCTGATGA | GGTTTGGGCT | 2100 |
| TTAAGGGACC | AAACTGCAGA | GTCACCGGTC | GAAGACAGCG | AGGAGGAAGA | CGACGACTCC | 2160 |
| TCGGACACCG | GCTCCGTCGT | CAGCCTGGGA | CACACAACAC | CGTCGTCCGA | TTACAACGAC | 2220 |
| GTCATTTCGC | CTCCCAGTCA | GACGCCCGAG | CAGTCGACGC | CGTCCAGAAT | ACGTAAAGCT | 2280 |
| AAGTTATCGT | CTCCAATGAC | GACGACATCC | ACGAGCCAGA | AACCGGTGCT | GGGCAAGCGA | 2340 |
| GTCGCGACGC | CGCACGCGTC | CGCCCGAGCG | CAGACGGTGA | CGTCGACACC | GGTTCAGGGA | 2400 |
| AGGGTAGAGA | AACAGGTATC | GGGCACGCCG | TCGACGGTAC | CCGCCACGCT | GTTGCAACCT | 2460 |

-continued

CAACCGGCTT CGTCTAAAAC AACGTCATCA AGGAACGTGA CTTCTGGCGC GAGAACCTCT 2520

TCCGCTTCGG CTCGACAGCC GTCAGCCTCG GCGTCCGTTT TGTCGCCCAC GGAGGATGAT 2580

GTCGTGTCCC CCGTCACGTC GCCGCTGTCC ATGCTTTCGT CAGCCTCTCC GTCCCCGGCC 2640

AAGAGTGCCC CTCCGTCTCC GGTGAAAGGT CGGGGCAGCC GCGTCGGTGT TCCTTCTTTG 2700

AAACCTACTT TGGGCGGCAA GGCGGTGGTA GGTCGACCGC CCTCGGTCCC CGTGAGCGGT 2760

AGCGCGCCGG GTCGCCTGTC CGGCACCAGC CGGGCCGCCT CGACCACGCC GACGTATCCC 2820

GCGGTAACCA CCGTTTACCC ACCGTCGTCT ACGGCCAAAA GCAGCGTATC GAATGCGCCG 2880

CCTGTGGCCT CCCCCTCCAT CCTGAAACCG GGGGCGAGCG CGGCTTTGCA ATCACGCCGC 2940

TCGACGGGGA CCGCCGCCGT AGGTTCCCCC GTCAAGAGCA CGACGGGCAT GAAAACGGTG 3000

GCTTTCGACC TATCGTCGCC CCAGAAGAGC GGTACGGGGC CGCAACCGGG TTCTGCCGGC 3060

ATGGGGGGCG CCAAAACGCC GTCGGACGCC GTGCAGAACA TCCTCCAAAA GATCGAGAAG 3120

ATTAAGAACA CGGAGGAATA G 3141

(2) INFORMATION FOR SEQ ID NO:31:

(i) SEQUENCE CHARACTERISTICS:
(A) LENGTH: 4075 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:31:

AAGCTTGCGG CCGCTCATTA GACAAGCGAA TGAGGGACGA AAACGTGGAG GAGGTATTAA 60

GTTTGGAGAA ATGGAGAGAG ACTGTTTAAT AGCGCATGGC GCAGCCAATA CTATTACAGA 120

AGTTTTGAAA GATTCGGAAG AAGATTATCA AGATGTGTAT GTTTGTGAAA ATTGTGGAGA 180

CATAGCAGCA CAAATCAAGG GTATTAATAC ATGTCTTAGA TGTTCAAAAC TTAATCTCTC 240

TCCTCTCTTA ACAAAAATTG ATACCACGCA CGTATCTAAA GTATTTCTTA CTCAAATGAA 300

CGCCAGAGGC GTAAAAGTCA AATTAGATTT CGAACGAAGG CCTCCTTCGT TTTATAAACC 360

ATTAGATAAA GTTGATCTCA AGCCGTCTTT TCTGGTGTAA TAAAAATTAA TTAATTACTC 420

GAGCCCCTAG CAATAAAAAC TATTCCTCCG TGTTCTTAAT CTTCTCGATC TTTTGGAGGA 480

TGTTCTGCAC GGCGTCCGAC GGCGTTTTGG CGCCCCCCAT GCCGGCAGAA CCCGGTTGCG 540

GCCCCGTACC GCTCTTCTGG GGCGACGATA GGTCGAAAGC CACCGTTTTC ATGCCCGTCG 600

TGCTCTTGAC GGGGGAACCT ACGGCGGCGG TCCCCGTCGA GCGGCGTGAT TGCAAAGCCG 660

CGCTCGCCCC CGGTTTCAGG ATGGAGGGGG AGGCCACAGG CGGCGCATTC GATACGCTGC 720

TTTTGGCCGT AGACGACGGT GGGTAAACGG TGGTTACCGC GGGATACGTC GGCGTGGTCG 780

AGGCGGCCCG GCTGGTGCCG GACAGGCGAC CCGGCGCGCT ACCGCTCACG GGTACCGAGG 840

GCGGTCGACC TACCACCGCC TTGCCGCCCA AAGTAGGTTT CAAAGAAGGA ACACCGACGC 900

GGCTGCCCCG ACCTTTCACC GGAGACGGAG GGGCACTCTT GGCCGGGGAC GGAGAGGCTG 960

ACGAAAGCAT GGACAGCGGC GACGTGACGG GGGACACGAC ATCATCCTCC GTGGGCGACA 1020

AAACGGACGC CGAGGCTGAC GGCTGTCGAG CCGAAGCGGA AGAGGTTCTC GCGCCAGAAG 1080

TCACGTTCCT TGATGACGTT GTTTTAGACG AAGCCGGTTG AGGTTGCAAC AGCGTGGCGG 1140

GTACCGTCGA CGGCGTGCCC GATACCTGTT TCTCTACCCT TCCCTGAACC GGTGTCGACG 1200

TCACCGTCTG CGCTCGGGCG GACGCGTGCG GCGTCGCGAC TCGCTTGCCC AGCACCGGTT 1260

-continued

TCTGGCTCGT GGATGTCGTC GTCATTGGAG ACGATAACTT AGCTTTACGT ATTCTGGACG 1320
GCGTCGACTG CTCGGGCGTC TGACTGGGAG GCGAAATGAC GTCGTTGTAA TCGGACGACG 1380
GTGTTGTGTG TCCCAGGCTG ACGACGGAGC CGGTGTCCGA GGAGTCGTCG TCTTCCTCCT 1440
CGCTGTCTTC GACCGGTGAC TCTGCAGTTT GGTCCCTTAA AGCCCAAACC TCATCAGCGG 1500
CGTTCTGAGA CGCTGTTTGT GTCACCGCGG CGCGTGGAGT CGACGGCCTC CGAGGGGTGG 1560
TGGACACGTT GTTTTGAGAA GTCGTGGAAG TCGTAGGCAT CCTGAAGGGA TTGTAAGCCA 1620
GGTGAGGATT CTTGAGGGCC CACGCGCGTT CGCGCGGCCA GTTGGCGGGG TTCATATCCC 1680
CGGGCAACGG CGCCGTCGGA GCCCAGGGCG AGTTACCGTT GACCGGGGTT TGGGTACCCG 1740
CGAAGGTAGG TGTCGGGGCC GGAGCGGGGG CCGTGGAAGG ATTGACAGGC GTCGGCGTGA 1800
GGATGGCAGC GCCGGCGCCA GCAGGGACGT TAACTCCGGC GCCGAACGTC AACGTCGGTT 1860
GCTCGAACTT GTACGCGGTG GTGACGGGCG GTTTGGCGCT CGTCTCGGTA TCCGTGATGT 1920
CCACCAGCGT GTCGGTGAAA CGCGGATCTT GACGGTTGGG GGGATAGCCA TCCGAGCTGT 1980
CGGAATCCTC GTCGCCCGAG AAAAGATCCC CTCTTGTCTC CGTGAGCGGC CTCACGTCCC 2040
ACGCGCTGTC CCGACGGACC CTTCCCGGGC TGGCCTTGGT TACCTGCGGG GAGACGAGAC 2100
TGAAAGCCGC GTGACGCTGT TGTTGCTGCG GGATGTTCAA GGGACCGCTG GTCGGTTTCT 2160
GACTGCCCGA GGATAACATG CCGCTGAAAA TGCTGGAAAC ACCGTTGCCA CTAGCGGCGC 2220
CCTTGCCGCT AGTTCCCGGT TTCTTGATGG GCGTAAAGAT GTTTTTCTCG TCATCATCAT 2280
CGTCGTCGTC CTCATCGGCA CTGGAGCCAA AGAGCCTCCG GGAGGCGCCC GGTTTACGTG 2340
TCGGGGGCGG CGGTTGCTGC TGACGTTGCT GCAGGTTCTG CTGCCTCTCC TCCCAAGCCT 2400
TCAGCTGCTG TTTCTCACGC TGCACCACCT CGTCGTCCAC CCGTTTCTGC CGCTCGCGAC 2460
GCTTTTCCTC TTCGTCGTAA TAGCCGACGC GCGCCGAACG GGCGGCGTGG GCGTCGGCGG 2520
CCGGTGCCAG AGAACCATGG GCCTCGAAGC GGAACGGTTT GTGTCCCTTC CAGGGACTGG 2580
CGATCCAGCT CCAGCCGTCC AGCGGCTGCG TGGGGACATG TTTCTTGGGT ACCGACGAGA 2640
AGGCTGAACC GCCGCCGAGC GAGAGGAGAT TGGCGTCATC GTCAAACTCC AACGACGGCG 2700
GGCGCGCGCC CAAAAAGGTG TGCGCCGACT GCGGGAAGCT GTCCACGTAG ATGTCAAAGT 2760
CCTCGATGAG CAGCTCCAGC AGCGTGTCGG CCGAGTCACC GTTTTCCACG GCGTGTTTGA 2820
GGATATTGCG ACAGTAGTTG GAATCAAAGG AAAGGCACAT GCGCAGCTCC TTGACCAGCA 2880
GCTTGCAGCG CTCCTGAATG CGCGCCAGAC ATTTGCGCTC CAGCTCCTCC CAAGACCTGC 2940
GCACGTTCAT GATGAGACGG CCCGTGTACA CGAGCTTGTT GACGGCGTTG ACCAGCGCCG 3000
TGTTGGCGTG CCGGTCCAGG TTAAGGTCGA GCGGTTTCAC GCAGAACATG TTACGGCGCA 3060
CACCCTCCAG GTTTTCTTCA ATGCGCTGCA CCTCCGTATC CTTGAGGTGC ACAAAAGCGA 3120
TGGGTTCCGT CTGGCCGATG GCTGTGACCA GCGTCTCGCG CACCGACATC TTGGCCAGAA 3180
TGACCGCGCT TACGAGCGCG CGCTCCACAA TCTCAGCATC GTGGCGTACG TCCGTATCGA 3240
ATTCGGTACG GTCTAGCACA GCCAGGTGGT CACGCGCCTT ACCACGATCA CCGAACGGGT 3300
AAGTGTAGCC GCGACGCGCC ACGGCCGCGC AACGCACCTC GAACTCCTCG AGAACCGAGG 3360
AGAGGTCGGG GTTGTGGAAA CGCAGCTCGC GGTAGTATCC CAACCAAAGC ATGAGCTCGT 3420
TGAACAGCAC CGTACGCCGG TGCAGGCGTT TTTCGCCACA TTTTTTCAGG ATCTTGGGGT 3480
GTGCCTCGAG ATCCACGTCG GGCTTTTGCG TGAGATGGCG CAGAAAGTTG ACCAGGGCCA 3540
CCACATCGCG CCGCTGTAGA CCGATAAACT GCAAACTCAT TTTATATTGT AATTATATAT 3600

-continued

```
TTTCAATTTT GAAATCCCAA AATATTATCA TATCTTCCCA ATAAAGCTAG GGGAGATCTA   3660

ATTTAATTTA ATTTATATAA CTTATTTTTT GAATATACTT TTAATTAACA AAAGAGTTAA   3720

GTTACTCATA TGGACGCCGT CCAGTCTGAA CATCAATCTT TTTAGCCAGA GATATCATAG   3780

CCGCTCTTAG AGTTTCAGCG TGATTTTCCA ACCTAAATAG AACTTCATCG TTGCGTTTAC   3840

AACACTTTTC TATTTGTTCA AACTTTGTTG TTACATTAGT AATCTTTTTT TCCAAATTAG   3900

TTAGCCGTTG TTTGAGAGTT TCCTCATTGT CGTCTTCATC GGCTTTAACA ATTGCTTCGC   3960

GTTTAGCCTC CTGGCTGTTC TTATCAGCCT TTGTAGAAAA AAATTCAGTT GCTGGAATTG   4020

CAAGATCGTC ATCTCCGGGG AAAAGAGTTC CGTCCATTTA AAGCCGCGGG AATTC        4075
```

(2) INFORMATION FOR SEQ ID NO:32:

(i) SEQUENCE CHARACTERISTICS:
(A) LENGTH: 4909 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:32:

```
GAGCTCGCGG CCGCCTATCA AAAGTCTTAA TGAGTTAGGT GTAGATAGTA TAGATATTAC     60

TACAAAGGTA TTCATATTTC CTATCAATTC TAAAGTAGAT GATATTAATA ACTCAAAGAT    120

GATGATAGTA GATAATAGAT ACGCTCATAT AATGACTGCA AATTTGGACG GTTCACATTT    180

TAATCATCAC GCGTTCATAA GTTTCAACTG CATAGATCAA AATCTCACTA AAAAGATAGC    240

CGATGTATTT GAGAGAGATT GGACATCTAA CTACGCTAAA GAAATTACAG TTATAAATAA    300

TACATAATGG ATTTTGTTAT CATCAGTTAT ATTTAACATA AGTACAATAA AAAGTATTAA    360

ATAAAAATAC TTACTTACGA AAAAATGACT AATTAGCTAT AAAAACCCGG GGGATCCTTA    420

ATTAATTAGT TATTAGACAA GGTGAAAACG AAACTATTTG TAGCTTAATT AATTAGCTGC    480

AGGGCTGCAG GAATTCTAGC AATAAAAACT ATTCCTCCGT GTTCTTAATC TTCTCGATCT    540

TTTGGAGGAT GTTCTGCACG GCGTCCGACG GCGTTTTGGC GCCCCCCATG CCGGCAGAAC    600

CCGGTTGCGG CCCCGTACCG CTCTTCTGGG GCGACGATAG GTCGAAAGCC ACCGTTTTCA    660

TGCCCGTCGT GCTCTTGACG GGGGAACCTA CGGCGGCGGT CCCCGTCGAG CGGCGTGATT    720

GCAAAGCCGC GCTCGCCCCC GGTTTCAGGA TGGAGGGGGA GGCCACAGGC GGCGCATTCG    780

ATACGCTGCT TTTGGCCGTA GACGACGGTG GGTAAACGGT GGTTACCGCG GGATACGTCG    840

GCGTGGTCGA GGCGGCCCGG CTGGTGCCGG ACAGGCGACC CGGCGCGCTA CCGCTCACGG    900

GTACCGAGGG CGGTCGACCT ACCACCGCCT TGCCGCCCAA AGTAGGTTTC AAAGAAGGAA    960

CACCGACGCG GCTGCCCCGA CCTTTCACCG GAGACGGAGG GGCACTCTTG GCCGGGGACG   1020

GAGAGGCTGA CGAAAGCATG GACAGCGGCG ACGTGACGGG GGACACGACA TCATCCTCCG   1080

TGGGCGACAA AACGGACGCC GAGGCTGACG GCTGTCGAGC CGAAGCGGAA GAGGTTCTCG   1140

CGCCAGAAGT CACGTTCCTT GATGACGTTG TTTTAGACGA AGCCGGTTGA GGTTGCAACA   1200

GCGTGGCGGG TACCGTCGAC GGCGTGCCCG ATACCTGTTT CTCTACCCTT CCCTGAACCG   1260

GTGTCGACGT CACCGTCTGC GCTCGGGCGG ACGCGTGCGG CGTCGCGACT CGCTTGCCCA   1320

GCACCGGTTT CTGGCTCGTG GATGTCGTCG TCATTGGAGA CGATAACTTA GCTTTACGTA   1380

TTCTGGACGG CGTCGACTGC TCGGGCGTCT GACTGGGAGG CGAAATGACG TCGTTGTAAT   1440

CGGACGACGG TGTTGTGTGT CCCAGGCTGA CGACGGAGCC GGTGTCCGAG GAGTCGTCGT   1500
```

-continued

```
CTTCCTCCTC GCTGTCTTCG ACCGGTGACT CTGCAGTTTG GTCCCTTAAA GCCCAAACCT   1560

CATCAGCGGC GTTCTGAGAC GCTGTTTGTG TCACCGCGGC GCGTGGAGTC GACGGCCTCC   1620

GAGGGGTGGT GGACACGTTG TTTTGAGAAG TCGTGGAAGT CGTAGGCATC CTGAAGGGAT   1680

TGTAAGCCAG GTGAGGATTC TTGAGGGCCC ACGCGCGTTC GCGCGGCCAG TTGGCGGGGT   1740

TCATATCCCC GGGCAACGGC GCCGTCGGAG CCCAGGGCGA GTTACCGTTG ACCGGGGTTT   1800

GGGTACCCGC GAAGGTAGGT GTCGGGGCCG GAGCGGGGGC CGTGGAAGGA TTGACAGGCG   1860

TCGGCGTGAG GATGGCAGCG CCGGCGCCAG CAGGGACGTT AACTCCGGCG CCGAACGTCA   1920

ACGTCGGTTG CTCGAACTTG TACGCGGTGG TGACGGGCGG TTTGGCGCTC GTCTCGGTAT   1980

CCGTGATGTC CACCAGCGTG TCGGTGAAAC GCGGATCTTG ACGGTTGGGG GGATAGCCAT   2040

CCGAGCTGTC GGAATCCTCG TCGCCCGAGA AAAGATCCCC TCTTGTCTCC GTGAGCGGCC   2100

TCACGTCCCA CGCGCTGTCC CGACGGACCC TTCCCGGGCT GGCCTTGGTT ACCTGCGGGG   2160

AGACGAGACT GAAAGCCGCG TGACGCTGTT GTTGCTGCGG GATGTTCAAG GGACCGCTGG   2220

TCGGTTTCTG ACTGCCCGAG GATAACATGC CGCTGAAAAT GCTGGAAACA CCGTTGCCAC   2280

TAGCGGCGCC CTTGCCGCTA GTTCCCGGTT TCTTGATGGG CGTAAAGATG TTTTTCTCGT   2340

CATCATCATC GTCGTCGTCC TCATCGGCAC TGGAGCCAAA GAGCCTCCGG GAGGCGCCCG   2400

GTTTACGTGT CGGGGGCGGC GGTTGCTGCT GACGTTGCTG CAGGTTCTGC TGCCTCTCCT   2460

CCCAAGCCTT CAGCTGCTGT TTCTCACGCT GCACCACCTC GTCGTCCACC CGTTTCTGCC   2520

GCTCGCGACG CTTTTCCTCT TCGTCGTAAT AGCCGACGCG CGCCGAACGG GCGGCGTGGG   2580

CGTCGGCGGC CGGTGCCAGA GAACCATGGG CCTCGAAGCG GAACGGTTTG TGTCCCTTCC   2640

AGGGACTGGC GATCCAGCTC CAGCCGTCCA GCGGCTGCGT GGGGACATGT TTCTTGGGTA   2700

CCGACGAGAA GGCTGAACCG CCGCCGAGCG AGAGGAGATT GGCGTCATCG TCAAACTCCA   2760

ACGACGGCGG GCGCGCGCCC AAAAAGGTGT GCGCCGACTG CGGGAAGCTG TCCACGTAGA   2820

TGTCAAAGTC CTCGATGAGC AGCTCCAGCA GCGTGTCGGC CGAGTCACCG TTTTCCACGG   2880

CGTGTTTGAG GATATTGCGA CAGTAGTTGG AATCAAAGGA AAGGCACATG CGCAGCTCCT   2940

TGACCAGCAG CTTGCAGCGC TCCTGAATGC GCGCCAGACA TTTGCGCTCC AGCTCCTCCC   3000

AAGACCTGCG CACGTTCATG ATGAGACGGC CCGTGTACAC GAGCTTGTTG ACGGCGTTGA   3060

CCAGCGCCGT GTTGGCGTGC CGGTCCAGGT TAAGGTCGAG CGGTTTCACG CAGAACATGT   3120

TACGGCGCAC ACCCTCCAGG TTTTCTTCAA TGCGCTGCAC CTCCGTATCC TTGAGGTGCA   3180

CAAAAGCGAT GGGTTCCGTC TGGCCGATGG CTGTGACCAG CGTCTCGCGC ACCGACATCT   3240

TGGCCAGAAT GACCGCGCTT ACGAGCGCGC GCTCCACAAT CTCAGCATCG TGGCGTACGT   3300

CCGTATCGAA TTCGGTACGG TCTAGCACAG CCAGGTGGTC ACGCGCCTTA CCACGATCAC   3360

CGAACGGGTA AGTGTAGCCG CGACGCGCCA CGGCCGCGCA ACGCACCTCG AACTCCTCGA   3420

GAACCGAGGA GAGGTCGGGG TTGTGGAAAC GCAGCTCGCG GTAGTATCCC AACCAAAGCA   3480

TGAGCTCGTT GAACAGCACC GTACGCCGGT GCAGGCGTTT TTCGCCACAT TTTTTCAGGA   3540

TCTTGGGGTG TGCCTCGAGA TCCACGTCGG GCTTTTGCGT GAGATGGCGC AGAAAGTTGA   3600

CCAGGGCCAC CACATCGCGC CGCTGTAGAC CGATAAACTG CAAACTCATT TTATATTGTA   3660

ATTATATATT TTCAATTTTG AAATCCCAAA ATATTATCAT ATCTTCCCAA TAAAGCTAGA   3720

TTCTTTTTAT TGATTAACTA GTCAAATGAG TATATATAAT TGAAAAAGTA AAATATAAAT   3780

CATATAATAA TGAAACGAAA TATCAGTAAT AGACAGGAAC TGGCAGATTC TTCTTCTAAT   3840

GAAGTAAGTA CTGCTAAATC TCCAAAATTA GATAAAAATG ATACAGCAAA TACAGCTTCA   3900
```

-continued

TTCAACGAAT TACCTTTTAA TTTTTTCAGA CACACCTTAT TACAAACTAA CTAAGTCAGA 3960

TGATGAGAAA GTAAATATAA ATTTAACTTA TGGGTATAAT ATAATAAAGA TTCATGATAT 4020

TAATAATTTA CTTAACGATG TTAATAGACT TATTCCATCA ACCCCTTCAA ACCTTTCTGG 4080

ATATTATAAA ATACCAGTTA ATGATATTAA AATAGATTGT TTAAGAGATG TAAATAATTA 4140

TTTGGAGGTA AAGGATATAA AATTAGTCTA TCTTTCACAT GGAAATGAAT TACCTAATAT 4200

TAATAATTAT GATAGGAATT TTTTAGGATT TACAGCTGTT ATATGTATCA ACAATACAGG 4260

CAGATCTATG GTTATGGTAA AACACTGTAA CGGGAAGCAG CATTCTATGG TAACTGGCCT 4320

ATGTTTAATA GCCAGATCAT TTTACTCTAT AAACATTTTA CCACAAATAA TAGGATCCTC 4380

TAGATATTTA ATATTATATC TAACAACAAC AAAAAAATTT AACGATGTAT GGCCAGAAGT 4440

ATTTTCTACT AATAAAGATA AAGATAGTCT ATCTTATCTA CAAGATATGA AAGAAGATAA 4500

TCATTTAGTA GTAGCTACTA ATATGGAAAG AAATGTATAC AAAAACGTGG AAGCTTTTAT 4560

ATTAAATAGC ATATTACTAG AAGATTTAAA ATCTAGACTT AGTATAACAA AACAGTTAAA 4620

TGCCAATATC GATTCTATAT TTCATCATAA CAGTAGTACA TTAATCAGTG ATATACTGAA 4680

ACGATCTACA GACTCAACTA TGCAAGGAAT AAGCAATATG CCAATTATGT CTAATATTTT 4740

AACTTTAGAA CTAAAACGTT CTACCAATAC TAAAAATAGG ATACGTGATA GGCTGTTAAA 4800

AGCTGCAATA AATAGTAAGG ATGTAGAAGA AATACTTTGT TCTATACCTT CGGAGGAAAG 4860

AACTTTAGAA CAACTTAAGT TTAATCAAAC TTGTATTTAT GAAGGTACC 4909

(2) INFORMATION FOR SEQ ID NO:33:

(i) SEQUENCE CHARACTERISTICS:
(A) LENGTH: 3567 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

AAGACTAATT TGTAAACCAT CTTACTCAAA ATATGTAACA ATAGTACGAT GCAATGAGTA 60

AGACAATAGG AAATCTATCT TATATACACA TAATTATTCT ATCAATTTTA CCAATTAGTT 120

AGTGTAATGT TATAAAAACT AATTAATCAC TCGAGCCCCT AGCAATAAAA ACTATTCCTC 180

CGTGTTCTTA ATCTTCTCGA TCTTTTGGAG GATGTTCTGC ACGGCGTCCG ACGGCGTTTT 240

GGCGCCCCCC ATGCCGGCAG AACCCGGTTG CGGCCCCGTA CCGCTCTTCT GGGGCGACGA 300

TAGGTCGAAA GCCACCGTTT TCATGCCCGT CGTGCTCTTG ACGGGGGAAC CTACGGCGGC 360

GGTCCCCGTC GAGCGGCGTG ATTGCAAAGC CGCGCTCGCC CCCGGTTTCA GGATGGAGGG 420

GGAGGCCACA GGCGGCGCAT TCGATACGCT GCTTTTGGCC GTAGACGACG GTGGGTAAAC 480

GGTGGTTACC GCGGGATACG TCGGCGTGGT CGAGGCGGCC CGGCTGGTGC CGGACAGGCG 540

ACCCGGCGCG CTACCGCTCA CGGGTACCGA GGGCGGTCGA CCTACCACCG CCTTGCCGCC 600

CAAAGTAGGT TTCAAAGAAG GAACACCGAC GCGGCTGCCC CGACCTTTCA CCGGAGACGG 660

AGGGGCACTC TTGGCCGGGG ACGGAGAGGC TGACGAAAGC ATGGACAGCG GCGACGTGAC 720

GGGGGACACG ACATCATCCT CCGTGGGCGA CAAAACGGAC GCCGAGGCTG ACGGCTGTCG 780

AGCCGAAGCG GAAGAGGTTC TCGCGCCAGA AGTCACGTTC CTTGATGACG TTGTTTTAGA 840

CGAAGCCGGT TGAGGTTGCA ACAGCGTGGC GGGTACCGTC GACGGCGTGC CCGATACCTG 900

TTTCTCTACC CTTCCCTGAA CCGGTGTCGA CGTCACCGTC TGCGCTCGGG CGGACGCGTG 960

-continued

CGGCGTCGCG ACTCGCTTGC CCAGCACCGG TTTCTGGCTC GTGGATGTCG TCGTCATTGG 1020
AGACGATAAC TTAGCTTTAC GTATTCTGGA CGGCGTCGAC TGCTCGGGCG TCTGACTGGG 1080
AGGCGAAATG ACGTCGTTGT AATCGGACGA CGGTGTTGTG TGTCCCAGGC TGACGACGGA 1140
GCCGGTGTCC GAGGAGTCGT CGTCTTCCTC CTCGCTGTCT TCGACCGGTG ACTCTGCAGT 1200
TTGGTCCCTT AAAGCCCAAA CCTCATCAGC GGCGTTCTGA GACGCTGTTT GTGTCACCGC 1260
GGCGCGTGGA GTCGACGGCC TCCGAGGGGT GGTGGACACG TTGTTTTGAG AAGTCGTGGA 1320
AGTCGTAGGC ATCCTGAAGG GATTGTAAGC CAGGTGAGGA TTCTTGAGGG CCCACGCGCG 1380
TTCGCGCGGC CAGTTGGCGG GGTTCATATC CCCGGGCAAC GGCGCCGTCG GAGCCCAGGG 1440
CGAGTTACCG TTGACCGGGG TTTGGGTACC CGCGAAGGTA GGTGTCGGGG CCGGAGCGGG 1500
GGCCGTGGAA GGATTGACAG GCGTCGGCGT GAGGATGGCA GCGCCGGCGC CAGCAGGGAC 1560
GTTAACTCCG GCGCCGAACG TCAACGTCGG TTGCTCGAAC TTGTACGCGG TGGTGACGGG 1620
CGGTTTGGCG CTCGTCTCGG TATCCGTGAT GTCCACCAGC GTGTCGGTGA AACGCGGATC 1680
TTGACGGTTG GGGGGATAGC CATCCGAGCT GTCGGAATCC TCGTCGCCCG AGAAAAGATC 1740
CCCTCTTGTC TCCGTGAGCG GCCTCACGTC CCACGCGCTG TCCCGACGGA CCCTTCCCGG 1800
GCTGGCCTTG GTTACCTGCG GGGAGACGAG ACTGAAAGCC GCGTGACGCT GTTGTTGCTG 1860
CGGGATGTTC AAGGGACCGC TGGTCGGTTT CTGACTGCCC GAGGATAACA TGCCGCTGAA 1920
AATGCTGGAA ACACCGTTGC CACTAGCGGC GCCCTTGCCG CTAGTTCCCG GTTTCTTGAT 1980
GGGCGTAAAG ATGTTTTTCT CGTCATCATC ATCGTCGTCG TCCTCATCGG CACTGGAGCC 2040
AAAGAGCCTC CGGGAGGCGC CCGGTTTACG TGTCGGGGGC GGCGGTTGCT GCTGACGTTG 2100
CTGCAGGTTC TGCTGCCTCT CCTCCCAAGC CTTCAGCTGC TGTTTCTCAC GCTGCACCAC 2160
CTCGTCGTCC ACCCGTTTCT GCCGCTCGCG ACGCTTTTCC TCTTCGTCGT AATAGCCGAC 2220
GCGCGCCGAA CGGGCGGCGT GGGCGTCGGC GGCCGGTGCC AGAGAACCAT GGGCCTCGAA 2280
GCGGAACGGT TTGTGTCCCT TCCAGGGACT GGCGATCCAG CTCCAGCCGT CCAGCGGCTG 2340
CGTGGGGACA TGTTTCTTGG GTACCGACGA GAAGGCTGAA CCGCCGCCGA GCGAGAGGAG 2400
ATTGGCGTCA TCGTCAAACT CCAACGACGG CGGGCGCGCG CCCAAAAAGG TGTGCGCCGA 2460
CTGCGGGAAG CTGTCCACGT AGATGTCAAA GTCCTCGATG AGCAGCTCCA GCAGCGTGTC 2520
GGCCGAGTCA CCGTTTTCCA CGGCGTGTTT GAGGATATTG CGACAGTAGT TGGAATCAAA 2580
GGAAAGGCAC ATGCGCAGCT CCTTGACCAG CAGCTTGCAG CGCTCCTGAA TGCGCGCCAG 2640
ACATTTGCGC TCCAGCTCCT CCCAAGACCT GCGCACGTTC ATGATGAGAC GGCCCGTGTA 2700
CACGAGCTTG TTGACGGCGT TGACCAGCGC CGTGTTGGCG TGCCGGTCCA GGTTAAGGTC 2760
GAGCGGTTTC ACGCAGAACA TGTTACGGCG CACACCCTCC AGGTTTTCTT CAATGCGCTG 2820
CACCTCCGTA TCCTTGAGGT GCACAAAAGC GATGGGTTCC GTCTGGCCGA TGGCTGTGAC 2880
CAGCGTCTCG CGCACCGACA TCTTGGCCAG AATGACCGCG CTTACGAGCG CGCGCTCCAC 2940
AATCTCAGCA TCGTGGCGTA CGTCCGTATC GAATTCGGTA CGGTCTAGCA CAGCCAGGTG 3000
GTCACGCGCC TTACCACGAT CACCGAACGG GTAAGTGTAG CCGCGACGCG CCACGGCCGC 3060
GCAACGCACC TCGAACTCCT CGAGAACCGA GGAGAGGTCG GGGTTGTGGA AACGCAGCTC 3120
GCGGTAGTAT CCCAACCAAA GCATGAGCTC GTTGAACAGC ACCGTACGCC GGTGCAGGCG 3180
TTTTTCGCCA CATTTTTTCA GGATCTTGGG GTGTGCCTCG AGATCCACGT CGGGCTTTTG 3240
CGTGAGATGG CGCAGAAAGT TGACCAGGGC CACCACATCG CGCCGCTGTA GACCGATAAA 3300

-continued

```
CTGCAAACTC ATTTTATATT GTAATTATAT ATTTTCAATT TTGAAATCCC AAAATATTAT   3360

CATATCTTCC CAATAAAGCT AGGGGGAATT CGGATCCTCG CGACTGCAGG GTACCTGAGT   3420

AGCTAATTTT TAAACAAAAA TGTGGGAGAA TCTAATTAGT TTTTCTTTAC ACAATTGACG   3480

TACATGAGTC TGAGTTCCTT GTTTTTGCTA ATTATTTCAT CCAATTTATT ATTCTTGACG   3540

ATATCGAGAT CTTTTGTATA GGAGTCA                                       3567
```

(2) INFORMATION FOR SEQ ID NO:34:

(i) SEQUENCE CHARACTERISTICS:
(A) LENGTH: 4893 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

```
CTGCAGGTCG ACGGATCTGA GAATGGATGA TTCTCCAGCC GAAACATATT CTACCATGGC     60

TCCGTTTAAT TTGTTGATGA AGATGGATTC ATCCTTAAAT GTTTTCTCTG TAATAGTTTC    120

CACCGAAAGA CTATGCAAAG AATTTGGAAT GCGTTCCTTG TGCTTAATGT TTCCATAGAC    180

GGCTTCTAGA AGTTGATACA ACATAGGACT AGCCGCGGTA ACTTTTATTT TTAGAAAGTA    240

TCCATCGCTT CTATCTTGTT TAGATTTATT TTTATAAAGT TTAGTCTCTC CTTCCAACAT    300

AATAAAAGTG GAAGTCATTT GACTAGATAA ACTATCAGTA AGTTTTATAG AGATAGACGA    360

ACAATTAGCG TATTGAGAAG CATTTAGTGT AACGTATTCG ATACATTTTG CATTAGATTT    420

ACTAATCGAT TTTGCATACT CTATAACACC CGCACAAGTC TGTAGAGAAT CGCTAGATGC    480

AGTAGGTCTT GGTGAAGTTT CAACTCTCTT CTTGATTACC TTACTCATGA TTAAACCTAA    540

ATAATTGTAC TTTGTAATAT AATGATATAT ATTTTCACTT TATCTCATTT GAGAATAAAA    600

AGATCACAAA AATTAACTAA TCAGGATCTC GAGATAAAAA TCAGCATGTC TTGAGCATGC    660

GGTAGAGCAG ATAGATGCCG ATGATGGCCG ATAGCGCGTA GACGGACATC ATGAGGAGAC    720

GACTGTCGGT AGCGTCCACG ACGACGTCAG TTACTTCTAG GACCGTACCG TTTTTCAAAA    780

GCATGAGGTA GTGAGTTCGC GGAGATGAGA CCACCACTTC GTTGTAGGGA TCCAGGGCGA    840

AAAGGACGTC GTCCGAGTCG TGCATGTACA TGATGTTGAT GACGCCTTGC GTGTCGTCGT    900

ATTCTAGTAG GGCGCTTTGG CAAAAGGCGC AGTTTTCTAG GGAAATGTTG AGCGCCGCTG    960

TGATGCTGTG TGTGGTATGC ATGTTGCGCG TCAGTTCGCA TTTAGTTTGA CTGTCCGTCT   1020

GGGTGATGAT GAGGCTCTGG CCTACGACGG TGGTGGAGAC AGGGTAGGAG ATACCTTTGA   1080

TCAGGTACTG GTTTGTTACG ACATAACTGA CGTGTTCGGA GACGGTCAGC GCGGAGAAGG   1140

ATTCGCCGAG CGGCAGACAA AACAGGTCGG GGAAGGTTTC TAGCGTGCTT GGTTGCATGG   1200

TAGATAGGAT GGAGAGGGCG GCGGGAACGG TAGTGGGGAC GGTGGCATCG GGGAAGAGAC   1260

GTGTGAGGCG TTCGAGCGAG TGATCGCGTC GCCCGCTACT GGAACAGGGT GTGTACAGGT   1320

CGCTGAGGTA TTCGTGGTGC GGATGAGCTA GCAACTGCGT AAAGTGTGAT AGCTCGGCTA   1380

ATGAACAGAG GCCCGTTTCT ACGATGAAGA TTTCGCGTCT CTCCGTCGTA TGTACTAGCA   1440

TGGAGTGGAC GAGGCTGCCC ATGAGGTAGA GTTCTTGACG CGCGAAGGCT GAAAGAAAAG   1500

AGGCCAGGTG CGTTTTGTGT AGTTTTAGGG CAAAGTCGGC GATCTGTCGT AGTGCCCACT   1560

GGGGGATGAG ATGTTGCTGA TTCTGTTTAG AGAGTATGTA GACCAGGCGT ACGAGGCTGG   1620

TGATGTCGGT GATCTGATTC GGTGTCCAAA GGGCTCGTTT GGCCAGGTCC ACGGCCGTGG   1680
```

-continued

```
GATACAGCAG CAACGTGGTG CGTGGTGGTG TTTGTGAGAG GCAGGTGATC ATAAATTCTT   1740

GTATTTGTAA GAGTGCGGCC TGGCGGTCTA GGGCCCGTGG GACGGAGACT TGGGCGCCGG   1800

CCTCTTCTTG TCGGGCTGCT GCGAACAGTG CTAATGCGTA GGCGAAGGCC ATTTCTACCG   1860

TGCGGCGGTC CAGCATCTGA CATCGACCGC TTTTGAGTAC ATCCACGGCG TAACGGTGAA   1920

AGCTGTTACG TAGTAGTGCG CTGAGGTCCA GGTAGTTGAA GTCAAGTGCG GCGTCAAGAA   1980

AGTCCGGGTC TTTGAGATAA GAGTGACGGT TCAGTTGATC TTTCTTAACT AGCACCAGGA   2040

GCTCGTGTTT TTCAGTTTGT CGTAGTATAA AGTTGTCGCG TTGATAGGGC GCTTTAAAGA   2100

GTACGCGTGG AAGATGGCCG AAGATAAGCA GCATGGGTGT GTCGTCGTCT ATGGACACCG   2160

TAACTACGAA GAAGTCCTCG GTCAGTGTTA TTTTAACGTA ACGTAGTTCG TCGATGAGGT   2220

AAAAGCCTTG GTGCAAACAA GGTGTGACGG TGCTGAATAG TAGATCGTGT CCATCAAAGA   2280

GGATACAGGT CTGGTTAAAG TGTGGTCGGT GTAGTCCTGA GGTGGTATGT GATTCTGTCC   2340

AGCCGTGTGG AGTGGTTTGC GGTGGCATCC AAACGTGAGG TATTGACAGG TCAATGGGTG   2400

GTGGCACAGT GGTGGGCTGT TCACCTAGGC TGTCCTGTGC CTTTAGCTGC TGCGAAAAAG   2460

ATCGGTAGCT GGCCAGGTCT TTGGATACCA GCGCGTAAGT GTTAAGTCTC TGTTGGTATC   2520

TTTCCAGGGT TTCGGTCAGA TCTACCTGGT TCAGAAACTG CTCCGCCAGA GGACCCGCAA   2580

AAAGACATCG AGGCATATGG AATACATAGT ATTGATTATA GCTTTGGAAA AAGTTGAAAC   2640

TGATGGCGTT TTCCCTGACG ACCGTGCTGT TACGGAGGCT GCTATTGTAG GTACACTGGG   2700

TGGTGTTTTC ACGCAGGAAG CGGATGGGTC TCCCGTAGGT GTTGAGCAGT AGGTGAAACG   2760

CTTTGTCCAG CGGTTCGGAT ATGGCTTCTG CGCCATATCG TGACGAAAGT AGGTGGCTGA   2820

GGAGACAGAC GGCGAGGACG ATGAGGTAGG AGGGGAGCCC GGGCCGCATT TTATATTGTA   2880

ATTATATATT TTCAATTTTG AAATCCCAAA ATATTATCAT ATTCTTCCCA ATAAACTCGA   2940

GATCCTTCTT TATTCTATAC TTAAAAAGTG AAAATAAATA CAAAGGTTCT TGAGGGTTGT   3000

GTTAAATTGA AAGCGAGAAA TAATCATAAA TTATTTCATT ATCGCGATAT CCGTTAAGTT   3060

TGTATCGTAA TGAAACAGAT TAAGGTTCGA GTGGACATGG TGCGGCATAG AATCAAGGAG   3120

CACATGCTGA AAAAATATAC CCAGACGGAA GAGAAATTCA CTGGCGCCTT TAATATGATG   3180

GGAGGATGTT TGCAGAATGC CTTAGATATC TTAGATAAGG TTCATGAGCC TTTCGAGGAG   3240

ATGAAGTGTA TTGGGCTAAC TATGCAGAGC ATGTATGAGA ACTACATTGT ACCTGAGGAT   3300

AAGCGGGAGA TGTGGATGGC TTGTATTAAG GAGCTGCATG ATGTGAGCAA GGGCGCCGCT   3360

AACAAGTTGG GGGGTGCACT GCAGGCTAAG GCCCGTGCTA AAAAGGATGA ACTTAGGAGA   3420

AAGATGATGT ATATGTGCTA CAGGAATATA GAGTTCTTTA CCAAGAACTC AGCCTTCCCT   3480

AAGACCACCA ATGGCTGCAG TCAGGCCATG GCGGCACTGC AGAACTTGCC TCAGTGCTCC   3540

CCTGATGAGA TTATGGCTTA TGCCCAGAAA ATATTTAAGA TTTTGGATGA GGAGAGAGAC   3600

AAGGTGCTCA CGCACATTGA TCACATATTT ATGGATATCC TCACTACATG TGTGGAAACA   3660

ATGTGTAATG AGTACAAGGT CACTAGTGAC GCTTGTATGA TGACCATGTA CGGGGGCATC   3720

TCTCTCTTAA GTGAGTTCTG TCGGGTGCTG TGCTGCTATG TCTTAGAGGA GACTAGTGTG   3780

ATGCTGGCCA AGCGGCCTCT GATAACCAAG CCTGAGGTTA TCAGTGTAAT GAAGCGCCGC   3840

ATTGAGGAGA TCTGCATGAA GGTCTTTGCC CAGTACATTC TGGGGGCCGA TCCTCTGAGA   3900

GTCTGCTCTC CTAGTGTGGA TGACCTACGG GCCATCGCCG AGGAGTCAGA TGAGGAAGAG   3960

GCTATTGTAG CCTACACTTT GGCCACCGCT GGTGTCAGCT CCTCTGATTC TCTGGTGTCA   4020

CCCCCAGAGT CCCCTGTACC CGCGACTATC CCTCTGTCCT CAGTAATTGT GGCTGAGAAC   4080
```

-continued

AGTGATCAGG AAGAAAGTGA GCAGAGTGAT GAGGAAGAGG AGGAGGGTGC TCAGGAGGAG 4140

CGGGAGGACA CTGTGTCTGT CAAGTCTGAG CCAGTGTCTG AGATAGAGGA AGTTGCCCCA 4200

GAGGAAGAGG AGGATGGTGC TGAGGAACCC ACCGCCTCTG GAGGTAAGAG TACCCACCCT 4260

ATGGTGACTA GAAGCAAGGC TGACCAGTAA TTTTTATCTC GAGCCCGGGA GATCTTAGCT 4320

AACTGATTTT TCTGGGAAAA AAATTATTTA ACTTTTCATT AATAGGGATT TGACGTATGT 4380

AGCGTACAAA ATTATCGTTC CTGGTATATA GATAAAGAGT CCTATATATT TGAAAATCGT 4440

TACGGCTCGA TTAAACTTTA ATGATTGCAT AGTGAATATA TCATTAGGAT TTAACTCCTT 4500

GACTATCATG GCGGCGCCAG AAATTACCAT CAAAAGCATT AATACAGTTA TGCCGATCGC 4560

AGTTAGAACG GTTATAGCAT CCACCATTTA TATCTAAAAA TTAGATCAAA GAATATGTGA 4620

CAAAGTCCTA GTTGTATACT GAGAATTGAC GAAACAATGT TTCTTACATA TTTTTTTCTT 4680

ATTAGTAACT GACTTAATAG TAGGAACTGG AAAGCTAGAC TTGATTATTC TATAAGTATA 4740

GATACCCTTC CAGATAATGT TCTCTTTGAT AAAAGTTCCA GAAAATGTAG AATTTTTTAA 4800

AAAGTTATCT TTTGCTATTA CCAAGATTGT GTTTAGACGC TTATTATTAA TATGAGTAAT 4860

GAAATCCACA CCGCCTCTAG ATATGGGGAA TTC 4893

(2) INFORMATION FOR SEQ ID NO:35:

(i) SEQUENCE CHARACTERISTICS:
(A) LENGTH: 6749 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

GAGCTCGCGG CCGCCTATCA AAAGTCTTAA TGAGTTAGGT GTAGATAGTA TAGATATTAC 60

TACAAAGGTA TTCATATTTC CTATCAATTC TAAAGTAGAT GATATTAATA ACTCAAAGAT 120

GATGATAGTA GATAATAGAT ACGCTCATAT AATGACTGCA AATTTGGACG GTTCACATTT 180

TAATCATCAC GCGTTCATAA GTTTCAACTG CATAGATCAA AATCTCACTA AAAAGATAGC 240

CGATGTATTT GAGAGAGATT GGACATCTAA CTACGCTAAA GAAATTACAG TTATAAATAA 300

TACATAATGG ATTTTGTTAT CATCAGTTAT ATTTAACATA AGTACAATAA AAAGTATTAA 360

ATAAAAATAC TTACTTACGA AAAAATGACT AATTAGCTAT AAAAACCCAA CAAAAACTAA 420

TCAGCTATCG GGGTTAATTA ATTAGTTATT AGACAAGGTG AAAACGAAAC TATTTGTAGC 480

TTAATTAATT AGAGCTTCTT TATTCTATAC TTAAAAAGTG AAAATAAATA CAAAGGTTCT 540

TGAGGGTTGT GTTAAATTGA AAGCGAGAAA TAATCATAAA TTATTTCATT ATGGCGATAT 600

CCGTTAAGTT TGTATCGTAA TGGAGTCGCG CGGTCGCCGT TGTCCCGAAA TGATATCCGT 660

ACTGGGTCCC ATTTCGGGGC ACGTGCTGAA AGCCGTGTTT AGTCGCGGCG ACACGCCGGT 720

GCTGCCGCAC GAGACGCGAC TCCTGCAGAC GGGTATCCAC GTGCGCGTGA GCCAGCCCTC 780

GCTGATCCTG GTGTCGCAGT ACACGCCCGA CTCGACGCCA TGCCACCGCG GCGACAATCA 840

GCTGCAGGTG CAGCACACGT ACTTTACGGG CAGCGAGGTG GAGAACGTGT CGGTCAACGT 900

GCACAACCCC ACGGGCCGGA GCATCTGCCC CAGCCAAGAG CCCATGTCGA TCTATGTGTA 960

CGCGCTGCCG CTCAAGATGC TGAACATCCC CAGCATCAAC GTGCACCACT ACCCGTCGGC 1020

GGCCGAGCGC AAACACCGAC ACCTGCCCGT AGCTGACGCT GTGATTCACG CGTCGGGCAA 1080

GCAGATGTGG CAGGCGCGTC TCACGGTCTC GGGACTGGCC TGGACGCGTC AGCAGAACCA 1140

-continued

GTGGAAAGAG CCCGACGTCT ACTACACGTC AGCGTTCGTG TTTCCCACCA AGGACGTGGC 1200

ACTGCGGCAC GTGGTGTGCG CGCACGAGCT GGTTTGCTCC ATGGAGAACA CGCGCGCAAC 1260

CAAGATGCAG GTGATAGGTG ACCAGTACGT CAAGGTGTAC CTGGAGTCCT TCTGCGAGGA 1320

CGTGCCCTCC GGCAAGCTCT TTATGCACGT CACGCTGGGC TCTGACGTGG AAGAGGACCT 1380

GACGATGACC CGCAACCCGC AACCCTTCAT GCGCCCCCAC GAGCGCAACG GCTTTACGGT 1440

GTTGTGTCCC AAAAATATGA TAATCAAACC GGGCAAGATC TCGCACATCA TGCTGGATGT 1500

GGCTTTTACC TCACACGAGC ATTTTGGGCT GCTGTGTCCC AAGAGCATCC CGGGCCTGAG 1560

CATCTCAGGT AACCTATTGA TGAACGGGCA GCAGATCTTC CTGGAGGTGC AAGCGATACG 1620

CGAGACCGTG GAACTGCGTC AGTACGATCC CGTGGCTGCG CTCTTCTTTT TCGATATCGA 1680

CTTGCTGCTG CAGCGCGGGC CTCAGTACAG CGAACACCCC ACCTTCACCA GCCAGTATCG 1740

CATCCAGGGC AAGCTTGAGT ACCGACACAC CTGGGACCGG CACGACGAGG GTGCCGCCCA 1800

GGGCGACGAC GACGTCTGGA CCAGCGGATC GGACTCCGAC GAGGAACTCG TAACCACCGA 1860

GCGCAAGACG CCCCGCGTTA CCGGCGGCGG CGCCATGGCG GGCGCCTCCA CTTCCGCGGG 1920

CCGCAAACGC AAATCAGCAT CCTCGGCGAC GGCGTGCACG GCGGGCGTTA TGACACGCGG 1980

CCGCCTTAAG GCCGAGTCCA CCGTCGCGCC CGAAGAGGAC ACCGACGAGG ATTCCGACAA 2040

CGAAATCCAC AATCCGGCCG TGTTCACCTG GCCGCCCTGG CAGGCCGGCA TCCTGGCCCG 2100

CAACCTGGTG CCCATGGTGG CTACGGTTCA GGGTCAGAAT CTGAAGTACC AGGAGTTCTT 2160

CTGGGACGCC AACGACATCT ACCGCATCTT CGCCGAATTG GAAGGCGTAT GGCAGCCCGC 2220

TGCGCAACCC AAACGTCGCC GCCACCGGCA AGACGCCTTG CCCGGGCCAT GCATCGCCTC 2280

GACGCCCAAA AAGCACCGAG GTTGATTTTT ATGGATCCGG TACCCTCGAG GAATTCTAGC 2340

AATAAAAACT ATTCCTCCGT GTTCTTAATC TTCTCGATCT TTTGGAGGAT GTTCTGCACG 2400

GCGTCCGACG GCGTTTTGGC GCCCCCCATG CCGGCAGAAC CCGGTTGCGG CCCCGTACCG 2460

CTCTTCTGGG GCGACGATAG GTCGAAAGCC ACCGTTTTCA TGCCCGTCGT GCTCTTGACG 2520

GGGGAACCTA CGGCGGCGGT CCCCGTCGAG CGGCGTGATT GCAAAGCCGC GCTCGCCCCC 2580

GGTTTCAGGA TGGAGGGGGA GGCCACAGGC GGCGCATTCG ATACGCTGCT TTTGGCCGTA 2640

GACGACGGTG GGTAAACGGT GGTTACCGCG GGATACGTCG GCGTGGTCGA GGCGGCCCGG 2700

CTGGTGCCGG ACAGGCGACC CGGCGCGCTA CCGCTCACGG GTACCGAGGG CGGTCGACCT 2760

ACCACCGCCT TGCCGCCCAA AGTAGGTTTC AAAGAAGGAA CACCGACGCG GCTGCCCCGA 2820

CCTTTCACCG GAGACGGAGG GGCACTCTTG GCCGGGGACG GAGAGGCTGA CGAAAGCATG 2880

GACAGCGGCG ACGTGACGGG GGACACGACA TCATCCTCCG TGGGCGACAA AACGGACGCC 2940

GAGGCTGACG GCTGTCGAGC CGAAGCGGAA GAGGTTCTCG CGCCAGAAGT CACGTTCCTT 3000

GATGACGTTG TTTTAGACGA AGCCGGTTGA GGTTGCAACA GCGTGGCGGG TACCGTCGAC 3060

GGCGTGCCCG ATACCTGTTT CTCTACCCTT CCCTGAACCG GTGTCGACGT CACCGTCTGC 3120

GCTCGGGCGG ACGCGTGCGG CGTCGCGACT CGCTTGCCCA GCACCGGTTT CTGGCTCGTG 3180

GATGTCGTCG TCATTGGAGA CGATAACTTA GCTTTACGTA TTCTGGACGG CGTCGACTGC 3240

TCGGGCGTCT GACTGGGAGG CGAAATGACG TCGTTGTAAT CGGACGACGG TGTTGTGTGT 3300

CCCAGGCTGA CGACGGAGCC GGTGTCCGAG GAGTCGTCGT CTTCCTCCTC GCTGTCTTCG 3360

ACCGGTGACT CTGCAGTTTG GTCCCTTAAA GCCCAAACCT CATCAGCGGC GTTCTGAGAC 3420

GCTGTTTGTG TCACCGCGGC GCGTGGAGTC GACGGCCTCC GAGGGGTGGT GGACACGTTG 3480

-continued

```
TTTTGAGAAG TCGTGGAAGT CGTAGGCATC CTGAAGGGAT TGTAAGCCAG GTGAGGATTC   3540
TTGAGGGCCC ACGCGCGTTC GCGCGGCCAG TTGGCGGGGT TCATATCCCC GGGCAACGGC   3600
GCCGTCGGAG CCCAGGGCGA GTTACCGTTG ACCGGGGTTT GGGTACCCGC GAAGGTAGGT   3660
GTCGGGGCCG GAGCGGGGGC CGTGGAAGGA TTGACAGGCG TCGGCGTGAG GATGGCAGCG   3720
CCGGCGCCAG CAGGGACGTT AACTCCGGCG CCGAACGTCA ACGTCGGTTG CTCGAACTTG   3780
TACGCGGTGG TGACGGGCGG TTTGGCGCTC GTCTCGGTAT CCGTGATGTC CACCAGCGTG   3840
TCGGTGAAAC GCGGATCTTG ACGGTTGGGG GGATAGCCAT CCGAGCTGTC GGAATCCTCG   3900
TCGCCCGAGA AAAGATCCCC TCTTGTCTCC GTGAGCGGCC TCACGTCCCA CGCGCTGTCC   3960
CGACGGACCC TTCCCGGGCT GGCCTTGGTT ACCTGCGGGG AGACGAGACT GAAAGCCGCG   4020
TGACGCTGTT GTTGCTGCGG GATGTTCAAG GGACCGCTGG TCGGTTTCTG ACTGCCCGAG   4080
GATAACATGC CGCTGAAAAT GCTGGAAACA CCGTTGCCAC TAGCGGCGCC CTTGCCGCTA   4140
GTTCCCGGTT TCTTGATGGG CGTAAAGATG TTTTTCTCGT CATCATCATC GTCGTCGTCC   4200
TCATCGGCAC TGGAGCCAAA GAGCCTCCGG GAGGCGCCCG GTTTACGTGT CGGGGGCGGC   4260
GGTTGCTGCT GACGTTGCTG CAGGTTCTGC TGCCTCTCCT CCCAAGCCTT CAGCTGCTGT   4320
TTCTCACGCT GCACCACCTC GTCGTCCACC CGTTTCTGCC GCTCGCGACG CTTTTCCTCT   4380
TCGTCGTAAT AGCCGACGCG CGCCGAACGG GCGGCGTGGG CGTCGGCGGC CGGTGCCAGA   4440
GAACCATGGG CCTCGAAGCG GAACGGTTTG TGTCCCTTCC AGGGACTGGC GATCCAGCTC   4500
CAGCCGTCCA GCGGCTGCGT GGGGACATGT TTCTTGGGTA CCGACGAGAA GGCTGAACCG   4560
CCGCCGAGCG AGAGGAGATT GGCGTCATCG TCAAACTCCA ACGACGGCGG GCGCGCGCCC   4620
AAAAAGGTGT GCGCCGACTG CGGGAAGCTG TCCACGTAGA TGTCAAAGTC CTCGATGAGC   4680
AGCTCCAGCA GCGTGTCGGC CGAGTCACCG TTTTCCACGG CGTGTTTGAG GATATTGCGA   4740
CAGTAGTTGG AATCAAAGGA AAGGCACATG CGCAGCTCCT TGACCAGCAG CTTGCAGCGC   4800
TCCTGAATGC GCGCCAGACA TTTGCGCTCC AGCTCCTCCC AAGACCTGCG CACGTTCATG   4860
ATGAGACGGC CCGTGTACAC GAGCTTGTTG ACGGCGTTGA CCAGCGCCGT GTTGGCGTGC   4920
CGGTCCAGGT TAAGGTCGAG CGGTTTCACG CAGAACATGT TACGGCGCAC ACCCTCCAGG   4980
TTTTCTTCAA TGCGCTGCAC CTCCGTATCC TTGAGGTGCA CAAAAGCGAT GGGTTCCGTC   5040
TGGCCGATGG CTGTGACCAG CGTCTCGCGC ACCGACATCT TGGCCAGAAT GACCGCGCTT   5100
ACGAGCGCGC GCTCCACAAT CTCAGCATCG TGGCGTACGT CCGTATCGAA TTCGGTACGG   5160
TCTAGCACAG CCAGGTGGTC ACGCGCCTTA CCACGATCAC CGAACGGGTA AGTGTAGCCG   5220
CGACGCGCCA CGGCCGCGCA ACGCACCTCG AACTCCTCGA GAACCGAGGA GAGGTCGGGG   5280
TTGTGGAAAC GCAGCTCGCG GTAGTATCCC AACCAAAGCA TGAGCTCGTT GAACAGCACC   5340
GTACGCCGGT GCAGGCGTTT TTCGCCACAT TTTTTCAGGA TCTTGGGGTG TGCCTCGAGA   5400
TCCACGTCGG GCTTTTGCGT GAGATGGCGC AGAAAGTTGA CCAGGGCCAC CACATCGCGC   5460
CGCTGTAGAC CGATAAACTG CAAACTCATT TTATATTGTA ATTATATATT TTCAATTTTG   5520
AAATCCCAAA ATATTATCAT ATCTTCCCAA TAAAGCTAGA ATTCTTTTTA TTGATTAACT   5580
AGTCAAATGA GTATATATAA TTGAAAAAGT AAAATATAAA TCATATAATA ATGAAACGAA   5640
ATATCAGTAA TAGACAGGAA CTGGCAGATT CTTCTTCTAA TGAAGTAAGT ACTGCTAAAT   5700
CTCCAAAATT AGATAAAAAT GATACAGCAA ATACAGCTTC ATTCAACGAA TTACCTTTTA   5760
ATTTTTTCAG ACACACCTTA TTACAAACTA ACTAAGTCAG ATGATGAGAA AGTAAATATA   5820
AATTTAACTT ATGGGTATAA TATAATAAAG ATTCATGATA TTAATAATTT ACTTAACGAT   5880
```

-continued

```
GTTAATAGAC TTATTCCATC AACCCCTTCA AACCTTTCTG GATATTATAA AATACCAGTT   5940

AATGATATTA AAATAGATTG TTTAAGAGAT GTAAATAATT ATTTGGAGGT AAAGGATATA   6000

AAATTAGTCT ATCTTTCACA TGGAAATGAA TTACCTAATA TTAATAATTA TGATAGGAAT   6060

TTTTTAGGAT TTACAGCTGT TATATGTATC AACAATACAG GCAGATCTAT GGTTATGGTA   6120

AAACACTGTA ACGGGAAGCA GCATTCTATG GTAACTGGCC TATGTTTAAT AGCCAGATCA   6180

TTTTACTCTA TAAACATTTT ACCACAAATA ATAGGATCCT CTAGATATTT AATATTATAT   6240

CTAACAACAA CAAAAAAATT TAACGATGTA TGGCCAGAAG TATTTTCTAC TAATAAAGAT   6300

AAAGATAGTC TATCTTATCT ACAAGATATG AAAGAAGATA ATCATTTAGT AGTAGCTACT   6360

AATATGGAAA GAAATGTATA CAAAAACGTG GAAGCTTTTA TATTAAATAG CATATTACTA   6420

GAAGATTTAA AATCTAGACT TAGTATAACA AAACAGTTAA ATGCCAATAT CGATTCTATA   6480

TTTCATCATA ACAGTAGTAC ATTAATCAGT GATATACTGA AACGATCTAC AGACTCAACT   6540

ATGCAAGGAA TAAGCAATAT GCCAATTATG TCTAATATTT TAACTTTAGA ACTAAAACGT   6600

TCTACCAATA CTAAAAATAG GATACGTGAT AGGCTGTTAA AAGCTGCAAT AAATAGTAAG   6660

GATGTAGAAG AAATACTTTG TTCTATACCT TCGGAGGAAA GAACTTTAGA ACAACTTAAG   6720

TTTAATCAAA CTTGTATTTA TGAAGGTAC                                     6749
```

(2) INFORMATION FOR SEQ ID NO:36:

(i) SEQUENCE CHARACTERISTICS:
(A) LENGTH: 837 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

```
ATGTGCCGCC GCCCGGATTG CGGCTTCTCT TTCTCACCTG GACCGGTGGC ACTGCTGTGG     60

TGTTGCCTTC TGCTGCCCAT CGTTTCCTCA GCCACCGTCA GCGTCGCTCC TACCGTCGCC    120

GAGAAAGTTC CCGCGGAGTG CCCCGAACTA ACGCGTCGAT GCCTGTTGGG TGAGGTGTTT    180

CAGGGTGACA AGTATGAAAG TTGGCTGCGC CCGTTGGTGA ATGTTACCAG ACGCGATGGC    240

CCGCTATCGC AACTTATTCG TTACCGTCCC GTTACGCCGG AGGCCGCCAA CTCCGTGCTG    300

TTGGACGATG CTTTCCTGGA CACTCTGGCC CTGCTGTACA ACAATCCGGA TCAATTGCGG    360

GCCTTGCTGA CGCTGTTGAG CTCGGACACA GCGCCGCGCT GGATGACGGT GATGCGCGGT    420

TACAGCGAGT GCGGCGATGG CTCGCCGGCC GTGTACACGT GCGTGGACGA CCTGTGCCGC    480

GGCTACGACC TCACGCGACT GTCATACGGG CGCAGCATCT TCACGGAACA CGTGTTAGGC    540

TTCGAGCTGG TGCCACCGTC TCTCTTTAAC GTGGTGGTGG CCATACGCAA CGAAGCCACG    600

CGTACCAACC GCGCCGTGCG TCTGCCCGTG AGCACCGCTG CCGCGCCCGA GGGCATCACG    660

CTCTTTTACG GCCTGTACAA CGCAGTGAAG GAATTCTGCC TGCGTCACCA GCTGGACCCG    720

CCGCTGCTAC GCCACCTAGA TAAATACTAC GCCGGACTGC CGCCCGAGCT GAAGCAGACG    780

CGCGTCAACC TGCCGGCTCA CTCGCGCTAT GGCCCTCAAG CAGTGGATGC TCGCTAA       837
```

(2) INFORMATION FOR SEQ ID NO:37:

(i) SEQUENCE CHARACTERISTICS:
(A) LENGTH: 5234 base pairs
(B) TYPE: nucleic acid
(C) STRANDEDNESS: single -continued (D) TOPOLOGY: linear (ii) MOLECULE TYPE: DNA (genomic)

(xi) SEQUENCE DESCRIPTION: SEQ ID NO:37:

AAGCTTTTGC GATCAATAAA TGGATCACAA CCAGTATCTC TTAACGATGT TCTTCGCAGA 60

TGATGATTCA TTTTTTAAGT ATTTGGCTAG TCAAGATGAT GAATCTTCAT TATCTGATAT 120

ATTGCAAATC ACTCAATATC TAGACTTTCT GTTATTATTA TTGATCCAAT CAAAAAATAA 180

ATTAGAAGCC GTGGGTCATT GTTATGAATC TCTTTCAGAG GAATACAGAC AATTGACAAA 240

ATTCACAGAC TCTCAAGATT TTAAAAAACT GTTTAACAAG GTCCCTATTG TTACAGATGG 300

AAGGGTCAAA CTTAATAAAG GATATTTGTT CGACTTTGTG ATTAGTTTGA TGCGATTCAA 360

AAAAGAATCC TCTCTAGCTA CCACCGCAAT AGATCCTATT AGATACATAG ATCCTCGTCG 420

CGATATCGCA TTTTCTAACG TGATGGATAT ATTAAAGTCG AATAAAGTGA ACAATAATTA 480

ATTCTTTATT GTCATCATGT AATTAACTAG CTACCCGGGA GATCTCTCGA GCTGCAGAAG 540

CTTATAAAAA TCACAAGTCT CTGTCACTTT TTTTGTCTAG TTTTTTTTTC TCCTCTTGGT 600

TCAGACGTTC TCTTCTTCGT CGGAGTCTTT CAAGTGTCGG TAGCCGTTTT TGCGGTGTCG 660

CAGTCGGTCT AGCAGGTTGG GCTTCTGTCC CTTGTCCTGC GTGCCAGTCT GTCCGTCCAA 720

AGAATCTGTA CCGTTCTCGT GCGCTCGCTG CTCTGCGTCC AGACGGACCA GGGCCAGAAG 780

CATCTGGTAA GCCTGCTCGT TGGTGTAAGG CGGAGCCGCC GTGGATGCAT CAGACGACGG 840

TGGTCCCGGT CCTTTGCGAC CAGAATTATA AACACTTTCC TCGTAGGAAG GCGGAGCCTG 900

TAACGACGTG TCTTTGGTGT TGCCCGACGT CACGGTGGTC CCGTCGGCGG ACACCAGATA 960

GGGAAAGAGG TTCTGCAGCG GCTGCATGCA GAGACGCCGC TGTCGAGTAT AGATCAAATA 1020

AATGATAATG ACGACGGCTA TGGCCACGAG GATGATGGTG AAGGCTCCGA AGGGGTTTTT 1080

GAGGAAGGTG GCAACGCCTT CGACCACGGA GGCCACCGCG CCACCCACGG CCCCAATGGC 1140

TACGCCAACG GCCTTTCCCG CGGCGCCCAG GCCGCTCATG AGGTCGTCCA GACCCTTGAG 1200

GTAGGGCGGC AGCGGGTCGA CTACCTTGTC CTCCACGTAC TTTACCCGCT GCTTATACGA 1260

ATTGAACTCG CGCATGATCT CCTCGAGATC AAAAACGTTG CTGGAACGCA ATTCTTTCTG 1320

CGAGTAAAGT TCCAGTACCC TGAAGTCGGT GTTTTCCAGC GGGTCGATGT CTAGGGCGAT 1380

CATGCTGTCG ACGGTGGAGA TGCTGCTGAG GTCAATCATG CGTTTGAAGA GGTAGTCCAC 1440

GTACTCGTAG GCCGAGTTGC CGGCGATGAA GATCTTGAGG CTGGGAAGCT GACATTCCTC 1500

AGTGCGGTGG TTGCCCAACA GGATTTCGTT ATCCTCGCCC AGTTGACCGT ACTGCACGTA 1560

CGAGCTGTTG GCGAAATTAA AGATGACCAC TGGTCGTGAG TAGCAGCGTC CTGGCGATTC 1620

CTTCACATTC ATATCACGCA GCACCTTGAC GCTGGTTTGG TTAATGGTCA CGCAGCTGGC 1680

CAGACCCAGG ACATCACCCA TGAAACGCGC GGCAATCGGT TTGTTGTAGA TGGCCGAGAG 1740

AATAGCTGAC GGGTTGATCT TGCTAAGTTC CTTGAAGACC TCTAGGGTGC GCCGTTGATC 1800

CACACACCAG GCTTCTGCGA TTTCGGCCAG CGCCCGGTTG ATGTAACCGC GCAACGTGTC 1860

ATAGGTGAAC TGCAGCTGGG CGTAGACCAG ATTGTGCACC GACTCCATGT TGGATAAATG 1920

AGTTGCATTG TTGCCATCTG TACTTCTTTT GGTTCTATTA TGAGTAAGAT TCAGACTGGA 1980

GCGGTTGGCC AAACGTTCGA GTTCCACCAG AGATTTTTGC TTGATACCTT GCCAGAACAC 2040

CACCAAACCA CCAGTGGTTT CAAAGACGGA CACGTTTCCA TATTTTTCAT ATGTTTGATT 2100

GTATGAAGTA TTGAAAATCT GCTGTAACTT ATTTATGGCC TCATCACGTA CACAGTCCAG 2160

CCCAGAGTCG GACATGTTCA CCTCTTGCTT CTTAGATAAG AAAGTGGCGG TCATTTTGGC 2220

-continued

```
AGAAGAAAAG TGATACGAGT CCTCGGCTTC GGAACGAATG GTGCGTTCCG AGGCTTCCCA   2280
GAAAGTGAGT TGACAAGTAA CATTCTTCTC GTCCTGTATA TCCCAGGAGA TCACTGAGTC   2340
CGCACGTTCA AGAAAAGCCA CCAACCTGTG GGTCTCTAAC GCAGAATTCG GTCTTTCAAA   2400
GTCGGAGACG ATAGTGTAGT TCGGAAAAAT GAAAAACTTG TCGGCGTTTT CTCCAAAATA   2460
GCTGGCATTG CGATTAGTTC CGTTGTAGAA AGGAGAAATG TCAACCACAT CACCCGTGGA   2520
AGTTGCGAAA AAATGATAGG GATACTTGGA GCGCGCAGTA GTGATGGTCA CCATACAATT   2580
CAGATTACAG GTCTCACGAT AGAGCCAGGT GCTGCCGCGG CTGTGCCATT GATCCTTGAC   2640
CGTCACGTAA CGGGTACTGT GGGTGTTGGA ATAATCGTCG GGCATTAATT GCATGGTTTT   2700
GTTTTCATAG CTGTCCCTAT GATAAGCCAC GAAAACCGTG CCTGCTATAA CGCGGCTGTA   2760
GGAACTGTAG CACTGACTGT GACTGTTGAT ATGATGAATC TCCCACATAG GAGGCGCCAC   2820
GTATTCCGTG TTGCTGCCCA GCAGATAAGT GGTGTGGATG TAAGCGTAGC TACGACGAAA   2880
CGTCAAAACC TTCTGGTAGA CTCGTACCTT AAAGGTGTGC GCGACGATGT TGCGTTTGTA   2940
GACCACCATG ATGCCCTCGT CCAGGTCTTC ATTGATGGGC TTCATCGAGG TGCAGACGAT   3000
ATTACGTTCA AAGCGAATAA GATCCGTACC CTGTGCCATA GAACACACGC GATAGGGGTA   3060
CTTGGTGGTG TTGACCCCCA CCACATCTCC GTACTTGAGG GTAGTGTTGT AGATGGTCTC   3120
GTTAACACCA TGGCTGACCG TTTGGGAAGA AGTTACGCGT TGAGAGACTG AACCGGATCG   3180
AGAATGAGCA GCAGACGTCG TATGAGAGGA ATGGTGACTG TGAGTAGCAG AAGTTCCACG   3240
AGTAGAAGAT GAGGAAACCG CAGCACCCAG ACAGACGATA CACAAGTTAA CGCAGACTAC   3300
CAGGCACCAG ATCCTGGATT CCATTACGAT ACAAACTTAA CGGATATCGC GATAATGAAA   3360
TAATTTATGA TTATTTCTCG CTTTCAATTT AACACAACCC TCAAGAACCT TTGTATTTAT   3420
TTTCACTTTT AAGTATAGAA TAAAGAAGCT TGCATGCCAC GCGTCTCGAG GGCCCCTGCA   3480
GGTCGACTCT AGAGGATCCT TCTTTATTCT ATACTTAAAA AGTGAAAATA AATACAAAGG   3540
TTCTTGAGGG TTGTGTTAAA TTGAAAGCGA GAAATAATCA TAAATTATTT CATTATCGCG   3600
ATATCCGTTA AGTTTGTATC GTAATGTGCC GCCGCCCGGA TTGCGGCTTC TCTTTCTCAC   3660
CTGGACCGGT GGCACTGCTG TGGTGTTGCC TTCTGCTGCC CATCGTTTCC TCAGCCACCG   3720
TCAGCGTCGC TCCTACCGTC GCCGAGAAAG TTCCCGCGGA GTGCCCCGAA CTAACGCGTC   3780
GATGCCTGTT GGGTGAGGTG TTTCAGGGTG ACAAGTATGA AAGTTGGCTG CGCCCGTTGG   3840
TGAATGTTAC CAGACGCGAT GGCCCGCTAT CGCAACTTAT TCGTTACCGT CCCGTTACGC   3900
CGGAGGCCGC CAACTCCGTG CTGTTGGACG ATGCTTTCCT GGACACTCTG GCCCTGCTGT   3960
ACAACAATCC GGATCAATTG CGGGCCTTGC TGACGCTGTT GAGCTCGGAC ACAGCGCCGC   4020
GCTGGATGAC GGTGATGCGC GGTTACAGCG AGTGCGGCGA TGGCTCGCCG GCCGTGTACA   4080
CGTGCGTGGA CGACCTGTGC CGCGGCTACG ACCTCACGCG ACTGTCATAC GGGCGCAGCA   4140
TCTTCACGGA ACACGTGTTA GGCTTCGAGC TGGTGCCACC GTCTCTCTTT AACGTGGTGG   4200
TGGCCATACG CAACGAAGCC ACGCGTACCA ACCGCGCCGT GCGTCTGCCC GTGAGCACCG   4260
CTGCCGCGCC CGAGGGCATC ACGCTCTTTT ACGGCCTGTA CAACGCAGTG AAGGAATTCT   4320
GCCTGCGTCA CCAGCTGGAC CCGCCGCTGC TACGCCACCT AGATAAATAC TACGCCGGAC   4380
TGCCGCCCGA GCTGAAGCAG ACGCGCGTCA ACCTGCCGGC TCACTCGCGC TATGGCCCTC   4440
AAGCAGTGGA TGCTCGCTAA TTTTTATAGA TCCTGATCCT TTTTCTGGGT AAGTAATACG   4500
TCAAGGAGAA AACGAAACGA TCTGTAGTTA GCGGCCGCCT AATTAACTAA TATTATATTT   4560
```

-continued

```
TTTATCTAAA AAACTAAAAA TAAACATTGA TTAAATTTTA ATATAATACT TAAAAATGGA   4620

TGTTGTGTCG TTAGATAAAC CGTTTATGTA TTTTGAGGAA ATTGATAATG AGTTAGATTA   4680

CGAACCAGAA AGTGCAAATG AGGTCGCAAA AAAACTGCCG TATCAAGGAC AGTTAAAACT   4740

ATTACTAGGA GAATTATTTT TTCTTAGTAA GTTACAGCGA CACGGTATAT TAGATGGTGC   4800

CACCGTAGTG TATATAGGAT CGGCTCCTGG TACACATATA CGTTATTTGA GAGATCATTT   4860

CTATAATTTA GGAATGATTA TCAAATGGAT GCTAATTGAC GGACGCCATC ATGATCCTAT   4920

TTTAAATGGA TTGCGTGATG TGACTCTAGT GACTCGGTTC GTTGATGAGG AATATCTACG   4980

ATCCATCAAA AAACAACTGC ATCCTTCTAA GATTATTTTA ATTTCTGATG TGAGATCCAA   5040

ACGAGGAGGA AATGAACCTA GTACGGCGGA TTTACTAAGT AATTACGCTC TACAAAATGT   5100

CATGATTAGT ATTTTAAACC CCGTGGCGTC TAGTCTTAAA TGGAGATGCC CGTTTCCAGA   5160

TCAATGGATC AAGGACTTTT ATATCCCACA CGGTAATAAA ATGTTACAAC CTTTTGCTCC   5220

TTCATATTCA GCTG                                                      5234
```

(2) INFORMATION FOR SEQ ID NO:38:

(i) SEQUENCE CHARACTERISTICS:
(A) LENGTH: 6749 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

```
GAGCTCGCGG CCGCCTATCA AAAGTCTTAA TGAGTTAGGT GTAGATAGTA TAGATATTAC     60

TACAAAGGTA TTCATATTTC CTATCAATTC TAAAGTAGAT GATATTAATA ACTCAAAGAT    120

GATGATAGTA GATAATAGAT ACGCTCATAT AATGACTGCA AATTTGGACG GTTCACATTT    180

TAATCATCAC GCGTTCATAA GTTTCAACTG CATAGATCAA AATCTCACTA AAAAGATAGC    240

CGATGTATTT GAGAGAGATT GGACATCTAA CTACGCTAAA GAAATTACAG TTATAAATAA    300

TACATAATGG ATTTTGTTAT CATCAGTTAT ATTTAACATA AGTACAATAA AAAGTATTAA    360

ATAAAAATAC TTACTTACGA AAAAATGACT AATTAGCTAT AAAAACCCAA CAAAAACTAA    420

TCAGCTATCG GGGTTAATTA ATTAGTTATT AGACAAGGTG AAAACGAAAC TATTTGTAGC    480

TTAATTAATT AGAGCTTCTT TATTCTATAC TTAAAAAGTG AAAATAAATA CAAAGGTTCT    540

TGAGGGTTGT GTTAAATTGA AAGCGAGAAA TAATCATAAA TTATTTCATT ATGGCGATAT    600

CCGTTAAGTT TGTATCGTAA TGGAGTCGCG CGGTCGCCGT TGTCCCGAAA TGATATCCGT    660

ACTGGGTCCC ATTTCGGGGC ACGTGCTGAA ACCCGTGTTT AGTCGCGGCG ACACGCCGGT    720

GCTGCCGCAC GAGACGCGAC TCCTGCAGAC GGGTATCCAC GTGCGCGTGA GCCAGCCCTC    780

GCTGATCCTG GTGTCGCAGT ACACGCCCGA CTCGACGCCA TGCCACCGCG GCGACAATCA    840

GCTGCAGGTG CAGCACACGT ACTTTACGGG CAGCGAGGTG GAGAACGTGT CGGTCAACGT    900

GCACAACCCC ACGGGCCGGA GCATCTGCCC CAGCCAAGAG CCCATGTCGA TCTATGTGTA    960

CGCGCTGCCG CTCAAGATGC TGAACATCCC CAGCATCAAC GTGCACCACT ACCCGTCGGC   1020

GGCCGAGCGC AAACACCGAC ACCTGCCCGT AGCTGACGCT GTGATTCACG CGTCGGGCAA   1080

GTAGATGTGG CAGGCGCGTC TCACGGTCTC GGGACTGGCC TGGACGCGTC ACCAGAACCA   1140

GTGGAAAGAG CCCGACGTCT ACTACACGTC AGCGTTCGTG TTTCCCACCA AGGACGTGGC   1200

ACTGCGGCAC GTGGTGTGCG CGCACGAGCT GGTTTGCTCC ATGGAGAACA CGCGCGCAAC   1260
```

-continued

CAAGATGCAG GTGATAGGTG ACCAGTACGT CAAGGTGTAC CTGGAGTCCT TCTGCGAGGA 1320

CGTGCCCTCC GGCAAGCTCT TTATGCACGT CACGCTGGGC TCTGACGTGG AAGAGGACCT 1380

GACGATGACC CGCAACCCGC AACCCTTCAT GCGCCCCCAC GAGCGCAACG GCTTTACGGT 1440

GTTGTGTCCC AAAAATATGA TAATCAAACC GGGCAAGATC TCGCACATCA TGCTGGATGT 1500

GGCTTTTACC TCACACGAGC ATTTTGGGCT GCTGTGTCCC AAGAGCATCC CGGGCCTGAG 1560

CATCTCAGGT AACCTATTGA TGAACGGGCA GCAGATCTTC CTGGAGGTGC AAGCGATACG 1620

CGAGACCGTG GAACTGCGTC AGTACGATCC CGTGGCTGCG CTCTTCTTTT TCGATATCGA 1680

CTTGCTGCTG CAGCGCGGGC CTCAGTACAG CGAACACCCC ACCTTCACCA GCCAGTATCG 1740

CATCCAGGGC AAGCTTGAGT ACCGACACAC CTGGGACCGG CACGACGAGG GTGCCGCCCA 1800

GGGCGACGAC GACGTCTGGA CCAGCGGATC GGACTCCGAC GAGGAACTCG TAACCACCGA 1860

GCGCAAGACG CCCCGCGTTA CCGGCGGCGG CGCCATGGCG GGCGCCTCCA CTTCCGCGGG 1920

CCGCAAACGC AAATCAGCAT CCTCGGCGAC GGCGTGCACG GCGGGCGTTA TGACACGCGG 1980

CCGCCTTAAG GCCGAGTCCA CCGTCGCGCC CGAAGAGGAC ACCGACGAGG ATTCCGACAA 2040

CGAAATCCAC AATCCGGCCG TGTTCACCTG GCCGCCCTGG CAGGCCGGCA TCCTGGCCCG 2100

CAACCTGGTG CCCATGGTGG CTACGGTTCA GGGTCAGAAT CTGAAGTACC AGGAGTTCTT 2160

CTGGGACGCC AACGACATCT ACCGCATCTT CGCCGAATTG GAAGGCGTAT GGCAGCCCGC 2220

TGCGCAACCC AAACGTCGCC GCCACCGGCA AGACGCCTTG CCCGGGCCAT GCATCGCCTC 2280

GACGCCCAAA AAGCACCGAG GTTGATTTTT ATGGATCCGG TACCCTCGAG GAATTCTAGC 2340

TTTATTGGGA AGATATGATA ATATTTTGGG ATTTCAAAAT TGAAAATATA TAATTACAAT 2400

ATAAAATGAG TTTGCAGTTT ATCGGTCTAC AGCGGCGCGA TGTGGTGGCC CTGGTCAACT 2460

TTCTGCGCCA TCTCACGCAA AAGCCCGACG TGGATCTCGA GGCACACCCC AAGATCCTGA 2520

AAAAATGTGG CGAAAAACGC CTGCACCGGC GTACGGTGCT GTTCAACGAG CTCATGCTTT 2580

GGTTGGGATA CTACCGCGAG CTGCGTTTCC ACAACCCCGA CCTCTCCTCG GTTCTCGAGG 2640

AGTTCGAGGT GCGTTGCGCG GCCGTGGCGC GTCGCGGCTA CACTTACCCG TTCGGTGATC 2700

GTGGTAAGGC GCGTGACCAC CTGGCTGTGC TAGACCGTAC CGAATTCGAT ACGGACGTAC 2760

GCCACGATGC TGAGATTGTG GAGCGCGCGC TCGTAAGCGC GGTCATTCTG GCCAAGATGT 2820

CGGTGCGCGA GACGCTGGTC ACAGCCATCG GCCAGACGGA ACCCATCGCT TTTGTGCACC 2880

TCAAGGATAC GGAGGTGCAG CGCATTGAAG AAAACCTGGA GGGTGTGCGC CGTAACATGT 2940

TCTGCGTGAA ACCGCTCGAC CTTAACCTGG ACCGGCACGC CAACACGGCG CTGGTCAACG 3000

CCGTCAACAA GCTCGTGTAC ACGGGCCGTC TCATCATGAA CGTGCGCAGG TCTTGGGAGG 3060

AGCTGGAGCG CAAATGTCTG GCGCGCATTC AGGAGCGCTG CAAGCTGCTG GTCAAGGAGC 3120

TGCGCATGTG CCTTTCCTTT GATTCCAACT ACTGTCGCAA TATCCTCAAA CACGCCGTGG 3180

AAAACGGTGA CTCGGCCGAC ACGCTGCTGG AGCTGCTCAT CGAGGACTTT GACATCTACG 3240

TGGACAGCTT CCCGCAGTCG GCGCACACCT TTTTGGGCGC GCGCCCGCCG TCGTTGGAGT 3300

TTGACGATGA CGCCAATCTC CTCTCGCTCG GCGGCGGTTC AGCCTTCTCG TCGGTACCCA 3360

AGAAACATGT CCCCACGCAG CCGCTGGACG GCTGGAGCTG GATCGCCAGT CCCTGGAAGG 3420

GACACAAACC GTTCCGCTTC GAGGCCCATG GTTCTCTGGC ACCGGCCGCC GACGCCCACG 3480

CCGCCCGTTC GGCGCGCGTC GGCTATTACG ACGAAGAGGA AAAGCGTCGC GAGCGGCAGA 3540

AACGGGTGGA CGACGAGGTG GTGCAGCGTG AGAAACAGCA GCTGAAGGCT TGGGAGGAGA 3600

GGCAGCAGAA CCTGCAGCAA CGTCAGCAGC AACCGCCGCC CCCGACACGT AAACCGGGCG 3660

-continued

```
CCTCCCGGAG GCTCTTTGGC TCCAGTGCCG ATGAGGACGA CGACGATGAT GATGACGAGA   3720
AAAACATCTT TACGCCCATC AAGAAACCGG GAACTAGCGG CAAGGGCGCC GCTAGTGGCA   3780
ACGGTGTTTC CAGCATTTTC AGCGGCATGT TATCCTCGGG CAGTCAGAAA CCGACCAGCG   3840
GTCCCTTGAA CATCCCGCAG CAACAACAGC GTCACGCGGC TTTCAGTCTC GTCTCCCCGC   3900
AGGTAACCAA GGCCAGCCCG GGAAGGGTCC GTCGGGACAG CGCGTGGGAC GTGAGGCCGC   3960
TCACGGAGAC AAGAGGGGAT CTTTTCTCGG GCGACGAGGA TTCCGACAGC TCGGATGGCT   4020
ATCCCCCCAA CCGTCAAGAT CCGCGTTTCA CCGACACGCT GGTGGACATC ACGGATACCG   4080
AGACGAGCGC CAAACCGCCC GTCACCACCG CGTACAAGTT CGAGCAACCG ACGTTGACGT   4140
TCGGCGCCGG AGTTAACGTC CCTGCTGGCG CCGGCGCTGC CATCCTCACG CCGACGCCTG   4200
TCAATCCTTC CACGGCCCCC GCTCCGGCCC CGACACCTAC CTTCGCGGGT ACCCAAACCC   4260
CGGTCAACGG TAACTCGCCC TGGGCTCCGA CGGCGCCGTT GCCCGGGGAT ATGAACCCCG   4320
CCAACTGGCC GCGCGAACGC GCGTGGGCCC TCAAGAATCC TCACCTGGCT TACAATCCCT   4380
TCAGGATGCC TACGACTTCC ACGACTTCTC AAAACAACGT GTCCACCACC CCTCGGAGGC   4440
CGTCGACTCC ACGCGCCGCG GTGACACAAA CAGCGTCTCA GAACGCCGCT GATGAGGTTT   4500
GGGCTTTAAG GGACCAAACT GCAGAGTCAC CGGTCGAAGA CAGCGAGGAG GAAGACGACG   4560
ACTCCTCGGA CACCGGCTCC GTCGTCAGCC TGGGACACAC AACACCGTCG TCCGATTACA   4620
ACGACGTCAT TTCGCCTCCC AGTCAGACGC CCGAGCAGTC GACGCCGTCC AGAATACGTA   4680
AAGCTAAGTT ATCGTCTCCA ATGACGACGA CATCCACGAG CCAGAAACCG GTGCTGGGCA   4740
AGCGAGTCGC GACGCCGCAC GCGTCCGCCC GAGCGCAGAC GGTGACGTCG ACACCGGTTC   4800
AGGGAAGGGT AGAGAAACAG GTATCGGGCA CGCCGTCGAC GGTACCCGCC ACGCTGTTGC   4860
AACCTCAACC GGCTTCGTCT AAAACAACGT TATCAAGGAA CGTGACTTCT GGCGCGAGAA   4920
CCTCTTCCGC TTCGGCTCGA CAGCCGTCAG CCTCGGCGTC CGTTTTGTCG CCCACGGAGG   4980
ATGATGTCGT GTCCCCCGTC ACGTCGCCGC TGTCCATGCT TTCGTCAGCC TCTCCGTCCC   5040
CGGCCAAGAG TGCCCCTCCG TCTCCGGTGA AAGGTCGGGG CAGCCGCGTC GGTGTTCCTT   5100
CTTTGAAACC TACTTTGGGC GGCAAGGCGG TGGTAGGTCG ACCGCCCTCG GTACCCGTGA   5160
GCGGTAGCGC GCCGGGTCGC CTGTCCGGCA CCAGCCGGGC CGCCTCGACC ACGCCGACGT   5220
ATCCCGCGGT AACCACCGTT TACCCACCGT CGTCTACGGC CAAAAGCAGC GTATCGAATG   5280
CGCCGCCTGT GGCCTCCCCC TCCATCCTGA AACCGGGGGC GAGCGCGGCT TTGCAATCAC   5340
GCCGCTCGAC GGGGACCGCC GCCGTAGGTT CCCCCGTCAA GAGCACGACG GGCATGAAAA   5400
CGGTGGCTTT CGACCTATCG TCGCCCCAGA AGAGCGGTAC GGGGCCGCAA CCGGGTTCTG   5460
CCGGCATGGG GGGCGCCAAA ACGCCGTCGG ACGCCGTGCA GAACATCCTC CAAAAGATCG   5520
AGAAGATTAA GAACACGGAG GAATAGTTTT TATTGCTAGA ATTCTTTTTA TTGATTAACT   5580
AGTCAAATGA GTATATATAA TTGAAAAAGT AAAATATAAA TCATATAATA ATGAAACGAA   5640
ATATCAGTAA TAGACAGGAA CTGGCAGATT CTTCTTCTAA TGAAGTAAGT ACTGCTAAAT   5700
CTCCAAAATT AGATAAAAAT GATACAGCAA ATACAGCTTC ATTCAACGAA TTACCTTTTA   5760
ATTTTTTCAG ACACACCTTA TTACAAACTA ACTAAGTCAG ATGATGAGAA AGTAAATATA   5820
AATTTAACTT ATGGGTATAA TATAATAAAG ATTCATGATA TTAATAATTT ACTTAACGAT   5880
GTTAATAGAC TTATTCCATC AACCCCTTCA AACCTTTCTG GATATTATAA AATACCAGTT   5940
AATGATATTA AAATAGATTG TTTAAGAGAT GTAAATAATT ATTTGGAGGT AAAGGATATA   6000
```

-continued

```
AAATTAGTCT ATCTTTCACA TGGAAATGAA TTACCTAATA TTAATAATTA TGATAGGAAT   6060

TTTTTAGGAT TTACAGCTGT TATATGTATC AACAATACAG GCAGATCTAT GGTTATGGTA   6120

AAACACTGTA ACGGGAAGCA GCATTCTATG GTAACTGGCC TATGTTTAAT AGCCAGATCA   6180

TTTTACTCTA TAAACATTTT ACCACAAATA ATAGGATCCT CTAGATATTT AATATTATAT   6240

CTAACAACAA CAAAAAAATT TAACGATGTA TGGCCAGAAG TATTTTCTAC TAATAAAGAT   6300

AAAGATAGTC TATCTTATCT ACAAGATATG AAAGAAGATA ATCATTTAGT AGTAGCTACT   6360

AATATGGAAA GAAATGTATA CAAAAACGTG GAAGCTTTTA TATTAAATAG CATATTACTA   6420

GAAGATTTAA AATCTAGACT TAGTATAACA AAACAGTTAA ATGCCAATAT CGATTCTATA   6480

TTTCATCATA ACAGTAGTAC ATTAATCAGT GATATACTGA AACGATCTAC AGACTCAACT   6540

ATGCAAGGAA TAAGCAATAT GCCAATTATG TCTAATATTT TAACTTTAGA ACTAAAACGT   6600

TCTACCAATA CTAAAAATAG GATACGTGAT AGGCTGTTAA AAGCTGCAAT AAATAGTAAG   6660

GATGTAGAAG AAATACTTTG TTCTATACCT TCGGAGGAAA GAACTTTAGA ACAACTTAAG   6720

TTTAATCAAA CTTGTATTTA TGAAGGTAC                                     6749
```

(2) INFORMATION FOR SEQ ID NO:39:

(i) SEQUENCE CHARACTERISTICS:
(A) LENGTH: 5798 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

```
TCTAGAACTA GTGGATCTTC TGGTAATGAC AAATTAAACT GTTTAGCGTA TATTATATAC     60

TCGTATAAAA AATCATGATC TATATTCTTA ATAGCTTTTA GAAGGTTCAT ATCGTAGAAA    120

TAAACATAAG TTCCTTTCAT CACTCTACCT ACACGACCTT TACGTTGCGT CATCATAGAT    180

TTTGATATAA ACATCTGAAC ACCACCAAAA GGTCTAGGTA CGTATACTCT ACCGGTATCG    240

TATACGTGAG TCGCTGTACG TATAGTAATA CTAGATTCCA AATAAGGGGT AGATACTAGA    300

ATACAAGGTC TTTCTCTATT AGGTCGTTGA ACATCTTGTA GGATTTCTGC TATATTTTTT    360

AATTTTCCAT GTATTACTAT AAAATCAATA TTCTTATTCT TAGATTCTAA GTACTCTTTA    420

TACTTAATAC ATTCTGATAC AGAAGGTAAG AATAAAATAC CACACATTCC ATTATCTGGC    480

TTACACCACA ATAAAGTAGA CGATATATTC TTTCTCTCAT TATCAAAATA AACTCTCTTA    540

TCCGGAGAAT ACCTATTTTT TACGTATATT TCTTTTATGG AGTAAAGAAC TGGTCCTTCT    600

ATATGGTAAA ATTCAACATC AGGAAGAAAT TCCATTAGTC TATCTTTATC ATCTTCTAGA    660

GTGGCAGACA TCAATACTAG CGAATGAATG CTATCTATAT TTTTTCTTAG AACGGCTATC    720

ATAATATCGG CTATCCTATC ATGTTCATGT ATTTCATCTA TTATGACTAT ATTATACTTT    780

GATAGAGAGT AACTAGTCAG TTTATTAGTA GAAAGTACTA TACCTTGAAA TCCTTTTTTG    840

GTTTTTTCTG TATGTCCTCC GTATTTAAGT TCTACAGGAG AACCTTCGAA CTGTGAAAAT    900

CCCAACGATT GTAAAAAATT ATTTCCGTTG CTCTTTACCA AAGTCACCCT AGGAAGAGAT    960

AAAACTATAG GTTTGGGTAT AAAATCTAGC CTTATCCTGT CTATATCATC CCATCCTCCG   1020

AATAAATAGT TATACCACAT TATTACTTTT GGTAACTGAG ATGTTTTACC TATGCCTGTA   1080

CTACCGGTAA CTACTATCTG TTTCCTCTTC TTTAACATAT CAAAGATATG AACCTGTGTT   1140

GTTAAACTAA GGGATTTGAA CGATATGATA GCGAAAGGAT TTGGATTATT GAGTATTCCT   1200
```

-continued

```
ATAGAATTCT TAATGGGTAC CTTCTTATTG GAAGAGAAAA TAGACAGATG ATTTCCAGCT   1260
ACTAGTAATC CTCTTTTATC GTCAAGCGTT ATATCAGATA CATGATTATA ACCGATACAT   1320
TTTACGTAAC TATAGCATTC AAACGTTATA AATCTATCGT TACCTATATA GTATACCTGT   1380
TTACTGTAGT TGATACTGAC GGGTATTATA TCTATAAGTT TACTAACAGG TATTTTAGCG   1440
GGTATTGAAT TAGTAGTTTC TATATTCAGC ATATAAGTAT CGTCCTTTAA GCAGATAAAT   1500
ACTTTATTCC ACCTATGTTT TATTATAGGA AATACAGAAT GAGAAAAAAA TAACGTATCT   1560
TTATTATGAT ATTCTTCTAA TTCTTTTTGG GTATACTTAC TTGGGAATAT ATCGTACATA   1620
TTAGGGAAAG CGTATATCGA AAATAGCTCG TTAGTGGCCA TAGTTCCTAC AGTATGTATA   1680
TTTAGTTAGT AATAAATGGA TAGATACACA GAACTAGTTA TTAATAAAAT ACCAGAATTA   1740
GGATTCGTTA ACTTGCTTTC TCATATCTAT CAAACAGTTG GGTTATCCTA CGATATAGAT   1800
GTATCAAAAT TCAAAACTAA TTGCAATGGT TACGTCGTAG AGAGATTTGA TAACTCAGAA   1860
ACAGTTGGCA AAGTGTCCTG CGTGCCTATA TCTATACTGT TAGAATTGGT AGACAGAAAA   1920
ATATTATCTA AACCAGATAC GTCTAAAACA GAAATAGAGA TTAAAGAAGA TTTAGTAAAC   1980
GAATTAATTG AAAATACCAA TAGTTTCGAA GATATAATGA CTATACCTAC CAGTATCCCT   2040
ATGAGATATT TTTTTAAACC GGTACTAAGA GAAAAAGTAT CTAAAGCTGT AGATTTTTCC   2100
AGAATGGATA TTAAGGGAGA TGATATTAGC AAAATGGGAA TAAAACACGG AGAAAAAAGT   2160
AATAATATAT CTAATATTAA GATTGTACCA GAAAAAGATG CCTGGATGAC TAATACTAGT   2220
ATTCAGCAAT TAATAGGACC TATGTCGTAC GGAACAGAAG TTAGCTATAT AGGTCAATTT   2280
AACTTTAATT TTATTAACAC ATATCCTGTA TACGAAAAAT CTGCAGCCCT TAACAGAAGT   2340
CCAGAACTTT TTAAGATTAA AGATAGAATT AAAGGATTAC GTACAAGATT TGTTATGTTC   2400
GGTTTCTGTT ATATGTTCCA TTGGAAATGT TTGATATATG ATAGAGAAAA CGATTTTGTA   2460
TGTTTCTATG ATTCAGGAGG ATCTAATCCA AATGACTTTG ATCACTATGA TAATTTTTTC   2520
TACTATAGTC ATTCGAGAGG ATTCAATAGA AATTCTAAGA GGTCATCTAG CTTATCTAAT   2580
GAAAATGCAG ATATAGATAT TCTGTTCAAC TTTTTCGTGG ATAATTACGA AGTTACTTCA   2640
GGATGTATAA ACGTAGAAGT CAATCAGCTG ATGGAATCAG AATGTGGTAT GTTTACTTGT   2700
TTGTTTATGA CTATGTGCTG TCTCCATCCT CCTAAAGGAT TTAAAGGGAT AAGAAAGACA   2760
TATACCTATT TTAAGTTTTT AGCCGATAAA AAAATGACTA TGCTAAAGTC TATACTTTTC   2820
AACGCTGACA AGATGGAATT TAAAGTGAAA GAATCAAGCA GTAAAGGCAT ACAAGAATAT   2880
AAAAAAATGG AAGAGTGGTG TGGTAAAACT ATAAACATTT TAGCTGATAA AATAACAACA   2940
CGTGTAAATA GTATAATAGA GTAGTAAAAT GGATAATTTT ATAAAGCAGA TATCGTCAAA   3000
GATAGTAAAA CCTATAGCAG AATTAGAACC TCCAGATTCT AAAGTACAAT ATTATTACAT   3060
GACTATATCG TTTAATTTTC CTGACTTATA TTATTGTAAT AAAAATTTAT TTGCGAAACC   3120
CGATAATACT TTGCTAGATG TTTCTAAGTC TTTGCTTACT TTAAACTCAT TTCCGTATGA   3180
AAACTTTGTG ATAAATGATT TACTAAGAAC TATTAGGCGT TACTGTCACG TATATGATGT   3240
CTATTTTTTA CCCGTAGGGT GGTTTGTAGG AAAAGAAGAT GTATTACCCA ATTACCAAGT   3300
ATCGATAAAA ATAATAAGAA GTACTAATCA AGAAGTAATA GAAAACATTA TTAGGAATTA   3360
TTTATCACGA CACGGTATTT ATGGAGATAA CCTATCTATA GAAACAGACC GATTAAACGA   3420
AGTATCTATA AACAGACATT CTATTGTAGG AGCTAGACAG TTAGCACCTA TATGCGTTGT   3480
TTCTTTTTAT CCTTTCGACC CTGAAAATAA AATACTTTTC GTTATATATG TAGGTAGATA   3540
CAAAGACAGA CATTGCGGTG TATCTTATGT AGTTGATAGA GAGGATATGT ATAAAGTAAT   3600
```

-continued

```
TAACAGAATA TATTCTTACG TAGTTTGTAT TTATCTAGTT TCCGATGATA TGGTCACGTT   3660
TCATACTACT CCTCTAGCTA ATCACAGTAA AAAATTAATA CCGTTACCCA TAAATCATTG   3720
CAATACCTTA TGCGAGATAG TTCACGACTT TGAGTTTTTA AGATTTGAGC AATCCACTAT   3780
GCCAATACCC GTTTTCACTC CTTTTATTCC TAAACAGCTA GTTAATATAA TCAACTTACC   3840
TGATGATATA CCTATTACTT GTGCATCAAT AAACAGATTA GAATATGTTA CACATATAGA   3900
TGATAAAAAA TTAAAAAGAG TACTGATTAT CGTAAAGGAT AAATTTCTTA GAAATACTAT   3960
TCTTCACGGT ACATTTAAAA AAAGGAATAT AGTCAGAAAC AGGAAATATA CTTTCACTAT   4020
AACATGGTCT AATTTCGAAT GTCCGACGTT AGGAGACGTT AAGTCTTCTT CACCTAATAC   4080
CTGTAATAGA GTAGTTTTAG ACGGTAGTAG ATACGTTACA AAAACCTTTA ATGATACAAT   4140
ATAAATGGAA CTAACTAGAG AAACGCTGAT ATTTGTAGGC ATTACTGTAC TAGTAGTAGT   4200
AATGATCATA TCTGGTTTCT CACTAATATT GCGATTGATA CCTGGTGTAT ATTCATCAGT   4260
TATTAGATCG TCGTTCGTAG GAGGGAAAAT ATTAAGATTT ATGGAGGTAT TCTCTACTGT   4320
TATGTTTATA CCATCATTAG TAATACTTTA TACAGCATAT ATAAGGAAAT CTAAAGTGAA   4380
AAATAACTAA ATATTATAGT ATTTGTAATA AATGGCTACT GGAGAGATTC GTCTTATTAT   4440
AGGGCCTATG TTTTCAGGTA AAACAACAGA ATTAGTTAGA TTAATAAGAA GATTTATGAT   4500
ATCGGGACGT AAATGTATAA TAATAAAACA TTGTAGTGAT TCCCGTTATA CCGAAGGAGA   4560
TTTAGAAGCT ATATATACTC ATGATAAAAT TTCGATGGAA GCACTATCGT GTAGCAAATT   4620
ATTACCTTTA ATACCTAAAA TTGATAACTT TGAAGTAATA GGTATAGACG AAGGACAGTT   4680
TTTTGAAGAT ATAGTAGAAT TTAGTGAGAT TATGGCTAAT AAGGGTAAAA CTGTAATCAT   4740
AGCGGCTTTA AATGGAGATT TCAAACGACA ATTATTTGGA AACATATTTA AACTATTATC   4800
TTTATCAGAA TCAGTTACTA GTTTAACTGC TATTTGTGCA GTTTGTAAAA ACGAAGCATC   4860
TTTTTCTAAG CGCATGACTG ATGATAAAGA TGTAAAAGTT ATAGGAGGTA AAGAAATGTA   4920
TACTGCTGTT TGTAGAAAAT GCTTTTTATG AGTCTAATAT ACGTACTAAA TACTTGTACG   4980
TACAACTATG TTAGAATAAT TTGCTTAGTA TAGTATATAA ACAAGTATGT AAAAAATAAA   5040
ATTGATATAA AAGTAGTCTT CTATTCCGAA CAATAACTAT ACAAAATGGA TTTAGATATT   5100
AAATCTTGCA GAAGTATTTA CAAAATATGG GATAAATATC ATTTTATGAC AGGGTATAAA   5160
TATAAAAATG ATAAACAGAG ATTTAAAATT ACAATTTACT GTAAATGTGA TTGTTCTATC   5220
AAAGAATATC CTTATAGATT TGTTACTGAG AAACTGCTTT TAATGTATAT TATTAATAAG   5280
TTTAGAGGAA AGTATCTAAT CAAAATTAGG ATAGAACCCA TAGTTAAAAA TTAAATCATA   5340
TATCAATACA TGTCAGTTTT TTATCGAAAA ATGGATTTAT AAATAAAATG AAAAATAACT   5400
TGAATGAAGG AAAAAATAAC CATGAGTAAA AAACCAGTAA AGACGGTCCA GCGTAGACGT   5460
GGAAACGATG AGGATAATAA GTTTACTTGT ATCCAAGCGC TAGAACATGC AAAAAGCTTA   5520
TGTACTAAAA ATAATAAAAT AGTTAAATCT GTTAAACTAT CACAATCTCT CTTTAAGTCA   5580
TCTAACAATA TTTCTGTGAT ATTAGAACCA GAATATAAAG ACAAATTAGT GACTCCTCTT   5640
ATTATTGTAG AAGGTGAAGG AAAAATATAC CATAATAAGA ATGATAGTTT TAATCGTGAA   5700
GAACCGTATT TTCTAAAAAT ACGACCTACG TTAATGAATC CTATATTATA TCAGATTATG   5760
GAATGCATTT ATAGAGATCC CCCGGGCTGC AGGAATTC                           5798
```

(2) INFORMATION FOR SEQ ID NO:40:

(i) SEQUENCE CHARACTERISTICS:

-continued (A) LENGTH: 5302 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

```
GCCCTTAACA GAAGTCCAGA ACTTTTTAAG ATTAAAGATA GAATTAAAGG ATTACGTACA     60
AGATTTGTTA TGTTCGGTTT CTGTTATATG TTCCATTGGA AATGTTTGAT ATATGATAGA    120
GAAAACGATT TTGTATGTTT CTATGATTCA GGAGGATCTA ATCCAAATGA CTTTGATCAC    180
TATGATAATT TTTTCTACTA TAGTCATTCG AGAGGATTCA ATAGAAATTC TAAGAGGTCA    240
TCTAGCTTAT CTAATGAAAA TGCAGATATA GATATTCTGT TCAACTTTTT CGTGGATAAT    300
TACGAAGTTA CTTCAGGATG TATAAACGTA GAAGTCAATC AGCTGATGGA ATCAGAATGT    360
GGTATGTTTA CTTGTTTGTT TATGACTATG TGCTGTCTCC ATCCTCCTAA AGGATTTAAA    420
GGGATAAGAA AGACATATAC CTATTTTAAG TTTTTAGCCG ATAAAAAAAT GACTATGCTA    480
AAGTCTATAC TTTTCAACGC TGACAAGATG GAATTTAAAG TGAAAGAATC AAGCAGTAAA    540
GGCATACAAG AATATAAAAA AATGGAAGAG TGGTGTGGTA AAACTATAAA CATTTTAGCT    600
GATAAAATAA CAACACGTGT AAATAGTATA ATAGAGTAGT AAAATGGATA ATTTTATAAA    660
GCAGATATCG TCAAAGATAG TAAAACCTAT AGCAGAATTA GAACCTCCAG ATTCTAAAGT    720
ACAATATTAT TACATGACTA TATCGTTTAA TTTTCCTGAC TTATATTATT GTAATAAAAA    780
TTTATTTGCG AAACCCGATA ATACTTTGCT AGATGTTTCT AAGTCTTTGC TTACTTTAAA    840
CTCATTTCCG TATGAAAACT TTGTGATAAA TGATTTACTA AGAACTATTA GGCGTTACTG    900
TCACGTATAT GATGTCTATT TTTTACCCGT AGGTGGTTTG TAGGAAAAGA AGATGTATTA    960
CCCAATTACC AAGTATCGAT AAAAATAATA AGAAGTACTA ATCAAGAAGT AATAGAAAAC   1020
ATTATTAGGA ATTATTTATC ACGACACGGT ATTTATGGAG ATAACCTATC TATAGAAACA   1080
GACCGATTAA ACGAAGTATC TATAAACAGA CATTCTATTG TAGGAGCTAG ACAGTTAGCA   1140
CCTATATGCG TTGTTTCTTT TTATCCTTTC GACCCTGAAA ATAAAATACT TTTCGTTATA   1200
TATGTAGGTA GATACAAAGA CAGACATTGC GGTGTATCTT ATGTAGTTGA TAGAGAGGAT   1260
ATGTATAAAG TAATTAACAG AATATATTCT TACGTAGTTT GTATTTATCT AGTTTCCGAT   1320
GATATGGTCA CGTTTCATAC TACTCCTCTA GCTAATCACA GTAAAAAATT AATACCGTTA   1380
CCCATAAATC ATTGCAATAC CTTATGCGAG ATAGTTCACG ACTTTGAGTT TTTGAGATTT   1440
GAGCAATCCA CTATGCCAAT ACCCGTTTTC ACTCCTTTTA TTCCTAAACA GCTAGTTAAT   1500
ATAATCAACT TACCTGATGA TATACCTATT ACTTGTGCAT CAATAAACAG ATTAGAATAT   1560
GTTACACATA TAGATGATAA AAAATTAAAA AGAGTACTGA TTATCGTAAA GGATAAATTT   1620
CTTAGAAATA CTATTCTTCA CGGTACATTT AAAAAAAGGA ATATAGTCAG AAACAGGAAA   1680
TATACTTTCA CTATAACATG GTCTAATTTC GAATGTCCGA CGTTAGGAGA CGTTAAGTCT   1740
TCTTCACCTA ATACCTGTAA TAGAGTAGTT TTAGACGGTA GTAGATACGT TACAAAAACC   1800
TTTAATGATA CAATATAAAT GGAACTAACT AGAGAAACGC TGATATTTGT AGGCATTACT   1860
GTACTAGTAG TAGTAATGAT CATATCTGGT TTCTCACTAA TATTGCGATT GATACCTGGT   1920
GTATATTCAT CAGTTATTAG ATCGTCGTTC GTAGGAGGGA AAATATTAAG ATTTATGGAG   1980
GTATTCTCTA CTGTTATGTT TATACCATCA TTAGTAATAC TTTATACAGC ATATATAAGG   2040
AAATCTAAAG TGAAAAATAA CTAAATATTA TAGTATTTGT AATAAGTACT AATTAGCTAT   2100
```

-continued

```
AAAAACCCGG GCTCGAGATA AAAATTACTG GTCAGCCTTG CTTCTAGTCA CCATAGGGTG   2160
GGTACTCTTA CCTCCAGAGG CGGTGGGTTC CTCAGCACCA TCCTCCTCTT CCTCTGGGGC   2220
AACTTCCTCT ATCTCAGACA CTGGCTCAGA CTTGACAGAC ACAGTGTCCT CCCGCTCCTC   2280
CTGAGCACCC TCCTCCTCTT CCTCATCACT CTGCTCACTT TCTTCCTGAT CACTGTTCTC   2340
AGCCACAATT ACTGAGGACA GAGGGATAGT CGCGGGTACA GGGGACTCTG GGGGTGACAC   2400
CAGAGAATCA GAGGAGCTGA CACCAGCGGT GGCCAAAGTG TAGGCTACAA TAGCCTCTTC   2460
CTCATCTGAC TCCTCGGCGA TGGCCCGTAG GTCATCCACA CTAGGAGAGC AGACTCTCAG   2520
AGGATCGGCC CCCAGAATGT ACTGGGCAAA GACCTTCATG CAGATCTCCT CAATGCGGCG   2580
CTTCATTACA CTGATAACCT CAGGCTTGGT TATCAGAGGC CGCTTGGCCA GCATCACACT   2640
AGTCTCCTCT AAGACATAGC AGCACAGCAC CCGACAGAAC TCACTTAAGA GAGAGATGCC   2700
CCCGTACATG GTCATCATAC AAGCGTCACT AGTGACCTTG TACTCATTAC ACATTGTTTC   2760
CACACATGTA GTGAGGATAT CCATAAATAT GTGATCAATG TGCGTGAGCA CCTTGTCTCT   2820
CTCCTCATCC AAAATCTTAA ATATTTTCTG GGCATAAGCC ATAATCTCAT CAGGGGAGCA   2880
CTGAGGCAAG TTCTGCAGTG CCGCCATGGC CTGACTGCAG CCATTGGTGG TCTTAGGGAA   2940
GGCTGAGTTC TTGGTAAACA ACTCTATATT CCTGTAGCAC ATATACATCA TCTTTCTCCT   3000
AAGTTCATCC TTTTTAGCAC GGGCCTTAGC CTGCAGTGCA CCCCCCAACT TGTTAGCGGC   3060
GCCCTTGCTC ACATCATGCA GCTCCTTAAT ACAAGCCATC CACATCTCCC GCTTATCCTC   3120
AGGTACAATG TAGTTCTCAT ACATGCTCTG CATAGTTAGC CCAATACACT TCATCTCCTC   3180
GAAAGGCTCA TGAACCTTAT CTAAGATATC TAAGGCATTC TGCAAACATC CTCCCATCAT   3240
ATTAAAGGCG CCAGTGAATT TCTCTTCCGT CTGGGTATAT TTTTTCAGCA TGTGCTCCTT   3300
GATTCTATGC CGCACCATGT CCACTCGAAC CTTAATCTGT TTCATTACGA TACAAACTTA   3360
ACGGATATCG CGATAATGAA ATAATTTATG ATTATTTCTC GCTTTCAATT TAACACAACC   3420
CTCAAGAACC TTTGTATTTA TTTTCACTTT TTAAGTATAG AATAAAGAAG GATCCTTCTT   3480
TATTCTATAC TTAAAAAGTG AAAATAAATA CAAAGGTTCT TGAGGGTTGT GTTAAATTGA   3540
AAGCGAGAAA TAATCATAAA TTATTTCATT ATCGCGATAT CCGTTAAGTT TGTATCGTAA   3600
TGTGCCGCCG CCCGGATTGC GGCTTCTCTT TCTCACCTGG ACCGGTGGCA CTGCTGTGGT   3660
GTTGCCTTCT GCTGCCCATC GTTTCCTCAG CCACCGTCAG CGTCGCTCCT ACCGTCGCCG   3720
AGAAAGTTCC CGCGGAGTGC CCCGAACTAA CGCGTCGATG CCTGTTGGGT GAGGTGTTTC   3780
AGGGTGACAA GTATGAAAGT TGGCTGCGCC CGTTGGTGAA TGTTACCAGA CGCGATGGCC   3840
CGCTATCGCA ACTTATTCGT TACCGTCCCG TTACGCCGGA GGCCGCCAAC TCCGTGCTGT   3900
TGGACGATGC TTTCCTGGAC ACTCTGGCCC TGCTGTACAA CAATCCGGAT CAATTGCGGG   3960
CCTTGCTGAC GCTGTTGAGC TCGGACACAG CGCCGCGCTG GATGACGGTG ATGCGCGGTT   4020
ACAGCGAGTG CGGCGATGGC TCGCCGGCCG TGTACACGTG CGTGGACGAC CTGTGCCGCG   4080
GCTACGACCT CACGCGACTG TCATACGGGC GCAGCATCTT CACGGAACAC GTGTTAGGCT   4140
TCGAGCTGGT GCCACCGTCT CTCTTTAACG TGGTGGTGGC CATACGCAAC GAAGCCACGC   4200
GTACCAACCG CGCCGTGCGT CTGCCCGTGA GCACCGCTGC CGCGCCCGAG GGCATCACGC   4260
TCTTTTACGG CCTGTACAAC GCAGTGAAGG AATTCTGCCT GCGTCACCAG CTGGACCCGC   4320
CGCTGCTACG CCACCTAGAT AAATACTACG CCGGACTGCC GCCCGAGCTG AAGCAGACGC   4380
GCGTCAACCT GCCGGCTCAC TCGCGCTATG GCCCTCAAGC AGTGGATGCT CGCTAATTTT   4440
TATAGATCCC TCGAGGGTAC CGCATGCCCT TTTTATTGAC TAGTTAATCA GTCTAATATA   4500
```

-continued

CGTACTAAAT ACTTGTACGT ACAACTATGT TAGAATAATT TGCTTAGTAT AGTATATAAA 4560

CAAGTATGTA AAAAATAAAA TTGATATAAA AGTAGTCTTC TATTCCGAAC AATAACTATA 4620

CAAAATGGAT TTAGATATTA AATCTTGCAG AAGTATTTAC AAAATATGGG ATAAATATCA 4680

TTTTATGACA GGGTATAAAT ATAAAAATGA TAAACAGAGA TTTAAAATTA CAATTTACTG 4740

TAAATGTGAT TGTTCTATCA AAGAATATCC TTATAGATTT GTTACTGAGA AACTGCTTTT 4800

AATGTATATT ATTAATAAGT TTAGAGGAAA GTATCTAATC AAAATTAGGA TAGAACCCAT 4860

AGTTAAAAAT TAAATCATAT ATCAATACAT GTCAGTTTTT TATCGAAAAA TGGATTTATA 4920

AATAAAATGA AAAATAACTT GAATGAAGGA AAAAATAACC ATGAGTAAAA AACCAGTAAA 4980

GACGGTCCAG CGTAGACGTG GAAACGATGA GGATAATAAG TTTACTTGTA TCCAAGCGCT 5040

AGAACATGCA AAAAGCTTAT GTACTAAAAA TAATAAAATA GTTAAATCTG TTAAACTATC 5100

ACAATCTCTC TTTAAGTCAT CTAACAATAT TTCTGTGATA TTAGAACCAG AATATAAAGA 5160

CAAATTAGTG ACTCCTCTTA TTATTGTAGA AGGTGAAGGA AAAATATACC ATAATAAGAA 5220

TGATAGTTTT AATCGTGAAG AACCGTATTT TCTAAAAATA CGACCTACGT TAATGAATCC 5280

TATATTATAT CAGATTATGG AA 5302

(2) INFORMATION FOR SEQ ID NO:41:

(i) SEQUENCE CHARACTERISTICS:
(A) LENGTH: 2151 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:41:

ATGCGGCCAG GCCTCCCCTC CTACCTCATC GTCCTCGCCG TCTGTCTCCT CAGCCACCTA 60

CTTTCGTCAC GATATGGCGC AGAAGCCATA TCCGAACCGC TGGACAAAGC GTTTCACCTA 120

CTGCTCAACA CCTACGGGAG ACCCATCCGC TTCCTGCGTG AAAACACCAC CCAGTGTACC 180

TACAATAGCA GCCTCCGTAA CAGCACGGTC GTCAGGGAAA ACGCCATCAG TTTCAACTTT 240

TTCCAAAGCT ATAATCAATA CTATGTATTC CATATGCCTC GATGTCTTTT TGCGGGTCCT 300

CTGGCGGAGC AGTTTCTGAA CCAGGTAGAT CTGACCGAAA CCCTGGAAAG ATACCAACAG 360

AGACTTAACA CTTACGCGCT GGTATCCAAA GACCTGGCCA GCTACCGATC TTTTTCGCAG 420

CAGCTAAAGG CACAGGACAG CCTAGGTGAA CAGCCCACCA CTGTGCCACC ACCCATTGAC 480

CTGTCAATAC CTCACGTTTG GATGCCACCG CAAACCACTC CACACGGCTG GACAGAATCA 540

CATACCACCT CAGGACTACA CCGACCACAC TTTAACCAGA CCTGTATCCT CTTTGATGGA 600

CACGATCTAC TATTCAGCAC CGTCACACCT TGTTTGCACC AAGGCTTTTA CCTCATCGAC 660

GAACTACGTT ACGTTAAAAT AACACTGACC GAGGACTTCT TCGTAGTTAC GGTGTCCATA 720

GACGACGACA CACCCATGCT GCTTATCTTC GGCCATCTTC CACGCGTACT CTTTAAAGCG 780

CCCTATCAAC GCGACAACTT TATACTACGA CAAACTGAAA AACACGAGCT CCTGGTGCTA 840

GTTAAGAAAG ATCAACTGAA CCGTCACTCT TATCTCAAAG ACCCGGACTT TCTTGACGCC 900

GCACTTGACT TCAACTACCT GGACCTCAGC GCACTACTAC GTAACAGCTT TCACCGTTAC 960

GCCGTGGATG TACTCAAAAG CGGTCGATGT CAGATGCTGG ACCGCCGCAC GGTAGAAATG 1020

GCCTTCGCCT ACGCATTAGC ACTGTTCGCA GCAGCCCGAC AAGAAGAGGC CGGCGCCCAA 1080

GTCTCCGTCC CACGGGCCCT AGACCGCCAG GCCGCACTCT TACAAATACA AGAATTTATG 1140

-continued

```
ATCACCTGCC TCTCACAAAC ACCACCACGC ACCACGTTGC TGCTGTATCC CACGGCCGTG   1200

GACCTGGCCA AACGAGCCCT TTGGACACCG AATCAGATCA CCGACATCAC CAGCCTCGTA   1260

CGCCTGGTCT ACATACTCTC TAAACAGAAT CAGCAACATC TCATCCCCCA GTGGGCACTA   1320

CGACAGATCG CCGACTTTGC CCTAAAACTA CACAAAACGC ACCTGGCCTC TTTTCTTTCA   1380

GCCTTCGCGC GTCAAGAACT CTACCTCATG GGCAGCCTCG TCCACTCCAT GCTAGTACAT   1440

ACGACGGAGA GACGCGAAAT CTTCATCGTA GAAACGGGCC TCTGTTCATT AGCCGAGCTA   1500

TCACACTTTA CGCAGTTGCT AGCTCATCCG CACCACGAAT ACCTCAGCGA CCTGTACACA   1560

CCCTGTTCCA GTAGCGGGCG ACGCGATCAC TCGCTCGAAC GCCTCACACG TCTCTTCCCC   1620

GATGCCACCG TCCCCACTAC CGTTCCCGCC GCCCTCTCCA TCCTATCTAC CATGCAACCA   1680

AGCACGCTAG AAACCTTCCC CGACCTGTTT TGTCTGCCGC TCGGCGAATC CTTCTCCGCG   1740

CTGACCGTCT CCGAACACGT CAGTTATGTC GTAACAAACC AGTACCTGAT CAAAGGTATC   1800

TCCTACCCTG TCTCCACCAC CGTCGTAGGC CAGAGCCTCA TCATCACCCA GACGGACAGT   1860

CAAACTAAAT GCGAACTGAC GCGCAACATG CATACCACAC ACAGCATCAC AGCGGCGCTC   1920

AACATTTCCC TAGAAAACTG CGCCTTTTGC CAAAGCGCCC TACTAGAATA CGACGACACG   1980

CAAGGCGTCA TCAACATCAT GTACATGCAC GACTCGGACG ACGTCCTTTT CGCCCTGGAT   2040

CCCTACAACG AAGTGGTGGT CTCATCTCCG CGAACTCACT ACCTCATGCT TTTGAAAAAC   2100

GGTACGGTCC TAGAAGTAAC TGACGTCGTC GTGGACGCTA CCGACAGTCG T            2151
```

(2) INFORMATION FOR SEQ ID NO:42:

(i) SEQUENCE CHARACTERISTICS:
(A) LENGTH: 5062 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

```
AAGCTTGCGG CCGCTCATTA GACAAGCGAA TGAGGGACGA AAACGTGGAG GAGGTATTAA     60

GTTTGGAGAA ATGGAGAGAG ACTGTTTAAT AGCGCATGGC GCAGCCAATA CTATTACAGA    120

AGTTTTGAAA GATTCGGAAG AAGATTATCA AGATGTGTAT GTTTGTGAAA ATTGTGGAGA    180

CATAGCAGCA CAAATCAAGG GTATTAATAC ATGTCTTAGA TGTTCAAAAC TTAATCTCTC    240

TCCTCTCTTA ACAAAAATTG ATACCACGCA CGTATCTAAA GTATTTCTTA CTCAAATGAA    300

CGCCAGAGGC GTAAAAGTCA AATTAGATTT CGAACGAAGG CCTCCTTCGT TTTATAAACC    360

ATTAGATAAA GTTGATCTCA AGCCGTCTTT TCTGGTGTAA TAAAAATTAA TTAATTACTC    420

GAGATAAAAA TCAACGACTG TCGGTAGCGT CCACGACGAC GTCAGTTACT TCTAGGACCG    480

TACCGTTTTT CAAAAGCATG AGGTAGTGAG TTCGCGGAGA TGAGACCACC ACTTCGTTGT    540

AGGGATCCAG GGCGAAAAGG ACGTCGTCCG AGTCGTGCAT GTACATGATG TTGATGACGC    600

CTTGCGTGTC GTCGTATTCT AGTAGGGCGC TTTGGCAAAA GGCGCAGTTT TCTAGGGAAA    660

TGTTGAGCGC CGCTGTGATG CTGTGTGTGG TATGCATGTT GCGCGTCAGT TCGCATTTAG    720

TTTGACTGTC CGTCTGGGTG ATGATGAGGC TCTGGCCTAC GACGGTGGTG GAGACAGGGT    780

AGGAGATACC TTTGATCAGG TACTGGTTTG TTACGACATA ACTGACGTGT TCGGAGACGG    840

TCAGCGCGGA GAAGGATTCG CCGAGCGGCA GACAAAACAG GTCGGGGAAG GTTTCTAGCG    900

TGCTTGGTTG CATGGTAGAT AGGATGGAGA GGGCGGCGGG AACGGTAGTG GGGACGGTGG    960
```

-continued

CATCGGGGAA GAGACGTGTG AGGCGTTCGA GCGAGTGATC GCGTCGCCCG CTACTGGAAC 1020

AGGGTGTGTA CAGGTCGCTG AGGTATTCGT GGTGCGGATG AGCTAGCAAC TGCGTAAAGT 1080

GTGATAGCTC GGCTAATGAA CAGAGGCCCG TTTCTACGAT GAAGATTTCG CGTCTCTCCG 1140

TCGTATGTAC TAGCATGGAG TGGACGAGGC TGCCCATGAG GTAGAGTTCT TGACGCGCGA 1200

AGGCTGAAAG AAAAGAGGCC AGGTGCGTTT TGTGTAGTTT TAGGGCAAAG TCGGCGATCT 1260

GTCGTAGTGC CCACTGGGGG ATGAGATGTT GCTGATTCTG TTTAGAGAGT ATGTAGACCA 1320

GGCGTACGAG GCTGGTGATG TCGGTGATCT GATTCGGTGT CCAAAGGGCT CGTTTGGCCA 1380

GGTCCACGGC CGTGGGATAC AGCAGCAACG TGGTGCGTGG TGGTGTTTGT GAGAGGCAGG 1440

TGATCATAAA TTCTTGTATT TGTAAGAGTG CGGCCTGGCG GTCTAGGGCC CGTGGGACGG 1500

AGACTTGGGC GCCGGCCTCT TCTTGTCGGG CTGCTGCGAA CAGTGCTAAT GCGTAGGCGA 1560

AGGCCATTTC TACCGTGCGG CGGTCCAGCA TCTGACATCG ACCGCTTTTG AGTACATCCA 1620

CGGCGTAACG GTGAAAGCTG TTACGTAGTA GTGCGCTGAG GTCCAGGTAG TTGAAGTCAA 1680

GTGCGGCGTC AAGAAAGTCC GGGTCTTTGA GATAAGAGTG ACGGTTCAGT TGATCTTTCT 1740

TAACTAGCAC CAGGAGCTCG TGTTTTTCAG TTTGTCGTAG TATAAAGTTG TCGCGTTGAT 1800

AGGGCGCTTT AAAGAGTACG CGTGGAAGAT GGCCGAAGAT AAGCAGCATG GGTGTGTCGT 1860

CGTCTATGGA CACCGTAACT ACGAAGAAGT CCTCGGTCAG TGTTATTTTA ACGTAACGTA 1920

GTTCGTCGAT GAGGTAAAAG CCTTGGTGCA AACAAGGTGT GACGGTGCTG AATAGTAGAT 1980

CGTGTCCATC AAAGAGGATA CAGGTCTGGT TAAAGTGTGG TCGGTGTAGT CCTGAGGTGG 2040

TATGTGATTC TGTCCAGCCG TGTGGAGTGG TTTGCGGTGG CATCCAAACG TGAGGTATTG 2100

ACAGGTCAAT GGGTGGTGGC ACAGTGGTGG GCTGTTCACC TAGGCTGTCC TGTGCCTTTA 2160

GCTGCTGCGA AAAAGATCGG TAGCTGGCCA GGTCTTTGGA TACCAGCGCG TAAGTGTTAA 2220

GTCTCTGTTG GTATCTTTCC AGGGTTTCGG TCAGATCTAC CTGGTTCAGA AACTGCTCCG 2280

CCAGAGGACC CGCAAAAAGA CATCGAGGCA TATGGAATAC ATAGTATTGA TTATAGCTTT 2340

GGAAAAAGTT GAAACTGATG GCGTTTTCCC TGACGACCGT GCTGTTACGG AGGCTGCTAT 2400

TGTAGGTACA CTGGGTGGTG TTTTCACGCA GGAAGCGGAT GGGTCTCCCG TAGGTGTTGA 2460

GCAGTAGGTG AAACGCTTTG TCCAGCGGTT CGGATATGGC TTCTGCGCCA TATCGTGACG 2520

AAAGTAGGTG GCTGAGGAGA CAGACGGCGA GGACGATGAG GTAGGAGGGG AGCCCGGGCC 2580

GCATTTTATA TTGTAATTAT ATATTTTCAA TTTTGAAATC CCAAAATATT ATCATATTCT 2640

TCCCAATAAA CTCGAGGGTA CCGGATCCTT CTTTATTCTA TACTTAAAAA GTGAAAATAA 2700

ATACAAAGGT TCTTGAGGGT TGTGTTAAAT TGAAAGCGAG AAATAATCAT AAATTATTTC 2760

ATTATCGCGA TATCCGTTAA GTTTGTATCG TAATGTGCCG CCGCCCGGAT TGCGGCTTCT 2820

CTTTCTCACC TGGACCGGTG GCACTGCTGT GGTGTTGCCT TCTGCTGCCC ATCGTTTCCT 2880

CAGCCACCGT CAGCGTCGCT CCTACCGTCG CCGAGAAAGT TCCCGCGGAG TGCCCCGAAC 2940

TAACGCGTCG ATGCCTGTTG GGTGAGGTGT TTCAGGGTGA CAAGTATGAA AGTTGGCTGC 3000

GCCCGTTGGT GAATGTTACC AGACGCGATG GCCCGCTATC GCAACTTATT CGTTACCGTC 3060

CCGTTACGCC GGAGGCCGCC AACTCCGTGC TGTTGGACGA TGCTTTCCTG GACACTCTGG 3120

CCCTGCTGTA CAACAATCCG GATCAATTGC GGGCCTTGCT GACGCTGTTG AGCTCGGACA 3180

CAGCGCCGCG CTGGATGACG GTGATGCGCG GTTACAGCGA GTGCGGCGAT GGCTCGCCGG 3240

CCGTGTACAC GTGCGTGGAC GACCTGTGCC GCGGCTACGA CCTCACGCGA CTGTCATACG 3300

-continued

```
GGCGCAGCAT CTTCACGGAA CACGTGTTAG GCTTCGAGCT GGTGCCACCG TCTCTCTTTA   3360
ACGTGGTGGT GGCCATACGC AACGAAGCCA CGCGTACCAA CCGCGCCGTG CGTCTGCCCG   3420
TGAGCACCGC TGCCGCGCCC GAGGGCATCA CGCTCTTTTA CGGCCTGTAC AACGCAGTGA   3480
AGGAATTCTG CCTGCGTCAC CAGCTGGACC CGCCGCTGCT ACGCCACCTA GATAAATACT   3540
ACGCCGGACT GCCGCCCGAG CTGAAGCAGA CGCGCGTCAA CCTGCCGGCT CACTCGCGCT   3600
ATGGCCCTCA AGCAGTGGAT GCTCGCTAAT TTTTATAGAT CCCCCGGGAA TCGATTCGCG   3660
ATAGCTGATT AGTTTTTGTT AACAAAAATG TGGGAGAATC TAATTAGTTT TTCTTTACAC   3720
AATTGACGTA CATGAGTCTG AGTTCCTTGT TTTTGCTAAT TATTTCATCC AATTTATTAT   3780
TCTTGACGAT ATCGAGATCT TTTGTATAGG AGTCAGACTT GTATTCAACA TGCTTTTCTA   3840
TAATCATCTT AGTTATTTCG GCATCATCCA ATAGTACATT TTCCAGATTA ACAGAGTAGA   3900
TATTAATGTC GTATTTGAAC AGAGCCTGTA ACATCTCAAT GTCTTTATTA TCTATAGCCA   3960
ATTTAATGTC CGGAATGAAG AGAAGGGAAT TATTGGTGTT TGTCGACGTC ATATAGTCGA   4020
GCAAGAGAAT CATCATATCC ACGTGTCCAT TTTTTATAGT GGTGTGAATA CAACTAAGGA   4080
GAATAGCCAG ATCAAAAGTA GATGGTATTT CTGAAAGAAA GTATGATACA ATACTTACAT   4140
CATTAAGCAT GACGGCATGA TAAAATGAAG TTTTCCATCC AGTTTTCCCA TAGAACATCA   4200
GTCTCCAATT TTTCTTAAAC AGTTTCACCG TTTGCATGTT ACCACTATCA ACCGCATAAT   4260
ACAATGCGGT GTTTCCTTTG TCATCAAATT GTGAATCATC CATTCCACTG AATAGCAAAA   4320
TCTTTACTAT TTTGGTATCT TCTAATGTGG CTGCCTGATG TAATGGAAAT TCATTCTCTA   4380
GAAGATTTTT CAATGCTCCA GCGTTCAACA ACGTACATAC TAGACGCACG TTATTATCAG   4440
CTATTGCATA ATACAAGGCA CTATGTCCAT GGACATCCGC CTTAAATGTA TCTTTACTAG   4500
AGAGAAAGCT TTTCAGCTGC TTAGACTTCC AAGTATTAAT TCGTGACAGA TCCATGTCTG   4560
AAACGAGACG CTAATTAGTG TATATTTTTT CATTTTTTAT AATTTTGTCA TATTGCACCA   4620
GAATTAATAA TATCTCTAAT AGATCTAATT TAATTTAATT TATATAACTT ATTTTTTGAA   4680
TATACTTTTA ATTAACAAAA GAGTTAAGTT ACTCATATGG ACGCCGTCCA GTCTGAACAT   4740
CAATCTTTTT AGCCAGAGAT ATCATAGCCG CTCTTAGAGT TTCAGCGTGA TTTTCCAACC   4800
TAAATAGAAC TTCATCGTTG CGTTTACAAC ACTTTTCTAT TTGTTCAAAC TTTGTTGTTA   4860
CATTAGTAAT CTTTTTTTCC AAATTAGTTA GCCGTTGTTT GAGAGTTTCC TCATTGTCGT   4920
CTTCATCGGC TTTAACAATT GCTTCGCGTT TAGCCTCCTG GCTGTTCTTA TCAGCCTTTG   4980
TAGAAAAAAA TTCAGTTGCT GGAATTGCAA GATCGTCATC TCCGGGGAAA AGAGTTCCGT   5040
CCATTTAAAG CCGCGGGAAT TC                                             5062
```

(2) INFORMATION FOR SEQ ID NO:43:

(i) SEQUENCE CHARACTERISTICS:
(A) LENGTH: 3209 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:43:

```
TGAATGTTAA ATGTTATACT TTGGATGAAG CTATAAATAT GCATTGGAAA AATAATCCAT     60
TTAAAGAAAG GATTCAAATA CTACAAAACC TAAGCGATAA TATGTTAACT AAGCTTATTC    120
TTAACGACGC TTTAAATATA CACAAATAAA CATAATTTTT GTATAACCTA ACAAATAACT    180
```

-continued

```
AAAACATAAA AATAATAAAA GGAAATGTAA TATCGTAATT ATTTTACTCA GGAATGGGGT    240
TAAATATTTA TATCACGTGT ATATCTATAC TGTTATCGTA TACTCTTTAC AATTACTATT    300
ACGAATATGC AAGAGATAAT AAGATTACGT ATTTAAGAGA ATCTTGTCAT GATAATTGGG    360
TACGACATAG TGATAAATGC TATTTCGCAT CGTTACATAA AGTCAGTTGG AAAGATGGAT    420
TTGACAGATG TAACTTAATA GGTGCAAAAA TGTTAAATAA CAGCATTCTA TCGGAAGATA    480
GGATACCAGT TATATTATAC AAAAATCACT GGTTGGATAA AACAGATTCT GCAATATTCG    540
TAAAAGATGA AGATTACTGC GAATTTGTAA ACTATGACAA TAAAAAGCCA TTTATCTCAA    600
CGACATCGTG TAATTCTTCC ATGTTTTATG TATGTGTTTC AGATATTATG AGATTACTAT    660
AAACTTTTTG TATACTTATA TTCCGTAAAC TATATTAATC ATGAAGAAAA TGAAAAAGTA    720
TAGAAGCTGT TCACGAGCGG TTGTTGAAAA CAACAAAATT ATACATTCAA GATGGCTTAC    780
ATGTACGTCT GTGAGGCTAT CATGGATAAT GACAATGCAT CTCTAAATAG GTTTTTGGAC    840
AATGGATTCG ACCCTAACAC GGAATATGGT ACTCTACAAT CTCCTCTTGA AATGGCTGTA    900
ATGTTCAAGA ATACCGAGGC TATAAAAATC TTGATGAGGT ATGGAGCTAA ACCTGTAGTT    960
ACTGAATGCA CAACTTCTTG TCTGCATGAT GCGGTGTTGA GAGACGACTA CAAAATAGTA   1020
AAAGATCTGT TGAAGAATAA CTATGTAAAC AATGTTCTTT ACAGCGGAGG CTTTACTCCT   1080
TTGTGTTTGG CAGCTTACCT TAACAAAGTT AATTTGGTTA AACTTCTATT GGCTCATTCG   1140
GCGGATGTAG ATATTTCAAA CACGGATCGG TTAACTCCTC TACATATAGC CGTATCAAAT   1200
AAAAATTTAA CAATGGTTAA ACTTCTATTG AACAAAGGTG CTGATACTGA CTTGCTGGAT   1260
AACATGGGAC GTACTCCTTT AATGATCGCT GTACAATCTG GAAATATTGA AATATGTAGC   1320
ACACTACTTA AAAAAAATAA AATGTCCAGA ACTGGGAAAA ATTGATCTTG CCAGCTGTAA   1380
TTCATGGTAG AAAAGAAGTG CTCAGGCTAC TTTTCAACAA AGGAGCAGAT GTAAACTACA   1440
TCTTTGAAAG AAATGGAAAA TCATATACTG TTTTGGAATT GATTAAAGAA AGTTACTCTG   1500
AGACACAAAA GAGGTAGCTG AAGTGGTACT CTCAAAATGC AGAACGATGA CTGCGAAGCA   1560
AGAAGTAGAG AAATAACACT TTATGACTTT CTTAGTTGTA GAAAAGATAG AGATATAATG   1620
ATGGTCATAG ATAACTCTGA TATTGCAAGT AAATGCAATA ATAAGTTAGA TTTATTTAAA   1680
AGGATAGTTA AAAATAGAAA AAAAGAGTTA ATTTGTAGGG TTAAAATAAT ACATAAGATC   1740
TTAAAATTTA TAAATACGCA TAATAATAAA AATAGATTAT ACTTATTACC TTCAGAGATA   1800
AAATTTAAGA TATTTACTTA TTTAACTTAT AAAGATCTAA AATGCATAAT TTCTAAATAA   1860
TGAAAAAAAA GTACATCATG AGCAACGCGT TAGTATATTT TACAATGGAG ATTAACGCTC   1920
TATACCGTTC TATGTTTATT GATTCAGATG ATGTTTTAGA AAAGAAAGTT ATTGAATATG   1980
AAAACTTTAA TGAAGATGAA GATGACGACG ATGATTATTG TTGTAAATCT GTTTTAGATG   2040
AAGAAGATGA CGCGCTAAAG TATACTATGG TTACAAAGTA TAAGTCTATA CTACTAATGG   2100
CGACTTGTGC AAGAAGGTAT AGTATAGTGA AAATGTTGTT AGATTATGAT TATGAAAAAC   2160
CAAATAAATC AGATCCATAT CTAAAGGTAT CTCCTTTGCA CATAATTTCA TCTATTCCTA   2220
GTTTAGAATA CTTTTCATTA TATTTGTTTA CAGCTGAAGA CGAAAAAAAT ATATCGATAA   2280
TAGAAGATTA TGTTAACTCT GCTAATAAGA TGAAATTGAA TGAGTCTGTG ATAATAGCTA   2340
TAATCAGAGA AGTTCTAAAA GGAAATAAAA ATCTAACTGA TCAGGATATA AAAACATTGG   2400
CTGATGAAAT CAACAAGGAG GAACTGAATA TAGCTAAACT ATTGTTAGAT AGAGGGGCCA   2460
AAGTAAATTA CAAGGATGTT TACGGTTCTT CAGCTCTCCA TAGAGCTGCT ATTGGTAGGA   2520
AACAGGATAT GATAAAGCTG TTAATCGATC ATGGAGCTGA TGTAAACTCT TTAACTATTG   2580
```

-continued

CTAAAGATAA TCTTATTAAA AAAAAATAAT ATCACGTTTA GTAATATTAA AATATATTAA 2640

TAACTCTATT ACTAATAACT CCAGTGGATA TGAACATAAT ACGAAGTTTA TACATTCTCA 2700

TCAAAATCTT ATTGACATCA AGTTAGATTG TGAAAATGAG ATTATGAAAT TAAGGAATAC 2760

AAAAATAGGA TGTAAGAACT TACTAGAATG TTTTATCAAT AATGATATGA ATACAGTATC 2820

TAGGGCTATA AACAATGAAA CGATTAAAAA TTATAAAAAT CATTTCCCTA TATATAATAC 2880

GCTCATAGAA AAATTCATTT CTGAAAGTAT ACTAAGACAC GAATTATTGG ATGGAGTTAT 2940

AAATTCTTTT CAAGGATTCA ATAATAAATT GCCTTACGAG ATTCAGTACA TTATACTGGA 3000

GAATCTTAAT AACCATGAAC TAAAAAAAAT TTTAGATAAT ATACATTAAA AAGGTAAATA 3060

GATCATCTGT TATTATAAGC AAAGATGCTT GTTGCCAATA ATATACAACA GGTATTTGTT 3120

TTTATTTTTA ACTACATATT TGATGTTCAT TCTCTTTATA TAGTATACAC AGAAAATTCA 3180

TAATCCACTT AGAATTTCTA GTTATCTAG 3209

(2) INFORMATION FOR SEQ ID NO:44:

(i) SEQUENCE CHARACTERISTICS:
(A) LENGTH: 1483 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:44:

GGTACGTGAC TAATTAGCTA TAAAAAGGAT CTTAATTAAT TAGTCATCAG GCAGGGCGAG 60

AACGAGACTA TCTGCTCGTT AATTAATTAG GTCGACGGAT CCCCCGGGTT CTTTATTCTA 120

TACTTAAAAA GTGAAAATAA ATACAAAGGT TCTTGAGGGT TGTGTTAAAT TGAAAGCGAG 180

AAATAATCAT AAATTATTTC ATTATCGCGA TATCCGTTAA GTTTGTATCG TAATGGAGGA 240

GCCGCAGTCA GATCCTAGCG TCGAGCCCCC TCTGAGTCAG GAAACATTTT CAGACCTATG 300

GAAACTACTT CCTGAAAACA ACGTTCTGTC CCCCTTGCCG TCCCAAGCAA TGGATGATTT 360

GATGCTGTCC CCGGACGATA TTGAACAATG GTTCACTGAA GACCCAGGTC CAGATGAAGC 420

TCCCAGAATG CCAGAGGCTG CTCCCCGCGT GGCCCCTGGA CCAGCAGCTC CTACACCGGC 480

GGCCCCTGCA CCAGCCCCCT CCTGGCCCCT GTCATCTTCT GTCCCTTCCC AGAAAACCTA 540

CCAGGGCAGC TACGGTTTCC GTCTGGGCTT CTTGCATTCT GGGACAGCCA AGTCTGTGAC 600

TTGCACGTAC TCCCCTGCCC TCAACAAGAT GTTTTGCCAA CTGGCCAAGA CCTGCCCTGT 660

GCAGCTGTGG GTTGATTCCA CACCCCCGCC CGGCACCCGC GTCCGCGCCA TGGCCATCTA 720

CAAGCAGTCA CAGCACATGA CGGAGGTTGT GAGGCGCTGC CCCCACCATG AGCGCTGCTC 780

AGATAGCGAT GGTCTGGCCC CTCCTCAGCA TCTTATCCGA GTGGAAGGAA ATTTGCGTGT 840

GGAGTATTTG GATGACAGAA ACACTTTTCG ACATAGTGTG GTGGTGCCCT ATGAGCCGCC 900

TGAGGTTGGC TCTGACTGTA CCACCATCCA CTACAACTAC ATGTGTAACA GTTCCTGCAT 960

GGGCGGCATG AACCGGAGGC CCATCCTCAC CATCATCACA CTGGAAGACT CCAGTGGTAA 1020

TCTACTGGGA CGGAACAGCT TTGAGGTGCG TGTTTGTGCC TGTCCTGGGA GAGACCGGCG 1080

CACAGAGGAA GAGAATCTCC GCAAGAAAGG GGAGCCTCAC CACGAGCTGC CCCCAGGGAG 1140

CACTAAGCGA GCACTGCCCA ACAACACCAG CTCCTCTCCC CAGCCAAAGA AGAAACCACT 1200

GGATGGAGAA TATTTCACCC TTCAGATCCG TGGGCGTGAG CGCTTCGAGA TGTTCCGAGA 1260

GCTGAATGAG GCCTTGGAAC TCAAGGATGC CCAGGCTGGG AAGGAGCCAG GGGGGAGCAG 1320

-continued

```
GGCTCACTCC AGCCACCTGA AGTCCAAAAA GGGTCAGTCT ACCTCCCGCC ATAAAAAACT   1380

CATGTTCAAG ACAGAAGGGC CTGACTCAGA CTGAACGCGT TTTTATCCCG GGCTCGAGTC   1440

TAGAATCGAT CCCGGGTTTT TATGACTAGT TAATCACGGC CGC                     1483
```

(2) INFORMATION FOR SEQ ID NO:45:

(i) SEQUENCE CHARACTERISTICS:
(A) LENGTH: 1173 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:45:

```
ATGACTGCCA TGGAGGAGTC ACAGTCGGAT ATCAGCCTCG AGCTCCCTCT GAGCCAGGAG     60

ACATTTTCAG GCTTATGGAA ACTACTTCCT CCAGAAGATA TCCTGCCATC ACCTCACTGC    120

ATGGACGATC TGTTGCTGCC CCAGGATGTT GAGGAGTTTT TTGAAGGCCC AAGTGAAGCC    180

CTCCGAGTGT CAGGAGCTCC TGCAGCACAG GACCCTGTCA CCGAGACCCC TGGGCCAGTG    240

GCCCCTGCCC CAGCCACTCC ATGGCCCCTG TCATCTTTTG TCCCTTCTCA AAAAACTTAC    300

CAGGGCAACT ATGGCTTCCA CCTGGGCTTC CTGCAGTCTG GGACAGCCAA GTCTGTTATG    360

TGCACGTACT CTCCTCCCCT CAATAAGCTA TTCTGCCAGC TGGCGAAGAC GTGCCCTGTG    420

CAGTTGTGGG TCAGCGCCAC ACCTCCAGCT GGGAGCCGTG TCCGCGCCAT GGCCATCTAC    480

AAGAAGTCAC AGCACATGAC GGAGGTCGTG AGACGCTGCC CCCACCATGA GCGCTGCTCC    540

GATGGTGATG GCCTGGCTCC TCCCCAGCAT CTTATCCGGG TGGAAGGAAA TTTGTATCCC    600

GAGTATCTGG AAGACAGGCA GACTTTTCGC CACAGCGTGG TGGTACCTTA TGAGCCACCC    660

GAGGCCGGCT CTGAGTATAC CACCATCCAC TACAAGTACA TGTGTAATAG CTCCTGCATG    720

GGGGGCATGA ACCGCCGACC TATCCTTACC ATCATCACAC TGGAAGACTC CAGTGGGAAC    780

CTTCTGGGAC GGGACAGCTT TGAGGTTCGT GTTTGTGCCT GCCCTGGGAG AGACCGCCGT    840

ACAGAAGAAG AAAATTTCCG CAAAAAGGAA GTCCTTTGCC CTGAACTGCC CCCAGGGAGC    900

GCAAAGAGAG CGCTGCCCAC CTGCACAAGC GCCTCTCCCC CGCAAAAGAA AAAACCACTT    960

GATGGAGAGT ATTTCACCCT CAAGATCCGC GGGCGTAAAC GCTTCGAGAT GTTCCGGGAG   1020

CTGAATGAGG CCTTAGAGTT AAAGGATGCC CATGCTACAG AGGAGTCTGG AGACAGCAGG   1080

GCTCACTCCA GCTACCTGAA GACCAAGAAG GGCCAGTCTA CTTCCCGCCA TAAAAAAACA   1140

ATGGTCAAGA AAGTGGGGCC TGACTCAGAC TGA                                1173
```

(2) INFORMATION FOR SEQ ID NO:46:

(i) SEQUENCE CHARACTERISTICS:
(A) LENGTH: 1182 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:46:

```
ATGGAGGAGC CGCAGTCAGA TCCTAGCGTC GAGCCCCCTC TGAGTCAGGA AACATTTTCA     60

GACCTATGGA AACTACTTCC TGAAAACAAC GTTCTGTCCC CCTTGCCGTC CCAAGCAATG    120

GATGATTTGA TGCTGTCCCC GGACGATATT GAACAATGGT TCACTGAAGA CCCAGGTCCA    180
```

-continued

```
GATGAAGCTC CCAGAATGCC AGAGGCTGCT CCCCGCGTGG CCCCTGCACC AGCAGCTCCT    240
ACACCGGCGG CCCCTGCACC AGCCCCCTCC TGGCCCCTGT CATCTTCTGT CCCTTCCCAG    300
AAAACCTACC AGGGCAGCTA CGGTTTCCGT CTGGGCTTCT TGCATTCTGG GACAGCCAAG    360
TCTGTGACTT GCACGTACTC CCCTGCCCTC AACAAGATGT TTTGCCAACT GGCCAAGACC    420
TGCCCTGTGC AGCTGTGGGT TGATTCCACA CCCCCGCCCG GCACCCGCGT CCGCGCCATG    480
GCCATCTACA AGCAGTCACA GCACATGACG GAGGTTGTGA GGCGCTGCCC CCACCATGAG    540
CGCTGCTCAG ATAGCGATGG TCTGGCCCCT CCTCAGCATC TTATCCGAGT GGAAGGAAAT    600
TTGCGTGTGG AGTATTTGGA TGACAGAAAC ACTTTTCGAC ATAGTGTGGT GGTGCCCTAT    660
GAGCCGCCTG AGGTTGGCTC TGACTGTACC ACCATCCACT ACAACTACAT GTGTAACAGT    720
TCCTGCATGG GCGGCATGAA CCGGAGGCCC ATCCTCACCA TCATCACACT GGAAGACTCC    780
AGTGGTAATC TACTGGGACG GAACAGCTTT GAGGTGCGTG TTTGTGCCTG TCCTGGGAGA    840
GACCGGCGCA CAGAGGAAGA GAATCTCCGC AAGAAAGGGG AGCCTCACCA CGAGCTGCCC    900
CCAGGGAGCA CTAAGCGAGC ACTGCCCAAC AACACCAGCT CCTCTCCCCA GCCAAAGAAG    960
AAACCACTGG ATGGAGAATA TTTCACCCTT CAGATCCGTG GGCGTGAGCG CTTCGAGATG   1020
TTCCGAGAGC TGAATGAGGC CTTGGAACTC AAGGATGCCC AGGCTGGGAA GGAGCCAGGG   1080
GGGAGCAGGG CTCACTCCAG CCACCTGAAG TCCAAAAAGG GTCAGTCTAC CTCCCGCCAT   1140
AAAAAACTCA TGTTCAAGAC AGAAGGGCCT GACTCAGACT GA                      1182
```

(2) INFORMATION FOR SEQ ID NO:47:

(i) SEQUENCE CHARACTERISTICS:
(A) LENGTH: 2336 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:47:

```
TATAAATCTC CTAACGCCGT TCGGGCAGTC ACAGTCTTCG GATCGGACGC CGTGGAACGC     60
AGTTCTCAGC GAAGAAGGAC ACCGCCCGAC TCCAGAAGAC ACCGCTGCCC GAAGAAGAGA    120
AGACTTCATC GGTAAGAGAC CCAGCTTCTC CTCCCCGGAG CTTCGGCCAC GCCGCTCCAC    180
ACCCGGGAAC CGAGGCTTCG GAGCCCGATA CCCGGACAGA AGCTTCTCCC CGGCCGCTCC    240
ACATCAGGGA GCCTTGACCG GCGAGCCTGC TATCCGGGTA GAGACTGTCC TGCGGCCGCT    300
TCAGCAGCTC CACGATCGAC GACTGTGACC GTTGAGCCCG CCGTTTAGGC AGAGGCTCCG    360
CTTCAACTAC CCTACCGACA CATTCGCGGT TCTTCCTCCA GAACATCTTA CCCTCTACTC    420
GGCCACTCTA CAAGGACCGG TAATGGATCC AACTCTTTTC ACACAATCAA GACTTCTCAG    480
AGTGAATGAT TATGATGAAG TGCGTGAGTC GGTAAATCAA CCGAGACAGG AACAGCAGCC    540
AGGAGACAGG TGCCCTAGAC ATGTGGCAAG AATCATTGCC GAGAACGATC CTCCAATCAG    600
ATGTGACCTG ACTCTCCAAG AGCTATTGAG TGAGGTGCAG GTGGATTTCG AACCATCGGC    660
ATCAGAGGTC GTGGCAATGG AAGGCCTGAT GGACGAACAA CACTTCATTC CACATGATCC    720
ACATTCTAAA AAAGCAGCCG TTCAAAGTCT TGTAATTGCC ATCAAGACCG CGGACCTCCT    780
GTTGCAAATG ATACATGAGA ATGTTAAAAG AGACATCCGC ACGACATGCA TCCAAATGGC    840
TAATGAATCT TATGCACGTG CGGACATAGT CAGAGATTCA CTGATAGCAG CATCGCAAGG    900
AAAATACACA GCACTCGGGA AAATAGTATT CCACTCCTAT ACAAATTTCA TGCCAGTGAA    960
```

-continued

```
TGCAAATGAG TCCGAAAAGA GAGCATGGAT GGAAATGCTA GGCGAGTGTA CCAGCCATGG   1020

AAACAAGCTG TGTGAGATGG CAAATGCGCA AGTAGAGCAG GAGACGCGCG ATATAATCAA   1080

TATAATGTTC AAAAATATAG ATGATGTAGT CACACAAACA ACAAGAGCAA TGAGAGGCGT   1140

GTTCGATCCA CCTGACACAG TTAAAGCTCT CTCTGCCGCA GCCCAACTGA TCAGAGTATG   1200

GGAACATGAT AACGTTATAA ATGACCAAAG TGTGTCAACA TCTTCTGTCG TAACGGCTGC   1260

ATTGGAGGCT AACGAGAATT TGGCAAAGGC ACTTAGAGAT GTGTCAGGGT ACGCTGAGGT   1320

GCAATTTAAC AGATTATGCC TTTCTATACT AACATCGGCA AAGGAACGAA TAGACATAAT   1380

CTATCATTCG GCAAGGTCCC AACACCTCGC GTGCAATGTC AGGATGAACG TGGCACAACA   1440

AAACCTAGCA ACTTTCATCC TAACGAATGC CAGAGAGAGG CCAAATGATG CTGTGATCAG   1500

AACACGCAGA GCAGTTGCAA ATACAGGTAT ACTGCTGTTC ACAGGACAAC ATATCACAAG   1560

AGATGCTTTA GATAAAGCTG CAGAGTCAAA AAGTGTAGAA GAAATTGTAG GGATGTCAGT   1620

ACAGGCTAGA CAAGCGCTAG TTGAACAAGA TATGCCTCCA CTAGAGGGAG AAGGTGAGGA   1680

AGCTAGAGAG GAACATGCCG GAGAAGGACA GGCTAGAGAA GGACAGGCCG AAGAAGAACA   1740

GGCCGGAGAA TCTGCGGGAG ATGAGTCCGA AGATGAAGAT GGCGAAGGAA CAAGGTCTCT   1800

GGTCCGTGTG ATCAACATTC CACTCGCGCA ACCTCAGCCG ATAGTGGCGC ACGAGCCTCC   1860

ACCTCAGCCC CAAGAATCGG ATGACAGCGA TACCGAATCT GATGGCGAAG ATCCAATCGC   1920

TAGGCAACAG AATCCCACAC CAACACAAGA GAGCGAACCC ATAACCGAAG ATCCTGAAGA   1980

CTGGCCGGAC GCTCAGAGAC TGATAGAAGA GGAATCTAGC CAAGAAACAC CCCAAGAACC   2040

GGCATCTGAG CAAGAACCAT CCACACCAGG TCCACGCACT AGGAGACGCT CACACCCCCC   2100

AACTGAAGGT TCAGCACCCA AGAGAGGCAG GAGATCATAA GGTGCCAACC AATATCAAAC   2160

CGATCGGGGT ACCAATCATA TAAATCATAA ATGCCAGGAT ACCAATCACA TAATCATATC   2220

AATATGCATC AATAAAATTT TATAATCATA CTCAGAGGGA ACTGCCCACC CTCAATTACC   2280

TATTGATTTT ACAATATATA ATGTAACTGC AATTAATAAA GTACACATGT ACATGA       2336
```

(2) INFORMATION FOR SEQ ID NO:48:

(i) SEQUENCE CHARACTERISTICS:
(A) LENGTH: 2115 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:48:

```
TATAAATCTC CTAACGCCGT TCGGGCAGTC ACAGTCTTCG GATCGGACGC CGTGGAACGC     60

AGTTCTCAGC GAAGAAGGAC ACCGCCCGAC TCCAGAAGAC ACCGCTGCCC GAAGAAGAGA    120

AGACTTCATC GGTAAGAGAC CCAGCTTCTC CTCCCCGGAG CTTCGGCCAC GCCGCTCCAC    180

ACCCGGGAAC CGAGGCTTCG GAGCCCGATA CCCGGACAGA AGCTTCTCCC CGGCCGCTCC    240

ACATCAGGGA GCCTTGACCG GCGAGCCTGC TATCCGGGTA GAGACTGTCC TGCGGCCGCT    300

TCAGCAGCTC CACGATCGAC GACTGTGACC GTTGAGCCCG CCGTTTAGGC AGAGGCTCCG    360

CTTCAACTAC CCTACCGACA CATTCGCGGT TCTTCCTCCA GAACATCTTA CCCTCTACTC    420

GGCCACTCTA CAAGGACCGG TAATGGATCC AACTCTTTTC ACACAATCAA GACTTCTCAG    480

AGTGAATGAT TATGATGAAG TGCGTGAGTC GGTAAATCAA CCGAGACAGG AACAGCAGCC    540

AGGAGACAGG TGCCCTAGAC ATGTGGCAAG AATCATTGCC GAGAACGATC CTCCAATCAG    600
```

-continued

```
ATGTGACCTG ACTCTCCAAG AGCTATTGAG TGAGGTGCAG GTGGATTTCG AACCATCGGC    660

ATCAGAGGTC GTGGCAATGG AAGGCCTGAT GGACGAACAA CACTTCATTC CACATGATCC    720

ACATTCTAAA AAAGCAGCCG GGCCTAACGT GAGGCATATA GACATTGTTA CCGCAGCCGC    780

GTCGATGTCA GGGATATCCG GATCAACAGA GAGACCATTA GATGATGGAC AGAGACCCTT    840

AGCTGATGGA TGTTATAGCA AGAAACATAA GAAGCAGAAA CACAGCGAAC CTATAGACAC    900

CAAGGTGCAC ATCCAACGGG GGGAGGAAAC AGACTCTGAT TCAGACTCAG ACACCGGTAA    960

ATCACCGGGA TGCGATGAAA TATCTTTTTA CTTGTCCAGT GCTTCGGATG ATGAACATGG   1020

CAATGGGAAT CGTTCTGGGT TAGAAGGAAA TTGTAGTTCA TATACTTCAC ATTCATCACG   1080

TAGATCAAAA TCGCCGCTAA GAAGTCCTTC AAACAGGCCC CAAAAGAGAA AATTATGTAA   1140

GAATATGTTT ATTACAAAAA GCAAACGTAG GGTAATATGT GAATCTGATT CAGATACAGA   1200

CTCCGAAATC GAGACCAGGC CATTTATCAG ACCACAAGAA CCTCCCAGAC AAAAGAATAA   1260

GGGGAAAAGA TGTCCCAAGA AACATAGAAA GATAAAAGAG CTCATGGATG GGCCAGGATT   1320

CGTGGCTCCG AATGCACACA AACGAGGTAA AAATAGAAAT GAGGGAAACA ACGATGGACG   1380

AGGGAAACCG ACCACACGAG CTTTAGAATA CAAACAGATG CCATACAAAC AGCAAACGGT   1440

CCAGTTTCTC TATGGAAATG CGATAAGGAC ATGTAGAGAG AGCACCGTAC ACGATAAAAT   1500

TATTATGGTG ATGTTTACAC GGGGTCAAGA TATCAGGCAG GCCATAGAAA AGTTGAGATC   1560

CCAACTTGGT CAAATAACCA ACCTTTCCAT ATCTGCTCCC TTCAACACAG AACACACAAA   1620

ACCACAGATA CACACACCAA ACACGGTTAA CATGACATCG CAGGCACTTG CGGCAGGTCT   1680

TCAAGCCTCC TGGAACCTAG ACGAGGATAA TAAACACAAT AATGCACCTA GGATGTCAGA   1740

TTACAGAACC ATGATAATCC AAGCGGCAAC ACCACCAGAT TTTCTAGGTG CACTCAAACT   1800

ATGCATACAG TTCGCACAAA CCTTTCCCAA GAATGCGTGT ATAAGGTTAT GTAATATAGT   1860

TGGAGGCCTA CAACCCCTTC CCATCTACGA AAAAGTCGTC ACCGCTTACA CTGACACGCA   1920

ATATAACTTT AGCCCAATCA CTAACAAAGA TAGTAACGGT GGTATGAGCA CAATATTGGA   1980

TCAGGACTCC GATTCAGAAT AATGAAGAAA CTATCATATT AAATCGTGTA CATATTTTAT   2040

TAAACACTAT TTCCAACCAT GAGACGAGGC TTGTTGATGC AGCTGCTGTT CCTTGGAATA   2100

AATGTAATAT ACTGT                                                    2115
```

(2) INFORMATION FOR SEQ ID NO:49:

(i) SEQUENCE CHARACTERISTICS:
(A) LENGTH: 5275 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:49:

```
AAGCTTGCGG CCGCTCATTA GACAAGCGAA TGAGGGACGA AAACGTGGAG GAGGTATTAA     60

GTTTGGAGAA ATGGAGAGAG ACTGTTTAAT AGCGCATGGC GCAGCCAATA CTATTACAGA    120

AGTTTTGAAA GATTCGGAAG AAGATTATCA AGATGTGTAT GTTTGTGAAA ATTGTGGAGA    180

CATAGCAGCA CAAATCAAGG GTATTAATAC ATGTCTTAGA TGTTCAAAAC TTAATCTCTC    240

TCCTCTCTTA ACAAAAATTG ATACCACGCA CGTATCTAAA GTATTTCTTA CTCAAATGAA    300

CGCCAGAGGC GTAAAAGTCA AATTAGATTT CGAACGAAGG CCTCCTTCGT TTTATAAACC    360

ATTAGATAAA GTTGATCTCA AGCCGTCTTT TCTGGTGTAA TAAAAATTAA TTAATTACTC    420
```

-continued

```
GAGATAAAAA TTATGATCTC CTGCCTCTCT TGGGTGCTGA ACCTTCAGTT GGGGGGTGTG    480
AGCGTCTCCT AGTGCGTGGA CCTGGTGTGG ATGGTTCTTG CTCAGATGCC GGTTCTTGGG    540
GTGTTTCTTG GCTAGATTCC TCTTCTATCA GTCTCTGAGC GTCCGGCCAG TCTTCAGGAT    600
CTTCGGTTAT GGGTTCGCTC TCTTGTGTTG GTGTGGGATT CTGTTGCCTA GCGATTGGAT    660
CTTCGCCATC AGATTCGGTA TCGCTGTCAT CCGATTCTTG GGGCTGAGGT GGAGGCTCGT    720
GCGCCACTAT CGGCTGAGGT TGCGCGAGTG GAATGTTGAT CACACGGACC AGAGACCTTC    780
TTCCTTCGCC ATCTTCATCT TCGGACTCAT CTCCCGCAGA TTCTCCGGCC TGTTCTTCTT    840
CGGCCTGTCC TTCTCTAGCC TGTCCTTCTC CGGCATGTTC CTCTCTAGCT TCCTCACCTT    900
CTCCCTCTAG TGGAGGCATA TCTTGTTCAA CTAGCGCTTG TCTAGCCTGT ACTGACATCC    960
CTACAATTTC TTCTACACTT TTTGACTCTG CAGCTTTATC TAAAGCATCT CTTGTGATAT   1020
GTTGTCCTGT GAACAGCAGT ATACCTGTAT TTGCAACTGC TCTGCGTGTT CTGATCACAG   1080
CATCATTTGG CCTCTCTCTG GCATTCGTTA GGATGAAAGT TGCTAGGTTT TGTTGTGCCA   1140
CGTTCATCCT GACATTGCAC GCGAGGTGTT GGGACCTTGC CGAATGATAG ATTATGTCTA   1200
TTCGTTCCTT TGCCGATGTT AGTATAGAAA GGCATAATCT GTTAAATTGC ACCTCAGCGT   1260
ACCCTGACAC ATCTCTAAGT GCCTTTGCCA AATTCTCGTT AGCCTCCAAT GCAGCCGTTA   1320
CGACAGAAGA TGTTGACACA CTTTGGTCAT TTATAACGTT ATCATGTTCC CATACTCTGA   1380
TCAGTTGGGC TGCGGCAGAG AGAGCTTTAA CTGTGTCAGG TGGATCGAAC ACGCCTCTCA   1440
TTGCTCTTGT TGTTTGTGTG ACTACATCAT CTATATTTTT GAACATTATA TTGATTATAT   1500
CGCGCGTCTC CTGCTCTACT TGCGCATTTG CCATCTCACA CAGCTTGTTT CCATGGCTGG   1560
TACACTCGCC TAGCATTTCC ATCCATGCTC TCTTTTCGGA CTCATTTGCA TTCACTGGCA   1620
TGAAATTTGT ATAGGAGTGG AATACTATTT TCCCGAGTGC TGTGTATTTT CCTTGCGATG   1680
CTGCTATCAG TGAATCTCTG ACTATGTCCG CACGTGCATA AGATTCATTA GCCATTTGGA   1740
TGCATGTCGT GCGGATGTCT CTTTTAACAT TCTCATGTAT CATTTGCAAC AGGAGGTCCG   1800
CGGTCTTGAT GGCAATTACA AGACTTTGAA CGGCTGCTTT TTTAGAATGT GGATCATGTG   1860
GAATGAAGTG TTGTTCGTCC ATCAGGCCTT CCATTGCCAC GACCTCTGAT GCCGATGGTT   1920
CGAAATCCAC CTGCACCTCA CTCAATAGCT CTTGGAGAGT CAGGTCACAT CTGATTGGAG   1980
GATCGTTCTC GGCAATGATT CTTGCCACAT GTCTAGGGCA CCTGTCTCCT GGCTGCTGTT   2040
CCTGTCTCGG TTGATTTACC GACTCACGCA CTTCATCATA ATCATTCACT CTGAGAAGTC   2100
TTGATTGTGT GAAAAGAGTT GGATCCATTA CGATACAAAC TTAACGGATA TCGCGATAAT   2160
GAAATAATTT ATGATTATTT CTCGCTTTCA ATTTAACACA ACCCTCAAGA ACCTTTGTAT   2220
TTATTTTCAC TTTTTAAGTA TAGAATAAAG AAGAATTGGG TTTTGGGATT TCAAAATTGA   2280
AAATATATAA TTACAATATA AAATGGATCC AACTCTTTTC ACACAATCAA GACTTCTCAG   2340
AGTGAATGAT TATGATGAAG TGCGTGAGTC GGTAAATCAA CCGAGACAGG AACAGCAGCC   2400
AGGAGACAGG TGCCCTAGAC ATGTGGCAAG AATCATTGCC GAGAACGATC CTCCAATCAG   2460
ATGTGACCTG ACTCTCCAAG AGCTATTGAG TGAGGTGCAG GTGGATTTCG AACCATCGGC   2520
ATCAGAGGTC GTGGCAATGG AAGGCCTGAT GGACGAACAA CACTTCATTC CACATGATCC   2580
ACATTCTAAA AAAGCAGCCG GGCCTAACGT GAGGCATATA GACATTGTTA CCGCAGCCGC   2640
GTCGATGTCA GGGATATCCG GATCAACAGA GAGACCATTA GATGATGGAC AGAGACCCTT   2700
AGCTGATGGA TGTTATAGCA AGAAACATAA GAAGCAGAAA CACAGCGAAC CTATAGACAC   2760
CAAGGTGCAC ATCCAACGGG GGGAGGAAAC AGACTCTGAT TCAGACTCAG ACACCGGTAA   2820
```

-continued

```
ATCACCGGGA TGCGATGAAA TATCTTTTTA CTTGTCCAGT GCTTCGGATG ATGAACATGG   2880
CAATGGGAAT CGTTCTGGGT TAGAAGGAAA TTGTAGTTCA TATACTTCAC ATTCATCACG   2940
TAGATCAAAA TCGCCGCTAA GAAGTCCTTC AAACAGGCCC CAAAAGAGAA AATTATGTAA   3000
GAATATGTTT ATTACAAAAA GCAAACGTAG GGTAATATGT GAATCTGATT CAGATACAGA   3060
CTCCGAAATC GAGACCAGGC CATTTATCAG ACCACAAGAA CCTCCCAGAC AAAAGAATAA   3120
GGGGAAAAGA CGTCCCAAGA AACATAGAAA GATAACAGAG CTCATGGATG GGCCAGGATT   3180
CGTGGCTCCG AATGCACACA AACGAGGTAA AAATAGAAAT GAGGGAAACA ACGATGGACG   3240
AGGGAAACCG ACCACACGAG CTTTAGAATA CAAACAGATG CCATACAAAC AGCAAACGGT   3300
CCAGTTTCTC TATGGAAATG CGATAAGGAC ATGTAGAGAG AGCACCGTAC ACGATAAAAT   3360
TATTATGGTG ATGTTTACAC GGGGTCAAGA TATCAGGCAG GCCATAGAAA AGTTGAGATC   3420
CCAACTTGGT CAAATAACCA ACCTTTCCAT ATCTGCTCCC TTCAACACAG AACACACAAA   3480
ACCACAGATA CACACACCAA ACACGGTTAA CATGACATCG CAGGCACTTG CGGCAGGTCT   3540
TCAAGCCTCC TGGAACCTAG ACGAGGATAA TAAACACAAT AATGCACCTA GGATGTCAGA   3600
TTACAGAACC ATGATAATCC AAGCGGCAAC ACCACCAGAT TTTCTAGGTG CACTCAAACT   3660
ATGCATACAG TTCGCACAAA CCTTTCCCAA GAATGCGTGT ATAAGGTTAT GTAATATAGT   3720
TGGAGGCCTA CAACCCCTTC CCATCTACGA AAAAGTCGTC ACCGCTTACA CTGACACGCA   3780
ATATAACTTT AGCCCAATCA CTAACAAAGA TAGTAACGGT GGTATGAGCA CAATATTGGA   3840
TCAGGACTCC GATTCAGAAT AATTTTTATC GCGATAGCTG ATTAGTTTTT GTTAACAAAA   3900
ATGTGGGAGA ATCTAATTAG TTTTTCTTTA CACAATTGAC GTACATGAGT CTGAGTTCCT   3960
TGTTTTTGCT AATTATTTCA TCCAATTTAT TATTCTTGAC GATATCGAGA TCTTTTGTAT   4020
AGGAGTCAGA CTTGTATTCA ACATGCTTTT CTATAATCAT CTTAGTTATT TCGGCATCAT   4080
CCAATAGTAC ATTTTCCAGA TTAACAGAGT AGATATTAAT GTCGTATTTG AACAGAGCCT   4140
GTAACATCTC AATGTCTTTA TTATCTATAG CCAATTTAAT GTCCGGAATG AAGAGAAGGG   4200
AATTATTGGT GTTTGTCGAC GTCATATAGT CGAGCAAGAG AATCATCATA TCCACGTGTC   4260
CATTTTTTAT AGTGGTGTGA ATACAACTAA GGAGAATAGC CAGATCAAAA GTAGATGGTA   4320
TTTCTGAAAG AAAGTATGAT ACAATACTTA CATCATTAAG CATGACGGCA TGATAAAATG   4380
AAGTTTTCCA TCCAGTTTTC CCATAGAACA TCAGTCTCCA ATTTTTCTTA AACAGTTTCA   4440
CCGTTTGCAT GTTACCACTA TCAACCGCAT AATACAATGC GGTGTTTCCT TTGTCATCAA   4500
ATTGTGAATC ATCCATTCCA CTGAATAGCA AAATCTTTAC TATTTTGGTA TCTTCTAATG   4560
TGGCTGCCTG ATGTAATGGA AATTCATTCT CTAGAAGATT TTTCAATGCT CCAGCGTTCA   4620
ACAACGTACA TACTAGACGC ACGTTATTAT CAGCTATTGC ATAATACAAG GCACTATGTC   4680
CATGGACATC CGCCTTAAAT GTATCTTTAC TAGAGAGAAA GCTTTTCAGC TGCTTAGACT   4740
TCCAAGTATT AATTCGTGAC AGATCCATGT CTGAAACGAG ACGCTAATTA GTGTATATTT   4800
TTTCATTTTT TATAATTTTG TCATATTGCA CCAGAATTAA TAATATCTCT AATAGATCTA   4860
ATTTAATTTA ATTTATATAA CTTATTTTTT GAATATACTT TTAATTAACA AAAGAGTTAA   4920
GTTACTCATA TGGACGCCGT CCAGTCTGAA CATCAATCTT TTTAGCCAGA GATATCATAG   4980
CCGCTCTTAG AGTTTCAGCG TGATTTTCCA ACCTAAATAG AACTTCATCG TTGCGTTTAC   5040
AACACTTTTC TATTTGTTCA AACTTTCTTG TTACATTAGT AATCTTTTTT TCCAAATTAG   5100
TTAGCCGTTG TTTGAGAGTT TCCTCATTGT CGTCTTCATC GGCTTTAACA ATTGCTTCGC   5160
```

-continued

```
GTTTAGCCTC CTGGCTGTTC TTATCAGCCT TTGTAGAAAA AAATTCAGTT GCTGGAATTG   5220

CAAGATCGTC ATCTCCGGGG AAAAGAGTTC CGTCCATTTA AAGCCGCGGG AATTC        5275
```

(2) INFORMATION FOR SEQ ID NO:50:

(i) SEQUENCE CHARACTERISTICS:
(A) LENGTH: 1740 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:50:

```
ATGGAGTCCT CTGCCAAGAG AAAGATGGAC CCTGATAATC CTGACGAGGG CCCTTCCTCC     60

AAGGTGCCAC GGCCCGAGAC ACCCGTGACC AAGGCCACGA CGTTCCTGCA GACTATGTTG    120

AGGAAGGAGG TTAACAGTCA GCTGAGTCTG GGAGACCCGC TGTTTCCAGA GTTGGCCGAA    180

GAATCCCTCA AAACTTTTGA ACAAGTGACC GAGGATTGCA ACGAGAACCC CGAGAAAGAT    240

GTCCTGGCAG AACTCGGTGA CATCCTCGCC CAGGCTGTCA ATCATGCCGG TATCGATTCC    300

AGTAGCACCG GCCCCACGCT GACAACCCAC TTCCGCAGCG TTAGACGCGC CCCTCTTAAC    360

AAGCCGACCC CCACCAGCGT CGCGGTTACT AACACTCCTC TCCCCGGGGC ATCCGCTACT    420

CCCGAGCTCA GCCCGCGTAA GAAACCGCGC AAAACCACGC GTCCTTTCAA GGTGATTATT    480

AAACCGCCCG TGCCTCCCGC GCCTATCATG CTGCCCCTCA TCAAACAGGA AGACATCAAG    540

CCCGAGCCCG ACTTTACCAT CCAGTACCGC AACAAGATTA TCGATACCGC CGGCTGTATC    600

GTGATCTCTG ATAGCGAGGA AGAACAGGGT GAAGAAGTCG AAACCCGCGG TGCTACCGCG    660

TCTTCCCCTT CCACCGGCAG CGGCACGCCG CGAGTGACCT CTCCCACGCA CCCGCTCTCC    720

CAGATGAACC ACCCTCCTCT TCCCGATCCC TTGGGCCGGC CCGATGAAGA TAGTTCCTCT    780

TCGTCTTCCT CCTGCAGTTC GGCTTCGGAC TCGGAGAGTG AGTCCGAGGA GATGAAATGC    840

AGCAGTGGCG GAGGAGCATC CGTGACCTCG AGCCACCATG GGCGCGGCGG TTTTGGTGGC    900

GCGGCCTCCT CCTCTCTGCT GAGCTGCGGC CATCAGAGCA GCGGCGGGGC GAGCACCGGA    960

CCCCGCAAGA AGAAGAGCAA ACGCATCTCC GAGTTGGACA ACGAGAAGGT GCGCAATATC   1020

ATGAAAGATA AGAACACCCC CTTCTGCACA CCCAACGTGC AGACTCGGCG GGGTCGCGTC   1080

AAGATTGACG AGGTGAGCCG CATGTTCCGC AACACCAATC GCTCTCTTGA GTACAAGAAC   1140

CTGCCCTTCA CGATTCCCAG TATGCACCAG GTGTTAGATG AGGCCATCAA AGCCTGCAAA   1200

ACCATGCAGG TGAACAACAA GGGCATCCAG ATTATCTACA CCCGCAATCA TGAGGTGAAG   1260

AGTGAGGTGG ATGCGGTGCG GTGTCGCCTG GGCACCATGT GCAACCTGGC CCTCTCCACT   1320

CCCTTCCTCA TGGAGCACAC CATGCCCGTG ACACATCCAC CCAAAGTGGC GCAGCGCACA   1380

GCCGATGCTT GTAACGAAGG CGTCAAGGCC GCGTGGAGCC TCAAAGAATT GCACACCCAC   1440

CAATTATGCC CCCGTTCCTC CGATTACCGC AACATGATCA TCCACGCTGC CACCCCCGTG   1500

GACCTGTTGG GCGCTCTCAA CCTGTGCCTG CCCCTGATGC AAAAGTTTCC CAAACAGGTC   1560

ATGGTGCGCA TCTTCTCCAC CAACCAGGGT GGGTTCATGC TGCCTATCTA CGAGACGGCC   1620

ACGAAGGCCT ACGCCGTGGG GCAGTTTGAG CAGCCCACCG AGACCCCTCC CGAAGACCTG   1680

GACACCCTGA GCCTGGCCAT CGAGGCAGCC ATCCAGGACC TGAGGAACAA GTCTCAGTAA   1740
```

(2) INFORMATION FOR SEQ ID NO:51:

(i) SEQUENCE CHARACTERISTICS:

-continued (A) LENGTH: 56 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:51:

GCCTCATCGC TGCTGGATAT CCGTTAAGTT TGTATCGTAA TGGAATCCAG GATCTG 56

(2) INFORMATION FOR SEQ ID NO:52:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:52:

GACAGAGACT TGTGATTTTT ATAAGCTTCG TAAGCTGTCA 40

(2) INFORMATION FOR SEQ ID NO:53:

(i) SEQUENCE CHARACTERISTICS:
(A) LENGTH: 55 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

AGCTTCTTTA TTCTATACTT AAAAAGTGAA AATAAATACA AAGGTTCTTG AGGGT 55

(2) INFORMATION FOR SEQ ID NO:54:

(i) SEQUENCE CHARACTERISTICS:
(A) LENGTH: 73 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:54:

TGTGTTAAAT TGAAAGCGAG AAATAATCAT AAATTATTTC ATTATCGCGA TATCCGTTAA 60

GTTTGTATCG TAC 73

(2) INFORMATION FOR SEQ ID NO:55:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:55:

TTATTAGTAT TTAATAAAGT AATAGCGCTA TAGGCAATTC AAACATAGCA TGAGCT 56

(2) INFORMATION FOR SEQ ID NO:56:

(i) SEQUENCE CHARACTERISTICS:
(A) LENGTH: 72 base pairs
(B) TYPE: nucleic acid

-continued (C) STRANDEDNESS: single
(D) TOPOLOGY: linear (ii) MOLECULE TYPE: DNA (genomic)

(xi) SEQUENCE DESCRIPTION: SEQ ID NO:56:

AGAAATAAGA TATGAATTTT TCACTTTTAT TTATGTTTCC AAGAACTCCC AACACAATTT 60

AACTTTCGCT CT 72

(2) INFORMATION FOR SEQ ID NO:57:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:57:

GGTCGACGGA TCCT 14

(2) INFORMATION FOR SEQ ID NO:58:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:58:

GATCAGGATC CGTCGACCTG CA 22

(2) INFORMATION FOR SEQ ID NO:59:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:59:

CAGTTGGTAC CACTGGTATT TTATTTCAG 29

(2) INFORMATION FOR SEQ ID NO:60:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:60:

TATCTGAATT CCTGCAGCCC GGGTTTTTAT AGCTAATTAG TCAAATGTGA GTTAATATTA 60

G 61

(2) INFORMATION FOR SEQ ID NO:61:

(i) SEQUENCE CHARACTERISTICS:
(A) LENGTH: 66 base pairs
(B) TYPE: nucleic acid

-continued (C) STRANDEDNESS: single
(D) TOPOLOGY: linear (ii) MOLECULE TYPE: DNA (genomic)

(xi) SEQUENCE DESCRIPTION: SEQ ID NO:61:

TCGCTGAATT CGATATCAAG CTTATCGATT TTTATGACTA GTTAATCAAA TAAAAAGCAT 60

ACAAGC 66

(2) INFORMATION FOR SEQ ID NO:62:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:62:

TTATCGAGCT CTGTAACATC AGTATCTAAC 30

(2) INFORMATION FOR SEQ ID NO:63:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:63:

TCCGGTACCG CGGCCGCAGA TATTTGTTAG CTTCTGC 37

(2) INFORMATION FOR SEQ ID NO:64:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:64:

TCGCTCGAGT AGGATACCTA CCTACTACCT ACG 33

(2) INFORMATION FOR SEQ ID NO:65:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:65:

TCGCTCGAGC TTTCTTGACA ATAACATAG 29

(2) INFORMATION FOR SEQ ID NO:66:

(i) SEQUENCE CHARACTERISTICS:
(A) LENGTH: 30 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:66:

TAGGAGCTCT TTATACTACT GGGTTACAAC 30

(2) INFORMATION FOR SEQ ID NO:67:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:67:

AATTCCTCGA GGGATCC 17

(2) INFORMATION FOR SEQ ID NO:68:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:68:

CGGGATCCCT CGAGG 15

(2) INFORMATION FOR SEQ ID NO:69:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:69:

TCGGGATCCG GGTTAATTAA TTAGTTATTA GACAAGGTG 39

(2) INFORMATION FOR SEQ ID NO:70:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:70:

TAGGAATTCC TCGAGTACGA TACAAACTTA AGCGGATATC G 41

(2) INFORMATION FOR SEQ ID NO:71:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:71:

-continued

GGGCTGAAGC TTGCTGGCCG CTCATTAGAC AAGCGAATGA GGGAC 45

(2) INFORMATION FOR SEQ ID NO:72:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:72:

AGATCTCCCG GGCTCGAGTA ATTAATTAAT TTTTATTACA CCAGAAAAGA CGGCTTGAGA 60

TC 62

(2) INFORMATION FOR SEQ ID NO:73:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:73:

TAATTACTCG AGCCCGGGAG ATCTAATTTA ATTTAATTTA TATAACTCAT TTTTTGAATA 60

TACT 64

(2) INFORMATION FOR SEQ ID NO:74:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:74:

TATCTCGAAT TCCCGCGGCT TTAAATGGAC GGAACTCTTT TCCCCC 46

(2) INFORMATION FOR SEQ ID NO:75:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:75:

GATCTTTTGT TAACAAAAAC TAATCAGCTA TCGCGAATCG ATTCCCGGGG GATCCGGTAC 60

CC 62

(2) INFORMATION FOR SEQ ID NO:76:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:76:

TCGAGGGTAC CGGATCCCCC GGGAATCGAT TCGCGATAGC TGATTAGTTT TTGTTAACAA 60

AA 62

(2) INFORMATION FOR SEQ ID NO:77:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:77:

GATCCATGGA CTCGACAGCG GCGTCTCTGC ATGCAGCCGC TGCAGA 46

(2) INFORMATION FOR SEQ ID NO:78:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:78:

AGCTTCTGCA GCGGCTGCAT GCAGAGACGC CGCTGTCGAG TCCATG 46

(2) INFORMATION FOR SEQ ID NO:79:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:79:

TACGAATTCT GCAGTTCACC TATGACACGT TGC 33

(2) INFORMATION FOR SEQ ID NO:80:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:80:

ATAGGATCCA TGGTCGTCCA GACCCTTGAG GTAGGGC 37

(2) INFORMATION FOR SEQ ID NO:81:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:81:

-continued

GCCCTACCTC AAGGGTCTGG ACGACACTCG ACAGCGGCGT CTCTGCAT 48

(2) INFORMATION FOR SEQ ID NO:82:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:82:

AATTGGTGAC CG 12

(2) INFORMATION FOR SEQ ID NO:83:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:83:

GATCCGGTCA CC 12

(2) INFORMATION FOR SEQ ID NO:84:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:84:

TGAAAGACCG AATTCTGCGT 20

(2) INFORMATION FOR SEQ ID NO:85:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:85:

TGCGATTCAT CGGTTTGTTG TAGAT 25

(2) INFORMATION FOR SEQ ID NO:86:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:86:

GACCCTTGAG GTAGGGCGGC 20

-continued (2) INFORMATION FOR SEQ ID NO:87:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:87:

ACTCATAATA GAACCATAAG ATCTACAGAT GGCAACAAT 39

(2) INFORMATION FOR SEQ ID NO:88:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:88:

CCGAAGCTTT CAGCATGTCT TGAGCATGC 29

(2) INFORMATION FOR SEQ ID NO:89:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:89:

CTCAAGACAT GCTGATTTTT ATCTCGAGA 29

(2) INFORMATION FOR SEQ ID NO:90:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:90:

AGCTTCTCGA GATAAAAATC AGCATGTCTT GAGCATG 37

(2) INFORMATION FOR SEQ ID NO:91:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:91:

AATTCTCGAG TTTATTGGGA AGAATATGAT AATATTTTGG GATTTC 46

(2) INFORMATION FOR SEQ ID NO:92:

(i) SEQUENCE CHARACTERISTICS:
(A) LENGTH: 42 base pairs

-continued (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:92:

AAAATTGAAA ATATATAATT ACAATATAAA ATGCGGCCCG GG 42

(2) INFORMATION FOR SEQ ID NO:93:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:93:

GATCCCCGGG CCGCATTTTA TATTGTAATT ATAT 34

(2) INFORMATION FOR SEQ ID NO:94:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:94:

ATTTTCAATT TTGAAATCCC AAAATATTAT CATATTCTTC CCAATAAACT CGAG 54

(2) INFORMATION FOR SEQ ID NO:95:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:95:

TTAGAATTCC CCGGGCTCCC CTCCTACCTC ATCGT 35

(2) INFORMATION FOR SEQ ID NO:96:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:96:

TTACTGCAGT AAGTGTTAAG TCTCTGTTGG TATC 34

(2) INFORMATION FOR SEQ ID NO:97:

(i) SEQUENCE CHARACTERISTICS:
(A) LENGTH: 66 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:97:

AGAAAAATCA GTTAGCTAAG ATCTCCCGGG CTCGAGGGTA CCGGATCCTG ATTAGTTAAT 60

TTTTGT 66

(2) INFORMATION FOR SEQ ID NO:98:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:98:

GATCACAAAA ATTAACTAAT CAGGATCCGG TACCCTCGAG CCCGGGAGAT CTTAGCTAAC 60

TGATTTTTCT 70

(2) INFORMATION FOR SEQ ID NO:99:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:99:

ATCATCGAAT TCTGAATGTT AAATGTTATA CTTTG 35

(2) INFORMATION FOR SEQ ID NO:100:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:100:

GGGGGTACCT TTGAGAGTAC CACTTCAG 28

(2) INFORMATION FOR SEQ ID NO:101:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:101:

GGGTCTAGAG CGGCCGCTTA TAAAGATCTA AAATGCATAA TTTC 44

(2) INFORMATION FOR SEQ ID NO:102:

(i) SEQUENCE CHARACTERISTICS:
(A) LENGTH: 35 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:102:

ATCATCCTGC AGGTATTCTA AACTAGGAAT AGATG 35

(2) INFORMATION FOR SEQ ID NO:103:

(i) SEQUENCE CHARACTERISTICS:
(A) LENGTH: 82 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:103:

GTACGTGACT AATTAGCTAT AAAAAGGATC CGGTACCCTC GAGTCTAGAA TCGATCCCGG 60

GTTTTTATGA CTAGTTAATC AC 82

(2) INFORMATION FOR SEQ ID NO:104:

(i) SEQUENCE CHARACTERISTICS:
(A) LENGTH: 82 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:104:

GGCCGTGATT AACTAGTCAT AAAAACCCGG GATCGATTCT AGACTCGAGG GTACCGGATC 60

CTTTTTATAG CTAATTAGTC AC 82

(2) INFORMATION FOR SEQ ID NO:105:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:105:

GATCTTAATT AATTAGTCAT CAGGCAGGGC GAGAACGAGA CTATCTGCTC GTTAATTAAT 60

TAGGTCGACG 70

(2) INFORMATION FOR SEQ ID NO:106:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:106:

GATCCGTCGA CCTAATTAAT TAACGAGCAG ATAGTCTCGT TCTCGCCCTG CCTGATGACT 60

AATTAATTAA 70

(2) INFORMATION FOR SEQ ID NO:107:

(i) SEQUENCE CHARACTERISTICS:
(A) LENGTH: 12 base pairs

-continued (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:107:

AATTGCGGCC GC 12

(2) INFORMATION FOR SEQ ID NO:108:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:108:

ATAAAAATTA GCTACTCAGG TACCCTGCAG TCGCGAGGAT CCGAATTCCC CGGGCTCGAG 60

TGATTAATTA GTTTTTAT 78

(2) INFORMATION FOR SEQ ID NO:109:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:109:

ATAAAAACTA ATTAATCACT CGAGCCCGGG GAATTCGGAT CCTCGCGACT GCAGGGTACC 60

TGAGTAGCTA ATTTTTAT 78

(2) INFORMATION FOR SEQ ID NO:110:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:110:

ACGGATCCAT AAAAATTACT GGTCAGCCTT GCTTC 35

(2) INFORMATION FOR SEQ ID NO:111:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:111:

ATCCGTTAAG TTTGTATCGT AATGGAGTCC TCTGCCAAGA GA 42

(2) INFORMATION FOR SEQ ID NO:112:

(i) SEQUENCE CHARACTERISTICS:
(A) LENGTH: 44 base pairs

-continued (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:112:

CGCGAATTCT CGCGATATCC GTTAAGTTTG TATCGTAATG GAGT 44

(2) INFORMATION FOR SEQ ID NO:113:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:113:

GCCTCTAGAG TTAACCTCCT TCCTCAACAT 30

(2) INFORMATION FOR SEQ ID NO:114:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:114:

CGGTCTAGAG GTTATCAGTG TAATGAAGC 29

(2) INFORMATION FOR SEQ ID NO:115:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:115:

CCGAAGCTTC TCGAGATAAA AATTACTGGT CAGCCTTGCT TCTAGT 46

(2) INFORMATION FOR SEQ ID NO:116:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:116:

CGATATCCGT TAAGTTTGTA TCGTAATCTG CAGCCCGGGG GGG 43

(2) INFORMATION FOR SEQ ID NO:117:

(i) SEQUENCE CHARACTERISTICS:
(A) LENGTH: 44 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:117:

GATCCCCCGG GCTGCAGATT ACGATACAAA CTTAACGGAT ATCG 44

(2) INFORMATION FOR SEQ ID NO:118:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:118:

CGCGAATTCT CGCGATATCC GTTAAGTTTG TATCGTAATG AAACAGATTA AGGTTCGAGT 60

(2) INFORMATION FOR SEQ ID NO:119:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:119:

GCCTCTAGAT GCCGCCATGG CCTGACT 27

(2) INFORMATION FOR SEQ ID NO:120:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:120:

TCGGGATCCG GGTTAATTAA TTAGTCATCA GGCAGGGCG 39

(2) INFORMATION FOR SEQ ID NO:121:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:121:

TAGCTCGAGG GTACCTACGA TACAAACTTA ACGGATATCG 40

(2) INFORMATION FOR SEQ ID NO:122:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:122:

-continued

TCGGGATCCT TCTTTATTCT ATACTTA 27

(2) INFORMATION FOR SEQ ID NO:123:

(i) SEQUENCE CHARACTERISTICS:
(A) LENGTH: 72 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:123:

AATTCTCGCG ATATCCGTTA AGTTTGTATC GTAATGACGA CGTTCCTGCA GACTATGTTG 60

AGGAAGGAGG TT 72

(2) INFORMATION FOR SEQ ID NO:124:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:124:

AACCTCCTTC CTCAACATAG TCTGCAGGAA CGTCGTCATT ACGATACAAA CTTAACGGAT 60

ATCGCGAG 68

(2) INFORMATION FOR SEQ ID NO:125:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:125:

CCCCCCGAAT TCGTCGACGA TTGTTCATGA TGGCAAGAT 39

(2) INFORMATION FOR SEQ ID NO:126:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:126:

CCCGGGGGAT CCCTCGAGGG TACCAAGCTT AATTAATTAA ATATTAGTAT AAAAAGTGAT 60

TTATTTTT 68

(2) INFORMATION FOR SEQ ID NO:127:

(i) SEQUENCE CHARACTERISTICS:
(A) LENGTH: 77 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:127:

AAGCTTGGTA CCCTCGAGGG ATCCCCCGGG TAGCTAGCTA ATTTTTCTTT TACGTATTAT    60

ATATGTAATA AACGTTC    77

(2) INFORMATION FOR SEQ ID NO:128:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

TTTTTTCTGC AGGTAAGTAT TTTTAAAACT TCTAACACC    39

(2) INFORMATION FOR SEQ ID NO:129:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

GATTATCGCG ATATCCGTTA AGTTTGTATC GTAATGGCAT CCGTACTGGG TCCCATTTCG    60

GG    62

(2) INFORMATION FOR SEQ ID NO:130:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

GCATAGGTAC CGGATCCATA AAAATCAACC TCGGTGCTTT TTGGGCG    47

(2) INFORMATION FOR SEQ ID NO:131:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:131:

TAGTTCGGAT CCCCGCTCAG TCGCCTACA    29

(2) INFORMATION FOR SEQ ID NO:132:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:132:

ATCAAGGGAT CCATCGAAAA AGAAGAGCG                                              29

(2) INFORMATION FOR SEQ ID NO:133:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:133:

GATTATCGCG ATATCCGTTA AGTTTGTATC GTAATGGAGT CGCGCGGTCG CCGTTGTCCC            60

G                                                                            61

(2) INFORMATION FOR SEQ ID NO:134:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:134:

ACCTGCATCT TGGTTGC                                                           17

(2) INFORMATION FOR SEQ ID NO:135:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:135:

ATCATCGAGC TCGCGGCCGC CTATCAAAAG TCTTAATGAG TT                               42

(2) INFORMATION FOR SEQ ID NO:136:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:136:

GAATTCCTCG AGCTGCAGCC CGGGTTTTTA TAGCTAATTA GTCATTTTTT CGTAAGTAAG            60

TATTTTATTT AA                                                                72

(2) INFORMATION FOR SEQ ID NO:137:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:137:

CCCGGGCTGC AGCTCGAGGA ATTCTTTTTA TTGATTAACT AGTCAAATGA GTATATATAA 60

TTGAAAAAGT AA 72

(2) INFORMATION FOR SEQ ID NO:138:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:138:

GATGATGGTA CCTTCATAAA TACAAGTTTG ATTAAACTTA AGTTG 45

(2) INFORMATION FOR SEQ ID NO:139:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:139:

TTCGGATCCG GTTCTGGAGA AAAGCC 26

(2) INFORMATION FOR SEQ ID NO:140:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:140:

GCTTCCAAGC TTTCCTGAAG GGATTGTAAG CC 32

(2) INFORMATION FOR SEQ ID NO:141:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:141:

TTCGGATCCG GCTTTCAGTC TCGTCTCC 28

(2) INFORMATION FOR SEQ ID NO:142:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:142:

-continued

TTCGGATCCA TGCAATTGCC CGCGGACAAC 30

(2) INFORMATION FOR SEQ ID NO:143:

(i) SEQUENCE CHARACTERISTICS:
(A) LENGTH: 99 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:143:

TTCGAATTCG CTAGCTTTAT TGGGAAGAAT ATGATAATAT TTTGGGATTT CAAAATTGAA 60

AATATATAAT TACAATATAA AATGAGTTTG CAGTTTATC 99

(2) INFORMATION FOR SEQ ID NO:144:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:144:

TTCTCTAGAT GAGCTCGTTG AACAGCAC 28

(2) INFORMATION FOR SEQ ID NO:145:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:145:

CCGAAGCTTG CTAGCAATAA AAACTATTCC TCCGTGTTCT TAAT 44

(2) INFORMATION FOR SEQ ID NO:146:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:146:

GCCTCTAGAT ACGTAAAGCT AAGTTATC 28

(2) INFORMATION FOR SEQ ID NO:147:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:147:

GCCTCTAGAA TGTGCCGCCG CCCGGATTGC 30

-continued (2) INFORMATION FOR SEQ ID NO:148:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:148:

CGCAAGCTTA GCGAGCATCC ACTGCTTGAG GGC 33

(2) INFORMATION FOR SEQ ID NO:149:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:149:

TCCAAGCTTA GATCTATAAA AATTAGCGAG CATCCACTGC TTGAGGGCCA TAGC 54

(2) INFORMATION FOR SEQ ID NO:150:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:150:

GCCTCTAGAT GCTGACGCTG TTGAGCTCGG AC 32

(2) INFORMATION FOR SEQ ID NO:151:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:151:

CGCGAATTCT CGCGATATCC GTTAAGTTTG TATCGTAATG TGCCGCCGCC CGGATTGC 58

(2) INFORMATION FOR SEQ ID NO:152:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:152:

GCCTCTAGAT TCCAGCGCGG CGCTGTGTCC GAGC 34

(2) INFORMATION FOR SEQ ID NO:153:

(i) SEQUENCE CHARACTERISTICS:

-continued (A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:153:

GTACATAAGC TTTTTGCATG 20

(2) INFORMATION FOR SEQ ID NO:154:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:154:

TATGAATTCC TCGAGGGATC CAGGCCTTTT TTATTGACTA GTTAATCAGT CTAATATACG 60

TACTAAATAC 70

(2) INFORMATION FOR SEQ ID NO:155:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:155:

CTAATTTCGA ATGTCCGACG 20

(2) INFORMATION FOR SEQ ID NO:156:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:156:

TTAGAATTCT CGCGACCCGG GTTTTTATAG CTAATTAGTA CTTATTACAA ATACTATAAT 60

ATTTAG 66

(2) INFORMATION FOR SEQ ID NO:157:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:157:

AATTCGTCGA CGGATCCCTC GAGGGTACCG CATGC 35

(2) INFORMATION FOR SEQ ID NO:158:

(i) SEQUENCE CHARACTERISTICS:

-continued (A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:158:

GCATGCGGTA CCCTCGAGGG ATCCGTCGAC G 31

(2) INFORMATION FOR SEQ ID NO:159:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:159:

CCGAAGCTTC TCGAGATAAA AATCAACGAC TGTCGGTAGC GTCCACGACG AC 52

(2) INFORMATION FOR SEQ ID NO:160:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:160:

TCCACTCCAT GCTAGT 16

(2) INFORMATION FOR SEQ ID NO:161:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:161:

GATCTGACTG CGGCTCCTCC ATTACGATAC AAACTTAACG G 41

(2) INFORMATION FOR SEQ ID NO:162:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:162:

GTGGGTAAGG GAATTCGGAT CCCCGGGTTA ATTAATTAGT GATAC 45

(2) INFORMATION FOR SEQ ID NO:163:

(i) SEQUENCE CHARACTERISTICS:
(A) LENGTH: 34 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:163:

GTTTGTATCG TAATGGAGGA GCCGCAGTCA GATC 34

(2) INFORMATION FOR SEQ ID NO:164:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:164:

CATTACGATA CAAACTTAAC GGATATCGCG ACGCGTTCAC ACAGGGCAGG TCTTGGC 57

(2) INFORMATION FOR SEQ ID NO:165:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:165:

TACTACCTCG AGCCCGGGAT AAAAAACGCG TTCAGTCTGA GTCAGGCCC 49

(2) INFORMATION FOR SEQ ID NO:166:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:166:

GTGTGAACGC GTCGCGATAT CCGTTAAGTT TGTATCGTAA TGCAGCTGCG TGGGCGTGAG 60

CGCTTC 66

(2) INFORMATION FOR SEQ ID NO:167:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:167:

ATCATCGGAT CCCCCGGGTT CTTTATTCTA TAC 33

(2) INFORMATION FOR SEQ ID NO:168:

(i) SEQUENCE CHARACTERISTICS:
(A) LENGTH: 1511 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:168:

GATTAAAGAA AGTTACTCTG AGACACAAAA GAGGTAGCTG AAGTGGTACT CTCAAAGGTA 60

CCCCCGGGTT AATTAATTAG TCATCAGGCA GGGCGAGAAC GAGACTATCT GCTCGTTAAT 120

TAATTAGGTG ACGGATCCCC GGGTTCTTTA TTCTATACTT AAAAAGTGAA AATAAATACA 180

AAGGTTCTTG AGGGTTGTGT TAAATTGAAA GCGAGAAATA ATCATAAATT ATTTCATTAT 240

CGCGATATCC GTTAAGTTTG TATCGTAATG GAGGAGCCGC AGTCAGATCC TAGCGTCGAG 300

CCCCCTCTGA GTCAGGAAAC ATTTTCAGAC CTATGGAAAC TACTTCCTGA AAACAACGTT 360

CTGTCCCCCT TGCCGTCCCA AGCAATGGAT GATTTGATGC TGTCCCCGGA CGATATTGAA 420

CAATGGTTCA CTGAAGACCC AGGTCCAGAT GAAGCTCCCA GAATGCCAGA GGCTGCTCCC 480

CGCGTGGCCC CTGGACCAGC AGCTCCTACA CCGGCGGCCC CTGCACCAGC CCCCTCCTGG 540

CCCCTGTCAT CTTCTGTCCC TTCCCAGAAA ACCTACCAGG GCAGCTACGG TTTCCGTCTG 600

GGCTTCTTGC ATTCTGGGAC AGCCAAGTCT GTGACTTGCA CGTACTCCCC TGCCCTCAAC 660

AAGATGTTTT GCCAACTGGC CAAGACCTGC CCTGTGCAGC TGTGGGTTGA TTCCACACCC 720

CCGCCCGGCA CCCGCGTCCG CGCCATGGCC ATCTACAAGC AGTCACAGCA CATGACGGAG 780

GTTGTGAGGC GCTGCCCCCA CCATGAGCGC TGCTCAGATA GCGATGGTCT GGCCCCTCCT 840

CAGCATCTTA TCCGAGTGGA AGGAAATTTG CGTGTGGAGT ATTTGGATGA CAGAAACACT 900

TTTCGACATA GTGTGGTGGT GCCCTATGAG CCGCCTGAGG TTGGCTCTGA CTGTACCACC 960

ATCCACTACA ACTACATGTG TAACAGTTCC TGCATGGGCG GCATGAACCG GAGGCCCATC 1020

CTCACCATCA TCACACTGGA AGACTCCAGT GGTAATCTAC TGGGACGGAA CAGCTTTGAG 1080

GTGCGTGTTT GTGCCTGTCC TGGGAGAGAC CGGCGCACAG AGGAAGAGAA TCTCCGCAAG 1140

AAAGGGGAGC CTCACCACGA GCTGCCCCCA GGGAGCACTA AGCGAGCACT GCCCAACAAC 1200

ACCAGCTCCT CTCCCCAGCC AAAGAAGAAA CCACTGGATG GAGAATATTT CACCCTTCAG 1260

ATCCGTGGGC GTGAGCGCTT CGAGATGTTC CGAGAGCTGA ATGAGGCCTT GGAACTCAAG 1320

GATGCCCAGG CTGGGAAGGA GCCAGGGGGG AGCAGGGCTC ACTCCAGCCA CCTGAAGTCC 1380

AAAAAGGGTC AGTCTACCTC CCGCCATAAA AAACTCATGT TCAAGACAGA AGGGCCTGAC 1440

TCAGACTGAA CGCGTTTTTA TCCCGGGCTC GAGTCTAGAA TCGATCCCGG GTTTTTATGA 1500

CTAGTTAATC A 1511

(2) INFORMATION FOR SEQ ID NO:169:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:169:

ATTATTATTG GATCCTTAAT TAATTAGTGA TACGC 35

(2) INFORMATION FOR SEQ ID NO:170:

(i) SEQUENCE CHARACTERISTICS:
(A) LENGTH: 35 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:170:

CTCCTCCATG GCAGTCATTA CGATACAAAC TTAAC 35

(2) INFORMATION FOR SEQ ID NO:171:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:171:

CGTTAAGTTT GTATCGTAAT GACTGCCATG GAGGAGTC 38

(2) INFORMATION FOR SEQ ID NO:172:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:172:

TAGTAGTAGT AGTAGCTTCT GGAGGAAGTA GTTTCC 36

(2) INFORMATION FOR SEQ ID NO:173:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:173:

CAGAAGCTAC TACTACTACT ACCCACCTGC ACAAGCGCC 39

(2) INFORMATION FOR SEQ ID NO:174:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:174:

AACTACTGTC CCGGGATAAA AATCAGTCTG AGTCAGGCCC CAC 43

(2) INFORMATION FOR SEQ ID NO:175:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:175:

-continued

TAGATAAAGC TGCAGAGTCA 20

(2) INFORMATION FOR SEQ ID NO:176:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:176:

AGACTCGAGA TAAAAATTAT GATCTCCTGC CTCTCT 36

(2) INFORMATION FOR SEQ ID NO:177:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:177:

CGCAAGCTTC GCGATAAAAA TTATTCTGAA TCGGAGTCCT 40

(2) INFORMATION FOR SEQ ID NO:178:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:178:

ATGATAATCC AAGCGGCAAC A 21

(2) INFORMATION FOR SEQ ID NO:179:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:179:

CTAGAGGATC CATTTTATAT TGTAATTATA TATTTTCAAT TTTGAAATCC CAAAACCCGG 60

GAGATCTG 68

(2) INFORMATION FOR SEQ ID NO:180:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:180:

AATTCAGATC TCCCGGGTTT TGGGATTTCA AAATTGAAAA TATATAATTA CAATATAAAA 60

-continued

```
TGGATCCT                                                            68


(2) INFORMATION FOR SEQ ID NO:181:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:181:

ATCCGTTAAG TTTGTATCGT AATGGATCCT                                    30


(2) INFORMATION FOR SEQ ID NO:182:

     (i) SEQUENCE CHARACTERISTICS:
          (A) LENGTH: 34 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:182:

CTAGAGGATC CATTACGATA CAAACTTAAC GGAT                               34


(2) INFORMATION FOR SEQ ID NO:183:

     (i) SEQUENCE CHARACTERISTICS:
          (A) LENGTH: 57 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:183:

GCCTCTAGAC TCGAGCGCCG ACCAGTTCTC CATTACGATA CAAACTTAAC GGATATC      57


(2) INFORMATION FOR SEQ ID NO:184:

     (i) SEQUENCE CHARACTERISTICS:
          (A) LENGTH: 27 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:184:

CGCGAATTCT TCTTTATTCT ATACTTA                                       27
```

RESTENOSIS/ATHEROSCLEROSIS DIAGNOSIS, PROPHYLAXIS AND THERAPY

FIELD OF THE INVENTION

The present invention relates to compositions and methods for the diagnosis, prophylaxis and/or therapy of restenosis and/or atherosclerosis.

The present invention relates to the use of an agent for decreasing viral load, e.g., an immunological composition, preferably a vaccine, against cytomegalovirus and/or p53 for therapy for restenosis and/or atherosclerosis; and, to a method for providing therapy for restenosis and/or atherosclerosis comprising administering the agent for decreasing viral load, e.g., an immunological composition or vaccine, against cytomegalovirus (CMV) and/or p53.

"Viral load" and "virus load", as used herein, can have their art-recognized definitions, and can refer to active virus, e.g. virus in circulation or infectious, non-dormant virus, as well as virus which is latent or dormant awaiting reactivation or reactivating, or virus which is having an abortive replication cycle. While restenosing patients may not have any increase in IgG or IgM, Applicants, without wishing to necessarily be bound by any one particular theory, submit that viral reactivation following angioplasty/atherectomy can occur; and, that this viral reactivation, in some instances, may only proceed as far as the turn-on of IE genes and not up to viremia. Thus, "viral activation" is included in "viral load" and "virus load" herein. Further, "atherectomy" is included in "angioplasty" herein.

The CMV antigen can derive from any CMV protein, including immediate early (IE), early, or late gene products. The antigen can be the entire protein or an antigenic portion thereof.

The p53 can be wild-type or a mutant, e.g., full-length p53 or a truncated antigenic portion thereof.

The antigen(s) can be derived recombinantly, e.g., from expression by a virus, bacteria, or plasmid, in vitro, with subsequent isolation and purification; or from expression by a recombinant in vivo. Preferred expression systems include generally adenovirus, baculovirus, poxvirus, and DNA vector systems. For in vivo use, a recombinant adenovirus or poxvirus, such as a vaccinia virus or avipox virus (e.g., canarypox virus), or a DNA vector system are preferred; but, any suitable vector system, including naked DNA, may be employed. Indeed, as herpesvirus vectors are known, a replication-deficient herpesvirus vector, e.g., a replication-defective HSV or CMV vector could even be used in embodiments of the invention.

The invention thus relates to stimulating an immune response, preferably a cellular immune response, directed against CMV and/or p53 to inhibit or prevent restenosis and/or atherosclerosis and/or smooth muscle proliferation. Such a response can cause cell lysis and thus inhibition of smooth muscle cell proliferation and/or inhibition of atherosclerosis and/or restenosis. Thus, the invention relates to methods for inducing cell lysis of smooth muscle cells and/or inhibition of smooth muscle cell proliferation to treat or prevent restenosis and/or atherosclerosis.

The administration of the immunological composition or vaccine can be before or at the time of angioplasty, e.g., coronary and/or peripheral angioplasty, to prevent the development of restenosis, or independently of angioplasty, to provide treatment for atherosclerosis. It can also be administered any time during the lifetime of the individual, from childhood to adulthood, to prevent the development or progression of atherosclerosis. Thus, the invention relates to a therapeutic method for treatment of atherosclerosis and/or restenosis.

The immunological composition or vaccine can be administered alone or with additional therapeutic treatment; and, the invention further relates to additional methods for therapeutic treatment of restenosis and/or atherosclerosis.

The additional therapeutic treatment can comprise therapy for decreasing viral burden, e.g., the administration of: antioxidants which inhibit the replication of CMV and the cytopathic effect of viral infection, and/or compositions which reduce the transcriptional activity of CMV (transcriptional activity reducer) and/or compositions which decrease reactive oxygen species (ROS) generated by the arachidonic cascade and/or the xanthine/xanthine oxidase system (ROS reducer). Additionally or alternatively, the additional therapeutic treatment can comprise administration of an antiviral agent such as gancyclovir and/or acyclovir.

Thus, the invention still further relates to a method for treatment of atherosclerosis and/or restenosis comprising administering a sufficient dose or doses of at least one agent for decreasing viral burden and/or directed to interfering with SMC proliferation, e.g., antioxidant which inhibits the cytopathic effect of viral infection and/or transcriptional activity reducer and/or ROS reducer, either alone, or in conjunction with the aforementioned immunological composition or vaccine therapy.

The antioxidant can be one or more of Vitamin C, Vitamin E, NAC, PDTC, and the like.

The transcriptional activity reducer can be an antiviral drug such as gancyclovir and/or acyclovir (which interfere with viral replication), and/or an antioxidant, or the like.

The ROS reducer can be aspirin (acetylsalicylic acid) or a derivative thereof, ASA, Indomethacin, oxypurinol, and the like.

Accordingly, the invention additionally relates to a method for treating restenosis and/or atherosclerosis comprising, after angioplasty: administering a sufficient dose or doses of an immunological composition, preferably a vaccine, against CMV and/or p53; or administering a sufficient dose or doses of an immunological composition, preferably a vaccine, against CMV and/or p53, with or without a sufficient dose or doses of an antioxidant which inhibits viral infection and/or the cytopathic effect of viral infection and/or transcriptional activity reducer and/or ROS reducer; or administering a sufficient dose or doses of one or more antioxidant which inhibits viral replication and/or the cytopathic effect of viral infection and/or transcriptional activity reducer and/or ROS reducer.

The compositions administered after angioplasty can be used before angioplasty, to prevent, i.e., as a prophylaxis against, restenosis and/or atherosclerosis.

Accordingly, the invention relates to a method for preventing restenosis and/or atherosclerosis comprising, before angioplasty: administering a sufficient dose or doses of an immunological composition, preferably a vaccine, against CMV and/or p53; or administering a sufficient dose or doses of an immunological composition, preferably a vaccine, against CMV and/or p53 with or without a sufficient dose or doses of at least one composition for decreasing viral burden and/or directed to interfering with SMC proliferation, e.g., antioxidant which inhibits the cytopathic effect of viral infection and/or transcriptional activity reducer and/or ROS reducer; or administering a sufficient dose or doses of at least one agent for decreasing viral burden and/or directed to interfering with SMC proliferation, e.g., antioxidant which inhibits the cytopathic effect of viral infection and/or transcriptional activity reducer and/or ROS reducer. Thus, the invention can relate to treatment or prophylaxis directed at both decreasing viral loads, and decreasing SMC proliferation.

Interesting therapeutic or prophylactic compositions and methods of the invention relate to recombinants, especially for in vivo use, expressing a CMV antigen or portion thereof, or p53 or a portion thereof, or a combination of a CMV antigen or portion thereof and p53 or a portion thereof. These recombinants can additionally express or be used in conjunction with another form of molecular based therapy, e.g., expression of cytotoxic molecules to inhibit proliferation of smooth muscle cells, gene therapy, or antisense strategies to inhibit expression of gene products for cell proliferation. Thus, an embodiment can be providing treatment directed at decreasing viral load and treatment directed at reducing SMC proliferation.

Accordingly in certain aspects, the present invention relates to vaccine or immunological compositions for treatment or prophylaxis of restenosis and/or atherosclerosis, including compositions containing a CMV antigen or portion thereof, e.g., IE1, IE2, IE1 and IE2, or antigenic portions thereof or any other CMV antigens from IE, early, or late gene products, p53 or an antigenic portion thereof, or a CMV antigen or portion thereof and p53 or portion thereof. The present invention can include compositions containing naked DNA expressing the CMV antigen or protion thereof, or a recombinant or recombinants expressing the CMV antigen or portion thereof and/or p53 or an antigenic portion thereof or such an antigen or portion thereof from recombinant expression. The present invention further includes uses of such compositions with additional treatment or therapy, including compositions containing a recombinant or recombinants expressing a component of such additional treatment or therapy or co-expressing the component of such additional treatment or therapy with the CMV antigen or portion thereof and/or p53 or an antigenic portion thereof, and methods of making and using such compositions. Naked DNA or recombinants used in the present invention can be of varied type; for instance, one antigen or portion thereof or component of additional therapy may be expressed in one type of system, and another antigen or portion thereof or component of additional therapy (if present) may be from the same, or a different, system.

The method for diagnosis to ascertain a susceptibility to atherosclerosis and/or restenosis can comprise immunologically detecting CMV antibodies, either against the whole or any part of the virus, or preferably against specific viral proteins that more specifically reflect reactivation of the virus such as IE72, IE84, IE55 and the like. The immunologically detecting can be by ELISA and/or immunoblotting. Alternatively, detection can be for the CMV antigen.

The method can include, in addition or alternatively to detecting the neutralizing antibodies or antigens elicited thereby, detecting whether CMV mRNA is present in peripheral blood monocytes (PBMCs), e.g., by PCR (such as RT-PCR) and/or detecting whether a cellular-mediated immune response to CMV peptides or proteins is present, e.g., whether PBMCs recognize and/or respond to CMV peptides or proteins.

This aspect of the invention can relate to a skin test whereby the CMV proteins or peptides are administered subcutaneously or intradermally or intramuscularly, which reflects the patient's capacity to mount a cellular-mediated response targeted to the CMV proteins or peptides. A negative vs. a positive skin test for patients with prior CMV infection reflects the capacity to not develop, or to develop, respectively, a cell-mediated immune response to CMV. Such a test allows a prediction of who is susceptible and who is resistant to atherosclerosis and/or restenosis.

This aspect of the invention can relate more generally to presenting the patient's PBMCs with CMV proteins or peptides and measuring either the proliferative response of the cells or the cytokine profile to determine whether there is a dominant Th1 (e.g., IL-2, IFN-12, IFNγ) or Th2 (IL-4, IL-10) response.

This aspect of the invention can also relate to HLA phenotyping and/or HLA genotyping, as such phenotyping and/or genotyping can be used to predict the susceptibility to CMV-induced vascular disease.

This aspect of the invention can further relate to detection of p53. CMV interacts with p53 in smooth muscle cells (SMCs). p53 present in increased amounts binds to MHC Class I antigens in the SMCs and is processed and presented at the cell surface at an increased rate, resulting in stimulation of T cell response, underlying the antibody responses (whereas normal p53 is immunologically silent). Increased or steady state levels of p53 are present in cancers or when viral oncoproteins bind to p53 (as is the case with CMV).

Thus, the diagnostic method can comprise screening a sample from a patient (e.g., sera, blood, SMCs, etc.) for antibodies to CMV. The method can further comprise: screening a sample from a patient for specific viral proteins or antibodies thereto that are more specific predictors of whether the virus has been reactivated such as IE72, IE84, IE55 and the like; and/or detecting whether CMV mRNA is present in PBMCs, e.g., by PCR (such as RT-PCR); and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCs) or the cytokine profile; and/or HLA phenotyping and/or HLA genotyping; and optionally screening a sample from a patient (e.g., sera, blood, SMCS, lesions,) for p53.

The initial screening for antibodies to CMV may optionally be omitted, such that the diagnostic method can comprise: screening a sample from a patient for specific viral proteins that predict whether the virus has been reactivated such as IE72, IE84, IE55 and the like; and/or detecting whether CMV mRNA is present in PBMCs, e.g., by PCR (such as RT-PCR); and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCs) or the cytokine profile; and/or HLA phenotyping and/or HLA genotyping; and optionally screening a sample from a patient (e.g., sera, blood, SMCs, lesions, etc.) for p53.

The diagnostic method of the invention can also be used to test for stratification of atherosclerosis and/or restenosis risk factors.

The CMV proteins or peptides can be purified CMV proteins or peptides from lysates of cells previously infected with CMV, or from recombinant expression of the CMV proteins or peptides. Antibodies to such may also be used in diagnostic and therapeutic and/or preventative composition and methods of the invention. And, the CMV in the various aspects to which the invention pertains can be of any suitable cytomegalovirus, including, human CMV (HCMV) murine CMV (MCMV) or rat CMV (RCMV) origin, with HCMV and RCMV embodiments preferred.

Various documents are cited in the following text, or in a reference section preceding the claims. Each of the documents cited herein, and each of the references cited in each of those various documents, is hereby incorporated herein by reference. None of the documents cited in the following text is admitted to be prior art with respect to the present invention.

BACKGROUND OF THE INVENTION

As discussed generally by Jean Marx at page 320 of Science, Vol. 265 (Jul. 15, 1994), each year about 330,000 patients in the United States undergo coronary and/or peripheral angioplasty, a procedure designed to open up blood vessels, e.g., coronary arteries, clogged by dangerous atherosclerotic plaques (atherosclerosis) and thereby restore normal blood flow. For a majority of these patients, the operation works as intended. Nearly 33% of these patients (and maybe more by some accounts), however, develop restenosis, wherein the treated arteries become quickly clogged again. These patients are no better off, and sometimes worse off, than they were before angioplasty. Excessive proliferation of smooth muscle cells in blood vessel walls contributes to restenosis.

Improvements in the therapy, prophylaxis and diagnosis of restenosis and/or atherosclerosis, especially in compositions therefore and methods thereof, would be an advance over the state of the art.

In 1950, Patterson and Cottral, in Arch. Pathol. 1950; 49:699, called attention to the development of coronary atherosclerosis in chickens ill with Marek's lymphomatosis, the etiological agent of which was subsequently discovered to be a herpesvirus now known as Marek's Disease Virus.

Melnick et al. in European Heart Journal (1993) 14 (Supplement K), 30–38, and BioEssays Vol. 17, No. 10 pp. 899–903 (1995) report that the finding in chickens prompted studies of human herpesviruses with respect to human atherosclerosis.

In Melnick et al., European Heart Journal, supra, circumstantial evidence for involvement of CMV is presented. This evidence includes finding CMV antigen and nucleic acid sequences in arterial smooth muscle cells of humans, seroepidemiological studies showing high levels of CMV antibodies found associated with clinically manifest atherosclerotic disease, suggesting that a periodically activated latent infection or a continuously active infection is present in patients with atherosclerosis. However, the viral genome, but not the infectious virus, was found in arterial cells, leading the authors to assert that the artery itself may be the site of CMV latency. The authors caution that their observations do not demonstrate that viruses have a role in the pathogenesis of atherosclerosis.

In Melnick et al., BioEssays, supra, the authors report that antigens and nucleic acid sequences of CMV, a widespread member of the herpesvirus family, were found in arterial lesions in human atherosclerosis; but, infectious virus has not been observed. In atherosclerosis patients, high levels of CMV antibodies are present, suggesting the presence of virus that had been activated from a latent state.

There is no teaching or suggestion in Melnick et al., BioEssays, supra, of any particular CMV vaccine or any particular strategy for treatment, prevention or diagnosis of restenosis or atherosclerosis.

Speir et al., Science 265:391–394 (Jul. 15, 1994) postulate that restenosis may be triggered by activation of latent CMV, e.g., by angioplasty-induced injury to the vessel wall, that causes multiple cellular changes and predispose SMCs to proliferate. For instance, Speir et al. postulate that CMV protein IE84 combines with and inactivates p53 in smooth muscle cells, which, in turn could predispose the cells towards increased growth, analogous to the way p53 inactivation is believed to contribute to the formation of malignant tumors. This CMV-mediated inhibition of p53, assert Speir et al., may in part explain the monoclonality observed in some atherosclerotic lesions (see Benditt and Benditt, PNAS USA 70: 1753 (1973)).

As Jean Marx, supra, observed, the Speir et al. hypothesis is just one of many potential mechanisms by which the virus may produce restenotic lesions. Jean Marx, supra, further observed that CMV activation cannot explain all cases of restenosis, as signs of a CMV-p53 interaction have not been found in about 67% of the restenosis samples.

Golubev et al., U.S. Pat. No. 5,534,258 (not admitted to be prior art), relates to four polypeptides from certain herpesviruses; specifically two polypeptides from HSV-1, and two polypeptides from CMV. Golubev et al., without any data, speculates that this shotgun approach of a combination of all four of these polypeptides, in equal proportion, is a prophylactic vaccine against pathogenic development of atherosclerotic plaque. No protection data is presented.

Literature involving CMV and/or restenosis and/or atherosclerosis, as discussed above likewise fails to teach or suggest any therapy or prophylaxis or any detection methods, or any compositions therefor, for restenosis and/or atherosclerosis, as in the present invention. Indeed, heretofore there had not been a definitive teaching or suggestion in the art of a relation between the presence of antibodies to CMV at the time of angioplasty, indicating prior exposure to CMV, and the subsequent development of restenosis. And, even if, assuming arguendo (with no admission), one asserted some sort of teaching or suggestion of any relation between CMV or antibodies thereto and restenosis and/or atherosclerosis, there is still a failure to teach or suggest any therapy or prophylaxis or any detection methods, or any compositions therefor, for restenosis and/or atherosclerosis, as in the present invention.

It would indeed be an advance in the art to show a connection between CMV and restenosis and/or atherosclerosis, especially mechanisms involving the virus, including such as the virus, by inhibiting either the capacity of p53 to block cell cycle progression, or its capacity to initiate apoptosis, enhances SMC accumulation and thereby facilitates development of restenotic lesions, as herein.

Indeed, it is believed that heretofore there has been no evidence linking viremia and angioplasty, such as balloon angioplasty, and subsequent restenosis in humans, e.g., no boost of immune response, such that there is a fortiori no teaching or suggestion of any prophylaxis or treatment for restenosis and/or atherosclerosis or compositions therefor or methods for making such compositions.

OBJECTS AND SUMMARY OF THE INVENTION

It is therefore an object of the invention to provide methods and compositions for the diagnosis of, prophylaxis of and/or therapy for restenosis and/or atherosclerosis.

It is yet a further object of the invention to provide such methods and compositions for prophylaxis and/or therapy which comprise an agent for decreasing viral load, e.g., a vaccine or immunological compositions.

It is a still further object of the invention to provide such methods and compositions including gene products from in vitro and/or in vivo expression from plasmid DNA, or a vector system, such as a recombinant viral and/or DNA expression system.

It is yet another object to provide such methods and compositions wherein the gene products comprise a CMV antigen, e.g., IE1 and/or IE2 or a portion thereof; gB; gB with transmembrane deleted therefrom; gH; gL; pp150; pp65; IE1 with amino acids 2–32 deleted therefrom; IE1 with amino acids 292–319 deleted therefrom; IE1 exon 4 segment; gB and gH; gB and pp65; gB, gH and pp65; gB, gH, pp65 and IE1 exon 4 segment; gB, gH, pp65, pp150, and IE1 exon 4 segment; gB, gH, pp65 and pp150; gB, gH, gL, pp65, pp150and IE1 exon 4 segment; and gB, gH, gL, pp65 and pp150; gp64; or portion of such CMV antigens; or p53 or a portion thereof, or a CMV antigen or portion thereof and p53 or a portion thereof; and, such a portion thereof can be an antigenic portion; for instance, an epitope of interest.

It is a yet further object of the invention to provide such methods and compositions in conjunction with additional treatment methods and compositions.

It is another object of the invention to provide diagnostic methods and compositions.

It is a further object of the invention to provide such diagnostic methods and compositions, including screening a sample from a patient for specific viral proteins or antibodies thereto that predict whether the virus has been reactivated such as IE72, IE84, IE55 and the like; and/or detecting whether CMV nucleic acid such as mRNA is present in PBMCs, e.g., by PCR (such as RT-PCR); and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCs) or the cytokine profile; and/or HLA phenotyping and/or HLA genotyping; and optionally screening a sample from a patient (e.g., sera, blood, SMCs, lesions, etc.) for p53; with optional initial screening for antibodies to CMV, which may optionally be omitted.

It is yet another object of the invention to demonstrate a relation between the presence of antibodies to CMV at the time of angioplasty, indicating prior exposure to CMV, and the subsequent development of restenosis.

It is a still further object of the invention to provide compositions and methods arising as a consequence of demonstrating that there is such a relation.

It is still another object of the invention to show a connection between CMV and restenosis and/or atherosclerosis, especially mechanisms involving the virus, including such as the virus, by inhibiting either the capacity of p53 to block cell cycle progression, or its capacity to initiate apoptosis, enhances SMC accumulation and thereby facilitates development of restenotic lesions.

It is even a still further object of the invention to provide compositions and methods arising as a consequence of demonstrating that there is such a connection and/or mechanisms.

The present invention thus provides methods and compositions for the diagnosis of, prophylaxis of and/or therapy for restenosis and/or atherosclerosis.

The present invention further provides such methods and compositions for prophylaxis and/or therapy which comprise compositions for decreasing viral burden, e.g., vaccine or immunological compositions.

The present invention also provides such methods and compositions including gene products from in vitro and/or in vivo expression from plasmid DNA, a vector system, such as a recombinant viral or DNA expression system.

The present invention additionally provides such methods and compositions wherein the gene products comprise a CMV antigen, e.g., IE1 and/or IE2, or other viral gene products or portion thereof, or p53 or a portion thereof, or a CMV antigen or portion thereof and p53 or a portion thereof; and, such a portion thereof can be an antigenic portion; for instance, an epitope of interest.

The present invention even further provides such methods and compositions in conjunction with additional treatment methods and compositions.

The present invention thus provides an immunological composition, preferably a vaccine, against cytomegalovirus and/or p53 for therapy for restenosis and/or atherosclerosis; and, a method for providing therapy for restenosis and/or atherosclerosis comprising administering the immunological composition or vaccine against cytomegalovirus (CMV) and/or p53.

The CMV antigen can be IE1 or an antigenic portion thereof, IE2 or an antigenic portion thereof, or, or another CMV gene product or an antigenic portion thereof, wherein the antigenic portion can be an epitope of interest; and, can be of any suitable origin, e.g., human CMV, murine CMV or rat CMV origin, with human CMV (HCMV) preferred.

The p53 can be wild-type or a mutant, e.g., full-length p53 or a truncated antigenic portion thereof; again, wherein the antigenic portion can be an epitope of interest.

The antigen(s) can be derived recombinantly, e.g., from expression by a virus, bacteria, or plasmid, in vitro, with subsequent isolation and purification; or from expression by a recombinant or plasmid in vivo. Preferred vector systems include plasmid DNA, adenovirus, baculovirus, poxvirus, and DNA expression systems. For in vivo use, plasmid DNA, a recombinant adenovirus or poxvirus, such as a vaccinia virus or avipox virus (e.g., canarypox virus), or a DNA expression system are preferred; but, any suitable vector system, including may be employed. Thus, as herpesvirus vectors are known, a replication-deficient herpesvirus vector, e.g., a replication-defective HSV or CMV vector could even be used in embodiments of the invention.

The invention thus provides compositions and methods for stimulating an immune response, preferably a cellular immune response, directed against CMV and/or p53 to inhibit or prevent restenosis and/or atherosclerosis and/or smooth muscle proliferation. Such a response can cause lysis of infected cells thereby eliminating virus or reducing virus load, and thus inhibit smooth muscle cell proliferation and/or restenosis and/or atherosclerosis. Thus, the invention provides methods and compositions for inducing cell lysis of infected smooth muscle cells and/or inhibition of smooth muscle cell proliferation to treat or prevent restenosis and/or atherosclerosis.

The administration of the immunological composition or vaccine can be after angioplasty, coronary and/or peripheral angioplasty, to prevent the development of, or to provide treatment for, atherosclerosis and/or restenosis. Thus, the invention provides a therapeutic method for treatment of atherosclerosis and/or restenosis, and compositions therefor.

The immunological composition or vaccine can be administered alone or with additional therapeutic treatment; and, the invention further provides additional methods and compositions for therapeutic treatment of restenosis and/or atherosclerosis.

The additional therapeutic treatment can comprise the administration of: antioxidants which inhibit the cytopathic effect of viral infection, and/or compositions which reduce the transcriptional activity of CMV (transcriptional activity reducer) and/or compositions which decrease reactive oxygen species (ROS) generated by the arachidonic cascade and/or the xanthine/xanthine oxidase system (ROS reducer).

Thus, the invention still further provides to a method for treatment of atherosclerosis and/or restenosis comprising administering a sufficient dose or doses of at least one antioxidant which inhibits the cytopathic effect of viral infection and/or transcriptional activity reducer and/or ROS reducer, either alone, or in conjunction with the aforementioned immunological composition or vaccine therapy; and, the invention provides such compositions.

The antioxidant can be one or more of Vitamin C, Vitamin E, NAC, PDTC, and the like.

The transcriptional activity reducer can be an antiviral drug such as gancyclovir and/or acyclovir (which interfere with viral replication), and/or an antioxidant, or the like.

The ROS reducer can be aspirin (acetylsalicylic acid) or a derivative thereof, ASA, oxypurinol, and the like.

Accordingly, the invention additionally provides a method for treating restenosis and/or atherosclerosis comprising, before, during or after angioplasty, or at any time during the lifetime of the individual, from childhood to adulthood, to prevent the development or progression of atherosclerosis: administering a sufficient dose or doses of an immunological composition, preferably a vaccine, against CMV and/or p53; or administering a sufficient dose or doses of an immunological composition, preferably a vaccine, against CMV and/or p53 in conjunction with a sufficient dose or doses of at least one antioxidant which inhibits replication and the cytopathic effect of viral infection and/or transcriptional activity reducer and/or ROS reducer; or administering a sufficient dose or doses of at least one antioxidant which inhibits replication and the cytopathic effect of viral infection and/or transcriptional activity reducer and/or ROS reducer. And, the invention provides compositions for these methods.

The compositions are administered before, during, or after angioplasty; before angioplasty, to prevent, i.e., as a prophylaxis against, restenosis and/or atherosclerosis. They can also be administered any time during the lifetime of the individual, from childhood to adulthood, to prevent the development or progression of atherosclerosis.

Accordingly, the invention provides a method for preventing restenosis and/or atherosclerosis comprising, before, during, or after angioplasty to prevent, e.g., as a prophylaxis against restenosis and/or atherosclerosis, or at any time during the lifetime of the individual, from childhood to adulthood, to prevent the development or progression of atherosclerosis: administering a sufficient dose or doses of an immunological composition, preferably a vaccine, against CMV and/or p53; or administering a sufficient dose or doses of an immunological composition, preferably a vaccine, against CMV and/or p53 in conjunction with a sufficient dose or doses of at least one antioxidant which inhibits the cytopathic effect of viral infection and/or transcriptional activity reducer and/or ROS reducer; or administering a sufficient dose or doses of at least one antioxidant which inhibits the cytopathic effect of viral infection and/or transcriptional activity reducer and/or ROS reducer. And, the invention provides compositions for these methods.

The invention further provides therapeutic or prophylactic compositions and methods of the invention relating to plasmid DNA or recombinants, especially for in vivo use, expressing a CMV antigen or portion thereof, or p53 or a portion thereof, or a combination of a CMV antigen or portion thereof and p53 or a portion thereof; and, these recombinants can additionally express or be used in conjunction with another form of molecular based therapy, e.g., expression of cytotoxic molecules to proliferating smooth muscle cells, gene therapy, or antisense strategies to inhibit expression of gene products for cell proliferation. The invention can provide compositions and methods directed at reducing viral load and inhibiting SMC proliferation.

Accordingly in certain aspects, the present invention provides vaccine or immunological compositions for treatment or prophylaxis of restenosis and/or atherosclerosis, including compositions containing a CMV antigen or portion thereof, e.g., IE1, IE2, IE2 and IE2, or antigenic portions thereof, p53 or an antigen portion thereof, a CMV antigen or portion thereof and p53 or portion thereof, such as compositions containing a recombinant or recombinants expressing the CMV antigen or portion thereof and/or p53 or antigenic portion thereof or such an antigen or portion thereof from recombinant expression, uses of such compositions with additional treatment or therapy, including compositions containing a recombinant or recombinants expressing a component of such additional treatment or therapy or co-expressing the component of such additional treatment or therapy with the CMV antigen or portion thereof and/or p53 or antigenic portion thereof, and methods of making and using such compositions (wherein a portion of an antigen can be an epitope of interest).

Recombinants used in the present invention can be of varied type; for instance, one antigen or portion thereof or component of additional therapy may be expressed in one type of system, and another antigen or portion thereof or component of additional therapy (if present) may be from the same, or a different, system.

Plasmid DNA or recombinants of the present invention can have in vivo expression at any suitable level for treatment and/or prophylaxis of restenosis and/or atherosclerosis, which can be determined by the skilled artisan without undue experimentation.

Recombinants can be administered in an amount of about $10^7$ pfu; thus, the inventive compositions can contain, and the inventive methods involve, administering a composition containing recombinant(s), at least this amount; more preferably about $10^4$ pfu to about $10^{10}$ pfu, e.g., about $10^5$ pfu to about $10^9$ pfu, for instance about $10^6$ pfu to about $_{10}{}^8$ pfu. And, if more than one gene product is expressed by more than one recombinant, each recombinant can be administered in these amounts; or, each recombinant can be administered such that there is, in combination, a sum of recombinants comprising these amounts.

In naked DNA and DNA plasmid compositions, the dosage should be a sufficient amount of naked DNA or DNA plasmid to elicit a response analogous to the expressed antigen compositions; or expression analogous to dosages in expressed antigen compositions; or expression analogous to expression obtained in vivo by other, e.g., viral, recombinant compositions. For instance, suitable quantities of naked DNA or plasmid DNA in naked DNA or DNA plasmid compositions can be 1 ug to 100 mg, preferably 0.1 to 10 mg, but lower levels such as 0.1 to 2 mg or even 1–10 ug, may be employed.

And, if more than one gene product is expressed by more than one recombinant and/or DNA (naked or plasmid) system, each recombinant and/or DNA system can be administered in these amounts; or, each recombinant and/or DNA system can be administered such that there is, in combination, a sum of recombinants and/or DNA comprising these amounts.

Subcutaneous, intradermal or intramuscular administration are presently preferred.

The present invention includes diagnostic methods and compositions.

The present invention also provides such diagnostic methods and compositions, including screening a sample from a patient for specific viral proteins or antibodies thereto that predict whether the virus has been reactivated such as IE72, IE84, IE55 and the like; and/or detecting whether CMV nucleic acid, e.g., mRNA is present in PBMCS, e.g., by PCR (such as reverse transcriptase or RT-PCR); and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCs) or the cytokine profile; and/or HLA phenotyping and/or HLA genotyping; and optionally screening a sample from a patient (e.g., sera, blood, SMCs, lesions, etc.) for p53; with initial screening for antibodies to CMV or proteins from CMV, which may optionally be omitted.

The diagnostic method of the invention can also be used to test for stratification of atherosclerosis and/or restenosis risk factors.

The present invention includes demonstrating a relation between the presence of antibodies to CMV at the time of angioplasty, indicating prior exposure to CMV, and the subsequent development of restenosis.

The present invention also provides compositions and methods arising as a consequence of demonstrating that there is such a relation.

The present invention includes a showing of a connection between CMV and restenosis and/or atherosclerosis, especially mechanisms involving the virus, including such as the virus, by inhibiting either the capacity of p53 to block cell cycle progression, or its capacity to initiate apoptosis, enhances SMC accumulation and thereby facilitates development of restenotic lesions.

The present invention additionally provides compositions and methods arising as a consequence of demonstrating that there is such a connection and/or mechanisms.

The invention further comprehends methods for preparing the compositions of the invention.

These and other embodiments are disclosed or are obvious from and encompassed by, the following Detailed Description.

BRIEF DESCRIPTION OF FIGURES

The following Detailed Description, given by way of example, but not intended to limit the invention to specific embodiments described, may be understood in conjunction with the accompanying Figures, incorporated herein by reference, in which.

Figure 7:
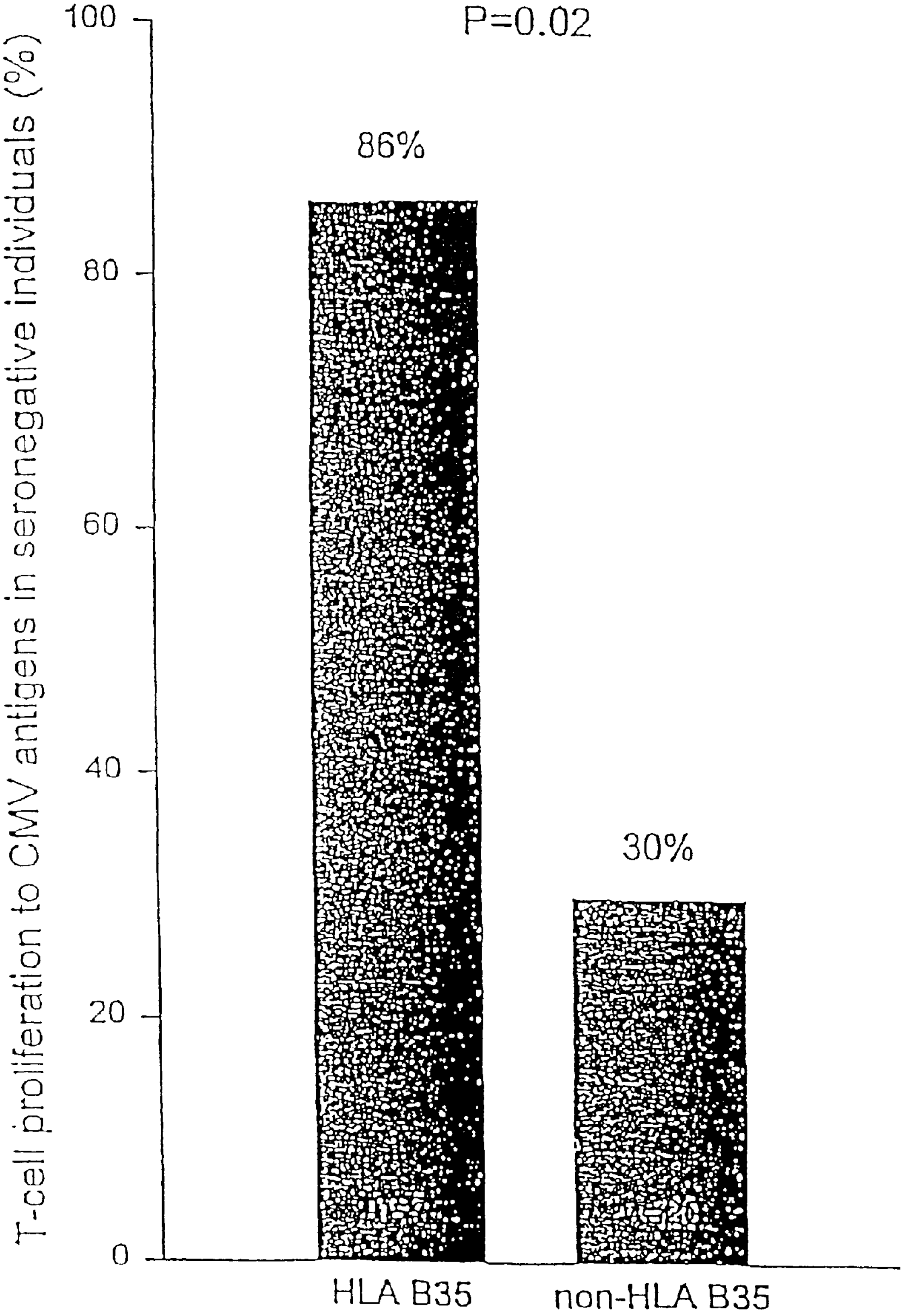
Figure 45:
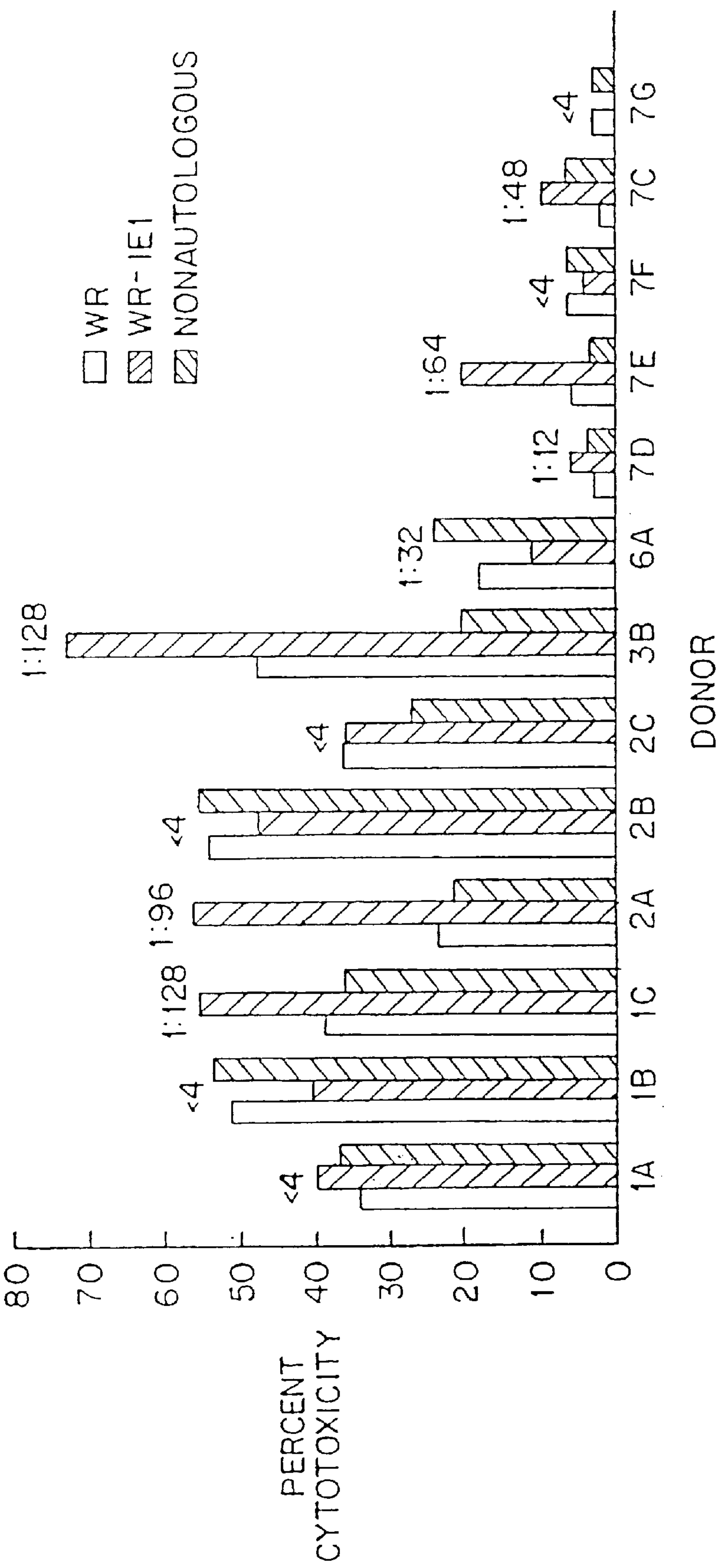
Figure 46:
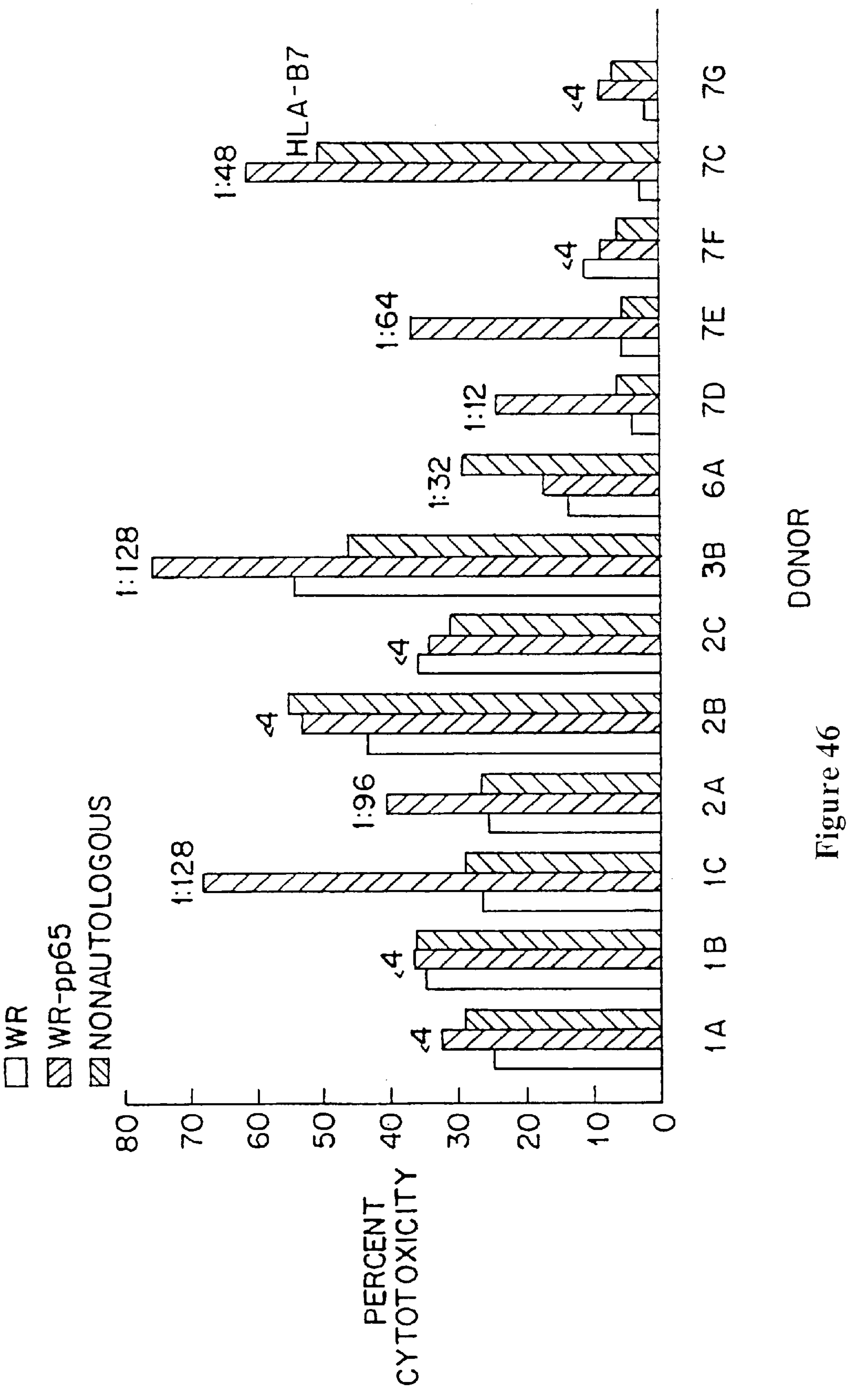
Figure 47:
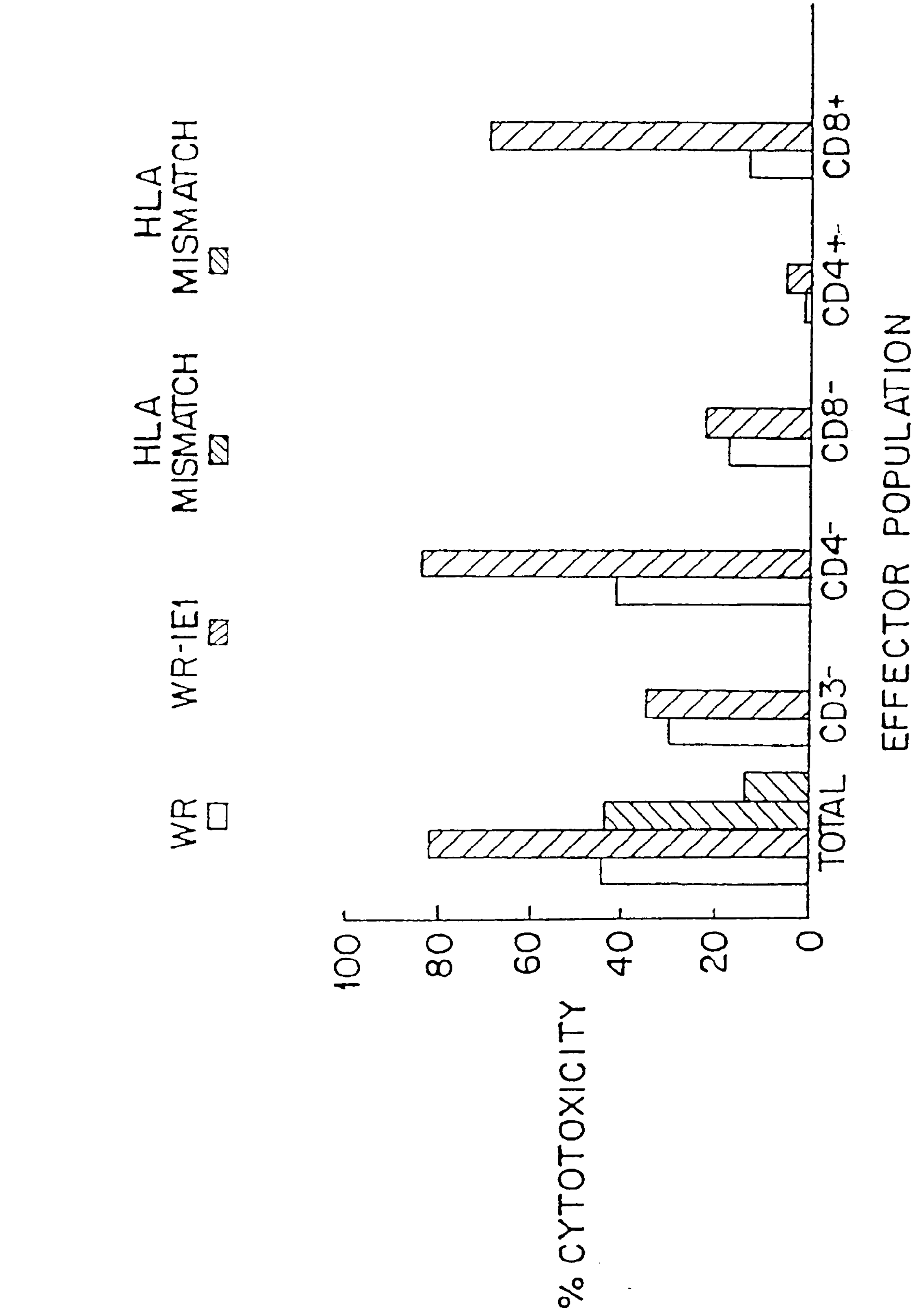
Figure 49A:
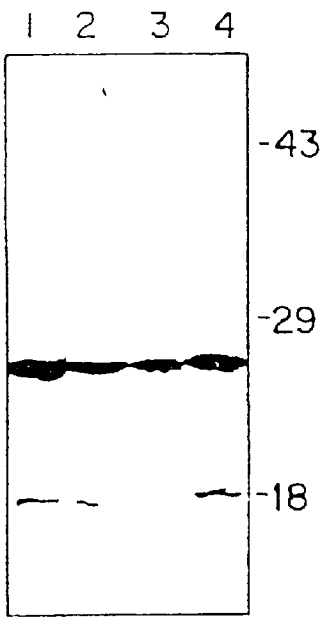
Figure 49B:
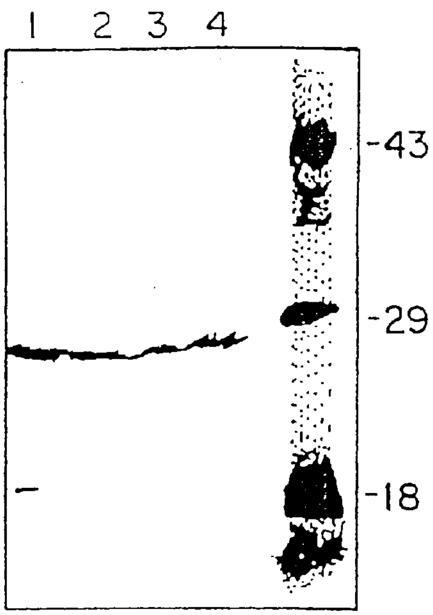
Figure 50:
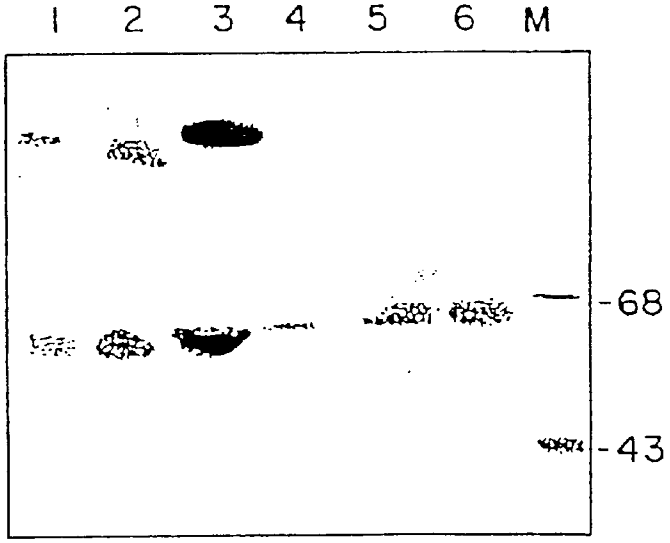
Figure 51:
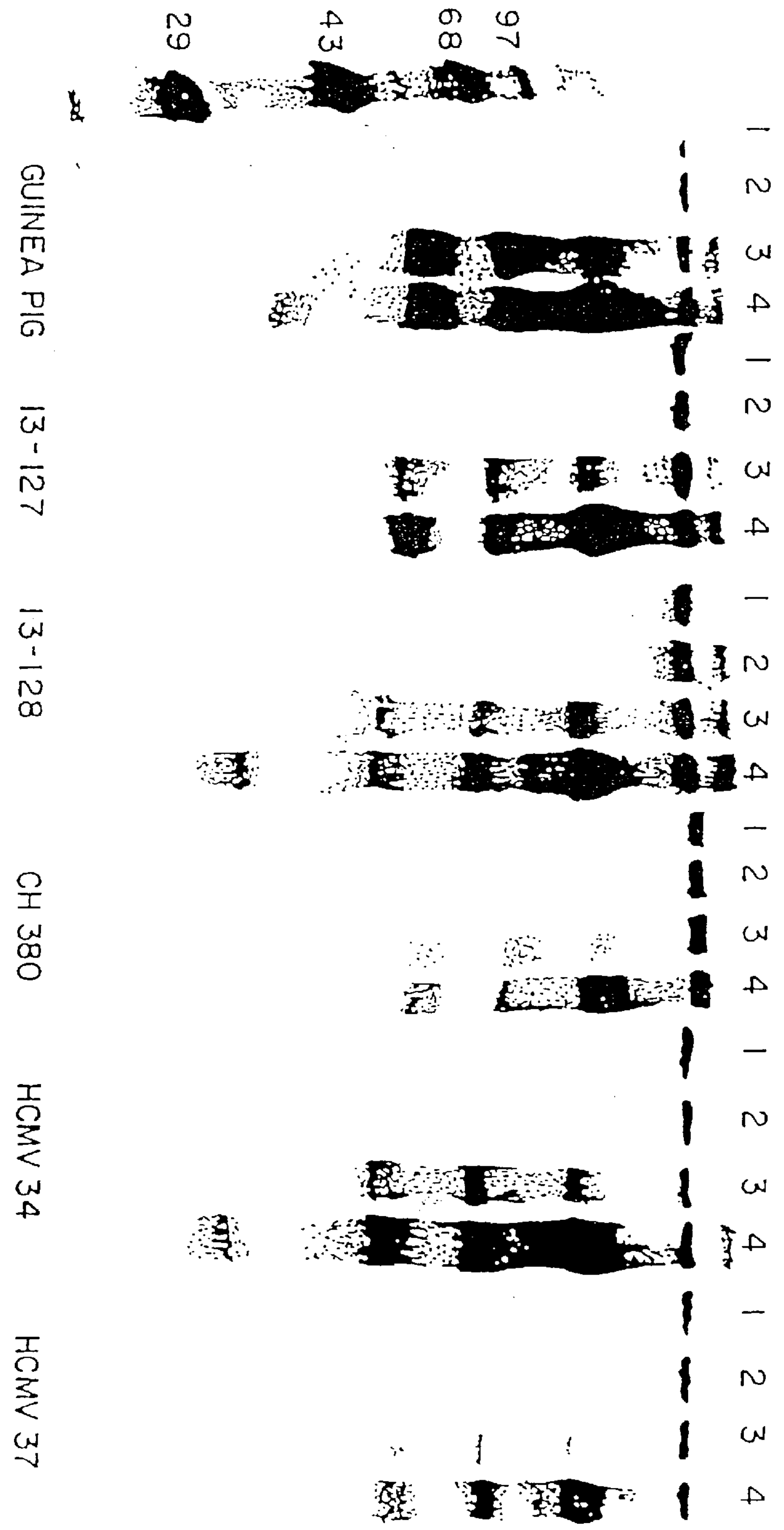
Figure 52:
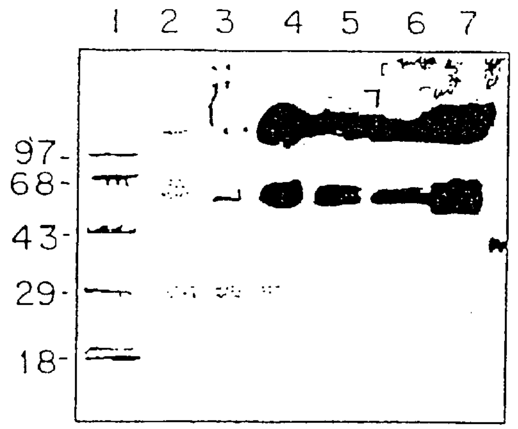
Figure 53:
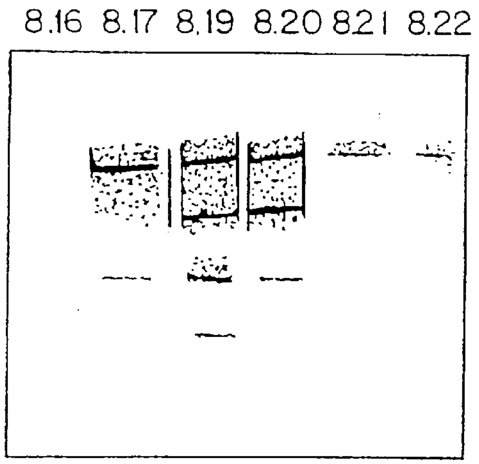
Figure 54:
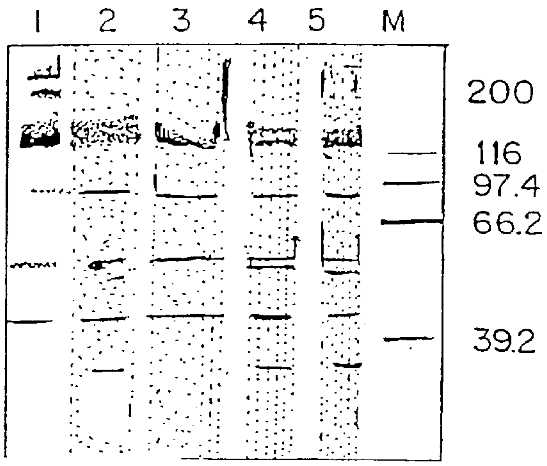
Figure 55A:
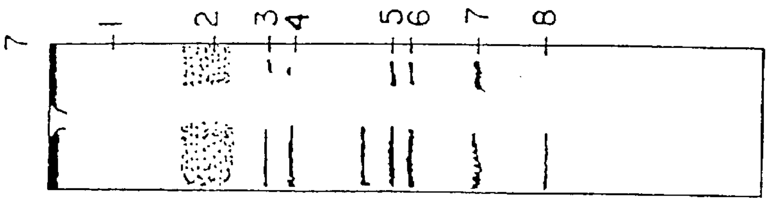
Figure 55:
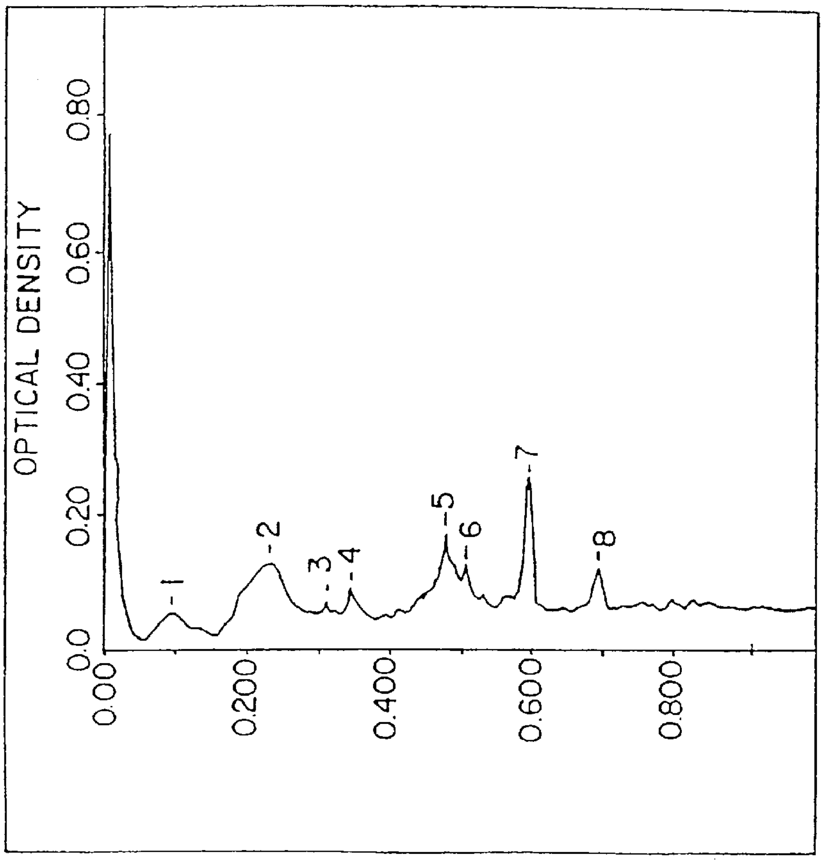
Figure 56A:
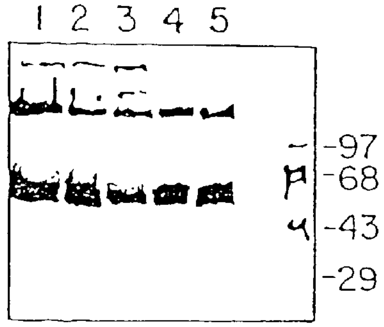
Figure 57A:
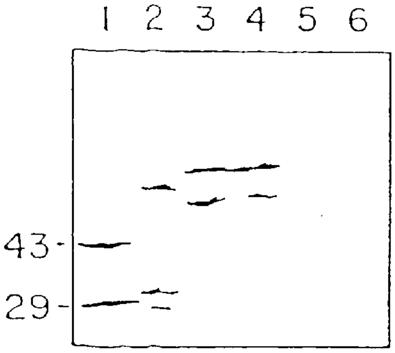
Figure 58A:
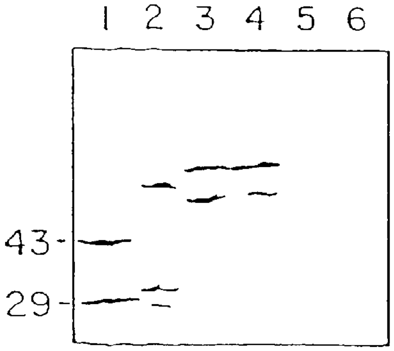

Zachary A. A. and G. A. Teresi, Eds., (Lenexa, Kans.: American Society for Histocompatibility and immunogenetics, 1990), pp. 195). Most class II types were determined by PCR (F. M. Marincola et al., J. Immunother. 18, 242 (1995)). Data were analyzed by the chi-square test or Fisher's exact test using the Instat program (GraphPAD Software, San Diego, Calif.). All tests were two-tailed. P values less than 0.05 were considered significant);

FIG. 7 shows HLA-B35 and positive T-cell proliferative response to CMV antigens in CMV-seronegative individuals (The percentage of seronegative individuals with HLA-B35 who developed a T-cell proliferative response to CMV antigens was significantly higher (P=0.02) than the percentage of seronegative individuals without HLA-B35);

FIG. 8 shows the DNA sequence of HCMVgB (Towne strain) (SEQ ID NO:1);

FIGS. 9A and B show the DNA sequence of the H6 promoted HCMVgB and NYVAC sequences flanking the TK locus (SEQ ID NO:2) (the 5' end of the H6 promoted CMVgB is at position 3447; the CKVgB coding sequence is from position 3324 through position 606);

FIGS. 10A to C show the DNA sequence of a 7351 base pair fragment of canarypox DNA containing the C3 ORF (SEQ ID NO:3) (the C3 ORF is initiated at position 1458 and terminates at position 2897);

FIGS. 11A to C show the DNA sequence of the H6 promoted HCMVgB and ALVAC sequences flanking the C3 locus (SEQ ID NO:4) (the 5' end of the H6 promoted CMVgB is at position 4425; the CMVgB coding sequence is from position 4301 through position 1581);

FIGS. 12A and B show the DNA sequence of the H6 promoted HCMVgB and NYVAC sequences flanking the ATI locus (SEQ ID NO:5) (the 5' end of the H6 promoted CMVgB is at position 3348; the CMVgB coding sequence is from position 3224 through position 504);

FIG. 13 shows the DNA sequence of HCMVgB (Towne strain) deleted of its transmembrane region (SEQ ID NO:6);

FIGS. 14A and B show the DNA sequence of the H6 promoted HCMVgB lacking its transmembrane region and NYVAC sequences flanking the ATI locus (SEQ ID NO:7) (the 5' end of the H6 promoted CMVgB is at position 3173; the CMVgB coding sequence is from position 3050 through position 504);

FIG. 15 shows the DNA sequence of HCMVgB (Towne strain) deleted of its transmembrane region and containing an altered cleavage site (SEQ ID NO:8);

FIGS. 16A and B show the DNA sequence of the H6 promoted HCMVgB lacking its transmembrane region and containing an altered cleavage site plus NYVAC sequences flanking the ATI locus (SEQ ID NO:9) (the 5' end of the H6 promoted CMVgB is at position 3173; the CMVgB coding sequence is from position 3050 through position 504);

FIG. 17 shows the DNA sequence of HCMVgH (Towne strain) (SEQ ID NO:10);

FIGS. 18A and B show the DNA sequence of the 42K promoted HCMVgH plus NYVAC sequences flanking the I4L locus (SEQ ID NO:11) (the 5' end of the 42K promoted CMVgH is at position 641; the CMVgH coding sequence is from position 708 through position 2933);

FIGS. 19A and B show the DNA sequence of the 42K promoted CMVgH and ALVAC sequences flanking the C5 locus (SEQ ID NO:13) (the 5' end of the 42K promoted CMVgH is at position 1664; the CMVgH coding sequence is from position 1730 through position 3955);

FIG. 20 shows the DNA sequence of the 42K promoted CMVgH and WR flanking sequences (SEQ ID NO:13) (the 5' end of the 42K promoted CMVgH is at position 2457; the CMVgH coding sequence is from position 2391 through 166);

FIG. 21 shows the DNA sequence of HCMV IE1 (AD169 strain) (SEQ ID NO:14);

FIG. 22 shows the DNA sequence of the H6 promoted CMVIE1 and WR flanking sequences (SEQ ID NO:15) (the 5' end of the H6 promoted CMVIE1 is at position 1796; the CMVIE1 coding sequence is from position 1673 through 201);

FIGS. 23A and B show the DNA sequence of the H6 promoted CMVIE1 and NYVAC sequences flanking the ATI locus (SEQ ID NO:16) (the 5' end of the H6 promoted CMVIE1 is at position 2030; the CMVIE1 coding sequence is from position 1906 through position 434);

FIG. 24 shows the DNA sequence of HCMVIE1 (AD169 strain) lacking amino acids 292–319 (SEQ ID NO:17);

FIGS. 25A and B show the DNA sequence of the H6 promoted CMVIE1 lacking amino acids 292–319 and NYVAC sequences flanking the ATI locus (SEQ ID NO:18) (the 5' end of the H6 promoted CHVIE1 is at position 1940; the CMVIE1 coding sequence is from position 1816 through position 434);

FIG. 26 shows the DNA sequence of the Exon 4 segment of HCMVIE1 (AD169 strain) (SEQ ID NO:19);

FIG. 27 shows the DNA sequence of the H6 promoted CMVIE1 Exon 4 segment and NYVAC sequences flanking the I4L locus (SEQ ID NO:20) (the 5' end of the H6 promoted IE1 Exon 4 is at position 630; the CMVIE1 Exon 4 coding sequence is from position 754 through position 1971);

FIGS. 28A and B show the DNA sequence of the H6 promoted CMVIE1 Exon 4 segment and ALVAC sequences flanking the C5 locus (SEQ ID NO:21) (the 5' end of the H6 promoted IE1 Exon 4 is at position 1647; the CMVIE1 Exon 4 coding sequence is from position 1771 through position 2988);

FIG. 29 shows the DNA sequence of HCMVIE1 (AD169 strain) lacking amino acids 2–32 (SEQ ID NO:22);

FIG. 30 shows the DNA sequence of the H6 promoted CMVIE1 lacking amino acids 2–32 and NYVAC sequences flanking the I4L locus (SEQ ID NO:23) (the 5' end of the H6 promoted IE1 lacking amino acids 2–32 is at position 630; the coding sequence for CMVIE1 lacking amino acids 2–32 is from position 754 through position 2133);

FIGS. 31A and B show the DNA sequence of the H6 promoted CMVIE1 lacking amino acids 2–32 and ALVAC sequences flanking the C5 locus (SEQ ID NO:24) (the 5' end of the H6 promoted IE1 lacking amino acids 2–32 is at position 1647; the CMVIE1 coding sequence for CMVIE1 lacking amino acids 2–32 is from position 1771 through position 3150);

FIG. 32 shows the DNA sequence of HCMV pp65 (Towne strain) (SEQ ID NO:25);

FIG. 33 shows the DNA sequence of the H6 promoted CMVpp65 and NYVAC sequences flanking the HA locus (SEQ ID NO:26) (the 5' end of the H6 promoted pp65 is at position 476; the CMVpp65 coding sequence is from position 600 through 2282);

FIGS. 34A and B show the DNA sequence of a 3706 base pair fragment of canarypox DNA containing the C6 ORF (SEQ ID NO:27) (the C6 ORF is initiated at position 377 and terminated at position 2254);

FIGS. 35A and B show the DNA sequence of the H6 promoted CMVpp65 and ALVAC sequences flanking the C6 locus (SEQ ID NO:28) (the 5' end of the H6 promoted pp65 is at position 496; the CMVpp65 coding sequence is from position 620 through 2302);

FIG. 36 shows the DNA sequence of the H6 promoted CMVpp65 and WR flanking sequences (SEQ ID NO:29) (the 5' end of the H6 promoted pp65 is at position 168; the CMVpp65 coding sequence is from position 292 through 1974);

FIG. 37 shows the DNA sequence of HCMVpp150 (Towne strain) (SEQ ID NO:30);

FIGS. 38A and B show the DNA sequence of the 42K promoted CMVpp150 and NYVAC sequences flanking the ATI locus (SEQ ID NO:31) (the 5' end of the 42K promoted pp150 is at position 3645; the CMVpp150 coding sequence is from position 3580 through 443);

FIGS. 39A and B show the DNA sequence of the 42K promoted CMVpp150 and ALVAC sequences flanking the C6 locus (SEQ ID NO:32) (the 5' end of the 42K promoted pp150 is at position 3714; the CMVpp150 coding sequence is from position 3649 through 512);

FIGS. 40A and B show the DNA sequence of the 42K promoted CMVpp150 gene and WR flanking sequences (SEQ ID NO:33) (the 5' end of the H6 promoted pp150 is at position 3377; the CMVpp150 coding sequence is from position 3312 through 175);

FIGS. 41A and B show the DNA sequence of the 42K promoted HCMVgH and H6 promoted HCMVIE Exon 4 and NYVAC sequences flanking the I4L locus (SEQ ID NO:34) (the 5' end of the 42K promoted CMVgH is at position 2935; the CMVgH coding sequence is from position 2869 through 644; the 5' end of the H6 promoted CMVIE Exon 4 is at position 2946; the CMVIE Exon 4 coding sequence is from position 3070 through position 4287);

FIGS. 42A to C show the DNA sequence of the H6 promoted HCMV pp65 and 42K promoted HCMVpp150 and ALVAC sequences flanking the C6 locus (SEQ ID NO:35) (the 5' end of the H6 promoted CMVpp65 is at position 496; the CMVpp65 coding sequence is from position 620 through 2302; the 5' end of the 42K promoted CMVpp150 is at position 5554; the CMVpp150 coding sequence is from position 5489 through position 2352);

FIG. 43 shows the DNA sequence of HCMVgL (Towne strain) (SEQ ID NO:36);

FIGS. 44A and B show the DNA sequence of the H6 promoted HCMVgB and H6 promoted HCMVgL and NYVAC sequences flanking the TK locus (SEQ ID NO:37) (the 5' end of the H6 promoted CMVgB is at position 3447; the CMVgB coding sequence is from position 3324 through position 606; the 5' end of the H6 promoted CMVgL is at position 3500; the CMVgL coding sequence is from position 3624 through position 4460);

FIG. 45 shows the results of HCMV IE1 CTL stimulation by ALVAC-IE1 (vCP256) (percent cytotoxicity; white bars=WR, black bars=WRIE1, striped bars=nonautologous);

FIG. 46 shows the results of stimulation of HCMV pp65-CTLs by ALVAC-pp65 (vCP260) (human CTLs stimulated in vitro and assayed for HCMV pp65 CTLs using methodology similar to that used for FIG. 49; percent cytotoxity; white bars=WR, black bars=WR-pp65, striped bars=nonautologous);

FIG. 47 shows the results of stimulation of HCMV IE1 CTLs by ALVAC-IE1 (vCP256) (methodology similar to that used for FIG. 49, except that following 6 days incubation for restimulation, the responder mononuclear cells were incubated with immunomagnetic beads coupled to monoclonal anti-human CD3, CD4 or CD8; percent cytotoxicity; white bars=WR, black bars=WR-IE1, striped bars=HLA mismatch);

FIGS. 48A to D show expression of CMV gB by COPAK recombinants in Vero and HeLa cells (cell and medium fractions from infected cells radiolabeled with [S 35] methionine were immune precipitated with guinea pig anti-CMV gB; Vero medium (A), HeLa medium (B), Vero cell (C), and HeLa cell (D) fractions derived from infections by vP993 COPAK parent (lanes 1), vP1126 expressing the entire gB (lanes 2), vP1128 expressing gB without the transmembrane site (lanes 3), and vP1145 expressing the gB without transmembrane and with altered cleavage sites (lanes 4) are shown; far right lane contains molecular weight markers);

FIGS. 49A and B show vaccinia infection of Vero and HeLa cells detected by expression of vaccinia early protein E3L (cell fractions from infected cells radiolabeled with [35 S] methionine were immune precipitated with rabbit anti-p25 (E3L); Vero (A) and HeLa (B) cell fractions derived from infections by vP993 (lanes 1), vP1126 (lanes 2), vP1128 (lanes 3), and vP1145 (lanes 4) are shown; far right lane contains molecular weight markers);

FIG. 50 shows comparison of CMV gB production by Vero, HeLa and MRC-5 cells (SDS-PAGE and western blot analysis were performed on the medium from MRC-5 cells (lanes 1, 4), Vero cells (lanes 2, 5), or HeLa cells (lanes 3, 6) after infection with vP1145 (lanes 1, 2, 3) or vP993 (lanes 4, 5, 6); CMV gB was detected with monoclonal CH380; molecular weight markers are present in lane M);

FIG. 51 shows immunoprecipitation of CMV gB by a panel of monoclonal antibodies and guinea pig anti-gB (radiolabeled medium fractions from Vero cells infected with vP993 (lanes 1), vP1126 (lanes 2), vP1128 (lanes 3), and vP1145 (lanes 4) were immune precipitated with guinea pig anti-CMV gB or with monoclonals 13–127, 13–128, CH380, HCMV 34, or HCMV 37; far left lane contains molecular weight markers);

FIG. 52 shows western blot analysis of fractions and bed material from CMV gB immunoaffinity chromatography columns (column 19 fractions representing eluted gB (lane 5), flow through material (lane 6), and crude gB material applied to the column (lane 7) were analyzed by SDS-PAGE and western blot using monoclonal CH380; included in the assay was bed material from column 19 (lane 2) and column 11 (lane 3), as well as gB purified on column 7 (lane 4); molecular weight markers are present in lane 1);

FIG. 53 shows SDS-PAGE analysis of CMV gB eluted from an immunoaffinity chromatography column (fractions 8.16 through 8.22, eluted from column 8, were electrophoretically separated on a 10% gel under reducing conditions, and stained with silver);

FIG. 54 shows SDS-PAGE analysis of five batches of immunoaffinity purified CMV gB (samples of batches 1 through 5 (lanes 1–5) were electrophoretically separated on a 10% gel under reducing conditions and stained with Coomassie Blue; Lane M contains molecular weight markers);

FIGS. 55, 55A shows characterization of immunoaffinity purified CMV gB (batch 5, analyzed by SDS-PAGE, as shown in FIGS. 54A and B, was scanned with a densitometer, and bands were defined (lane 7, labels 1 through 8) with FIG. 55A showing a densitometer tracing through lane 7);

FIGS. 56A and B show immunoblot analysis of immunoaffinity purified CMV gB (purified HIV env (lanes 1), affinity purified CMV gB (lanes 2), crude CMV gB (lane (B3), or monoclonal CH380 (lane A3) were electrophoretically separated on a 10% gel, blotted onto nitrocellulose paper and probed for the presence of mouse IgG H and L chains or CMVgB using goat anti-mouse IgG (A) or monoclonal CH380 (B), respectively; molecular weight markers are present in lanes 4);

FIGS. 57A and B show immunoprecipitation/immunoblot analysis of affinity purified gB (Batch 1 immunoaffinity purified gB(1) or crude gB (B) was immunoprecipitated with monoclonals CH380 (lanes 1), 13–127 (lanes 2), 13–128 (lanes 3), HCMV 37 (lanes 4), or HCMV 34 (lanes 5); the immunoprecipitates were electrophoretically separated on a 10% gel under reducing conditions, blotted onto nitrocellulose and probed for the presence of gB, using guinea pig anti-CMB gB; far left lanes are molecular weight markers);

FIGS. 58A and B show immunoblot analysis of affinity purified CMV gB (Vero cells lysates (lanes A3, B2), CEF lysates (lane A2), vaccinia-infected Vero cells (lane B3), crude CMV gB (lanes 4), affinity purified CMV gB (lanes 5), or purified HIV env (lanes 6) were electrophoretically separated on a 10% gel under reducing conditions, blotted onto nitrocellulose, and probed for the presence of Vero cell proteins using rabbit anti-Vero cells (A), or vaccinia proteins using rabbit anti-vaccinia (B); molecular weight markers are present in lanes 1);

FIGS. 59A–C show the DNA sequence of the H6 promoted HCMVpp65 and 42K promoted HCMVpp150 and ALVAC sequences flanking the C6 locus (SEQ ID NO:38) (The 5' end of the H6 promoted CMVpp65 is at position 496. The CMVpp65 coding sequence is from position 620 through 2302. The 5' end of the 42K promoted CMVpp150 is at position 2341. The CMVpp150 coding sequence is from position 2406 through 5543);

FIGS. 60A and B show the DNA sequence of a 5798 bp fragment of canarypox DNA containing the $C_7$ ORF (tk) (SEQ ID NO:39) (The $C_7$ ORF is initiated at position 4412 and terminated at position 4951);

FIGS. 61A and B show the DNA sequence of the H6 promoted HCMVgL gene and ALVAC sequences flanking the $C_7$ locus (The 5' end of the H6 promoted CMVgL gene is at position 2136. The CMVgL coding sequence is from position 2260 through 3093);

FIGS. 62A and B show the DNA sequence of the H6 promoted HCMVgL gene and H6 promoted HCMV IE1-exon4 gene and ALVAC sequences flanking the $C_7$ locus (SEQ ID NO:40) (The 5' end of the H6 promoted CMVgL gene is at position 3476. The CMVgL coding region is from position 3600 through 4433. The 5' end of the H6 promoted IE1-exon4 is at position 3469. The CMV IE1-exon4 coding region is from position 3345 through 2128);

FIG. 63 shows the DNA sequence of HCMVgH (SEQ ID NO:41)(Towne strain) deleted of its transmembrane region and cytoplasmic tail;

FIGS. 64A and B show the DNA sequence of the H6 promoted HCMVgL gene and 42K promoted truncated HCMVgH gene and NYVAC sequences flanking the ATI locus (SEQ ID NO:42) (The 5' end of the H6 promoted CMVgL gene is at position 2669. The CMVgL coding region is from position 2793 through 3626. The 5' end of the 42K promoted truncated CMVgH gene is at position 2650. The truncated CMVgH coding sequence is from position 2584 through 434);

FIG. 65 shows the DNA sequence of a 3209 base pair fragment of canarypox DNA containing the C5 ORF (SEQ ID NO:43) (the C5 ORF initiates at position 1537 and terminates at position 1857);

FIG. 66 shows the nucleotide sequence of the H6/p53 (wildtype) expression cassette and flanking regions from vCP207 (SEQ ID NO:44);

FIG. 67 shows the murine p53 gene (SEQ ID NO:45);

FIG. 68 shows the coding sequence for the human p53 gene (SEQ ID NO:46);

FIG. 69 shows the nucleotide sequence for RCMVIE1 (DNA) (SEQ ID NO:47);

FIG. 70 shows the nucleotide sequence for RCMVIE2 (DNA) (SEQ ID NO:48);

FIGS. 71A and B show the nucleotide sequence for RCNVIE2 (DNA) (SEQ ID NO:49);

FIG. 72 shows the generation of baculovirus and gene expression with the Bac-To-Bac Expression System;

FIG. 73 shows the map and restriction sites for the pFastBac HT expression vector;

FIG. 74 shows multiple cloning site sequences for the pFastBac HT expression vector;

FIG. 75 shows the nucleotide sequence for HCMVIE2 (DNA) (SEQ ID NO:50);

FIGS. 76A and B, respectively, show Western Blot and Coomassie Blue stained gel (FIG. 76A: lane 1=SF9 insect cell lysate, lane 2=baculovirus RCMVIE1 infected SF9 cell lysate, lane 3=RCMVIE1 purified protein preparation, lane 4=baculovirus RCMVIE2 infected SF9 cell lysate, lane 5=RK-13 cells, lane 6=vP1479 infected RK-13 cell lysate, lane 7=prestained molecular weight markers; FIG. 76B: lane 1=RCMVIE1 purified protein preparation, lane 2=prestained molecular weight markers); and FIG. 77 shows the nucleotide sequence of the wildtype p53 expression cassette and flanking regions within vP1101 (SEQ ID NO:168).

DETAILED DESCRIPTION

As discussed above, the present invention pertains to methods for diagnosis, prophylaxis and treatment of restenosis and/or atherosclerosis, including detecting cellular mediated immune responses and/or HLA phenotyping and/or genotyping, and administering an agent to reduce viral load in a patient in need of such, for instance administering a vaccine or immunological composition against CMV and/or p53. The vaccine or immunological composition can boost the immune response so that the patient's system consequently reduces viral load.

Examples 1 and 2 show the correlation between CMV and vascular disease, and that while there is a correlation between antibodies to CMV and chances of restenosis occurring, diagnostic methods should include detecting cellular mediated immune response and/or HLA phenotyping and/or genotyping, and methods for treatment or prophylaxis can be aimed at decreasing viral load, such as by administering a vaccine or immunological composition against CMV and/or p53.

Example 1, below, may be summarized as follows:

Background: Recent evidence suggests a potential role of cytomegalovirus (CMV) in the development of restenosis: CMV DNA is present in restenosis lesions from atherectomy specimens, and a CMV immediate early gene protein (IE84) binds to and inhibits p53, a gene product that can block cell cycle progression and initiate apoptosis. These p53-mediated effects may contribute to increased SMC accumulation and thereby predispose to restenosis.

Methods: Seventy-five consecutive patients undergoing directional coronary atherectomy (DCA) for symptomatic CAD were prospectively evaluated by measuring anti-CMV IgG antibodies (before DCA) to determine whether prior CMV exposure increases restenosis risk, as determined by a 6-month post-DCA angiogram.

Results: Following the DCA procedure, minimal luminal diameter was greater in CMV seropositive patients (n=49) than in seronegative patients (3.18±0.51 mm vs 2.89±0.45, P=0.01); at six months, however, the large late luminal diameter loss (1.24±0.83 mm vs 0.68±0.69, P=0.003) and loss index (0.68±0.47 vs 0.36±0.33, P<0.001) experienced by seropositive patients resulted in a significantly higher rate of restenosis (43% vs 8%, P=0.002). Both CMV seropositivity (odds ratio=12.9) and CMV titer (odds ratio=8.1) were independently predictive of restenosis (>50% narrowing) in a multivariable logistic regression model. There was no evidence of acute infection, as anti-CMV IgG antibody titers did not increase over time and anti-CMV IgM antibodies were negative in all patients.

Conclusions: Prior infection with CMV is a strong independent risk factor for restenosis.

Figures 1, 1A:
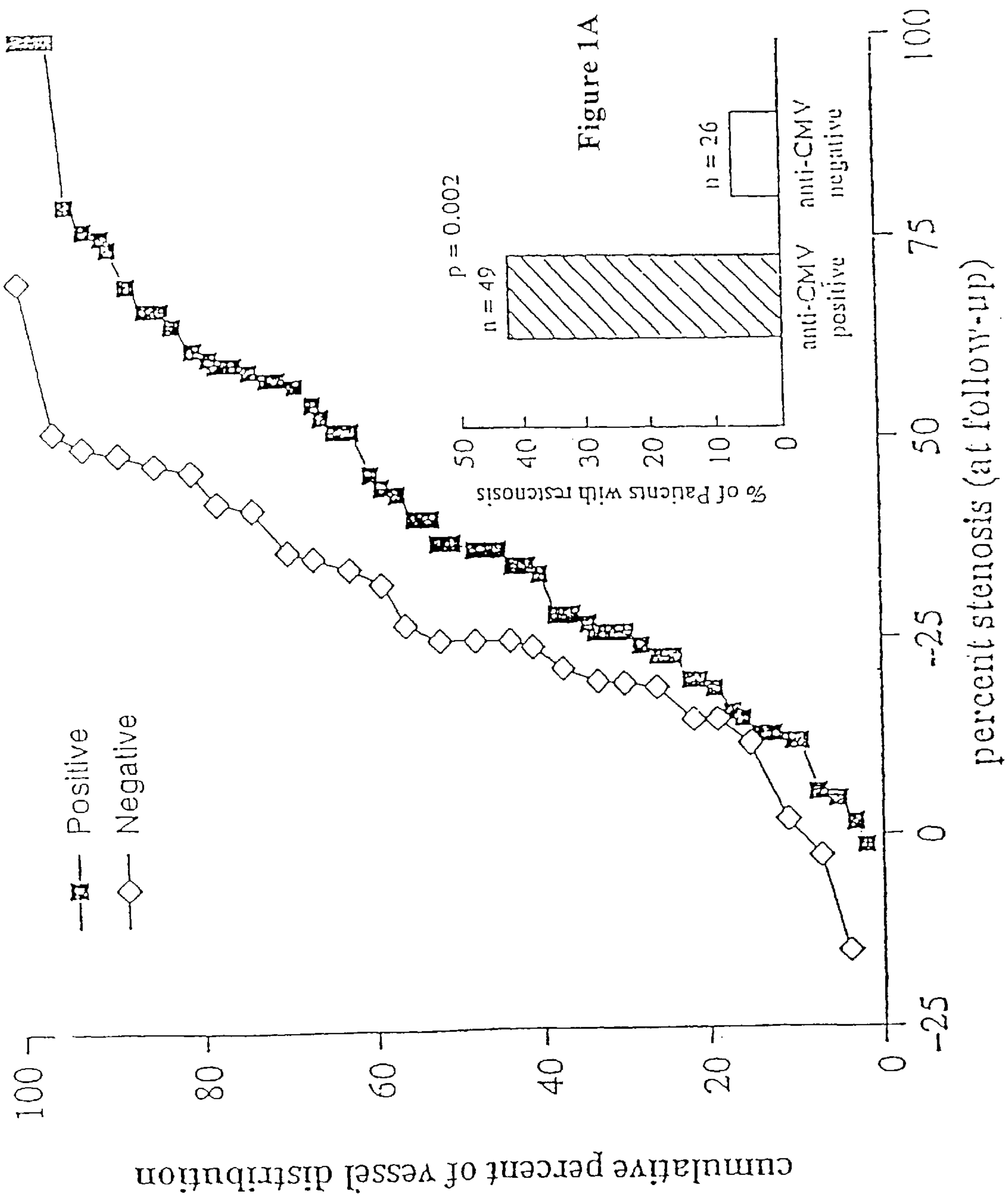
FIG. 1 shows the influence of prior HCMV infection on cumulative distribution of percent stenosis of target vessels determined by angiography 6 months following DCA (Eighty-five target vessels from 75 patients were divided into two groups based on anti-CMV IgG antibody seropositivity status at study entry. A positive CMV IgG antibody status was defined, prospectively, as a cytomegalisa value of ≧0.25. Vessels from seropositive patients had higher percent stenoses compared with those from seronegative patients (p=0.01))
FIG. 1A shows the incidence of restenosis (>50% diameter narrowing) in the seropositive/seronegative patients.

In more detail, Example 1 provides the first prospective evidence indicating that prior exposure to CMV, as indicated by the presence of CMV IgG antibodies at the time of coronary angioplasty, is a strong independent risk factor for the subsequent development of restenosis (p=0.002; FIG. 1). The importance of prior exposure to CNV infection as a risk factor is further emphasized by the odds ratio of developing restenosis, which was 9-fold greater in patients exposed to CMV than those without such exposure (Table 3). In contrast, no significantly increased risk was seen with any of the other variables tested, findings generally consistent with the results of other studies, e.g., Bach et al., Thromb. Res. 1994; 74:S55–S67; Hermans et al., J. Cardiovas. Pharmaco. 1993; 22(suppl.4):S445–S57; Feuvre et al., Am. J. Cardiol. 1994; 73:840–844; Dzavik et al., Am. J. Cardiol. 1995; 75:936–938; Stein et al., Circulation 1995; 91:979–989; Foley et al., Circulation 1994; 1239–1251.

Analyses believed to provide more complete information than the results of the simple dichotomous analysis described above (restenosis vs no restenosis), led to the same conclusion—that CMV is an important risk factor in the development of restenosis. Thus, when the degree of stenosis is considered as a continuous variable and the effects of CMV are assessed, seropositive patients had a greater degree of lesion stenosis (p=0.01; FIG. 1, Table 2). With MLD considered as a continuous variable (FIG. 2, Table 2), Applicants found that lesion MLD was greater immediately post DCA in the seropositive patients (p=0.01). However, the CMV seropositive patients experienced a markedly greater late loss (p=0.003) and late loss index (p=0.0005), resulting in a tendency for a smaller MLD and a significantly greater incidence of restenosis (p=0.002).

Given that the processes leading to restenosis are complex and undoubtedly multifactorial, it is all the more compelling that one factor—exposure to CMV—conveys such a high risk. Indeed, it is probably this very potency of CMV as a risk factor that accounts for the significant relation Applicants found between anti-CMV antibodies and the incidence of restenosis despite the moderate patient sample-size studied. Also helping the sensitivity and specificity of the study is the fact that the diagnosis of restenosis in this study was based on angiographic analysis rather than on clinical assessment, which is known to be highly inaccurate in predicting anatomic restenosis. Confidence in the results also derives from the fact that this study was prospective in design, that angiographic readers were blinded as to patients' anti-CMV antibody status, and that analysis of anti-CMV antibody levels was performed without knowledge of the angiographic results.

The association between the development of restenosis and CMV was based on anti-CMV IgG antibodies drawn at the time of the angioplasty procedure. Antibody levels did not increase over the ensuing months. This finding, in conjunction with the fact that IgM antibodies were not elevated, suggest that acute CMV infection with systemic viremia did not occur. Although Applicants do not rule out the possibility of acute viremia occurring shortly after angioplasty, with antibody levels returning to baseline by the 6 month repeat studies, Applicants' results are most compatible with the concept that the virus produced either an abortive infection (viral gene expression limited to immediate early gene products), or that viral replication occurred locally in the absence of systemic viremia.

CMV is a complex virus—it has a large genome with over 200 open reading frames. Thus, it undoubtedly possesses many viral proteins that might influence neointimal accumulation. In addition to the effects of IE84, which as noted hereinabove binds to and inactivates p53, infection of SMCs with CMV leads to the expression and secretion of growth factors, Gonczol et al., J. Gen. Virol. 1984; 65:1833–1837; Alcami et al., J. Gen. Virol. 1991; 72:2765–2770, and CMV infection has been shown to activate NFkB, Kowalik et al., Proc. Natl. Acad. Sci. USA 1993; 90:1107–1111, a transcription factor involved in stimulating a broad range of genes, including those involved in inflammatory and immune responses. The virus also increases leukocyte and platelet adhesion to endothelial cells through induction of cellular expression of adhesion molecules, Grundy et al., Immunology. 1993; 78:405–412; O'Brien et al., J. Clin. Invest. 1993; 92:945–951; Span et al., Eur. J. Clin. Invest. 1991; 21:331–338; Etingin et al., Proc. Natl. Acad. Sci. USA 1993; 90:5153–5156; and induces changes that are procoagulant, Van Dam-Mieras et al., Thromb. Haemost. 1992; 68:364–370; Etingin et al., Cell 1990; 61:657–662; Pryzdial et al., Blood 1994; 84:3749–3757. CMV also increases the activity of the scavenger receptor, and IE72, another IE gene product, increases scavenger receptor gene expression, Zhou et al., Circulation 1995; 92:1–162 (Abstr.); increased accumulation of oxidized LDL within lesion SMCs might contribute to an atherogenic-related process like restenosis. Finally, it has recently been shown that IE72 and IE84 inhibit apoptosis, which could increase neointimal accumulation, Zhu et al., J. Virol. 1995; 69:7960–7970.

Totally unexpectedly, Applicants found a strong association between CMV and hypertension. Thus, there may be an important CMV-hypertension link, such that testing for CMV may be indicative of a predisposition to hypertension and vice versa.

It is possible, although Applicants do not necessarily wish to be bound by any one particular theory, that the relation Applicants observed between CMV infection and subsequent development of restenosis is due to a specific relation between the particular angioplasty procedure used in the present investigation—atherectomy—and that very different results may be observed with other techniques such as balloon angioplasty. This possibility appears very remote, as it is generally believed that the final common pathway of the restenosis process is a healing response to vascular injury, a response that probably would be similar (and therefore influenced in a similar way by CMV) whether the injury were induced by balloon angioplasty or by directional atherectomy. Moreover, adjunct balloon dilatation was in fact performed in 87% of patients. Thus, the particular angioplasty procedure is believed to not be a factor.

It is possible that CMV seropositivity, instead of indicating a causal role of CMV per se in restenosis, is just a marker of another process that is actually the mechanistically contributing factor. However, CMV DNA is present in human restenosis, and a CMV gene product inhibits the transcriptional activity of p53 in human coronary artery smooth muscle cells, Speir et al., Science 1994; 265:391–394, and acute CMV infection increases neointimal formation in a rat balloon injury model, Zhou et al., J. Am. Cell. Cardiol. 1995; (suppl) 242a (Abstr.), which when taken together with the results presented herein, strongly suggest that CMV does indeed play a role in restenosis development. (However, the Abstract of Zhou et al., supra, either individually or in a combination with other documents, cannot be said to teach or suggest the present invention because, in addition to the surprising results in the Examples, Zhou et al., supra concerns an acute infection model, whereas human or animal patients are chronically infected).

The results of the present invention demonstrate that CMV seropositivity provides a powerful means of risk-stratifying patients for the development of restenosis. Thus, the determination (from a simple, standard blood test) that a given patient has less than a 10% chance of developing restenosis (CMV seronegative) vs over a 40% chance (CMV seropositive), when considered together with the patient's specific clinical profile, could importantly influence the clinician's decision as to whether that patient might best benefit from bypass surgery or from angioplasty.

However, as shown by Example 2, the CMV seropositive or seronegative status of a patient, while providing particular statistical chances of developing restenosis (Example 1), is not necessarily in and of itself sufficient in providing a diagnosis as to whether there is a predisposition towards or against (prevention of) restenosis and/or atherosclerosis; but rather, detecting a patient's cell mediated immune response to CMV and/or HLA phenotyping and/or genotyping may be more predictive of such a predisposition.

More particularly, because the type of immune response (cellular vs humoral) to infectious agents can determine disease expression or containment, and because cytomegalovirus (CMV) may contribute to restenosis and atherosclerosis, as reported in Example 2, Applicants tested whether there is a spectrum of humoral vs cellular immunodominant responses to CMV infection in healthy individuals. Four patterns were found: both cellular and humoral; humoral only; no detectable response; and, unexpectedly, cellular only. Applicants then determined whether HLA phenotype influenced the type of response: 50% of individuals with a cellular, but not humoral, immunodominant response had an HLA-B35 allele without HLA-B44; conversely, 43% with a humoral, but not cellular, immunodominant response had HLA-B44 without HLA-B35. These values significantly differed from those of control populations. Thus, genetically-determined, HLA-associated, immunodominant patterns of response to CMV occur and may influence susceptibility to CMV-induced disease, including vascular disease.

Pathogen-induced activation of the cellular and the humoral arms of the immune system are frequently inversely related. This observation has led to important insights relating to the type of immune response (cellular or humoral) that permits some hosts either to succeed in eliminating potential pathogens, or to develop persistence of pathogen and the establishment of chronic or recurrent disease.

Although the humoral arm of the immune system is important mainly for prevention of infection by extracelluar agents, if pathogens gain entry to intracellular sites, the cell-mediated immune response becomes essential to pathogen elimination or control. There is now evidence indicating that the cell-mediated immune response is an important mechanism for eliminating or controlling infectious pathogens that cause chronic disease in humans and in various animal species. Data compatible with this concept come from studies of infectious diseases such as acquired immune deficiency syndrome (AIDS) (S. Rowland-Jones et al., Nat. Med. 1, 59 (1995); M. Clerici, JAMA. 271, 42 (1994)), chronic hepatitis B (B. Rehermann, D. Lau, J. H. Hoofnagle, F. V. Chisari, J. Clin. Invest. 97, 1655 (1996)), and leishmaniasis (S. C. Mendonca, P. M. De Luca, W. Mayrink, T. G. Restom, Am. J. Trop. Med. Hyg. 53, 195 (1995); M. L. Guler et al., Science 271, 984 (1996); N. Noben-Trauth, P. Kropf, I. Muller, Science 271, 987 (1996)). On the other hand, a chronic cell-mediated immune inflammatory response can also lead to disease exacerbation.

Given, as shown in Example 2, that the same HLA molecule that predisposes to a cellular immunodominant response to CMV is also associated with a cellular immune response targeted to HIV and to the *P. falciparium* parasite (which seems to convey a protective effect in these diseases), these results herein have much broader implications.

Specific HLA molecules, such as HLA-B35, may have unique attributes that facilitate the development of a cellular immunodominant response, implying a mechanism whereby some individuals are resistant to certain infectious diseases (or to cancer), and some are susceptible to the development of diseases characterized by immunopathology (chronic granulomatous diseases and autoimmune disease).

There may be a correlation between this pattern of immune response and either protection from, or exacerbation of, any disease processes caused by CMV, including vascular disease.

Thus, novel therapeutic strategies, such as disclosed herein arise. For instance, the results reported herein allow for favorably altering disease outcome by directing attempts to change the immunodominant phenotype from one that increases disease susceptibility to one that promotes resistance.

More importantly, Example 2 shows that diagnosis for a predisposition towards restenosis from angioplasty or for a predisposition towards atherosclerosis cannot be predicated on merely whether an individual has antibodies against CMV, i.e., any prior correlations between CMV and vascular disease fail to teach or suggest the methods and compositions for diagnosis and therapy or treatment or prophylaxis of the present invention.

For instance, Example 2 demonstrates that detecting cellular immune responses and/or HLA genotyping and/or phenotyping can provide surprisingly better diagnosis. Detection of a cellular mediated response can be more predictive or predisposition to or against (prevention) of restenosis and/or atherosclerosis, since antibody-negative patients, as herein demonstrated can have T-cell responses.

Further, this Examples 1 and 2 show the importance in therapy or treatment or prophylaxis to boost the immune response to CMV and/or p53. Simply, the latent CMV infection is a low grade viral infection that the body cannot rid itself of because there is not sufficient stimulation of immune responses. Therapy, treatment or prophylaxis with a vaccine or immunological composition against CMV and/or p53 can thus boost the immune response to eliminate low levels of CMV, e.g., to reduce activation, and thus provide therapy, treatment or prophylaxis with respect to restenosis and/or atherosclerosis.

And, with the now disclosed causal role of CMV in the development of restenosis, and the showing that measuring antibodies against CMV is not sufficient for predicting predisposition towards or against restenosis and/or atherosclerosis, the therapeutic approaches to the prevention and/or treatment of restenosis and/or atherosclerosis, as herein disclosed, e.g., immunological or vaccine compositions comprising CMV antigens or portions thereof and/or p53 or portions thereof, or such compositions in conjunction with additional therapies or treatments, and methods employing them, as well as the diagnostic methods including detecting cell mediated immune response and/or HLA phenotyping and/or genotyping, are now provided.

Thus, in a general way, the invention provides a composition comprising a CMV antigen or antigens, or portions thereof and/or p53 or a portion thereof, and methods for making and using the composition in treatment, therapy or prophylaxis of restenosis and/or atherosclerosis. The composition can be a vaccine or immunological composition. The antigen(s) and/or p53 or portions thereof can be from in vitro and/or in vivo expression by a plasmid, a recombinant, or from isolation and/or purification from cells expressing the antigen(s) and/or p53, e.g., cells infected with HCMV and subsequent isolation and/or purification.

Techniques for protein purification of native proteins, in general, are as follows:

Briefly, the cells are disrupted and the protein of interest is released into an aqueous "extract". There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration.

Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method of cell disintegration based upon the starting material, and the teachings herein and in the art.

Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed.

Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immuno affinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the native proteins or epitopes of interest of CMV or p53, using the standard methodologies outlined hereinabove, and in the literature, as well as the teachings in the Examples below.

In regard to isolation and/or purification of CMV antigen (s) and/or p53 from cells expressing the antigen(s) and/or p53, in addition to methods discussed in the Examples, mention is made of U.S. Pat. Nos. 4,689,225 (HCMV gA subunit vaccine), 5,180,813 (early envelope glycoprotein and monoclonals to HCMV glycoproteins), and 4,716,104 (detection of HCMV antigens by antibodies reactive to IE of HCMV). The compositions and methods of these patents may be useful in the practice of the present invention.

Accordingly, the composition can comprise a vector comprising exogenous DNA encoding at least one CMV and/or p53 epitope. The epitope can be: IE1 and/or IE2 or a portion thereof; gB; gB with transmembrane deleted therefrom; gH; gL; pp150; pp65; IE1 with amino acids 2–32 deleted therefrom; IE1 with amino acids 292–319 deleted therefrom; IE1 exon 4 segment; gB and gH; gB and pp65; gB, gH and pp65; gB, gH, pp65 and IE1 exon 4 segment; gB, gH, pp65, pp150, and IE1 exon 4 segment; gB, gH, pp65 and pp150; gB, gH, gL, pp65, pp150 and IE1 exon 4 segment; and gB, gH, gL, pp65 and pp150; or portion of such CMV antigens; and/or p53, wild-type or mutant, or a portion thereof; or, more generally, a CMV antigen or portion thereof and/or p53 or a portion thereof; and, such a portion thereof can be an antigenic portion; for instance, an epitope of interest. The vector preferably induces an immune response, more preferably a protective immune response, when administered to a patient. Mention is made of U.S. Pat. Nos. 5,047,320 and 5,075,213, incorporated herein by reference, which relate to DNA probes for HCMV gp64 and HCMV gp64 as a vaccine, such that if desired, an epitope of interest in a composition of the invention can be gp64 or a portion thereof.

The methods for making a vector or recombinant can be by or analogous to the methods disclosed in U.S. Pat. Nos. 4,603,112, 4,769,330, 5,174,993, 5,505,941, 5,338,683, 5,494,807, 4,722,848, WO 94/16716, U.S. application Ser. No. 08/184,009, filed Jan. 19, 1994, WO 96/39491, U.S. application Ser. No. 08/658,665, filed Jun. 5, 1996, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573 U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068–3075, 1991; U.S. Pat. Nos. 5,591,439, 5,552,143 (recombinant adenovirus expressing HCMV gB and IE-exon 4), Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591,639, 5,589,466, and 5,580,859 relating to DNA expression vectors, inter alia.

Recombinant poxviruses can be constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,110,587, 5,179,993, 5,505,941, and 5,494,807, the disclosures of which, like the disclosures of all documents cited herein, are incorporated herein by reference.

First, the DNA gene sequence to be inserted into the virus, e.g., an open reading frame from a non-pox source, is placed into a plasmid construct such as an *E. coli* plasmid construct into which DNA homologous to a section of DNA of the poxvirus has been inserted. Separately, the DNA gene sequence to be inserted can be ligated to a promoter. The promoter-gene linkage is positioned in the plasmid construct so that the promoter-gene linkage is flanked on both ends by DNA homologous to a DNA sequence flanking a region of pox DNA; for instance, pox DNA containing a nonessential locus (although an essential locus may also be used). The resulting plasmid construct is then amplified, e.g., by growth within *E. coli* bacteria (Clewell, 1972) and isolated (Clewell et al., 1969; Maniatis et al., 1982). Alternatively, the DNA gene sequence can, without separate ligation to a promoter, merely be placed within the plasmid construct so that the DNA gene sequence is flanked on both ends by DNA homologous to a DNA sequence flanking a region of pox DNA; for instance, a region downstream from an endogenous promoter such that expression of the gene sequence is under control of the promoter and the promoter and coding portion of the DNA gene sequence are thus adjacent.

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, e.g., in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

However, the foregoing is not meant to limit the vectors or recombinants or means for obtaining vectors or recombinants in the present invention, as any vector or recombinant as well as any means for obtaining a vector or recombinant, e.g. a poxvirus-CMV and/or p53 epitope of interest recombinant, may be used to obtain the present invention.

In some embodiments, a poxvirus vector may be desired.

Paoletti, U.S. Pat. No. 5,338,683, incorporated herein by reference, provides poxvirus-herpesvirus recombinants, including vaccinia and avipox virus-herpesvirus recombinants, such as vaccinia and avipox virus-CMV recombinants, and gene products therefrom, useful in the practice of this invention.

A preferred vaccinia vector can have attenuated virulence, such as the NYVAC vector. Preferred avipox vectors include ALVAC (attenuated canarypox virus) and TROVAC (attenuated fowlpox virus). ALVAC and TROVAC are each unimolar species. ALVAC has been deposited with the ATCC, Accession No. VR-2547, under the terms of the Budapest Treaty. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox.

ALVAC-based recombinant viruses expressing extrinsic immunogens have also been demonstrated efficacious as vaccine vectors (Tartaglia et al., 1993a,b). So too have NYVAC-based recombinant viruses expressing extrinsic immunogens. In Paoletti et al., U.S. Pat. No. 5,494,807, incorporated herein by reference, ALVAC-HCMV and NYVAC-HCMV recombinants, e.g., such recombinants expressing HCMV gB, which elicit neutralizing antibodies, cell mediated immunity, and epitope-specific cytotoxic T-lymphocytes, and gene products therefrom, useful in the practice of this invention, are disclosed.

Paoletti et al., PCT publication WO 96/39491, based on U.S. applications Ser. Nos. 08/471,014, filed Jun. 6, 1995, and 08/658,665, filed Jun. 5, 1995, incorporated herein by reference, provides recombinant poxvirus-cytomegalovirus compositions and uses, including NYVAC and ALVAC recombinants, e.g., wherein the exogenous DNA codes for an HCMV protein selected from the group consisting of: gB; gB with transmembrane deleted therefrom; gH; gL; pp150; pp65; IE1; IE1 with amino acids 2–32 deleted therefrom; IE1 with amino acids 292–319 deleted therefrom; IE1 exon 4 segment; gB and gH; gB and pp65; gB, gH and pp65; gB, gH, pp65 and IE1 exon 4 segment; gB, gH, pp65, pp150, and IE1 exon 4 segment; gB, gH, pp65 and pp150; gB, gH, gL, pp65, pp150 and IE1 exon 4 segment; and gB, gH, gL, pp65 and pp150, and gene products therefrom, useful in the practice of this invention.

Paoletti et al. WO 94/16716 based on U.S. applications Ser. Nos. 007,115, filed Jan. 21, 1993, and 184,009, filed Jan. 19, 1994, incorporated herein by reference, provides recombinant viruses containing DNA encoding a cytokine and/or tumor associated antigen, including p53, wild-type or mutant, e.g., a NYVAC or ALVAC recombinant containing DNA coding for p53, wildtype or mutant, useful in the practice of this invention.

From the aforementioned Paoletti patent publications, and the teachings herein, including documents incorporated by reference into this specification, the skilled artisan can construct any desired poxvirus-HCMV and/or p53 recombinant expressing an epitope of interest, without undue experimentation.

Baculovirus, adenovirus, and DNA expression systems are also preferred for the practice of the invention.

With respect to certain vectors or recombinants, such as those whose DNA is infectious, e.g., adenovirus vectors, herpesvirus vectors, and the like, methods analogous to the above-described in vivo recombination technique for poxviruses may be employed for construction of the vector or recombinant containing desired exogenous DNA; but, such recombinants or vectors, with reference to adenovirus only for exemplification, may also be obtained by cleaving adenovirus DNA to obtain cleaved adenovirus DNA, ligating the exogenous DNA to the cleaved adenovirus DNA to obtain hybrid adenovirus-exogenous DNA, tranfecting a cell with the hybrid adenovirus-exogenous DNA, and optionally then recovering adenovirus modified by the presence of the exogenous DNA.

U.S. Pat. Nos. 5,591,439 and 5,552,143, incorporated herein by reference, provide adenovirus-HCMV gB or IE-exon 4 recombinants and gene products therefrom, useful in the practice of this invention. Furthermore, by employing the techniques of these patents, or of other literature concerning adenovirus recombinants, with exogenous DNA of any of U.S. Pat. Nos. 5,047,320, 5,075,213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995, Paoletti et al. WO 94/16716 based on U.S. applications Ser. Nos. 007,115, filed Jan. 21, 1993, and 184,009, filed Jan. 19, 1994, or other documents cited and incorporated herein, or literature concerning HCMV antigens, epitopes of interest, p53, p53 epitopes of interest, and DNA coding therefor, and the teachings herein, adenovirus embodiments expressing any desired HCMV and/or p53 epitope of interest and obtaining gene products therefrom, are within the ambit of the skilled artisan, without undue experimentation, for practice of this invention.

By employing the techniques of Smith et al., U.S. Pat. No. 4,745,051, incorporated herein by reference, or of other literature concerning baculovirus recombinants, with exogenous DNA of any of U.S. Pat. Nos. 5,047,320, 5,075,213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995, Paoletti et al. WO 94/16716 based on U.S. applications Ser. Nos. 007,115, filed Jan. 21, 1993, and 184,009, filed Jan. 19, 1994, or other documents cited and incorporated herein, or literature concerning HCMV antigens, epitopes of interest, p53, p53 epitopes of interest, and DNA coding therefor, and teachings herein, baculovirus embodiments expressing any desired HCMV and/or p53 epitope of interest and obtaining gene products therefrom, are within the ambit of the skilled artisan, without undue experimentation, for practice of this invention.

By employing the techniques of U.S. Pat. Nos. 5,591,639, 5,589,466, 5,580,589, incorporated herein by reference, or of other literature concerning DNA expression vectors with exogenous DNA of any of U.S. Pat. Nos. 5,047,320, 5,075, 213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995, Paoletti et al. WO 94/16716 based on U.S. applications Ser. Nos. 007,115, filed Jan. 21, 1993, and 184,009, filed Jan. 19, 1994, or other documents cited and incorporated herein or literature concerning HCMV antigens, epitopes of interest, p53, p53 epitopes of interest, and DNA coding therefor, and the teachings herein, DNA expression vector embodiments expressing any desired HCMV and/or p53 epitope of interest and obtaining gene products therefrom, are within the ambit of the skilled artisan, without undue experimentation, for practice of this invention.

Similarly, any other desired vector or recombinant expressing any desired HCMV and/or p53 epitope of interest and obtaining gene products therefrom, are within the ambit of the skilled artisan, without undue experimentation, from this disclosure and the knowledge in the art, for practice of this invention.

The expression product generated by vectors or recombinants in this invention can also be isolated from infected or transfected cells and used to inoculate patients in a subunit vaccine configuration (composition, or an antigenic or immunological composition).

Further, DNA encoding a CMV and/or p53 epitope(s) of interest can be administered through immunization using alternate appropriately engineered mammalian expression systems including but not limited to other poxviruses, herpesviruses, adenoviruses, alphavirus-based strategies, and naked or formulated DNA-based immunogens. Techniques for engineering such recombinant subunits are known in the art. With respect to techniques for these immunization vehicles and state-of-the-art knowledge mention is particularly made of: Hormaeche and Kahn, Perkus and Paoletti, Shiver et al. all in *Concepts in Vaccine Development*, Kaufman, S. H. E., ed., Walter deGruytes, New York, 1996, and vectors described in *Viruses in Human Gene Therapy*, Vos, J. -M. H., ed, Chapman and Hall, Carolina Academic Press, New York, 1995, and in *Recombinant Vectors in Vaccine Development,* Brown, F., ed., Karger, New York, 1994.

The invention still further provides an antigenic, immunogenic, immunological or vaccine composition for use in therapy, treatment and/or prophylaxis of restenosis and/or atherosclerosis containing the recombinant virus or expression product thereof, and an acceptable carrier or diluent. An immunological composition containing the vector or recombinant virus (or an expression product thereof) elicits an immunological response—local or systemic. The response can, but need not be, protective. An immunogenic composition containing the vector or recombinant virus (or an expression product thereof) likewise elicits a local or systemic immunological response which can, but need not be, protective. An antigenic composition similarly elicits a local or systemic immunological response which can, but need not be, protective. A vaccine composition elicits a local or systemic protective response. Accordingly, the terms "immunological composition", "antigenic composition" and "immunogenic composition" include a "vaccine composition" (as the three former terms can be protective compositions). A protective response is understood to be a response, such as a humoral and/or secretory and/or cell-mediated response which confers an immunity, with immunity understood to comprise the ability to resist or overcome infection or to overcome infection more easily as compared to a subject not administered the inventive composition, or to better tolerate infection as compared to a subject not administered the inventive composition, e.g., increased resistance to infection.

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology,* 1988.

As to size: the skilled artisan can maximize the size of the protein encoded by the DNA sequence to be inserted into the mammalian vector (keeping in mind the insertion limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD4+T cell response (which recognizes virus infected cells or cancerous cells). A minimum peptide length of 13 to 25 amino acids is useful to stimulate a CD8+T cell response (which recognizes special antigen presenting cells which have engulfed the pathogen). See Kendrew, *The Encyclopedia of Molecular Biology* (Blackwell Science Ltd 1995). However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides completed with MHC molecules. The method is less effective for determining B-cell epitopes" since B cell epitopes are often not linear amino acid sequence but rather result from the tertiary structure of the folded three dimensional protein. Janis Kuby, *Immunology*, pp. 79–80 (1992).

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology,* p. 81 (1992).

Yet another method for determining an epitope of interest is to perform an X-ray crystallographic analysis of the antigen (full length)-antibody complex. Janis Kuby, *Immunology*, p. 80 (1992).

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatibility complex MHC" located on another cell's surface. There are two classes of MHC complexes—class I and class II, and each class is made up of many different alleles. Different patients have different types of MHC complex alleles; they are said to have a "different HLA type".

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD4 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class I cells and kill the cell by exocytosis of lytic granules.

Some guidelines in determining whether a protein contains epitopes of interest which will stimulate a T cell response, include: Peptide length—the peptide should be at least 8 or 9 amino acids long to fit into the MHC class I complex and at least 13–25 amino acids long to fit into a class II MCH complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al., *Specific Binding of Leukemia Oncogene Fusion Protein Peptides to HLA Class I Molecules*, Blood 85:2680–2684; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the the protein was derived. The skilled artisan can use the other guidelines set forth in this disclosure and in the art for generating or expressing portions of a protein of interest for analysis as to whether antibodies thereto inhibit growth in vitro.

For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of a CMV and/or p53 epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

The administration procedure for the vector or recombinant or expression product thereof in the invention, and of compositions of the invention such as immunological, antigenic or vaccine compositions which are prophylactic and/or therapeutic compositions with respect to vascular disease, e.g., atherosclerosis and/or restenosis, can be via a parenteral route (intradermal, intramuscular or subcutaneous). Such an administration enables a systemic immune response. The administration can be via a mucosal route, e.g., oral, nasal, genital, etc. Such an administration enables a local immune response. Direct administration to blood vessels and SMCs (see, e.g., Epstein et al., JACC Vol. 23, No. 6, 1994:1278–88 (and documents cited therein, incorporated herein by reference); Chang et al., Science 267:518–22 (Jan. 27, 1995) (and documents cited therein, incorporated herein by reference)) and; French Patent Application 2723697) are also encompassed within the invention.

Epstein et al., JACC, 23(6): 1278–88 (1994) and Didier et al. (Rhone Poulenc Rorer SA), French Patent Application, publication no. 2,723,697 (Feb. 23, 1996) relate to treatments for restenosis, and Chang et al., Science 267:518–522 (Jan. 27, 1995) is directed to therapy for retinoblastoma.

More generally, the antigenic, immunological or vaccine compositions or therapeutic compositions which are prophylactic and/or therapeutic compositions with respect to vascular disease, e.g., atherosclerosis and/or restenosis (compositions containing the vectors or recombinants of the invention or expression products) can be prepared in accordance with standard techniques well known to those skilled in the pharmaceutical or veterinary arts. Such compositions can be administered in dosages and by techniques well known to those skilled in the medical arts taking into consideration such factors as the age, sex, weight, and condition of the particular patient (e.g., factors such as identified in Example 1), and the route of administration. The compositions can be administered alone, or can be co-administered or sequentially administered with other compositions of the invention or with other prophylactic or therapeutic compositions for decreasing viral load or for targeting SMC proliferation.

Such other compositions can include purified native antigens or epitopes or antigens or epitopes from the expression by a poxvirus recombinant or another vector system (such that compositions can contain more that one epitope of interest from CMV and/or p53); antioxidants which inhibit the cytopathic effect of viral infection, and/or compositions which reduce the transcriptional activity of CMV (transcriptional activity reducer) and/or compositions which decrease reactive oxygen species (ROS) generated by the arachidonic cascade and/or the xanthine/xanthine oxidase system (ROS reducer); or another form of molecular based therapy, e.g., expression of cytotoxic molecules to inhibit proliferation of smooth muscle cells and gene therapy, or antisense strategies to inhibit expression of gene products for cell proliferation. Mention is made of WO 96/24604 relating to compositions and methods for treatment of cardiovascular disease involving genes which are differentially expressed.

The antioxidant can be one or more of Vitamin C, Vitamin E, NAC, PDTC, and the like. For information on ROS, ROS reducers, and antioxidants, mention is made of Ian N. Acworth, Bruce Bailey, "The Handbook of Oxidative Metabolism (ESA, Inc.), e.g., pages i, 1-1, Chapter 2 ("Reactive Oxygen Species"), page 2-1 et seg., Chapter 4 ("Mechanisms of Oxygen Damage"), e.g., page 4-1 et seq., Chapter 5 ("Protection Against Oxidants"), page 5-1 et seq., Chapter 7 ("Diseases Associated With Free Radicals"); Davies, "Oxidative stress: the paradox of aerobic life", Biochem. Soc. Symp. 61, 1–31; Halliwell, "How to characterize an antioxidant: an update", Biochem. Soc. Symp. 61, 73–101; all incorporated herein by reference (including documents cited therein).

The transcriptional activity reducer can be an antiviral drug such as gancyclovir and/or acyclovir (which interfere with viral replication), and/or an antioxidant, or the like.

The ROS reducer can be aspirin (acetylsalicylic acid) or a derivative thereof, ASA, indomethacin, oxypurinol, and the like.

Compositions which also can be administered in conjunction with the immunological or vaccine composition in the practice of the invention for prevention or treatment of atherosclerosis and/or restenosis, directed to reducing viral load or burden, include, calcium influx blockers and cyclic nucleotide modulators for inhibiting CMV replication, e.g., as disclosed in U.S. Pat. Nos. 4,663,317, 4,800,081, 4,849,412, acyclic pyrrolo[2,3-D pyrimidine analogs, e.g., as disclosed in U.S. Pat. No. 4,927,830, polysubstituted benzimidazoles, e.g., as disclosed in U.S. Pat. No. 5,360,795, heterocyclic thioamides and analogs, e.g., as disclosed in U.S. Pat. No. 5,543,413, or anti-HCMV pharmaceutical compositions, e.g., as disclosed in U.S. Pat. No. 5,316,768. Mention is also made of U.S. Pat. No. 5,547,992, relating to anti-HCMV polycarbonate oligomers.

An interesting embodiment can include administration of an antiviral drug such as gancyclovir and/or acyclovir.

Such other composition(s) is (are) administered taking into account the aforementioned factors. It is believed that the present invention provides for the first time the use of compositions which target HCMV and are directed to lowering HCMV viral load or burden, as a means for prevention and/or treatment of vascular disease, e.g., restenosis and/or atherosclerosis. Thus, the aforementioned "other composition(s)" (other than HCMV and/or p53 epitope of interest or recombinant or DNA so expressing vaccine or immunological compositions), in another embodiment of the invention, may be administered for the prevention or treatment of atherosclerosis and/or restenosis, without necessarily also administering a HCMV and/or p53 epitope of interest vaccine or immunological composition.

Examples of compositions of the invention include liquid preparations for orifice, e.g., oral, nasal, anal, genital (e.g., vaginal), vascular and/or SMC, etc., administration such as suspensions, syrups or elixirs; and, preparations for parenteral, subcutaneous, intradermal, intramuscular, intravenous, intraarterial (e.g., at site of lesion or plaque), intralymphatic, or intraperitoneal administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions, can contain an adjuvant and an amount of the recombinant or expression product or isolated product to elicit the desired response (although embodiments of the invention do not necessarily need to contain an adjuvant; and, in some instances, embodiments of the invention may be without added adjuvant); or, the gene product or product expressed in vivo can be in a form which is exceptionally immunogenic (e.g., a fusion peptide wherein a first portion of the peptide enhances immunogenicity; see, e.g., Huebner et al., WO 96/40718, published Dec. 19, 1996).

In human applications, alum (aluminum phosphate or aluminum hydroxide) is a typical adjuvant. Saponin and its purified component Quil A, Freund's complete adjuvant and other adjuvants are used in research and veterinary applications. Chemically defined preparations such as muramyl dipeptide, monophosphoryl lipid A, phospholipid conjugates such as those described by Goodman-Snitkoff et al., *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vesicular Systems, Inc., Nashua, N.H.) can also be used.

The compositions of the invention may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, intravenous, intralymphatic, intraarterial (e.g., at site of lesion or plaque), intraperitoneal, and the like administration. And again, the effective dosage and route of administration are determined by the nature of the composition, by the nature of the expression product, by expression level if the vector or recombinant is directly used, and by known factors, such as age, sex, weight, condition and nature of patient, as well as $LD_{50}$ and other screening procedures which are known and do not require undue experimentation.

Dosages of expressed product or isolated product (e.g., isolated from CMV-infected cells) can range from a few to a few hundred micrograms, e.g., 5 to 500 $\mu$g. The inventive vector or recombinant can be administered in any suitable amount to achieve expression at these dosage levels. The inventive vector or recombinant can be administered to a patient or infected or transfected into cells in an amount of about at least $10^{3.5}$ pfu; more preferably about $10^4$ pfu to about $10^{10}$ pfu, e.g., about $10^5$ pfu to about $10^9$ pfu, for instance about $10^6$ pfu to about $10^8$ pfu. And, if more than one gene product is expressed by more than one recombinant, each recombinant can be administered in these amounts; or, each recombinant can be administered such that there is, in combination, a sum of recombinants comprising these amounts. Other suitable carriers or diluents can be water or a buffered saline, with or without a preservative. The expression product or isolated product or vector or recombinant may be lyophilized for resuspension at the time of administration or can be in solution.

In plasmid compositions, the dosage should be a sufficient amount of plasmid to elicit a response analogous to the expressed antigen compositions; or expression analogous to dosages in expressed antigen compositions; or expression analogous to expression obtained in vivo by recombinant compositions. For instance, suitable quantities of plasmid DNA in plasmid compositions can be 1 ug to 100 mg, preferably 0.1 to 10 mg, but lower levels such as 0.1 to 2 mg or preferably 1–10 ug may be employed. Documents cited herein regarding DNA plasmid vectors may be consulted for the skilled artisan to ascertain other suitable dosages for DNA plasmid vector compositions of the invention, without undue experimentation.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and NanoDarticles in Medicine and Pharmacology,* (M. Donbrow, ed.) CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al., *Current Tonics in Microbiology and Immunology,* 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Furthermore, the vector or recombinant or expression products therefrom or isolated products can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive patient, the reinfusion is to stimulate or boost the immune system against the CMV and/or p53, for prevention or treatment of vascular disease such as restenosis and/or atherosclerosis.

For treatment of restenosis, a HCMV and/or p53 vaccine or immunological composition, alone or with other treatment as herein discussed, may be administered as desired by the skilled medical practitioner, from this disclosure and knowledge in the art, e.g., at the first signs or symptoms of restenosis, or as soon thereafter as desired by the skilled medical practitioner, without any undue experimentation required; and, the administration of the vaccine or immunological composition, alone or with other treatment as herein discussed, may be continued as a regimen, e.g., monthly, bimonthly, biannually, annually, or in some other regimen, by the skilled medical practitioner for such time as is necessary to boost the immune response against CMV and keep it boosted so as to prevent further clogging of blood vessels or further symptoms or signs of restenosis, without any undue experimentation required.

For prevention of restenosis, a HCMV and/or p53 vaccine or immunological composition, alone or with other treatment as herein discussed, may be administered at the first indication of the patient being prone to restenosis, or as soon thereafter as desired by the skilled medical practitioner, e.g., within six months prior to, immediately prior to, or at angioplasty, such as within six weeks prior to, immediately prior to, or at angioplasty, in any desired regimen such as a single administration or multiple administrations in a regimen as desired, e.g., monthly, bi-monthly, biannually, or any combination thereof, without any undue experimentation required. Further, for prevention of restenosis, a HCMV and/or p53 vaccine composition, alone or with other treatment as herein discussed, may be administered after angioplasty in a regimen of single or multiple administrations as desired by the skilled medical practitioner, such as immediately after, within six weeks after, within six months after, and/or within a year after, e.g., monthly, bi-monthly, biannually, annually, or in some other regimen, by the skilled medical practitioner for such time as is necessary to boost the immune response against CMV and keep it boosted so as to prevent clogging of blood vessels or symptoms or signs of restenosis, without any undue experimentation required.

For treatment of atherosclerosis, a HCMV and/or p53 vaccine or immunological composition, alone or with other treatment as herein discussed, may be administered at the first signs or symptoms of atherosclerosis, or as soon thereafter as desired by the skilled medical practitioner, without any undue experimentation required; and, the administration of the vaccine or immunological composition, alone or with other treatment as herein discussed, may be continued as a regimen, e.g., monthly, bi-monthly, biannually, annually, or in some other regimen, by the skilled medical practitioner for such time as is necessary to boost the immune response against CMV and keep it boosted so as to prevent further clogging of blood vessels or further symptoms or signs of atherosclerosis, without any undue experimentation required.

For prevention of atherosclerosis, a HCMV and/or p53 vaccine or immunological composition, alone or with other treatment as herein discussed, may be administered at the first indication of the patient being prone to restenosis and/or atherosclerosis, or as soon thereafter as desired by the skilled medical practitioner, in any desired regimen such as a single administration or multiple administrations in a regimen as desired, e.g., monthly, bi-monthly, biannually, or any combination thereof, without any undue experimentation required, e.g., for such time as is necessary to boost the immune response against CMV and keep it boosted so as to prevent clogging of blood vessels or symptoms or signs of atherosclerosis, without any undue experimentation required.

Further, given the prevalence of HCMV in the population as correlated to age, as discussed above (CMV present: in about 10 to 15% of the adolescent population; in about 40 to 50% of the adult, age 35 population; and in more than 60 to 70% of the adult, over age 65 population), a program of administering a HCMV vaccine or immunological composition from childhood, to reduce the prevalence of HCMV in the population, is yet a further method for preventing atherosclerosis and/or restenosis; and, this program can be annual, bi-annual or some other regimen of administration as desired by the skilled medical practitioner, without undue experimentation.

The therapeutic vaccine or immunological composition of the invention can be administered before the angioplasty to induce maximal cellular immune responses at the time of angioplasty, since the restenotic process happens quickly; however, treatment after angioplasty is not excluded.

As discussed above, the present invention also pertains to diagnostic compositions and methods; and, these diagnostic methods and compositions may be used in conjunction with the therapy and/or treatment and/or prophylactic compositions and methods of the invention.

The method for diagnosis to ascertain a susceptibility to atherosclerosis and/or restenosis can comprise immunologically detecting CMV antibodies, preferably against specific viral proteins that are more specific indicators that the virus has been reactivated, such as IE72, IE84, IE55 and the like. The immunologically detecting can be by ELISA and/or immunoblotting. The Examples below discuss testing patients for antibodies against CMV, as well as testing samples for the presence of CMV epitope(s) of interest, antibodies thereto, and DNA coding therefor. Mention is also made of U.S. Pat. Nos. 5,180,813 and 4,716,104, incorporated herein by reference, relating to early envelop glycoprotein and monoclonals to HCMV glycoproteins, and detection of HCMV antigens by antibodies reactive to IE.

The method can include, in addition or alternatively to detecting the neutralizing antibodies, detecting whether CMV mRNA is present in peripheral blood monocytes (PBMCs), e.g., by PCR (such as RT-PCR) and/or detecting whether a cellular-mediated immune response to CMV peptides or proteins is present, e.g., whether PBMCs recognize and/or respond to CMV peptides or proteins.

To detect whether CMV nucleic acids are in a sample, the skilled artisan can employ DNA for primers, as used in the Examples below, or as in the art, e.g., the Paoletti and Paoletti et al. patents and patent publications discussed herein, U.S. Pat. Nos. 5,569,583, 5,173,402, and 4,762,780, incorporated herein by reference, relating to detection of CMV using primers or DNA sequences, U.S. Pat. Nos. 5,047,320 and 5,075,213, incorporated herein by reference, relating to DNA probes for HCMV gp64 (as well as use of HCMV gp64 as a vaccine), and U.S. Pat. Nos. 5,591,439 and 5,552,143, incorporated herein by reference, relating to adenovirus-HCMV gB and IE-exon 4 recombinants.

For instance, DNA as herein disclosed may be contacted with a specimen from a patient, with that DNA employed as a primer in a polymerase chain reaction. From that the skilled artisan can detect the presence or absence of CMV in the sample, and ergo propensity to or against vascular disease such as restenosis and/or atherosclerosis. The sample can be SMCs, sera, blood, or the like, or samples as used in the art.

This aspect of the invention can relate to a skin test whereby the CMV proteins or peptides are administered subcutaneously or intradermally or intramuscularly, which reflects the patient's capacity to mount a cellular-mediated response targeted to the CMV proteins or peptides. A negative or positive skin test shows patients with prior CMV infection and who are thus susceptible or resistant to atherosclerosis and/or restenosis. A negative skin test, for instance, may show either someone who has never seen the virus (Ab–T– of Example 2) or someone who has seen the virus, but did not make a cellular response (Ab+T– of Example 2).

This aspect of the invention can relate more generally to presenting the patient's PBMCs with CMV proteins or peptides and measuring either the proliferative response of the cells or the cytokine profile to determine whether there is a dominant Th1 (e.g., IL-2, IFN-12, IFNγ) or Th2 (IL-4, IL-10) response.

The CMV proteins or peptides can be purified CMV proteins or peptides from lysates of cells previously infected with CMV, or from recombinant expression of the CMV proteins or peptides or epitopes of interest; and, useful in this aspect of the invention is the CMV and p53 epitopes of interest discussed in the following Examples or as in the art, e.g., the Paoletti and Paoletti et al. patents and patent publications discussed herein, U.S. Pat. Nos. 5,047,320 and 5,075,213, incorporated herein by reference, relating to HCMV gp64 as a vaccine, and U.S. Pat. Nos. 5,591,439 and 5,552,143, incorporated herein by reference, relating to adenovirus-HCMV gB and IE-exon 4 recombinants and products therefrom.

This aspect of the invention can also relate to HLA phenotyping and/or HLA genotyping, as such phenotyping and/or genotyping can be used to predict the susceptibility to CMV-induced vascular disease such as restenosis and/or atherosclerosis (see, e.g., Example 2).

This aspect of the invention can further relate to detection of p53. CMV interacts with p53 in smooth muscle cells (SMCs). p53 present in increased amounts binds to MHC Class I antigens in the SMCs and is processed and presented at the cell surface at an increased rate, resulting in stimulation of T cell response, underlying the antibody responses (whereas normal p53 is immunologically silent). Increased or steady state levels of p53 are present in cancers or when viral oncoproteins bind to p53 (as is the case with CMV).

Thus, detection of p53, e.g., at lesions, can be indicative of the presence of CMV proteins, and an indicator of the presence or absence or restenosis and/or atherosclerosis, or of the propensity to develop vascular disease such as restenosis and/or atherosclerosis. p53, or an epitope thereon, can be obtained from cells, or by recombinant methods, e.g., as discussed in the Examples, for use in this aspect of the invention; or, for use in this aspect of the invention, one can use antibodies elicited by such p53, or an epitope thereon, for detection of the presence of p53.

Accordingly, the diagnostic method can comprise screening a sample from a patient (e.g., sera, blood, SMCs, lesions) for antibodies to CMV and/or for the presence of CMV proteins and/or p53. The method can further comprise: screening a sample from a patient for specific viral proteins and/or antibodies thereto that predict whether the virus has been reactivated such as IE72, IE84, IE55 and the like.

These screenings can employ epitopes of interest as in the Examples, or as in the art, e.g., the Paoletti and Paoletti et al. patents and patent publications discussed herein, U.S. Pat. Nos. 5,047,320 and 5,075,213, incorporated herein by reference, relating to HCMV gp64, and U.S. Pat. Nos. 5,591,439 and 5,552,143, incorporated herein by reference, relating to adenovirus-HCMV gB and IE-exon 4 recombinants, in binding assays, or antibodies elicited therefrom; and, binding assays and purification/isolation procedures with respect to epitopes of interest are included in the Examples, or as in the art, e.g., the Paoletti and Paoletti et al. patents and patent publications discussed herein, U.S. Pat. Nos. 5,047,320 and 5,075,213, incorporated herein by reference, relating to HCMV gp64, and U.S. Pat. Nos. 5,591,439 and 5,552,143, incorporated herein by reference, relating to adenovirus-HCMV gB and IE-exon 4 recombinants, and U.S. Pat. Nos. 5,180,813 and 4,716,104 relating to monoclonals to HCNV glycoproteins and detection of HCMV antigens by antibodies reactive to IE.

These screenings can further comprise detecting whether CMV mRNA is present in PBMCs, e.g., by PCR (such as RT-PCR), e.g., employing DNA as disclosed in the Examples herein, or as in the art, e.g., the Paoletti and Paoletti et al. patents and patent publications discussed herein, U.S. Pat. Nos. 5,047,320 and 5,075,213, incorporated herein by reference, relating to HCMV gp64, and U.S. Pat. Nos. 5,591,439 and 5,552,143, incorporated herein by reference, relating to adenovirus-HCMV gB and IE-exon 4 recombinants; and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCS) or the cytokine profile; and/or HLA phenotyping and/or HLA genotyping; and optionally screening a sample from a patient (e.g., sera, blood, lesions, SMCs, etc.) for p53. With respect to RT-PCR (reverse transcriptase-polymerase chain reaction), reference is made to Luehrsen et al., BioTechniques 22(1):168–174 (1996).

The initial screening for antibodies to CMV may optionally be omitted, such that the diagnostic method can comprise: screening a sample from a patient for specific viral proteins that predict whether the virus has been reactivated such as IE72, IE84, IE55 and the like; and/or detecting whether CKV mRNA is present in PBMCs, e.g., by PCR (such as RT-PCR); and/or detecting whether a cellular-mediated immune response to CMV peptides or proteins is present, e.g., whether PBMCs recognize and/or respond to CMV peptides or proteins, e.g., by administering a CMV skin test by administering CMV proteins or peptides intradermally or subcutaneously or intramuscularly and ascertaining the result of the skin test and/or presenting CMV proteins or peptides to a patient's PBMCs and measuring either the proliferative response of the cells (PMBCs) or the cytokine profile; and/or HLA phenotyping and/or HLA genotyping; and optionally screening a sample from a patient (e.g., sera, blood, SMCs, lesions, etc.) for p53.

In general, the diagnostic methods are to ascertain the presence of or propensity towards or against vascular disease such as restenosis and/or atherosclerosis which evaluate whether an individual has been infected by CMV and/or whether a cellular response is present, wherein the cellular mediated response may be predictive of an ability to fight infection, e.g., predictive of a predisposition to or against (prevention of) vascular disease such as restenosis and/or atherosclerosis. Alternatively, it may be predictive of immunopathology, and thereby predict susceptibility to restenosis and/or atherosclerosis. The diagnostic methods can be for stratification of atherosclerosis and/or restenosis risk.

For instance, the methods of the present invention may be useful in the following scenario: someone presents with coronary artery disease and angioplasty is being considered. The patient would be tested for CMV (Abs or cellular response, etc. as herein). If negative, the patient would be at low risk for restenosis (see Examples 1, 2), so angioplasty is indicated without therapy or treatment, e.g., without pre-angioplasty and/or follow-up treatment or therapy, such as aggresive follow-up. If positive, then the patient has a 40–50% risk of restenosis (see Examples 1, 2), and should probably get treatment or therapy, e.g., pre-angioplasty and/or follow-up to angioplasty, by the administration of a composition according to the invention (see description supra, Examples 3 et seq.), or a combination of both in doses such that the skilled artisan would consider such therapy or treatment "aggressive".

And, the CMV in the various aspects to which the invention pertains can be of human CMV (HCMV), murine CMV (MCMV) or rat CMV (RCMV) origin, with HCMV and RCMV embodiments preferred.

In addition, the therapeutic and prophylactic methods of the present invention can be performed with respect to other infectious agents causing cardiovascular disease. For instance, an antigen or portion thereof, such as an epitope of interest, or a recombinant, e.g., naked DNA, DNA plasmid, virus, etc. expressing such an antigen etc., in vivo and/or in vitro, of another infectious agent linked to cardiovascular disease may be employed instead of or in addition to the CMV antigen or portion thereof in the present invention.

An example of a particular additional infectious agent is Chlamydia pneumoniae, which has been implicated in coronary artery disease; see, e.g., Peeling et al. Emerging Infectious Diseases 2:307–319 (1996); Saikku et al., Chronic Chlamydia pneumoniae Infection as a Risk Factor for Coronary Heart Disease in the Helsinki Heart Study. Ann Intern Med 1992;116:273–8; Thom et al., Association of Prior Infection With Chlamydia pneumoniae and Angiographically Demonstrated Coronary Artery Disease. JAMA 1992;268:68–72; Melnick et al., Past Infection by Chlamydia pneumoniae Strain TWAR and Asymptomatic Carotid Atherosclerosis. Am J Med 1993;95:499–504; Shor et al., Detection of Chlamydia pneumoniae in coronary arterial fatty streaks and atheromatous plaques. S Afr Med J 1992;82:158–61; Kuo et al., Demonstration of Chlamydia pneumoniae in Atherosclerotic Lesions of Coronary Arteries. J Infect Dis 1993;167:841–9; Muhlestein et al., Increased incidence of Chlamydia species within the coronoary arteries of patients with symptomatic atherosclerotic versus other forms of cardiovascular disease. J Am Coll Cardiol 1996;27:1555–61; Godzik et al., In Vitro Susceptibility of Human Vascular Wall Cells to Infection with Chlamydia pneumoniae. J Clin Microbiol 1995;33:2411–4 (but see Weiss et al., Failure to detect Chlamydia pneumoniae in coronary atheromas of patients undergoing atherectomy. J Infect Dis 1996;173:957–62, which is discounted in view of the overwhelming foregoing citations to the contrary). Similarly, the diagnostic methods can be extended to detecting the presence of such other infectious agents. And, these additional therapeutic, prophylactic and diagnostic methods are all within the ambit of the present invention.

A better understanding of the present invention and of its many advantages will be had from the following examples, given by way of illustration.

EXAMPLES

Example 1

Relation Between Antibodies to CMV at Angioplasty and Restenosis

With respect to this Example, reference is made to Zhou et al., "Association Between Prior Cytomegalovirus Infection And The Risk Of Restenosis After Coronary Atherctomy," Aug. 29, 1996, New England Journal of Medicine, 335:624–630, incorporated herein by reference.

CMV infection of immunocompetent adults is common, see Melnick et al. European Heart Journal, supra, and usually asymptomatic, Jordan et al., Ann. Intern, Med. 1973; 79:153–160., Klacsmann, De. Med. J. 1977; 49:499–509. Like other herpesviruses, CMV persists indefinitely in certain host cells. Bruggeman, Vurchows Arch. B. Cell Pathol. 1993; 64:325–333; Banks et al., Clin. Infect. Dis. 1992; 14:933–941. Certain circumstances such as immunosuppression, Jacobson et al. Ann. Intern. Med. 1988; 108:585–94, or iatrogenically following organ transplantation, Schulman et al., Arch. Intern, Med. 1981; 151:1118–24, CMV can be reactivated and cause serious disease, as can other herpesviruses. Viral replication may contribute to the disease process.

CMV may also contribute to disease processes during abortive infections, Southern et al., Engl. J. Med. 1986; 314:359–67, wherein there is viral gene expression limited to immediate early (IE) gene products without viral replication, see Geist et al., Am. J. Respir. Cell. Mol. Biol. 1991; 5:292–296 (CMV IE gene products affecting expression of human cellular genes involved in inflammation and immunologic responses).

Methods

Patients and Study Design

Patients included in this investigation were part of the OARS trial (Optimal Atherectomy Restenosis Study), which was designed to determine the frequency of restenosis following directional coronary atherectomy (DCA). Follow-up angiographic evaluation was obtained approximately 6 months later. Patients derived solely from one of the four multicenter sites (Washington Hospital Center), which recruited 100 of the total 211 OARS patients. Of these 100 patients, 7 were "de-registered" due to an initial procedural complication or protocol violation; an additional 18 patients failed to obtain follow-up angiographic study, leaving a total of 75 patients included in this study.

The patients ranged from 35 to 78 years (mean 58), and there were 58 men and 17 women. Blood samples were collected before and six months after DCA to assay anti-CMV IgG and IgM antibody status. Blood samples were assayed for anti-CMV antibodies without knowledge of the patients' angiographic status.

Clinical Definitions

The following definitions were used: diabetes—if the patient was taking insulin or oral hypoglycemic agents, or had previously taken them and was currently diet controlled; hypertension—if the patient was diagnosed as having hypertension and/or was being treated with antihypertensive medications or diet; hypercholesterolemia—if the patient had a serum cholesterol value of >240 mg/dl at the time of angioplasty or if the patient was on cholesterol lowering treatment.

Directional Atherectomy Procedure

Optimal directional coronary atherectomy involves 1) initial localized plaque resection followed by 2) circumferential plaque resection using larger devices or higher support balloon pressures, and usually concluded with 3) adjunct low-pressure balloon dilatation. Ultrasound guidance is utilized to optimize results. Of the 75 patients, 65 (87%) had adjunct PTCA resulting in a mean 10% additional reduction in final percent diameter stenosis. Two patients (3%) had stents placed after the atherectomy procedure to treat severe lumen-compromising dissections.

Angiographic Analysis

Cineangiograms were forwarded to the core angiographic laboratory blinded to the results of patients' anti-CMV antibody status. Baseline, post DCA procedural, and late follow-up cineangiograms were analyzed using an automated edge detection algorithm (CMS, MEDIS). Minimal lumen diameter (MLD), interpolated reference diameter, and percent diameter stenosis before and after intervention and on follow-up angiography were measured from two projections; the average of these two values is reported. Acute gain was defined as MLD immediately post DCA minus MLD pre DCA; late loss was defined as MLD immediately post DCA minus MLD at six-month follow-up; loss index was defined as late loss divided by acute gain. Restenosis was defined as a dichotomous endpoint of >50% diameter stenosis at follow-up study in a lesion that had been opened to a <50% narrowing immediately after the DCA procedure.

Assays for CKV Antibodies

Anti-CMV IgG assay. Anti-CMV IgG antibodies were tested by using the ELISA kit (Cytomegelisa II test kit) from BioWhittaker (Walkersville, Md.) according to manufacturer's directions. Patient antibody titers ("cytomegelisa value") were determined from a standard curve. The threshold value for defining a result as seropositive was determined prospectively, as per the manufacturer: a cytomegelisa value <0.25 units is a negative response, while a value of ≧0.25 units indicates prior exposure to CMV.

Anti-CMV IgM test. Anti-CMV IgM antibodies were tested by using the enzyme-linked antibody capture assay kit (CMV CAP-M) from BioWhittaker (Walersville, Md.), according to the manufacturer's directions. As per the manufacturer, an index value of <0.9 was interpreted as negative for CMV IgM antibodies, while a value of >1.1 was interpreted as positive for CMV IgM.

Statistical Analysis

Statistical analyses of frequency counts were performed by the Chi-Square test or the Fisher's Exact test for small sample sizes, and means were compared by the two-sample t-test. All tests were 2-sided. The odds ratio, for comparing the odds of restenosis in those with a given risk factor to those without the risk factor, was chosen as a measure of risk in this prospective study. Modelling of the dichotomous definition of restenosis outcome was performed using the logistic regression model. Factors affecting loss index were identified using linear regression. The covariates considered were CMV status (as a dichotomous variable), CMV titer (as a continuous variable), diabetes, hypercholesterolemia, hypertension, left anterior descending coronary artery location, small reference vessel size (<3 mm in diameter), a history of recent smoking, gender, age, and whether or not the patient had unstable angina as the indication for DCA. All covariates were examined for importance as predictors of restenosis and loss index univariately, as a group in one multivariate model, and in a stepwise multivariable model.

Patient Characteristics

The patients in this study are of similar age and gender, and have similar vessel lesion distribution as the total OARS cohort (Table 1). suggesting that the subgroup is representative of patients undergoing DCA in the larger study.

Forty-nine of the 75 patients (65%) had positive anti-CMV IgG antibody status at study entry, suggesting that they had prior CMV exposure. This prevalence of CMV seropositivity is similar to that reported in several epidemiologic studies conducted in subjects of similar age. Geist et al., Am. J. Respir. Cell. Mol. Biol. 1991; 5:292–296. Of the 18 patients deleted from study because a 6-month angiogram was not obtained, 11 (61%) were CMV seropositive, a percentage virtually identical to that of the 75 patients included in the study. Restenosis developed in 23 of the 75 patients (31%).

Within the CMV seropositive and seronegative groups the relative prevalence of several factors suspected of conveying some increased risk of developing restenosis (see Table 4) did not differ. The one exception was hypertension, which was present in 59% of the seropositive and in 31% of the seronegative patients (p=0.02). Additional analyses showed, however, that hypertension was unrelated to restenosis (p=0.18).

Correlation Between CMV Seropositivity and Development of Restenosis

By comparing patients' anti-CMV IgG antibody status at study entry with six month angiographic outcome, we found that of the 49 patients with prior CMV exposure, 21 (43%) developed restenosis; only 2 of the 26 patients (8%) without prior CMV exposure developed restenosis (p=0.002; FIG. 1A). Analysis of the data using percent stenosis of target vessels at follow-up as a continuous variable indicated that CMV infection predisposes to more severe stenosis (p=0.01; FIG. 1, Table 2).

Figure 2:
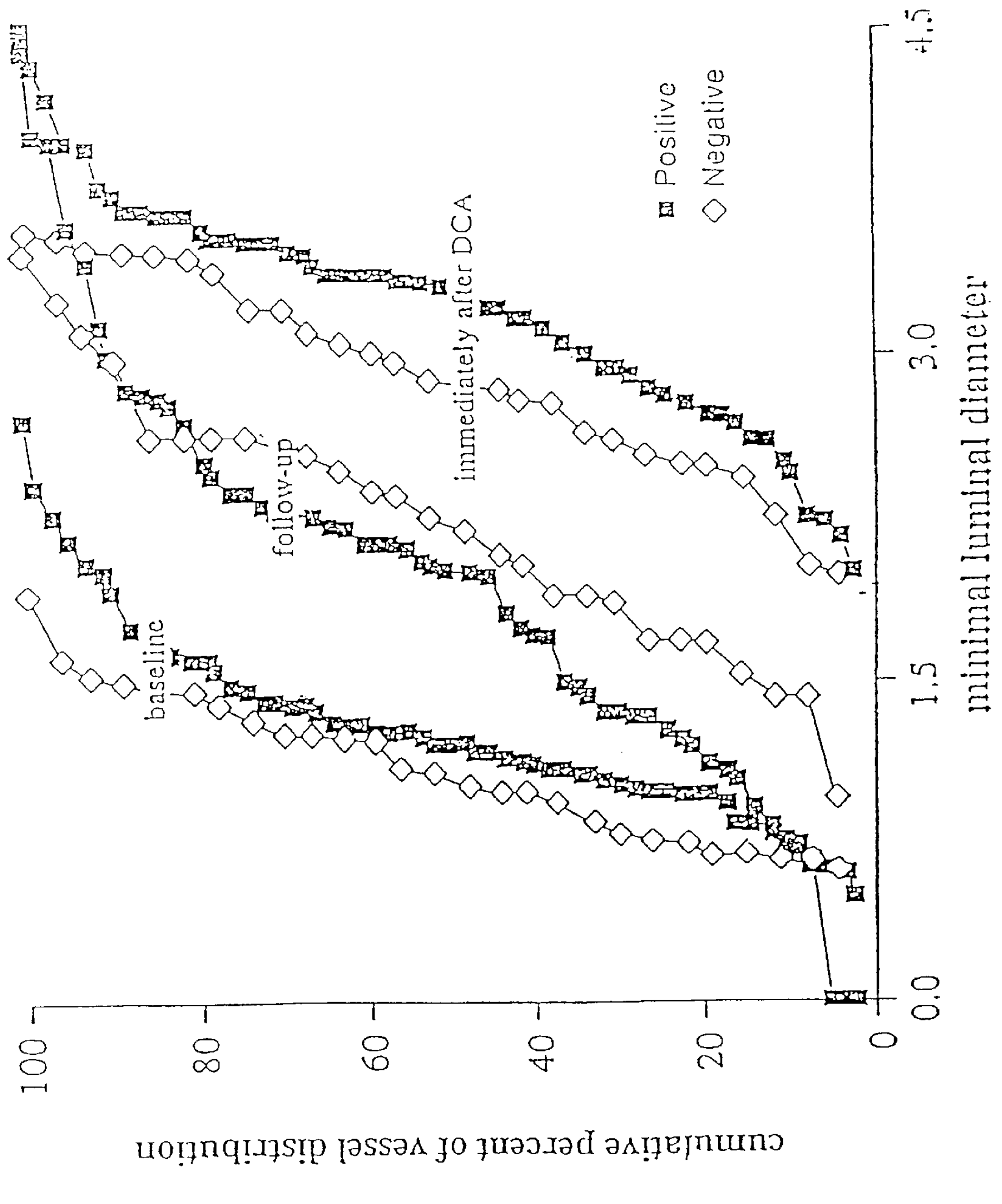
FIG. 2 shows the cumulative percent distribution of MLD at base line, immediately after the DCA procedure, and at six-month follow-up (See text and Table 2 for detailed statistical analysis)
Figure 3:
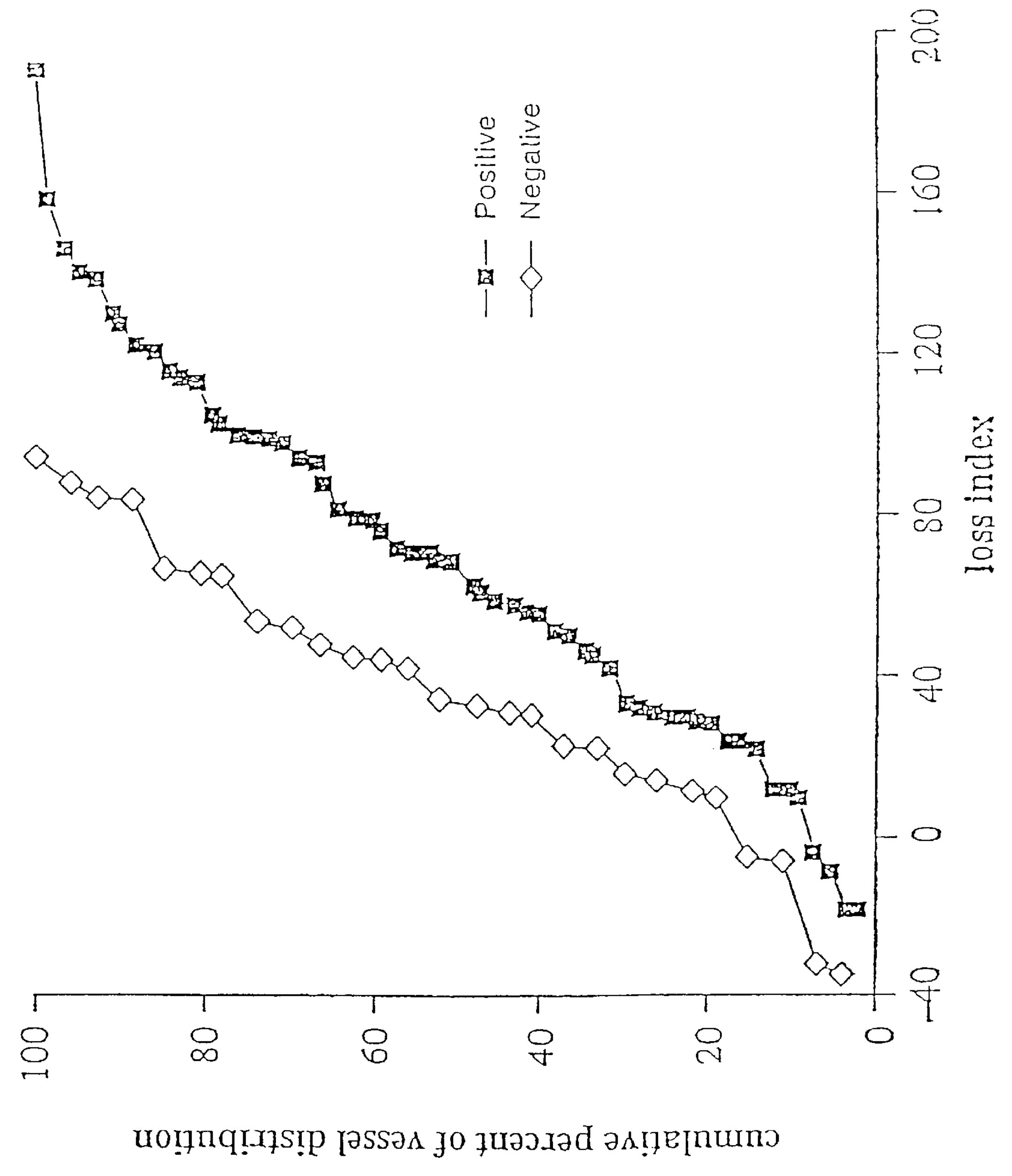
FIG. 3 shows the cumulative percent distribution of luminal diameter loss index (The loss index (late loss divided by acute gain) was higher in the seropositive than in the seronegative patients (p=0.0005))

The luminal dimensions and percent stenosis at baseline, immediately after the DCA procedure, and at follow-up are presented in Table 2. A plot of the cumulative percent of target vessels against MLD at each of the three time points, is shown in FIG. 2. At baseline, the reference vessel diameter and lesion MLD tended to be larger in the CMV seropositive patients, but there was no difference in percent stenosis. Immediately after the procedure, the seropositive group had a slightly larger lesion MLD (p=0.01), but the mean acute gain was similar. However, the seropositive group had a much greater late loss (p=0.003) and, most importantly, an almost 50% greater loss index than the seronegative group (p=0.0005; Table 2 and FIG. 3).

The Influence of CMV Seropositivity and Other Risk Factors on the Development of Restenosis Univariate analyses (Table 3) identified CMV status as the only statistically significant predictor of restenosis (odds ratio=9.0, p=0.002). An analysis of the association of mean IgG antibody titers on restenosis confirmed the finding (mean titer=0.66±0.30 units for restenosis patients and 0.44±0.35 for no restenosis; p=0.01). There were no other statistically significant predictors of restenosis among the remaining potential risk factors examined. CMV status and CMV titer maintained their relationship with restenosis in the full multivariate logistic regression models (odds ratios, with 95% confidence intervals:=12.9; 2.3, 71.11, p=0.003, and =8.1; 1.5, 43.2, p=0.01, respectively).

The Influence of CMV Seropositivity and Other Risk Factors on Loss Index

Simple linear regression models show that both CMV titer and the dichotomous CMV status (cytomegelisa values ≧0.25 considered positive for CMV, as defined prospectively) are each strong predictors of loss index (p=0.01 and p=0.002, respectively).

The full multiple regression model for loss index shows CMV, when analyzed either as a continuous titer or a dichotomous variable, to be a persistent and independent predictor over and above the effects of all other model covariates (p=0.03 and p=0.01, respectively). Table 4 contains the results for the full model with CMV titer. No other risk factors gained or lost appreciable importance between univariate and multivariate analysis. Also, a stepwise approach to model selection identified CMV titer (and CMV status) as the only significant prognostic variable for loss index. Although the relationship between CMV titer and restenosis was highly significant (p=0.01), CMV titer explained only 7% of the variation in late loss index ($r^2$=0.07). To put this into perspective, taken as a whole, all the risk factors analyzed in this investigation explain only 11.5% if the total variation in loss index.

To determine whether the effect of CMV differed in subgroups defined by the other potential risk variables analyzed in the study, a two-factor interaction of each with CMV was tested and none found significant.

Evidence Against the Presence of Acute Infection and Systemic Viremia

Figure 4:
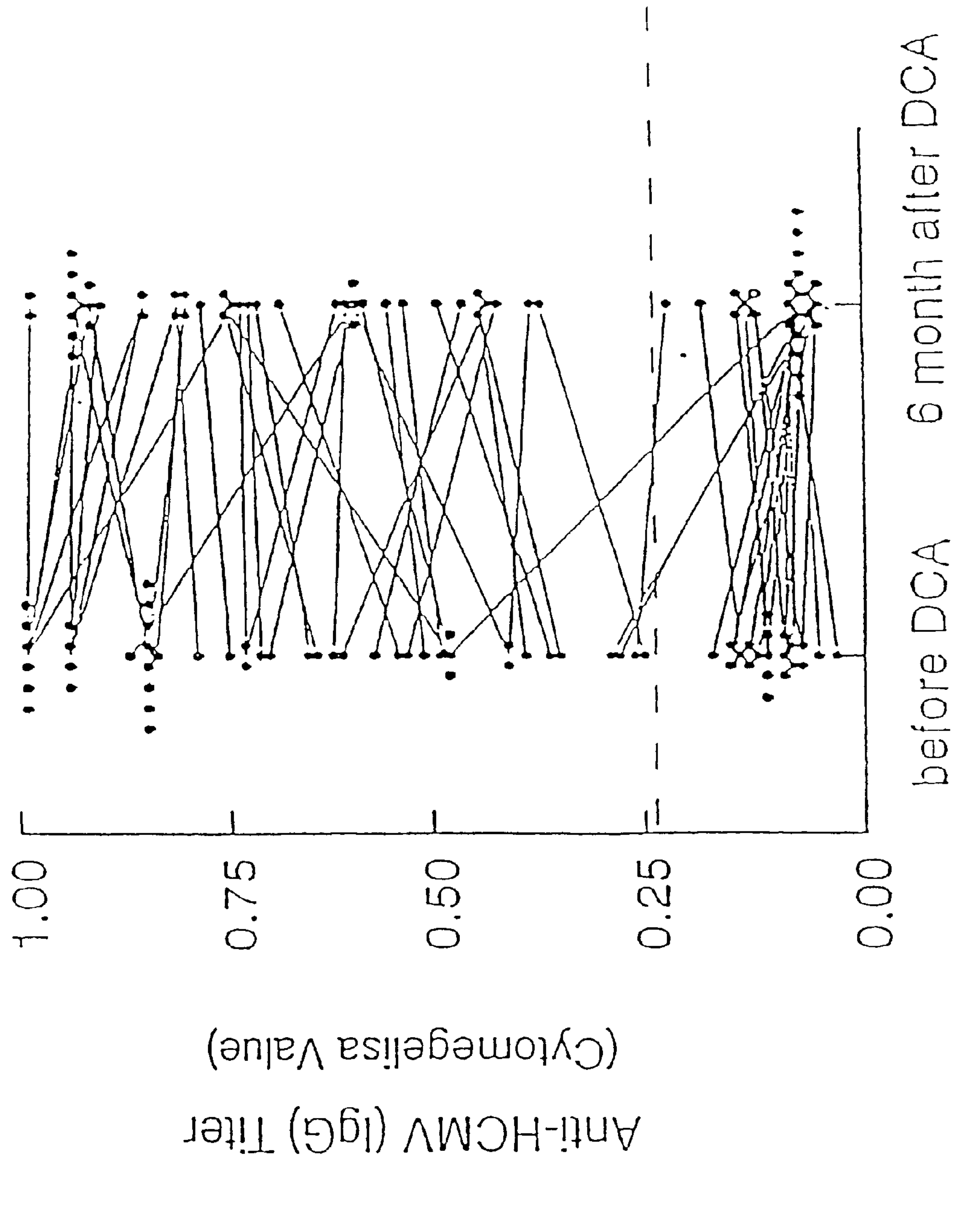
FIG. 4 shows the patients' anti-CMV IgG antibody titer status at study entry and six months following the DCA procedure.

Assays for anti-CMV IgM antibodies, usually present only early after acute infection, were performed. No anti-CMV IgM antibodies were detected in any of the patients. Also, at approximately the six month time-point of the study (the time of follow-up angioplasty), a second assay to determine IgG anti-CMV antibody titers was performed. There was no significant change in titers (FIG. 4). Most importantly, no patient in the original CMV immunopositive group exhibited a significant increase in titer (>2×), and titers fell to within the negative range in only four CMV seropositive patients (of these four patients, all developed restenosis). In addition, none of the original CMV seronegative patients became seropositive.

Immune Status Against Another Virus

To determine whether the correlation between CMV immunopositivity and restenosis was merely a reflection of either a generalized susceptibility to viral infection or a marker of an increased but non-specific immune responsiveness, we determined whether there was a correlation between pre-existing antibodies to Hepatitis A virus and restenosis (seroposivity to Hepatitis A has approximately the same frequency as seropositivity to CMV). Forty-one percent of the total patient group was seropositive for Hepatitis A virus. However, no significant association with restenosis was found; the restenosis rate was 35.7% for Hepatitis A seropositive patients and 37.5% for Hepatitis A seronegative patients.

This Example provides the first prospective evidence indicating that prior exposure to CMV, as indicated by the presence of CMV IgG antibodies, at the time of coronary angioplasty, is a strong independent risk factor for the subsequent development of restenosis (p=0.002; FIG. 1).

TABLE 1

Comparison between total patient cohort of OARS and the OARS subgroup included in the present study.

| | Total OARS (N = 199) | Subgroup studied (N = 75) | P value |
|---|---|---|---|
| Age | 58 ± 11 (36–80) | 58 ± 10 (35–78) | 100◆ |
| Gender (male) | 152 (76%) | 58 (77%) | 0.868† |
| SVD + DVD* | 187 (94%) | 73 (97%) | 0.525⁺ |

*SVD, DVD = number of patients with single and double vessel disease respectively.
◆By 2-sample T-test (two tailed)
†By $X^2$-text
⁺By Fisher's Exact test (two tailed)

TABLE 2

Influence of anti-CMV IgG seropositive/seronegative status on angiographic results of atherectomy

| | CMV + (N = 58 vessels) Mean ± SD mm | CMV − (N = 27 vessels) Mean ± SD mm | P-value* |
|---|---|---|---|
| PRE | | | |
| Reference diameter | 3.23 ± 0.42 | 3.05 ± 0.48 | 0.07 |
| MLD | 1.29 ± 0.44 | 1.09 ± 0.33 | 0.045 |
| Stenosis (%) | 60 ± 12 | 64 ± 11 | 0.21 |
| IMMED-POST | | | |
| Reference diameter | 3.37 ± 0.44 | 3.21 ± 0.47 | 0.13 |
| MLD | 3.18 ± 0.51 | 2.89 ± 0.45 | 0.01 |
| Stenosis (%) | 5 ± 13 | 10 ± 10 | 0.11 |
| FOLLOW-UP | | | |
| Reference diameter | 3.27 ± 0.49 | 3.08 ± 0.40 | 0.08 |
| MLD | 1.93 ± 0.94 | 2.20 ± 0.6 | 0.12 |
| Stenosis (%) | 42 ± 25 | 28 ± 18 | 0.01 |
| GAIN/LOSS | | | |
| Acute gain | 1.90 ± 0.56 | 1.80 ± 0.55 | 0.44 |
| Late loss | 1.24 ± 0.83 | 0.68 ± 0.69 | 0.003 |
| Loss index (%) | 68 ± 47 | 36 ± 33 | 0.0005 |

*by 2-sample T-test (two sided)

Reference diameter refers to diameter of the normal segment of vessel adjacent to the stenosis.

MLD=minimal luminal diameter of the stenotic lesion

Definition of gain/loss terms as per Example

TABLE 3

Univariate association of restenosis with potential risk factors.

| | Restenosis* (n = 23) N (%) | No restenosis (n = 52) N (%) | Odds Ratio (95% Cl) | P Value+ |
|---|---|---|---|---|
| DMV + | 21 (91%) | 28 (54%) | 9.00 (1.91, 42.38) | 0.002 |
| Diabetes | 4 (17%) | 8 (15%) | 1.16 (0.31, 4.31) | 1.00 |
| LAD lesion | 11 (48%) | 25 (48) | 0.99 (0.37, 2.64) | 0.98 |
| Vessel size (<3 mm dia) | 8 (35%) | 21 (40%) | 0.79 (0.28, 2.19) | 0.65 |
| Hypertension | 14 (61%) | 23 (44%) | 1.96 (0.72, 5.33) | 0.18 |
| Hypercholesterolemia | 7 (30%) | 21 (40%) | 0.65 (0.23, 1.84) | 0.41 |
| smoking | 5 (22%) | 17 (33%) | 0.57 (0.18, 1.8) | 0.34 |
| Gender (men) | 20 (87%) | 38 (73%) | 2.44 (0.63, 9.09) | 0.19 |
| Unstable angina | 17 (74%) | 40 (77%) | 0.85 (0.27, 2.64) | 0.78 |

*Restenosis defined as dichotomous variable (>50% luminal diameter narrowing)
+All p-values by $x^2$-text except† by Fisher's Exact Test (two-tailed).

TABLE 4

Association of potential risk factors with loss index (Full multiple linear regression model)

| Risk factor | Slope | p value |
|---|---|---|
| CMV titer* | 0.36 | 0.025 |
| Diabetes | −0.03 | 0.83 |
| LAD lesion | 0.09 | 0.42 |
| Vessel size (<3 mm dia) | −0.03 | 0.78 |
| Hypertension | −0.06 | 0.62 |
| Hypercholesterolemia | 0.06 | 0.58 |
| Unstable angina | −0.06 | 0.64 |
| Smoking | −0.03 | 0.81 |
| Gender (male) | −0.13 | 0.35 |
| Age | 0.01 | 0.30 |

*When CMV status is defined as a dichotomous value the association when loss index is even stronger (p = 0.007) than when defined as titer, a continuous variable.

Example 2

Immunodominant Cellular and Rumoral Responses to CNV and their Regulation by Specific HLA Alleles Human cytomegalovirus (CMV) rarely produces clinically recognizable disease in immunocompetent individuals. However, like other herpesviruses, it persists in the infected host for life and, under certain circumstances, can be reactivated to cause clinically important disease. Most known CMV-related diseases occur in immune-compromised patients—such as the CMV-associated diseases experienced by many patients following organ transplantation (R. H. Rubin and R. B. Colvin, in *Kidney transplant rejection; Diagnosis and treatment,* G. M. Williams, J. F. Burdick, K. Solez Eds. (New York: Dekker, 1986) pp. 283), and the CMV-induced diseases that complicate the course of AIDS patients (R. D. Schrier, W. R. Freeman, C. A. Wiley, J. A. McCutchan, and the HNRC group, J. Clin. Invest. 95, 1741 (1995)). Clinically important CMV-induced disease, however, may not be limited to immune-compromised subjects, as Example 1 provides the first prospective evidence indicating that prior exposure to CMV, as indicated by the presence of CMV IgG antibodies, at the time of coronary angioplasty, is a strong independent risk factor for the subsequent development of restenosis (p=0.002; FIG. 1); with respect to CMV and the development of vascular diseases such as restenosis following coronary angioplasty, and atherosclerosis, see E. Speir et al., Science 256, 391 (1994); Y. F. Zhou et al., N. Engl. J. Med. 335, 624 (1996); J. L. Melinick, B. L. Petrie, G. R. Dreesman, J. Burek, C. H. McCollum, M. E. DeBakey, Lancet 2, 644 (1983); M. T. Grattan, C. E. Moreno-Cabral, V. A. Starnes, P. E. Oyer, E. B. Stinson, N. E. Shumway, JAMA. 261, 3561 (1989); L. Melnick, E. Adam, M. E. DeBakey, JAMA. 263, 2204 (1990).

With CMV related to these diseases, it is of interest that many more individuals exhibit evidence of prior CMV infection than develop vascular disease. Applicants therefore speculated that certain hosts infected with CMV, although immunocompetent, lack an efficient immune-surveillance system targeted to CMV, and, thereby, have an impaired capacity to eliminate the virus or to prevent its reactivation from latency.

To test this prediction, Applicants determined whether, in immunocompetent individuals, there is a spectrum of humoral vs cellular immunodominant responses to CMV infection. In addition, evidence in studies of patients with HIV and patients with malaria indicate there is a relationship between human leucocyte antigen (HLA) phenotypes to both the type of immunodominant response and the susceptibility or resistance to disease (S. Rowland-Jones et al., Nat. Med. 1, 59 (1995); R. D. Schrier, W. R. Freeman, C. A. Wiley, J. A. McCutchan, and the HNRC group, J. Clin. Invest. 95, 1741 (1995); A. S. Hill et al., Phil. Trans. R. Soc. Lond. B. 346, 379 (1994); A. S. Hill et al., Nature 360, 434 (1992)).

Applicants therefore also determined whether, if divergent immune responses to CMV were found in the study population, the type of response is related to HLA phenotypes. Based on data indicating an association between specific HLA phenotypes and 1) cellular immune protection against the development of AIDS in HIV exposed subjects (S. Rowland-Jones et al., Nat. Med. 1, 59 (1995)), 2) susceptibility to CMV-induced retinitis in patients suffering from AIDS (R. D. Schrier, W. R. Freeman, C. A. Wiley, J. A. McCutchan, and the HNRC group, J. Clin. Invest. 95, 1741 (1995)), and 3) susceptibility to CMV-induced disease in renal transplant patients (G. Blancho, R. Josien, D. Douiliard, J. D. Bignon, A. Cesbron, J. P. Soulillou, Transplantation 54, 871 (1992); Y. J. Kraat, M. H. L. Christiaans, F. H. M. Nieman, P. M. van den Berg-Loonen, J. P. van Hooff, C. A. Bruggeman, Lancet 341, 494 (1993).14, 15), Applicants prospectively examined the hypothesis that in immunocompetent individuals with prior CMV exposure the presence of a cellular immune response to CMV would be associated with HLA-B35, whereas its lack would be associated with HLA-DR7 and HLA-B44.

Fifty healthy individuals who volunteered, under an NIH IRB-approved protocol, to donate blood to the Transfusion Medicine Department, National Institute of Health (NIH) were entered into this study. They consisted of 32 (64%) men and 18 (36%) women, and 32 (64%) Caucasians, 17 (34%) Blacks and 1 (2%) Asian. Their ages ranged from 25 to 62 years (mean 40). The HLA frequencies in these study individuals were similar to the reported HLA frequencies in the North American population (T. D. Lee, in *The HLA system; Distribution of HLA antigens,* J. Lee, Ed. (New York: Springer-Verlag, 1990), pp. 141) (see also below).

To determine whether there are immunodominant humoral and cellular responses to CMV antigens in healthy individuals, all blood samples were tested for 1) anti-CMV IgG antibodies, using an enzyme-linked immunosorbent assay (ELISA), and 2) the ability of T lymphocytes, obtained from peripheral blood mononuclear cells (PBMCs), to proliferate in response to CMV antigens.

In particular, a blood sample from each individual was obtained from the Transfusion Medicine Department, NIH (Bethesda, Md.). PBMCs were separated from whole blood on lymphocyte separation medium (Organon Teknika Corp., Durham, N.C.) by centrifugation at 1,800 rpm for 25 min at room temperature. The separated cells were collected and washed twice in PBS (Gibco, Laboratories, Grand Island, N.Y.). The number of viable cells was determined by trypan blue exclusion and hemacytometer. PBMCs were then cryopreserved in aliquots in liquid nitrogen until used.

CMV antigens were derived from CMV-infected human fibroblasts.

In particular, Human CMV, Towne strain, was obtained from the American Type Culture Collection (ATCC) (Rockville, Md.) and grown in human fibroblasts (HEL299; ATCC) for preparation of the viral antigens. Growth media consisted of Minimum Essential Medium (Gibco) supplemented with 2% fetal bovine serum and antibiotics. Virus titer was measured on HEL299 cells.

The published protocols for CMV antigen preparations were followed, and were as follows:

Briefly, CMV antigens were prepared with 1) heat inactivated CMV (1 hour at 56° C.) that was obtained from supernatants of CMV-infected fibroblasts—final concentration of virus was $10^5$ plaque-forming units (pfu) before inactivation (R. D. Schrier et al., in Y. F. Zhou et al., N. Engl. J. Med. 335, 624 (1996)); 2) cell lysates of CMV-infected fibroblasts by repeated freezing and thawing (G. J. Boland, R. J. Hene, C. Ververs, M. A. M. De Haan, G. C. De Gast, Clin. Exp. Immunol. 94, 306 (1993); and 3) 0.08% glutaraldehyde fixed CMV-infected fibroblast cells (P. J. Converse, A. D. Hess, P. J. Tutschka, G. W. Santos, Infect. Immun. 41, 1226 (1983). Both cell lysates and fixed cells were prepared from $2\times10^6$/ml cells by infecting a 90% confluent monolayer of human fibroblasts with CMV at a multiplicity of infection (MOI) of 10. Cells were collected by centrifugation when they showed 50% cytopathic effect. The large stocks were aliquoted and stored at −70° C. Controls for the CMV antigens were obtained from noninfected fibroblasts (mock-infected cells), prepared exactly as described for CMV-infected cells.

Anti-CMV IgG antibodies were detected in 23/50 (46%) of individuals, and CMV-induced T lymphocyte proliferative responses developed in 21/50 (42%). No proliferative response was observed in these individuals when their PBMCs were stimulated with antigens derived from mock-infected fibroblasts, or cultured with medium alone.

Positive controls included: 1) 3 days of stimulation with PHA (Gibco) diluted 1:200; 2) influenza A/Bangkok RX73 (grown in embryonated eggs and used as infectious allantoic fluid at an infectivity of $2\times10^4$ tissue culture infectious $dose_{50}$/well) at a final dilution of 1:1,000; 3) Candida antigen (Greer Laboratories, Inc., Lenoir, N.C.), at a final dilution of 20 mg/ml; 4) a pool of irradiated (5,000 rad) PBMCs from three unrelated healthy donors ($2\times10^6$/ml). Negative controls were derived from non-infected (mock-infected) fibroblasts and culture medium alone.

The positive proliferative responses to other antigenic stimuli were: 29/50 (58%) to influenza A plus candida antigens, and 35/50 (70%) to allogenic cells. All 50 individuals responded to phytohaemagglutinin (PHA).

Figure 5:
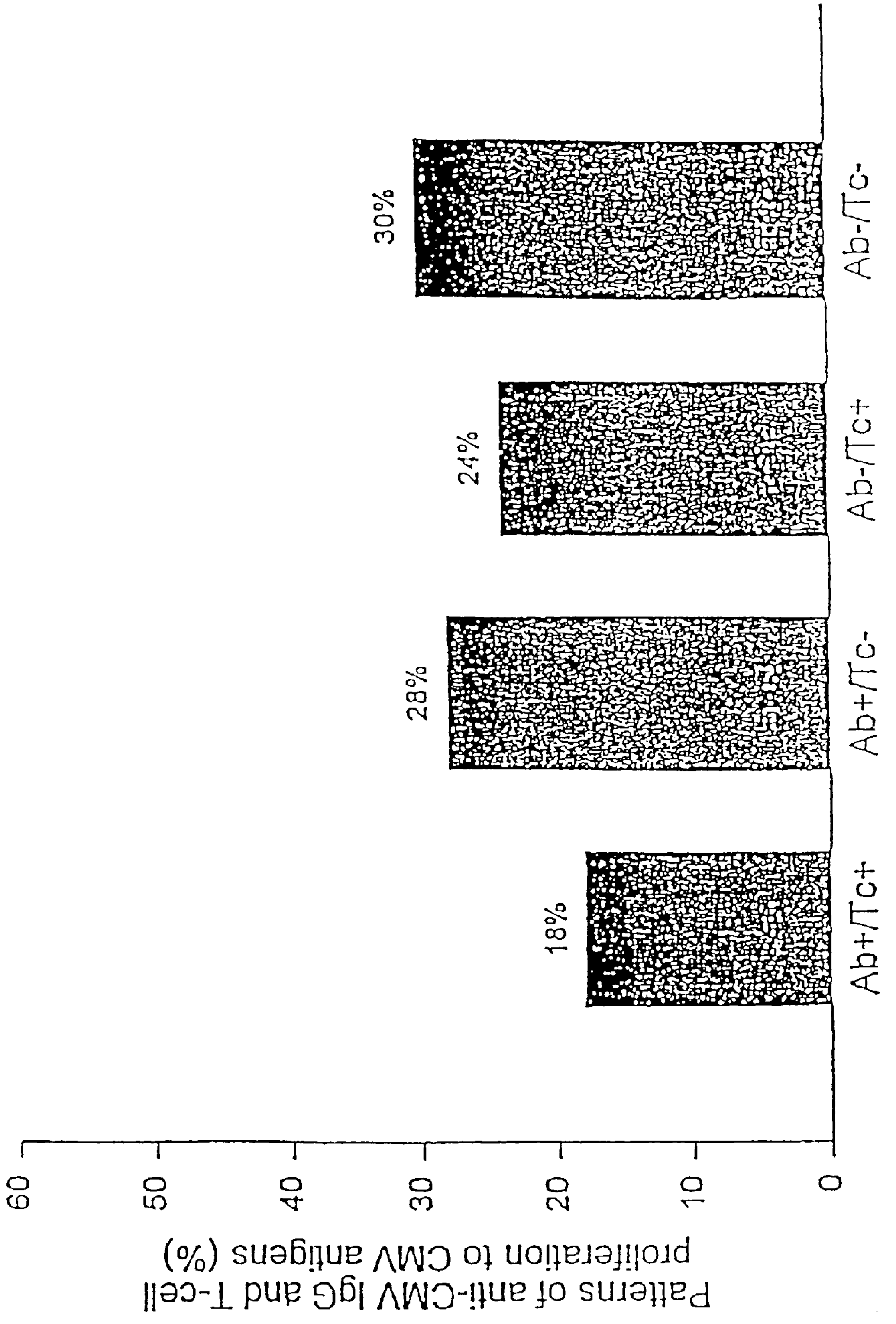
FIG. 5 shows patterns of anti-CMV IgG antibodies and T lymphocyte proliferation to CMV antigens in healthy individuals (Serum IgG antibodies for CMV were determined using an ELISA kit (CYTOMEGELISA II, Biowhittaker, Walkersville, Md.). Antibody titers were calculated from standard curves provided by the manufacturer. The threshold value for a "positive" result was that provided by the company, which we used prospectively: an ELISA value of less than 0.25 units was considered a negative result, and a value of 0.25 unit or higher was considered a positive result, indicating prior exposure to CMV. Samples for anti-CMV IgG antibodies were tested in triplicate and in two separate experiments. T lymphocyte proliferative responses were performed in 96-well flat-bottom plates (Costar, Cambridge, Mass.). 100 μl of PBMCs ($3\times10^6$/ml) was added to each well. PBMCs were cultured at 37° C. with 5% $CO_2$ in RPMI 1640 (Gibco) containing 5% human AB serum, 2 mM L-glutamine, 100 U/ml penicillin, 100 μg/ml streptomycin and Herpes buffer, with or without exposure to CMV antigens. After 6 days of culture (3 days for PHA stimulation), each well was pulsed with 1 μCi of [$^3$H]thymidine, and harvested 18 hours later. Thymidine incorporation was determined using a model LS1801 β-spectrometer (Beckman Instruments, Fullerton, Calif.). All samples were assayed in triplicate and expressed as the mean counts per minute (cpm). The data are presented as stimulation index (cpm of cultures in the presence of CMV antigens divided by cpm of cultures in the absence of CMV antigens). If a sample had a response to two of the three CMV antigen preparations (heat inactivated supernatants of CMV-infected fibroblasts, CMV-infected cell lysates, or fixed CMV-infected fibroblasts) and the stimulation index in each was above 4.0, the response was considered positive)

FIG. 5 shows the patterns of anti-CMV IgG antibodies and T lymphocyte proliferation to CMV antigens. Of the 50 individuals, nine (18%) had both anti-CMV IgG antibodies and a T-cell proliferative response to CMV antigens (referred to as the antibody positive/T lymphocyte proliferation positive subgroup). Fourteen (28%) who had anti-CMV antibodies did not show a CMV-induced T-lymphocyte response (referred to as the antibody positive/T lymphocyte proliferation negative subgroup). There were 15 individuals (30%) who were negative for both antibodies and T lymphocyte proliferation to CMV (referred to as the antibody negative/T lymphocyte proliferation negative subgroup).

Unexpectedly, 12 (24%) individuals who did not produce anti-CMV IgG antibodies had positive proliferative responses to CMV antigens (referred to as the antibody negative/T lymphocyte proliferation positive subgroup).

These results demonstrate that immunodominant phenotypes directed against CMV are present in immunocompetent individuals. Of interest, 44% of the 27 individuals who were seronegative for CMV antibodies (and therefore, by conventional criteria, would not be considered to have been exposed to CMV) had T lymphocyte proliferative responses to CMV antigens. This particular subgroup, which displayed a dominant cellular immune response to CMV, constituted 24% of the total population.

To determine whether the immune response to CMV infection is related to specific HLA phenotypes, allelic frequencies for HLA class I and class II molecules were analyzed.

Figures 6A, 6B, 6C, 6D:
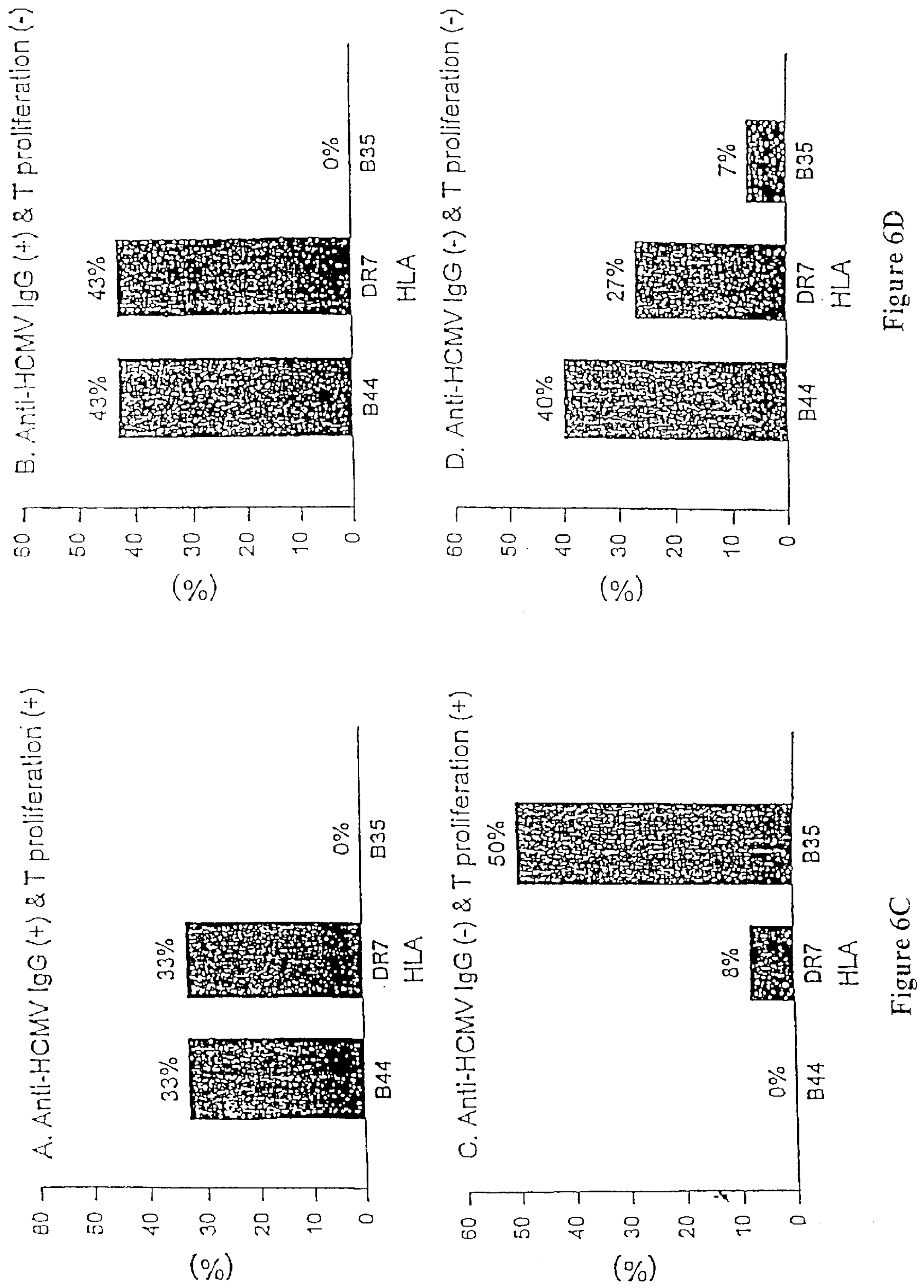
FIGS. 6A to D show the percentage of individuals with HLA-B44, DR7 and B35 in different CMV-induced immune response subgroups (HLA typing was performed on PBMCs by the NIH HLA laboratory. The standard NIH microcytotoxicity method was used for HLA class I and some class II typing (K. A. Hopkins, A. van Leeuwen, G. N. Tardiff, W. M. LeFor, in *ASHI laboratory manual; Lymophotoxicity testing,*

The frequency in the North American population (T. D. Lee, in *The HLA system; Distribution of HLA antigens,* J. Lee, Ed. (New York: Springer-Verlag, 1990), pp. 141) of the specific HLA alleles we prospectively examined is 24% for B44, 26% for DR7, and 18% for B35. There were no significant differences in the HLA allelic frequencies between this control population and the total population, which had allelic frequencies of 30% for B44, 28% for DR7, and 14% for B35. Nor were there significant differences in allelic frequencies between either of these two groups and the antibody negative/T lymphocyte proliferation negative subgroup, which had allelic frequencies of 40% for HLA-B44, 27% for DR7 and 7% for B35 (FIG. 6D). This latter subgroup can probably be considered to consist of individuals who have not been exposed to CMV infection (although some may have had a prior infection following which the virus was either successfully cleared or has remained latent).

In contrast, the remaining subgroups, characterized by their immunodominant response to CMV antigens, demonstrated marked differences in HLA allelic frequency when compared to that of the North American population or the total study population. Thus, neither of the two antibody-positive groups (one characterized by a positive T lymphocyte proliferative response to CMV antigens (FIG. 6A) and the other with a negative proliferative response (FIG. 6B)) contained any individuals carrying the HLA-B35 allele (P<0.05 vs North American and total study populations).

Conversely, in the cellular immunodominant subgroup (CMV-seronegative individuals who were positive for CMV-induced T lymphocyte proliferation; FIG. 6C), none carried HLA-B44, only 8% had DR7, but 50% carried HLA-B35. Both the lower frequency of HLA-B44 (but not DR7) and the higher frequency of HLA-B35 in this cellular immunodominant subgroup are significantly different from the corresponding allelic frequencies in our total study population (P=0.03 for HLA-B44 and P=0.01 for B35) and in antibody negative/proliferation negative individuals (P=0.02 for HLA-B44 and P=0.02 for B35). Although the difference remained highly significant when the allelic frequency for HLA-B35 was compared to that of the North American population, that for HLA-B44 was only of marginal significance (P=0.01 for B35 and P=0.08 for HLA-B44).

To determine whether carrying the HLA-B35 allele uniquely predisposes to a cellular immune response to CMV, the relative frequency of a positive T-cell proliferative response to CMV antigens of those individuals with and those without HLA-B35 was compared. A total of 7 individuals carried HLA-B35, and all were CMV-seronegative. Most importantly, 6 of these 7 (86%) had positive T lymphocyte proliferative responses to CMV antigens (FIG. 7). This is in contrast to 6/20 (30%) of the seronegative individuals without B35 (P=0.02).

Applicants also determined the presence of additional HLA alleles (18 HLA-A alleles, 25 HLA-B, 8 HLA-Cw, 11 HLA-DR, 7 HLA-DRw and 8 HLA-DQ) not prospectively identified as potential determinants of immunodominant response.

Additional HLA phenotypes analyzed were: A1–3, A11, A23, A24, A26, A28–34, A36, A66, A68, A74; B7, B8, B13, B14, B18, B27, B37–42, B51, B53, B55, B57, B58, B60–63, B70–72, B81; Cw1–8; DR1, DR3, DR4, DR9–15, DR18, DRw52, DRw53, DRw3*01–3*03, DRw4*01, DRw5*01 and DQ1–8.

Analysis failed to reveal any significant correlations with cell or antibody immunodominant responses.

Without wishing to necessarily be bound by any one particular theory, Applicants do not rule out that the association between HLA-B35 and a cellular immunodominant response to CMV may be due to a closely-linked but unrelated gene. However, it is of note that HLA-B35, which now has been identified as consisting of a large family of homologous gene products, also is associated with an immunodominant cellular response characterized by the presence of cytotoxic T lymphocytes (CTLs) in subjects exposed to HIV-1 or HIV-2 (S. Rowland-Jones et al., Nat. Med. 1, 59 (1995)), and with the recognition of epitopes of the *Plasmodium falciparum* malaria parasite, resulting in the generation of specific CTLs (A. S. Hill et al., Phil. Trans. R. Soc. Lond. B. 346, 379 (1994)). The data from these studies further suggested that the cellular immune responses associated with HLA-B35 conveyed protection against the development of AIDS (Rowland et al., supra) and of severe malaria (Hill et al., supra).

Applicants findings demonstrate the association of HLA-B35 with T cell proliferative responses to CMV antigens. This proliferative response has not been shown to be restricted by $CD4^+$ and/or $CD8^+$ T cells, it is noteworthy that the most common CMV-specific CTLs present in CMV-seropositive healthy blood donors was recently demonstrated to be targeted to pp65, a CMV matrix protein, which was found to contain at least three pp65-specific CTL peptides restricted by HLA-B35. CTLs of seronegative individuals may target the same or different CMV proteins.

It has been pointed out that the high polymorphism and redundancy of the mammalian MHC makes it difficult to identify a particular MHC haplotype determining resistance or susceptibility to an infectious pathogen in humans. Although Applicants have not demonstrated a correlation between HLA phenotype and resistance or susceptibility to CMV-related disease, these results demonstrate that some immune competent individuals are genetically predisposed, in an HLA dependent manner, to respond to CMV with a cellular immune response in the absence of a humoral response. Given that the same HLA molecule that predisposes to a cellular immunodominant response to CMV is also associated with a cellular immune response targeted to HIV and to the *P. falciparium* parasite (which seems to convey a protective effect in these diseases), these results have much broader implications.

Specific HLA molecules, such as HLA-B35, may have unique attributes that facilitate the development of a cellular immunodominant response, implying a mechanism whereby some individuals are resistant to certain infectious diseases (or to cancer), and some are susceptible to the development of diseases characterized by immunopathology (chronic granulomatous diseases and autoimmune disease).

There may be a correlation between this pattern of immune response and either protection from, or exacerbation of, any disease processes caused by CMV. Thus, novel therapeutic strategies, such as herein arise. For instance, these results allow for favorably altering disease outcome by directing attempts to change the immunodominant phenotype from one that increases disease susceptibility to one that promotes resistance.

More importantly, this Example shows that diagnosis for a predisposition towards restenosis from angioplasty or for a predisposition towards atherosclerosis cannot be predicated on merely whether an individual has antibodies against CMV, i.e., any prior correlations between CMV and vascular disease fail to teach or suggest the methods and compositions for diagnosis and therapy or treatment or prophylaxis of the present invention. For instance, this Example demonstrates that detecting cellular immune responses and/or HLA genotyping and/or phenotyping can provide surprisingly better diagnosis. Detection of a cellular mediated response can be more predictive or predisposition to or against (prevention) of restenosis and/or atherosclerosis, since antibody-negative patients, as herein demonstrated can have T-cell responses.

Further, this Example, with Example 1 shows the importance in therapy or treatment or prophylaxis to boost the immune response to CMV and/or p53. Simply, the latent CMV infection is a low grade viral infection that the body cannot rid itself of because there is not sufficient stimulation of immune responses. Therapy, treatment or prophylaxis with a vaccine or immunological composition against CMV and/or p53 can thus boost the immune response to knock out low levels of CMV from the body, and thus provide therapy, treatment or prophylaxis with respect to restenosis and/or atherosclerosis.

Example 3

Poxvirus-CXV Recombinants

Reference is made to PCT WO 96/39491, incorporated herein by reference, with respect to this Example, especially the Examples thereof from Example 12, and the Figures thereof cited in those Examples such as Figures from FIG. 12, and FIG. 8.

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Example 3.1

Cloning of HCMV gB in Poxvirus Vectors

Cloning of the HCMV gB gene into vaccinia donor plasmid, pMP22BHP. The 4800 bp HindIII-BamHI fragment of the HindIII D fragment of the HCMV DNA (Towne strain) was cloned into the 2800 bp HindIII-BamHI fragment of the plasmid pIBI24 (International Biotechnologies, Inc., New Haven, Conn.). By in vitro mutagenesis (Kunkel, 1985) using the oligonucleotides CMVM5 (SEQ ID NO:51) (5'-GCCTCATCGCTGCTGGATATCCGTTAAGTTTGTATCGTAATGGAATCCAGGATCTG-3') and CMVM3 (SEQ ID NO:52) (5"-GACAGAGACTTGTGATTTTTATAAGCTTCGTAAGCTGTCA-3'), the gB gene was modified to be expressed under the control of the vaccinia H6 promoter (Taylor et al., 1988a,b; Perkus et al., 1989). The plasmid containing the modified gB was designated 24CMVgB (5+3). The DNA sequence of the CMVgB gene is shown in FIG. 8 (SEQ ID NO:1).

Plasmid pMP2VCL (containing a polylinker region with vaccinia sequences upstream of the K1L host range gene) was digested within the polylinker with HindIII and XhoI and ligated to annealed oligonucleotides SPHPRHA A through D generating SP131 containing a HindIII site, H6 promoter −124 through −1 (Perkus et al., 1989) and a polylinker region.

```
SPHPRHA A (SEQ ID NO: 53) (5'-
AGCTTCTTTATTCTATACTTAAAAAGTGAAAATAAATACAAAGGTTCTTGAGGGT-3')

SPHPRHA B (SEQ ID NO: 54) (5'-
TGTGTTAAATTGAAAGCGAGAAATAATCATAAATTATTTCATTATCGCGATATCCGTTAA
GTTTGTATCGTAC-3')

SPHPRHA C (SEQ ID NO: 55) (3'-
TTATTAGTATTTAATAAAGTAATAGCGCTATAGGCAATTCAAACATAGCATGAGCT-5')

SPHPRHA D (SEQ ID NO: 56) (3'-
AGAAATAAGATATGAATTTTTCACTTTTATTTATGTTTCCAAGAACTCCCAACACAATTT
AACTTTCGCTCT-5').
```

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The 2900 bp EcoRV-BamHI fragment of 24CMVgB (5+3) was cloned into the 3100 bp EcoRV-BglII fragment of SP131. This cloning step put the gB gene under the control of the H6 promoter. The resulting plasmid was designated SP131CMVgB.

Plasmid pSD22-H contains a 2.9 kb BglII fragment derived from the HindIII F region of the WR strain of vaccinia virus ligated into the BamHI site of pUC8. The unique BamHI site in pSD22-H is a nonessential site used as an insertion locus for foreign genes (Panicali and Paoletti, 1982). Plasmid pMP22BHP is a derivative of pSD22-H in which the unique BamHI site was modified by the addition of an expanded polylinker region for the insertion of foreign DNA. Plasmid pMP22BHP was digested with HindIII and ligated to a 2.9 kb HindIII fragment from SP131CMVgB (containing the H6 promoted gB gene) generating plasmid SAg22CMVgB. To modify the polylinker region in sAg22CMVgB, the plasmid was digested with BamHI followed by partial digestion with HindIII and purified. Ligation to a 50 bp BamHI/HindIII polylinker derived from IBI24 resulted in plasmid 22CMVgB.

Cloning of the HCMVgB gene into NYVAC donor plasmid pSD542. Plasmid pSD542 (a NYVAC TK locus donor plasmid) was derived from plasmid pSD513 (Tartaglia et al., 1992). The polylinker region in pSD513 was modified by cutting with PstI/BamHI and ligating to annealed synthetic oligonucleotides MPSYN288 (SEQ ID NO:57) (5'-GGTCGACGGATCCT-3') and MPSYN289 (SEQ ID NO:58) (5'-GATCAGGATCCGTCGACCTGCA-3') resulting in plasmid pSD542.

22CMVgB was digested with BamHI and NsiI to generate a fragment containing the H6 promoter and part of the gB gene, and with NsiI and PstI to generate a fragment containing the remainder of the gB gene. These two fragments were ligated to pSD542 that had been digested with BamHI and PstI within its' polylinker creating the NYVAC donor plasmid 542CMVgB. The DNA sequence of the CMVgB gene and flanking sequences contained in 542CMVgB is shown in FIGS. 9A and B (SEQ ID NO:2).

Cloning of the HCMV gB gene into the ALVAC donor plasmid CP3LVOH6. An 8.5 kb canarypox BglII fragment was cloned in the BaHI site of pBS-SK plasmid vector (Stratagene, La Jolla, Calif.) to form pWW5. Nucleotide sequence analysis revealed a reading frame designated C3 initiated at position 1458 and terminated at position 2897 in the sequence in FIGS. 10A–C (SEQ ID NO:3). In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:59) (5'-CAGTTGGTACCACTGGTATTTTATTTCAG-3') and RG278 (SEQ ID NO:60) (5'-TATCTGAATTCCTGCAGCCCGGGTTTT-TATAGCTAATTAGTCAAATGTGAGTTAATATTAG -3').

Primers for the 3' sequences were RG279 (SEQ ID NO:61) (5'-TCGCTGAATTCGATATCAAGCTTATC-GATTTTTATGACTAGTTAAT-CAAATAAAAAGCATACAAG C-3') and RG280 (SEQ ID NO:62) (5'-TTATCGAGCTCTGTAACATCAGTATCTAAC-3'). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

A 908 bp fragment of canarypox DNA, immediately upstream of the C3 locus was obtained by digestion of plasmid pWW5 with NsiI and SspI. A 604 bp fragment of canarypox DNA was derived by PCR (Engelke et al., 1988) using plasmid PWW5 as template and oligonucleotides CP16 (SEQ ID NO:63) (5'-TCCGGTACCGCGGCCGCAGATATTTGTTAGCTTCT GC-3') and CP17 (SEQ ID NO:64) (5'-TCGCTCGAGTAGGATACCTACCTACTACCTACG-3'). The 604 bp fragment was digested with Asp 718 and XhoI (sites present at the 5' ends of oligonucleotides CP16 and CP17, respectively) and cloned into Asp718-XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI and ligated to the 908 bp NsiI-SspI fragment generating SPCPLAX which contains 1444 bp of canarypox DNA upstream of the C3 locus.

A 2178 bp BglII-StyI fragment of canarypox DNA was isolated from plasmids pXX4 (which contains a 6.5 kb NsiI fragment of canarypox DNA cloned into the PstI site of pBS-SK). A 279 bp fragment of canarypox DNA was isolated by PCR (Engelke et al., 1988) using plasmid pXX4 as template and oligonucleotides CP19 (SEQ ID NO:65) (5'-TCGCTCGAGCTTTCTTGACAATAACATAG-3') and CP20 (SEQ ID NO:66) (5'-TAGGAGCTCTTTATACTACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA.

To add additional unique sites to the polylinker, pC3I was digested within the polylinker region with EcoRI and ClaI, treated with alkaline phosphatase and ligated to kinased and annealed oligonucleotides CP12 (SEQ ID NO:67) (5'-AATTCCTCGAGGGATCC-3') and CP13 (SEQ ID NO:68) (5'-CGGGATCCCTCGAGG-3') (containing an EcoRI sticky end, XhoI site, BamHI site and a sticky end compatible with ClaI) generating plasmid SPCP3S. SPCP3S was digested within the canarypox sequences downstream of the C3 locus with StyI and SacI (pBS-SK) and ligated to a 261 bp BglII-SacI fragment from SPC3RA and the 2178 bp BglII-StyI fragment from pXX4 generating plasmid CPRAL containing 2572 bp of canarypox DNA downstream of the C3 locus. SPCP3S was digested within the canarypox sequences upstream of the C3 locus with Asp718 (in PBS-SK) and AccI and ligated to a 1436 bp Asp718-AccI fragment from SPCPLAX generating plasmid CPLAL containing 1457 bp of canarypox DNA upstream of the C3 locus. CPLAL was digested within the canarypox sequences downstream of the C3 locus with StyI and SacI (in pBS-SK) and ligated to a 2438 bp StyI-SacI fragment from CPRAL generating plasmid CP3L containing 1457 bp of canarypox DNA upstream of the C3 locus, stop codons in six reading frames, early transcription termination signal, a polylinker region, early transcription termination signal, stop codons in six reading frames, and 2572 bp of canarypox DNA downstream of the C3 locus.

The early/late H6 vaccinia virus promoter (Taylor et al., 1988a,b; Perkus et al., 1989) was derived by PCR (Engelke et al., 1988) using pRW838 (a plasmid containing the rabies glycoprotein gene (Kieny et al., 1984) linked to the H6 promoter) as template and oligonucleotides CP21 (SEQ ID NO:69) (5'-TCGGGATCCGGGTTAATTAATTAGTTATTAGACAA GGTG-3') and CP22 (SEQ ID NO:70) (5'-TAGGAATTCCTCGAGTACGATACAAACTTAAGCG GATATCG-3'). The PCR product was digested with BamHI and EcoRI (sites present at the 5' ends of oligonucleotides CP21 and CP22, respectively) and ligated to CP3L that was digested with BamHI and EcoRI in the polylinker generating plasmid VQH6CP3L.

ALVAC donor plasmid VQH6CP3L was digested within the polylinker with XhoI and within the H6 promoter with NruI and ligated to a NruI/HindIII fragment from 22CMVgB containing part of the H6 promoter and gB gene and a polylinker derived from pIBI24 by XhoI and HindIII digestion generating the ALVAC donor plasmid CP3LCMVgB. The DNA sequence of the CMVgB gene plus additional flanking DNA sequences in plasmid CP3LCMVgB is shown in FIGS. 11A–C (SEQ ID NO:4).

Cloning of the HCMV gB gene deleted of its transmembrane region into the NYVAC donor plasmid pSD553. Plasmid pSD553 is a vaccinia deletion/insertion plasmid of the COPAK series (rescuing virus vP866 (NYVAC), a derivative of the Copenhagen strain of vaccinia, contains a large deletion encompassing C7L and K1L; COPAK plasmids insert K1L plus a foreign gene into the ATI (A26L) insertion locus; selection on RK13 and MRC-5 cell possible.) It contains the vaccinia K1L host range gene (Gillard et al., 1986; Perkus et al., 1990) within flanking Copenhagen vaccinia arms, replacing the ATI region (ORFs A25L, A26L; Goebel et al., 1990a,b). pSD553 was constructed as follows.

Left and right vaccinia flanking arms were constructed by polymerase chain reaction (PCR) using pSD414, a pUC8-based clone of vaccinia SalI B (Goebel et al., 1990a,b) as template. The left arm was synthesized using synthetic deoxyoligonucleotides MPSYN267 (SEQ ID NO:71) (5'-GGGCTGAAGCTTGCTGGCCGCTCATTAGACAAGC GAATGAGGGAC-3') and MPSYN268 (SEQ ID NO:72) (5'-AGATCTCCCGGGCTCGAGTAATTAAT-TAATTTTTATTACACCAGAAAAGACGGCTTGAGAT C-3') as primers. The right arm was synthesized using synthetic deoxyoligonucleotides MPSYN269 (SEQ ID NO:73) (5'-TAATTACTCGAGCCCGGGAGATCTAATTTAATTTA ATTTATATAACTCATTTTTTGAATATACT-3') and MPSYN270 (SEQ ID NO:74) (5'-TATCTCGAATTCCCGCGGCTTTAAATGGACGGAAC TCTTTTCCCCC-3') as primers. The two PCR-derived DNA fragments containing the left and right arms were combined in a further PCR reaction. The resulting product was cut with EcoRI/HindIII and a 0.9 kb fragment isolated. The 0.9 kb fragment was ligated with pUC8 cut with EcoRI/HindIII, resulting in plasmid pSD541. The polylinker region located at the vaccinia ATI deletion locus was expanded as follows. pSD541 was cut with BglII/XhoI and ligated with annealed complementary synthetic oligonucleotides MPSYN333 (SEQ ID NO:75) (5'-GATCTTTTGTTAACAAAAACTAATCAGCTATCGCG AATCGATTCCCGGGGGATCCGGTACCC-3') and MPSYN334 (SEQ ID NO:76) (5'-TCGAGGGTACCGGATCCCCCGGGAATC-GATTCGCGATAGCTGATTAGTTTTTGTTAACAAA A-3') generating plasmid pSD552. The K1L host range gene was isolated as a 1 kb BglII (partial)/HpaI fragment from plasmid pSD452 (Perkus et al., 1990). pSD552 was cut with BglII/HpaI and ligated with the K1L containing fragment, generating pSD553.

A HindIII fragment from SP131CMVgB (containing the HCMVgB gene under the control of the H6 promoter) was filled in with the klenow fragment of DNA polymerase I and ligated into plasmid pSD553 which had been SmaI digested and alkaline phosphatase treated. The resulting NYVAC donor plasmid (in which the H6 promoted gB is in the same orientation as K1L) was designated 553H6CMVgB. The DNA sequence of the CMVgB gene plus additional flanking DNA sequences in plasmid 553H6CMVgB is shown in FIGS. 12A and B (SEQ ID NO:5).

The sequence of CMVgB deleted of its transmembrane region is presented in FIG. 13 (SEQ ID NO:6). The nucleotides encoding the transmembrane region were deleted in the following manner. Oligonucleotides SPgB3 (SEQ ID NO:77) (5'-GATCCATGGACTCGACAGCGGCGTCTCTGCATGC AGCCGCTGCAGA-3') and SPgB4 (SEQ ID NO:78) (5'-AGCTTCTGCAGCGGCTGCATGCAGAGACGCCGCT GTCGAGTCCATG-3') were kinased, annealed and cloned into BamHI/HindIII digested and alkaline phosphatase treated IBI24 generating plasmid SPCMVgB2. Oligonucleotides SPgB1 (SEQ ID NO:79) (5'-TACGAATTCTGCAGTTCACCTATGACACGTTGC-3') and SPgB2 (SEQ ID NO:80) (5'-ATAGGATCCATGGTCGTCCAGACCCTTGAGGTAG GGC-3') were used in PCR with plasmid SP131CMVgB as template to generate a 0.7 kb fragment. This fragment was digested with EcoRI/BamHI and cloned into EcoRI/BamHI digested and alkaline phosphase treated IBI24 generating plasmid SPCMVgB1. A 0.7 kb EcoRI/NcoI fragment from SPCMVgB1 was ligated to EcoRI/NcoI digested and phosphatase treated SPCMVgB2 generating plasmid SPCMVgB3. The unique NcoI site in SPCMVgB3 was deleted by mutagenesis (Mandecki, 1986) using oligonucleotide SPgB5 (SEQ ID NO:81) (5'-GCCCTACCTCAAGGGTCTGGACGACACTCGACAG CGGCGTCTCTGCAT-3') generating plasmid SPCMVgB4. A 0.7 kb PstI fragment from SPCMVgB4 was ligated to a 6.6 kb PstI fragment from 553H6CMVgB generating NYVAC donor plasmid 553H6CMVgBTM$^-$. This plasmid contains the gB gene under the control of the H6 promoter with its transmembrane region deleted (amino acids 715–772; Spaete et al., 1988). The DNA sequence of the transmembrane deleted CMVgB gene plus additional flanking DNA sequences in plasmid 553H6CMVgBTM$^-$ is shown in FIGS. 14A and B (SEQ ID NO:7).

Cloning the HCMVgB gene deleted of its transmembrane region and containing an altered cleavage site into NYVAC donor plasmid pSD553. The sequence of CMVgB deleted of its transmembrane region and containing an altered cleavage site is presented in FIG. 15 (SEQ ID NO:8). The alteration of the cleavage site was accomplished in the following manner. Oligonucleotides SPgB8 (SEQ ID NO:82) (5'-AATTGGTGACCG-3') and SPgB9 (SEQ ID NO:83) (5'-GATCCGGTCACC-3') were kinased, annealed and cloned into EcoRI/BamHI digested and alkaline phosphatase treated IBI24 generating plasmid BstIBI. A 1.4 kb BstEII/SpHI fragment from 553H6CMVgBTM$^-$ was cloned into BstEII/SpHI digested and alkaline phosphatase treated BstIBI generating plasmid SPCMVgB5.

Oligonucleotides SPgB10 (SEQ ID NO:84) (5'-TGAAAGACCGAATTCTGCGT-3') plus SPgB11 (SEQ ID NO:85) (5'-TGCGATTCATCGGTTTGTTGTAGAT-3') and SPgB12 (SEQ ID NO:86) (5'-GACCCTTGAGGTAGGGCGGC-3') plus SPgB13 (SEQ ID NO:87) (5'-ACTCATAATAGAACCATAAGATCTACAGATGGCAA CAAT-3') were used in PCR with plasmid 553H6CMVgBTM$^-$ to generate 0.7 and 0.8 kb fragments. These two fragments were combined in a PCR with oligonucleotides SPgB10 plus SPgB12 to generate a 1.2 kb fragment. The 1.2 kb fragment was digested with EcoRI and PstI and a 0.5 kb fragment isolated and cloned into EcoRI/PstI digested and alkaline phosphatase treated IBI24 generating plasmid SPCMVgB6. The 0.5 kb EcoRI/PstI fragment from SPCMVgB6 was used to replace the corresponding fragment in SPCMVgB5 generating plasmid SPCMVgB7. A 1.4 kb BstEII/SpHI fragment from SPCMVgB7 was used to replace the corresponding fragment in 553H6CMVgB generating NYVAC donor plasmid 553H6gBC$^-$TM$^-$. This plasmid contains the gB gene under the control of the H6 promoter with its transmembrane region deleted (amino acids 715–772) and an alteration at the cleavage site (RTKR*ST modified to RTIRST where the asterisk indicated where cleavage normally occurs (Spaete et al., 1988) the S codon was modified to create a BglII restriction site). The DNA sequence of the cleavage site altered and transmembrane deleted CMVgB gene plus additional flanking DNA sequences in plasmid 553H6gBC$^-$TM$^-$ is shown in FIGS. 16A and B (SEQ ID NO:9).

Example 3.2

Construction of Recombinant Poxviruses Containing HCMVgB

Procedures for transfection of recombinant donor plasmids into tissue culture cells infected with a rescuing poxvirus and identification of recombinants by in situ hybridization on nitrocellulose filters have been described (Guo et al., 1989; Panicali and Paoletti, 1982; Piccini et al., 1987; Perkus et al., 1993). Plasmid 542CMVgB was transfected into NYVAC (vP866) infected Vero cells (ATCC CCL#81) to generate the recombinant vP1001 (NYVAC-gB). Plasmid CP3LCMVgB was transfected into ALVAC infected primary chicken embryo fibroblast (CEF) cells to generate the recombinant vCP139 (ALVAC-gB). Plasmids 553H6CMVgB, 553H6CMVgBTM$^-$ and 553H6gBC$^-$TM$^-$ were transfected into NYVAC infected Vero cells to generate the recombinants vP1126, vP1128 and vP1145, respectively. Plasmid 22CMVgB was transfected into Vero cells infected with the WR L variant vaccinia virus (Panicali et al., 1981) to generate the recombinant vP992.

Example 3.3

Immunoprecipetation of HCMVgB Expressed by Poxvirus Recombinants

Immunoprecipitation assays were performed as described previously (Taylor et al., 1990) using gB specific guinea pig polyclonal serum (Gönczöl et al., 1990). The apparent molecular weights of the gB specific bands corresponded to previously published results (Britt and Auger, 1986; Britt and Vugler, 1989; Reis et al., 1993). The intracellular fraction from vP992, vP1001, vCP139, vP1126, vP1128 and vP1145 contained a major band of apparent molecular weight 130–140 kDa, identifiable as the glycosylated uncleaved gB precursor. Fainter bands at approximately 110 kDa and 55 kDa, representing the N-terminal and C-terminal processed fragments were also seen in the cell fractions. The extracellular medium from vP1128 and vP1145 infected cells contained the uncleaved precursor and N-terminal and C-terminal processed fragments.

Example 3.4

Humoral Response of Laboratory Animals Inoculated with ALVAC-gB and NYVAC-gB

Following a single immunization of CBA mice with vP1001 (NYVAC-gB), neutralizing antibody titers of the sera of inoculated mice were assessed (Gönczöl et al., 1986). Antibodies capable of neutralizing HCMV were detected (Table 5) in the sera of mice 14–21 days later (geometric mean titers of 1:16) and between 28–60 days post-immunization (gmt=1:26). A single immunization of CBA mice with vCP139 (ALVAC-gB) generated HCMV neutralizing antibody titers of 1:64 gmt (14–21 days pi) and 1:111 gmt (between 28 and 60 days pi). Thus, immunization of mice with NYVAC and ALVAC recombinants expressing HCMV gB elicited antibodies able to neutralize the infectivity of HCMV.

ALVAC-gB (vCP139) was evaluated for safety and immunogenicity in human volunteers. After two inoculations with $10^{6.3}$TCID$_{50}$ of this recombinant, no serious reactions were noted.

TABLE 5

HCMV Neutralizing Antibodies in CBA mice

| | Days After Immunization | | |
|---|---|---|---|
| Immunization | 14–21 | 21–28 | 28–60 |
| NYVAC-gB | 16 | | |
| | 16 | | |
| | | | 32 |
| | | | 24 |
| | | | 32 |
| | | | 24 |
| ALVAC-gB | 32 | | |
| | 64 | | |
| | 128 | | |
| | 64 | | |
| | | 64 | |
| | | 128 | |
| | | | 128 |
| | | | 96 |

Immunization was i.p. with 2–4 × $10^8$ PFU of recombinant viruses.

Guinea pigs were immunized twice with ALVAC-gB (days 0 and 28) and sera were tested for the presence of HCMV neutralizing antibody. HCMV neutralizing antibody was detected (Table 6) in the sera on day 34 (gmt=60), day 42 (gmt=60) and day 56(gmt=60). Thus, immunization of guinea pigs with ALVAC-gB elicited antibodies able to neutralize the infectivity of HCMV.

TABLE 6

HCMV Neutralizing Antibodies in Guinea Pigs Inoculated with ALVAC-gB

| | Days | | | | | |
|---|---|---|---|---|---|---|
| Guinea Pig # | 0 | 14 | 28 | 34 | 42 | 56 |
| 19 | <4 | <4 | <4 | 64 | 64 | 64 |
| 20 | <4 | <4 | <4 | 32 | 64 | 64 |
| 21 | <4 | <4 | <4 | 12 | 32 | 64 |
| 22 | <4 | <4 | <4 | 48 | 48 | 32 |
| 23 | <4 | <4 | 4 | 96 | 46 | 46 |
| 24 | <4 | <4 | <4 | 46 | 46 | 32 |

Guinea pigs were inoculated by intramuscular route on days 0 and 28 with $10^{63}$ TCID$_{50}$ Example 3.5

Cloning of HCMVgH in Poxvirus Vectors

Cloning of the HCMVgH gene into the NYVAC donor plasmid pSD550. The HCMVgH gene was isolated from genomic DNA (Towne strain) by PCR using oligonucleotides SPgH1 (SEQ ID NO:87) (5'-TATCTGCAGATGCGGCCAGGCCTCCCCTCCTAC-3') and SPgH2 (SEQ ID NO:88) (5'-CCGAAGCTTTCAGCATGTCTTGAGCATGC-3'). The resulting 2.3 kb fragment was digested with PstI (site at the 5' end of SPgH1) and HindIII (site at the 5' end of SPgH2) and cloned into PstI/HindIII digested and alkaline phosphatase treated IBI24 generating plasmid SPgH1. The sequence of CMVgH is presented in FIG. 17 (SEQ ID NO:10).

The 3' end of the gH gene in SPgH1 was modified to contain a vaccinia virus early transcription termination signal (Yuen and Moss, 1987) and a unique XhoI restriction site in the following manner. SPgH1 was digested within the 3' end of the gH gene with SpHI and within IBI24 with HindIII and the fragment containing gH was purified and ligated to kinased and annealed oligonucleotides SPgH16 (SEQ ID NO:89) (5'-CTCAAGACATGCTGATTTTTATCTCGAGA-3') and SPgH17 (SEQ ID NO:90) (5'-AGCTTCTCGAGATAAAAATCAGCATGTCTTGAGCATG-3') generating plasmid SPgH2.

Kinased and annealed oligonucleotides SPgH12 (SEQ ID NO:91) (5'-AATTCTCGAGTTTATTGGGAAGAATATGATAATATTTTGGGATTTC-3'), SPgH13 (SEQ ID NO:92) (5'-AAAATTGAAAATATATAATTACAATATAAAATGCGGCCCGGG-3'), SPgH14 (SEQ ID NO:93) (5'-GATCCCCGGGCCGCATTTTATATTGTAATTATAT-3') and SPgH15 (SEQ ID NO:94) (5'-ATTTTCAATTTTGAAATCCCAAAATATTATCATATTCTTCCCAATAAACTCGAG-3") were ligated to EcoRI/BamHI digested and alkaline phosphatase treated IBI24 generating plasmid SPgH3 which contains a unique XhoI site, the entomopox 42K promoter and nucleotide sequences encoding the first four amino acids of HCMVgH (underlined bases in codons three and four in oligonucleotides SPgH13 (SEQ ID NO:92) and SPgH14 (SEQ ID NO:93) were modified to create a SmaI site without altering the amino acid sequence). Oligonucleotides SPgH18 (SEQ ID NO:95) (5'-TTAGAATTCCCCGGGCTCCCCTCCTACCTCATCGT-3') and SPgH19 (SEQ ID NO:96) (5'-TTACTGCAGTAAGTGTTAAGTCTCTGTTGGTATC-3') were used in PCR with plasmid SPgH1 as template to derive a 0.4 kb fragment. This fragment was digested with SmaI and PstI and cloned into SmaI/PstI digested and alkaline phosphatase treated SPgH3 generating plasmid SPgH5 which contains a unique XhoI site, the 42K promoter and 5' 15% of the HCMVgH gene. A 0.4 kb EcoRI/BglII fragment from SPgH5 was ligated to a 4.7 kb EcoRI/BglII fragment from SPgH3 generating plasmid SPgH6 which contains the 42K promoted gH gene flanked by XhoI sites.

Plasmid pSD550 (an I4L locus donor plasmid) was derived from plasmid pSD548 (Tartaglia et al., 1992). The polylinker region in pSD548 was modified by cutting with BglII and SmaI and ligating to annealed synthetic oligonucleotides 539A (SEQ ID NO:97) (5'-AGAAAAATCAGTTAGCTAAGATCTCCCGGGCTCGAGGGTACCGGATCCTGATTAGTTAATTTTTGT-3') and 539B (SEQ ID NO:98) (5'-GATCACAAAAATTAACTAATCAGGATCCGGTACCCTCGAGCCCGGGAGATCTTAGCTAACTGATTTTTCT-3') resulting in plasmid pSD550. The 2.3 kb XhoI fragment from SPgH6 was cloned into XhoI digested and alkaline phosphatase treated pSD550 generating the NYVAC donor plasmid I4L42KgH in which the orientation of gH is in the same direction as the replaced I4L gene. The DNA sequence of CMVgH plus additional flanking DNA sequences in plasmid I4L42KgH are shown in FIGS. 18A and B (SEQ ID NO:11).

Cloning of the HCMVgH gene into the ALVAC donor plasmid NVOC5LSP. A C5 insertion vector containing 1535 bp upstream of C5, polylinker containing KpnI/SmaI/XbaI and NotI sites and 404 bp of canarypox DNA (31 base pairs of C5 coding sequence and 373 bp of downstream sequence) was derived in the following manner. A genomic library of canarypox DNA was constructed in the cosmid vector puK102 (Knauf and Nester, 1982) probed with pRW764.5 (a PuC9 based plasmid containing an 880 bp canarypox PvuII fragment which includes the C5 ORF Nucleotides 1372 to 2251 in FIG. 65 (SEQ ID NO:43)) and a clone containing a 29 kb insert identified (pHCOS1). A 3.3 kb ClaI fragment from pHCOS1 containing the C5 region was identified. The C5 open reading frame is initiated at position 1537 and terminated at position 1857 in the sequence shown in FIG. 65 (SEQ ID NO:43).

The C5 insertion vector was constructed in two steps. The 1535 bp upstream sequence was generated by PCR amplification using oligonucleotides C5A (SEQ ID NO:99) (5'-ATCATCGAATTCTGAATGTTAAATGTTATACTTTG-3') and C5B (SEQ ID NO:100) (5'-GGGGGTACCTTTGAGAGTACCACTTCAG-3') and purified genomic canarypox DNA as template. This fragment was digested with EcoRI (within oligoC5A) and cloned into EcoRI/SmaI digested pUC8 generating C5LAB. The 404 bp arm was generated by PCR amplification using oligonucleotides C5C (SEQ ID NO:101) (5'-GGGTCTAGAGCGGCCGCTTATAAAGATCTAAAATGCATAATTTC-3') and C5DA (SEQ ID NO:102) (5'-ATCATCCTGCAGGTATTCTAAACTAGGAATAGATG-3'). This fragment was digested with PstI (within oligoC5DA) and cloned into SmaI/PstI digested C5LAB generating pC5L.

pC5L was digested within the polylinker with Asp718 and NotI, treated with alkaline phosphatase and ligated to kinased and annealed oligonucleotides CP26 (SEQ ID NO:103) (5'-GTACGTGACTAATTAGCTATAAAAAG-GATCCGGTACCCTCGAGTCTAGAATC-GATCCCGGGTTTTTATGA CTAGTTAATCAC-3') and CP27 (SEQ ID NO:104) (5'-GGCCGTGATTAACTAGTCATAAAAACCCGGGATCGATTCTAGACTCGAGGGTACCGGATCCTTTTTATAGCTAATTAGTCAC-3') (containing a disabled Asp 718 site, translation stop codons in six reading frames, vaccinia early transcription termination signal (Yuen and Moss, 1987), BamHI KpnI XhoI XbaI ClaI and SmaI restriction sites, vaccinia early transcription termination signal, translation stop codons in six reading frames, and a disabled NotI site) generating plasmid C5LSP. The polylinker region in C5LSP was further modified by digesting with BamHI and ligating to annealed oligonucleotides CP32 (SEQ ID NO:105) (5'-GATCTTAATTAATTAGTCATCAGGCAGGGCGAGAACGAGACTATCTGCTCGTTAATTAATTAGGTCGACG-3') and CP33 (SEQ ID NO:106) (5'-GATCCGTCGACCTAATTAATTAACGAGCAGATAGTCTCGTTCTCGCCCTGCCTGATGACTAATTAATTAA-3') generating plasmid VQC5LSP. VQC5LSP was digested with EcoRI, treated with alkaline phosphatase, ligated with kinased and annealed oligonucleotide CP29 (SEQ ID NO:107) (5'-AATTGCGGCCGC-3') and digested with NotI. The linearized plasmid was purified and self ligated to generate plasmid NVQC5LSP. The 2.3 kb XhoI fragment from SPgH6 was cloned into XhoI digested and alkaline phosphatase treated NVQC5LSP generating the ALVAC donor plasmid NVQC5L42KgH in which the orientation of gH is in the same direction as the deleted C5 gene. The DNA sequence of CMVgH plus additional flanking DNA sequences in plasmid NVQC5L42KgH are shown in FIGS. 19A and B (SEQ ID NO:12).

Cloning of the HCMVgH gene into the vaccinia donor plasmid pSD157K1LINS. Plasmid pHK (which contains the WR vaccinia HindIII K fragment cloned in pBR322) was digested with HindIII/BglII and a 1.2 kb fragment isolated and cloned into BamHI/HindIII digested pBS-SK$^+$ yielding plasmid pBS-HKARM. pBS-HKARM was digested with Asp718 in the polylinker region, blunt ended with the klenow fragment of *E. Coli* DNA polymerase, and digested with HindIII at the pBS/vaccinia junction. The resulting 4.1 kb vector fragment was ligated to a 2.0 kb NruI/HindIII fragment from pHM-1 (pHM-1 contains the WR vaccinia virus HindIII M fragment cloned in pBR322) resulting in plasmid pMPWRMK. pMPWRMK was cut with HpaI and ligated with annealed synthetic oligonucleotides MPSYN527 (SEQ ID NO:108) (5'-ATAAAAATTAGCTACTCAGGTACCCTGCAGTCGCG AGGATCCGAATTCCCCGGGCTCGAGTGATTAATTA GTTTTTAT-3') and MPSYN528 (SEQ ID NO:109) (5'-ATAAAAACTAATTAATCACTCGAGCCCGGGGAATT CGGATCCTCGCGACTGCAGGGTACCTGAGTAGCT AATTTTTAT-3'). The resulting plasmid is pSD157K1LINS. pSD157K1LINS was digested within its polylinker region with XhoI, treated with alkaline phosphatase and ligated to the 2.3 kb XhoI fragment from SPgH6 yielding plasmid MP804-42KgH (which contains the HCMVgH gene and vaccinia K1L gene both in the same orientation.) The DNA sequence of CMVgH plus additional flanking DNA sequences in plasmid MP804-42KgH are shown in FIG. 20 (SEQ ID NO:13).

Example 3.6

Construction of Recombinant Poxviruses Containing HCMVgH

Plasmid I4L42kgH was transfected into NYVAC infected CEF cells to generate the recombinant vP1173 (containing HCMVgH). The same plasmid was transfected into vP1001 infected Vero cells to generate the recombinant vP1183 (containing HCMVgB and gH).

Plasmid NVQC5L42KgH was transfected into ALVAC infected CEF cells to generate the recombinant vCP236 (containing HCMVgH). The same plasmid was transfected into vCP139 infected CEF cells to generate the recombinant vCP233 (containing HCMVgB and gH). Vaccinia virus vP1170 (which contains Ecogpt under the transcriptional control of the entomopoxvirus 42K promoter in place of the deleted K1L gene) was used to infect Vero cells transfected with plasmid MP804-42KgH to generate the recombinant vP1205B.

Example 3.7

Immunoprecipitation of HCMVgH Expressed by Poxvirus Recombinants

Immunoprecipitation performed with a monoclonal antibody specific for HCMVgH demonstrated the expression of an 86 kDa gH protein (Pachl et al., 1989) by recombinants vP1173, vP1183, vP1205B, vCP233 and vCP236. Immunoprecipitation with the gB specific guinea pig polyclonal serum demonstrated correct expression of gB by recombinants vP1183 and vCP233.

The HCMV 72-kDa immediate early 1 protein (IE1) is a target for $CD8^+$ cytotoxic T cells in humans (Borysiewicz et al., 1988) and is recognized by $CD4^+$ T cells (Alp et al., 1991). For one individual the peptide specificities of proliferative and MHC-class I-restricted cytotoxic determinants on IE1 were determined and found to be spatially distinct segments of the exon 4 coding region (Alp et al., 1991).

The IE1 protein has been shown to up-regulate expression from its own promoter (Cherrington and Mocarski, 1989) as well as expression from the HIV LTR (Biegalke and Geballe, 1991; Ghazal et al., 1991) and expression of the promoters for the cellular genes c-myc, c-fos and hsp70 (Hagemeier et al., 1992; Santomenna and Colberg-Poley, 1990; Colberg-Poley et al., 1992). Lafemina et al., (1989) reported that the IE1 protein expressed in stable cell lines preferentially associates with metaphase chromosomes and proposed that this protein may be involved in maintenance of a putative plasmid state for HCMV DNA during latency.

In the following Examples 3.8 to 3.19, the development of poxvirus recombinants expressing the entire IE1 gene, IE1 deleted of amino acids 2–32, IE1 deleted of amino acids 292–319 or the exon 4 segment of IE1 are provided. These studies were performed in order to develop a form of the IE1 gene product that would be incapable of translocation to the nucleus, thus decreasing its potential to act as a transactivator, while maintaining its ability to be recognized by $CD8^+$ cytotoxic T cells. Example 3.34 demonstrates that an ALVAC recombinant expressing an altered form of the IE1 protein (deleted of amino acids 2–32) which unlike the full length gene product is found in both the nucleus and cytoplasm of infected cells, can re-stimulate cytotoxic effector cells from HCMV seropositive individuals.

Example 3.8

Cloning of the Entire HCMV IE1 Gene in Poxvirus Vectors

Cloning of the HCMV IE1 gene into the vaccinia donor plasmid pSD22-H. The entire HCMV IE1 gene (AD169 strain) was derived as a 1.5 kb fragment by PCR using plasmid pJD083 as template (Akrigg et al., 1985) along with oligonucleotides IE3 (SEQ ID NO:110) (5'-ACGGATCCATAAAAATTACTGGTCAGCCTTGCTTC-3') and IE5 (SEQ ID NO:111) (5'-ATCCGTTAAGTTTGTATCGTAATGGAGTCCTCTGC CAAGAGA-3'). The DNA sequence of CMV IE1 is presented in FIG. 21 (SEQ ID NO:14). Plasmid pSD486H6340 (which contains an irrelevant gene linked precisely to H6 promoter) was digested (within the H6 promoter) with NruI and (at the 3' end of the irrelevant gene) with BamHI and ligated to the BamHI digested 1.5 kb PCR fragment (BamHI site located at the 5' end of oligonucleotide IE3) generating plasmid pSD486H6HCMVIE1.

The H6 promoted IE1 gene was obtained from pSD486H6HCMVIE1 as a 1.6 kb fragment by digestion with BamHI followed by partial BglII digestion and ligated to BamHI digested pSD22-H yielding plasmid pSD22-HCMVIE1. The DNA sequence of CMV IE1 plus additional flanking DNA sequences in plasmid pSD22-HCMVIE1 are shown in FIG. 22 (SEQ ID NO:15).

Cloning of the HCMVIE1 gene into the vaccinia donor plasmid pSD554. Oligonucleotides SPIE1 (SEQ ID NO:112) (5'-CGCGAATTCTCGCGATATCCGTTAAGTTTGTATCG TAATGGAGT-3') and SPIE2 (SEQ ID NO:113) (5'-GCCTCTAGAGTTAACCTCCTTCCTCAACAT-3') were used in PCR with plasmid pSD486H6HCMVIE1 as template to generate a 181 bp fragment. This fragment was digested with EcoRI and XbaI and cloned into EcoRI/XbaI digested and alkaline phosphatase treated IBI24 generating plasmid SPIE1 containing part of the H6 promoter and the first 135 bp of the IE1 gene. Oligonucleotides SPIE3 (SEQ ID NO:114) (5'-CGGTCTAGAGGTTATCAGTGTAATGAAGC-3') and SPIE4 (SEQ ID NO:115) (5'-CCGAAGCTTCTCGAGATAAAAATTACTGGTCAGC CTTGCTTCTAGT-3') were used in PCR with plasmid pSD486H6HCMVIE1 as template to generate a 506 bp fragment. This fragment was digested with XbaI and HindIII and cloned into XbaI/HindIII digested and alkaline phosphatase treated IBI24 generating plasmid SPIE2 containing the 3' end of the IE1 gene, a vaccinia early transcription termination signal and an XhoI site. SPIE1 was digested at the 3' end of the inserted fragment of the IE1 gene with HindII and within the IBI24 polylinker with HindIII, alkaline phosphatase treated and ligated to a 903 bp HindII-BglII fragment from pSD486H6HCMVIE1 and a 464 bp BglII-HindIII fragment from SPIE2 generating plasmid SPIE3 containing the entire IE1 gene linked to part of the H6 promoter.

Plasmid pSD553 was cut with NruI and ligated with a SmaI/NruI fragment containing the synthetic H6 promoter (Perkus et al., 1989) upstream from the NruI site located at −26 relative to the translation initiation codon. The resulting plasmid, pMP553H6, was digested with NruI and BamHI and ligated to annealed oligonucleotides MPSYN347 (SEQ ID NO:116) (5'-CGATATCCGTTAAGTTTGTATCGTAATCTGCAGCC CGGGGGGG-3') and MPSYN348 (SEQ ID NO:117) (5'-GATCCCCCGGGCTGCAGATTACGATACAAACTTAA CGGATATCG-3'). The resulting plasmid, pSD554, contains the entire H6 promoter region through nucleotide −1 relative to the initiation codon, followed by a polylinker region. pSD554 was digested with NruI and XhoI and ligated to a 1.5 kb NruI/XhoI fragment from SPIE3 generating plasmid COPAKH6IE. The DNA sequence of CMV IE1 plus flanking DNA sequences in plasmid COPAKH6IE are shown in FIGS. 23A and B (SEQ ID NO:16).

Example 3.9

Construction of Recombinant Poxviruses Containing the Entire HCMVIE1 Gene

Plasmid pSD22-HCMVIE1 was transfected into Vero cells infected with the WR L variant to generate the recombinant vP893. Plasmid COPAKH6IE was transfected into NYVAC infected Vero cells to generate the recombinant vP1161.

Example 3.10

Expression of the Entire IE1 Gene by Poxvirus Recombinants

Immunoprecipitation studies performed with a monoclonal antibody specific for HCMVIE1 demonstrated the expression of a 72 kDa IE1 protein (Blanton and Tevethia, 1981; Cameron and Preston, 1981) by recombinants vP893 and vP1161. Immunofluorescence studies (performed as described in Taylor et al., 1990) revealed nuclear localization of the IE1 gene product.

Example 3.11

Cloning of the HCMVIE1 Gene (Lacking Amino Acids 292–319) Into the vaccinia Donor Plasmid The DNA sequence of CMVIE1 lacking amino acids 292–319 is shown in FIG. 24 (SEQ ID NO:17). This deletion was made in the following manner. Plasmid SPIE3 was digested with SpeI and a 4239 bp fragment isolated (which lacks nucleotides 868–958 encoding amino acids 292–319). This fragment was self ligated generating plasmid SPIE4. A 1.4 kb NruI/XhoI fragment from SPIE4 was ligated to NruI/XhoI digested pSD554 generating plasmid COPAKH6IEN⁻. The DNA sequence of CMVIE1 lacking amino acids 292–319 plus flanking DNA sequences in plasmid COPAKH6IEN⁻ are shown in FIGS. 25A and B (SEQ ID NO:18).

Example 3.12

Construction of a Recombinant Poxvirus Containing the HCMV IE1 Gene Lacking Amino Acids 292–319

Plasmid COPAKH6IEN⁻ was transfected into NYVAC infected Vero cells to generate the recombinant vP1160.

Example 3.13

Expression of the HCMVIE1 Gene Lacking Amino Acids 292–319

Immunoprecipitation assays demonstrated the expression of a 69 kDa protein in cells infected with vP1160 consistent with the deletion of amino acids 292–319. Immunofluorescence studies revealed nuclear localization of this gene product.

Example 3.14

Cloning of the Exon 4 Segment of HCMVIE1 in Poxvirus Vectors

Cloning of the Exon 4 segment of HCMVIE1 in NYVAC donor plasmid SPI4LH6. The DNA sequence of the Exon 4 segment of HCMVIE1 is shown in FIG. 26 (SEQ ID NO:19). This segment of the gene was obtained in the following manner. Oligonucleotides SPIE5 (SEQ ID NO:118) (5'-CGCGAATTCTCGCGATATCCGTTAAGTTTGTATCGT AATGAAACAGATTAAGGTTCGAGT-3') and SPIE6 (SEQ ID NO:119) (5'-GCCTCTAGATGCCGCCATGGCCTGACT-3') were used in PCR with plasmid pSD486H6HCMVIE1 to generate a 0.5 kb fragment. This fragment was digested with EcoRI and XbaI and cloned into EcoRI/XbaI digested and alkaline phosphatase treated IBI24 generating plasmid SPIE5. Plasmid SPIE3 was digested with EcoRI and NcoI and a 3.6 kb fragment purified and ligated to a 0.47 kb EcoRI-NcoI fragment from SPIE5 generating plasmid SPIE6 which contains the Exon 4 segment of IE1 linked to part of the H6 promoter.

The early/late H6 vaccinia virus promoter (Guo et al., 1989; Perkus et al., 1989) was derived by PCR using PRW823 as template (a plasmid containing the H6 promoter linked to an irrelevant gene) and oligonucleotides CP30 (SEQ ID NO:120) (5'-TCGGGATCCGGGTTAATTAATTAGTCATCAGGCAG GGCG-3') and CP31 (SEQ ID NO:121) (5'-TAGCTCGAGGGTACCTACGATACAAACTTAACGG ATATCG-3'). The PCR product was digested with BamHI and XhoI (sites present at the 5' end of CP30 and CP31, respectively) and ligated to BamHI/XhoI digested C5LSP generating plasmid VQH6C5LSP. This plasmid was used as template in PCR with oligonucleotides CP31 and RUB1 (SEQ ID NO:122) (5'-TCGGGATCCTTCTTTATTCTATACTTA-3'). The PCR product was digested with BamHI and XhoI (site present at the 5' ends of RUB1 and CP31, respectively) and ligated to BamHI/XhoI digested pSD550 generating plasmid SPI4LH6. A 1.3 kb NruI/XhoI fragment isolated from SPIE6 was cloned into NruI/XhoI digested and alkaline phosphatase treated SPI4LH6 generating plasmid I4LH6IE-Ex4 (in which the H6 promoted IE1 Exon 4 gene is in the same orientation as the replaced I4L gene). The DNA sequence of the Exon 4 segment of HCMVIE1 plus flanking DNA sequences in plasmid I4LH6IE-Ex4 are shown in FIG. 27 (SEQ ID NO:20).

Cloning of the Exon 4 fragment of HCMVIE1 in ALVAC donor plasmid NVQH6C5LSP. Plasmid VQH6C5LSP was digested with EcoRI, treated with alkaline phosphatase, ligated with kinased and annealed oligonucleotide CP29 and digested with NotI. The linearized plasmid was purified and self ligated generating plasmid NVQH6C5LSP. The 1.3 kb NruI/XhoI fragment from SPIE6 was cloned into NruI/XhoI digested and alkaline phosphatase treated NVQH6C5LSP generating plasmid NVQH6IE-Ex4 (in which the H6 promoted IE1 Exon 4 gene is in the same orientation as the replaced C5 gene). The DNA sequence of the Exon 4 segment of HCMVIE1 plus flanking DNA sequences in plasmid NVQH6IE-Ex4 are shown in FIGS. 28A and B (SEQ ID NO:21).

Example 3.15

Construction of Recombinant Poxviruses Containing the EXON 4 Segment of IE1

Plasmid I4LH6IE-Ex4 was transfected into NYVAC infected CEF cells to generate the recombinant vP1186. Plasmid NVQH6IE-Ex4 was transfected into ALVAC infected CEF cells to generate the recombinant vCP244.

Example 3.16

Expression of the EXON 4 Segment of HCMVIE1 by Poxvirus Recombinants

Immunofluorescence experiments revealed cytoplasmic localization of the IE-Exon 4 protein expressed by recombinants vP1186 and vCP244. Immunoprecipitation experiments with a monoclonal antibody specific for IE-Exon 4 demonstrated the expression of a 60 kDa protein in cells infected with vCP244 consistent with the predicted size of the exon 4 segment. Immunoprecipitation with a polyclonal rabbit serum raised against a bacterial Exon 4 fusion protein revealed the expression of a 60 kDa protein in cells infected with vP1186 and VCP244.

Example 3.17

Cloning of the HCMVIE1 Gene (Lacking Amino Acids 2–32) in Poxvirus Vectors

Cloning of the HCMVIE1 gene (lacking amino acids 2–32) in NYVAC donor Rlasmid SPI4LH6. The DNA sequence of HCMVIE1 lacking amino acids 2–32 is shown in FIG. 29 (SEQ ID NO:22). This segment was obtained in the following manner. Oligonucleotides SPIE9 (SEQ ID NO:123) (5'-AATTCTCGCGATATCCGTTAAGTTTGTATCGTAATG ACGACGTTCCTGCAGACTATGTTGAGGAAGGAG GTT-3') and SPIE10 (SEQ ID NO:124) (5'-AACCTCCTTCCTCAACATAGTCTGCAGGAACGTC GTCATTACGATACAAACTTAACGGATATCGCGAG-3') were kinased, annealed and ligated to a 4.2 kb HindII/EcoRI digested and alkaline phosphatase treated fragment from SPIE3 generating plasmid SPIE8. A 1.4 kb NruI/XhoI fragment from SPIE8 (containing part of the H6 promoter and IE1 lacking amino acids 2–32) was ligated to NruI/XhoI digested and alkaline phosphatase treated SPI4LH6 generating plasmid I4LH6IEd32. The DNA sequence of HCM-VIE1 lacking amino acids 2–32 plus flanking DNA sequences in plasmid I4LH6IEd32 are shown in FIG. 30 (SEQ ID NO:23).

Cloning of the HCMVIE1 gene (lacking amino acids 2–32) in ALVAC donor Plasmid NVQH6C5LSP. The 1.4 kb NruI/XhoI fragment from SPIE8 was cloned into NruI/XhoI digested and alkaline phosphatase treated NVQH6C5LSP generating plasmid NVQH6IEd32. The DNA sequence of HCMVIE1 lacking amino acids 2–32 plus flanking DNA sequences in plasmid NVQH6IEd32 are shown in FIGS. 31A and B (SEQ ID NO:24).

Example 3.18

Construction of Poxvirus Recombinants Containing the IE1 Gene Lacking Amino Acids 2–32

Plasmid I4LH6IEd32 was transfected into NYVAC infected CEF cells to generate the recombinant vP1201. Plasmid NVQH6IEd32 was transfected into ALVAC infected CEF cells to generate the recombinant vCP256.

Example 3.19

Expression of IE1 Lacking Amino Acids 2–32 by Poxvirus Recombinants

Immunofluorescence experiments revealed both nuclear and cytoplasmic localization of the IE1 protein lacking amino acids 2–32 by recombinants vP1201 and vCP256. Immunoprecipitation with a polyclonal rabbit serum raised against a bacterial exon 4 fusion protein revealed the expression of a 68 kDa protein in cells infected with vP1201 consistent with the predicted size.

Example 3.20

Cloning of the HCMV pp65 Gene in Poxvirus Vectors

Cloning of the HCMV pp65 aene in NYVAC donor plasmid SPHA-H6. pSD456 is a subclone of Copenhagen vaccinia DNA containing the HA gene (A56R; Goebel et al., 1990a,b) and surrounding regions. pSD456 was used as a template in PCR for synthesis of left and right vaccinia arms flanking the A56R ORF. The left arm was synthesized using oligonucleotides MPSYN279 (SEQ ID NO:125) (5'-CCCCCCGAATTCGTCGACGATTGTTCATGATGGCA AGAT-3') and MPSYN280 (SEQ ID NO:126) (5'-CCCGGGGGATCCCTCGAGGGTACCAAGCTTAATT AATTAAATATTAGTATAAAAAGTGATTTATTTTT-3'). The right arm was synthesized using oligonucleotides MPSYN281 (SEQ ID NO:127) (5'-AAGCTTGGTACCCTCGAGGGATCCCCCGGGTAGC TAGCTAATTTTTCTTTTACGTATTATATATGTAATAA ACGTTC-3') and MSYN312 (SEQ ID NO:128) (5'-TTTTTTCTGCAGGTAAGTATTTTTAAAACTTCTAA CACC-3'). The purified PCR fragments for the left and right arms were combined in a further PCR reaction. The resulting product was digested with EcoRI/HindIII. The resulting 0.9 kb fragment was cloned into EcoRI/HindIII digested pUC8 resulting in plasmid pSD544.

pSD544 was digested within its polylinker with XhoI, filled in with klenow and treated with alkaline phosphatase. Plasmid SP126 (equivalent to SP131) was digested with HindIII, treated with klenow and the H6 promoter isolated by digestion with SmaI. Ligation of the H6 promoter fragment to pSD544 generated SPHA-H6.

The HCMV pp65 gene was PCR amplified using HCMV genomic DNA as template (Towne strain) and oligonucleotides pp651 (SEQ ID NO:129) (5'-GATTATCGCGATATCCGTTAAGTTTGTATCGTAATG GCATCCGTACTGGGTCCCATTTCGGG-3') and pp651R (SEQ ID NO:130) (5'-GCATAGGTACCGGATCCATAAAAATCAACCTCGGT GCTTTTTGGGCG-3'). The DNA sequence of CMVpp65 is shown in FIG. 32 (SEQ ID NO:32). The 1.6 kb product was digested with NruI and BamHI (site present at the 5' end of oligonucleotides pp651 and pp651R, respectively) and cloned into NruI/BamHI digested SPHA-H6 generating plasmid CMV65.1. This plasmid contained the pp65 gene linked to the H6 promoter, however, the first 30 bp of the pp65 gene were missing.

To derive a plasmid containing the first 30 bp of the pp65 gene oligonucleotides RNApp65I (SEQ ID NO:131) (5'-TAGTTCGGATCCCCGCTCAGTCGCCTACA-3') and pp65R4 (SEQ ID NO:132) (5'-ATCAAGGGATCCATCGAAAAAGAAGAGCG-3') were used in PCR with genomic DNA. The resulting 1 kb fragment was digested with BamHI (BamHI sites present at the 5' ends of both oligonucleotides) and cloned into BamHI digested IBI24 generating plasmid pp65.7. Plasmid pp65.7 was used in PCR with oligonucleotides pp651B (SEQ ID NO:133) (5'-GATTATCGCGATATCCGTTAAGTTTGTATCGTAATG GAGTCGCGCGGTCGCCGTTGTCCCG-3') and pp65BstXI (SEQ ID NO:134) (5'-ACCTGCATCTTGGTTGC-3') to generate a 0.5 kb fragment. This fragment was digested with NruI and BstXI (sites at the 5' ends of oligonucleotides pp651B and pp65BstXI, respectively) and ligated to a 4.8 kb NruI/BstXI fragment of CMV65.1 generating plasmid pCMV65.2. This plasmid contains the entire pp65 gene linked precisely to the H6 promoter oriented in the same direction as the replaced HA gene. The DNA sequence of CMVpp65 plus flanking DNA sequences in plasmid pCMV65.2 are shown in FIG. 33 (SEQ ID NO:26).

Cloning of the HCMV pp65 gene in ALVAC donor plasmid pMPC616E6VQ. FIGS. 34A and B (SEQ ID NO:27) is the sequence of a 3.7 kb segment of canarypox DNA. Analysis of the sequence revealed a reading frame designate C6L initiated at position 377 and terminated at position 2254. A C6 insertion vector containing 370 bp upstream of C6, polylinker containing SmaI, PstI, XhoI and EcoRI sites, and 1156 bp of downstream sequence was derived in the following manner. The 0.4 bp upstream sequence was generated by PCR amplification of a cosmid clone derived from purified genomic canarypox DNA using oligonucleotides C6A1SG (SEQ ID NO:135) (5'-ATCATCGAGCTCGCGGCCGCCTATCAAAAGTCTTA ATGAGTT-3') and C6B1SG (SEQ ID NO:136) (5'-GAATTCCTCGAGCTGCAGCCCGGGTTTTTATAGCT AATTAGTCATTTTTTCGTAAGTAAGTATTTTTATTTAA-3'). The 1.2 kb downstream arm was generated by PCR amplification of the same template using oligonucleotides C6C1SG (SEQ ID NO:137) (5'-CCCGGGCTGCAGCTCGAGGAATTCTTTTTATTGAT TAACTAGTCAAATGAGTATATATAATTGAAAAAGT AA-3') and C6D1SG (SEQ ID NO:138) (5'-GATGATGGTACCTTCATAAATACAAGTTTGATTA AACTTAAGTTG-3'). These fragments were fused by a third PCR employing gel purified 0.4 and 1.2 kb fragments as template for primers C6A1SG (SEQ ID NO:135) and C6D1SG (SEQ ID NO:138). The resulting 1.6 kb fragment was isolated from an agarose gel, digested with SacI and KpnI and ligated to similarly digested pBS generating C6 insertion plasmid pC6L.

Plasmid pMPC616E6VQ was derived by cloning a HpaI-XhoI fragment containing the H6 promoter precisely linked to an irrelevant gene into Sma-XhoI digested pC6L. pMPC616E6VQ was digested with NruI and BamHI and the 4 kb vector fragment (NruI-BamHI) and 0.6 kb C6 flanking arm fragment (BamHI-BamHI) isolated. These two fragments were combined in a ligation with a 1.7 kb NruI-BamHI fragment from pCMV65.2 (containing part of the H6 promoter linked to the p65 gene) generating plasmid CMV65C6.1 which contained a C6 flanking arm, H6 promoter and the pp65 gene but lacked the 0.6 kb C6 flanking arm. CMV65C6.1 was digested with BamHI, treated with alkaline phosphatase and ligated to the 0.6 kb C6 flanking arm generating plasmid CMV65C6.2 in which C6 flanking arms are present on both sides of the H6-pp65 insert. The DNA sequence of CMVpp65 plus flanking DNA sequences in plasmid CMV65C6.2 are shown in FIGS. 35A and B (SEQ ID NO:28).

Cloning of the HCMVpp65 gene into the vaccinia donor plasmid pSD157 K1LINS. Plasmid pCMV65.2 was digested with KpNI, treated with Mung Bean Nuclease and digested with BamHI generating a 1.7 kb fragment containing H6-pp65. PSD157K1LINS was digested with BamHI and SmaI and ligated to the 1.7 kb fragment generating plasmid CMV65.WR. The DNA sequence of CMVpp65 plus flanking DNA sequences in plasmid CMV65.WR are shown in FIG. 36 (SEQ ID NO:29).

Example 3.21

Construction of Recombinant Poxviruses Containing HCMVpp65

Plasmid pCMV65.2 was transfected into NYVAC infected Vero cells to generate the recombinant vP1184 (containing HCMVpp65), into vP1001 infected Vero cells to generate the recombinant vP1196 (containing HCMVgB and pp65) and into vP1183 infected Vero cells to generate the recombinant vP1210 (containing HCMVgB, gH and pp65).

Plasmid CMV65C6.2 was transfected into ALVAC infected CEF cells to generate the recombinant vCP260 (containing HCMVpp65).

Plasmid CMV65.WR was transfected into vP1170 infected Vero cells to generate the recombinant vP1214 (WR-pp65).

Example 3.22

Expression of HCMVpp65 by Poxvirus Recombinants

Immunoprecipitation experiments with a monoclonal antibody specific for HCMV pp65 demonstrated the expression of a 65 kDa protein (Pande et al., 1991) by recombinants vP1184, vP1214, vCP260, vP1196 and vP1210. In addition, immunoprecipitation with gB specific guinea pig polyclonal sera demonstrated correct expression of gB by recombinants vP1196 and vP1210 and immunoprecipitation with a gH specific monoclonal antibody demonstrated correct expression of gH by recombinant vP1210.

Example 3.23

Cloning of the HCMV pp150 Gene in Poxvirus Vectors

Cloning of the pp150 gene into the NYVAC donor plasmid pSD541. The DNA sequence of CMVpp150 is shown in FIG. 37 (SEQ ID NO:30). Oligonucleotides pp150.1B (SEQ ID NO:139) (5'-TTCGGATCCGGTTCTGGAGAAAAGCC-3') and pp150R6 (SEQ ID NO:140) (5'-GCTTCCAAGCTTTCCTGAAGGGATTGTAAGCC-3') were used in PCR with Towne genomic DNA to generate a 2 kb fragment from the 5' end of pp150. This fragment was digested with BamHI and HindIII and cloned into BamHI/HindIII digested and alkaline phosphatase treated IBI24 generating plasmid pp150.5.

Oligonucleotides pp150.9 (SEQ ID NO:141) (5'-TTCGGATCCGGCTTTCAGTCTCGTCTCC-3') and pp150END2 (SEQ ID NO:142) (5'-TTCGGATCCATGCAATTGCCCGCGGACAAC-3') were used in PCR with Towne DNA to generated a 1.8 kb fragment which includes the 3' end of the gene. This fragment was digested with BamHI and cloned into BamHI digested and alkaline phosphatase treated PUC8 yielding pp150.3.

Oligonucleotides SP150–3 (SEQ ID NO:143) (5'-TTCGAATTCGCTAGCTTTATTGGGAAGAATATGATA ATATTTTGGGATTTCAAAATTGAAAATATATAATTA CAATATAAAATGAGTTTGCAGTTTATC-3') and SP150–4 (SEQ ID NO:144) (5'-TTCTCTAGATGAGCTCGTTGAACAGCAC-3') were used in PCR with plasmid pp150.5 as template to generate a 259 bp fragment. This fragment was digested with EcoRI and XbaI and cloned into EcoRI/XbaI digested and alkaline phosphatase treated IBI24 generating plasmid 150.5MP. This plasmid contains a NheI site, 65 bp entomopoxvirus 42K promoter and bases 1–170 from the 5' end of the pp150 gene. The underlined base in the sequence of oligonucleotide SP150-3 (position −53 of the promoter) is missing in this clone.

Oligonucleotides SP150-1 (SEQ ID NO:145) (5'-CCGAAGCTTGCTAGCAATAAAAACTATTCCTCCGT GTTCTTAAT-3') and SP150-2 (SEQ ID NO:146) (5'-GCCTCTAGATACGTAAAGCTAAGTTATC-3') were used in PCR with plasmid pp150.3 as template to generate a 907 bp fragment. This fragment was digested with XbaI and HindIII and cloned into XbaI/HindIII digested and alkaline phosphatase treated IBI24 yielding plasmid 150.3MP. This plasmid contains nucleotides 2273–3141 from pp150 followed by a vaccinia early transcription termination signal ($T_5$ATT) (Yuen and Moss, 1987) and a NheI site. pp150 nucleotide 2748 (FIG. 37; SEQ ID NO:30) in this clone is an A not a C as in pp150.3, this change is silent.

Plasmid pp150.3 was digested with SnaBI and HindIII and a 3451 bp fragment isolated. Plasmid 150.3MP was digested with SnaBI and HindIII and 873 bp fragment isolated. Ligation of these two fragments yielded plasmid 150.3MC which contains pp150 nucleotides 1473–3141 followed by $T_5$ATT and a NheI site.

Plasmid 150.5MP was digested with SacI and HindIII and a 3056 bp fragment isolated. Plasmid pp150.5 was digested with SacI and HindIII and a 1816 bp fragment isolated. Ligation of these two fragments yielded plasmid 150.5MC which contains a NheI site, 65 bp 42K promoter and pp150 nucleotides 1–1981.

Plasmid 150.5MC was digested with HpaI and HindIII and a 4634 bp fragment isolated. Plasmid 150.3MC was digested with HaI and HindIII and a 1412 bp fragment isolated. Ligation of these two fragments yielded plasmid 150.1 which contains a NheI site, 65 bp 42K promoter, nucleotides 1–3141 pp150, $T_5$ATT and a NheI site.

Plasmid pSD541 is a vaccinia insertion plasmid which is deleted for vaccinia sequences encompassing the A25L and A26L ORFS (Goebel et al., 1990a,b). The deletion junction consists of a polylinker region containing XhoI, SmaI and BglII restriction sites, flanked on both sides by stop codons and early vaccinia transcriptional terminators (Yuen and Moss, 1987). pSD541 was constructed by polymerase chain reaction (PCR) using cloned vaccinia SalI E plasmid pSD414 as template. Synthetic oligonucleotides MPSYN267 (SEQ ID NO:71) (5'-GGGCTCAAGCTTGCGGCCGCTCATTAGACAAGCG AATGAGGGAC-3') and MPSYN268 (SEQ ID NO:72) (5'-AGATCTCCCGGGCTCGAGTAATTAATTAATTTTTAT TACACCAGAAAAGACGGCTTGAGATC-3') were used as primers to generate the left vaccinia arm and synthetic oligonucleotides MPSYN269 (SEQ ID NO:73) (5'-TAATTACTCGAGCCCGGGAGATCTAATTTAATTTA ATTTATATAACTCATTTTTTGAATATACT-3') and MPSYN270 (SEQ ID NO:74) (5'-TATCTCGAATTCCCGCGGCTTTAAATGGACGGAA CTCTTTTCCCC-3') were used to generate the right vaccinia arm. PCR products consisting of the left and right vaccinia arms were combined, and subjected to PCR amplification. The PCR product was digested with EcoRI and HindIII and electrophoresed on a agarose gel. The 0.8 kb fragment was isolated and ligated into pUC8 cut with EcoRI/HindIII, resulting in plasmid pSD541.

Plasmid pSD541 was digested in its polylinker region with SmaI and alkaline phosphatase treated. Plasmid 150.1 was digested with NheI, treated with klenow and a 3224 bp fragment (containing 42K-pp150) isolated. Ligation of these two fragments yielded plasmid 150.7. The DNA sequence of CMVpp150 plus flanking DNA sequences in plasmid 150.7 are shown in FIGS. 38A and B (SEQ ID NO:31).

Cloning of the pp150 gene into ALVAC donor plasmid PMM117. Plasmid PMM117 is a derivative of pC6L with a modified polylinker region. PMM117 was digested in its polylinker with EcoRI filled in with klenow and treated with alkaline phosphatase. Plasmid 150.1 was digested with NheI, treated with klenow and a 3224 bp fragment (containing 42K-pp150) isolated. Ligation of these two fragments generated plasmid 150.6. The DNA sequence of CMVpp150 plus flanking DNA sequences in plasmid 150.6 are shown in FIGS. 39A and B (SEQ ID NO:32).

Cloning of the pp150 gene into vaccinia donor plasmid pSD157K1LINS. Plasmid pSD1571LINS was digested in its polylinker region with SmaI and alkaline phosphatase treated. Plasmid 150.1 was digested with NheI, treated with klenow and a 3224 bp fragment (containing 42K-pp150) isolated. Ligation of these two fragments generated plasmid 150.4. The DNA sequence of CMVpp150 plus flanking DNA sequences in plasmid 150.4 are shown in FIGS. 40A and B (SEQ ID NO:33).

Example 3.24

Construction of Recombinant Poxviruses Containing HCMVMpp150

Plasmid 150.4 was transfected into vP1170 infected CEF cells to generate the recombinant vP1238 (WR-pp150).

Plasmid 150.7 was transfected into NYVAC infected CEF cells to generate the recombinant vP1247 (NYVAC-pp150).

Plasmid 150.6 was transfected into ALVAC infected CEF cells to generate the recombinant vCP284 (ALVAC-pp150).

Example 3.25

Expression of HCMVpp150 by Poxvirus Recombinants

Western blot (Harlow and Lane, 1988) with a monoclonal antibody specific for HCMVpp150 demonstrated the expression of a 150 kDa protein in cells infected with vP1238 which comigrated with a protein present in HCMV infected cells. Expression of a 150 kDa protein was observed in vP1247 and vCP284 infected cells by immunoprecipitation with the pp150 specific monoclonal antibody.

Example 3.26

Developing a NYVAC Donor Plasmid Containing the HCMVgH and IE1 Exon 4 Genes

Plasmid I4LH6IE-Ex4 was linearized with BamHI, filled in with klenow and treated with alkaline phosphatase yielding a 4.9 kb fragment. Plasmid gH6-3 was digested with XhoI, filled in with klenow and a 2.3 kb fragment (containing 42K-gH) isolated. These two fragments were ligated to generate plasmid I4L42KgHH6IE-Ex4. The DNA sequence of CMVgH and IE-Exon4 plus additional flanking sequences in plasmid I4L42KgHH6IE-Ex4 are shown in FIGS. 41A and B (SEQ ID NO:34).

Example 3.27

Construction of NYVAC Recombinants Containing HCKVgB.+gH.+pp65.+IE-Exon 4, HCMVgB.+gh.+ pp65.+pp150 OR HCMVgB.+gH.+pp65.+IE-Exon 4 and pp150

Plasmid I4L42KgHH6IE-Ex 4 was transfected into vP1196 infected Vero cells to generate the recombinant vP1216 (containing HCMVgB, gH, pp65, IE-Exon 4). Plasmid 150.7 was transfected into vP1216 infected CEF cells to generate the recombinant vP1251 (containing HCMVgB, gH, IE-Exon 4, pp65, pp150). Plasmid 150.7 was transfected into vP1210 infected Vero cells to generate the recombinant vP1262 (containing HCMV-gB, gH, pp65, pp150).

Example 3.28

Expression of the HCMV Genes in vP1216, vP1251. vP1262

Immunoprecipitation with monoclonal antibodies specific for gB, gH, pp65 and IE-Exon 4 demonstrated the correct expression of all four genes by recombinant vP1216. Immunoprecipitation with monoclonal antibodies specific for gB, gH, pp65 and IE-Exon 4 demonstrated the correct expression of these four genes by recombinant vP1251. Immunoprecipitation with monoclonal antibodies specific for gB, gH and pp65 demonstrated the correct expression of these three genes by recombinant vP1262. Western blot with a monoclonal antibody specific for ppl50 demonstrated the correct expression of this gene by recombinants vP1251 and vP1262.

Example 3.29

Developing an ALVAC Donor Plasmid Containing the HCMV pp65 and pp150 Genes

Plasmid CMV65C6.2 was linearized with EcoRI, filled in with klenow and treated with alkaline phosphatase generating a 6.3 kb fragment. Plasmid 150.1 was digested with NheI, filled in with klenow and a 3.2 kb fragment (42K-pp150) isolated. Ligation of these two fragments yielded plasmid 150.8. The DNA sequence of CMVpp65 and pp150 plus additional flanking sequences in plasmid 150.8 are shown in FIGS. 42A to C (SEQ ID NO:35).

Example 3.30

Construction of an ALVAC Recombinant Containing HCMVgB, gH, pp65 and pp150

Plasmid 150.8 was transfected into vPC233 infected CEF cells to generate an ALVAC-gB, gH, pp65, pp150 recombinant (vCP280).

Example 3.31

Expression of the HCMV Genes in vCP280

Immunoprecipitation with monoclonal antibodies specific for gB, gH and pp65 demonstrated the correct expression of these three genes by recombinant vCP280.

Example 3.32

Cloning of HCMVgL in Poxvirus Vectors Deriving a NYVAC Donor Plasmid Containing gB and gL Oligonucleotides UL115A (SEQ ID NO:147) (5'-GCCTCTAGAATGTGCCGCCGCCCGGATTGC-3') and UL115B (SEQ ID NO:148) (5'-CGCAAGCTTAGCGAGCATCCACTGCTTGAGGGC-3') were used in PCR with Towne DNA as template to generate a 853 bp fragment. This fragment was digested with XbaI and HindIII and cloned into XbaI/HindIII digested and alkaline phosphatase treated IBI24 generating plasmid UL115.1. The sequence of CMVgL is presented in FIG. 43 (SEQ ID NO:65).

Oligonucleotides UL115M (SEQ ID NO:149) (5'-TCCAAGCTTAGATCTATAAAAATTAGCGAGCATCC ACTGCTTGAGGGCCATAGC-3') and UL115N (SEQ ID NO:150) (5,'-GCCTCTAGATGCTGACGCTGTTGAGCTCGGAC-3') were used in PCR with plasmid UL115.1 as template to generate a 498 bp fragment. This fragment was digested with HindIII and XbaI and cloned into HindIII/XbaI digested and alkaline phosphatase treated IBI24 generating plasmid UL115.2.

Oligonucleotides UL115G2 (SEQ ID NO:151) (5'-CGCGAATTCTCGCGATATCCGTTAAGTTTGTATCGT AATGTGCCGCCGCCCGGATTGC-3') and UL115H2 (SEQ ID NO:152) (5'-GCCTCTAGATTCCAGCGCGGCGCTGTGTCCGAGC-3') were used in PCR with plasmid UL115.1 as template to generate a 450 bp fragment. This fragment was digested with EcoRI and XbaI and cloned into EcoRI/XbaI digested and alkaline phosphatase treated IBI24 generating plasmid UL115.3.

Plasmid UL115.3 was digested with HindIII and SacI and a 3226 bp fragment isolated. Plasmid UL115.2 was digested with HindIII and SacI and a 469 bp fragment isolated. Ligation of these two fragments yielded plasmid UL115.4.

Plasmid UL115.4 was digested with NruI and BglII and a 865 bp fragment isolated. Plasmid I4LH6 was digested with NruI and BglII and a 3683 bp fragment isolated. Ligation of these two fragments yielded plasmid I4LH6gL.

To correct a one base deletion in the H6 promoter in I4LH6gL this plasmid was digested with EcoRV treated with alkaline phosphatase and a 3805 bp fragment isolated. Plasmid I4LH6 was digested with EcoRV and a 736 bp fragment isolated. Ligation of these two fragments yielded plasmid I4LH6CgL.

Plasmid 542CMVgB was linearized with BamHI and treated with alkaline phosphatase. Plasmid I4LH6CgL was digested with BamHI and BalII and a 968 bp fragment (containing the H6 promoted gL gene) isolated. Ligation of these two fragments generated plasmid 542CMVgBgL. The DNA sequence of CMVgL and CMVgB plus additional flanking DNA sequences in plasmid 542CMVgBgL are shown in FIGS. 44A and B (SEQ ID NO:37).

Example 3.33

Developing a NYVAC Recombinant Containing gB, gH, gL, pp65, pp150, IE1-Exon 4 or gB, gH, gL, pp65, pp150

Plasmid 542CMVgBgL was transfected into vP1251 infected CEF cells to generate a NYVAC gB, gH, gL, pp65, pp150, IE1-Exon 4 recombinants (NYVAC-CMV6: vP1302 and vP1302B).

Plasmid 542CMVgBgL is transfected into vP1262 infected cells to generate NYVAC recombinant vP1312 (NYVAC-CMV5).

Example 3.34

Human Cytotoxic T Lymphocyte Responses to HCMV Proteins

Lymphocytes comprising the antigen-specific segment of the immune system may functionally react to antigen by producing antibodies (B-lymphocytes) or by becoming cytotoxic T lymphocytes (CD8+ T-lymphocytes). ALVAC recombinants expressing HCMV proteins that are known to be recognized by human cytotoxic T lymphocytes (CTLs) are capable of re-stimulating human cellular immune responses with characteristics of classical CTLs.

Thirteen individuals for which there was previously established EBV-transformed B-cell lines (LBCL) for use as CTL targets were screened for CTL responses to HCMV gB, IE1, and pp65. Although only one of these volunteer blood donors had an established clinical history of HCMV infection, seven were found to be HCMV seropositive by virtue of their sera containing antibodies which neutralized HCMV.

Stimulation of HCMV 1E1 CTLs by ALVAC-1E1 (vCP256): Whole blood was collected into heparinized Vacutainer tubes from each volunteer donor by venipuncture. The mononuclear cell fraction was separated from the remainder of the blood components by centrifugation over Leucoprep gradients, washed several times by centrifugation in Stim Medium (MEM containing 5% fetal bovine serum [FBS], 2 mM L-glutamine, $10^{-4}$ M 2-mercaptoethanol, 100 IU/ml penicillin, and 100 $\mu$g/ml streptomycin), counted for viable cells with trypan blue, and resuspended at $5\times10^6$ cells/ml in Stim Medium (responder cells). A portion of the mononuclear cells were resuspended at $10^7$ cells/ml in MEM containing 2% FBS and infected with recombinant ALVAC expressing HCMV 1E1 (vCP256) at a multiplicity of infection of 25 for approximately 1 hour at 37 C. Following incubation, sufficient Stim Medium was added to dilute the infected cells to $5\times10^5$ cells/ml (stimulator cells). Equal volumes of responder cells and stimulator cells were added to upright 25 $cm^2$ tissue culture flasks or to the wells of 24-well tissue culture plates and incubated in 5% $CO_2$/95% air at 37° C. for 6 days. Target cells were prepared by infecting LBCLs with recombinant WR vaccinia virus expressing HCMV 1E1 (vP893) similarly to the infection of stimulator cells except the target cells were incubated overnight at $4\times10^5$ cells/ml in RPMI 1640 medium containing 20% FBS. Following incubation, the mononuclear cells and the target cells were washed by centrifugation in Assay Medium (RPMI 1640 medium containing 10% FBS, 2 mM L-glutamine, $5\times10^{-5}$ M 2-mercaptoethanol, 100 IU/ml penicillin, and 100 $\mu$g/ml streptomycin). Target cells were incubated in $Na_2{}^{51}CrO_4$ for 1 hour, washed by centrifugation in Assay Medium, resuspended to $10^5$ cells/ml in Assay Medium, and held on ice until use. Following centrifugation, the mononuclear cells were diluted to $2\times10^6$ cells/ml in Assay Medium. One tenth ml of mononuclear cells and 0.1 ml of $^{51}$Cr labelled, infected target cells were added to the wells of 96-well round bottom tissue culture plates. These volumes and cell densities resulted in an effector to target ratio (E:T) of 20:1. The tissue culture plates were centrifuged at 250 g for 2 minutes and incubated in 5% $CO_2$/95% air at 37 C. for 4 to 5 hours. Following incubation, 0.1 ml of supernatant fluid from each well was collected using Skatron filter wicks and counted for released radioactivity. Percent cytoxicity was calculated as:

(EXPERIMENTAL $^{51}$CR RELEASE−SPONTANEOUS $^{51}$CR RELEASE)/(MAXIMUM $^{51}$CR RELEASE−SPONTANEOUS $^{51}$CR RELEASE)×100.

Maximum release was determined by the addition of 5% sodium dodecyl sulfate to target cells while spontaneous release was determined by incubating target cells in the absence of effector cells. In none of the experiments presented did spontaneous release of $^{51}$Cr from target cells exceed 20% of maximum $^{51}$Cr release.

Following in vitro stimulation with ALVAC recombinants expressing a single HCMV protein, mononuclear cells from four of the seven seropositive volunteer donors lysed autologous targets expressing HCMV IE1 (FIG. 45) and mononuclear cells from six of the seven seropositive donors lysed autologous targets expressing HCMV pp65 (FIG. 46). Re-stimulated mononuclear cells from none of the HCMV seropositive donors lysed autologous targets expressing HCMV gB.

The mononuclear cells from HCMV seronegative volunteer donors, when re-stimulated similarly to the mononuclear cells of the HCMV seropositive donors, failed to lyse autologous target cells expressing HCMV IE1 or HCMV pp65 (FIG. 45 and FIG. 46, respectively).

In all cases except one, the cytotoxic effector cells only lysed autologous, but not nonautologous, target cells expressing the appropriate HCMV protein. The single exception, mononuclear cells from Donor 7C, following re-stimulation with ALVAC pp65 (vCP260), was capable of lysing nonautologous target cells expressing HCMV pp65. However, it was later demonstrated that Donor 7C and the donor for the nonautologous target cell line share HLA-B7 of the human major histocompatibility complex (MHC).

Stimulation of HCMV IE1 CTLs by ALVAC-IE1 (vCP256): Human CTLs were stimulated in vitro and assayed for HCMV IE1 CTLs using similar methodology as in FIG. 45 except that following 6 days incubation for restimulation, the responder mononuclear cells were incubated with immunomagnetic beads coupled to monoclonal anti-human CD3, CD4, or CD8. Following incubation, the beads were removed by a magnet and therefore the CD3+, CD4+ or CD8+ cells. The cells adhering to the magnetic beads were uncoupled, washed and used in the cytotoxicity assay.

Representative of the phenotype of the cytotoxic responses of this HCMV seropositive cohort, the ALVAC-IE1 (vCP256) re-stimulated mononuclear cells from Donor 2A failed to lyse IE1-expressing targets following depletion of lymphocytes expressing CD3 and CD8, but not CD4 (FIG. 47). Furthermore, re-stimulated mononuclear cells that had been enriched for CD8, but not CD4, retained cytotoxic activity.

Thus, the cytotoxic effector cells derived from HCMV seropositive volunteer donors by re-stimulation in vitro with ALVAC recombinants expressing HCMV IE1 (vCP256) or HCMV pp65 (vCP260) were antigen specific, MHC-restricted, and expressed CD3 and CD8. These characteristics are consistent with those of classical cytotoxic T lymphocytes (CTLs).

These results show that ALVAC recombinants expressing HCNV proteins can serve as vaccines for the purpose of eliciting human cytotoxic T lymphocytes capable of mediating the destruction of HCMV-infected human cells. Furthermore, these data also show that these recombinant viruses can serve as reagents for the ex vivo stimulation and expansion of cytotoxic T lymphocyte clones for the purpose of immunotherapeutic applications (Riddell et al., 1992).

As discussed earlier, HCMV-gB can serve to elicit protective immunity in humans since 1) HCMV neutralizing antibody titer is reduced significantly when gB specific antibody is absorbed from human sera (Gönczöl et al., 1991; Marshall et al., 1992) and 2) there is evidence for the activation of helper T cells by the gB protein in seropositive individuals (Liu et al., 1991). Gönczöl et al., (1990) reported the immunoaffinity purified gB was immunogenic in human volunteers. In this study a single injection of the purified gB was able to induce high titers of HCMV neutralizing antibodies and lymphocyte proliferation in naturally seropositive individuals. In seronegative individuals three injections of the gB preparation induced transient HCMV neutralizing antibodies, a fourth injection induced a rapid reappearance and increase in titer of HCMV neutralizing antibodies.

These studies show the use of purified gB as a subunit vaccine. Additionally purified gB can also be used in prime/boost protocols in combination with NYVAC or ALVAC-gB recombinants. Recent studies have indicated that a prime/boost protocol, whereby immunization with a poxvirus recombinant expressing a foreign gene product is followed by a boost with a purified form of that gene product, elicits an enhanced immune response relative to the response elicited with either product alone. For example, humans immunized with a vaccinia recombinant expressing the HIV-1 envelope glycoprotein and boosted with purified HIV-1 envelope glycoprotein from a baculovirus recombinant exhibit higher HIV-1 neutralizing antibody titers than individuals immunized with just the vaccinia recombinant or purified envelope glycoprotein alone (Graham et al., 1993; Cooney et al., 1993). Humans immunized with two injections of ALVAC-HIV (vCP125) failed to develop HIV specific antibodies. Boosting with purified rgp160 from a vaccinia virus recombinant resulted in detectable HIV-1 neutralizing antibodies. Furthermore, specific lymphocyte T cell proliferation to rgp160 was clearly increased by the boost with rgp160. Envelope specific cytotoxic lymphocyte activity was also detected with this vaccination regimen (Pialoux et al., 1995). Macaques immunized with a vaccinia recombinant expressing the simian immunodeficiency virus (SIV) envelope glycoprotein and boosted with SIV envelope glycoprotein from a baculovirus recombinant are protected against a SIV challenge (Hu et al., 1991; 1992).

Example 3.35

Purification of HCMV Glycoprotein B

This Example involves purification of CMV glycoprotein B produced by a vaccinia recombinant, and the testing of its immunogenicity in laboratory animals in combination with ALVAC-CMV gB (vCP139).

COPAK recombinants vP1126, vP1128, and vP1145, each expressing a different form of gB, elicit CMV neutralizing antibodies in mice (Table 8) and therefore express gB in an immunogenic form. To select a virus and cell system, and an immunological reagent for CMV gB purification, gB expression by the three COPAK recombinants was compared by an immunoprecipitation assay, utilizing 5 different gB-specific monoclonal antibodies. Based on the assay results, a scheme was developed to purify gB from the medium of vP1145-infected VERO cells.

Immunoaffinity column bed material was prepared by crosslinking CMV gB-specific monoclonal antibody (mAb) CH380 to Protein A-agarose. This material was used to purify gB in a one-step procedure. Batches of gB were produced and evaluated for purity, as described in section III.

Immunoprecivitation Assay. Vero and HeLa cell monolayers in 60 mm dishes were infected with vP1126, vP1128, vP1145, or vP993 (described below) at an moi of 5 pfu/cell in serum-free medium. Medium and cells were harvested separately at 24 hours post infection. Immunoprecipitation (IP) assays were performed (Taylor et al., 1990) using the reagents described below, with rat anti-mouse IgG as a bridge to protein A for the monoclonals.

Virus

| | |
|---|---|
| vP1126: | COPAK-CMV gB (entire). Full length wild type gB |
| vP1128: | COPAK-CMV gB ($TM^-$). Lacks transmembrane region |
| vP1145: | COPAK-CMV gB ($TM^-$, $Cl^-$ lacks transmembrane region and has an altered cleavage site. |
| vP993: | COPAK control |

Reagents

| | |
|---|---|
| Guinea pig anti-CMV gB: | Obtained from Eva Gönczöl (Wistar Institute) |
| Monoclonal CH380: | Obtained from PMs&v (Pereria and Hoffman, 1986) |
| Monoclonal 13-127 | Advanced Biotechnologies, Inc. |
| Monoclonal 13-128 | Advanced Biotechnologies, Inc., neutralizing, conformationally dependent |
| Monoclonal HCMV-34 | Cogent Diagnostics, neutralizing |
| Monoclonal HCMV-37 | Cogent Diagnostics, neutralizing |
| Rabbit anti-p25 (Vaccinia E3L) | (obtained from Bert Jacobs, U. Arizona) |

Preparation of immunoaffinity chromatography bed material. One ml of immunoaffinity column bed material consisting of approximately 2.4 mg of mAb CH380 coupled to Protein A-agarose with the crosslinking agent dimethylpimelimidate was provided by Stephen Cockle, Connaught Laboratories, Limited (Willowdale, Ontario, Canada). mAb CH380 (Pereria and Hoffman, 1986) was used previously to purify CMV gB from a CMV viral envelope preparation (Gönczöl et.al., 1990). The material from S. Cockle was used in preliminary experiments to further determine its utility in gB purification. To scale up gB production, additional bed material was prepared by the same method used by S. Cockle, as described below.

Preparation of monoclonal ch380. Four vials of lyophilized monoclonal CH380 (lot S1705, obtained from PMsv) were reconstituted in PBS (137 mM NaCl, 2.7 mM KCl, 1.5 mM $KH_2PO_4$, 8.1 mM $Na_2HPO_4$, pH 7.4)(1 ml each) and dialyzed overnight versus PBS (final volume 3.5 ml). Protein concentration was determined to be 4.9 mg/ml by bicinchoninic acid assay (BCA assay, reagents obtained from Pierce, Rockford, Ill.). This preparation was then diluted in an equal volume of MAPS binding buffer (Bio-Rad cat# 153-6161; 31.4% w/v in milli-Q water, adjusted to pH 9, and filtered through a 22 mm membrane). To remove particulate material, the antibody preparation in MAPS buffer was centrifuged at 16,000×g for 30 min, and the protein concentration of the supernate was calculated from the absorbance at 280 nm, using 1.44 as the absorbance coefficient for IgG.

Preparation of protein a-agarose beads. Three ml of protein A-agarose beads (Bio-Rad cat# 153-6153) were washed 4 times with 2 volumes of MAPS binding buffer by gentle mixing in a closed tube and centrifugation for 5 min at 1000×g (1400 rpm in Beckman GPKR centrifuge, GH 3.7 rotor). The supernate was discarded after the last wash.

Binding of monoclonal antibody to the beads. All of the mAb antibody from step 1 was added to the washed beads from step 2 and the mixture was rotated in a closed tube at 4° C. The amount of mAb bound to the beads was determined at 6–12 hour intervals by pelleting the beads (1000 g/5 min) and determining concentration of IgG in the supernatant by reading OD at 280 nm, as described above. Approximately 48 hour of incubation at 4° C. were required to reach 90% depletion of IgG from the supernate.

Covalent crosslinking of monoclonal antibody to the beads. After binding was 90% complete, the beads were washed 4 times with 6 ml (2 volumes) of 50 mM borate, 3M NaCl, pH9. The beads were then resuspended in 30 ml (10 volumes) of 200 mM borate, 3M NaCl, pH9, and the pH adjusted to 9±0.1. A sample of beads (100 μl) was removed for later evaluation of cross-linking. Cross linking reagent dimethylpimelimidate (DMP) was prepared immediately before use at a concentration of 500 mM in 200 mM borate, 3M NaCl, pH9. DMP was added to the beads to produce a final concentration of 20 mM, and the beads were mixed in a closed tube, end-over-end, for 30 min at room temperature. Another sample of beads (100 μl) was removed for evaluation of cross-linking. To quench residual crosslinking reagent, the beads were washed 2 times with 6 ml (2 volumes) of 200 mM ethanolamine, pH8 and then incubated in 30 ml (10 volumes) of 200 mM ethanolamine, pH8 by mixing end-over-end for 2 hours at room temperature. Finally the beads were washed 4 times with 6 ml (2 volumes) of PBS and stored in 6 ml of PBS with 0.01% $NaN_3$.

To determine the extent of crosslinking, the gel bead samples taken before and after DMP incubation were pelleted, supernates discarded, and the beads mixed with 2×SDS-PAGE sample buffer containing reducing agent. These samples were boiled and electrophoretically separated on a 10% polyacrylamide gel. After staining with Coomassie Blue, IgG heavy and light chains could be detected in the "before" samples, but not in the "after" samples, indicating good efficiency of crosslinking.

Based on protein concentration before and after incubation of the antibody with the beads, the resulting bed material was estimated to contain approximately 5 mg of monoclonal antibody per ml of protein A-agarose beads.

Purification of CMV gB by immunoaffinity column chromatography. Column buffers. PBS (137 mM NaCl, 2.7 mM KCl, 1.5 mM $KH_2PO_4$, 8.1 mM $Na_2HPO_4$), pH 7 (batch 1), pH 7.4 (batches 2–5), or pH 6.8 (batches 2–5); 0.1 M glycine, pH 2.5; 1 M tris, pH 8.5.

Columns. Column sizes varied from 0.3 to 4 ml volumes. When a new column was poured, it was stripped with 10 bed volumes (bv) of 0.1 M glycine, pH 2.5, followed by 10–20 bv of PBS, pH 7 or 7.4. At the end of each column run, the column was washed with at least 10 bv of PBS, pH 7. At the beginning of each run, it was washed again with at least 10 bv of PBS, pH 7. The columns were run at room temperature and, when not in use, stored at 4° C. in PBS+0.01% $NaN_3$.

Preparation of the crude gB sample. Roller bottles (850 $cm^2$) were seeded with Vero cells in MEM+10% FBS. Medium was changed to serum-free MEM 2–12 hours before infection. Cells were infected with vP1145 at an MOI of 5 pfu/cell in a volume of 10 ml/RB of serum-free MEM. Virus was absorbed at 37° C. for 60 min and then 30 ml of serum-free MEM was added to each RB and incubation continued at 37° C. Medium was harvested at 16–24 hours post infection. The medium was clarified by centrifugation at 3000 rpm (Beckman GPKR centrifuge GH 3.7 rotor) for 15 min. The supernatant was recovered and further clarified by centrifugation at 20,000 rpm in a Beckman SW28 rotor for 60 min. The clarified medium was then concentrated (10 to 40-fold) by ultrafiltration with buffer exchange to PBS, pH 7.4, using one or more of the following ultrafiltration devices having 30,000 MWCO: Centricell-60 (Polysciences #19182-6), Centriprep-30 (Amicon #4306), or polysulfone immersible filter units (Polysciences #2250). This material was applied to the column as described below.

Column procedure. The crude gB sample was applied to the column at a flow rate of 0.03–0.09 ml/min, controlled by stopcock or peristaltic pump. After application of the sample, the column was washed at a flow rate of 0.2–0.6 ml/min with 10 bv PBS, pH7 (batch 1), or 20 bv of PBS, pH7.4 followed by 20 bv of PBS, pH6.8 (batches 2–5). Bound material was eluted with 10 bv of 0.1 M glycine, pH 2.5, collecting 500 μl (Batch 1,3) or 1 ml (batch 2,4,5) fractions into tubes containing 50 μl (Batch 1,3) or 100 μl (batch 2,4,5) of 1.0 M Tris, pH 8.5. One column (#28) was eluted with 0.1N glycine+0.1M Tris, pH7. CMV gB fractions were identified by SDS-PAGE on a 10% gel, under reducing conditions, followed by silver stain (Bio-Rad kit #161-0443).

Treatment of eluted qB. After identification by SDS-PAGE and silver stain the CMV gB fractions were pooled and concentrated in one of 2 ways: 1) Dialysis against 0.1×PBS and 10-fold vacuum concentration (majority of batch 1), or 2) Precipitation with 70% ammonium sulfate and resuspension in PBS. Protein concentration of the gB samples was determined by bicinchoninic acid microplate assay (BCA reagents from Pierce, Rockford, Ill.). Five batches of gB were prepared and frozen in aliquots at −70° C.

Evaluation of purified gB. Slot blot. Slot blot analysis was utilized to measure relative quantities of CMV gB in crude preparations, flow-through fractions, and elution fractions from affinity column purification. Serial two-fold dilutions in PBS were made of each test sample, and these were applied to nitrocellulose paper with the Schleicher and Scheull Manifold II slot blot apparatus. Each test included serially diluted samples of purified gB with a known protein concentration (determined by BCA microplate assay) as a standard. CMV gB was detected with monoclonal CH380 diluted 1:100 followed by $^{125}I$ goat anti-mouse (NEN#NEX159, at 0.1 Ci/ml). Slot blot signals on the autoradiograph were scanned and analyzed by densitometry (PDI, Inc., Huntington Station, N.Y., Quantity One densitometer program). The amount of CMV gB in each test sample was determined by linear regression analysis as compared to a gB standard curve.

Western blot. Test samples were electrophoretically separated on a 10% gel under reducing conditions, and blotted onto nitrocellulose paper (Harlow and Lane, 1988). The blot was probed for the presence of CMVgB, mouse IgG, vaccinia, and Vero cell proteins with the following reagents:

TABLE 7

Detection Methods

| ANTIGEN | PRIMARY ANTIBODY | DETECTION |
|---|---|---|
| CMV gB | Monoclonal CH380 diluted 1:100 | $^{125}I$ goat anti-mouse (NEN # NEX159), 0.1 μ |

TABLE 7-continued

| Detection Methods | | |
|---|---|---|
| ANTIGEN | PRIMARY ANTIBODY | DETECTION |
| | | Ci/ml |
| Mouse IgG | $^{125}$I goat anti-mouse (NEN # NEX159, at 0.1 μ Ci/ml | (See primary antibody) |
| Vaccinia proteins | Rabbit anti-vP410, rabbit #W29 week 39, 9/13/91, preabsorbed against Vero cells and diluted 1:100 | $^{125}$I Protein A (NEN #NEX-146), 0.1 μ Ci/ml |
| Vero cell proteins | Rabbit anti-Vero cells, obtained from B. Meignier, PMsv, preabsorbed against ALVAC-infected CEF and diluted 1:100 | $^{25}$I Protein A (NEN #NEX-146), 0.1 μ Ci/ml |

Immunoprecipitation/western blot assay. A combination IP/Western Blot was performed on Batch 1 gB utilizing the panel of monoclonal antibodies. Unlabeled crude and purified gB was subjected to immunoprecipitation followed by SDS-PAGE, the gel was blotted onto nitrocellulose, and gB-specific proteins detected with guinea pig anti-CMV gB (from Eva Gönczöl), diluted 1:1000, and $^{125}$I Protein A (NEN#NEX-146), 0.1 μCi/ml.

Analysis of the purity of the gB product. Samples from each batch of gB were analyzed by electrophoretic separation on a 10% gel under reducing conditions, followed by staining with Coomassie Blue. The dried gel was scanned and analyzed by densitometry (PDI, Inc., Huntington Station, N.Y., Quantity One densitometer program).

Immunoprecipitation assay comparing expression of CMV gB by three vaccinia COPAK recombinants. To choose a suitable recombinant, cell substrate and antibody for production and immunoaffinity purification of CMV gB, COPAK recombinants expressing 3 different forms of gB were compared by immunoprecipitation assay using guinea pig anti-gB and a panel of monoclonal antibodies. Recombinants vP1126, vP1128, and vP1145 elicit CMV neutralizing antibodies in mice and therefore express gB in an immunogenic form (Table 8). All of the CMV gB antibodies tested produced similar IP results. A representative assay, with guinea pig serum using both medium and cell fractions from HeLa and Vero cell infections, is shown in FIGS. 48A to D. As expected, CMV gB specific material was precipitated from both the cell and medium fractions of vP1128 and vP1145 infected cells, but in only the cell fraction with vP1126 infected cells. The apparent molecular weights of the gB specific bands correspond to previously published results (Britt and Auger, 1986; Britt and Vugler, 1989; Reis et.al., 1993). The cell fractions of all three CMV gB recombinants contained a major band of apparent molecular weight 130–140 kDa, consistent with the apparent molecular weight of the glycosylated uncleaved gB precursor. Less intense protein species with apparent MW of 110 kDa and 55 kDa were observed in the cell fractions and are consistent with the proteolytically processed mature protein species. The N-terminal product was previously reported to be 90–110 kDa and the C-terminal product 55–58 kDa (Britt and Auger, 1986). In HeLa cells a protein species with an apparent higher molecular mass (approximately 150 kDa) was also present (e.g., FIG. 48D, lane 4). This species probably also represents an uncleaved precursor form that is more highly glcosylated. In the medium fractions three gB bands were precipitated from vP1128 and vP1145 infected cells, representing the uncleaved precursor, and N-terminal and C-terminal processed polypeptides. By densitometric analysis, there was more gB-specific material precipitated from the medium fractions of Vero cells compared to HeLa, with recombinant vP1145 producing more gB-specific material than vP1128. This difference may be explained by the observation that more vaccinia E3L was precipitated from the cell fraction of vP1145 than the vP1128 cell fraction, indicating an overall higher level of vaccinia expression in this sample (FIGS. 49A and B). With vP1145, there was more gB specific material precipitated from the medium fraction than from the cell fraction in both HeLa and Vero cells (compare FIGS. 48A,B vs. C,D).

The three different sizes of gB precipitated from the medium of HeLa infected cells appear to have higher molecular weights than the three species produced in Vero cells (compare FIG. 48A vs. 48B). These differences may be due to different levels of glycosylation in HeLa cells compared to Vero, but this hypothesis was not examined further. To determine if the higher molecular weight gB-specific proteins would also be produced by another human cell line, MRC-5, a western blot assay was performed comparing the gB proteins in the medium of vP1145 infected HeLa, MRC-5, and Vero cells using monoclonal CH380 (FIG. 50). The result shows that the two gB bands detectable in this assay, gB precursor (approx. 140 kDa) and C terminal processing fragment (55–58 kDa), had apparently higher molecular weights in HeLa and MRC-5 than in VERO cells. The N-terminal processing fragment is not detectable by western blot using either monoclonal CH380 or the guinea pig anti-CMV gB serum.

MAb CH380 was chosen for use in immunoaffinity purification of gB, since a large quantity was readily available and no apparent differences were seen in the gB-specific proteins detected by the five different monoclonals in the IP assay (FIG. 51). Based on the IP analysis and the considerations that purification of secreted gB from the medium of infected cells eliminates the need to solubilize gB from cell membranes and purify it from cellular proteins, purification of CMV gB was initiated using the medium fraction of vPl145-infected Vero cells. Infection was done in serum-free medium, further reducing contaminating proteins in the crude material.

Purification of CMV gB. Fifteen separate immunoaffinity chromatography column runs, yielding a total of 3.1 mg of gB, are summarized in Table 9. Some of the material was used for further assays and the remainder was pooled in 5 separate batches of purified product, totaling 2.6 mg (Table 10). Column runs 7, 8, 10, and 11 were sequential runs in the same column. The bed material from columns 19A, 19B, 19C, 21A, 21B, and 21C were pooled to make the column used for runs 28, 29, and 32, from which the largest amount of gB was obtained. Table 9 lists the Crude gB material applied to each column in terms of the number of vP1145-infected Vero roller bottles (b 1×10$^8$ cells per RB) from which the crude material was derived, and amount of total protein and gB-specific protein in the crude. Based on analysis of 8 samples, the total protein content of the crude preparations ranged from 1.2 to 3.7 mg/RB with a mean value of 2.4 mg/RB (24 μg per $10^6$ cells). Utilizing a slot blot assay with purified gB as standard, the amount of gB present in the crude material was measured for 7 of the preparations: values ranged from 50 to 350 μg/RB with a mean of 153 μg/RB (1.5 μg/$10^6$ cells). Together these calculations indicate that the protein in the crude preparations consisted of approximately 6% gB. CMV gB yields ranged from 8 to 29 μg/RB with a mean of 20 μg/RB (0.2 μg/$10^6$ cells) (Table 9). Approximately fifty roller bottles (1×$10^9$ cells) were required to produce 1 mg of CMV gB.

The capacity of the immunoabsorbent gel for gB was not fully evaluated. The 4 ml bed material used for column runs 28, 29, and 32, was initially divided into 0.6 ml mini-columns (column runs 19A, 19B, 19C, 21A, 21B, and 21C) and varying amounts of crude gB were applied to each column to determine where saturation of binding would occur. Unfortunately, the quantity of gB in the crude material applied to the columns was overestimated, and saturation was not demonstrated. The highest binding result (from column 19C) was used as an estimate of column capacity (300 μg/ml bed material). The amount of gB eluted from the mini-columns represented 8 to 25% of the gB protein applied to the columns (Table 9). Therefore, if the capacity of the 4 ml column is at least 1.2 mg and 25% of the gB applied is recovered, it was estimated that 4.9 mg of crude gB (from approximately 33 RB) must be applied to the column to obtain 1.2 mg of purified gB. The result from column 28 is close to this estimate: material from 36 roller bottles was applied to the column #28, and 1 mg of gB was eluted.

The gB applied to the columns but not eluted as purified material has not been quantitatively accounted for. Since only 8–25% of the gB applied to the column was recovered as purified gB, the remainder of the gB must be present in flow-through fractions, wash fractions, eluted fractions not pooled with the product, or bound to the column. CMV gB could be detected by western blot in the flow-through fractions (e.g., FIG. 52, lane 6). However, when the amount of gB in the flow-through fractions was estimated by slot blot analysis, it did not account for more than 20% of the applied gB. The wash fractions have not been evaluated. The pooled fractions chosen for the final gB product were peak fractions only and therefore trace amounts of gB in adjacent fractions could account for some of the missing gB. For example, FIG. 53 shows sequential fractions eluted from column 8. Fractions 8.17–8.21 were pooled for the gB product, but trace amounts remained in fractions 8.16 and 8.22. Evidence exists also for the retention of gB in the immunoabsorbent gel. Gel material, taken from columns 11 and 19C after elution and washes, contains gB specific material detectable by western blot (FIG. 52, lanes 2 and 3). The amount of gB remaining on the column has not been quantitatively evaluated.

Reapplication of flow-through material to the column was attempted when flow-through material from column run #7 was applied to column #10 (Table 9). The amount of gB eluted from column 10 (4.5 μg) was only 4% of that obtained from column 7 (110 μg). It was not possible to evaluate this result since the capacity of the bed material for gB, and the amounts of gB applied to the column and present in the flow-through fractions were not known. Because of the poor yield, this approach was not used again.

Evaluation of purified gB. After pooling gB-containing eluted fractions, evaluation of purified gB consisted of 1) determination of total protein concentration, 2) SDS-PAGE analysis to identify gB specific and non-specific bands, and 3) confirmation of these bands with immunological reagents. Additionally, the purified gB was analyzed for degree of purity by densitometer scan, and for native conformation by ability to bind to a panel of CMV monoclonal antibodies.

Figure 56B:
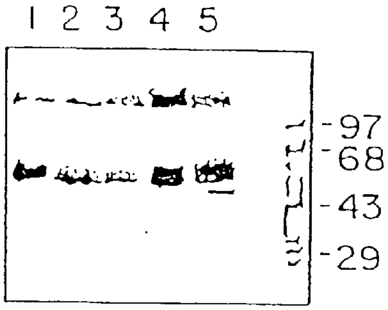

Fractions containing CMV gB eluted from each column were analyzed initially by SDS-PAGE and silver staining, and gB fractions were identified and pooled for each run. A typical elution profile is shown in FIG. 53. A portion of the eluted gB was used for analysis, and the remainder of the material was combined into 5 separate batches (Table 10). Each batch was analyzed by SDS-PAGE on a 10% gel under reducing conditions and stained with Coomassie Blue (FIG. 54). The stained gel was scanned on a densitometer and the molecular weight and relative quantity of each band was calculated: a typical scan is shown in FIGS. 55, 55A and analysis of the 5 batches is summarized in Table 11. By SDS-PAGE analysis batches 1–5 appear very similar (FIG. 54). The two major bands, having apparent molecular weights 120–130 and 51–59 kDa, represent the precursor gB protein and the C-terminal processing fragment. The wide diffuse appearance of these bands is probably due to variable glycosylation of this normally heavily glycosylated protein. The identity of these bands as gB-specific is supported by results from western blot analysis with monoclonal CH380 (FIG. 56B). The bands of apparent molecular weight 77–100 kDa, which appear as doublets in batches 2–5 (FIG. 54), are the correct size for the gB N-terminal processing fragment, identified in the medium of vP1145-infected cells by IP analysis (FIGS. 48A and B). These bands could not be verified as gB-specific by either western blot analysis (FIG. 56B), or a combination immunoprecipitation-western blot assay (FIGS. 57A and B), but the possibility should not be ruled out since neither the guinea pig anti-gB serum nor monoclonal CH380 are able to detect N-terminal processing fragments by western blot. A contaminating protein of approximately 39–45 kDa is present in each batch at a level of 6–15% of total protein (FIG. 54 and Table 11). Two more possible gB protein bands, one of greater than 200 kDa and the other 30–35 kDa are present in every batch (FIGS. 54, 55, and 55A; Table 11). Evidence that the large (~200 kDa) protein is gB is derived from western blot analysis with monoclonal CH380 which detects two proteins with molecular weights greater than 200 kDa (FIG. 56B, lanes 2 & 3). It is possible that the protein of approximately 30–35 kDa is also gB-specific (FIG. 54). In the IP analysis of medium of vP1145-infected cells, a protein of approximately 35 kDa was detected by 3 monoclonals (13–128, HCMV 34, and HCMV 37)(FIG. 51) and by the guinea pig serum (FIGS. 48A and B). A protein of this size was described by Reis et al. (1993) as a degradation product of gB.

Figure 58B:
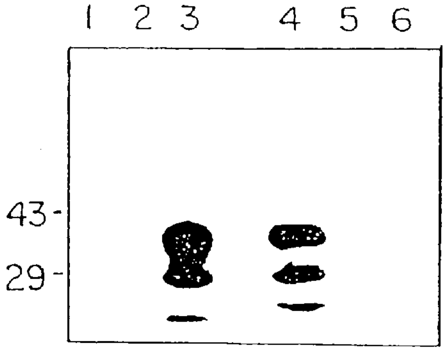

Assuming that contaminating proteins in the gB preparation would be derived from the cell substrate, the virus vector or the immunoabsorbent bed material, the preparation was probed for the presence of mouse IgG, Vero cell proteins, and vaccinia proteins. Proteins derived from Vero cells or mouse IgG could not be detected by western blot analysis (FIGS. 56A and 58A). However, contaminating vaccinia-specific proteins with molecular weights of approximately 35 and 20 kDa were detected in trace amounts (FIG. 58B, lane 5).

Figure 57B:
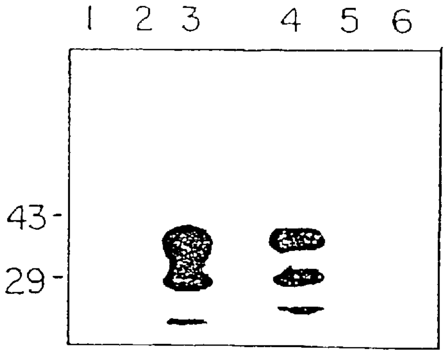

To determine if the eluted gB retained its native conformation, a combination immunoprecipitation/western blot assay was performed with a panel of monoclonals which included 3 neutralizing and one conformationally dependent antibody. Each monoclonal antibody precipitated the precursor and C-terminal fragment from purified gB (FIG. 57), suggesting that the gB eluted from the immunoaffinity column retained its native conformation.

In summary, the analysis of eluted gB in batches 1–5 demonstrates that the product contains at least two known gB-specific proteins, the precursor gB and C-terminal fragment, which together account for approximately 50% of the protein content (FIG. 54 and Table 11). Three other protein species, which account for 20–25% of total protein content (Table 11), could also be gB-specific although direct evidence has not been provided.

Furthermore, this Example provides both general and specific techniques for isolation and/or purification of HCMV epitope(s) of interest, which can be applied analogously to whole cell preparations infected with HCMV.

Immunogenicity of purified gB. The five CMV gB batches were pooled and the final concentration determined. Several amounts of purified gB were adjuvanted with either alum or QS21 and used to inoculate mice. Serum from the mice was evaluated for the presence of HCMV neutralizing antibody. Table 12 demonstrates that all of the amounts of purified gB tested with both adjuvants were able to elicit HCMV neutralizing antibody.

Purified gB was used in a prime/boost protocol in combination with ALVAC-gB (vCP139) in mice. Table 13 demonstrates that mice receiving ALVAC gB (vCP139) on day 0 and boosted on Day 29 with purified gB adjuvanted with QS21 or Alum developed higher levels of HCMV neutralizing antibody than mice receiving a second dose of ALVAC-gB (vCP1319).

TABLE 8

Induction of HCMV Neutralizing Antibody in Mice

| Immunogen[1] | Days After Immunization: 30 | 48 | 135 |
|---|---|---|---|
| vP1126 | 16[2] | 8 | 256 |
| vP1128 | 16 | 8 | 106 |
| vP1145 | 16 | 8 | 106 |

[1]Mice were immunized with 1 × $10^8$ PFU of recombinant viruses (ip.) on day 0 and day 49.
[2]HCMV Neutralizing titer

TABLE 9

SUMMARY OF IMMUNOAFFINITY PURIFICATION COLUMNS

| COLUMN RUN | # VERO ROLLER BOTTLES[a] | COLUMN SIZE | CRUDE MATERIAL APPLIED TO COLUMN: Total Protein[b] | gB-specific protein[c] | gB YIELD (% of applied) |
|---|---|---|---|---|---|
| 7 | 4 | 1 ml | 13.3 mg | nd[d] | 110 μg[b] |
| 8 | 6 | 1 ml | 14.4 mg | 2.2 mg | 84 μg[b] |
| 10 | Col 7 flow thru | 1 ml | nd | nd | 4.8 μg[b] |
| 11 | 4 | 1 ml | nd | nd | 100 μg[b] |
| 13 | 1 | 0.3 ml | nd | nd | 12 μg[d] |
| 19A | 1 | 0.6 ml | 2.9 mg | 240 μg | 41 μg[c] (17%) |
| 19B | 2 | 0.6 ml | 5.8 mg | 480 μg | 93 μg[c](19%) |
| 19C | 3 | 0.6 ml | 8.7 mg | 720 μg | 185 μg[c] (25%) |
| 21A | 3 | 0.6 ml | 5.7 mg | 300 μg | 29 μg[c](8%) |
| 21B | 5 | 0.6 ml | 9.5 mg | 500 μg | 120 μg[c] (13%) |
| 21C | 7 | 0.6 ml | 13.3 mg | 700 μg | 150 μg[c] (19%) |
| 23 | 3 | 6 ml | 5.7 mg | 300 μg | 25 μg[c] (8%) |
| 28 | 36 | 4 ml | 64.8 mg | nd | 1000 μg[b] |
| 29 | 24 | 4 ml | 30 mg | nd | 480 μg[b] |
| 32 | 24 | 4 ml | nd | nd | 700 μg[b] |

[a]Cell density: 1 × $10^8$ cells per roller bottle
[b]Protein concentration determined by Pierce BCA assay
[c]Estimated by slot blot analysis, using purified gB as standard
[d]Not determined

TABLE 10

CMV gB BATCHES

| BATCH # | TOTAL gB | VOLUME | CONCENTRATION | COLUMN RUN |
|---|---|---|---|---|
| 1 | 0.16 mg | 0.55 ml | 0.29 mg/ml | 7 |
| | | | | 8 |
| | | | | 10 |
| | | | | 11 |
| | | | | 13 |
| 2 | 1.0 mg | 1.0 ml | 1.0 mg/ml | 28 |
| 3 | 0.26 mg | 0.5 ml | 0.52 mg/ml | 21A |
| | | | | 21B |
| | | | | 21C |
| | | | | 23 |
| 4 | 0.48 mg | 0.5 ml | 0.96 mg/ml | 29 |
| 5 | 0.7 mg | 0.5 ml | 1.4 mg/ml | 32 |

TABLE 11

| DENSITOMETRY ANALYSIS OF 5 BATCHES OF CMV gB | | | | | | | | | | |
|---|---|---|---|---|---|---|---|---|---|---|
| PROTEIN | APPARENT MOLECULAR WEIGHT (kDa)[a] | | | | | RELATIVE QUANTITY (%)[b] | | | | |
| BAND | B1 | B2 | B3 | B4 | B5 | B1 | B2 | B3 | B4 | B5 |
| >200 kDa | 222 | 208 | 221 | 225 | 217 | 10.6 | 6.7 | 7.5 | 8.3 | 7.4 |
| (gB?) | 192 | | | | | 8 | | | | |
| Precursor gB | 128 | 120 | 124 | 128 | 134 | 39 | 30 | 36.1 | 30 | 27.4 |
| N fragment | 83 | 94 | 99 | 101 | 100 | 9.6 | 3.6 | 3.2 | 4.5 | 3.5 |
| (?) | | 77 | 84 | 88 | 89 | 9.7 | 6.3 | 6.6 | 6.3 | 6.3 |
| C fragment | 55 | 51 | 55.4 | 56.4 | 59 | 21 | 15.6 | 13.7 | 22.6 | 21 |
| Unknown contaminant | 42 | 39 | 42 | 44 | 45 | 6.1 | 12 | 15.4 | 14.3 | 15.8 |
| gB degradation product (?) | 32 | 30 | 35 | 35 | 37 | 4.3 | 9.7 | 11.3 | 8.6 | 10 |

[a]Calculated from densitometer scan using molecular weight markers as standards (refer to FIG. 55, 55A)
[b]The density of each band is calculated from a 2 dimensional scan line through the band: the average pixel OD across the sample width is integrated under the curve to the baseline to obtain density (OD × cm). Relative quantity is the percentage of the total density of all bands in the lane. (refer to FIG. 55, 55A).

TABLE 12

HCMV Neutralizing Antibodies Elicited by purified gB protein in CBA Mice[1]

| Mouse | dose[3] | Adjuvant[3] | NT[2] 4w | NT[2] 6w | NT[2] 8w | NT[2] 9w |
|---|---|---|---|---|---|---|
| 201 | 2.5 | Alum | 32 | 256 | 256 | 256 |
| 203 | | | 8 | 64 | 128 | 128 |
| 204 | | | 8 | 12 | 16 | 16 |
| 206 | 5.0 | Alum | 48 | 512 | 192 | 192 |
| 207 | | | 12 | 192 | 512 | 512 |
| 208 | | | 16 | 192 | 192 | 192 |
| 209 | | | 16 | 128 | 256 | 256 |
| 210 | | | 8 | 128 | 256 | 256 |
| 211 | 10.0 | Alum | 32 | 256 | | |
| 213 | | | 32 | 96 | 256 | 256 |
| 214 | | | 32 | 256 | 256 | |
| 216 | 20.0 | Alum | 64 | 128 | 128 | 128 |
| 217 | | | 64 | 256 | 256 | 256 |
| 218 | | | 32 | 128 | 512 | 256 |
| 219 | | | 16 | 128 | 256 | 256 |
| 220 | | | 32 | 192 | 512 | 256 |
| 222 | 2.5 | QS21 | 8 | 192 | 512 | |
| 223 | | | 32 | >4096 | >4096 | 2048 |
| 224 | | | 16 | 1536 | | |
| 225 | | | 64 | 1024 | 1024 | 1024 |
| 226 | 5.0 | QS21 | 64 | >4096 | 1024 | 1024 |
| 227 | | | 96 | >4096 | | |
| 228 | | | 64 | >4096 | >4096 | >4096 |
| 229 | | | 64 | >256 | >4096 | |
| 230 | | | 32 | >4096 | 1536 | 2048 |
| 231 | 10.0 | QS21 | 64 | 2048 | 2048 | >4096 |
| 232 | | | 96 | 1536 | 2048 | |
| 233 | | | 96 | >4096 | | |
| 234 | | | 64 | 2048 | 2048 | 1024 |
| 236 | 20.0 | QS21 | 128 | 3072 | | |
| 239 | | | 96 | >4096 | >4096 | >4096 |

[1]Mice were inoculated S.C. at weeks 0 and 4.
[2]Sera were obtained at 4, 6, 8 or 9 weeks after priming.
[3]μg gB in either 15 μg QS21 or 25 μl Alum were used for each inoculation.

TABLE 13

Summary Of Prime-Boost Experiment

| Mice | NT | antigen adj. | NT | antigen adj. | NT | NT |
|---|---|---|---|---|---|---|
| | Day 0 | | Day 29 | | Day 42 | Day 56 |
| 381 | 4 | ALV | 32 | gB + Alu | 384 | 768 |
| 382 | <4 | ALV | 8 | gB + Alu | 192 | 192 |
| 383 | 4 | ALV | 4 | gB + Alu | 192 | 256 |
| 384 | <4 | ALV | 48 | gB + Alu | 512 | 512 |
| 385 | 4 | ALV | 16 | gB + Alu | 256 | ND |
| 397 | 4 | ALV | 8 | gB + Alu | 128 | 192 |
| G.m. | 4 | | 13.5 | | 248 | 326 |
| 392 | <4 | ALV | <4 | gB + QS | 128 | 128 |
| 393 | <4 | ALV | 4 | gB + QS | >1024 | >1024 |
| 394 | <4 | ALV | 8 | gB + QS | >1024 | >1024 |
| 395 | <4 | ALV | 16 | gB + QS | 512 | 384 |
| 396 | <4 | ALV | 4 | gB + QS | 256 | 384 |
| 398 | 4 | ALV | 8 | gB + QS | >1024 | >1024 |
| G.m. | 4 | | 6.3 | | >512 | >522 |
| 373 | 4 | ALV | 16 | ALV | 128 | 96 |
| 376 | 4 | ALV | 4 | ALV | 8 | 12 |
| 378 | 8 | ALV | 4 | ALV | 8 | 4 |
| 379 | 4 | ALV | 8 | ALV | 128 | 128 |
| 380 | 4 | ALV | 16 | ALV | 64 | 64 |
| 399 | 4 | ALV | 4 | ALV | 96 | 192 |
| 400 | <4 | ALV | 4 | ALV | 64 | 128 |
| G.m. | 4 | | 6.5 | | 45.6 | 51.2 |

$5 \times 10^5$ $TCD_{50}$ of ALVAC-gB (vCP139), 5 ug gB + Alu, 1 ug gB + QS21 were given, s.c.
G.m. = geometric mean The results presented here demonstrate the ability of the NYVAC and ALVAC-HCNV recombinants and products therefrom to be employed in the compositions and utilities aforementioned, for instance, immunological, antigenic or vaccine compositions, or for use in preparing antigens or antibodies for assays, kits or tests, and, for example, as suitable for uses in vaccine or immunization strategies capable of preventing vascular disease such as restenosis and/or atherosclerosis arising from infection by HCMV; and, that the DNA of the recombinants is useful for probes or for preparing PCR primers for diagnosis of restenosis and/or atherosclerosis or whether a patient is prone thereto or not prone thereto due to HCMV status.

Example 3.36

Expression of CMV Genes in NYVAC-CMV6 (vP1302B) and NYVAC-CMV5

Immunoprecipitation with monoclonal antibodies specific for gB, gH, pp65, pp150 and IE1-exon4 demonstrated the correct expression of these five genes by NYVAC-CMV6. FACScan analysis (Becton-Dickinson) demonstrated surface expression of gH in vP1302B infected cells but not in cells infected with its parent (vP1251) indicating that a functional gL gene product is expressed in vP1302B.

Immunoprecipitation with monoclonal antibodies specific for gB, gH, pp65 and pp150 demonstrated the correct expression of these four genes by NYVAC-CMV5 (vP1312). FACScan analysis demonstrated surface expression of gH in vP1312 infected cells but not in cells infected with its parent (vP1262) indicating that a functional gL gene product is expressed in vP1312.

Example 3.37

Developing an ALVAC Donor Plasmid Containing the HCMV pp65 and pp150 Genes

Plasmid CMV65C6.2 was linearized with EcoRI, filled in with klenow and treated with alkaline phosphatase generating a 6.3 kb fragment. Plasmid 150.1 was digested with NheI, filled in with klenow and a 3.2 kb fragment (42K-pp150) isolated. Ligation of these two fragments yielded plasmid 150.8R1 in which transcription of pp65 and pp150 are in the same direction and pp150 is reversed from plasmid 150.8 in Example 3.29. The DNA sequence of CMVpp65 and CMVpp150 plus additional flanking sequences in plasmid 150.8R1 are shown in FIGS. 59A–C (SEQ ID NO:38).

Example 3.38

Construction of ALVAC-CMV4 (gB, gH, pp65, pp150)

Plasmid 150.8R1 was transfected into vCP233 infected CEF cells to generate ALVAC-CMV4 (vP1360).

Example 3.39

Expression of CMV Genes in ALVAC-CMV4

Immunoprecipitation with monoclonal antibodies specific for gB, gH, pp65 and pp150 demonstrated the correct expression of all four genes by ALVAC-CMV4 (vP1360).

Example 3.40

Developing ALVAC Donor Plasmids Containing HCMV gL OR gL Plus IE1-exon4

FIGS. 60A and B (SEQ ID NO:39) is the sequence of a 5.8 kd segment of canarypox DNA contained in plasmid pCPtk. The canarypox thymidine kinase gene (tk) is encoded within this segment initiating at nucleotide 4412 and terminating at nucleotide 4951. A tk (C7) insertion vector containing 2085 bp upstream of C7, polylinker containing SmaI, NruI, EcoRI, XhoI and StuI sites, and 812 bp downstream of C7 was derived in the following manner. A 3450 bp PstI/NsiI fragment from pCPtk was cloned into the blunt ended Asp718/XbaI sites of PBS-SK+ generating plasmid pEU1. To delete the tk ORF and replace it with a polylinker, two PCR fragments were amplified from pCPtk using oligonucleotides RG578 (SEQ ID NO:153) (5'-GTACATAAGCTTTTTGCATG-3') plus RG581 (SEQ ID NO:154) (5'-TATGAATTCCTCGAGGGATCCAGGC-CTTTTTTATTGACTAGTTAAT-CAGTCTAATATACGTACTA AATAC-3') and RG579 (SEQ ID NO:155) (5'-CTAATTTCGAATGTCCGACG-3') plus RG580 (SEQ ID NO:156) (5'-TTAGAATTCTCGCGACCCGGGTTTTTAT-AGCTAATTAGTACTTATTACAAATACTATAATATTTAG-3'). These fragments were purified, digested with HindIII/EcoRI or BstBI/EcoRI and ligated to pEU1 cut with HindIII/BstBI resulting in plasmid pC7.

The polylinker region in pC7 was modified in the following manner. pC7 was digested with EcoRI and StuI, purified and ligated to annealed oligonucleotides SDSYN154 (SEQ ID NO:157) (5'-AATTCGTCGACGGATCCCTCGAGGGTACCGCATGC-3') and SDSYN155 (SEQ ID NO:158) (5'-GCATGCGGTACCCTCGAGGGATCCGTCGACG-3') generating plasmid pC7$^+$.

Plasmid pC7$^+$ was digested with BamHI and treated with alkaline phosphatase. Plasmid I4LH6CgL was digested with BamHI and BglII and a 968 bp fragment (containing the H6 promoted gL gene ) isolated. Ligation of these two fragments generated plasmid C7gL in which transcription of gL is in the same direction as the deleted tk gene. The DNA sequence of HCMV gL plus additional flanking sequences in plasmid C7 gL is shown in FIGS. 61A and B.

Plasmid C7 gL was digested with BamHI and PspAI and treated with alkaline phosphatase. Plasmid I4LH6IEEX4 was digested with BamHI and PspAI and a 1363 bp fragment (containing the H6 promoted IE1-exon4 gene) isolated. Ligation of these two fragments yielded plasmid C7gLIES2. The DNA sequence of HCMV gL and IE1-exon4 plus additional flanking sequences in plasmid C7gLIES2 is shown in FIGS. 62A and B.

Example 3.41

Construction of ALVAC-CMV6 (gB, gH, gL, pp65, pp150, IE1-exon4 and ALVAC-CMV5 (gB, gH, gL, pp65, pp150)

Plasmid C7gLIES2 is transfected into vP1360 infected cells to generate ALVAC-CMV6 (gB, gH, gL, pp65, pp150 , IE1-exon4).

Plasmid C7 gL is transfected into vP1360 infected cells to generate ALVAC-CMV5 (gB, gH, gL, pp65, pp150).

Example 3.42

Cloning of HCMV gL and A gH Lacking its Transmembrane Region and Cyoplasmic Tail in NYVAC Donor Plasmid RSD553

The sequence of HCMV gH lacking its transmembrane region and cytoplasmic tail is presented in FIG. 63 (SEQ ID NO:41). Plasmid SPgH1 was used in PCR with oligonucleotides SPgHS1 (SEQ ID NO:159) (5'-CCGAAGCTTCTCGAGATAAAAATCAACGACTGTC GGTAGCGTCCACGACGAC-3') and SPgH8 (SEQ ID NO:160) (5'-TCCACTCCATGCTAGT-3') to generate a 756 bp fragment. This fragment was digested with NsiI and HindIII and a 275 bp fragment isolated. Plasmid SPgH6 was digested with NsiI and HindIII and a 4779 bp fragment isolated. Ligation of these two fragments yielded plasmid SPgH7 which contains the 42K promoted gH gene lacking its transmembrane region and cytoplasmic tail.

NYVAC insertion plasmid pSD553 was digested with BamHI and treated with alkaline phosphatase. Plasmid I4LH6CgL was digested with BamHI and BglII and a 970 bp fragment (containing the H6 promoter and gL gene) isolated. Ligation of these two fragments generated plasmid COPAKgL-24.

Plasmid gH7 was digested with XhoI and ScaI and a 2239 bp fragment isolated (containing the 42K promoter and truncated gH gene). Plasmid COPAKgL-24 was digested with XhoI, treated with alkaline phosphatase and ligated to the 2239 bp fragment generating plasmid COPAKHL-15. The DNA sequence of gL and the truncated gH plus additional flanking DNA sequences in plasmid COPAKHL-15 is shown in FIGS. 64A and B (SEQ ID NO:42).

Example 3.43

Constructing a Poxvirus Recombinant Containing gL and gH Lacking Transmembrane Region and Cytoplasmic Tail Plasmid COPAKHL-15 was transfected into NYVAC infected CEF cells to generate the recombinant vP1399.

Example 3.44

Expression of gH by Recombinant VP1399

Immunoprecipitation with a monoclonal antibody specific for gH revealed the expression of a secreted gH protein of approximately 97 kDa by recombinant vP1399.

Example 4

Poxvirus-p53 Epitope of Interest Recombinants

Reference is made to WO 94/16716, incorporated herein by reference, with respect to this Example, especially Examples 15, 32 and 33, and FIGS. 17, 18, 38 and 39 of WO 94/16716. Methods and Materials are as in Example 3.

Example 4.1

NYVAC- and ALVAC-p53 Recombinant Viruses

The nuclear phosphoprotein, p53, is found in normal cells at very low steady state levels. Expression of p53 is tightly regulated throughout the cell cycle and may be involved in controlling cell proliferation. The molecular mechanisms by which p53 exerts its tumor suppressor activity remain unknown, although p53 appears to exist in two conformational states. One form is unique to wildtype p53 and is associated with the ability to block cell cycle progression while the second form is associated with the ability to promote cell proliferation and is common to wildtype and mutant forms (reviewed by Ulrich et al., 1992). p53 is the gene most frequently found to be mutated in a wide variety of human tumors (reviewed by Hollstein et al., 1991).

Probably the most studied cancer associated with p53 mutation is breast cancer. It is known that p53 mutation results in the overexpression of the p53 gene product in primary breast cancer patients (Davidoff et al., 1991). The basis for p53 overexpression was found to result from a post-transcriptional mechanism, since p53-specific mRNA levels were similar in tumors with high and low level protein expression. Further, the p53 mRNA from overexpressing tumors were found to contain missense mutations in highly conserved regions of the gene. These mutations were subsequently found to give rise to more stable p53 protein forms which form complexes with heat shock protein 70 (HSP-70). Since HSP-70 proteins have been implicated in antigen processing, not only may the humoral response to p53 observed in a subset of breast cancer patients have resulted from unique processing/presentation modes for complexes, such an association may also elicit cellular anti-p53 protein responses (Davidoff et al., 1992). Such anti-p53 cellular immune responses are responses more germane to the immunotherapy of such cancers.

Generation of Poxvirus-based Recombinant Viruses Expressing Wildtype and Mutant Forms of the Human p53 Gene Product Three plasmids, p53wtXbaISP6/T3, p53-217XbaI, and p53-238XbaI containing wildtype human p53 gene sequences, and two mutant forms of p53, respectively, were obtained from Dr. Jeffrey Marks (Duke University). The p53-217XbaI contains a p53 gene encoding a p53 product lacking codon 217 while p53-238XbaI encodes a p53 gene product with an cysteine to arginine substitution at amino acid 238. The sequence of the wildtype p53 cDNA and the deduced amino acid sequence was described previously (Lamb and Crawford, 1986).

All three p53 genes were individually juxtaposed 3' to the modified vaccinia virus H6 promoter described by Perkus et al., 1989. These manipulations were performed in the following manner. A 227 bp PCR-derived fragment was generated using oligonucleotides MM002 (SEQ ID NO:161) (5'-GATCTGACTGCGGCTCCTCCATTACGATACAAACT TAACGG-3') and RW425 (SEQ ID NO:162) (5'-GTGGGTAAGGGAATTCGGATCCCCGGGTTAATTAA v TTAGTGATAC-3') and plasmid pRW825 as template. PCR using these oligonucleotides amplifies the vaccinia H6 promoter sequences from pRW825 such that the 3' end of the promoter is precisely linked to the 5'-most region of the p53 coding sequence. Plasmid pRW825 contains the vaccinia virus H6 promoter (Perkus et al., 1989) linked to a nonpertinent gene.

PCR was also used to generate a 480 bp and 250 bp fragment from p53wtXbaISP6/T3. The 480 bp fragment was derived with oligonucleotides MM003 (SEQ ID NO:163) (5'-GTTTGTATCGTAATGGAGGAGCCGCAGTCAGATC-3') and MM008 (SEQ ID NO:164) (5'-CATTACGATACAAACTTAACGGATATCGCGACGCG TTCACACAGGGCAGGTCTTGGC-3'). This fragment contains the 3' portion of the vaccinia virus H6 promoter sequences and the 5' portion of the p53 coding sequences through the SgrAI site. The 250 bp fragment was derived by amplification with oligonucleotides MM005 (SEQ ID NO:165) (5'-TACTACCTCGAGCCCGGGATAAAAAACGCGTTCA GTCTGAGTCAGGCCC-3') and MM007 (SEQ ID NO:166) (5'-GTGTGAACGCGTCGCGATATCCGTTAAGTTTGTAT CGTAATGCAGCTGCGTGGGCGTGAGCGCTTC-3'). This PCR fragment contains the 3' end of the p53 coding sequences beginning at the StuI restriction site. The 480 bp and 250 bp PCR fragments were generated such that the 5' end of the MM005/MM007-derived (SEQ ID NO:165/166) fragment overlaps the 3' end of the MM003/MM008-derived (SEQ ID NO:163/164) fragment.

The 227 bp, 480 bp, and 250 bp PCR-derived fragments were pooled and fused by PCR using oligonucleotides MM006 (SEQ ID NO:167) (5'-ATCATCGGATCCCCCGGGTTCTTTATTCTATAC-3') and MM005 (SEQ ID NO:165). The 783 bp fused PCR product contains the H6 promoter juxtaposed 5' to the 5' portion of the p53 coding sequence (through the SgrAI restriction site) followed by the end of the p53 coding sequence beginning at the StuI site. Following the end of the p53 coding sequence, a $T_5NT$ sequence motif providing early vaccinia transcription termination (Yuen and Moss, 1986) and a unique XhoI site were added. It should be noted that the final H6-p53 PCR fusion product (783 bp) does not contain the p53 coding sequences between the SgrAI and StuI restriction sites.

The 783 bp fusion was digested with BamHI (5' end) and XhoI (3' end) and inserted into plasmid pSD550 to yield plasmid pMM105.

Plasmids containing intact p53 gene (wildtype or mutant forms) juxtaposed 3' to the H6 promoter were generated by first digesting pMM105 with SgrAI and StuI. A 795 bp SgrAI/StuI fragment was isolated from p53wtXbaISP6/T3 and p53-238XbaI, while a 792 bp fragment was isolated from p53-217XbaI. These fragments were individually ligated to the SgrAI/StuI digested pMM105 plasmid to yield pMM106, pMM108, and pMM107, respectively.

Plasmids pMM106, pMM107, and pMM108 were used in standard in vitro recombination experiments (Piccini et al., 1987) with NYVAC (vP866; Tartaglia et al., 1992) as the rescue virus to generate recombinant viruses vP1101, vP1096, and vP1098, respectively. FIG. 77 presents the nucleotide sequence of the wildtype p53 expression cassette and flanking regions within vP1101 (SEQ ID NO:168). The H6 promoter starts at position 145. The p53 start codon is at position 269, and the p53 stop codon is at position 1450. Positions 1 through 144 and positions 1451 through 1512 flank the H6/p53 expression cassette. The sequences within vP1096 and vP1098 are identical except vP1096 contains a 3 base deletion from nucleotide 920 to 922 while vP1101 contains a point mutation at nucleotide 980 (T or C).

Both immunofluorescence and immunoprecipitation assays were performed using a p53-specific monoclonal antibody (pAB1801, Oncogene Science provided by Dr. J. Marks) to demonstrate expression of p53 in vP1101, vP1098 and vP1096 infected Vero cells. These assays were performed as described previously (Taylor et al., 1990). Immunofluorescence assay demonstrated p53-specific fluorescent staining of cells infected with vP1101, vP1096, or vP1098. The p53 antigen was located in both the nucleus and cytoplasm of the infected cells. The nuclear staining, however, was more intense in vP1101 infected cells. These results are similar to those reported by Ronen et al. (1992) using replication-competent vaccinia to express wildtype and mutant forms of p53. No p53-specific fluorescent staining was observed in Vero cells infected with the parental NYVAC virus, vP866.

ALVAC (CPpp) p53 insertion plasmids were engineered by excising the p53 expression cassettes from pMM106, pMM107, and pMM108 by digestion with BamHI and XhoI and inserting them individually into BamHI/XhoI digested NVQC5LSP. The 1320 bp BamHI/XhoI fragment containing the H6-p53 expression cassette from pMM106 and pMM108 was inserted into NVQC5LSP to yield pMM110 and pMM112, respectively, while the 1317 bp BamHI/XhoI fragment derived from pMM107 and inserted into NVQC5LSP yielded pMM111. (NVQC5LSP generated by introducing a NotI site in pVQC5LSP6, generated from pC5LSP, which in turn was generated from pCL5, which in further turn was generated from pC5LAB, which was generated from PHCOS1, which originated from 1535 bp upstream polylinker containing KpnI, SmaI, XbaI, and NotI sites and 404 bp of canarypox DNA, e.g., 31 bp of C5 coding sequence and 373 bp of downstream sequence, and cosmid vector pVK102; see FIG. 65 (SEQ ID NO:43), providing nucleotides 1–1372 of ClaI fragment from pHCOS1 containing C5 region.)

Insertion plasmids pMM110, pMM111, and pMM112 were used in standard in vitro recombination experiments (Piccini et al., 1987) with ALVAC (CPpp) as the rescue virus to yield vCP207, vCP193 and vCP191, respectively. Confirmation of expression of the p53 gene product was accomplished by immunoprecipitation assays performed as described above. FIG. 66 presents the nucleotide sequence of the H6/p53 (wildtype) expression cassette and flanking regions from vCP207 (SEQ ID NO:44). The H6 promoter starts at position 109. The p53 start codon is at position 233, and the p53 stop codon is at position 1414. Positions 1 through 232 and positions 1415 through 1483 flank the H6/p53 expression cassette. The nucleotide sequence is identical to that within vCP193 and vCP191 except vCP193 contains a 3 nucleotide deletion from nucleotide 973 to 975 while vCP191 contains a point mutation at nucleotide 94 to (T to C).

A listing of the NYVAC- and ALVAC- based p53 recombinant viruses is provided in Table 14.

TABLE 14

NYVAC and ALVAC-based p53 recombinant viruses

| Recombinant Virus | Parent Virus | Gene Insert |
|---|---|---|
| vP1101 | NYVAC | w.t. 53 |
| pP1096 | NYVAC | p53(−aa 217) |
| pP1098 | NYVAC | p53 (aa238; C to R) |
| vCP207 | ALVAC | w.t. 53 |
| vCP193 | ALVAC | p53 (−aa 217) |
| vCP191 | ALVAC | p53 (−aa 238; C to R) |

Example 4.2

Insertion of Wildtype and Mutant Forms of Murine P53 into ALVAC

The gene for the nuclear phosphoprotein p53 is the gene most frequently found to be mutated in a wide variety of human tumors (reviewed in Hollstein et al., 1991). NYVAC and ALVAC-based p53 recombinant virus are described in Example 4.1.

Insertion of wildtype Murine p53 into ALVAC. Plasmid p11-4 containing murine wild-type p53 was received from Arnold Levine (Princeton University, Princeton, N.J.). The p53 sequence is described in Pennica et al., (1984). The murine wild-type p53 gene was placed under the control of the vaccinia H6 promoter and the p53 3' non coding end was removed with PCR-derived fragments.

A fragment containing the H6 promoted 5' end of the p53 gene fused to the 3' end of the p53 gene was generated by several PCRs as described below.

PCR I: Plasmid pRW825, containing the H6 promoter and a nonpertinent gene, was used as template with oligonucleotides MM080 (SEQ ID NO:169) 5'ATTATTATTGGATCCTTAATTAATTAGTGATACGC 3' and MM081 (SEQ ID NO:170) 5'CTCCTCCATGGCAGTCATTACGATACAAACTTAAC 3' producing a 228 bp fragment containing the H6 promoter and the 5'-most base pairs of the murine p53 gene. MM080 anneals to the 5' end of the H6 promoter and primes toward the 3' end. MM081 anneals to the 3' end of the H6 promoter and primes toward the 5' end.

PCR II: Plasmid p11-4 was used as template with oligonucleotides MM082 (SEQ ID NO:171) 5'CGTTAAGTTTG- TATCGTAATGACTGCCATGGAGGAGTC 3' and MM083 (SEQ ID NO:172) 5'TAGTAGTAGTAGTAGCTTCTG-GAGGAAGTAGTTTCC 3' to generate a 129 bp fragment with the 3'-end of the H6 promoter, the 5' end of the p53 gene followed by 15 bp which overlaps PCR fragment PCRIII (described below). MM082 contains the 3' end of the H6 promoter and primes from the 5' end of the murine p53 gene. MM083 anneals to position 97 (FIG. 67) of the murine p53 gene and primes toward the 5' end.

PCRIII: Plasmid p11-4 was used as template with oligonucleotides MM084 (SEQ ID NO:173) 5'CAGAAGCTAC-TACTACTACTACCCACCTGCACAAGCGCC 3' and MM085 (SEQ ID NO:174) 5'AACTACTGTCCCGG-GATAAAAATCAGTCTGAGTCAGGCCCCAC 3' to generate a 301 bp fragment. The 301 bp PCR-derived fragment contains the 3' end of the p53 gene, and the 5' end overlaps the 3' end of the PCRII product. MM084 (SEQ ID NO:173) primes from position 916 of the murine p53 gene toward the 3' end. MM085 (SEQ ID NO:174) primes from position 1173 toward the p53 gene 5' end. The three PCR products were pooled and primed with MM080and MM085. The resultant 588 bp fragment contains a BamHI site followed by the H6 promoted 5' end of the p53 gene fused to the p53 gene 3' end followed by a SmaI site; the 5' end of the p53 gene ends at the XhoI site at position 37, and the 3' end starts at the SacII site at position 990 (FIG. 67). The 588 bp PCR-derived fragment was digested with BamHI and SmaI generating a 565 bp fragment which was inserted into BamHI/SmaI digested pNC5LSP5 (described below). The resultant plasmid, designated pMM136, was digested with KspI and XhoI to remove a 149 bp fragment, and the 953 bp KspI/XhoI fragment from p11-4 was inserted. The resultant plasmid, pMM148, contains the H6 promoted wild-type murine p53 in the ALVAC C5 insertion locus.

The construction of pNC5LSP5 is as follows. A C5 insertion vector plasmid C5LSP (Example 3.5) was digested with EcoRI, treated with alkaline phosphatase and ligated to self-annealed oligonucleotide CP29 (SEQ ID NO:107) 5' AATTGCGGCCGC 3', then digested with NotI and linear purified followed by self-ligation. This procedure introduced a NotI site to pC5LSP, generating pNC5LSP5.

The nucleotide sequence of the wildtype murine p53 gene is presented in FIG. 67 (SEQ ID NO:45). The start codon is at position 1 and the stop codon is at position 1171.

Recombination between donor plasmid pMM148 and ALVAC rescuing virus generated recombinant virus vCP263. vCP263 contains the wild type murine p53 gene under the control of the vaccinia H6 promoter in the C5 locus. Analysis confirms expression.

Insertion of a mutant form of Murine D53 into ALVAC. Plasmid pSVK215 containing a mutant form of the murine p53 gene was received from Arnold Levine (Princeton University, Princeton, N.J.). The mutation in pSVKH215 changes the sequence GTAC of the murine p53 coding sequence (FIG. 67) nt positions 643 through 646 to CCAAGCTTGG. The insertion between nt positions 643 and 646 changes the predicted amino acid coding sequence from val-pro to pro-ser-leu-ala; and the insertion replaces a KpnI site with a HindIII site. The construction of pSVKH215 is described in Tan et al. (1986).

Plasmid pMM136 (described above) contains the vaccinia H6 promoted 5' end of the p53 gene fused to the 3' end of the p53 gene in an ALVAC C5 locus insertion plasmid. pMM136 was digested with KspI and XhoI to remove 149 bp, and the 960 bp KspI/XhoI fragment containing the mutation described above from pSVKH215 was inserted. The resultant plasmid, pMM149, contains the H6 promoted murine mutant p53 gene in the C5 locus.

Recombination between donor plasmid pMM149 and ALVAC rescuing virus generated recombinant virus vCP267. vCP267 contains the mutant form of the murine p53 gene under the control of the vaccinia H6 promoter in the C5 locus. Analysis confirms expression.

Example 4.3

Insertion of Mutant Forms of Human P53 into ALVAC and NYVAC

Mutant forms of Human P53 into ALVAC. FIG. 66 (see Example 4.1) presented the sequence of the vaccinia H6 promoted human wild type p53 gene cassette in an ALVAC-based recombinant, vCP207. In this example, to facilitate description of the mutant forms of the human p53 gene being described, FIG. 68 (SEQ ID NO:46) presents only the coding sequence for the human wild type p53 gene. The start codon is at position 1 and the stop codon is at position 1180.

Plasmid Cx22A, containing a mutant form of the human p53 gene, was received from Arnold Levine (Princeton University, Princeton, N.J.). Relative to the wild type p53 sequence presented in FIG. 68, the G at nucleotide position 524 is substituted with an A, changing the arg amino acid at codon 175 of the wild type protein to a his amino acid in Cx22A.

Plasmid pMM110 (see Example 4.1, FIG. 66) contains the vaccinia H6 promoted wildtype human p53 gene in the ALVAC C5 insertion site. The human p53 gene contains two PflmI sites. p53 coding sequences upstream from the first PflmI site and downstream from the second PflmI site are the same in pMM110 as in Cx22A. pMM110 was digested with PflmI to remove the 853 central base pairs of the p53 gene. The 853 bp PflmI fragment from Cx22A containing the base change at position 524 was inserted. The resultant plasmid, pMM143, contains the H6 promoted mutant p53 gene.

Recombination between donor plasmid pMM143 and ALVAC rescuing virus generated recombinant virus vCP270. vCP270 contains the mutant form of the human p53 gene under the control of the vaccinia H6 promoter in the C5 locus.

Plasmid pR4-2 containing a mutant form of the human p53 gene was received from Arnold Levine (Princeton University, Princeton, N.J.). Relative to the wild type p53 sequence presented in FIG. 68, the G at nucleotide position 818 is substituted by an A, changing the arg codon at amino acid position 273 to a his codon in pR4-2.

Plasmid pMM110 (Example 4.1, FIG. 66) contains the vaccinia H6 promoted human wildtype p53 gene in the ALVAC C5 insertion site. p53 coding sequences upstream from the first PflmI site and p53 coding sequences downstream from the second PflmI site are the same in pMM110 as in pR4-2. pMM110 was digested with PflmI to remove the 853 central base pairs of the p53 gene. The 853 bp PflmI fragment from pR4-2 containing the base change at nucleotide position 818 was inserted. The resultant plasmid, pMM144, contains the H6 promoted mutant form of the human p53 gene in the C5 insertion locus.

Recombination between donor plasmid pMM144 and ALVAC rescuing virus generated recombinant virus vCP269. vCP269 contains the mutant form of the human p53 gene under the control of the vaccinia H6 promoter in the C5 locus.

Mutant forms of Human p53 into NYVAC. Plasmid Cx22A, described above, contains a mutant form of the human p53 gene, in which the G at nucleotide position 524 (FIG. 68) is substituted by an A, changing the arg codon at amino acid position 175 to a his codon in Cx22A.

Plasmid pMM106 (Example 4.1) contains the vaccinia H6 promoted wild-type human p53 gene in the NYVAC I4L insertion locus. p53 coding sequences upstream from the first PflmI site and p53 coding sequences downstream from the second PflmI site are the same in pMM106 as in Cx22A. pMM106 was digested with PflmI to remove the 853 central base pairs of the p53 gene. The 853 bp PflmI fragment from Cx22A containing the base change at position 524 was inserted. The resultant plasmid, pMM140, contains the H6 promoted mutant p53 gene.

Recombination between donor plasmid pMM140 and NYVAC rescuing virus generated recombinant virus vP1234. vP1234 contains the mutant form of the human p53 gene under the control of the vaccinia H6 promoter in the I4L locus.

Plasmid pR4-2, described above, contains a mutant form of the human p53 gene, in which the G at nucleotide position 818 (FIG. 68) is substituted by an A, changing the arg codon at amino acid position 273 to a his codon in pR4-2. pMM106 (Example 4.1) contains the H6 promoted wild-type human p53 gene in the I4L locus. p53 coding sequences upstream from the first PflmI site and p53 coding sequences downstream from the second PflmI site are the same in pMM106 as in pR4-2. pMM106 was digested with PflmI to remove the 853 central base pairs of the p53 gene. The 853 bp PflmI fragment from pR4-2 containing the base change at position 818 was inserted. The resultant plasmid, pMM141, contains the H6 promoted mutant p53 gene.

Recombination between donor plasmid pMM141 and NYVAC rescuing virus generated recombinant virus vP1233. vP1233 contains the mutant form of the human p53 gene under the control of the vaccinia H6 promoter in the I4L locus.

A listing of the wildtype and mutant forms of murine p53 and the mutant forms of human p53 present in ALVAC and NYVAC recombinants described in Examples 4.2 and 4.3 is provided in Table 15.

TABLE 15

| Recombinant Virus | Parent Virus | Species | Gene Insert |
|---|---|---|---|
| vCP263 | ALVAC | *murine* | w.t. p53 |
| vCP267 | ALVAC | *murine* | p53 (+3 aa) |
| vCP270 | ALVAC | *human* | p53 (aa 175; R to H) |
| vCP269 | ALVAC | *human* | p53 (aa 273; R to H) |
| vP1234 | NYVAC | *human* | p53 (aa 175; R to H) |
| vP1233 | NYVAC | *human* | p53 (aa 273; R to H) |

Immunoprecipitation. ALVAC and NYVAC based recombinants vP1101, vP1096, vP1098, vCP207, vCP193, vCP191 (all described in Example 4.1; Table 14, as well as ALVAC and NYVAC based recombinants vCP270, vCP269, vP1233, vP1234 described in this Example, Table 15), contain wild type or mutant forms of the human p53 gene. All of these recombinant virus were assayed for expression of the human p53 gene using immunoprecipitation.

Recombinant or parental virus were inoculated onto preformed monolayers of tissue culture cells in the presence of radiolabelled $^{35}S$-methionine and treated as previously described (Taylor et al., 1990). Immunoprecipitation reactions were performed using a human p53 specific monoclonal antibody 1801. A protein of between 47 and 53 kDa was precipitated from cells infected with any of the recombinant viruses, vP1101, vP1096, vP1098, vCP207, vCP193, vCP191, vCP270, vCP269, vP1233, or vP1234, but not from uninfected cells or cells infected with parental ALVAC or NYVAC virus.

Based upon the properties of the poxvirus vector systems, NYVAC, ALVAC and TROVAC cited above, such vectors expressing either wildtype or mutant forms of p53 provide valuable reagents to determine whether endogenous CTL activities can be detected in patient effector populations (TILS, PBMC, or lymph node cells); and, valuable vehicles for the stimulation or the augmenting of such activities; for instance, augmenting such activities by in vitro or ex vivo stimulation with these recombinant viruses. Further, the highly attenuated properties of both NYVAC and ALVAC allow the recombinants of the invention to be used for interventive immunotherapeutic modalities discussed above, e.g., in vivo interventive immunotherapy.

Example 5

Poxvirus-Rat CMV IE1 and IE2 Recombinants

Plasmids RCMVIE1 and RCMVIE2 were obtained from Dr. Toren Finkel (NIH-NHLBI), and transformed into bacteria MN522 (available from Stratgene). In FIG. 69 RCMVIE1 the coding sequence for the Rat CMV IE1 gene is depicted from nucleotides 443–2140 (SEQ ID NO:47). In FIG. 70 RCMVIE2 the coding sequence for the Rat CMV IE1 gene is depicted from nucleotides 443–2002 (SEQ ID NO:48).

Oligonucleotides SPIE1C (5'-TAG-ATA-AAG-CTG-CAG-AGT-CA-3') (SEQ ID NO:176) and SPIE1D (5'-AGA-CTC-GAG-ATA-AAA-ATT-ATG-ATC-TCC-TGC-CTC-TCT-3') (SEQ ID NO:177) were used in PCR with plasmid RCMVIE1 to generate a 585 bp fragment containing the C-terminal end of the IE1 gene. This fragment was digested with PstI and XhoI (yielding a 565 bp fragment) and cloned into BamHI/XhoI digested and alkaline phosphatase treated IBI25 along with a 1132 bp BamHI/PstI fragment from RCMVIE1 generating plasmid IE1-2-21.

Oligonucleotides SPIE2C (5'-CGC-AAG-CTT-CGC-GAT-AAA-AAT-TAT-TCT-GAA-TCG-GAG-TCC-T-3') (SEQ ID NO:178) and SPIE2D (5'-ATG-ATA-ATC-CAA-GCG-GCA-ACA-3') (SEQ ID NO:179) were used in PCR with plasmid RCMVIE2 to generate a 272 bp fragment containing the C-terminal end of the IE2 gene. This fragment was digested with NsiI and PstI (yielding a 210 bp fragment) and cloned into BamHI/HindIII digested IBI25 along with a 1361 bp BamHI/NsiII fragment from RCMVIE2 generating plasmid IE2-2-4.

Plasmid IBI25 was digested with EcoRI and XbaI, treated with alkaline phosphatase and ligated to kinased and annealed oligonucleotides SPIE2A (5'-CTA-GAG-GAT-CCA-TTT-TAT-ATT-GTA-ATT-ATA-TAT-TTT-CAA-TTT-TGA-AAT-CCC-AAA-ACC-CGG-GAG-ATC-TG-3') (SEQ ID NO:180) and SPIE2B (5'-AAT-TCA-GAT-CTC-CCG-GGT-TTT-GGG-ATT-TCA-AAA-TTG-AAA-ATA-TAT-AAT-TAC-AAT-ATA-AAA-TGG-ATC-CT-3') (SEQ ID NO:181) yielding plasmid IE2-1-1.

Plasmid IE2-1-1 was digested with BamHI and HindIII, treated with alkaline phosphatase and ligated to a 1570 bp BamHI/HindIII fragment derived from plasmid IE2-2-4 yielding plasmid IE2-3-1 which contains the Rat CMV IE2 gene under the control of the entemopoxvirus 42K early promoter.

NYVAC donor plasmid pSD553 (which contains the K1L host range gene, a polylinker and sequences flanking the ATI locus; see U.S. Pat. No. 5,494,807) was digested with BamHI and NruI, treated with alkaline phosphatase and ligated to a 1618 bp BglII/NruI fragment from plasmid IE2-3-1 generating plasmid IE2-4-16.

Plasmid MCP1-3 (which contains the vaccinia early/late H6 promoter) was derived from SPHA-H6. Plasmid SPHA-H6 was used in PCR with oligonucleotides SPMCP1 (5'-GCCTCTAGACTCGAGCGCCGACCAGTTCTCCATT ACGATACAAACTTAACGGATATC-3') (SEQ ID NO:184) and SPMCP2 (5'-CGCGAATTCTTCTTTATTCTATACTTA-3') (SEQ ID NO:185) and the resulting 166 bp fragment was digested with Eco RI and XbaI and ligated to EcoRI/XbaI digested and alkaline phosphatase-treated IBI24 generating plasmid MCP1-3.

Plasmid MCP1-3 was digested with EcoRV (within the H6 promoter) and XbaI (within the polylinker), treated with alkaline phosphatase and ligated to kinased and annealed oligonucleotides SPIE1A (5'-ATC-CGT-TAA-GTT-TGT-ATC-GTA -ATG-GAT-CCT-3') (SEQ ID NO:182) and SPIE1B (5'-CTA-GAG-GAT-CCA-TTA-CGA-TAC-AAA-CTT-AAC-GGA-T-3') (SEQ ID NO:183) yielding plasmid IE1-1-3.

Plasmid IE1-1-3 was digested with BamHI and XhoI, treated with alkaline phosphatase and ligated to a 1703 bp BamHI/XhoI fragment from plasmid IE1-2-21 yielding plasmid IE1-3-2 (which contains the Rat CMV IE1 gene under the control of the vaccinia H6 promoter).

Plasmid IE2-4-16 was digested with SmaI and XhoI and treated with alkaline phosphatase. Plasmid IE1-3-2 was digested with EcoRI, filled in with Klenow, digested with XhoI and a 1838 bp fragment isolated. Ligation of these two fragments yielded plasmid COPAKIE1.2-2. The DNA sequence of Rat CMV IE1 and IE2 plus additional flanking DNA sequences in plasmid COPAKIE1.2-2 is shown in FIGS. 71A and B providing the nucleotide sequence (DNA) of COPIE$1_{13}$ 2 (SEQ ID NO:49). The H6 promoted Rat CMV IE1 gene is located between nucleotides 2252 and 431. The 42K promoted Rat CMV IE2 gene is located between nucleotides 2261 and 3862.

Plasmid COPAKIE1.2-2 was transfected into NYVAC infected CEF cells to generate recombinant vP1479. Analysis confirms expression.

Example 6

Baculovirus Rat CMV IE1 OR IE2 Recombinants

Baculovirus recombinants expressing Rat CMV IE1 or IE2 were derived using the BAC-TO-BAC BACULOVIRUS EXPRESSION SYSTEM (Life technologies) as described in the instruction manual. This system is based on the site specific transposition of an expression cassette into a baculovirus shuttle vector (bacmid) propagated in *E. coli*. The recombinant bacmid DNA is isolated and used to transfect insect cells. Viral stocks harvested from transfected cells are amplified and used to infect insect cells for subsequent protein expression, purification (by virtue of the His tag present on the recombinant protein) and analysis (see FIG. 72, Generation of recombinant baculovirus and gene expression with the Bac-to-Bac Expression system).

The donor plasmid pFASTBACHTa (FIG. 73) was digested within the multiple cloning sites (FIG. 74) with BamHI and HindIII and a 4771 bp fragment isolated. Plasmid IE1-2-21 was digested with BamHI and HindIII and a 1716 bp fragment isolated. Ligation of these two fragments yielded plasmid BacRIE1-3 which encodes a fusion protein containing 25 amino acids derived from pFASTBACHTa and the entire rat CMV IE1 amino acid sequence.

Plasmid IE2-2-4 was digested with BamHI and HindIII and a 1570 bp fragment was isolated and ligated to the 4771 bp BamHI/HindIII fragment from pFASTBACHTa yielding plasmid BacRIE2-4. This plasmid encodes a fusion protein containing 25 amino acids derived from pFASTBACHTa and the entire rat CMV IE2 amino acid sequence.

BacRIE1-3 and BacRIE2-4 were transformed into DH10Bac cells and transposition allowed to occur. Recombinant bacmid DNA was isolated from appropriate colonies and used to transfect Sf9 insect cells to generate recombinant baculoviruses A6 (Rat CMV IE1 recombinant) and B2 (Rat CMV IE2 recombinant). Analysis confirms expression (FIG. 76A, lane 6).

FIG. 75 (SEQ ID NO: 50) provides the nucleotide sequence (DNA) of HCMV IE2, which is useful in generating vectors or recombinants for use in this invention.

Proteins expressed by the recombinant baculovirus were isolated and purified as follows:

Purification of Recombinant Proteins Expressed by Baculovirus

Baculovirus proteins were purified using the His Trap chelating column from Pharmacia Biotech. A suspension culture of SF9 insect cells at a density of $2\times10^6$ per ml was inoculated with recombinant baculovirus at a multiplicity of 1 plaque forming unit of virus per cell. Cells were incubated at 28° and harvested at 72 hours post infection. Cells were spun out at 2000 rpm for 10 minutes at 4° C. and stored at −80° C. until processing. Cells were lysed using 5 ml of lysis buffer per gram of cells. Lysis buffer was composed of 1×Phosphate buffer (supplied with kit), 10 mM Imidazole (supplied with kit), 1% NP-40, 1 mM PMSF, and 0.01M Mercaptoethanol. Cells were sonicated to release the virus and spun out at 8000 rpm for 10 minutes, 4° C. The supernatant was filtered through a 0.45 micron disc filter to remove particulates. The column was prepared for use by washing with 5 ml water and charging with 0.5 ml 0.1M nickel salt solution (supplied with kit); this was followed by a 5 ml water wash. The column was equilibrated with 10 ml of the lysis buffer prior to loading. The sample was applied to the column at a flow rate of 1 ml per minute. Next, the column was washed with 10 ml of lysis buffer. Fractions were eluted with a buffer composed of 1×Phosphate, 500 mM Imidazole, 10% NP-40, 0.01M Mercaptoethanol in 1 ml aliquots. Fractions were tested by Western Blot using an ECL kit. The primary antiserum was Rabbit anti Rat Cytomegalovirus IE1 and IE2 specific serum from Gordon Sandford, Johns Hopkins at a 1:300 dilution in PBS containing 1% Tween (such serum can be generated by the skilled artisan from isolation of native IE1 and IE2). The conjugate used was an HRP swine anti rabbit (DAKO) at 1:1000. Positive fractions were pooled and dialyzed against PBS (Spectra/Por 1 6,000–8,000 dialysis membrane). Protein determinations were made using the BCA microtiter plate method and samples were examined for purity by Coomassie Blue stain and Western Blot.

FIGS. 76A and B, respectively, show Western Blot and Coomassie Blue stained gel. In FIG. 76A: lane 1=SF9 insect cell lysate, lane 2=baculovirus RCMVIE1 infected SF9 cell lysate, lane 3=RCMVIE1 purified protein preparation, lane 4=baculovirus RCMVIE2 infected SF9 cell lysate, lane 5=RK-13 cells, lane 6=vP1479 infected RK-13 cell lysate, and lane 7=prestained molecular weight markers. In FIG. 76B: lane 1=RCMVIE1 purified protein preparation, and lane 2=prestained molecular weight markers.

Example 7

Additional Baculovirus Recombinants

By employing the techniques of Smith et al., U.S. Pat. No. 4,745,051, incorporated herein by reference, or of other literature concerning baculovirus recombinants, including the techniques of Example 6, with exogenous DNA of any of U.S. Pat. Nos. 5,047,320, 5,075,213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995 (see Example 3), Paoletti et al. WO 94/16716 based on U.S. applications Ser. Nos. 007,115, filed Jan. 21, 1993, and 184,009, filed Jan. 19, 1994 (see Example 4), or other documents cited and incorporated herein, or literature concerning HCMV antigens, epitopes of interest, p53, p53 epitopes of interest, and DNA coding therefor, baculovirus embodiments expressing any desired HCMV and/or p53 epitope of interest, including those set forth in Examples 3 and 4 for various HCMV epitopes of interest and p53 epitopes of interest, and gene products therefrom, are obtained, for practice of this invention. Analysis confirms expression.

Example 8

Adenovirus Recombinants

By employing the techniques of U.S. Pat. Nos. 5,591,439 and 5,552,143, or of other literature concerning adenovirus recombinants with exogenous DNA of any of U.S. Pat. Nos. 5,047,320, 5,075,213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995 (see Example 3), Paoletti et al. WO 94/16716 based on U.S. applications Ser. Nos. 007,115, filed Jan. 21, 1993, and 184,009, filed Jan. 19, 1994 (see Example 4), or other documents cited and incorporated herein, or literature concerning HCPV antigens, epitopes of interest, p53, p53 epitopes of interest, and DNA coding therefor, adenovirus embodiments expressing any desired HCMV and/or p53 epitope of interest, including the HCMV and p53 epitopes of interest of Examples 3 and 4 are obtained, for practice of this invention. Analysis confirms expression.

Example 9

DNA Expression System Embodiments

By employing the techniques of U.S. Pat. Nos. 5,591,639, 5,589,466, 5,580,589, incorporated herein by reference, or of other literature concerning DNA expression vectors with exogenous DNA of any of U.S. Pat. Nos. 5,047,320, 5,075,213, Paoletti, U.S. Pat. No. 5,338,683, Paoletti et al., U.S. Pat. No. 5,494,807, Paoletti et al., PCT publication WO 96/39491, based on U.S. applications Ser. Nos. 08/471,014, filed Jun. 6, 1995, and 08/658,665, filed Jun. 5, 1995 (see Example 3), Paoletti et al. WO 94/16716 based on U.S. applications Ser. Nos. 007,115, filed Jan. 21, 1993, and 184,009, filed Jan. 19, 1994 (see Example 4), or other documents cited and incorporated herein or literature concerning HCMV antigens, epitopes of interest, p53, p53 epitopes of interest, and DNA coding therefor, DNA expression vector embodiments expressing any desired HCMV and/or p53 epitope of interest, including HCMV and p53 epitopes as in Examples 3 and 4 and gene products therefrom, are obtained, for practice of this invention. Analysis confirms expression.

Example 10

Formulations and Use

Native HCMV epitopes are obtained from cells infected with HCMV, and native p53 epitopes are also obtained from cells wherein expression thereof is detected. Recombinant HCMV and p53 epitopes are obtained from recombinants expressing these products, e.g., as in the previous Examples. These proteins are admixed with carrier, diluent etc., as herein described in amounts as herein described to obtain formulations. Recombinants and DNA expression systems expressing HCMV epitopes and p53 epitopes are obtained, e.g., as in the previous Examples; and, these recombinants and DNA expression systems are admixed with carrier, diluent, etc., as herein described to obtain formulations. Patients are administered the formulations as herein described for the prevention and/or treatment of vascular disease such as atherosclerosis and/or restenosis, including in a manner analogous to gene therapy directed against SMC proliferation, as described in literature cited herein. Propensity towards or against such disease is determined using diagnostic methods as herein described.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Akrigg, A., Wilkinson, G. W. G., and Oram, J. D., Virus Res. 2:107–121 (1985).
2. Alp, N. J., Allport, T. D., Zanten, J. Van, Rodgers, B., Patrick Sissons, J. G. and Borysiewicz, L. K., J. Virol. 65:4812–4820 (1991).
3. Biegalke, B. J. and Geballe, A. P., Virology 183:381–385 (1991).
4. Blanton, R., and Tevethia, M., Virology 112:262–273 (1981).
5. Borysiewicz, L. K., Hickling, J. K., Graham, S., Sinclair, J., Cranage, M. P., Smith, G. L., and Sissons, J. G. P., J. Exp. Med. 168:919–931 (1988).
6. Britt, W. J. and Auger, D., J. Virol. 58:185–191 (1986).
7. Britt, W. J. and Vugler, L. G., J. Virol. 63:403–410 (1989).
8. Cameron, J., and Preston, C., J. Gen. Virol. 54:421–424 (1981).
9. Cherrington, J. M. and Mocarski, E. S., J. Virol. 63:1435–1440 (1989).
10. Clewell, D. B. and D. R. Helinski, Proc. Natl. Acad. Sci. USA 62, 1159–1166 (1969).
11. Clewell, D. B., J. Bacteriol 110, 667–676 (1972).
12. Colberg-Poley, A. M., Santomenna, L. D., Harlow, P. P., Benfield, P. A. and Tenney, D. J., J. Virol. 66:95–105 (1992).
13. Cooney, E., McElrath, M., Corey, L., Hu, S., Collier, A., Arditti, D., Hoffman, M., Coombs, R., Smith, G., and Greenberg, P., Proc. Natl. Acad. Sci. USA 90:1882–1886 (1993).
14. Davidoff, A. M., Kerns, B. J. M., Iglehart, J. D., Marks, J. R., Cancer Res. 51, 2605–2610 (1991).
15. Davidoff, A. M., J. D. Iglehart, and J. R. Marks, PNAS USA 89, 3439–3442 (1992).
16. Engelke, D. R., Hoener, P. A., and Collins, F. S., Proc. Natl. Acad. Sci. 85:544–548 (1988).
17. Ghazal, P., Young, J., Giuletti, E., DeMattei, C., Garcia, J., Gaynor, J., Stenberg, R. M. and Nelson, J. A., J. Virol. 65:6735–6742 (1991).
18. Gillard, S., Spehner, D., Drillien, R., and Kirn, A., Proc. Natl. Acad. Sci. USA 83:5573–5577 (1986).
19. Goebel, S. J., Johnson, G. P., Perkus, M. E., Davis, S. W., Winslow, J. P., Paoletti, E., Virology 179:247–266 (1990a).

20. Goebel, S. J., G. P. Johnson, M. E. Perkus, S. W. Davis, J. P. Winslow and E. Paoletti, Virology 179:517–563 (1990b).

21. Gönczöl E., Furlini, G., Ianacone, J., and Plotkin, S., J. Virol. Meth. 14:37–41 (1986).

22. Gönczöl, E., De Taisne, C., Hirka, G., Berencsi, K., Lin, W., Paoletti, E. and Plotkin, S., Vaccine 9:631–637 (1991).

23. Gönczöl, E., Ianacone, W. H. O., Starr, S., Meignier, B., and Plotkin, S. A., Vaccine 8:130–136 (1990).

24. Graham, B., Mathes, T., Belshe, R., Clements, M., Dolin, R., Wright, P., Gorse, G., Schwartz, D., Keefer, M., Bolognesi, D., Corey, L., Stablein, D., Esterlitz, J., Hu, S. -L., Smith, G., Fast, P., Koff, W. and the HIAID AIDS Vaccine Clinical Trials Network, J. Infect. Dis. 167:533–537 (1993).

25. Guo, P., Goebel, S., Davis, S., Perkus, M. E., Languet, B., Desmettre, P., Allen, G., and Paoletti, E., J. Virol. 63:4189–4198 (1989).

26. Hagemeier, C., Walker, S. M., Sissons, P. J. G. and Sinclair, J. H., J. Gen. Virol. 73:2385–2393 (1992).

27. Harlow, E. and Lane D., In Antibodies: A Laboratory Manual (Cold Spring Harbor University, Cold Spring Harbor, N.Y.) (1988).

28. Hollstein, M., Sidransky, D., Vogeistein, B., Harris, C. C., Science 253, 49–53 (1991).

29. Hu, S. -L., Klaniecki, J., Dykers, T., Sridhar, P. and Travis, B., AIDS RES. Hum. Retroviruses 3:615–620 (1991).

30. Hu, S. -L., Abrams, K., Barber, G., Moran, P., Zarling, J., Langlois, A., Kuller, L., Morton, W. and Benveniste, R., Science 255:456–459 (1992).

31. Kieny, M. P., Lathe, R., Drillien, R., Spehner, D., Skory, S., Schmitt, D., Wiktor, T., Koprowski, H., and Lecocq, J. P., Nature (London) 312:163–166 (1984).

32. Knauf, V. C., and Nester, E. W., Plasmid 8:45–54 (1982).

33. Kunkel, T. A., Proc. Natl. Acad. Sci. USA 82:488–492 (1985).

34. Lafemina, R., Pizzorno, M. C., Mosca, J. D. and Hayward, G. S., Virology 172:584–600 (1989).

35. Lamb, P. and Crawford, L., Mol. Cell. Biol. 6, 1379–1385 (1986).

36. Liu, Y. -N. C., Klaus, A., Kari, B., Stinski, M. F., Eckhardt, J. and Gehrz, R. C., J. Virology 65:1644–1648 (1991).

37. Mandecki, W., Proc. Natl. Acad. Sci. USA 83:7177–7182 (1986).

38. Maniatis, T., Fritsch, E. F., and Sambrook, J. In Molecular cloning: a laboratory manual, (Cold Spring Harbor Laboratory, Cold Spring Harbor, N.Y.) (1982).

39. Marshall, G. S., Rabalais, G. P., Stout, G. G. and Waldeyer, S. L., J. Infect. Dis. 165:381–384 (1992).

40. Pachl, C., Probert, W. S., Hermsen, K. M., Masiarz, F. R., Rasmussen, L., Merigan, T. C. and Spaete, R. C., Virology 169:418–426 (1989).

41. Pande, H., Campo, K., Tanamachi, B. and Zaia, J. A., Virology 182:220–228 (1991).

42. Panicali, D. and E. Paoletti, Proc. Natl. Acad. Sci. USA 79:4927–4931 (1982).

43. Panicali, D., Davis, S. W., Mercer, S. R., and Paoletti, E., J. Virol. 37:1000–1010 (1981).

44. Pennica, D., D. V. Goeddel, J. S. Hayflick, N. C. Reich, C. W. Anderson and A. J. Levine, Virology 134, 477–482 (1984).

45. Pereira, L. and Hoffman, M., In Human Herpesvirus Infections: Pathogenesis, Diagnosis and Treatments, eds. Lopez, C. and Roizman, B. Second International Conference on Immunobiology and Prophyaxis of Human Herpesvirus Infections Oct. 13–16, 1985 (Raven Press, New York) pp. 69–92 (1986).

46. Perkus, M. E., Goebel, S. J., Davis, S. W., Johnson, G. P., Limbach, K., Norton, E. K., and Paoletti, E., Virology 179:276–286 (1990).

47. Perkus, M. E., Limbach, K., and Paoletti, E., J. Virol. 63:3829–3836 (1989).

48. Perkus, M. E., A. Piccini, B. R. Lipinskas and E. Paoletti, Science 229:981–984 (1985).

49. Perkus, M. E., Kauffman, E. B., Taylor, J., Mercer, S., Smith, D., VanderHoeven, J. and Paoletti, E., J. Tiss. Cult. Meth. 15:72–81 (1993).

50. Pialoux, G., Excler, J. -L., Riviere, Y. et al., AIDS Research and Human Retroviruses 11:373–381 (1995).

51. Piccini, A., M. E. Perkus, and E. Paoletti, Methods in Enzymology 153:545–563 (1987).

52. Reis, B., Bogner, E., Reschke, M., Richter, A., Mockenhaupt, T. and Radsak, K., J. Gen. Virol. 74:1371–1379 (1993).

53. Riddell, S. R., Watanabe, K. S., Goodrich, J. M., Li, C. R., Agha, M. E. and Greenberg, P. D., Science 257:238–241 (1992).

54. Ronen, D., Teitz, Y., Goldfinger, N., Rotter, V. Nucleic Acids Research 20, 3435–3441 (1992).

55. Santomenna, L. D. and Colberg-Poley, A. M., J. Virol. 64:2033–2040 (1990).

56. Sanger, F., Nickel, S. Coulson, A. R., Proc. Natl. Acad. Sci. 74:5463–5467 (1977).

57. Spaete, R. R., Thayer, R. M., Probert, W. S., Masiarz, F. R., Chamberlain, S. H., Rasmussen, L., Merigan, T. C. and Pachl, C., Virology 167:207–225 (1988).

58. Tabor, S. and C. C. Richardson, Proc. Natl. Acad. Sci. USA 84:4767–4771 (1987).

59. Tan, T., Wallis, J., Levine, A., Journal of Virology 59, 574–583 (1986).

60. Tartaglia, J., J. Taylor, W. I. Cox, J. -C. Audonnet, M. E. Perkus, A. Radaelli, C. de Giuli Morghen, B. Meignier, M. Riviere, K. Weinhold & E. Paoletti, In AIDS Research Reviews, W. Koff, F. Wong-Staal & R. C. Kenedy, Eds., Vol. 3, Marcel Dekker, NY, pp. 361–378 (1993a).

61. Tartaglia, J., Pincus, S., Paoletti, E., Critical Reviews in Immunology 10:13–30 (1990a).

62. Tartaglia, J. and Paoletti, E., In Immunochemistry of Viruses, II, eds. M. H. V. van Regenmortel & A. R. Neurath, (Elsevier Science Publishers, Amsterdam) pp. 125–151 (1990b).

63. Tartaglia, J., Perkus, M. E., Taylor, J., Norton, E. K., Audonnet, J -C., Cox, W. I., Davis, S. W., Van der Hoeven, J., Meignier, B., Riviere, M., Languet, B., Paoletti, E., Virology 188:217–232 (1992).

64. Tartaglia, J., Jarrett, O., Desmettre, P., Paoletti, E., J. Virol. 67, 2370–2375 (1993b).

65. Taylor, J., Edbauer, C., Rey-Senelonge, A., Bouquet, J. -F., Norton, E., Goebel, S., Desmettre, P., Paoletti, E., J. Virol. 64:1441–1450 (1990).

66. Taylor, J., Weinberg, R., Kawaoka, Y., Webster, R. G., and Paoletti, E., Vaccine 6:504–508 (1988a).

67. Taylor, J., R. Weinberg, B. Lanquet, P. Desmettre, and E. Paoletti, Vaccine 6:497–503 (1988b).

68. Ulrich, S. J., Anderson, C. W., Mercer, W. E., Appella, E., J. Biol. Chem. 267:15259–15262 (1992).

69. Yuen, L. and B. Moss, J. Virol. 60:320–323 (1986).

70. Yuen, L., and Moss, B., Proc. Natl. Acad. Sci. USA 84:6417–6421 (1987).

What is claimed is:

1. A composition comprising: an expression system which expresses at least one exogenous epitope of interest of CMV and at least one epitope of interest of p53.

2. A method of inducing a response against cytomegalovirlis comprising administering to a patient in need of such a response a composition comprising: (I) at least one epitone of interest of CMV and/or an expression system which expresses at least one epitope of interest of CMV: and (II) at least one enitope of interest of p53 and/or an expression system which expresses the at least one enitope of p53.

3. The method of claim 2 further comprising administering treatment for reducing CMV viral burden and/or for inhibiting smooth muscle cell proliferation.

4. A method of treating conditions associated with cytomegalovirus comprising administering to a patient in need of such treatment a composition comprising: (I) at least one epitope of interest of CMV and/or an expression system which expresses at least one epitope of interest or CMV; and (II) at least one epitope of interest of p53 and/or an expression system which expresses the at least one epitope of p53.

5. The method of claim 4 further comprising administering treatment for reducing CMV viral burden and/or for inhibiting smooth muscle cell proliferation.

6. A method of preventing conditions associated with cytomegalovirus comprising administering to a patient in need of such prevention a composition comprising: (I) at least one epitope of interest of CMV and/or an expression system which expresses at least one epitope of interest of CMV; and (II) at least one epitope of interest of p53 and/or an expression system which expresses the at least one epitope of p53.

7. The method of claim 6, further comprising administering an agent for reducing CMV viral burden and/or for inhibiting smooth muscle cell proliferation.

8. The method according to any one of claims 2, 4 or 6 wherein the composition comprises an expression system which expresses at least one enitope of interest of CMV and at least one enitope of interest of p53.

9. The method of claim 8 further comprising administering an agent for reducing CMV viral burden and/or for inhibiting smooth muscle cell proliferation.

10. The method according to any one of claims 2, 4 or 6 wherein in the composition, (I) comprises the expression system which expresses at least one epitope of interest of CMV.

11. The method of claim 10 wherein in the composition, the expression system is an adenovirus, poxvirus or DNA plasmid expression system.

12. The method according to any one of claims 2, 4 or 6 wherein in the composition, (I) comprises the at least one epitope of interest of CMV.

13. The method of claim 12 wherein in the composition, the at least one epitope of interest is from expression by at least one recombinant.

14. The method of claim 13 wherein in the composition, the recombinant is an adenovinis, poxvirus, baculovirus, or DNA plasmid expression system.

15. The method according to any one of claims 2, 4 or 6 wherein in the composition, (II) comprises the at least one epitope of interest of p53.

16. The method according to any one of claims 2, 4 or 6 wherein in the composition, the CMV is human CMV.

17. The method according to any one of claims 2, 4 or 6 wherein in the composition, the CMV epitope of interest is selected from IE1 and/or IE2 or a portion thereof; gB; gB with transmembrane deleted therefrom; gH; gL; pp150; pp65; IE1 with amino acids 2–32 deleted therefrom; IE1 with amino acids 292–319 deleted therefrom; IE1 exon 4 segment; gB and gH; gB and pp65; gB, gH and pp65; gB, gH, pp65 and IE1 exon 4 segment; gB, gH, pp65, pp150, and IE1 exon 4 segment; gB, gH, pp65 and pp150; gB, gH, gL, pp65, pp150 and IE1 exon 4 segment; and gB, gH, gL, pp65 and pp150 ; gp64; or portion of such CMV antigens.

18. The method of claim 17 wherein in the composition, (II) comprises a p53 epitope of interest.

19. The method according to any one of claims 2, 4 or 6, wherein in the composition, (II) comprises the expression system that expresses the at least one epitope of interest of p53.

20. The method of claim 19 wherein in the composition, the CMV is human CMV.

21. The method of claim 19 wherein in the composition, the CMV epitope of interest is selected from IE1 and/or IE2 or a portion thereof; gB; gB with transmembrane deleted therefrom; gH; gL; pp150; pp65; IE1 with amino acids 2–32 deleted therefrom; IE1 with amino acids 292–319 deleted therefrom; IE1 exon 4 segment; gB and gH; gB and pp65; gB, gII and pp65; gB, gH, pp65 and IE1 exon 4 segment; gB, gH, pp65, pp150, and IE1 exon 4 segment; gB, gH, pp65 and pp150; gB, gH, gL, pp65, pp150 and IE1 exon 4 segment; and gB, gH, gL, pp65 and pp150; gp64; or portion of such CMV antigens.

22. The method of claim 19 wherein in the composition, (I) comprises the expression system which expresses at least one epitope of interest of CMV.

* * * * *

UNITED STATES PATENT AND TRADEMARK OFFICE

CERTIFICATE OF CORRECTION

PATENT NO. : 6,183,752 B1
DATED : February 6, 2001
INVENTOR(S) : Stephen E. Epstein et al.

It is certified that error appears in the above-identified patent and that said Letters Patent is hereby corrected as shown below:

Claim 2,
Line 3, change "epitone" to -- epitope --;
Line 6, change "enitope" to -- epitope --;
Line 7, change "enitope" to -- epitope --.

Claim 8,
Line 3, change "enitope" to -- epitope --;
Line 4, change "enitope" to -- epitope --.

Signed and Sealed this

Second Day of October, 2001

Attest:

Nicholas P. Godici

NICHOLAS P. GODICI

*Attesting Officer* *Acting Director of the United States Patent and Trademark Office*